US012679823B2

(12) United States Patent
Shirude et al.

(10) Patent No.: US 12,679,823 B2
(45) Date of Patent: Jul. 14, 2026

(54) OXOPYRROLIDINE FPR2 AGONISTS

(71) Applicant: BRISTOL-MYERS SQUIBB COMPANY, Princeton, NJ (US)

(72) Inventors: Pravin Sudhakar Shirude, Bangalore (IN); Chandrasekhar Reddy Rachamreddy, Kadapa District (IN); Amit Kumar Chattopadhyay, Bangalore (IN); Balaji Seshadri, Bangalore (IN); Vishweshwaraiah Baligar, Bangalore (IN); Sudhakara Reddy Madduri, Bangalore (IN); Ellen K. Kick, Pennington, NJ (US); Nicholas R. Wurtz, Pennington, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 646 days.

(21) Appl. No.: 18/004,731

(22) PCT Filed: Jul. 8, 2021

(86) PCT No.: PCT/US2021/040798
§ 371 (c)(1),
(2) Date: Jan. 9, 2023

(87) PCT Pub. No.: WO2022/011084
PCT Pub. Date: Jan. 13, 2022

(65) Prior Publication Data

US 2023/0348426 A1 Nov. 2, 2023

Related U.S. Application Data

(60) Provisional application No. 63/049,838, filed on Jul. 9, 2020.

(51) Int. Cl.

| | |
|---|---|
| *C07D 401/14* | (2006.01) |
| *C07D 207/14* | (2006.01) |
| *C07D 401/04* | (2006.01) |
| *C07D 403/04* | (2006.01) |
| *C07D 405/14* | (2006.01) |
| *C07D 413/14* | (2006.01) |
| *C07D 471/04* | (2006.01) |
| *C07D 487/04* | (2006.01) |
| *C07D 487/08* | (2006.01) |
| *C07D 491/08* | (2006.01) |
| *C07D 491/107* | (2006.01) |
| *C07D 498/04* | (2006.01) |
| *C07F 9/572* | (2006.01) |
| *C07F 9/6558* | (2006.01) |

(52) U.S. Cl.
CPC ......... *C07D 401/14* (2013.01); *C07D 207/14* (2013.01); *C07D 401/04* (2013.01); *C07D 403/04* (2013.01); *C07D 405/14* (2013.01); *C07D 413/14* (2013.01); *C07D 471/04* (2013.01); *C07D 487/04* (2013.01); *C07D 487/08* (2013.01); *C07D 491/08* (2013.01); *C07D 491/107* (2013.01); *C07D 498/04* (2013.01); *C07F 9/572* (2013.01); *C07F 9/65583* (2013.01)

(58) Field of Classification Search
CPC ... C07D 401/14; C07D 207/14; C07D 401/04
USPC .......................................................... 514/89
See application file for complete search history.

(56) References Cited

U.S. PATENT DOCUMENTS

| | | | | |
|---|---|---|---|---|
| 9,822,069 | B2 | 11/2017 | Takahashi et al. | |
| 10,029,983 | B2 * | 7/2018 | Takahashi et al. | .. C07D 207/46 |
| 2019/0270704 | A1 | 9/2019 | Shirude et al. | |

FOREIGN PATENT DOCUMENTS

| | | | |
|---|---|---|---|
| EP | 3075726 | A1 | 10/2016 |
| WO | 2015079692 | A1 | 6/2015 |
| WO | 2016189876 | A1 | 12/2016 |
| WO | 2016189877 | A1 | 12/2016 |
| WO | 2017091496 | A1 | 6/2017 |
| WO | 2017100390 | A1 | 6/2017 |
| WO | 2018217684 | A1 | 11/2018 |

(Continued)

OTHER PUBLICATIONS

Christopher R. McCurdy & Claude Cohen, Bioisosterism, Drug Design Org, Feb. 2007, p. 133. (Year: 2007).*

(Continued)

*Primary Examiner* — Jeffrey S Lundgren
*Assistant Examiner* — Heather Dahlin
(74) *Attorney, Agent, or Firm* — Hong Liu

(57) ABSTRACT

The disclosure relates to compounds of Formula (I), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, chronic obstructive pulmonary disease (COPD), and related diseases.

(I)

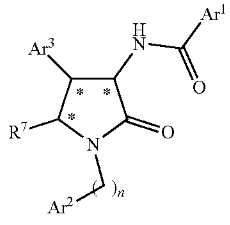

10 Claims, No Drawings

(56) References Cited

FOREIGN PATENT DOCUMENTS

| | | | | |
|---|---|---|---|---|
| WO | 2018227058 A9 | 12/2018 | | |
| WO | 2018227061 A1 | 12/2018 | | |
| WO | 2018227065 A1 | 12/2018 | | |
| WO | 2018227067 A1 | 12/2018 | | |
| WO | 2019173182 A1 | 9/2019 | | |
| WO | WO 2019170904 A1 * | 9/2019 | ........... | C07D 401/14 |
| WO | 2020102643 A1 | 5/2020 | | |
| WO | 2020112583 A1 | 6/2020 | | |
| WO | 2020257161 A1 | 12/2020 | | |
| WO | 2022011083 A1 | 1/2022 | | |
| WO | 2022/035923 A1 | 2/2022 | | |
| WO | 2022076764 A1 | 4/2022 | | |

OTHER PUBLICATIONS

U.S. Appl. No. 18/040,831, filed Feb. 7, 2023, Oxopyrrolidine Urea FPR2 Agonists.*

Christopher R. McCurdy & Claude Cohen, Bioisosterism, Drug Design Org, Feb. 2007, p. 133. (Year: 2007) (Year: 2007).*

Klapars et al., "A General and Efficient Copper Catalyst for the Amidation of Aryl Halides", J. Am. Chem. Soc. 2002, 124, 7421-7428.

Yin et al., "Palladium-Catalyzed Intermolecular Coupling of Aryl Halides and Amides" Organic Letters vol. 2(8)1101-1104 (2000).

Yin, et al., "Pd-Catalyzed Intermolecular Amidation of Aryl Halides: The Discovery that Xantphos Can Be Trans-Chelating in a Palladium Complex", J. Am. Chem. Soc. 2002, 124, 6043-6048.

Allen, Jr., Loyd V., "Remington: The Science and Practice of Pharmacy, vol. I and vol. II. Twenty-second edition", Pharmaceutical Press, 2012, p. 2724.

Burli et al., "Potent hFPRLI (ALXR) agonists as potential anti-inflammatory agents", Bioorganic & Medicinal Chemistry Letters, vol. 16(14), pp. 3713-3718 (2006).

Cattaneo et al., "Distinct Signaling Cascades Elicited by Different Formyl Peptide Receptor 2 (FPR2) Agonists" Int. J. Mol. Sci., vol. 14, pp. 7193-7230 (2013).

Chandrasekharan et al., "Lipoxins: nature's way to resolve inflammation", Journal of Inflammation Research, 2015:8 181-192.

Chen et al., "Regulation of inflammation by members of the formyl-peptide receptor family", Journal of Autoimmunity vol. 85, pp. 64-77 (2017).

Fredman et al.,"Targeted nanoparticles containing the pro resolving peptide Ac2-26 protect against advanced atherosclerosis in hypercholesterolemic mice", Sci. Trans. Med., vol. 7(275) 2015.

Gavins, Felicity N.E., "Are formyl peptide receptors novel targets for therapeutic intervention ischaemia-reperfusion injury?" Trends in Pharmacological Sciences, vol. 31(6), pp. 266-276 (2010).

Greene, T.W. et al., Protecting Groups in Organic Synthesis, 4th Edition, Wiley (2007).

Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).

Kiyomor, et al., "An Efficient Copper-Catalyzed Coupling of Aryl Halides with Imidazoles", Tetrahedron Letters 40 (1999) 2657-2660.

Klapars, et al., "A General and Efficient Copper Catalyst for the Amidation of Aryl Halides and the N-Arylation of Nitrogen Heterocycles", J. Am. Chem. Soc. 2001, 123, 7727-7729.

Liu et al., "Lipoxin A4 ameliorates ischemia/reperfusion induced spinal cord injury in rabbit model", Int. J. Clin.Exp. Medicine, Vo. 8(8), pp. 12826-12833 (2015.

Perretti, et al., "Resolution Pharmacology: Opportunities for Therapeutic Innovationin Inflammation", Trends in Pharmacological Sciences, vol. 36(11) 2015.

Petri et al., "The role of the FPR2/ALX receptor in atherosclerosis development and plaque stability", Cardiovascular Research, vol. 105, pp. 65-74 (2015).

Romano et al., "Lipoxins and aspirin-triggered lipoxinsin resolution of inflammation", European Journal of Pharmacology vol. 760 pp. 49-63 (2015).

Ye et al., "International Union of Basic and Clinical Pharmacology. LXXIII. Nomenclature for the Formyl Peptide Receptor (FPR) Family", Pharmacological Reviews, vol. 61(2), 2009.

* cited by examiner

OXOPYRROLIDINE FPR2 AGONISTS

CROSS REFERENCE TO RELATED APPLICATIONS

This application is a 371 application of PCT/US2021/040798, filed Jul. 8, 2021, which is entitled to priority pursuant to 35 U.S.C. § 119(e) to U.S. provisional patent application No. 63/049,838, filed Jul. 9, 2020, which is incorporated herein in its entirety.

BACKGROUND OF THE INVENTION

The present invention relates to novel oxopyrrolidine compounds, which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to a small group of seven-transmembrane domain, G protein-coupled receptors that are expressed in multiple human tissues including immune cells and are known to be important in host defense and inflammation. FPR2 shares significant sequence homology with FPR1 and FPR3 (Journal of Autoimmunity 85, 2017, 64-77). Collectively, these receptors bind a number of structurally diverse agonists, including N-formyl and nonformyl peptides which act as chemo attractants and activate phagocytes. The endogenous peptide Annexin A1 and its N-terminal fragments are examples of ligands that bind human FPR1 and FPR2. Fatty acids such as eicosanoid, lipoxin A4, which belongs to a class of small pro-resolution mediators (SPMs), has also been identified as an agonist for FPR2 (Ye R D., et al., Pharmacol. Rev., 2009, 61, 119-61).

Endogenous FPR2 pro-resolution ligands, such as lipoxin $A_4$ and Annexin A1, have been reported to trigger a wide array of cytoplasmatic cascades such as Gi coupling, $Ca^{2+}$ mobilization and β-arrestin recruitment. (Int J Mol Sci. 2013 April; 14(4): 7193-7230). FPR2 regulates both innate and adaptive immune systems including neutrophils, macrophages, T-, and B-cells. In neutrophils, FPR2 ligands modulate movement, cytotoxicity and life span. In macrophages, agonism of FPR2 prevents apoptosis and enhances efferocytosis. (Chandrasekharan J A, Sharma-Walia N. J. Inflamm. Res., 2015, 8, 181-92). The initiation of resolution of inflammation by FPR2 agonism is responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive loss of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 receptor with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, inflammatory bowel syndrome, Crohn's disease, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

SUMMARY OF THE INVENTION

The present invention provides novel oxopyrrolidines, and their analogues thereof, which are useful as FPR2 agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in therapy.

The compounds of the invention may be used in the treatment and/or prophylaxis of multiple diseases or disorders associated with FPR2, such as inflammatory diseases, heart diseases, chronic airway diseases, cancers, septicemia, allergic symptoms, HIV retrovirus infection, circulatory disorders, neuroinflammation, nervous disorders, pains, prion diseases, amyloidosis, and immune disorders. The heart diseases are selected from the group consisting of angina pectoris, unstable angina, myocardial infarction, acute coronary disease, cardiac iatrogenic damage, and heart failure including, but not limited to, acute heart failure, chronic heart failure of ischemic and non-ischemic origin, systolic heart failure, diastolic heart failure, heart failure with reduced ejection fraction ($HF_REF$), and heart failure with preserved ejection fraction ($HF_PEF$).

The compounds of the invention can be used alone, in combination with other compounds of the present invention, or in combination with one or more other agent(s).

Other features and advantages of the invention will be apparent from the following detailed description and claims.

DESCRIPTION OF THE INVENTION

The invention encompasses compounds of Formulae (I)—(VII), which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of Formula (I):

(I)

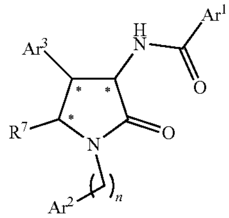

or a pharmaceutically acceptable salt thereof, wherein:

* is an asymmetric carbon atom;

$Ar^1$ is aryl or pyridyl, each substituted with 1-3 $R^1$;

$Ar^2$ is $C_{3-6}$ cycloalkyl, aryl, or 5- to 12-membered heterocyclyl comprising 1-4 heteroatoms selected from O, $S(O)_p$, N, and $NR^{2a}$, and each substituted with 0-3 $R^2$;

$Ar^3$ is phenyl or pyridyl, each substituted with 1 $R^{5a}$, 1 $R^{5b}$, and 1 $R^{5c}$;

$R^1$ is halo, $C_{1-4}$ haloalkyl, $C_{1-4}$ alkoxy, or $C_{1-4}$ haloalkoxy;

$R^2$ is oxo, cyano, halo, $C_{1-6}$ alkyl substituted with 0-5 $R^e$, —$OR^b$, —$NR^3R^4$, —$NR^4C(O)R^b$, —$NR^4(CR^dR^d)_{0-1}C(O)NR^3R^4$, $(C_{1-4}\ alkyl)_2(O)P$—, $C_{3-6}$ cycloalkyl, aryl, 5 to 6-membered heterocyclyl comprising 1-4 heteroatoms selected from O, $S(O)_p$, N, and $NR^a$;

$R^{2a}$ is hydrogen, $C_{1-4}$ alkyl substituted with 0-5 $R^e$, —$(CR^dR^d)_{1-4}$—$NR^3R^4$, —$(CR^dR^d)_{1-4}$—$OR^b$, —$(CR^dR^d)_{1-4}$—$C(O)NR^3R^4$, —$(CR^dR^d)_r$—$C_{3-6}$ cycloalkyl substituted with 0-5 $R^e$, —$(CR^dR^d)_r$-aryl substituted with 0-5 $R^e$, or —$(CR^dR^d)_r$-heterocyclyl comprising 1-4 heteroatoms selected from O, $S(O)_p$, N, and $NR^a$ and substituted with 0-5 $R^e$;

$R^3$ is hydrogen, $C_{1-4}$ alkyl substituted with 0-5 $R^e$, $C_{3-6}$ cycloalkyl substituted with 0-5 $R^e$, or heterocyclyl comprising 1-4 heteroatoms selected from O, $S(O)_p$, N, and $NR^8$ and substituted with 0-5 $R^e$;

$R^4$ is hydrogen or $C_{1-4}$ alkyl;

alternatively, $R^3$ and $R^4$ together with the nitrogen to which they are both attached form a 4- to 9-membered heterocyclyl comprising 1-4 heteroatoms selected from O, $S(O)_p$, N, and $NR^8$ and substituted with 1-3 $R^6$;

$R^{5a}$ is hydrogen or halo;

$R^{5b}$ is hydrogen or halo;

$R^{5c}$ is halo, $C_{1-4}$ alkyl, $C_{1-4}$ haloalkyl, $C_{1-4}$ alkoxy, or deuteroalkoxy;

$R^6$ is hydrogen, halo, oxo, hydroxy, or $C_{1-4}$ alkyl substituted with 0-5 $R^e$;

$R^7$ is hydrogen or $C_{1-4}$ alkyl;

$R^8$ is hydrogen, $C_{1-4}$ alkyl, or —$S(O)_pR^c$;

$R^a$ is hydrogen or $C_{1-6}$ alkyl substituted with 0-5 $R^e$, $C_{3-6}$ cycloalkyl substituted with 0-5 $R^e$, aryl substituted with 0-5 $R^e$, or heterocyclyl comprising 1-4 heteroatoms selected from O, $S(O)_p$, $NR^d$ and substituted with 0-5 $R^e$;

$R^b$ is hydrogen, $C_{1-6}$ alkyl substituted with 0-5 $R^e$, $C_{3-6}$ cycloalkyl substituted with 0-5 $R^e$, aryl substituted with 0-5 $R^e$, or heterocyclyl comprising 1-4 heteroatoms selected from O, $S(O)_p$, $NR^d$ and substituted with 0-5 $R^e$;

$R^c$ is $C_{1-4}$ alkyl substituted with 0-5 $R^e$;

$R^d$ is hydrogen or $C_{1-4}$ alkyl substituted with 0-5 $R^e$;

$R^e$ is halo, cyano, oxo, —$OR^g$, —$NR^gR^g$, —$C(O)NR^gR^g$, —$S(O)_pC_{1-4}$ alkyl, $C_{1-6}$ alkyl substituted with 0-5 $R^f$, —$(CH_2)_r$-$C_{3-6}$ cycloalkyl substituted with 0-5 $R^f$, —$(CH_2)_r$-aryl substituted with 0-5 $R^f$, or —$(CH_2)_r$-heterocyclyl comprising 1-4 heteroatoms selected from O, $S(O)_p$, N, and $NR^g$ and substituted with 0-5 $R^f$;

$R^f$ is halo, cyano, hydroxy, oxo, $C_{1-5}$ alkyl, $C_{3-6}$ cycloalkyl, or phenyl;

$R^g$ is hydrogen, $C_{1-5}$ alkyl, $C_{3-6}$ cycloalkyl, aryl, or heterocyclyl; or $R^g$ and $R^g$ together with the nitrogen atom to which they are both attached form a heterocyclyl;

n is zero or 1;

p is zero, 1, or 2; and r is zero, 1, 2, 3, or 4.

Another aspect of the invention is a compound of Formula (II):

(II)

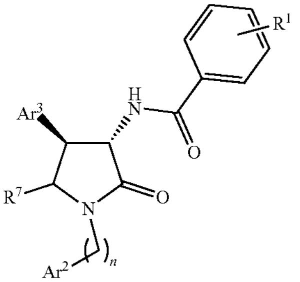

or a pharmaceutically acceptable salt thereof, wherein.

$Ar^2$ is $C_{3-6}$ cycloalkyl, phenyl, 5- to 6-membered heterocyclyl comprising 1-2 N or $NR^{2a}$, each substituted with 0-2 $R^2$ $Ar^3$ is phenyl substituted with 1 $R^{5a}$, 1 $R^{5b}$, and 1 $R^{5c}$;

$R^1$ is halo, $C_{1-4}$haloalkyl, or $C_{1-4}$haloalkoxy;

$R^2$ is oxo, cyano, halo, $C_{1-5}$ alkyl substituted with 0-5 $R^e$, —$OR^b$, —$NR^3R^4$, —$NR^4C(O)R^b$, $(C_{1-3}\ alkyl)_2(O)P$—, $C_{3-6}$ cycloalkyl, aryl, 5- to 6-membered heterocyclyl comprising 1-4 heteroatoms selected from O, S, N, and $NR^a$;

$R^{2a}$ is hydrogen, $C_{1-4}$ alkyl substituted with 0-4 $R^e$, —$(CHR^d)_{1-3}$—$C(O)NR^3R^4$, —$(CHR^d)_r$—$C_{3-6}$ cycloalkyl substituted with 0-4 $R^e$, —$(CHR^d)_r$-aryl substituted with 0-4 $R^e$, or —$(CHR^d)_r$-heterocyclyl comprising 1-4 heteroatoms selected from O, S, N, and $NR^a$ and substituted with 0-4 $R^e$;

$R^3$ is hydrogen, $C_{1-4}$ alkyl substituted with 0-4 $R^e$, $C_{3-6}$ cycloalkyl, or heterocyclyl comprising 1-4 heteroatoms selected from O, S, N, and $NR^8$ and substituted with 0-4 $R^e$;

$R^4$ is hydrogen or $C_{1-3}$ alkyl;

alternatively, $R^3$ and $R^4$ together with the nitrogen to which they are both attached form a 4- to 8-membered heterocyclyl comprising 1-4 heteroatoms selected from O, S, N, and $NR^8$ and substituted with 1-3 $R^6$;

$R^{5a}$ is hydrogen or halo;

$R^{5b}$ is hydrogen or halo;

$R^{5c}$ is halo, $C_{1-4}$ alkyl, $C_{1-4}$ haloalkyl, or $C_{1-4}$ alkoxy;

$R^6$ is hydrogen, halo, oxo, hydroxy, or $C_{1-4}$ alkyl substituted with 0-4 $R^e$;

$R^7$ is hydrogen or $C_{1-3}$ alkyl;

$R^8$ is hydrogen, $C_{1-3}$ alkyl, or —$S(O)_pR^e$;

$R^a$ is hydrogen or $C_{1-6}$ alkyl substituted with 0-5 $R^e$;

$R^b$ is hydrogen, $C_{1-6}$ alkyl substituted with 0-5 $R^e$, or heterocyclyl comprising 1-4 heteroatoms selected from O, S, N, $NR^d$ and substituted with 0-5 $R^e$;

$R^c$ is $C_{1-3}$ alkyl substituted with 0-5 $R^e$;

$R^d$ is hydrogen or $C_{1-4}$ alkyl substituted with 0-1 —$OC_{1-4}$ alkyl;

$R^e$ is halo, cyano, oxo, —$OR^g$, —$NR^gR^g$, —C(O)$NR^gR^g$, —$S(O)_pC_{1-4}$ alkyl, $C_{1-4}$ alkyl substituted with 0-5 $R^f$, —$(CH_2)_r$—$C_{3-6}$ cycloalkyl substituted with 0-5 $R^f$, —$(CH_2)_r$-aryl substituted with 0-5 $R^f$, or —$(CH_2)_r$-heterocyclyl comprising 1-4 heteroatoms selected from O, S, N, and $NR^g$ and substituted with 0-5 $R^f$;

$R^f$ is halo, cyano, hydroxy, $C_{1-5}$ alkyl, or $C_{3-6}$ cycloalkyl;

$R^g$ is hydrogen, $C_{1-5}$ alkyl, or heterocyclyl;

n is zero; and r is zero, 1, 2, or 3.

Another aspect of the invention is a compound of Formula (III):

(III)

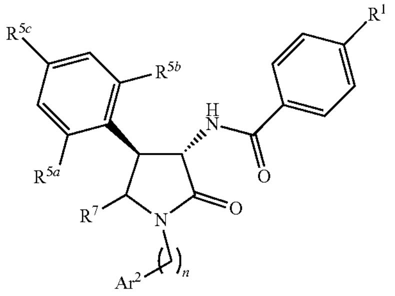

or a pharmaceutically acceptable salt thereof, wherein:

$Ar^2$ is

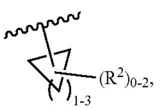

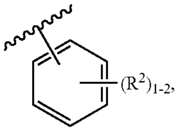

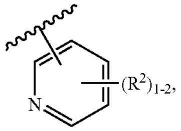

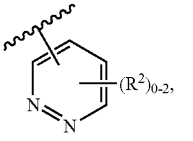

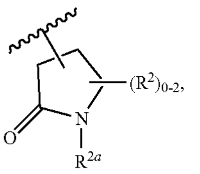

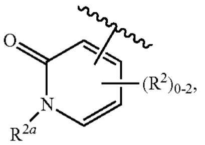

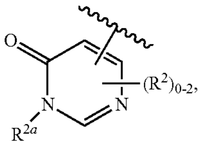

or

-continued

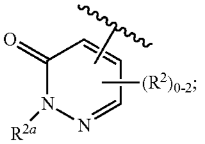

$R^1$ is halo, $C_{1-3}$ haloalkyl, or $C_{1-3}$ haloalkoxy;

$R^2$ is cyano, halo, $C_{1-4}$ alkyl substituted with 0-5 $R^e$, —$OR^b$, —$NR^3R^4$, —$NR^4C(O)R^b$, $(C_{1-4}$ alkyl$)_2$(O)P—, $C_{3-6}$ cycloalkyl, aryl, or 5- to 6-membered heterocyclyl comprising 1-4 heteroatoms selected from O, S, N, and $NR^a$;

$R^{2a}$ is hydrogen, $C_{1-4}$ alkyl substituted with 0-3 $R^e$, —$(CHR^d)_{1-2}$—C(O)$NR^3R^4$, —$(CH_2)_r$—$C_{3-6}$ cycloalkyl substituted with 0-3 $R^e$, —$(CH_2)_r$-aryl substituted with 0-3 $R^e$, or —$(CH_2)_r$-heterocyclyl comprising 1-4 heteroatoms selected from O, S, N, and $NR^a$ and substituted with 0-3 $R^e$;

$R^3$ is hydrogen, $C_{1-4}$ alkyl substituted with 0-3 $R^e$, $C_{3-6}$ cycloalkyl, or heterocyclyl comprising 1-4 heteroatoms selected from O, S, N, and $NR^8$ and substituted with 0-3 $R^e$;

$R^4$ is hydrogen or $C_{1-2}$ alkyl;

alternatively, $R^3$ and $R^4$ together with the nitrogen to which they are both attached form a 4- to 8-membered heterocyclyl comprising 1-3 heteroatoms selected from O, S, N, and $NR^8$ and substituted with 1-3 $R^6$;

$R^{5a}$ is hydrogen or halo;

$R^{5b}$ is hydrogen or halo;

$R^{5c}$ is halo or $C_{1-2}$ alkoxy;

$R^6$ is hydrogen, halo, oxo, hydroxy, or $C_{1-4}$ alkyl substituted with 0-3 $R^e$;

$R^7$ is hydrogen or $CH_3$;

$R^8$ is hydrogen, $C_{1-2}$ alkyl, or $S(O)_2C_{1-4}$ alkyl;

$R^a$ is hydrogen or $C_{1-5}$ alkyl substituted with 0-4 $R^e$;

$R^b$ is hydrogen, $C_{1-5}$ alkyl substituted with 0-4 $R^e$, heterocyclyl comprising 1-4 heteroatoms selected from O, S, N, $NR^d$ and substituted with 0-4 $R^e$;

$R^d$ is hydrogen or $C_{1-2}$ alkyl substituted with 0-1 —$OC_{1-4}$ alkyl;

$R^e$ is halo, cyano, oxo, —$OR^g$, —$NR^gR^g$, C(O)$NR^gR^g$, —$S(O)_pC_{1-4}$ alkyl, $C_{1-4}$ alkyl substituted with 0-4 $R^f$, —$(CH_2)_r$—$C_{3-6}$ cycloalkyl substituted with 0-4 $R^f$, —$(CH_2)_r$-aryl substituted with 0-4 $R^f$, or —$(CH_2)_r$-heterocyclyl comprising 1-4 heteroatoms selected from O, S, N, and $NR^g$ and substituted with 0-4 $R^f$;

$R^f$ is halo, cyano, hydroxy, or $C_{1-5}$ alkyl;

$R^g$ is hydrogen or $C_{1-4}$ alkyl;

n is zero; and r is zero, 1, or 2.

Another aspect of the invention is a compound of Formula (IVa):

(IVa)

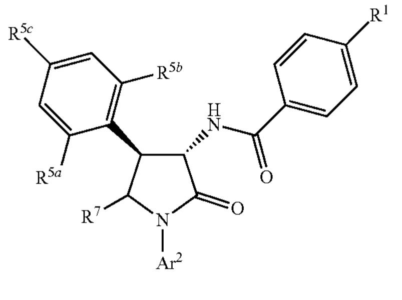

or a pharmaceutically acceptable salt thereof, wherein:
$Ar^2$ is

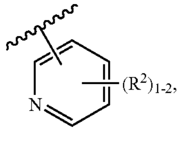
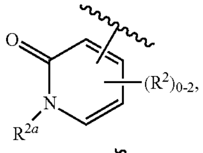

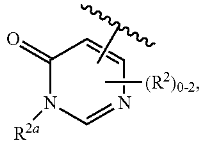
or
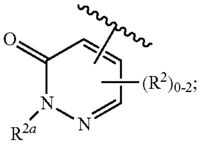

$R^1$ is Cl, $-CF_3$, $-OCHF_2$, or $-OCF_3$;
$R^2$ is cyano, halo, $C_{1-4}$ alkyl substituted with 0-4 $R^e$, $-OR^b$, $-NR^3R^4$, $-NR^4C(O)R^b$, $(C_{1-2}\ alkyl)_2(O)P$, $-C_{3-6}$ cycloalkyl, or heterocyclyl comprising 1-4 heteroatoms selected from O, S, N, and $NR^a$;
$R^{2a}$ is hydrogen, $C_{1-4}$ alkyl substituted with 0-4 $R^e$, $-(CHR^d)_{1-2}-C(O)NR^3R^4$, $-(CH_2)_r-C_{3-6}$ cycloalkyl substituted with 0-2 $R^e$, $-(CH_2)_r$-aryl substituted with 0-2 $R^e$, or $-(CH_2)_r$-heterocyclyl comprising 1-4 heteroatoms selected from O, S, N, and $NR^a$ and substituted with 0-2 $R^e$;
$R^3$ is hydrogen, $C_{1-4}$ alkyl substituted with 0-3 $R^e$, or heterocyclyl comprising 1-4 heteroatoms selected from O, S, N, and $NR^8$ and substituted with 0-3 $R^e$;
$R^4$ is hydrogen or $C_{1-2}$ alkyl;
alternatively, $R^3$ and $R^4$ together with the nitrogen to which they are both attached form a 4- to 8-membered heterocyclyl comprising 1-3 heteroatoms selected from O, S, N, and $NR^8$ and substituted with 1-3 $R^6$;
$R^{5a}$ is hydrogen, F, or Cl;
$R^{5b}$ is hydrogen, F, or Cl;
$R^{5c}$ is Cl or $-OCH_3$;
$R^6$ is hydrogen, halo, oxo, hydroxy, or $C_{1-3}$ alkyl substituted with 0-3 $R^e$;
$R^7$ is hydrogen or $C_{1-2}$ alkyl;
$R^8$ is hydrogen, $C_{1-2}$ alkyl, or $S(O)_2C_{1-3}$ alkyl;
$R^a$ is hydrogen, $C_{1-4}$ alkyl substituted with 0-3 $R^e$;
$R^b$ is hydrogen, $C_{1-4}$ alkyl substituted with 0-3 $R^e$, heterocyclyl comprising 1-4 heteroatoms selected from O, S, N, and $NR^d$ and substituted with 0-3 $R^e$;
$R^d$ is hydrogen or $C_{1-2}$ alkyl substituted with 0-1 $-OC_{1-4}$ alkyl;
$R^e$ is halo, cyano, oxo, $-OR^g$, $-NR^gR^g$, $-C(O)NR^gR^g$, $-S(O)_2C_{1-4}$ alkyl, $C_{1-6}$ alkyl substituted with 0-3 $R^f$, $-(CH_2)_r-C_{3-6}$ cycloalkyl substituted with 0-3 $R^f$, or $-(CH_2)_r$-heterocyclyl comprising 1-4 heteroatoms selected from O, S, N, and $NR^g$ and substituted with 0-3 $R^f$;
$R^f$ is halo, cyano, hydroxy, or $C_{1-4}$ alkyl;
$R^g$ is hydrogen or $C_{1-3}$ alkyl; and
r is zero or 1.

Another aspect of the invention is a compound of Formula (IVa), or a pharmaceutically acceptable salt thereof, wherein:
$Ar^2$ is

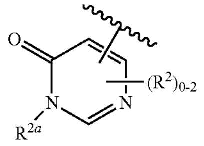
or
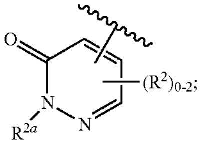

$R^2$ is F, Cl, $-CH_2OH$, $-CH_3$, $-CF_3$, or $-CHF_2$; and
$R^{2a}$ is $-CH_3$, $-CH_2CH_3$, $-CH_2CHF_2$, $-CH_2CF_3$, $-CH_2CH_2OCH_3$, $-CH_2CH(OH)CF_3$, $-CH_2CH(OH)CH_3$, $-CH_2CH_2OH$, $-CH_2CH(CH_3)OH$, $-CH_2CH(CF_3)OH$, $-CH_2CH_2CF_3$, $-CH(CH_2OH)CH_2OCH_3$, $-CH(CH_2NH_2)OCH_3$, $-CH_2CH(CH_3)OCH_3$, or $-CH_2CH(CF_3)OCH_3$;
other variables are as defined in Formula (IVa).

Another aspect of the invention is a compound of Formula (IVb):

(IVb)

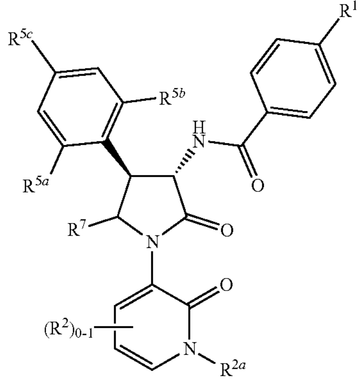

or a pharmaceutically acceptable salt thereof, wherein:
$R^1$ is Cl, $-CF_3$, $-OCHF_2$, or $-OCF_3$;
$R^2$ is cyano, F, Cl, $CH_3$, $CF_3$, $CHF_2$, or $-NHC(O)CH_3$;
$R^{2a}$ is $-CH_3$, $-CH_2CH_3$, $-CH_2CN$, $-CH_2CHF_2$, $-CH_2CH_2OCH_3$, $-CH_2CH(OH)CF_3$, $-CH_2CH(OH)CH_3$, $-CH_2CH_2OH$, $-CF_2CH_2OH$, $-CH_2CH(CH_3)OH$, $-CH_2CH_2CF_3$, $-CH(CH_2OH)CH_2OCH_3$, $-CH(CH_2NH_2)OCH_3$, $-CH_2CH(CH_3)OCH_3$, $-CH_2CH(CF_3)OCH_3$, $-CH(CH_2NH_2)CH_2OCH_3$, $-CH(C(O)N(CH_3)_2)CH_2OCH_3$, $-CH_2C(CH_3)(CH_2OH)_2$, $-CH_2CH_2N(CH_3)_2$, $-CH_2CH_2S(O)_2C_{1-4}$ alkyl, $-CHR^dC(O)NR^3R^4$, $-(CH_2)_{0-1}-C_{3-6}$ cycloalkyl, $-(CH_2)_{0-3}$-heterocyclyl selected from

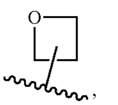,
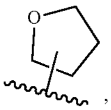, and
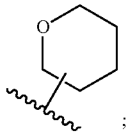;

$R^3$ and $R^4$ together with the nitrogen to which they are both attached form a heterocyclyl selected from

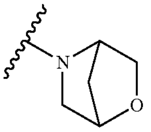 [SMILES: *N1CC2CC1CO2]

and

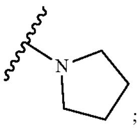 [SMILES: *N1CCCC1]

;

$R^5$ is hydrogen or F;

$R^{5b}$ is hydrogen or F;

$R^{5c}$ is Cl or —$OCH_3$;

$R^6$ is hydrogen, oxo, halo, or —$CH_3$, —$CHF_3$, —$CF_3$, or —$CH_2OH$;

$R^7$ is hydrogen or $C_{1-2}$ alkyl;

$R^8$ is hydrogen, $C_{1-2}$ alkyl, or —$S(O)_2C_{1-3}$ alkyl; and $R^d$ is —$CH_2OCH_3$.

Another aspect of the invention is a compound of Formula (IVc):

(IVc)

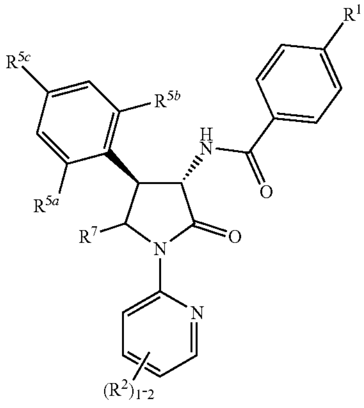

or a pharmaceutically acceptable salt thereof, wherein:

$R^1$ is Cl, —$CF_3$, —$OCHF_2$, or —$OCF_3$;

$R^2$ is cyano, F, Cl, $CH_2OH$, $CH_3$, $CHF_2$, $CF_3$, —$OCH_3$, —$OCH(CH_3)_2$, —$NR^3R^4$, $(CH_3)_2(O)P$—, $C_{3-6}$ cycloalkyl

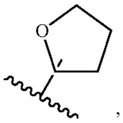 , 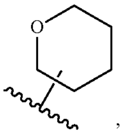 , or 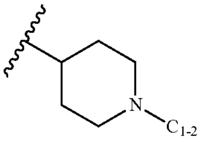

alkyl;

$R^3$ is hydrogen or $C_{1-4}$ alkyl substituted with 0-2 $R^e$,

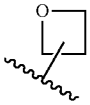 , or 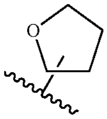 ;

$R^4$ is hydrogen;

alternatively, $R^3$ and $R^4$ together with the nitrogen to which they are both attached form a heterocyclyl selected from

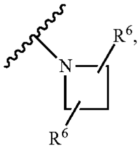 , 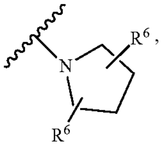 , 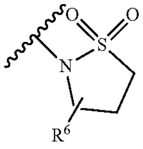 ,

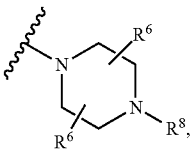 , 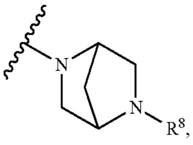 ,

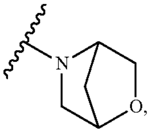 , 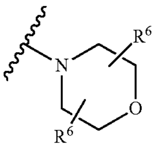 , 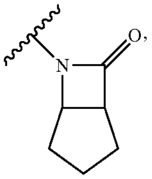

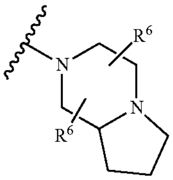 , or 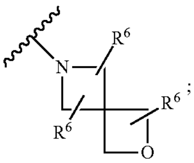 ;

$R^{5a}$ is hydrogen or F;

$R^{5b}$ is hydrogen or F;

$R^{5c}$ is Cl or $OCH_3$ $R^6$ is hydrogen, halo, oxo, $CH_3$, —$CH_2CH_3$, or —$CH_2OH$;

$R^7$ is hydrogen or $C_{1-4}$ alkyl; and $R^8$ is hydrogen, $C_{1-4}$ alkyl, or —$S(O)_2C_{1-3}$ alkyl.

Another aspect of the invention is a compound of Formula (IVd):

(IVd)

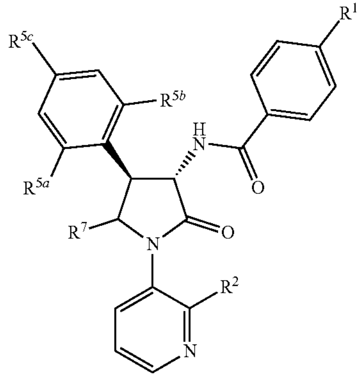

or a pharmaceutically acceptable salt thereof, wherein:

$R^1$ is Cl, $-CF_3$, $-OCHF_2$, or $-OCF_3$;

$R^2$ is $-OR^b$ or $(C_{1-2}\ alkyl)_2(O)P-$;

$R^{5a}$ is hydrogen or F;

$R^{5b}$ is hydrogen or F;

$R^{5c}$ is Cl or $-OCH_3$;

$R^7$ is hydrogen or $-CH_3$;

$R^b$ is hydrogen, $C_{1-4}$ alkyl substituted with 0-3 $R^e$, or

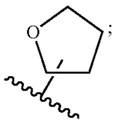;

$R^e$ is F, Cl, or $-OR^g$; and $R^g$ is hydrogen or $C_{1-3}$ alkyl.

Another aspect of the invention is a compound of Formula (IVe):

(IVe)

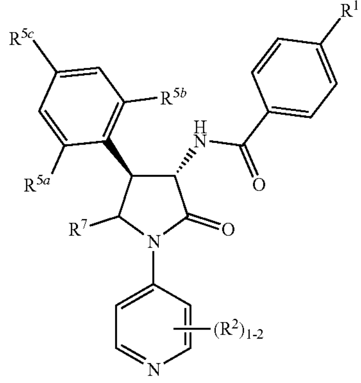

or a pharmaceutically acceptable salt thereof, wherein:

$R^1$ is Cl, $-CF_3$, $-OCHF_2$, or $-OCF_3$;

$R^2$ is cyano, F, Cl, $-CH_2OH$, $-CH_3$, $-CHF_2$, $-CF_3$, $-OCH_3$, $-OCH(CH_3)_2$, or $-NR^3R^4$;

$R^3$ is hydrogen or $C_{1-4}$ alkyl;

$R^4$ is hydrogen or $C_{1-2}$ alkyl;

alternatively, $R^3$ and $R^4$ together with the nitrogen to which they are both attached form a heterocyclyl selected from

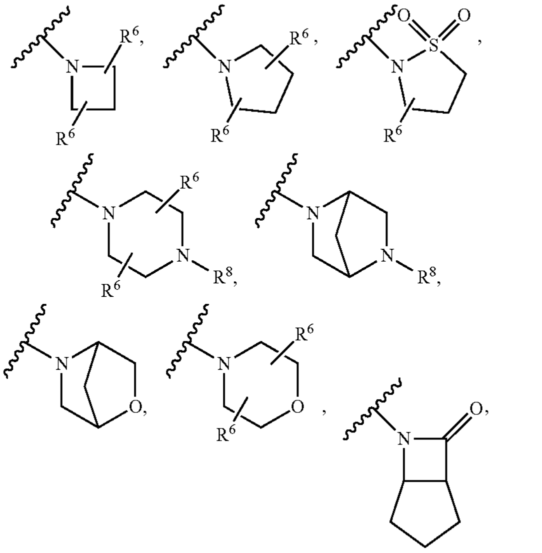

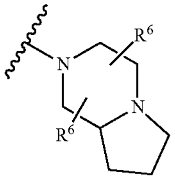

, and

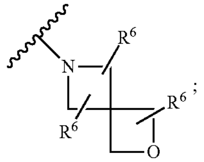;

$R^{5a}$ is hydrogen or F;

$R^{5b}$ is hydrogen or F;

$R^5$, is Cl or $-OCH_3$;

$R^6$ is hydrogen, halo, oxo, $CH_3$, $-CH_2CH_3$, or $-CH_2OH$;

$R^7$ is hydrogen or $C_{1-4}$ alkyl; and $R^8$ is hydrogen or $C_{1-2}$ alkyl.

Another aspect of the invention is a compound of Formula (IVf):

(IVf)

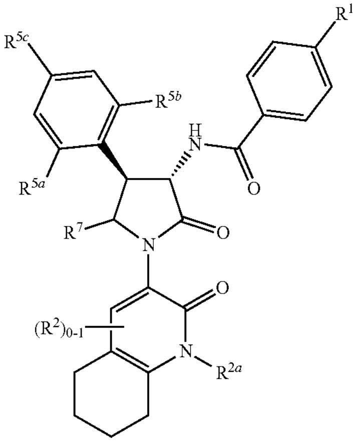

or a pharmaceutically acceptable salt thereof, wherein:

$R^1$ is Cl, $-CF_3$, $-OCH_3$, $-OCHF_2$, or $-OCF_3$;

$R^2$ is cyano, F, Cl, $-CH_2OH$, $-CH_3$, $-CHF_2$, or $-CF_3$;

$R^{2a}$ is $—CH_3$, $—CH_2CH_3$, $—CH_2CHF_2$, $—CH_2CH_2OCH_3$, $—CH_2CH(OH)CF_3$, $—CH_2CH(OH)CH_3$, $—CH_2CH_2OH$, $—CH_2CH(CH_3)OH$, or $—CH_2CH_2CF_3$;

$R^{5a}$ is hydrogen, F, or Cl;

$R^{5b}$ is hydrogen, F, or Cl;

$R^5$, is Cl or $—OCH_3$; and $R^7$ is hydrogen or $—CH_3$.

Another aspect of the invention is a compound of Formula (V):

(V)

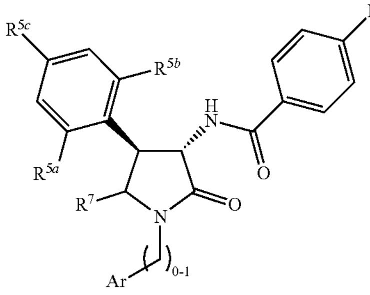

or a pharmaceutically acceptable salt thereof, wherein:

$Ar^2$ is $C_{3-5}$ cycloalkyl;

$R^1$ is Cl, $—CF_3$, $—OCHF_2$, or $—OCF_3$;

$R^{5a}$ is F or Cl;

$R^{5b}$ is F or Cl; and $R^{5c}$ is $—OCH_3$.

Another aspect of the invention is a compound of Formula (Va):

(Va)

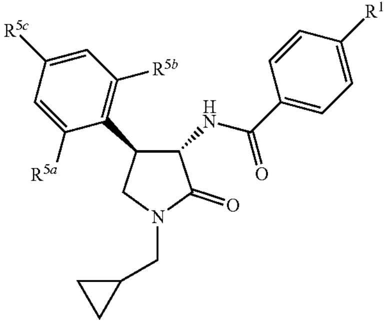

or a pharmaceutically acceptable salt thereof, wherein:

$R^1$ is $CF_3$, $OCHF_2$, or $OCF_3$;

$R^{5a}$ is F or Cl;

$R^{5b}$ is F or Cl; and $R^{5c}$ is $OCH_3$.

Another aspect of the invention is a compound of Formula (VI):

(VI)

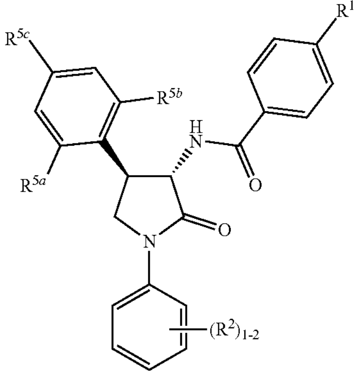

or a pharmaceutically acceptable salt thereof, wherein:

$R^1$ is $—CF_3$, $—OCHF_2$, or $—OCF_3$;

$R^2$ is F, Cl, $—CH_2OH$, $—CF_3$, $—CHF_2$, $—OCH_3$, $—OCH(CH_3)_2$, or $(CH_3)_2(O)P—$;

$R^{5a}$ is F or Cl;

$R^{5b}$ is F or Cl; and $R^{5c}$ is $—OCH_3$.

Another aspect of the invention is a compound of Formula (VII):

(VII)

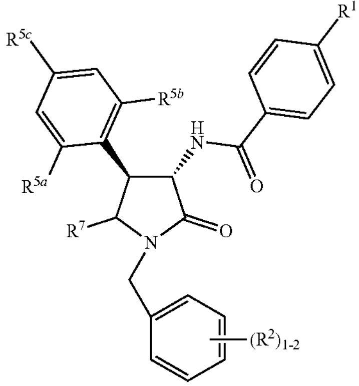

or a pharmaceutically acceptable salt thereof, wherein:

$R^1$ is $—CF_3$, $—OCHF_2$, or $—OCF_3$;

$R^2$ is F, Cl, or $(CH_3)_2(O)P—$;

$R^{5a}$ is F;

$R^{5b}$ is F; and $R^{5c}$ is $—OCH_3$.

For a compound of Formula (I), (II), (III), (IVa), (IVb), (IVc), (IVd), (IVe), (IVf), (V), (Va), (VI), or (VII), i.e., Formulae (I-VII), the scope of any instance of a variable substituent, including $Ar^1$, $Ar^2$, $Ar^3$, $R^1$, $R^2$, $R^{2a}$, $R^3$, $R^4$, $R^{5a}$, $R^{5b}$, $R^{5c}$, $R^6$, $R^7$, $R^8$, $R^a$, $R^b$, $R^c$, $R^d$, $R^e$, $R^f$, and $R^g$ can be used independently with the scope of any other instance of a variable substituent. As such, the invention includes combinations of the different aspects.

In one non-limiting embodiment, for a compound of Formula (I), (II), or (III), $Ar^1$ is phenyl substituted with 1 $R^1$; $R^1$ is $CF_3$, $OCHF_2$, or $OCF_3$; n is zero or 1; $Ar^2$ is phenyl, pyridinyl, or $C_{3-6}$ cycloalkyl, each substituted with 0-2 $R^2$; $R^2$ is F, Cl, $CH_2OH$, $CF_3$, $OCH_3$, $OCH(CH_3)_2$, $CHF_2$, $CF_3$, or $(CH_3)_2(O)P$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), or (III), $Ar^1$ is phenyl substituted with 1 $R^1$; $R^1$ is $CF_3$; n is zero; $Ar^2$ is phenyl, pyridinyl, or $C_{3-6}$ cycloalkyl, each substituted with 0-2 $R^2$; $R^2$ is F, Cl, $CH_2OH$, $CF_3$, $OCH_3$, $OCH(CH_3)_2$, $CHF_2$, $CF_3$, or $(CH_3)_2(O)P$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), or (III), $Ar^1$ is phenyl substituted with 1 $R^1$; $R^1$ is $OCHF_2$; n is zero; $Ar^2$ is phenyl, pyridinyl, or $C_{3-6}$ cycloalkyl, each substituted with 0-2 $R^2$; $R^2$ is F, Cl, $CH_2OH$, $CF_3$, $OCH_3$, $OCH(CH_3)_2$, $CHF_2$, $CF_3$, or $(CH_3)_2(O)P$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), or (III), $Ar^1$ is phenyl substituted with 1 $R^1$; $R^1$ is $OCF_3$; n is zero; $Ar^2$ is phenyl, pyridinyl, or $C_{3-6}$ cycloalkyl, each substituted with 0-2 $R^2$; $R^2$ is F, Cl, $CH_2OH$, $CF_3$, $OCH_3$, $OCH(CH_3)_2$, $CHF_2$, $CF_3$, or $(CH_3)_2(O)P$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), or (III), $Ar^1$ is phenyl substituted with 1 $R^1$; $R^1$ is $CF_3$, $OCHF_2$, or $OCF_3$; n is 1; $Ar^2$ is phenyl substituted with 0-2 $R^2$; $R^2$ is halo or alkoxy; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), or (III), $Ar^1$ is phenyl substituted with 1 $R^1$; $R^1$ is $CF_3$, $OCHF_2$, or $OCF_3$; n is 1; $Ar^2$ is cyclopropyl; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

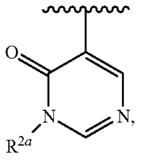

$R^{2a}$ is $—CH_3$, $—CH_2CH_3$, $—CH_2CHF_2$, $—CH_2CF_3$, $—CH_2CH_2OCH_3$, $—CH_2CH(OH)CF_3$, $—CH_2CH(OH)CH_3$, $—CH_2CH_2OH$, $—CH_2CH(CH_3)OH$, $—CH_2CH(CF_3)OH$, or $—CH_2CH_2CF_3$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

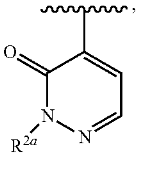

$R^{2a}$ is $—CH_3$, $—CH_2CH_3$, $—CH_2CHF_2$, $—CH_2CF_3$, $—CH_2CH_2OCH_3$, $—CH_2CH(OH)CF_3$, $—CH_2CH(OH)CH_3$, $—CH_2CH_2OH$, $—CH_2CH(CH_3)OH$, $—CH_2CH(CF_3)OH$, $—CH_2CH_2CF_3$, $—CH(CH_2OH)CH_2OCH_3$, $—CH(CH_2NH_2)OCH_3$, $—CH_2CH(CH_3)OCH_3$, or $—CH_2CH(CF_3)OCH_3$; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

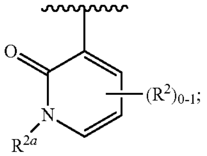

$R^2$ is cyano, F, Cl, $CH_3$ or $—NHC(O)\ CH_3$; $R^{2a}$ is $—CH_3$, $—CH_2CH_3$, $—CH_2CN$, $—CH_2CHF_2$, $—CH_2CH_2OCH_3$, $—CH_2CH(OH)CF_3$, $—CH_2CH(OH)CH_3$, $—CH_2CH_2OH$, $—CF_2CH_2OH$, $—CH_2CH(CH_3)OH$, $—CH_2CH_2CF_3$, $—CH(CH_2OH)CH_2OCH_3$, $—CH(CH_2NH_2)OCH_3$, $—CH_2CH(CH_3)OCH_3$, $—CH_2CH(CF_3)OCH_3$, $—CH(CH_2NH_2)CH_2OCH_3$, $—CH(C(O)N(CH_3)_2)CH_2OCH_3$, $—CH_2C(CH_3)(CH_2OH)_2$, $—CH_2CH_2N(CH_3)_2$, $—CH_2CH_2S(O)_2C_{1-4}$ alkyl, $—(CH_2)_{0-1}—C_{3-6}$ cycloalkyl, $—(CH_2)_{0-3}$-heterocyclyl selected from

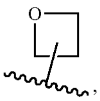, 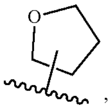, and 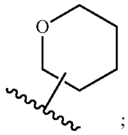;

$Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

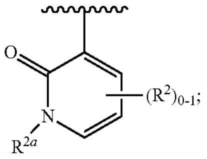

$R^2$ is cyano, F, Cl, $CH_3$ or $—NHC(O)CH_3$; $R^{2a}$ is $—CH_3$, $—CH_2CH_3$, $—CH_2CN$, $—CH_2CHF_2$, $—CH_2CH_2OCH_3$, $—CH_2CH(OH)CF_3$, $—CH_2CH(OH)CH_3$, $—CH_2CH_2OH$, $—CF_2CH_2OH$, $—CH_2CH(CH_3)OH$, $—CH_2CH_2CF_3$, $—CH(CH_2OH)CH_2OCH_3$, $—CH(CH_2NH_2)OCH_3$, $—CH_2CH(CH_3)OCH_3$, $—CH_2CH(CF_3)OCH_3$, $—CH(CH_2NH_2)CH_2OCH_3$, $—CH(C(O)N(CH_3)_2)CH_2OCH_3$, $—CH_2C(CH_3)(CH_2OH)_2$, $—CH_2CH_2N(CH_3)_2$, $—CH_2CH_2S(O)_2C_{1-4}$ alkyl, $—(CH_2)_{0-1}—C_{3-6}$ cycloalkyl, $—(CH_2)_{0-3}$-heterocyclyl selected from

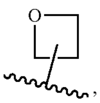, 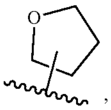, and 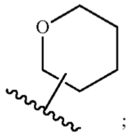;

$Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

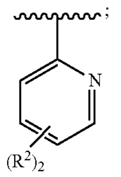

$R^2$ is cyano, F, Cl, $CH_2OH$, $CH_3$, $CF_3$, $CHF_2$, $CF_3$, $-OCH_3$, $-OCH(CH_3)_2$, $-NR^3R^4$, $(CH_3)_2(O)P-$, $C_{3-6}$ cycloalkyl,

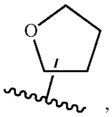 , 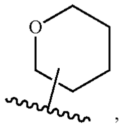 , 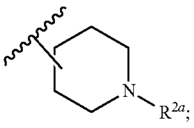 ; or

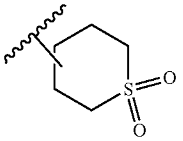

$R^{2a}$ is $-CH_3$, $-CH_2CH_3$, $-CH_2CN$, $-CH_2CHF_2$, $-CH_2CH_2OCH_3$, $-CH_2CH(OH)CF_3$, $-CH_2CH(OH)CH_3$, or $-CH_2CH_2OH$; $R^3$ is hydrogen or $C_{1-4}$ alkyl substituted with 0-2 $R^e$,

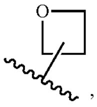 , or 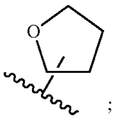 ;

$R^4$ is hydrogen or $C_{1-2}$ alkyl; alternatively, $R^3$ and $R^4$ together with the nitrogen to which they are both attached form a heterocyclyl selected from

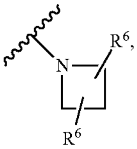 , 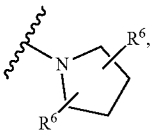 , 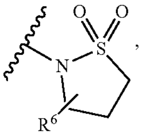 ,

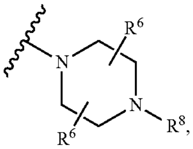 , 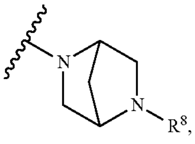 , 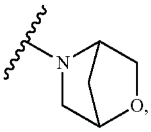 ,

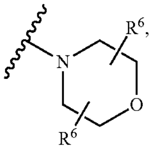 , 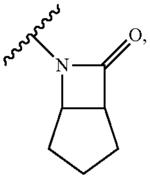 , 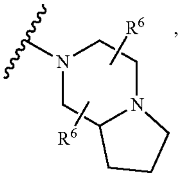 , or

-continued

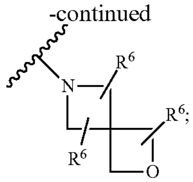

$Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), $Ar^1$ is phenyl substituted with 1 $R^1$; $R^1$ is Cl, $CF_3$, $OCHF_2$, or $OCF_3$; n is zero; $Ar^2$ is

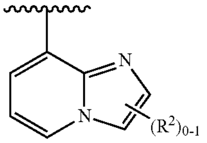

or

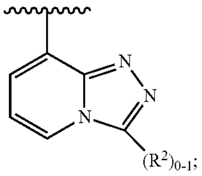

$R^2$ is alkyl, haloalkyl, hydroxyalkyl, or cycloalkyl; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

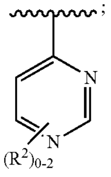

$R^2$ is cyano, F, Cl, $CH_2OH$, $CF_3$, $CHF_2$, $CF_3$, $-OCH_3$, $-OCH(CH_3)_2$, $-NR^3R^4$, $(CH_3)_2(O)P-$, $C_{3-6}$ cycloalkyl,

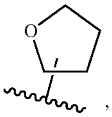 , 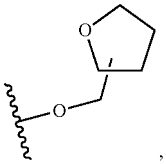 , 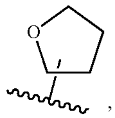 , 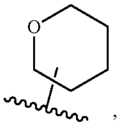 , or

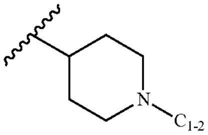

alkyl; $R^3$ is hydrogen or $C_{1-4}$ alkyl substituted with 0-2 $R^e$,

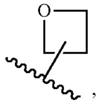, or 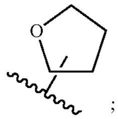;

$R^4$ is hydrogen or $C_{1-2}$ alkyl; alternatively, $R^3$ and $R^4$ together with the nitrogen to which they are both attached form a heterocyclyl selected from

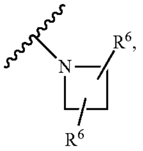, 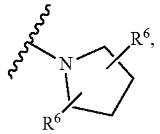, 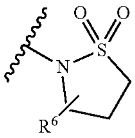,

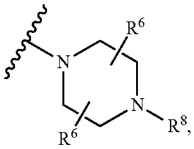, 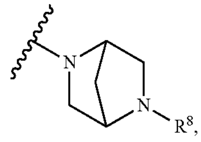, 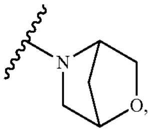,

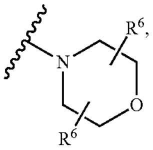, 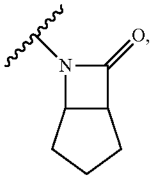, 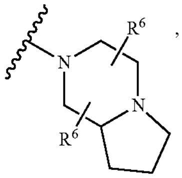, or

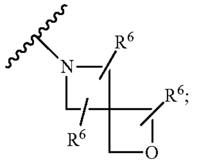;

$Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), (II), (III), or (IVa), $Ar^1$ is phenyl substituted with 1 $R^1$; $R^1$ is Cl, $CF_3$, $OCHF_2$, or $OCF_3$; n is zero; $Ar^2$ is

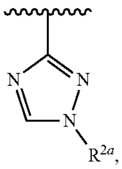, 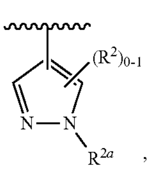, 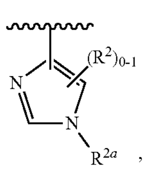, or

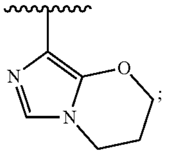;

$R^2$ is alkoxy; $R^{2a}$ is alkyl or haloalkyl; $Ar^3$ is phenyl substituted with $R^{5a}$, $R^{5b}$, and $R^{5c}$; $R^{5a}$, $R^{5b}$, and $R^{5c}$ are halo and alkoxy, respectively.

In one non-limiting embodiment, for a compound of Formula (I), $Ar^1$ is phenyl substituted with 1 $R^1$; $R^1$ is Cl, $CF_3$, $OCHF_2$, or $OCF_3$; n is zero; $Ar^2$ is

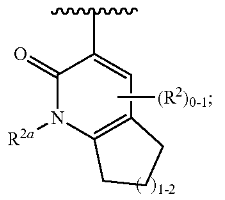;

$R^2$ is cyano, F, Cl, $CH_3$ or —NHC(O) $CH_3$; $R^{2a}$ is —$CH_3$, —$CH_2CH_3$, —$CH_2CN$, —$CH_2CHF_2$, —$CH_2CH_2OCH_3$, —$CH_2CH(OH)CF_3$, —$CH_2CH(OH)CH_3$, —$CH_2CH_2OH$, —$CF_2CH_2OH$, —$CH_2CH(CH_3)OH$, —$CH_2CH_2CF_3$, —$CH(CH_2OH)CH_2OCH_3$, —$CH(CH_2NH_2)OCH_3$, —$CH_2CH(CH_3)OCH_3$, —$CH_2CH(CF_3)OCH_3$, —$CH(CH_2NH_2)CH_2OCH_3$, —$CH(C(O)N(CH_3)_2)CH_2OCH_3$, —$CH_2C(CH_3)(CH_2OH)_2$, —$CH_2CH_2N(CH_3)_2$, —$CH_2CH_2S(O)_2C_{1-4}$ alkyl, —$(CH_2)_{0-1}$—$C_{3-6}$ cycloalkyl, —$(CH_2)_{0-3}$-heterocyclyl selected from

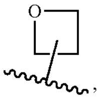, 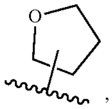, and 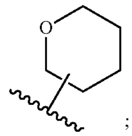;

$Ar^3$ is phenyl substituted with $R^{5a}$, $R^{5b}$, and $R^{5c}$; $R^{5a}$, $R^{5b}$, and $R^{5c}$ are halo and alkoxy, respectively.

In another embodiment, the compounds of the present invention have FPR2 $EC_{50}$ values≤1 μM.

In another embodiment, the compounds of the present invention have FPR2 $EC_{50}$ values≤0.5 μM.

In another embodiment, the compounds of the present invention have FPR2 $EC_{50}$ values≤0.1 μM.

In another embodiment, the compounds of the present invention have FPR2 $EC_{50}$ values≤0.05 μM.

In another embodiment, the compounds of the present invention have FPR2 $EC_{50}$ values≤0.01 μM.

In another embodiment, the compounds of the present invention have FPR2 $EC_{50}$ values≤0.001 μM.

Unless specified otherwise, these terms have the following meanings.

A dash "—" that is not between two letters or symbols is used to indicate a point of attachment for a substituent. For example, —$CONH_2$ is attached through the carbon atom.

A bond pointing to a wave line, such as

, as used in structural formulas herein, depicts the bond that is the point of attachment of the moiety or substituent to the core or backbone structure.

"Cyano" means —CN.

"Hydroxy" means —OH.

"Alkyl" means a straight or branched hydrocarbon group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. Terms with a hydrocarbon moiety (e.g. alkoxy) include straight and branched isomers for the hydrocarbon portion.

"Halo" includes fluoro, chloro, bromo, and iodo. "Haloalkyl" and "haloalkoxy" include all halogenated isomers from monohalo to perhalo.

"Haloalkoxy" and derivatives such as "$C_{1-6}$ haloalkoxy" are used interchangeably and mean halo substituted alkyl groups linked through the oxygen atom. Haloalkoxy include mono-substituted as well as multiple halo substituted alkoxy groups, up to perhalo substituted alkoxy. For example trifluoromethoxy and difluoromethoxy are included.

"Alkoxy" means an alkyl group attached via an oxygen linkage to the rest of the molecule. Representative examples of such groups are $—OCH_3$ and $—OC_2H_5$. Unless set forth or recited to the contrary, all alkoxy groups described or claimed herein may be straight chain or branched.

"Alkoxyalkyl" means an alkoxy group as defined above directly bonded to an alkyl group as defined above, e.g., $—CH_2—O—CH_3$, $—CH_2CH_2—O—CH_3$ and the like.

"Cycloalkyl" means a non-aromatic mono or multicyclic ring system having 3 to 12 carbon atoms, such as cyclopropyl, cyclobutyl, cyclopentyl, cyclohexyl and the like.

"Aryl" means a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl.

"Heterocycle," "heterocyclyl," or "heterocyclic ring" means a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. When the term "heterocyclyl" is used, it is intended to include heteroaryl.

Bridged rings are also included in the definition of heterocyclyl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

"Heteroaryl" means a 5 to 7 membered monocyclic or 8 to 11 membered bicyclic aromatic ring system with 1-5 heteroatoms independently selected from nitrogen, oxygen, and sulfur.

Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms including the structure below with the indicated carbon. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, $Ca^{2+}$ mobilization and transcription. The family interacts with a diverse set of ligands that includes proteins, polypeptides and fatty acid metabolites which activate both pro-inflammatory and pro-resolution downstream responses. FPR2 and FPR1 Cyclic Adenosine Monophosphate (cAMP) Assays were used to measure the activity of the compounds in this patent.

FPR2 and FPR1 Cyclic Adenosine Monophosphate (cAMP) Assays. A mixture of forskolin (5 μM final for FPR2 or 10 μM final for FPR1) and IBMX (200 μM final) were added to 384-well Proxiplates (Perkin-Elmer) pre-dotted with test compounds in DMSO (1% final) at final concentrations in the range of 0.020 nM to 100 μM. Chinese Hamster Ovary cells (CHO) overexpressing human FPR1 or human FPR2 receptors were cultured in F-12 (Ham's) medium supplemented with 10% qualified FBS, 250 μg/ml zeocin and 300 μg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 μM to 0.1 μM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. Table 1 below lists $EC_{50}$ values in the FPR2 and FPR1 cAMP assays measured for the following examples.

TABLE 1

| Example | hFPR2 cAMP2 $EC_{50}$ (μM) | hFPR1 cAMP $EC_{50}$ (μM) |
|---|---|---|
| 1 | 0.028 | 4.2 |
| 2 | 0.022 | 0.086 |
| 3 | 0.029 | 1.7 |
| 4 | 0.0017 | 0.29 |
| 5 | 0.0029 | 0.014 |
| 6 | 0.0051 | 0.65 |
| 7 | 0.010 | 1.3 |
| 8 | 0.015 | 0.28 |
| 9 | 0.0067 | 4.4 |
| 10 | 0.050 | 0.29 |
| 11 | 0.031 | 0.086 |
| 12 | 0.091 | >10 |
| 13 | 0.045 | 0.085 |
| 14 | 0.037 | 0.043 |
| 15 | 0.022 | 1.1 |
| 16 | 0.180 | 0.48 |
| 17 | 0.036 | 0.069 |
| 18 | 0.037 | 0.20 |
| 19 | 0.024 | 0.54 |
| 20 | 0.032 | 0.56 |
| 21 | 0.035 | 2.3 |
| 22 | 0.013 | 3.2 |
| 23 | 0.028 | 1.5 |
| 24 | 0.045 | 0.30 |
| 25 | 0.035 | >10 |
| 26 | 0.035 | 0.027 |
| 27 | 0.027 | 0.57 |

TABLE 1-continued

| Example | hFPR2 cAMP2 $EC_{50}$ (μM) | hFPR1 cAMP $EC_{50}$ (μM) |
|---|---|---|
| 28 | 0.007 | 1.1 |
| 29 | 0.051 | 0.11 |
| 30 | 0.010 | 0.75 |
| 31 | 0.010 | 0.15 |
| 32 | 0.018 | 0.96 |
| 33 | 0.005 | 1.61 |
| 34 | 0.0038 | 0.30 |
| 35 | 0.0031 | >10 |
| 36 | 0.0055 | 0.030 |
| 37 | 0.0089 | 0.016 |
| 38 | 0.0051 | 0.018 |
| 39 | 0.0005 | 0.072 |
| 40 | 0.0006 | 2.6 |
| 41 | 0.0006 | 0.11 |
| 42 | 0.0007 | 0.73 |
| 43 | 0.0008 | >5 |
| 44 | 0.001 | 0.010 |
| 45 | 0.001 | 0.0043 |
| 46 | 0.001 | 0.002 |
| 47 | 0.0011 | 0.15 |
| 48 | 0.0011 | 0.94 |
| 49 | 0.0011 | 2.0 |
| 50 | 0.0012 | 1.7 |
| 51 | 0.0012 | 5.5 |
| 52 | 0.0013 | 0.027 |
| 53 | 0.0014 | 0.0023 |
| 54 | 0.0014 | 0.82 |
| 55 | 0.0014 | 0.0086 |
| 56 | 0.0014 | 0.004 |
| 57 | 0.0014 | 0.000066 |
| 58 | 0.0015 | 0.0035 |
| 59 | 0.0015 | 0.0066 |
| 60 | 0.0016 | 0.0026 |
| 61 | 0.0016 | 0.034 |
| 62 | 0.0016 | 0.11 |
| 63 | 0.0017 | 0.016 |
| 64 | 0.0017 | 0.0072 |
| 65 | 0.0017 | 0.18 |
| 66 | 0.0018 | 0.049 |
| 67 | 0.0018 | 0.0044 |
| 68 | 0.0018 | 0.50 |
| 69 | 0.0019 | 0.0042 |
| 70 | 0.0019 | >10 |
| 71 | 0.0019 | 0.29 |
| 72 | 0.0019 | 0.0057 |
| 73 | 0.0019 | 0.0032 |
| 74 | 0.0019 | 0.094 |
| 75 | 0.002 | 0.0028 |
| 76 | 0.002 | 0.28 |
| 77 | 0.002 | 0.17 |
| 78 | 0.002 | 0.0052 |
| 79 | 0.002 | 0.012 |
| 80 | 0.0021 | 0.13 |
| 81 | 0.0022 | 0.0027 |
| 82 | 0.0022 | 0.0053 |
| 83 | 0.0022 | 0.0076 |
| 84 | 0.0023 | 0.12 |
| 85 | 0.0023 | 0.16 |
| 86 | 0.0023 | 0.0041 |
| 87 | 0.0023 | 0.75 |
| 88 | 0.0024 | 0.0079 |
| 89 | 0.0024 | 0.045 |
| 90 | 0.0025 | 0.0035 |
| 91 | 0.0026 | 0.016 |
| 92 | 0.0026 | 0.0036 |
| 93 | 0.0026 | 0.068 |
| 94 | 0.0027 | 0.095 |
| 95 | 0.0027 | 0.16 |
| 96 | 0.0027 | 0.046 |
| 97 | 0.0027 | 0.35 |
| 98 | 0.0027 | 0.043 |
| 99 | 0.0027 | 0.33 |
| 100 | 0.0027 | 0.022 |
| 101 | 0.0028 | 0.15 |
| 102 | 0.0028 | 0.0047 |
| 103 | 0.0028 | 0.0019 |

TABLE 1-continued

| Example | hFPR2 cAMP2 $EC_{50}$ (μM) | hFPR1 cAMP $EC_{50}$ (μM) |
|---|---|---|
| 104 | 0.0029 | 0.12 |
| 105 | 0.0029 | 0.065 |
| 106 | 0.0029 | 0.87 |
| 107 | 0.0029 | 0.0057 |
| 108 | 0.0029 | 0.0004 |
| 109 | 0.0029 | 0.50 |
| 110 | 0.0029 | 0.020 |
| 111 | 0.003 | 1.1 |
| 112 | 0.003 | 0.0028 |
| 113 | 0.003 | 0.016 |
| 114 | 0.003 | 0.0059 |
| 115 | 0.0031 | 0.0024 |
| 116 | 0.0031 | 0.034 |
| 117 | 0.0031 | 0.21 |
| 118 | 0.0031 | 0.0041 |
| 119 | 0.0031 | 0.067 |
| 120 | 0.0031 | 0.013 |
| 121 | 0.0031 | 0.0014 |
| 122 | 0.0032 | 1.08 |
| 123 | 0.0032 | 0.041 |
| 124 | 0.0033 | 0.047 |
| 125 | 0.0033 | 1.1 |
| 126 | 0.0033 | 2.3 |
| 127 | 0.0033 | 0.39 |
| 128 | 0.0033 | 0.0063 |
| 129 | 0.0033 | 0.38 |
| 130 | 0.0034 | 0.34 |
| 131 | 0.0034 | 0.0008 |
| 132 | 0.0034 | 0.0008 |
| 133 | 0.0034 | 0.012 |
| 134 | 0.0035 | 0.0016 |
| 135 | 0.0035 | 0.058 |
| 136 | 0.0035 | 0.0022 |
| 137 | 0.0035 | 0.19 |
| 138 | 0.0035 | 0.0017 |
| 139 | 0.0035 | 0.57 |
| 140 | 0.0035 | 0.61 |
| 141 | 0.0036 | 0.029 |
| 142 | 0.0036 | 0.087 |
| 143 | 0.0036 | 0.053 |
| 144 | 0.0036 | 0.0231 |
| 145 | 0.0037 | 0.0082 |
| 146 | 0.0038 | 0.15 |
| 147 | 0.0038 | 0.0022 |
| 148 | 0.0038 | 0.019 |
| 149 | 0.0038 | 0.0001 |
| 150 | 0.0039 | 0.007 |
| 151 | 0.0039 | 0.0005 |
| 152 | 0.0039 | 0.46 |
| 153 | 0.004 | 0.0042 |
| 154 | 0.004 | 0.0033 |
| 155 | 0.004 | 0.0093 |
| 156 | 0.004 | 0.0013 |
| 157 | 0.004 | 0.10 |
| 158 | 0.0041 | 0.19 |
| 159 | 0.0041 | 0.074 |
| 160 | 0.0041 | 1.1 |
| 161 | 0.0041 | 0.0034 |
| 162 | 0.0041 | 0.0094 |
| 163 | 0.0042 | 1.2 |
| 164 | 0.0042 | 0.29 |
| 165 | 0.0042 | 0.0017 |
| 166 | 0.0043 | 2.3 |
| 167 | 0.0043 | >10 |
| 168 | 0.0043 | 1.6 |
| 169 | 0.0043 | 0.021 |
| 170 | 0.0044 | 0.0009 |
| 171 | 0.0044 | 2.4 |
| 172 | 0.0045 | 0.039 |
| 173 | 0.0045 | 0.012 |
| 174 | 0.0045 | 0.067 |
| 175 | 0.0046 | 0.0093 |
| 176 | 0.0046 | 0.0065 |
| 177 | 0.0046 | 0.015 |
| 178 | 0.0047 | 0.0001 |
| 179 | 0.0047 | 0.092 |

TABLE 1-continued

| Example | hFPR2 cAMP2 $EC_{50}$ (μM) | hFPR1 cAMP $EC_{50}$ (μM) |
|---|---|---|
| 180 | 0.0047 | >10 |
| 181 | 0.0048 | 0.99 |
| 182 | 0.0048 | 0.0018 |
| 183 | 0.0048 | 0.0006 |
| 184 | 0.0048 | 0.0098 |
| 185 | 0.0048 | 0.0007 |
| 186 | 0.0049 | 0.003 |
| 187 | 0.0049 | 0.038 |
| 188 | 0.0049 | 0.038 |
| 189 | 0.005 | 3.4 |
| 190 | 0.005 | 0.13 |
| 191 | 0.005 | 0.090 |
| 192 | 0.0051 | 0.0008 |
| 193 | 0.0051 | 0.57 |
| 194 | 0.0051 | 0.15 |
| 195 | 0.0052 | 0.0013 |
| 196 | 0.0052 | 0.16 |
| 197 | 0.0052 | 0.0017 |
| 198 | 0.0052 | 0.013 |
| 199 | 0.0052 | 0.13 |
| 200 | 0.0052 | 0.29 |
| 201 | 0.0053 | 0.018 |
| 202 | 0.0053 | 0.062 |
| 203 | 0.0053 | 0.77 |
| 204 | 0.0053 | 0.52 |
| 205 | 0.0054 | 0.22 |
| 206 | 0.0054 | 0.024 |
| 207 | 0.0054 | >5 |
| 208 | 0.0054 | 0.0014 |
| 209 | 0.0055 | 0.13 |
| 210 | 0.0055 | 0.19 |
| 211 | 0.0055 | 0.025 |
| 212 | 0.0056 | 0.10 |
| 213 | 0.0056 | 1.8 |
| 214 | 0.0056 | 2.4 |
| 215 | 0.0056 | 0.041 |
| 216 | 0.0057 | 0.27 |
| 217 | 0.0057 | 0.042 |
| 218 | 0.0057 | 0.14 |
| 219 | 0.0058 | 0.14 |
| 220 | 0.0058 | 0.99 |
| 221 | 0.006 | 0.050 |
| 222 | 0.006 | 1.4 |
| 223 | 0.0061 | 0.1 |
| 224 | 0.0061 | 1.9 |
| 225 | 0.0062 | 0.63 |
| 226 | 0.0062 | 0.023 |
| 227 | 0.0062 | 0.24 |
| 228 | 0.0062 | 0.0012 |
| 229 | 0.0062 | 0.013 |
| 230 | 0.0062 | 0.088 |
| 231 | 0.0063 | 0.46 |
| 232 | 0.0063 | 0.0032 |
| 233 | 0.0063 | >5 |
| 234 | 0.0063 | 1.1 |
| 235 | 0.0065 | 0.084 |
| 236 | 0.0065 | 0.030 |
| 237 | 0.0065 | 0.44 |
| 238 | 0.0066 | 1.5 |
| 239 | 0.0066 | 0.65 |
| 240 | 0.0066 | 0.13 |
| 241 | 0.0066 | 0.038 |
| 242 | 0.0067 | 0.11 |
| 243 | 0.0067 | 0.17 |
| 244 | 0.0068 | 0.95 |
| 245 | 0.0068 | 0.0011 |
| 246 | 0.0069 | 0.28 |
| 247 | 0.0069 | 0.25 |
| 248 | 0.0069 | 0.0007 |
| 249 | 0.0069 | 0.013 |
| 250 | 0.0069 | 4.8 |
| 251 | 0.007 | >5 |
| 252 | 0.007 | 0.044 |
| 253 | 0.007 | 0.011 |
| 254 | 0.007 | 0.052 |
| 255 | 0.007 | 0.052 |

TABLE 1-continued

| Example | hFPR2 cAMP2 $EC_{50}$ (μM) | hFPR1 cAMP $EC_{50}$ (μM) |
|---|---|---|
| 256 | 0.0072 | 0.53 |
| 257 | 0.0073 | 0.0016 |
| 258 | 0.0074 | 0.083 |
| 259 | 0.0074 | 0.58 |
| 260 | 0.0075 | 0.0012 |
| 261 | 0.0075 | 0.94 |
| 262 | 0.0075 | 0.018 |
| 263 | 0.0075 | 1.3 |
| 264 | 0.0075 | 0.37 |
| 265 | 0.0076 | 0.0015 |
| 266 | 0.0076 | 0.41 |
| 267 | 0.0077 | 1.6 |
| 268 | 0.0077 | 0.14 |
| 269 | 0.0077 | 0.027 |
| 270 | 0.0078 | 0.18 |
| 271 | 0.0078 | 1.4 |
| 272 | 0.0078 | 0.014 |
| 273 | 0.0078 | 1.4 |
| 274 | 0.008 | 0.019 |
| 275 | 0.008 | 6.1 |
| 276 | 0.008 | 0.013 |
| 277 | 0.008 | 0.21 |
| 278 | 0.0081 | 0.34 |
| 279 | 0.0081 | 5.8 |
| 280 | 0.0082 | 0.026 |
| 281 | 0.0082 | 0.56 |
| 282 | 0.0083 | 0.70 |
| 283 | 0.0084 | 0.019 |
| 284 | 0.0084 | 0.58 |
| 285 | 0.0029 | 0.22 |
| 286 | 0.0085 | 0.13 |
| 287 | 0.0086 | 4.6 |
| 288 | 0.0086 | 0.0008 |
| 289 | 0.0086 | 0.062 |
| 290 | 0.0086 | 1.8 |
| 291 | 0.0087 | 0.0066 |
| 292 | 0.0087 | 0.95 |
| 293 | 0.0087 | 0.044 |
| 294 | 0.0088 | 0.0091 |
| 295 | 0.0089 | 0.0006 |
| 296 | 0.009 | 0.44 |
| 297 | 0.009 | 0.0001 |
| 298 | 0.009 | 0.0085 |
| 299 | 0.0092 | 1.9 |
| 300 | 0.0093 | 0.36 |
| 301 | 0.0093 | 0.15 |
| 302 | 0.010 | 0.022 |
| 303 | 0.0096 | 0.39 |
| 304 | 0.0096 | 0.090 |
| 305 | 0.0096 | 1.3 |
| 306 | 0.0098 | 0.25 |
| 307 | 0.0099 | 0.0018 |
| 308 | 0.0099 | 0.18 |
| 309 | 0.01 | 0.41 |
| 310 | 0.01 | 0.067 |
| 311 | 0.010 | 1.9 |
| 312 | 0.010 | 0.0005 |
| 313 | 0.010 | 5.4 |
| 314 | 0.010 | 0.0004 |
| 315 | 0.010 | 0.0096 |
| 316 | 0.010 | 0.095 |
| 317 | 0.010 | 0.0026 |
| 318 | 0.010 | >10 |
| 319 | 0.010 | 0.20 |
| 320 | 0.010 | 0.044 |
| 321 | 0.010 | 0.57 |
| 322 | 0.01 | 0.097 |
| 323 | 0.011 | 0.75 |
| 324 | 0.011 | 0.13 |
| 325 | 0.011 | 0.0016 |
| 326 | 0.011 | 0.035 |
| 327 | 0.012 | 1.7 |
| 328 | 0.012 | 0.61 |
| 329 | 0.012 | 2.5 |
| 330 | 0.013 | 3.7 |
| 331 | 0.013 | 5.6 |

TABLE 1-continued

| Example | hFPR2 cAMP2 $EC_{50}$ (μM) | hFPR1 cAMP $EC_{50}$ (μM) |
|---|---|---|
| 332 | 0.013 | 5.8 |
| 333 | 0.014 | 5.7 |
| 334 | 0.014 | 0.48 |
| 335 | 0.015 | 0.45 |
| 336 | 0.017 | 0.06 |
| 337 | 0.017 | 4.3 |
| 338 | 0.018 | 1.8 |
| 339 | 0.023 | 0.0006 |
| 340 | 0.023 | 0.0011 |
| 341 | 0.023 | 4.1 |
| 342 | 0.032 | 0.83 |
| 343 | 0.033 | 0.12 |
| 344 | 0.046 | 2.0 |
| 345 | 0.089 | 0.0031 |
| 346 | 0.097 | 1.9 |
| 347 | 0.11 | 0.84 |
| 348 | 0.1107 | 1.4 |
| 349 | 0.57 | 5.5 |
| 350 | 0.0009 | 0.0006 |
| 351 | 0.008 | 0.005 |
| 352 | 0.0048 | 0.003 |
| 353 | 0.0042 | 0.017 |
| 354 | 0.0032 | 0.007 |
| 355 | 0.0045 | 0.004 |
| 356 | 0.0035 | 0.031 |
| 357 | 0.0031 | 0.012 |
| 358 | 0.0020 | 0.014 |
| 359 | 0.0045 | 0.006 |
| 360 | 0.0032 | 0.018 |
| 361 | 0.0017 | 0.003 |
| 362 | 0.0001 | 0.012 |
| 363 | 0.0008 | 0.003 |
| 364 | 0.0023 | 0.001 |
| 365 | 0.0026 | 0.001 |
| 366 | 0.0030 | 0.003 |
| 367 | 0.0012 | 0.003 |
| 368 | 0.0017 | 0.086 |
| 369 | 0.0037 | 1.1 |
| 370 | 0.0037 | 1.4 |
| 371 | 0.0019 | 0.008 |
| 372 | 0.0028 | 0.017 |
| 373 | 0.0125 | 0.233 |
| 374 | 0.0041 | 0.014 |
| 375 | 0.0016 | 0.003 |
| 376 | 0.0004 | 0.004 |
| 377 | 0.0016 | 0.005 |
| 378 | 0.0046 | 3.8 |
| 379 | 0.0026 | 0.32 |
| 380 | 0.0018 | 0.003 |
| 381 | 0.0040 | 0.010 |
| 382 | 0.0052 | 0.002 |
| 383 | 0.0055 | 0.002 |
| 384 | 0.0019 | 0.001 |
| 385 | 0.0071 | 0.001 |
| 386 | 0.0024 | 0.001 |
| 387 | 0.0022 | 0.001 |
| 388 | 0.0046 | 0.002 |
| 389 | <0.005 | <0.005 |
| 390 | 0.0048 | 0.076 |
| 391 | 0.0055 | 0.036 |
| 392 | 0.0149 | 0.005 |
| 393 | 0.0024 | 0.002 |
| 394 | 0.0019 | 0.011 |
| 395 | 0.0024 | 0.001 |
| 396 | 0.0095 | 0.039 |
| 397 | 0.0027 | 0.015 |
| 398 | 0.0072 | 0.011 |
| 399 | 0.0027 | 0.013 |
| 400 | 0.0029 | 0.000 |
| 401 | 0.0037 | 0.007 |
| 402 | 0.0028 | 0.003 |
| 403 | 0.0040 | 0.002 |
| 404 | 0.0059 | 0.003 |
| 405 | 0.0047 | 0.002 |
| 406 | 0.0029 | 0.009 |
| 407 | 0.0078 | 0.64 |

TABLE 1-continued

| Example | hFPR2 cAMP2 $EC_{50}$ (μM) | hFPR1 cAMP $EC_{50}$ (μM) |
|---|---|---|
| 408 | 0.0035 | 0.009 |
| 409 | 0.0063 | 0.036 |
| 410 | 0.0117 | 3.3 |
| 411 | 0.0026 | 0.12 |
| 412 | 0.0076 | 0.093 |
| 413 | 0.0006 | 0.12 |
| 414 | 0.0047 | 0.019 |
| 415 | 0.0068 | 0.003 |
| 416 | 0.0017 | 0.001 |
| 417 | 0.0029 | 0.017 |
| 418 | 0.0027 | 0.004 |
| 419 | 0.0048 | 0.11 |
| 420 | 0.0073 | 0.051 |
| 421 | 0.0033 | 0.015 |
| 422 | 0.0011 | 0.003 |
| 423 | 0.0047 | 1.1 |
| 424 | 0.0022 | 0.011 |
| 425 | 0.0079 | 0.001 |
| 426 | 0.0023 | 0.004 |
| 427 | 0.0044 | 0.002 |
| 428 | 0.0090 | 0.008 |
| 429 | 0.0015 | 0.000 |
| 430 | 0.0033 | 0.005 |
| 431 | 0.0034 | 0.008 |
| 432 | 0.0091 | 3.8 |
| 433 | 0.0018 | 0.001 |
| 434 | 0.0044 | 0.010 |
| 435 | 0.0028 | 0.004 |
| 436 | <0.005 | 0.009 |
| 437 | 0.0010 | 0.001 |
| 438 | 0.0039 | 0.007 |
| 439 | 0.0055 | 0.007 |
| 440 | 0.0013 | 0.011 |
| 441 | 0.0052 | 0.003 |
| 442 | 0.0096 | 0.001 |
| 443 | 0.0051 | 0.002 |
| 444 | 0.0018 | 0.001 |
| 445 | 0.0042 | 0.62 |
| 446 | <0.005 | 0.003 |
| 447 | 0.0047 | 2.8 |
| 448 | 0.0080 | 0.009 |
| 449 | 0.0035 | 0.0002 |
| 450 | 0.0030 | 0.003 |
| 451 | 0.002 | 1.9 |
| 452 | 0.0096 | 0.004 |
| 453 | 0.0095 | 2.9 |
| 454 | 0.0044 | 0.017 |
| 455 | 0.0029 | 0.010 |
| 456 | 0.0028 | 0.001 |
| 457 | 0.0032 | 0.002 |
| 458 | 0.0012 | 0.0008 |
| 459 | 0.0009 | 0.0002 |
| 460 | 0.0014 | 0.001 |
| 461 | 0.0037 | 0.003 |
| 462 | 0.0006 | 1.4 |
| 463 | 0.0039 | 0.006 |
| 464 | 0.0016 | 0.004 |
| 465 | 0.0029 | 0.013 |
| 466 | 0.0030 | 0.004 |
| 467 | 0.0018 | 1.5 |
| 468 | 0.0021 | 0.018 |
| 469 | 0.0014 | 0.002 |
| 470 | 0.0019 | 0.008 |
| 471 | 0.0011 | 0.002 |
| 472 | 0.0012 | 0.0017 |
| 473 | 0.0018 | 0.002 |
| 474 | 0.0021 | 0.004 |
| 475 | 0.0020 | 0.020 |
| 476 | 0.0017 | 0.014 |
| 477 | 0.0010 | 0.013 |
| 478 | 0.0059 | 0.001 |
| 479 | 0.0094 | 0.005 |
| 480 | 0.0057 | 0.3 |
| 481 | 0.0012 | 2.2 |
| 482 | 0.0025 | 0.001 |
| 483 | 0.0056 | 0.016 |

TABLE 1-continued

| Example | hFPR2 cAMP2 $EC_{50}$ (μM) | hFPR1 cAMP $EC_{50}$ (μM) |
|---|---|---|
| 484 | 0.0030 | 0.42 |
| 485 | 0.0017 | 0.002 |
| 486 | 0.0043 | 0.036 |
| 487 | 0.0019 | 0.72 |
| 488 | 0.0026 | 0.79 |
| 489 | 0.0007 | 0.005 |
| 490 | 0.001 | 0.001 |
| 491 | 0.0018 | >5 |
| 492 | 0.0087 | >5 |
| 493 | 0.0022 | 0.27 |
| 494 | 0.0034 | 0.44 |
| 495 | 0.0016 | 0.86 |
| 496 | 0.0030 | 1.1 |
| 497 | 0.0012 | 0.72 |
| 498 | 0.0018 | >5 |
| 499 | 0.029 | 0.060 |
| 500 | 0.0022 | 0.71 |
| 501 | 0.0016 | 2.5 |
| 502 | 0.0077 | 0.90 |
| 503 | 0.0043 | 3.5 |
| 504 | 0.0022 | 3.3 |
| 505 | 0.10 | 3.4 |
| 506 | 0.0008 | 0.068 |
| 507 | 0.0023 | 0.15 |
| 508 | 0.0064 | 0.11 |
| 509 | 0.041 | 0.079 |
| 510 | 0.0035 | 0.29 |
| 511 | 0.066 | 0.39 |
| 512 | 0.0037 | 2.1 |
| 513 | 0.0024 | 1.5 |
| 514 | 0.0026 | 0.27 |
| 515 | 0.0021 | 2.2 |
| 516 | 0.0013 | 1.7 |
| 517 | 0.0028 | 1.8 |
| 518 | 0.0020 | 3.3 |
| 519 | 0.0031 | 0.48 |
| 520 | 0.0049 | 1.3 |
| 521 | 0.0090 | 0.33 |
| 522 | 0.0054 | >5 |
| 523 | 0.0014 | 3.6 |
| 524 | 0.0008 | 1.4 |
| 525 | 0.0014 | 0.42 |
| 526 | 0.0011 | 2.3 |
| 527 | 0.0013 | 0.77 |
| 528 | 0.0002 | 0.60 |
| 529 | 0.0067 | >5 |
| 530 | 0.0031 | 0.68 |
| 531 | 0.0016 | 3.2 |
| 532 | 0.0023 | 0.63 |
| 533 | 0.0040 | 0.90 |
| 534 | 0.0034 | >5 |
| 535 | 0.0010 | 0.20 |
| 536 | 0.0021 | 0.65 |
| 537 | 0.0099 | 0.035 |
| 538 | 0.0013 | 2.0 |
| 539 | 0.0068 | 0.47 |
| 540 | 0.0027 | >5 |
| 541 | 0.020 | 0.81 |
| 542 | 0.0057 | 1.2 |
| 543 | 0.0069 | 1.9 |
| 544 | 0.034 | 1.7 |
| 545 | 0.0060 | 0.33 |
| 546 | 0.0021 | 1.8 |
| 547 | 0.0045 | 2.4 |
| 548 | 0.28 | >5 |
| 549 | 0.0041 | 0.028 |
| 550 | 0.010 | 0.0035 |
| 551 | 0.0015 | 0.077 |
| 552 | 0.13 | 0.44 |
| 553 | 0.0007 | 1.2 |
| 554 | 0.0043 | 2.4 |
| 555 | 0.031 | 0.53 |
| 556 | 0.0022 | 2.0 |
| 557 | 0.0018 | 0.13 |
| 558 | 0.0064 | 2.0 |
| 559 | 0.0066 | 0.45 |

TABLE 1-continued

| Example | hFPR2 cAMP2 $EC_{50}$ (μM) | hFPR1 cAMP $EC_{50}$ (μM) |
|---|---|---|
| 560 | 0.0008 | 0.12 |
| 561 | 0.0043 | 0.17 |
| 562 | 0.0016 | 0.75 |
| 563 | 0.0023 | 0.0023 |
| 564 | 0.0036 | 0.0005 |
| 565 | 0.0082 | 0.72 |
| 566 | 0.0011 | 0.99 |
| 567 | 0.0096 | >5 |
| 568 | 0.0028 | 0.44 |
| 569 | 0.0012 | 1.6 |
| 570 | 0.0012 | 1.5 |
| 571 | 0.0060 | 0.58 |
| 572 | 0.0035 | 1.6 |
| 573 | 0.0087 | 1.3 |
| 574 | 0.015 | 0.55 |
| 575 | 0.48 | >5 |
| 576 | 0.0014 | 0.0015 |
| 577 | 0.0006 | 0.0002 |
| 578 | 0.0015 | 0.006 |
| 579 | 0.0058 | 0.0055 |
| 580 | 0.0036 | 0.74 |
| 581 | 0.0013 | 0.010 |
| 582 | 0.0047 | 0.55 |
| 583 | 0.0038 | 0.057 |
| 584 | 0.0218 | 0.66 |
| 585 | 0.0218 | 1.2 |
| 586 | 0.0098 | 1.3 |
| 587 | 0.0011 | 0.60 |
| 588 | 0.0069 | 0.41 |
| 589 | 0.13 | 2.6 |
| 590 | 0.0019 | 1.6 |
| 591 | 0.0105 | 0.0085 |
| 592 | 0.0071 | 0.0062 |
| 593 | 0.0033 | 0.040 |
| 594 | 0.0024 | 0.0014 |
| 595 | 0.0024 | 0.013 |
| 596 | 0.0437 | 0.86 |
| 597 | 0.0015 | 0.21 |
| 598 | 0.0062 | 0.59 |
| 599 | 0.0041 | 0.040 |
| 600 | 0.0078 | 0.17 |
| 601 | 0.0020 | 0.17 |
| 602 | 0.0038 | 0.088 |
| 603 | 0.0039 | 0.056 |
| 604 | 0.0005 | 0.015 |
| 605 | <0.005 | 0.0019 |
| 606 | 0.0200 | 0.053 |
| 607 | 0.0133 | 0.030 |
| 608 | 0.0041 | 0.0042 |
| 609 | 0.0018 | 0.028 |
| 610 | 0.0010 | 0.0003 |
| 611 | 0.0024 | 0.0059 |
| 612 | 0.0135 | 0.033 |
| 613 | 0.0118 | 0.0093 |
| 614 | 0.0060 | 0.033 |
| 615 | 0.0087 | 0.0053 |
| 616 | 0.0094 | 0.020 |
| 617 | 0.0091 | 0.018 |
| 618 | 0.0010 | 0.0095 |
| 619 | 0.0094 | 0.064 |
| 620 | 0.0074 | 0.0065 |
| 621 | 0.090 | 0.064 |
| 622 | 0.0084 | 0.0022 |
| 623 | 0.0115 | 0.16 |
| 624 | 0.0015 | 0.0093 |
| 625 | 0.0019 | 0.012 |
| 626 | 0.0007 | 0.013 |
| 627 | 0.0086 | 0.0020 |
| 628 | 0.0047 | 0.059 |
| 629 | 0.0099 | 0.67 |
| 630 | 0.0052 | 1.1 |
| 631 | 0.0100 | 0.16 |
| 632 | 0.0009 | 0.0037 |
| 633 | 0.0014 | 0.0043 |
| 634 | 0.0020 | 0.0023 |
| 635 | 0.0037 | 0.0063 |

TABLE 1-continued

| Example | hFPR2 cAMP2 $EC_{50}$ (μM) | hFPR1 cAMP $EC_{50}$ (μM) |
|---|---|---|
| 636 | 0.0016 | 0.0032 |
| 637 | 0.0066 | 0.0057 |
| 638 | 0.014 | 0.29 |
| 639 | 0.0058 | 0.057 |
| 640 | 0.0022 | 1.2 |
| 641 | 0.0028 | 1.0 |
| 642 | 0.015 | 0.57 |
| 643 | 0.0026 | 0.075 |
| 644 | 0.0021 | 0.064 |
| 645 | 0.0028 | 0.19 |
| 646 | 0.016 | 0.67 |
| 647 | 0.0015 | 0.022 |
| 648 | 0.0007 | 0.0041 |
| 649 | 0.0013 | 0.0078 |
| 650 | 0.011 | 1.7 |
| 651 | 0.0035 | 0.78 |
| 652 | 0.0072 | 0.70 |
| 653 | 0.0033 | 0.012 |
| 654 | 0.0010 | 0.012 |
| 655 | 0.0038 | 0.0012 |
| 656 | 0.0025 | 0.013 |
| 657 | 0.0020 | 0.045 |
| 658 | 0.0034 | 0.0017 |
| 659 | 0.0010 | 0.0013 |
| 660 | 0.0014 | 0.029 |
| 661 | 0.0012 | 0.11 |
| 662 | 0.0040 | 0.014 |
| 663 | 0.0011 | 1.7 |
| 664 | 0.0087 | 0.19 |
| 665 | <0.010 | 0.0074 |
| 666 | 0.015 | 0.015 |
| 667 | 0.063 | 0.0077 |
| 668 | 0.0088 | 0.21 |
| 669 | 0.011 | 0.27 |
| 670 | 0.0065 | |
| 671 | 0.0058 | |
| 672 | 0.0079 | 0.005 |
| 673 | 0.0031 | 0.012 |
| 674 | 0.0068 | 0.023 |
| 675 | 0.0055 | 0.005 |
| 676 | 0.013 | 0.295 |
| 677 | 0.0053 | 0.230 |
| 678 | 0.011 | 0.092 |
| 679 | 0.006 | 0.028 |
| 680 | 0.0028 | 0.78 |
| 681 | 0.010 | 1.000 |
| 682 | 0.015 | 0.001 |
| 683 | 0.013 | |
| 684 | 0.007 | 0.005 |
| 685 | 0.014 | 0.0014 |
| 686 | 0.013 | 0.00070 |
| 687 | 0.0018 | 0.00028 |
| 688 | 0.012 | 0.0015 |
| 689 | 0.0045 | 0.0015 |
| 690 | 0.011 | 0.024 |
| 691 | 0.011 | 0.011 |
| 692 | 0.0038 | 0.0028 |
| 693 | 0.0020 | 0.0025 |
| 694 | 0.0061 | 0.056 |
| 695 | 0.0035 | 0.004 |
| 696 | 0.0072 | 0.0083 |
| 697 | 0.0036 | 0.0067 |
| 698 | 0.0057 | 0.0025 |
| 699 | 0.0066 | 0.0030 |
| 700 | 0.0030 | 0.00067 |
| 701 | 0.012 | 0.027 |
| 702 | 0.0085 | 0.0075 |
| 703 | 0.057 | 0.099 |
| 704 | 0.0024 | 0.001 |
| 705 | 0.0006 | 0.0039 |
| 706 | 0.0094 | 0.019 |
| 707 | 0.0054 | 0.13 |
| 708 | 0.011 | >1 |
| 709 | 0.014 | 0.21 |
| 710 | 0.0040 | 0.49 |
| 711 | 0.0042 | 3.4 |

TABLE 1-continued

| Example | hFPR2 cAMP2 $EC_{50}$ (μM) | hFPR1 cAMP $EC_{50}$ (μM) |
|---|---|---|
| 712 | 0.0021 | 2.8 |
| 713 | 0.0040 | >5 |
| 714 | 0.0064 | 3.6 |
| 715 | 0.0055 | >5 |
| 716 | 0.0057 | >5 |
| 717 | 0.0007 | 0.15 |
| 718 | 0.0009 | 0.84 |
| 719 | 0.0014 | 1.9 |
| 720 | 0.0039 | >5 |
| 721 | 0.0056 | >5 |

Pharmaceutical Compositions and Methods of Use

The compounds of the present invention may be administered to mammals, preferably humans, for the treatment of a variety of conditions and disorders including atherosclerosis, heart failure, lung diseases including asthma, COPD, and cystic fibrosis; neuroinflammatory diseases including multiple sclerosis, Alzheimer's disease, and stroke; and chronic inflammatory diseases such as inflammatory bowel disease, rheumatoid arthritis, psoriasis, sepsis, and kidney fibrosis.

Unless otherwise specified, the following terms have the stated meanings. The term "subject" refers to any human or other mammalian species that could potentially benefit from treatment with a FPR2 and/or FPR1 agonist as understood by practioners in this field. Some subjects include human beings of any age with risk factors for cardiovascular disease. Common risk factors include age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). The term "patient" means a person suitable for therapy as determined by practitioners in the field. "Treating" or "treatment" cover the treatment of a patient or subject as understood by practitioners in this field. "Preventing" or "prevention" cover the preventive treatment (i.e., prophylaxis and/or risk reduction) of a subclinical disease-state in a patient or subject aimed at reducing the probability of the occurrence of a clinical disease-state as understood by practitioners in this field. Patients are selected for preventative therapy based on factors that are known to increase risk of suffering a clinical disease state compared to the general population. "Therapeutically effective amount" means an amount of a compound that is effective as understood by practitioners in this field.

Another aspect of the invention are pharmaceutical compositions comprising a therapeutically effective amount of a compound of Formulae (I)—(VII) in combination with a pharmaceutical carrier.

Another aspect of the invention are pharmaceutical compositions comprising a therapeutically effective amount of a compound of Formulae (I)—(VII) in combination with at least one other therapeutic agent and a pharmaceutical carrier.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Another aspect of the invention is a method for treating heart disease comprising administering a therapeutically effective amount of a compound of Formulae (I)—(VII) to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

It will be understood that treatment or prophylaxis of heart failure may involve treatment or prophylaxis of a cardiovascular event as well. Treatment or prophylaxis as referred to herein may refer to treatment or prophylaxis of certain negative symptoms or conditions associated with or arising as a result of a cardiovascular event. By way of example, treatment or prophylaxis may involve reducing or preventing negative changes in fractional shortening, heart weight, lung weight, myocyte cross sectional area, pressure overload induced cardiac fibrosis, stress induced cellular senescence, and/or cardiac hypertrophy properties, or any combination thereof, associated with or arising as a result of a cardiovascular event. Treatment may be administered in preparation for or in response to a cardiovascular event to alleviate negative effects. Prevention may involve a pro-active or prophylactic type of treatment to prevent the cardiovascular event or to reduce the onset of negative effects of a cardiovascular event.

In one embodiment, the present invention provides the use of a compound of Formulae (I)—(VII) or a pharmaceutically acceptable salt thereof for the preparation of a pharmaceutical composition for the treatment or prophylaxis of heart failure, for example, heart failure results from hypertension, an ischemic heart disease, a non-ischemic heart disease, exposure to a cardiotoxic compound, myocarditis, Kawasaki's disease, Type I and Type II diabetes, thyroid disease, viral infection, gingivitis, drug abuse, alcohol abuse, pericarditis, atherosclerosis, vascular disease, hypertrophic cardiomyopathy, dilated cardiomyopathy, myocardial infarction, atrial fibrosis, left ventricular systolic dysfunction, left ventricular diastolic dysfunction, coronary bypass surgery, pacemaker implantation surgery, starvation, an eating disorder, muscular dystrophies, and a genetic defect. Preferably, the heart failure to be treated is diastolic heart failure, heart failure with reduced ejection fraction ($HF_{R}EF$), heart failure with preserved ejection fraction ($HF_{P}EF$), acute heart failure, and chronic heart failure of ischemic and non-ischemic origin.

In one embodiment, the present invention provides the use of a compound of Formulae (I)—(VII) to treat systolic and/or diastolic dysfunction, wherein the compound is administered in a therapeutically effective amount to increase the ability of the cardiac muscle cells to contract and relax thereby increasing the filling and emptying of both the right and left ventricles, preferably, the left ventricle.

In another embodiment, the present invention provides the use of a compound of Formulae (I)—(VII) to treat heart failure wherein the compound is administered in a therapeutically effective amount to increase ejection fraction in the left ventricle.

In still another embodiment, the present invention provides the use of a compound of Formulae (I)—(VII) to treat heart failure wherein the compound is administered in a therapeutically effective amount to reduce fibrosis in heart tissue.

Another aspect of the invention is a method for treating heart disease wherein the treatment is post myocardial infarction.

Another aspect of the invention is a method for treating heart disease comprising administering a therapeutically effective amount of a compound of Formulae (I)—(VII) to a patient in conjunction with other therapeutic agents.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with at least one of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention may be employed in combination with at least one of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination at least one of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The compounds of the invention may be used in combination with at least one of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with at least one of the following anti-obesity agents selected from phenylpropanolamine, phentermine, diethylpropion, mazindol, fenfluramine, dexfenfluramine, phentiramine, $\beta_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries. The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product. The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached. The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemistry Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "wave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Ac acetic
AcOH acetic acid
Acn (or MeCN) acetonitrile
Bn benzyl
Boc tert-butyl carbonyl
$Boc_2O$ di-tert-butyl dicarbonate
Bu butyl
Dba as in dibenzylideneacetone
($Pd_2(dba)_3$)
Cbz carboxybenzyl
DCM dichloromethane
DEA diethylamine
DIEA or DIPEA diisopropylethylamine
DMAP 4-dimethylaminopyridine
DMF dimethylformamide
DMSO dimethyl sulfoxide
dppf 1,1'-bis(diphenylphosphino)ferrocene
Et ethyl
EtOH ethanol
EtOAc ethyl acetate
HATU 2-(7-Aza-1H-benzotriazole-1-yl)-1,1,3,3-tetramethyluronium hexafluorophosphate
HBTU 2-(1H-Benzotriazole-1-yl)-1,1,3,3-tetramethyluronium
hexafluorophosphate
i-Bu isobutyl
IPA isopropyl alcohol
i-Pr isopropyl
LAH lithium aluminum hydride
Me methyl
MeOH methanol
pet petroleum
Ph phenyl
Pr propyl
t-Bu tert-butyl
TEA triethylamine
TFA trifluoroacetic acid
THF tetrahydrofuran
Ts tosyl The disclosed compounds can be made by various methods known in the art including those of the following schemes and in the specific embodiments section. The structure numbering and variable numbering shown in the synthetic schemes are distinct from and should not be confused with the structure or variable numbering in the claims or the rest of the specification. The variables in the schemes are meant only to illustrate how to make some of the compounds of this invention.

A consideration in the planning of any synthetic route in this field is the choice of the protecting group used for protection of the reactive functional groups present in the compounds described in this invention. An authoritative account describing the many alternatives to the trained practitioner is Greene, T. W. et al., *Protecting Groups in Organic Synthesis,* 4th Edition, Wiley (2007)).

Compounds having the general Formula (I): wherein A, B and C are defined above as $Ar^1$, $Ar^2$ and $Ar^3$, respectively and Formula (II): wherein A, B and Y are defined above as $Ar^1$, $Ar^2$ and alkyl and/or cycloalkyl groups, respectively and can be prepared by the following one or more of the synthetic Schemes.

(I)

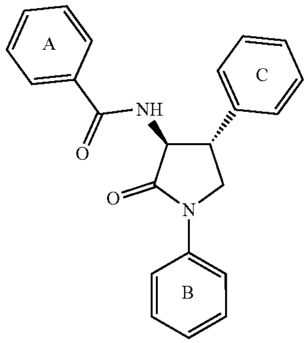

((II)

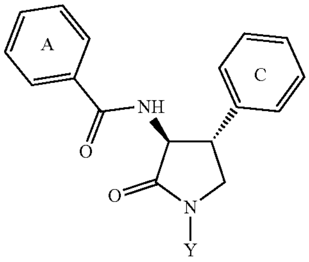

1-Arylpyrrolidinone compounds of this invention (Formula I) wherein ring A is a substituted phenyl or cycloalkyl ring, ring B is phenyl or heteroaryl ring and ring C is a substituted phenyl or heteroaryl ring can be prepared by the general route shown in Scheme 1. Compound 1a was synthesized as per the procedure reported in the patent literature (WO2015079692). Compound 1a was treated with diphenylphosphoryl azide (DPPA) and a tertiary amine such as triethylamine (TEA). Subsequent addition of benzyl alcohol yielded Cbz protected compound 1b. Removal of the Cbz protecting group from 1b with Pd/C in the presence of hydrogen, followed by amide coupling of the resulting free amine with a suitably substituted phenyl acid provided amides 1c. Other deprotection conditions and protecting groups known to those skilled in the art could also be used in this sequence. Copper or Pd-catalyzed coupling of 1c to a substituted iodobenzene or bromobenzene or other suitable halo aryl or heteroaryl compounds in a suitable solvent such as butanol or dioxane or toluene, in the presence of a base such as potassium carbonate or cesium carbonate and a suitable ligand such as N,N'-dimethylethylenediamine, or Xanthphos can afford desired compounds 1d. Suitable aryl or heteroaryl halides are either commercially available or can be readily obtained from the corresponding readily available starting materials by methods known to one skilled in the art. Additional methods for this transformation include other variations of Ullmann, Goldberg, and Buchwald copper-catalyzed amidation or Buchwald Pd-catalyzed C—N coupling depending on the nature of ring B, using methods known to one skilled in the art for these types of couplings (see for example Yin & Buchwald, Organic Lett. 2000, 2, 1101; Klapers et al., JACS, 2001, 123, 7727; Klapars et al., JACS, 2002, 124, 7421; Yin & Buchwald, JACS. 2002, 124, 6043; Kiyomor, Madoux & Buchwald, Tet. Lett., 1999, 40, 2657). Similarly, 1-arylpyrrolidinone compounds of this invention (Formula I) wherein rings A and C are substituted phenyl rings or heteroaryl or cycloalkyl and ring B is phenyl or heteroaryl can be prepared by the general route shown in Scheme 2.

Scheme 1

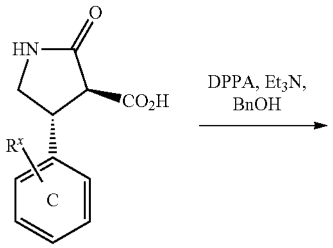

1a

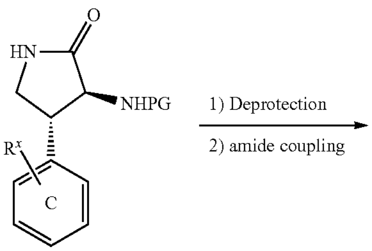

1b

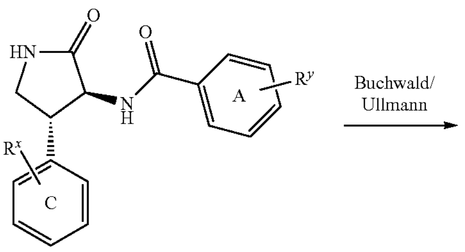

1c

-continued

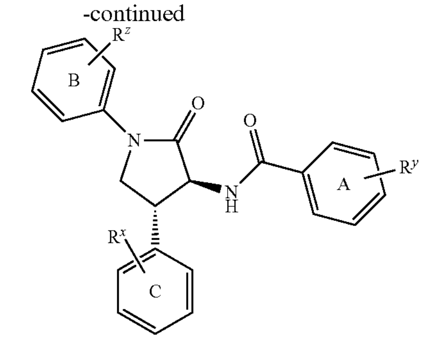

1d

Scheme 2

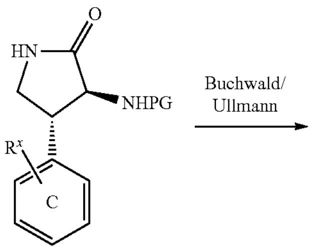

1b

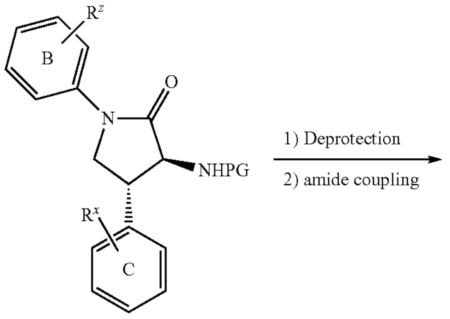

1e

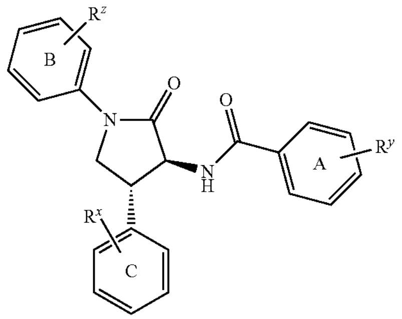

1f

1-Arylpyrrolidinone compounds of this invention (Formula II) wherein rings A and C are phenyl rings and Y is a substituted benzyl, heteroaryl alkyl, alkyl and or cycloalkyl group, can be prepared by the general route shown in Scheme 3, starting from an intermediate 1c, prepared as shown in Scheme 1.

Scheme 3

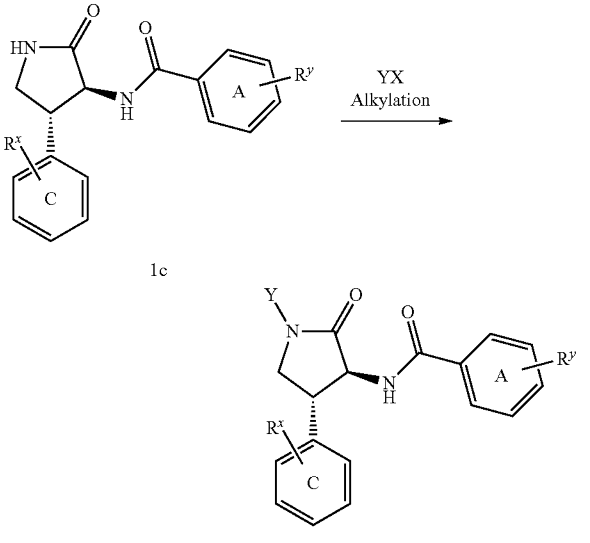

1c

1e

In the Scheme 3, Y is a $C_{1-6}$ alkyl group, benzyl, and heteroaryl with an alkyl spacer and X is a leaving group such as chloride, bromide, iodide, a methane sulfonyloxy group, a trifluoromethane sulfonyloxy group or the other known groups. Compound 1e can be obtained by reacting compound 1c with alkylating reagent YX in a solvent in the presence of a suitable base with heating in an appropriate solvent such as DMF or DMSO or obtained by other methods known to one skilled in the art.

Other features of the invention will become apparent in the course of the following descriptions of exemplary embodiments that are given for illustration of the invention and are not intended to be limiting thereof.

The following methods were used in the exemplified Examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% Acn, 0.1% TFA) and Solvent B (5% water, 95% Acn, 0.1% TFA) or with gradients of Solvent A (95% water, 2% Acn, 0.1% HCOOH) and Solvent B (98% Acn, 2% water, 0.1% HCOOH) or with gradients of Solvent A (95% water, 5% Acn, 10 mM $NH_4OAc$) and Solvent B (98% Acn, 2% water, 10 mM $NH_4OAc$) or with gradients of Solvent A (98% water, 2% Acn, 0.1% $NH_4OH$) and Solvent B (98% Acn, 2% water, 0.1% $NH_4OH$).

LC/MS Methods Employed in Characterization of Examples. Reverse phase analytical HPLC/MS was performed on a Waters Acquity system coupled with a Waters MICROMASS® ZQ Mass Spectrometer.

Method A: Linear gradient of 0 to 100% B over 3 min, with 0.75 min hold time at 100% B;

UV visualization at 220 nm

Column: Waters BEH C18 2.1×50 mm

Flow rate: 1.0 mL/min

Solvent A: 0.1% TFA, 95% water, 5% Acn

Solvent B: 0.1% TFA, 5% water, 95% Acn

Method B: Linear gradient of 0 to 100% B over 3 min, with 0.75 min hold time at 100% B;

UV visualization at 220 nm

Column: Waters BEH C18 2.1×50 mm

Flow rate: 1.0 mL/min

Solvent A: 10 mM ammonium acetate, 95% water, 5% Acn

Solvent B: 10 mM ammonium acetate, 5% water, 95% Acn

Analytical HPLC: Methods Employed in Characterization of Examples

Products were analyzed by reverse phase analytical HPLC: carried out on a Shimadzu Analytical HPLC: system running Discovery VP software. RT=retention time.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

The following representative conditions were used to screen compounds for chiral purity. Other conditions were used as well.

Columns: Chiralpak IA, 250×4.6 mm, 5.0-μm particles, Chiralpak IB, 250×4.6 mm, 5.0-μm particles, Chiralpak IC, 250×4.6 mm, 5.0-μm particles, Chiralpak ID, 250×4.6 mm, 5.0-μm particles, Chiralpak IE, 250×4.6 mm, 5.0-μm particles and Chiralpak IF, 250×4.6 mm, 5.0-μm particles;

Mobile Phase: 0.2% ammonia in Acn:MeOH (1:1).

NMR Employed in Characterization of Examples. $^1H$ NMR spectra were obtained with Bruker or JEOL® Fourier transform spectrometers operating at frequencies as follows: $^1H$ NMR: 300 MHz (Bruker or JEOL®) or 400 MHz (Bruker or JEOL®) or 500 MHz (Bruker or JEOL®). $^{13}C$ NMR: 100 MHz (Bruker or JEOL®). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1H$ NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}C$ NMR spectra appear at 39.7 ppm for $CD_3SOCD_3$, 49.0 ppm for $CD_3OD$, and 77.0 ppm for $CDCl_3$. All $^{13}C$ NMR spectra were proton decoupled.

Intermediate 1: benzyl ((3S,4R)-4-(2,6-difluoro-4-methoxyphenyl)-2-oxopyrrolidin-3-yl)carbamate

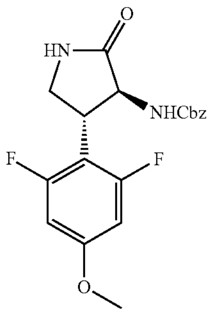 [SMILES: COc1cc(F)c([C@@H]2CNC(=O)[C@H]2NC(=O)OCc2ccccc2)c(F)c1]

To a stirred solution of (3S,4R)-4-(2,6-difluoro-4-methoxyphenyl)-2-oxopyrrolidine-3-carboxylic acid (6.0 g, 22 mmol), TEA (3.7 mL, 27 mmol) in toluene (60 mL) and acetonitrile (12 mL) was added diphenylphosphoryl azide (5.7 mL, 27 mmol). The mixture was stirred at rt for 3 h, and then at 80° C. for 30 min. After the mixture was cooled to rt, benzyl alcohol (12 mL, 110 mmol) was added, and the mixture was stirred at 100° C. for 16 h. The reaction mixture was cooled and concentrated under reduced pressure. The residue was purified via column chromatography (pet. ether-ethyl acetate) to afford Intermediate 1 (4.0 g, 11 mmol, 50%) as a colorless liquid. MS (ESI) m/z: 377.3 $[M+H]^+$ Intermediate 2: (3S,4R)-3-amino-4-(2,6-difluoro-4-methoxyphenyl)pyrrolidin-2-one

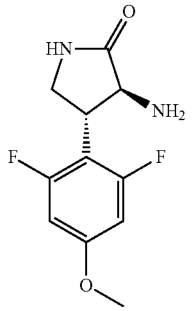 [SMILES: COc1cc(F)c([C@@H]2CNC(=O)[C@H]2N)c(F)c1]

To a degassed solution of Intermediate 1 (4.0 g, 11 mmol) in EtOH (60 mL) was added Pd—C(0.11 g, 1.1 mmol). The reaction mixture was purged with $H_2$ and stirred under an $H_2$ atmosphere for 16 h at rt. The mixture was filtered through a pad of Celite and concentrated under reduced pressure to afford (3S,4R)-3-amino-4-(2,6-difluoro-4-methoxyphenyl)pyrrolidin-2-one (2.5 g, 10.3 mmol, 97%) as a white solid. The crude material was used in the next synthetic step without further purification. MS (ESI) m/z: 243.2 $[M+H]^+$ Intermediate 3: N-((3S,4R)-4-(2,6-difluoro-4-methoxyphenyl)-2-oxopyrrolidin-3-yl)-4-(difluoromethoxy)benzamide

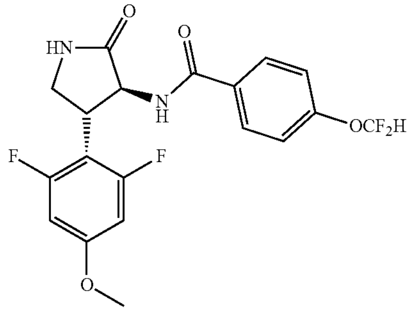

To a stirred solution of Intermediate 2 (1.2 g, 5.0 mmol) in DMF (10 mL) under argon atmosphere at rt were added DIEA (1.0 mL, 6.0 mmol), 4-(difluoromethoxy)benzoic acid (1.1 g, 6.0 mmol), and HATU (2.3 g, 6.0 mmol). After 16 h, the reaction mixture was quenched with water (20 mL) and extracted with EtOAc (20 mL×3). The combined organic layers were washed with water and brine (20 mL each), dried over $Na_2SO_4$ and concentrated under reduced pressure to give the crude product, which was purified via column chromatography (pet. ether-ethyl acetate) to afford Intermediate 3 (1.2 g, 2.9 mmol, 59% yield) as a white solid. MS(ESI) m/z: 413.1 [M+H]+. $^1H$ NMR (300 MHz, DMSO-d6) δ 8.85 (d, J=8.6 Hz, 1H), 8.19 (s, 1H), 7.86 (d, J=8.6 Hz, 2H), 7.35 (t, J=75.0 Hz, 1H), 7.26 (d, J=8.6 Hz, 2H), 6.75 (d, J=12.0 Hz, 2H), 4.90-4.80 (m, 1H), 4.06-3.79 (m, 1H), 3.75 (s, 3H), 3.60-3.45 (m, 1H), 3.42-3.32 (m, 1H).

Intermediate 4: N-((3S,4R)-4-(2,6-difluoro-4-methoxyphenyl)-2-oxopyrrolidin-3-yl)-4-(trifluoromethoxy)benzamide

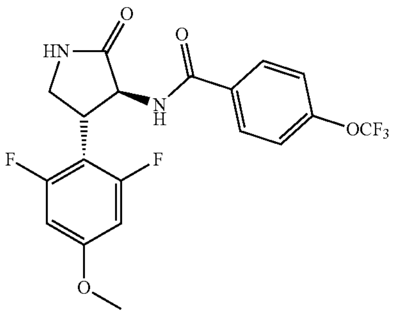

A similar protocol to the above procedure for Intermediate 3 was followed to synthesize Intermediate 4. MS(ESI) m/z: 431.1 [M+H]+. $^1H$ NMR (300 MHz, $CDCl_3$) δ=7.77 (d, J=8.4 Hz, 2H), 7.19 (d, J=7.9 Hz, 2H), 6.47 (m, 3H), 6.23 (s, 1H), 5.14-4.97 (m, 1H), 4.07-3.95 (m, 1H), 3.82-3.75 (m, 4H), 3.68-3.63 (m, 1H).

Intermediate 5A and 5B: 3-Bromo-4-methyl-1-(3,3,3-trifluoro-2-hydroxypropyl) pyridin-2(1H)-one

5A

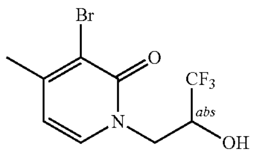

Enantiomer-1

5B

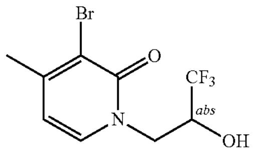

Enantiomer-2

To a stirred solution of 3-bromo-4-methylpyridin-2(1H)-one (1.5 g, 8.0 mmol) in DMF (15 mL) at rt, were added 3-bromo-1,1,1-trifluoropropan-2-ol (2.3 g, 12 mmol) and $K_2CO_3$ (3.3 g, 24 mmol). The reaction mixture was heated at 90° C. for 16 h. The reaction mixture was cooled, filtered through Celite pad, and concentrated under reduced pressure. The crude compound was purified by silica gel chromatography (pet. ether-ethyl acetate) and the enantiomers were separated via chiral SFC separation to yield Intermediate 5A (0.80 g, 2.7 mmol, 33.4% yield) and Intermediate 5B (0.80 g, 2.7 mmol, 33% yield). SFC prep conditions: Column/dimensions: Whelk (R,R)(250×4.6) mm, 5p; $CO_2$: 85%, % Co-solvent: 15% of 0.2% DEA in IPA. Total flow: 3.0 g/min, back pressure: 100 bar, temperature: 40° C., UV: 220 nm. Retention time peak 1=3.2 min and peak 2=4.4 min. Enantiomer 1: MS(ESI) m/z: 299.9 [M+H]+. $^1$H NMR (400 MHz, DMSO-$d_6$) δ=7.60 (d, J=7.0 Hz, 1H), 6.62 (d, J=6.5 Hz, 1H), 6.29 (d, J=7.0 Hz, 1H), 4.42-4.29 (m, 2H), 3.87-3.79 (m, 1H), 2.28 (s, 3H). Enantiomer 2: MS(ESI) m/z: 299.9 [M+H]+. $^1$H NMR (400 MHz, DMSO-$d_6$) δ=7.60 (d, J=7.0 Hz, 1H), 6.62 (d, J=6.5 Hz, 1H), 6.29 (d, J=7.0 Hz, 1H), 4.42-4.29 (m, 2H), 3.87-3.79 (m, 1H), 2.28 (s, 3H).

Intermediate 6: 2-(2-Methoxyethyl)-5-methylpyridazin-3(2H)-one

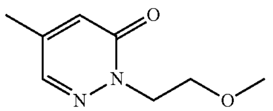

To a stirred solution of 5-methylpyridazin-3(2H)-one (1.0 g, 9.1 mmol) in DMF (10 mL) at rt, were added potassium carbonate (3.8 g, 27 mmol), and 1-bromo-2-methoxyethane (1.5 g, 11 mmol). The reaction mixture was heated at 70° C. for 15 h. Then, the reaction mixture was cooled, filtered through Celite pad, and concentrated under reduced pressure. The crude residue was purified by silica gel chromatography (pet. ether-ethyl acetate) to yield Intermediate 6 (1.0 g, 6.0 mmol, 66% yield) as a yellow liquid. MS(ESI) m/z: 169.1 $[M+H]^+$. $^1$H NMR (400 MHz, DMSO-$d_6$) δ=7.79 (d, J=2.0 Hz, 1H), 6.73 (m, 1H), 4.18 (t, J=5.8 Hz, 2H), 3.64 (t, J=5.8 Hz, 2H), 3.23 (s, 3H), 2.16 (d, J=2.0 Hz, 3H).

Intermediate 7: 4-Bromo-2-(2-methoxyethyl)-5-methylpyridazin-3(2H)-one

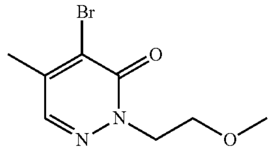

To a stirred solution of 2-(2-methoxyethyl)-5-methylpyridazin-3(2H)-one (500 mg, 3.0 mmol) in acetonitrile (5 mL) at rt, was added NBS (1060 mg, 5.95 mmol). Then, the reaction mixture was heated at 80° C. for 16 h. The reaction mixture was cooled, filtered through Celite pad and the filtrate was concentrated under reduced pressure. The crude compound was purified by silica gel chromatography (pet. ether-ethyl acetate) to afford the Intermediate 7 (350 mg, 1.4 mmol, 48% yield) as an orange solid. MS(ESI) m/z: 249.1 $[M+H]^+$. $^1$H NMR (400 MHz, DMSO-$d_6$) δ=7.86 (s, 1H), 4.26 (t, J=5.5 Hz, 2H), 3.67 (t, J=5.5 Hz, 2H), 3.22 (s, 3H), 2.27 (s, 3H).

Example 1: N-((3S,4R)-1-(2-cyanopyridin-3-yl)-4-(2,6-difluoro-4-methoxyphenyl)-2-oxopyrrolidin-3-yl)-4-(difluoromethoxy)benzamide

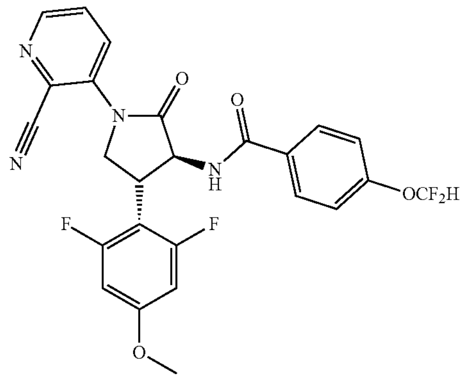

To a stirred solution of Intermediate 3 (80 mg, 0.19 mmol) in 1,4-dioxane (2 mL) were added 3-bromopicolinonitrile (43 mg, 0.23 mmol), and $Cs_2CO_3$ (130 mg, 0.39 mmol). The reaction mixture was purged with nitrogen for 5 min and charged with xanthphos (22 mg, 0.039 mmol) and $Pd_2(dba)_3$ (18 mg, 0.019 mmol). The reaction mixture was again purged with nitrogen for 3 min and heated at 100° C. for 16 h. The reaction mixture was cooled and filtered through a Celite pad. The filtrate was concentrated under reduced pressure, and the crude product was purified by reverse phase HPLC to afford Example 1 (26 mg, 0.051 mmol, 26% yield) as a white solid. MS(ESI) m/z: 515.2 $[M+H]^+$. $^1$H NMR (400 MHz, DMSO-$d_6$) δ=9.14 (d, J=8.3 Hz, 1H), 8.72 (d, J=4.6 Hz, 1H), 8.24 (d, J=8.3 Hz, 1H), 7.94-7.87 (m, 3H), 7.35 (s, 1H), 7.29 (d, J=8.8 Hz, 2H), 6.81 (d, J=10.8 Hz, 2H), 5.16-5.02 (m, 1H), 4.34-4.22 (m, 2H), 4.18-4.09 (m, 1H), 3.78 (s, 3H). RT=1.725 min, 100% (Method D).

Example 2: N-((3S,4R)-4-(2,6-difluoro-4-methoxyphenyl)-1-(1-methyl-6-oxo-1,6-dihydropyridin-3-yl)-2-oxopyrrolidin-3-yl)-4-(difluoromethoxy)benzamide

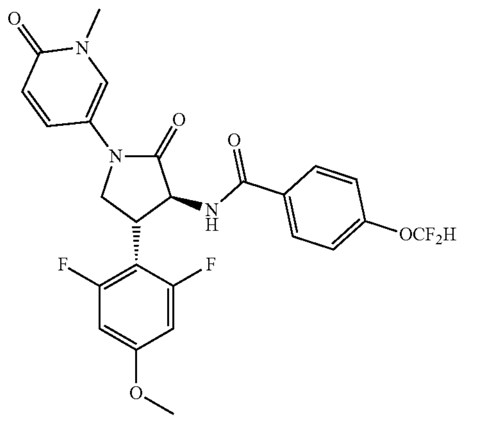

To a stirred solution of Intermediate 3 (60 mg, 0.15 mmol) in 1,4-dioxane (2 mL) at rt were added 5-bromo-1-methylpyridin-2(1H)-one (33 mg, 0.18 mmol), $Cs_2CO_3$ (95 mg, 0.29 mmol) and, N,N'-dimethylethylenediamine (2.6 mg, 0.029 mmol). The reaction mixture was purged with nitrogen for 5 min and then charged with copper (I) iodide (5.5 mg, 0.029 mmol), purged with nitrogen for 3 min and heated at 100° C. for 16 h. The reaction mixture was cooled, filtered through Celite pad and concentrated under reduced pressure to give the crude product, which was purified by reverse phase HPLC to afford the Example 2 (32 mg, 0.062 mmol, 42% yield) as a white solid. MS(ESI) m/z: 520.1 $[M+H]^+$. $^1H$ NMR (400 MHz, DMSO-$d_6$) δ=9.03 (d, J=8.6 Hz, 1H), 8.01 (d, J=2.7 Hz, 1H), 7.93-7.81 (m, 3H), 7.55-7.13 (m, 3H), 6.80 (d, J=10.8 Hz, 2H), 6.46 (d, J=10.0 Hz, 1H), 4.98 (m, 1H), 4.18-4.07 (m, 1H), 4.00 (t, J=8.8 Hz, 1H), 3.93-3.85 (m, 1H), 3.78 (s, 3H), 3.45 (s, 3H). RT=1.677 min, 100% (Method D).

Example 3: N-((3S,4R)-1-(cyclopropylmethyl)-4-(2,6-difluoro-4-methoxyphenyl)-2-oxopyrrolidin-3-yl)-4-(difluoromethoxy)benzamide

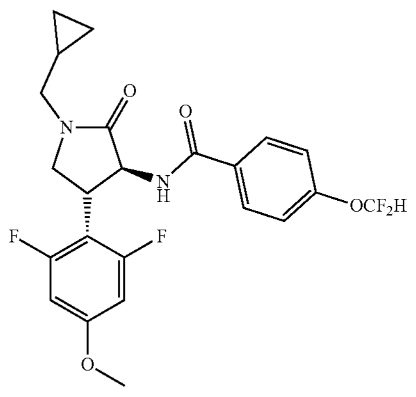

To a stirred solution of Intermediate 3 (60 mg, 0.15 mmol) in DMF (2 mL) under argon atmosphere at 0° C. was added NaH (8.7 mg, 0.22 mmol), and the resulting reaction mixture was stirred for 30 min. Then bromomethyl cyclopropane (24 mg, 0.18 mmol) was added to the reaction mixture, and the mixture was gradually warmed to rt over a period of 2 h. The reaction mixture was quenched with ice/water and extracted with EtOAc (20 mL×2). The combined organic layers were washed with water (10 mL) and brine (10 mL), dried over $Na_2SO_4$ and concentrated under reduced pressure. The crude product was purified by reverse phase HPLC to afford Example 3 (23 mg, 0.049 mmol, 33% yield) as a white solid. MS(ESI) m/z: 467.1 $[M+H]^+$. $^1H$ NMR (400 MHz, DMSO-$d_6$) δ=8.91 (d, J=8.8 Hz, 1H), 7.87 (d, J=8.8 Hz, 2H), 7.34 (s, 1H), 7.26 (d, J=8.6 Hz, 2H), 6.76 (d, J=10.8 Hz, 2H), 4.92 (t, J=9.5 Hz, 1H), 3.97-3.88 (m, 1H), 3.77 (s, 3H), 3.75-3.70 (m, 1H), 3.65-3.55 (m, 1H), 3.31-3.24 (m, 1H), 3.07 (m, 1H), 1.01-0.93 (m, 1H), 0.51 (d, J=8.1 Hz, 2H), 0.32-0.20 (m, 2H). RT=1.810 min, 99.2% (Method D).

Example 4 and 5: N-((3S,4R)-4-(2,6-Difluoro-4-methoxyphenyl)-2-oxo-1-(2-oxo-1-(3,3,3-trifluoro-2-hydroxypropyl)-1,2-dihydropyridin-3-yl)pyrrolidin-3-yl)-4-(difluoromethoxy)benzamide (Enantiomers 1 and 2)

4

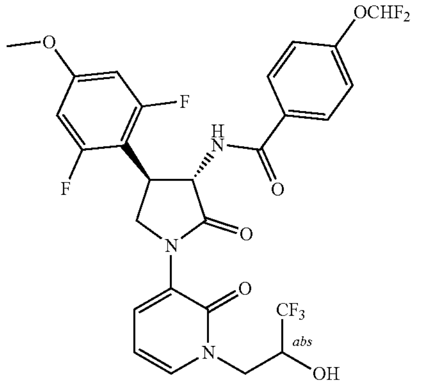

Enantiomer-1

5

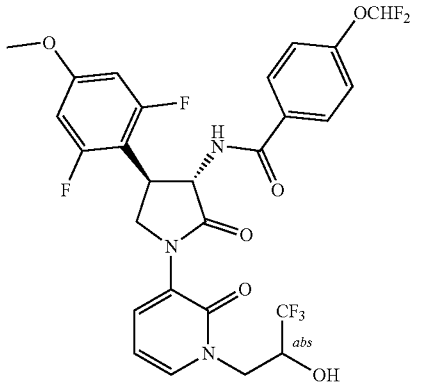

Enantiomer-2

To a stirred solution of N-((3S,4R)-4-(2,6-difluoro-4-methoxyphenyl)-2-oxopyrrolidin-3-yl)-4-(difluoromethoxy)benzamide (500 mg, 1.2 mmol) in 1,4-dioxane (10 mL) at rt, were added cesium carbonate (790 mg, 2.4 mmol), and 3-bromo-1-(3,3,3-trifluoro-2-hydroxypropyl) pyridin-2(1H)-one (382 mg, 1.34 mmol). The reaction mixture was purged with nitrogen for 5 min and then charged with N,N-dimethylethane-1,2-diamine (21 mg, 0.24 mmol) and copper (I) iodide (23 mg, 0.12 mmol). The reaction mixture was again purged with nitrogen for 3 min and heated at 100° C. for 16 h. The reaction mixture was cooled, filtered through Celite pad, concentrated under reduced pressure. The crude compound, which was purified reverse phase HPLC followed by chiral SFC to yield Example 4 (68 mg, 0.11 mmol, 9.1% yield), and Example 5 (65 mg, 0.10 mmol, 8.7% yield). SFC prep condition: Column/dimensions: Lux-cellulose (250×30) mm, 5μ; % $CO_2$: 60%, % Co-solvent: 40% of 4M methanolic ammonia in MeOH. Total flow: 120.0 g/min, back pressure: 100 bar, temperature: 30° C., UV: 220 nm; Retention time: peak 1=4.6 min and peak 2=9.7 min. Enantiomer 1: MS(ESI) m/z: 618.2 [M+H]*. $^1$H NMR (400 MHz, DMSO-$d_6$) δ=9.01 (br d, J=8.6 Hz, 1H), 7.93-7.81 (m, 2H), 7.70 (dd, J=6.8, 2.0 Hz, 1H), 7.65 (dd, J=7.3, 2.0 Hz, 1H), 7.34 (t, J=73.6 Hz, 1H), 7.27 (m, 2H), 6.76 (d, J=10.8 Hz, 2H), 6.37 (t, J=7.1 Hz, 1H), 5.16-5.04 (m, 1H), 4.45 (dd, J=13.1, 2.8 Hz, 1H), 4.39-4.27 (m, 1H), 4.17-4.06 (m, 1H), 4.06-3.98 (m, 1H), 3.97-3.88 (m, 1H), 3.88-3.80 (m, 1H), 3.76 (s, 3H), 3.35 (br s, 1H). Enantiomer 2: MS(ESI) m/z: 618.2 $[M+H]^+$. $^1$H NMR (400 MHz, DMSO-$d_6$) δ=9.02 (d, J=8.8 Hz, 1H), 7.93-7.83 (m, 2H), 7.69 (dd, J=6.7, 2.1 Hz, 1H), 7.64 (dd, J=7.3, 2.1 Hz, 1H), 7.34 (t, J=73.6 Hz, 1H), 7.28 (d, J=8.8 Hz, 2H), 6.77 (d, J=10.8 Hz, 2H), 6.37 (t, J=7.0 Hz, 1H), 5.08 (dd, J=10.9, 8.9 Hz, 1H), 4.44 (dd, J=13.1, 3.1 Hz, 1H), 4.39-4.26 (m, 1H), 4.15-3.99 (m, 2H), 3.97-3.90 (m, 1H), 3.84 (dd, J=13.3, 9.4 Hz, 1H), 3.76 (s, 3H), 3.36 (br s, 1H).

The following Examples in Table 2 were made by using analogous procedures as shown in Examples 1-5 and/or modifications thereof known to one skilled in the art.

TABLE 2

| Ex | Structure | LCMS (M + H)+ | HPLC Method, RT (min.) & Purity | $^1$H NMR |
|---|---|---|---|---|
| 6 | 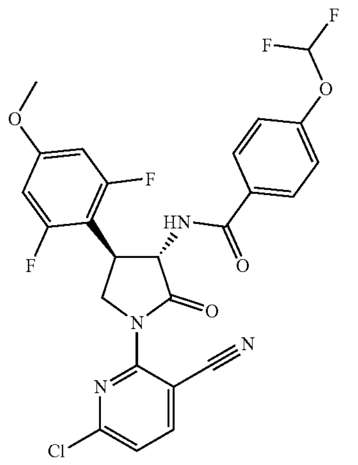 [SMILES: COc1cc(F)c([C@@H]2CN(c3nc(Cl)ccc3C#N)C(=O)[C@H]2NC(=O)c2ccc(OC(F)F)cc2)c(F)c1] | 549.1 | Method D, RT = 2.022 min, 96.2% | $^1$H NMR (400 MHz, DMSO-$d_6$) δ = 9.18 (d, J = 8.1 Hz, 1H), 8.50 (d, J = 8.3 Hz, 1H), 7.96-7.82 (m, 2H), 7.70 (d, J = 8.1 Hz, 1H), 7.58-7.13 (m, 3H), 6.81 (d, J = 10.8 Hz, 2H), 5.06 (m, 1H), 4.46-4.33 (m, 1H), 4.31-4.20 (m, 1H), 4.17-4.08 (m, 1H), 3.78 (s, 3H). |
| 7 | 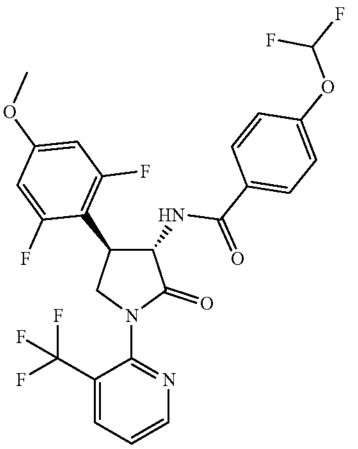 [SMILES: COc1cc(F)c([C@@H]2CN(c3ncccc3C(F)(F)F)C(=O)[C@H]2NC(=O)c2ccc(OC(F)F)cc2)c(F)c1] | 558.1 | Method D, RT = 1.907 min, 97.7% | 1H NMR (400 MHz, DMSO-d6) δ = 9.09 (d, J = 8.6 Hz, 1H), 8.94-8.85 (m, 1H), 8.39 (dd, J = 1.6, 7.9 Hz, 1H), 7.95-7.83 (m, 2H), 7.73 (dd, J = 5.3, 7.7 Hz, 1H), 7.57-7.09 (m, 3H), 6.80 (d, J = 10.8 Hz, 2H), 5.14 (m, 1H), 4.28 (m, 1H), 4.14 (m, J = 9.3 Hz, 1H), 4.02-3.94 (m, 1H), 3.77 (s, 3H). |

TABLE 2-continued

| Ex | Structure | LCMS (M + H)+ | HPLC Method, RT (min.) & Purity | $^1$H NMR |
|---|---|---|---|---|
| 8 | 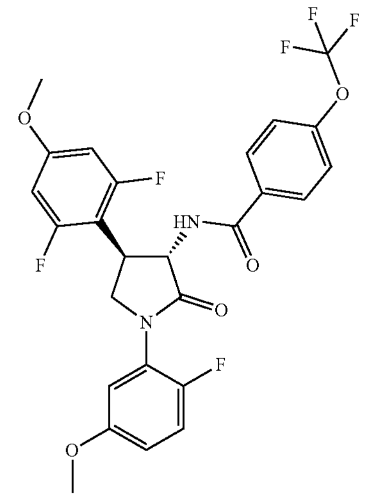 [SMILES: COc1cc(F)c([C@@H]2CN(c3cc(OC)ccc3F)C(=O)[C@H]2NC(=O)c2ccc(OC(F)(F)F)cc2)c(F)c1] | 555.1 | Method D, RT = 2.153 min, 97.9% | $^1$H NMR (400 MHz, DMSO-$d_6$) $\delta$ = 9.18 (d, J = 8.6 Hz, 1H), 8.05-7.87 (m, 2H), 7.50 (d, J = 8.1 Hz, 2H), 7.29 (m, 1H), 7.14 (m, 1H), 6.95 (m, 1H), 6.79 (d, J = 10.8 Hz, 2H), 5.13 (m, 1H), 4.24-4.13 (m, 1H), 4.05 (t, J = 8.8 Hz, 1H), 4.01-3.90 (m, 1H), 3.77 (s, 3H), 3.51 (s, 3H). |
| 9 | 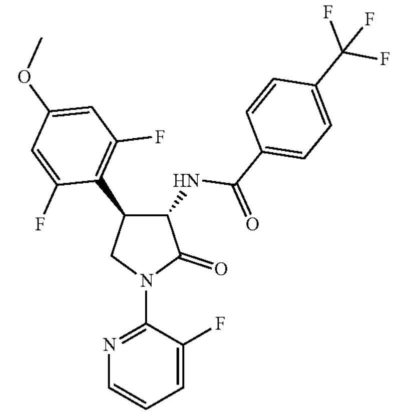 [SMILES: COc1cc(F)c([C@@H]2CN(c3ncccc3F)C(=O)[C@H]2NC(=O)c2ccc(C(F)(F)F)cc2)c(F)c1] | 510.2 | Method D, RT = 1.931 min, 97.7% | $^1$H NMR (400 MHz, DMSO-$d_6$) $\delta$ = 9.35 (d, J = 8.3 Hz, 1H), 8.38 (d, J = 4.6 Hz, 1H), 8.03 (d, J = 8.3 Hz, 2H), 7.96-7.82 (m, 3H), 7.49 (m, 1H), 6.81 (d, J = 11.0 Hz, 2H), 5.13 (t, J = 9.3 Hz, 1H), 4.33-4.16 (m, 2H), 4.15-4.03 (m, 1H), 3.78 (s, 3H). |
| 10 | 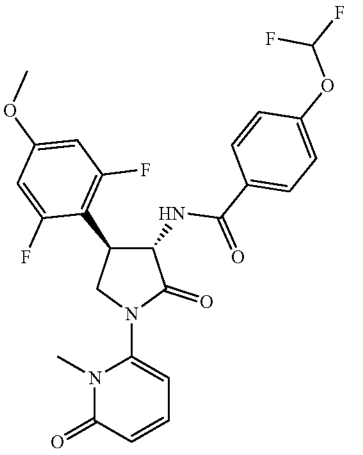 [SMILES: COc1cc(F)c([C@@H]2CN(c3cccc(=O)n3C)C(=O)[C@H]2NC(=O)c2ccc(OC(F)F)cc2)c(F)c1] | 520.1 | Method D, RT = 1.583 min, 90.7% | $^1$H NMR (400 MHz, DMSO-$d_6$) $\delta$ = 9.13 (d, J = 7.8 Hz, 1H), 7.89 (d, J = 8.8 Hz, 2H), 7.57-7.12 (m, 4H), 6.81 (d, J = 10.5 Hz, 2H), 6.46 (d, J = 9.3 Hz, 1H), 6.40 (m, 1H), 4.87-4.73 (m, 1H), 4.37-4.24 (m, 1H), 4.04 (t, J = 8.7 Hz, 1H), 3.99-3.92 (m, 1H), 3.78 (s, 3H), 3.45 (br s, 3H). |

TABLE 2-continued
| Ex | Structure | LCMS (M + H)+ | HPLC Method, RT (min.) & Purity | $^1$H NMR |
| --- | --- | --- | --- | --- |
| 11 | 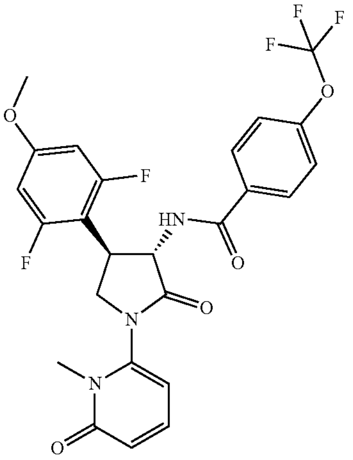 [SMILES: COc1cc(F)c([C@@H]2CN(c3cccc(=O)n3C)C(=O)[C@H]2NC(=O)c2ccc(OC(F)(F)F)cc2)c(F)c1] | 538.1 | Method D, RT = 1.759 min, 99.2% | $^1$H NMR (400 MHz, DMSO-$d_6$) δ = 9.23 (d, J = 8.1 Hz, 1H), 8.03-7.88 (m, 2H), 7.57-7.45 (m, 3H), 6.82 (d, J = 10.8 Hz, 2H), 6.50-6.44 (m, 1H), 6.40 (dd, J = 1.0, 7.1 Hz, 1H), 4.90-4.76 (m, 1H), 4.37-4.24 (m, 1H), 4.05 (t, J = 8.8 Hz, 1H), 4.00-3.92 (m, 1H), 3.78 (s, 3H), 3.44 (br s, 3H). |
| 12 | 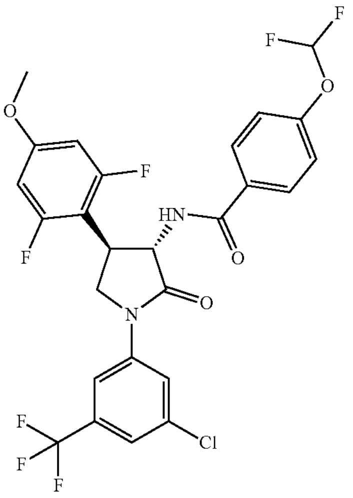 [SMILES: COc1cc(F)c([C@@H]2CN(c3cc(Cl)cc(C(F)(F)F)c3)C(=O)[C@H]2NC(=O)c2ccc(OC(F)F)cc2)c(F)c1] | 591 | Method D, RT = 2.381 min, 92.5% | $^1$H NMR (400 MHz, DMSO-$d_6$) δ = 9.11 (d, J = 8.1 Hz, 1H), 8.20 (s, 1H), 8.11 (s, 1H), 7.95-7.83 (m, 2H), 7.69 (s, 1H), 7.55-7.12 (m, 3H), 6.81 (d, J =10.8 Hz, 2H), 5.04 (m, 1H), 4.33-4.23 (m, 1H), 4.21-4.10 (m, 2H), 3.79 (s, 3H). |
| 13 | 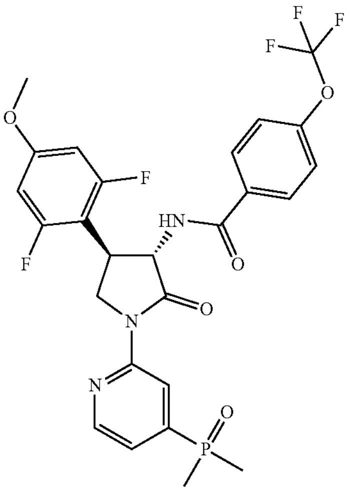 [SMILES: COc1cc(F)c([C@@H]2CN(c3cc(P(C)(C)=O)ccn3)C(=O)[C@H]2NC(=O)c2ccc(OC(F)(F)F)cc2)c(F)c1] | 584.2 | Method D, RT = 1.784 min, 98.7% | $^1$H NMR (400 MHz, DMSO-$d_6$) δ = 9.23 (d, J = 8.1 Hz, 1H), 8.72 (d, J = 12.7 Hz, 1H), 8.59 (m, 1H), 7.96 (d, J = 8.8 Hz, 2H), 7.62-7.42 (m, 3H), 6.80 (d, J = 10.5 Hz, 2H), 5.03 (m, 1H), 4.47 (t, J = 9.8 Hz, 1H), 4.18 (m, 1H), 4.09-3.99 (m, 1H), 3.79 (s, 3H), 1.75 (s, 3H), 1.70 (s, 3H). |

TABLE 2-continued
| Ex | Structure | LCMS (M + H)+ | HPLC Method, RT (min.) & Purity | $^1$H NMR |
|---|---|---|---|---|
| 14 | 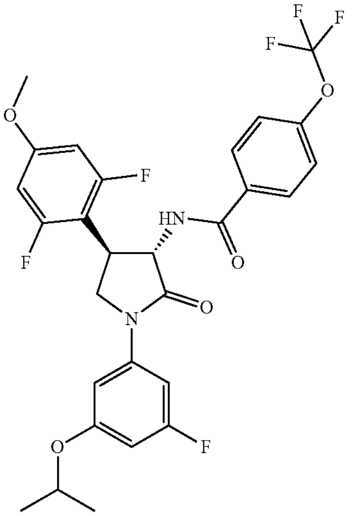 [SMILES: COc1cc(F)c([C@@H]2CN(c3cc(F)cc(OC(C)C)c3)C(=O)[C@H]2NC(=O)c2ccc(OC(F)(F)F)cc2)c(F)c1] | 583.2 | Method D, RT = 1.414 min, 99.8% | $^1$H NMR (400 MHz, DMSO-$d_6$) δ = 9.17 (d, J = 8.3 Hz, 1H), 7.95 (d, J = 8.8 Hz, 2H), 7.50 (d, J = 8.3 Hz, 2H), 7.25 (m, 1H), 7.17 (s, 1H), 6.80 (d, J = 10.5 Hz, 2H), 6.70-6.61 (m, 1H), 5.06 (m, 1H), 4.66 (m, 1H), 4.23-4.05 (m, 2H), 4.04-3.94 (m, 1H), 3.78 (s, 3H), 1.28 (d, J = 5.9 Hz, 6H). |
| 15 | 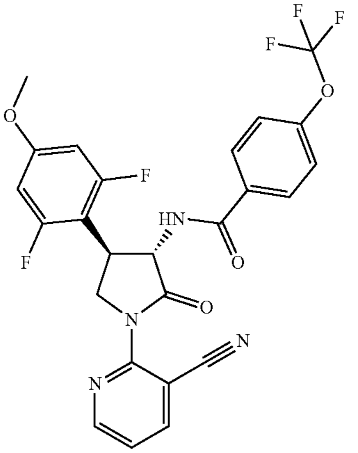 [SMILES: COc1cc(F)c([C@@H]2CN(c3ncccc3C#N)C(=O)[C@H]2NC(=O)c2ccc(OC(F)(F)F)cc2)c(F)c1] | 533.1 | Method D, RT = 1.951 min, 97.8% | $^1$H NMR (400 MHz, DMSO-$d_6$) δ = 9.27 (d, J = 8.1 Hz, 1H), 8.81 (m, 1H), 8.45 (m, 1H), 7.96 (d, J = 8.8 Hz, 2H), 7.57 (m, 1H), 7.51 (d, J = 8.3 Hz, 2H), 6.81 (d, J = 10.8 Hz, 2H), 5.11 (m, 1H), 4.49-4.37 (m, 1H), 4.26 (q, J = 9.5 Hz, 1H), 4.19-4.08 (m, 1H), 3.75 (s, 3H). |
| 16 | 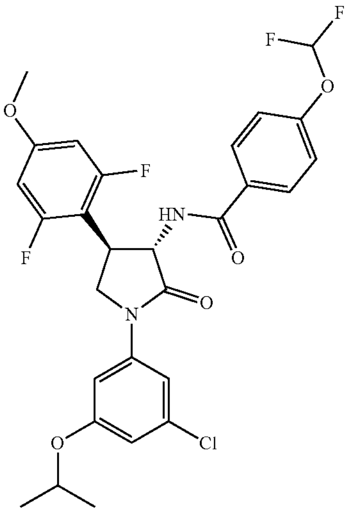 [SMILES: COc1cc(F)c([C@@H]2CN(c3cc(Cl)cc(OC(C)C)c3)C(=O)[C@H]2NC(=O)c2ccc(OC(F)F)cc2)c(F)c1] | 529.2 | Method D, RT = 2.370 min, 100.0% | $^1$H NMR (400 MHz, DMSO-$d_6$) δ = 9.08-9.02 (m, 1H), 7.89 (d, J = 8.8 Hz, 2H), 7.46 (m, 1H), 7.31-7.26 (m, 3H), 7.16 (s, 1H), 6.87-6.71 (m, 3H), 5.11-4.97 (m, 1H), 4.67 (m, 1H), 4.25-4.06 (m, 2H), 4.05-3.96 (m, 1H), 3.78 (s, 3H), 1.27 (d, J = 5.9 Hz, 6H). |

TABLE 2-continued
| Ex | Structure | LCMS (M + H)+ | HPLC Method, RT (min.) & Purity | $^1$H NMR |
|---|---|---|---|---|
| 17 | 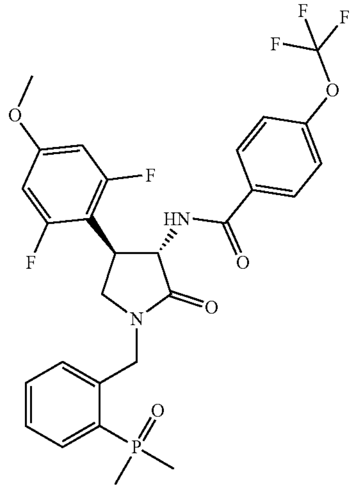 [SMILES: COc1cc(F)c([C@@H]2CN(Cc3ccccc3P(C)(C)=O)C(=O)[C@H]2NC(=O)c2ccc(OC(F)(F)F)cc2)c(F)c1] | 597.2 | Method D, RT = 1.763 min, 98.4% | $^1$H NMR (400 MHz, DMSO-$d_6$) δ = 9.10 (d, J = 8.3 Hz, 1H), 7.96 (d, J = 8.8 Hz, 2H), 7.71-7.60 (m, 2H), 7.52-7.42 (m, 4H), 6.75 (d, J = 10.8 Hz, 2H), 5.13-4.98 (m, 2H), 4.95-4.87 (m, 1H), 4.02 (m, 1H), 3.75 (s, 3H), 3.61 (m, 1H), 3.52-3.44 (m, 1H), 1.80 (s, 3H), 1.74 (s, 3H). |
| 18 | 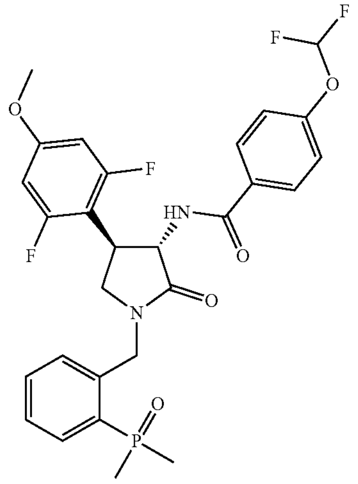 [SMILES: COc1cc(F)c([C@@H]2CN(Cc3ccccc3P(C)(C)=O)C(=O)[C@H]2NC(=O)c2ccc(OC(F)F)cc2)c(F)c1] | 579.2 | Method D, RT = 1.607 min, 100% | $^1$H NMR (400 MHz, DMSO-$d_6$) δ = 9.00 (d, J = 8.1 Hz, 1H), 7.90 (d, J = 8.8 Hz, 2H), 7.71-7.60 (m, 2H), 7.50-7.41 (m, 2H), 7.35 (s, 1H), 7.29 (d, J = 8.6 Hz, 2H), 6.75 (d, J = 10.5 Hz, 2H), 5.05 (m, 2H), 4.93-4.86 (m, 1H), 4.02 (m, 1H), 3.75 (s, 3H), 3.60 (m, 1H), 3.50-3.43 (m, 1H), 1.80 (s, 3H), 1.75 (s, 3H). |
| 19 | 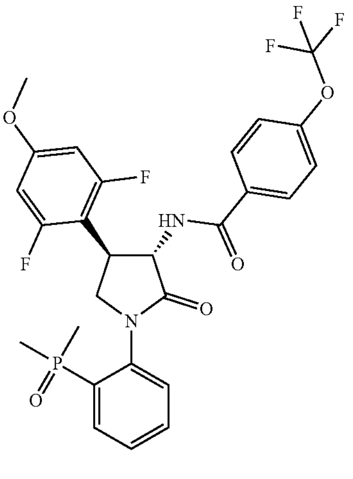 [SMILES: COc1cc(F)c([C@@H]2CN(c3ccccc3P(C)(C)=O)C(=O)[C@H]2NC(=O)c2ccc(OC(F)(F)F)cc2)c(F)c1] | 583.1 | Method D, RT = 1.723 min, 93.7% | $^1$H NMR (400MHz, DMSO-$d_6$) δ = 9.21-9.06 (m, 1H), 7.95 (d, J = 8.6 Hz, 2H), 7.89-7.79 (m, 1H), 7.74-7.66 (m, 1H), 7.60-7.52 (m, 1H), 7.52-7.44 (m, 3H), 6.85-6.72 (m, 2H), 5.12-4.90 (m, 1H), 4.31-4.16 (m, 1H), 4.13-3.89 (m, 2H), 3.77 (s, 3H), 1.86-1.58 (m, 6H). |

TABLE 2-continued
| Ex | Structure | LCMS (M + H)+ | HPLC Method, RT (min.) & Purity | $^1$H NMR |
|---|---|---|---|---|
| 20 | 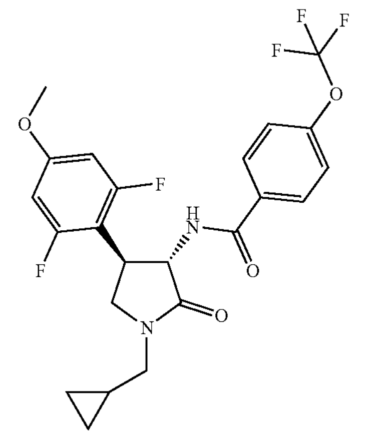 [SMILES: COc1cc(F)c([C@@H]2CN(CC3CC3)C(=O)[C@H]2NC(=O)c2ccc(OC(F)(F)F)cc2)c(F)c1] | 485.1 | Method D, RT = 1.965 min, 100% | $^1$H NMR (400 MHz, DMSO-$d_6$) δ = 9.01 (d, J = 8.6 Hz, 1H), 7.93 (d, J = 8.8 Hz, 2H), 7.48 (d, J = 8.3 Hz, 2H), 6.78 (s, 1H), 6.75 (s, 1H), 4.96-4.89 (m, 1H), 3.93 (m, 1H), 3.77 (s, 3H), 3.76-3.72 (m, 1H), 3.64-3.56 (m, 1H), 3.31-3.25 (m, 1H), 3.07 (m, 1H), 1.02-0.89 (m, 1H), 0.51 (d, J = 8.1 Hz, 2H), 0.30-0.20 (m, 2H). |
| 21 | 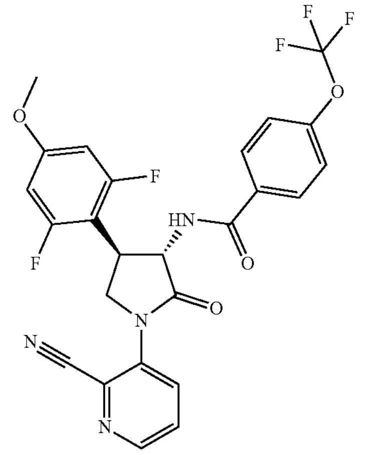 [SMILES: COc1cc(F)c([C@@H]2CN(c3cccnc3C#N)C(=O)[C@H]2NC(=O)c2ccc(OC(F)(F)F)cc2)c(F)c1] | 533.1 | Method D, RT = 1.897 min, 96.7% | $^1$H NMR (400 MHz, DMSO-$d_6$) δ = 9.25 (d, J = 8.3 Hz, 1H), 8.72 (m, 1H), 8.25 (m, 1H), 8.02-7.93 (m, 2H), 7.90 (m, 1H), 7.51 (d, J = 8.3 Hz, 2H), 6.82 (d, J = 10.8 Hz, 2H), 5.13 (m, 1H), 4.36-4.22 (m, 2H), 4.17-4.07 (m, 1H), 3.78 (s, 3H). |
| 22 | 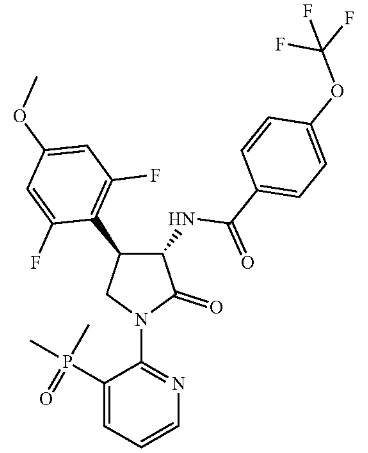 [SMILES: COc1cc(F)c([C@@H]2CN(c3ncccc3P(C)(C)=O)C(=O)[C@H]2NC(=O)c2ccc(OC(F)(F)F)cc2)c(F)c1] | 584.1 | Method D, RT = 1.620 min, 93.1% | $^1$H NMR (400 MHz, DMSO-$d_6$) δ = 9.16 (d, J = 8.1 Hz, 1H), 8.79-8.70 (m, 1H), 8.33-8.31 (m, 1H), 7.95 (d, J = 8.8 Hz, 2H), 7.61 (m, 1H), 7.59-7.50 (m, 2H), 6.79 (d, J = 10.8 Hz, 2H), 5.10-4.94 (m, 1H), 4.33-4.23 (m, 1H), 4.15-4.08 (m, 1H), 4.06-3.97 (m, 1H), 3.78 (s, 3H), 1.91-1.68 (m, 6H). |

TABLE 2-continued
| Ex | Structure | LCMS (M + H)+ | HPLC Method, RT (min.) & Purity | $^1$H NMR |
|---|---|---|---|---|
| 23 | 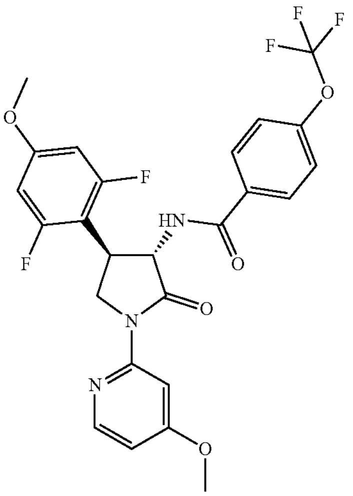 [SMILES: COc1ccnc(N2C[C@@H](c3c(F)cc(OC)cc3F)[C@H](NC(=O)c3ccc(OC(F)(F)F)cc3)C2=O)c1] | 538.1 | Method D, RT = 2.065 min, 94.0% | $^1$H NMR (400 MHz, DMSO-$d_6$) δ = 9.19 (d, J = 8.3 Hz, 1H), 8.25 (d, J = 5.9 Hz, 1H), 8.01-7.81 (m, 3H), 7.51 (d, J = 8.3 Hz, 2H), 6.85 (m, 1H), 6.79 (d, J = 10.8 Hz, 2H), 5.08 (m, 1H), 4.44 (m, 1H), 4.12 (m, 1H), 4.03-3.94 (m, 1H), 3.85 (s, 3H), 3.78 (s, 3H). |
| 24 | 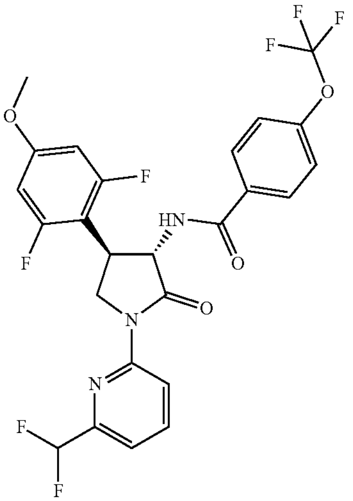 [SMILES: COc1cc(F)c([C@@H]2CN(c3cccc(C(F)F)n3)C(=O)[C@H]2NC(=O)c2ccc(OC(F)(F)F)cc2)c(F)c1] | 558.1 | Method D, RT = 2.223 min, 92.5% | $^1$H NMR (400 MHz, DMSO-$d_6$) δ = 9.23 (d, J = 8.1 Hz, 1H), 8.50 (d, J = 8.3 Hz, 1H), 8.09 (m, 1H), 7.96 (d, J = 8.6 Hz, 2H), 7.54-7.48 (m, 3H), 6.9 (s, 1 H), 6.82-6.74 (m, 2H), 5.11 (m, 1H), 4.46 (m, 1H), 4.17 (m, 1H), 4.06-3.96 (m, 1H), 3.78 (s, 3H). |
| 25 | 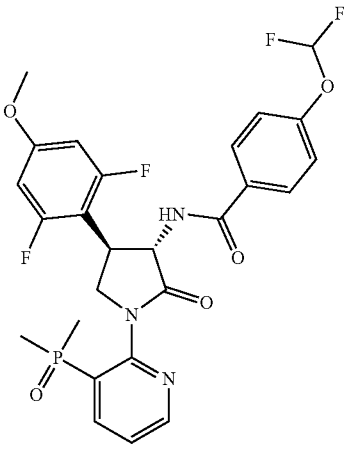 [SMILES: COc1cc(F)c([C@@H]2CN(c3ncccc3P(C)(C)=O)C(=O)[C@H]2NC(=O)c2ccc(OC(F)F)cc2)c(F)c1] | 566.2 | Method D, RT = 1.594 min, 100% | $^1$H NMR (400 MHz, DMSO-$d_6$) δ = 9.06 (d, J = 7.8 Hz, 1H), 8.82-8.68 (m, 1H), 8.41-8.28 (m, 1H), 7.89 (d, J = 8.8 Hz, 2H), 7.61 (m, 1H), 7.54-7.07 (m, 3H), 6.87-6.71 (m, 2H), 5.08-4.91 (m, 1H), 4.38-4.23 (m, 1H), 4.11 (m, 1H), 4.06-3.94 (m, 1H), 3.78 (s, 3H), 1.86-1.72 (m, 6H). |

TABLE 2-continued

| Ex | Structure | LCMS (M + H)+ | HPLC Method, RT (min.) & Purity | $^1$H NMR |
|---|---|---|---|---|
| 26 | 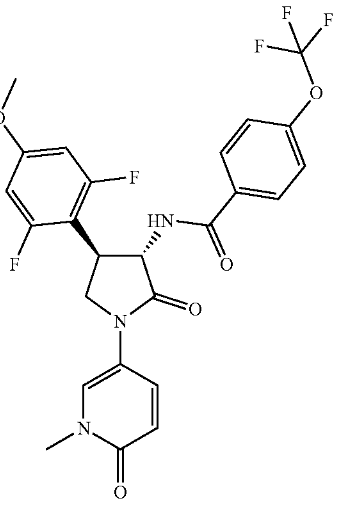 | 538.1 | Method D, RT = 1.677 min, 100% | $^1$H NMR (400 MHz, DMSO-$d_6$) δ = 9.13 (d, J = 8.3 Hz, 1H), 8.01 (d, J = 2.9 Hz, 1H), 7.94 (d, J = 8.8 Hz, 2H), 7.87 (m, 1H), 7.50 (d, J = 8.6 Hz, 2H), 6.80 (d, J = 10.8 Hz, 2H), 6.46 (d, J = 9.8 Hz, 1H), 5.08-4.91 (m, 1H), 4.12 (m, 1H), 4.00 (m, 1H), 3.94-3.87 (m, 1H), 3.78 (s, 3H), 3.45 (s, 3H). |
| 27 | 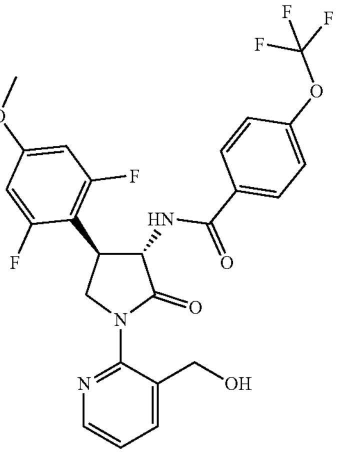 | 538.1 | Method D, RT = 1.874 min, 93.8% | $^1$H NMR (400 MHz, DMSO-$d_6$) δ = 9.20 (d, J = 8.3 Hz, 1H), 8.19 (d, J = 8.6 Hz, 1H), 7.96 (d, J = 8.8 Hz, 2H), 7.88 (m, 1H), 7.51 (d, J = 8.3 Hz, 2H), 7.29 (d, J = 7.3 Hz, 1H), 6.80 (d, J = 10.8 Hz, 2H), 5.40 (m, 1H), 5.10 (m, 1H), 4.52 (d, J = 5.9 Hz, 2H), 4.44 (m, 1H), 4.12 (q, J = 9.9 Hz, 1H), 4.01-3.98 (m, 1H), 3.78 (s, 3H). |
| 28 | 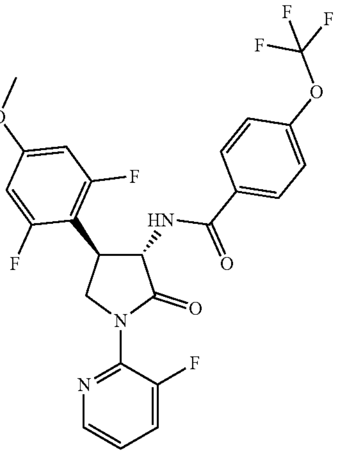 | 526.1 | Method D, RT = 1.926 min, 97.9% | $^1$H NMR (400 MHz, DMSO-$d_6$) δ = 9.22 (d, J = 8.3 Hz, 1H), 8.38 (d, J = 4.4 Hz, 1H), 8.03-7.78 (m, 3H), 7.57-7.39 (m, 3H), 6.80 (d, J = 10.8 Hz, 2H), 5.11 (m, 1H), 4.32-4.17 (m, 2H), 4.15-4.06 (m, 1H), 3.78 (s, 3H). |

TABLE 2-continued
| Ex | Structure | LCMS (M + H)+ | HPLC Method, RT (min.) & Purity | $^1$H NMR |
|---|---|---|---|---|
| 29 | 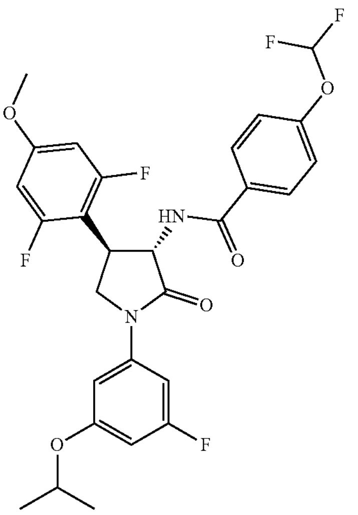 [SMILES: COc1cc(F)c([C@@H]2CN(c3cc(F)cc(OC(C)C)c3)C(=O)[C@H]2NC(=O)c2ccc(OC(F)F)cc2)c(F)c1] | 565.2 | Method D, RT = 2.289 min, 93.5% | $^1$H NMR (400 MHz, DMSO-$d_6$) δ = 9.07 (d, J = 8.3 Hz, 1H), 7.89 (d, J = 8.8 Hz, 2H), 7.55-7.10 (m, 5H), 6.80 (d, J = 10.8 Hz, 2H), 6.69-6.60 (m, 1H), 5.05 (m, 1H), 4.66 (m, 1H), 4.24-4.04 (m, 2H), 4.02-3.92 (m, 1H), 3.78 (s, 3H), 1.28 (d, J = 5.9 Hz, 6H). |
| 30 | 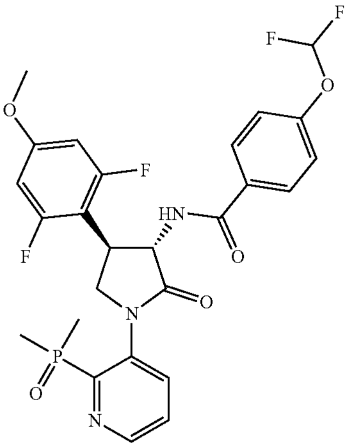 [SMILES: COc1cc(F)c([C@@H]2CN(c3ccccc3P(C)(C)=O)C(=O)[C@H]2NC(=O)c2ccc(OC(F)F)cc2)c(F)c1] # | 566.2 | Method D, RT = 1.529 min, 89.8% | $^1$H NMR (400 MHz, DMSO-$d_6$) δ = 9.02 (d, J = 8.3 Hz, 1H), 8.76 (d, J = 4.4 Hz, 1H), 8.01-7.94 (m, 1H), 7.92-7.87 (m, 2H), 7.74-7.67 (m, 1H), 7.31-7.21 (m, 3H), 6.79-6.71 (m, 2H), 5.14 (dd, J = 8.7, 10.6 Hz, 1H), 4.27-4.18 (m, 1H), 4.12-4.00 (m, 2H), 3.77 (s, 3H), 1.70-1.63 (m, 6H). |
| 31 | 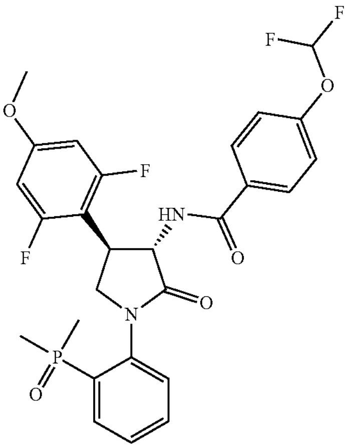 | 565.1 | Method D, RT = 1.604 min, 95.1% | $^1$H NMR (400 MHz, DMSO-$d_6$) δ = 9.09-8.98 (m, 1H), 7.94-7.77 (m, 3H), 7.70 (t, J = 7.8 Hz, 1H), 7.61-7.52 (m, 1H), 7.46 (dd, J = 3.4, 7.8 Hz, 1H), 7.35 (s, 1H), 7.31-7.15 (m, 3H), 6.82-6.71 (m, 1H), 5.09-4.94 (m, 1H), 4.29-4.18 (m, 1H), 4.12-3.89 (m, 2H), 3.77 (s, 3H), 1.83-1.68 (m, 6H). |

TABLE 2-continued
| Ex | Structure | LCMS (M + H)+ | HPLC Method, RT (min.) & Purity | $^1H$ NMR |
|---|---|---|---|---|
| 32 | 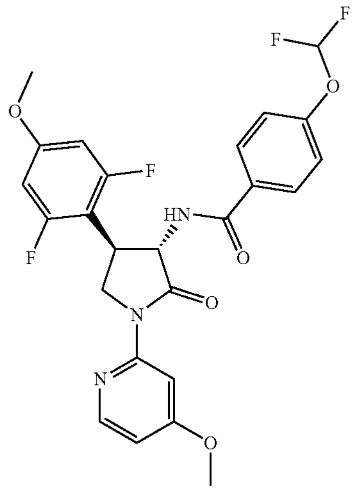 [SMILES: COc1ccnc(N2C[C@@H](c3c(F)cc(OC)cc3F)[C@H](NC(=O)c3ccc(OC(F)F)cc3)C2=O)c1] | 520.1 | Method D, RT = 1.886 min, 94.2% | $^1H$ NMR (400 MHz, DMSO-$d_6$) δ = 9.09 (d, J = 8.1 Hz, 1H), 8.25 (d, J = 5.9 Hz, 1H), 7.96 (d, J = 2.2 Hz, 1H), 7.92-7.86 (m, 2H), 7.36 (s, 1H), 7.29 (d, J = 8.8 Hz, 2H), 6.85 (m, 1H), 6.79 (d, J = 10.5 Hz, 2H), 5.06 (dd, J = 8.1, 11.0 Hz, 1H), 4.47-4.40 (m, 1H), 4.17-4.08 (m, 1H), 4.03-3.94 (m, 1H), 3.86 (s, 3H), 3.78 (s, 3H). |
| 33 | 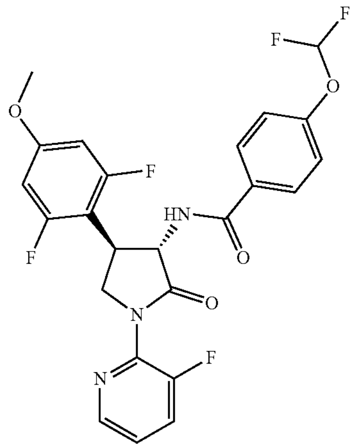 [SMILES: COc1cc(F)c([C@@H]2CN(c3ncccc3F)C(=O)[C@H]2NC(=O)c2ccc(OC(F)F)cc2)c(F)c1] | 508.1 | Method D, RT = 1.790 min, 90.9% | $^1H$ NMR (400 MHz, DMSO-$d_6$) δ = 9.12 (d, J = 8.6 Hz, 1H), 8.38 (d, J = 4.6 Hz, 1H), 7.96-7.84 (m, 3H), 7.56-7.13 (m, 4H), 6.80 (d, J = 10.8 Hz, 2H), 5.17-5.01 (m, 1H), 4.32-4.17 (m, 2H), 4.15-4.03 (m, 1H), 3.78 (s, 3H). |
| 34 | 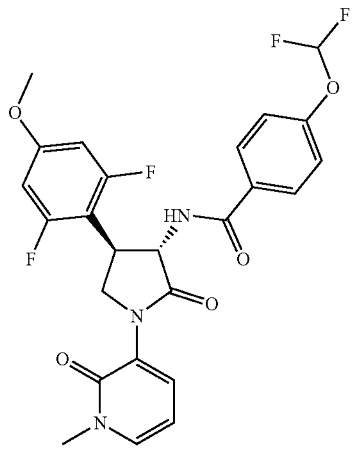 [SMILES: COc1cc(F)c([C@@H]2CN(c3cccn(C)c3=O)C(=O)[C@H]2NC(=O)c2ccc(OC(F)F)cc2)c(F)c1] | 520.2 | Method D, RT = 1.564 min, 99.4% | $^1H$ NMR (400 MHz, DMSO-d6) δ = 9.01 (d, J = 8.8 Hz, 1H), 7.96-7.82 (m, 2H), 7.76 (m, 1H), 7.59 (m, 1H), 7.55-7.11 (m, 3H), 6.77 (d, J = 10.8 Hz, 2H), 6.33 (m, 1H), 5.11 (m, 1H), 4.17-4.03 (m, 1H), 3.98 (m, 2H), 3.77 (s, 3H), 3.51 (s, 3H). |

TABLE 2-continued
| Ex | Structure | LCMS (M + H)+ | HPLC Method, RT (min.) & Purity | $^1$H NMR |
|---|---|---|---|---|
| 35 | 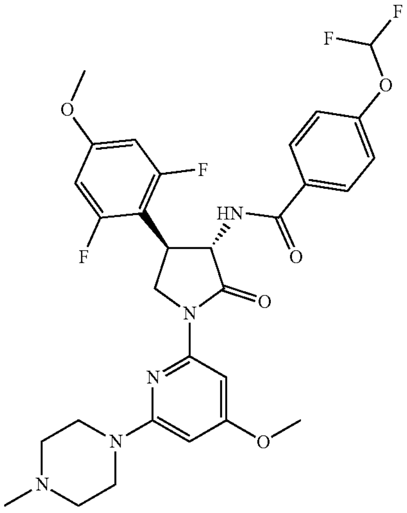 [SMILES: COc1cc(N2CCN(C)CC2)nc(N2C[C@@H](c3c(F)cc(OC)cc3F)[C@H](NC(=O)c3ccc(OC(F)F)cc3)C2=O)c1] | 618.3 | Method D, RT = 1.881 min, 94.8% | $^1$H NMR (400 MHz, DMSO-$d_6$) δ = 9.05 (d, J = 8.3 Hz, 1H), 7.89 (d, J = 8.8 Hz, 2H), 7.55-7.13 (m, 4H), 6.79 (d, J = 10.5 Hz, 2H), 6.14 (d, J = 1.5 Hz, 1H), 5.08 (m, 1H), 4.43 (m, 1H), 4.06 (m, 1H), 3.92-3.84 (m, 1H), 3.79 (d, J = 7.6 Hz, 6H), 3.48 (m, 4H), 2.49-2.35 (m, 4H), 2.25 (s, 3H). |
| 36 | 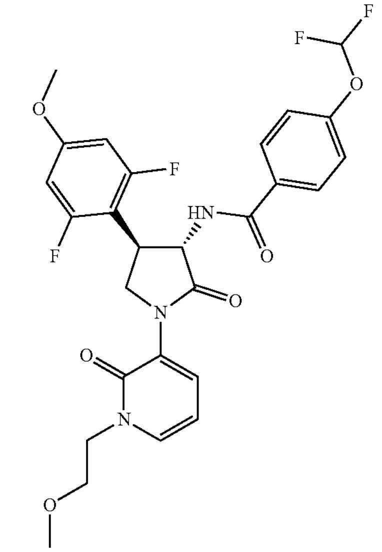 [SMILES: COCCn1cccc(N2C[C@@H](c3c(F)cc(OC)cc3F)[C@H](NC(=O)c3ccc(OC(F)F)cc3)C2=O)c1=O] | 564.2 | Method D, RT = 1.640 min, 97.8% | $^1$H NMR (400 MHz, DMSO-$d_6$) δ = 9.02 (d, J = 8.6 Hz, 1H), 7.93-7.83 (m, 2H), 7.67 (dd, J = 6.8, 2.0 Hz, 1H), 7.60 (dd, J = 7.3, 2.0 Hz, 1H), 7.34 (t, J = 73.6 Hz, 1H), 7.27 (d, J = 8.8 Hz, 2H), 6.77 (d, J = 10.8 Hz, 2H), 6.33 (t, J = 7.0 Hz, 1H), 5.12 (dd, J = 11.0, 8.6 Hz, 1H), 4.20-4.03 (m, 3H), 4.02-3.94 (m, 2H), 3.77 (s, 3H), 3.60 (t, J = 5.3 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 37 | 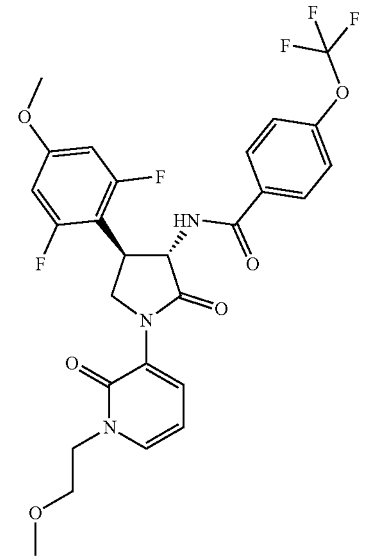 [SMILES: COCCn1cccc(N2C[C@@H](c3c(F)cc(OC)cc3F)[C@H](NC(=O)c3ccc(OC(F)(F)F)cc3)C2=O)c1=O] | 582.2 | Method D, RT = 1.808 min, 95.8% | $^1$H NMR (400 MHz, DMSO-$d_6$) δ = 9.13 (d, J = 8.6 Hz, 1H), 8.00-7.87 (m, 2H), 7.67 (dd, J = 6.8, 2.0 Hz, 1H), 7.60 (dd, J = 7.3 Hz, 2.0, 1H), 7.49 (d, J = 7.8 Hz, 2H), 6.78 (d, J = 10.8 Hz, 2H), 6.33 (t, J = 7.0 Hz, 1H), 5.13 (dd, J = 11.0, 8.6 Hz, 1H), 4.19-3.93 (m, 5H), 3.77 (s, 3H), 3.60 (t, J = 5.3 Hz, 2H), 3.25 (s, 3H). |
| 38 | 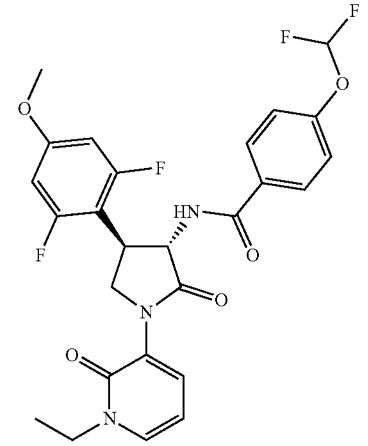 [SMILES: CCn1cccc(N2C[C@@H](c3c(F)cc(OC)cc3F)[C@H](NC(=O)c3ccc(OC(F)F)cc3)C2=O)c1=O] | 534.2 | Method D, RT = 1.651 min, 100% | $^1$H NMR (400 MHz, DMSO-$d_6$) δ = 9.02 (d, J = 8.6 Hz, 1H), 7.94-7.84 (m, 2H), 7.77 (dd, J = 6.8, 2.0 Hz, 1H), 7.58 (dd, J = 7.1, 2.0 Hz, 1H), 7.34 (t, J = 73.6 Hz, 1H), 7.27 (d, J = 8.6 Hz, 2H), 6.77 (d, J = 10.8 Hz, 2H), 6.35 (t, J = 7.0 Hz, 1H), 5.12 (dd, J = 11.0, 8.6 Hz, 1H), 4.16-4.04 (m, 1H), 4.02-3.92 (m, 4H), 3.77 (s, 3H), 1.25 (t, J = 7.1 Hz, 3H). |
| 39 | 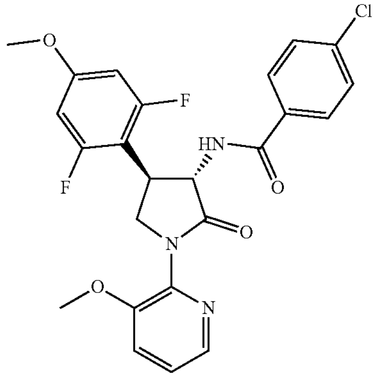 [SMILES: COc1cc(F)c([C@@H]2CN(c3ncccc3OC)C(=O)[C@H]2NC(=O)c2ccc(Cl)cc2)c(F)c1] | 488.1 | Method D, RT = 1.73 min, 99% | $^1$H NMR (400 MHz, DMSO-$d_6$) δ = 9.14 (d, J = 8.8 Hz, 1H), 8.10 (dd, J = 4.6, 1.2 Hz, 1H), 7.90-7.77 (m, 2H), 7.64 (dd, J = 8.4, 1.2 Hz, 1H), 7.61-7.53 (m, 2H), 7.44-7.41 (m, 1H), 6.79 (d, J = 10.8 Hz, 2H), 5.22 (dd, J = 11.1, 8.9 Hz, 1H), 4.23-4.11 (m, 1H), 4.05 (t, J = 8.9 Hz, 1H), 3.93-3.89 (m, 1H), 3.87 (s, 3H) 3.77 (s, 3H). |

TABLE 2-continued

| Ex | Structure | LCMS (M + H)+ | HPLC Method, RT (min.) & Purity | $^1$H NMR |
|---|---|---|---|---|
| 40 | 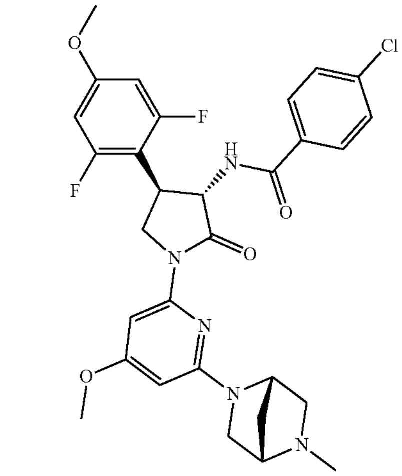 [SMILES: COc1cc(N2C[C@@H](c3c(F)cc(OC)cc3F)[C@H](NC(=O)c3ccc(Cl)cc3)C2=O)nc(N2C[C@@H]3C[C@H]2CN3C)c1] | 598.2 | Method D, RT = 1.68 min, 100% | $^1$H NMR (400 MHz, DMSO-$d_6$) δ = 9.11 (d, J = 8.3 Hz, 1H), 7.84-7.82 (m, 2H), 7.59-7.56 (m, 2H), 7.22 (d, J = 2.0 Hz, 1H), 6.79 (d, J =10.8 Hz, 2H), 5.80 (s, 1H), 5.11-5.06 (m, 1H), 4.59 (br s, 1H), 4.45 (t, J = 9.9 Hz, 1H), 4.08-3.98 (m, 1H), 3.90-3.81 (m, 2H), 3.78 (s, 3H), 3.77 (s, 3H), 3.45-3.38 (m, 2H), 3.25-3.22-3.19 (m, 1H), 2.82-2.76 (m, 1H), 2.24 (s, 3H), 1.83-1.79 (m, 1H), 1.71-1.63 (m, 1H). |
| 41 | 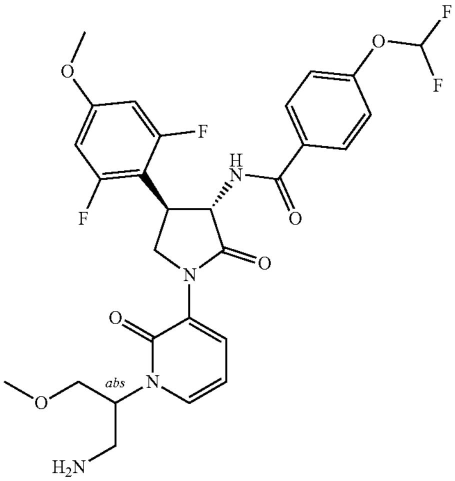 [SMILES: COCC(CN)n1cccc(N2C[C@@H](c3c(F)cc(OC)cc3F)[C@H](NC(=O)c3ccc(OC(F)F)cc3)C2=O)c1=O] | 593.3 | Method D, RT = 1.424 min, 100% | $^1$H NMR (400 MHz, DMSO-$d_6$) δ = 9.00 (d, J = 8.8 Hz, 1H), 7.96-7.81 (m, 2H), 7.68 (dd, J = 7.0, 1.8, Hz, 1H), 7.55 (dd, J = 7.2, 1.8 Hz, 1H), 7.34 (t, J = 73.6 Hz, 1H), 7.28 (d, J = 8.8 Hz, 2H), 6.76 (d, J = 10.8 Hz, 2H), 6.34 (t, J = 7.1 Hz, 1H), 5.10 (dd, J = 10.8, 8.6 Hz, 1H), 5.01-4.88 (m, 1H), 4.15-4.03 (m, 1H), 4.03-3.89 (m, 2H), 3.80-3.71 (m, 4H), 3.61 (dd, J = 10.5, 4.4 Hz, 1H), 3.34 (br s, 2H), 3.23 (s, 3H), 2.95-2.81 (m, 2H). |
| 42 | 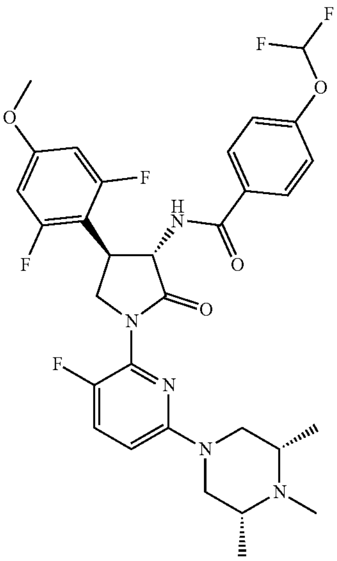 [SMILES: COc1cc(F)c([C@@H]2CN(c3nc(N4C[C@@H](C)N(C)[C@@H](C)C4)ccc3F)C(=O)[C@H]2NC(=O)c2ccc(OC(F)F)cc2)c(F)c1] | 634.2 | Method D, RT = 2.634 min, 99% | $^1$H NMR (400 MHz, DMSO-$d_6$) δ = 9.13-9.04 (m, 1H), 7.93-7.84 (m, 2H), 7.70-7.57 (m, 1H), 7.34 (t, J = 72 Hz, 1H), 7.29-7.27 (m, 2H), 6.89-6.74 (m, 3H), 5.16-5.07 (m, 1H), 4.26-4.15 (m, 2H), 4.06-3.93 (m, 3H), 3.76 (s, 3H), 2.56-2.47 (m, 2H), 2.17 (s, 3H), 2.16-2.10 (m, 2H), 1.12-1.03 (d, J = 6 Hz, 6H). |

TABLE 2-continued

| Ex | Structure | LCMS (M + H)+ | HPLC Method, RT (min.) & Purity | $^1$H NMR |
|---|---|---|---|---|
| 43 | 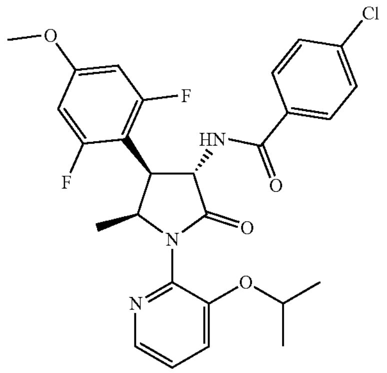 [SMILES: COc1cc(F)c([C@H]2[C@H](NC(=O)c3ccc(Cl)cc3)C(=O)N(c3ncccc3OC(C)C)[C@H]2C)c(F)c1] | 529.15 | Method D, RT = 1.97 min, 97% | $^1$H NMR (400 MHz, DMSO-$d_6$) δ = 8.96 (d, J = 8.6 Hz, 1H), 8.07 (dd, J = 4.6, 1.2 Hz, 1H), 7.90-7.79 (m, 2H), 7.61 (d, J = 7.3 Hz, 1 H), 7.57-7.49 (m, 2H), 7.37 (dd, J = 8.3, 4.6 Hz, 1H), 6.84-6.70 (m, 2H), 5.60 (dd, J = 11.5, 8.8 Hz, 1H), 4.74-4.68 (m, 1H), 4.54-4.44 (m, 1H), 4.40-4.35 (m, 1H), 3.77 (s, 3H), 1.28 (d, J = 6.0 Hz, 3H), 1.27 (d, J = 6.0 Hz, 3H), 0.90 (d, J = 6.6 Hz, 3H). |
| 44 | 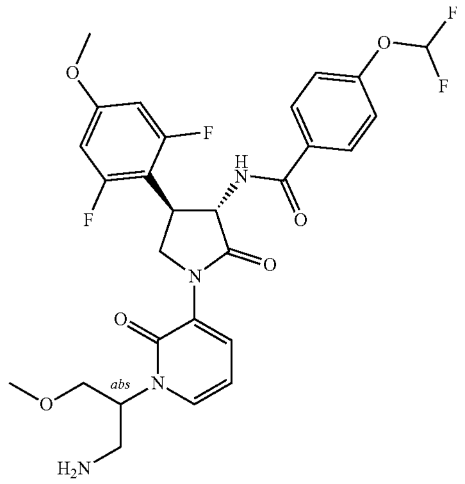 [SMILES: COCC(CN)n1cccc(N2C[C@@H](c3c(F)cc(OC)cc3F)[C@H](NC(=O)c3ccc(OC(F)F)cc3)C2=O)c1=O] | 593.3 | Method D, RT = 1.427 min, 100% | $^1$H NMR (400 MHz, DMSO-$d_6$) δ = 9.11 (d, J = 8.6 Hz, 1H), 7.95 (d, J = 8.8 Hz, 2H), 7.68 (dd, J = 7.0, 1.8 Hz, 1H), 7.56 (dd, J = 7.1, 1.8 Hz, 1H), 7.34 (t, J = 73.6 Hz, 1H), 7.28 (d, J = 8.8 Hz, 2H), 6.77 (d, J = 10.8 Hz, 2H), 6.34 (t, J = 7.1 Hz, 1H), 5.13 (dd, J = 10.8, 8.8 Hz, 1H), 5.02-4.90 (m, 1H), 4.15-3.88 (m, 3H), 3.81-3.70 (m, 4H), 3.61 (dd, J = 10.8, 4.4 Hz, 1H), 3.35-3.33 (br s, 2H), 3.20 (s, 3H), 2.96-2.84 (m, 2H). |
| 45 | 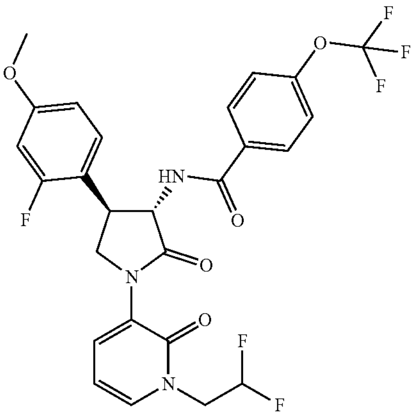 [SMILES: COc1ccc([C@@H]2CN(c3cccn(CC(F)F)c3=O)C(=O)[C@H]2NC(=O)c2ccc(OC(F)(F)F)cc2)c(F)c1] | 570.2 | Method D, RT = 1.84 min, 96.7% | $^1$H NMR (400 MHz, DMSO-$d_6$) δ = 9.06 (d, J = 8.8 Hz, 1H), 8.01-7.91 (m, 2H), 7.72 (dd, J = 7.0, 1.8 Hz, 1H), 7.66 (dd, J = 7.1, 1.8 Hz, 1H), 7.55-7.35 (m, 3H), 6.89-6.74 (m, 2H), 6.43-6.40 (m, 1H), 6.35 (t, J = 57.6 Hz, 1H), 5.14 (dd, J = 11.4, 8.7 Hz, 1H), 4.49-4.43 (m, 2H), 4.20-4.09 (m, 1H), 4.07-3.97 (m, 1H), 3.76 (s, 3H), 3.75-3.67 (m, 1H). |

TABLE 2-continued

| Ex | Structure | LCMS (M + H)+ | HPLC Method, RT (min.) & Purity | $^1$H NMR |
|---|---|---|---|---|
| 46 | 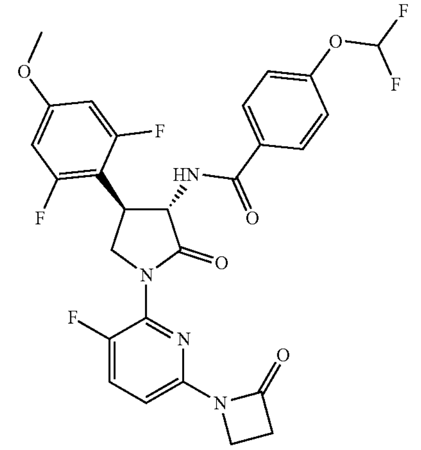 [SMILES: COc1cc(F)c([C@@H]2CN(c3nc(N4CCC4=O)ccc3F)C(=O)[C@H]2NC(=O)c2ccc(OC(F)F)cc2)c(F)c1] | 577.2 | Method D, RT = 1.862 min, 99% | $^1$H NMR (400 MHz, DMSO-d$_6$) δ = 9.12 (d, J = 8.3 Hz, 1H), 8.01-7.74 (m, 3H), 7.74-7.28 (m, 3H), 7.36 (t, J = 72 Hz, 1H), 6.81 (d, J = 10.8 Hz, 2H), 5.11 (m, 1H), 4.33-4.15 (m, 2H), 4.12-3.98 (m, 1H), 3.78 (s, 3H), 3.76-3.57 (m, 2H), 3.13 (t, J = 4.4 Hz, 2H). |
| 47 | 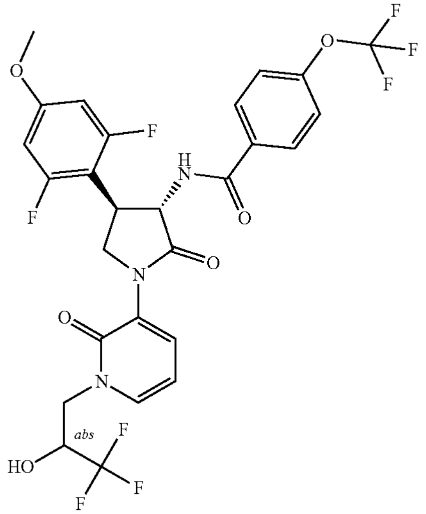 [SMILES: COc1cc(F)c([C@@H]2CN(c3cccn(CC(O)C(F)(F)F)c3=O)C(=O)[C@H]2NC(=O)c2ccc(OC(F)(F)F)cc2)c(F)c1] | 636.2 | Method D, RT = 1.904 min, 100% | $^1$H NMR (400 MHz, DMSO-d$_6$) δ = 9.18-9.04 (m, 1H), 7.99-7.86 (m, 2H), 7.70 (dd, J = 6.8, 2.0 Hz, 1H), 7.66 (dd, J = 7.3, 2.0 Hz, 1H), 7.53-7.39 (m, 2H), 6.77 (d, J = 10.8 Hz, 2H), 6.37 (t, J = 7.0 Hz, 1H), 5.16-5.02 (m, 1H), 4.45 (dd, J = 13.2, 2.9 Hz, 1H), 4.37-4.25 (m, 1H), 4.19-3.98 (m, 2H), 3.98-3.80 (m, 2H), 3.76 (s, 3H), 3.35-3.33 (brs, 1H). |
| 48 | 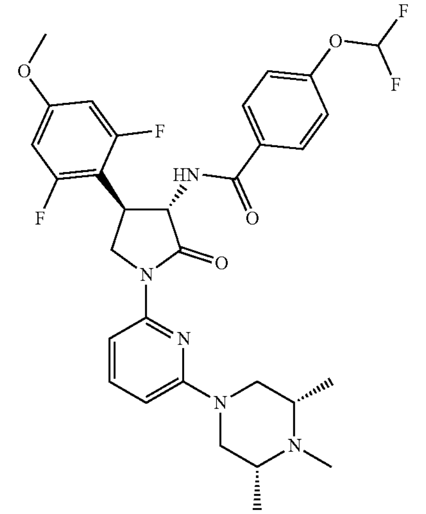 [SMILES: COc1cc(F)c([C@@H]2CN(c3cccc(N4C[C@@H](C)N(C)[C@@H](C)C4)n3)C(=O)[C@H]2NC(=O)c2ccc(OC(F)F)cc2)c(F)c1] | 616.3 | Method D, RT = 1.939 min, 99% | $^1$H NMR (400 MHz, DMSO-d$_6$) δ = 9.07 (d, J = 8.3 Hz, 1H), 7.94-7.82 (m, 2H), 7.64-7.56 (m, 2H), 7.36 (t, J = 72 Hz, 1H), 7.29-7.27 (m, 2H), 6.86-6.73 (m, 2H), 6.63 (dd, J = 6.1, 2.9 Hz, 1H), 5.07 (dd, J = 11.0, 9.0 Hz, 1H), 4.51-4.39 (m, 1H), 4.14-3.98 (m, 3H), 3.97-3.87 (m, 1H), 3.78 (s, 3H), 3.34-3.28 (m, 2H), 2.17 (s, 3H), 2.17-2.03 (m, 2H), 1.06 (d, J = 5.9 Hz, 6H). |

TABLE 2-continued

| Ex | Structure | LCMS (M + H)+ | HPLC Method, RT (min.) & Purity | $^1H$ NMR |
|---|---|---|---|---|
| 49 | 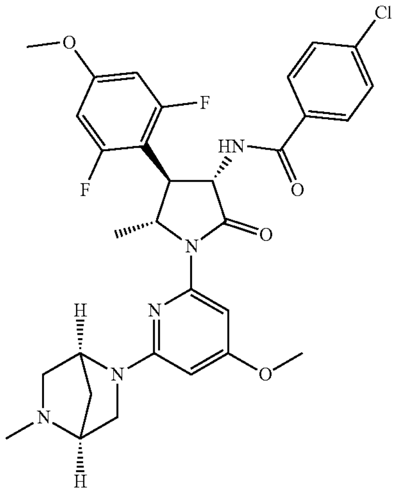 [SMILES: COc1cc(N2C[C@@H]3C[C@H]2CN3C)nc(N2C(=O)[C@@H](NC(=O)c3ccc(Cl)cc3)[C@H](c3c(F)cc(OC)cc3F)[C@H]2C)c1] | 612.3 | Method D, RT = 1.74 min, 100% | $^1H$ NMR (400 MHz, DMSO-$d_6$) δ = 9.11 (d, J = 8.6 Hz, 1H), 7.84 (d, J = 8.4 Hz, 2H), 7.57 (d, J = 8.4 Hz, 2H), 6.90-6.69 (m, 3H), 5.85 (s, 1H), 4.99 (dd, J = 10.8, 8.3 Hz, 1H), 4.61-4.38 (m, 2H), 3.79 (s, 3H), 3.78 (s, 3H), 3.64-3.61 (m, 2H), 3.45-3.42 (m, 1H), 3.23-3.21 (m, 1H), 2.80 (dd, J = 9.3, 2.0 Hz, 1H), 2.42-2.44 (m, 1H), 2.25 (s, 3H), 1.92-1.77 (m, 1H), 1.71-1.68 (m, 1H), 1.36 (d, J = 5.9 Hz, 3H). |
| 50 | 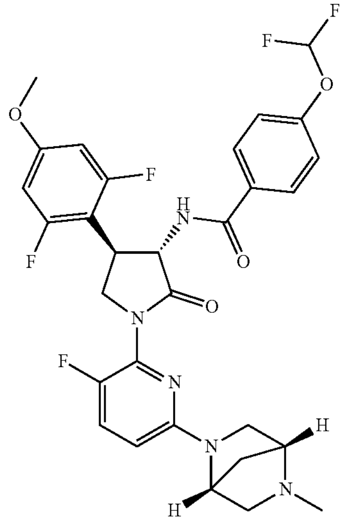 [SMILES: COc1cc(F)c([C@@H]2CN(c3nc(N4C[C@H]5C[C@@H]4CN5C)ccc3F)C(=O)[C@H]2NC(=O)c2ccc(OC(F)F)cc2)c(F)c1] | 618.2 | Method D, RT = 2.407 min, 96% | $^1H$ NMR (400 MHz, DMSO-$d_6$) δ = 9.10-9.03 (m, 1H), 7.93-7.86 (m, 2H), 7.59-7.56 (m, 1H), 7.35 (t, J = 72 Hz, 1H), 7.29-7.27 (m, 2H), 6.84-6.74 (m, 2H), 6.51-6.43 (m, 1H), 5.17-5.07 (m, 1H), 4.55-4.48 (m, 1H), 4.20-4.11 (m, 2H), 4.02-3.93 (m, 1H), 3.77 (s, 3H), 3.44-3.38 (m, 3H), 2.83-2.76 (m, 1H), 2.47-2.39 (m, 1H), 2.25 (s, 3H), 1.87-1.82 (m, 1H), 1.74-1.69 (m, 1H). |
| 51 | 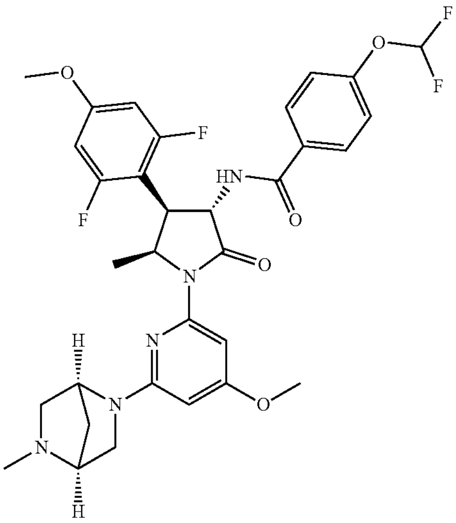 [SMILES: COc1cc(N2C[C@@H]3C[C@H]2CN3C)nc(N2C(=O)[C@@H](NC(=O)c3ccc(OC(F)F)cc3)[C@H](c3c(F)cc(OC)cc3F)[C@@H]2C)c1] | 644.3 | Method D, RT = 1.69 min, 100% | $^1H$ NMR (400 MHz, DMSO-$d_6$) δ = 8.86 (d, J = 8.6 Hz, 1H), 7.93-7.82 (m, 2H), 7.35 (t, J = 73.6 Hz, 1H), 7.27-7.25 (m, 3H), 6.87-6.70 (m, 2H), 5.78 (d, J = 1.7 Hz, 1H), 5.65 (dd, J = 12.8, 8.4 Hz, 1H), 4.94-4.83 (m, 1H), 4.58-4.53 (m, 1H), 4.26-4.21 (m, 1H), 3.77 (s, 3H), 3.76 (s, 3H), 3.43-3.37 (m, 1H), 3.40-3.36 (m, 1H), 3.26-3.24 (m, 1H), 2.79-2.76 (m, 1H), 2.46-2.37 (m, 1H), 2.27 (s, 3H), 1.82-1.7 (m, 1H), 1.75-1.64 (m, 1H), 1.18 (d, J = 6.4 Hz, 3H). |

TABLE 2-continued
| Ex | Structure | LCMS (M + H)+ | HPLC Method, RT (min.) & Purity | $^{1}$H NMR |
|---|---|---|---|---|
| 52 | 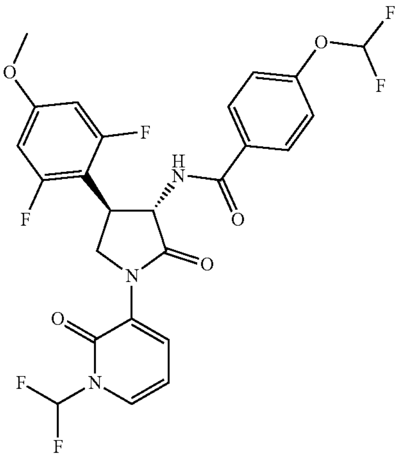 [SMILES: COc1cc(F)c([C@@H]2CN(c3cccn(C(F)F)c3=O)C(=O)[C@H]2NC(=O)c2ccc(OC(F)F)cc2)c(F)c1] | 556.2 | Method D, RT = 1.764 min, 100% | $^{1}$H NMR (400 MHz, DMSO-$d_6$) δ = 9.02 (d, J = 8.6 Hz, 1H), 7.92 (t, J = 59.2 Hz, 1H) 7.92 (t, J = 67.2 Hz, 1H), 7.89-7.74 (m, 3H), 7.34 (t, J = 73.6 Hz, 1H) 7.28 (d, J = 8.4 Hz, 2H), 6.78 (d, J = 10.8 Hz, 2H), 6.56 (t, J = 7.2 Hz, 1H), 5.08 (dd, J = 11.0, 8.6 Hz, 1H), 4.20-4.07 (m, 1H), 4.06-3.94 (m, 2H), 3.77 (s, 3H). |
| 53 | 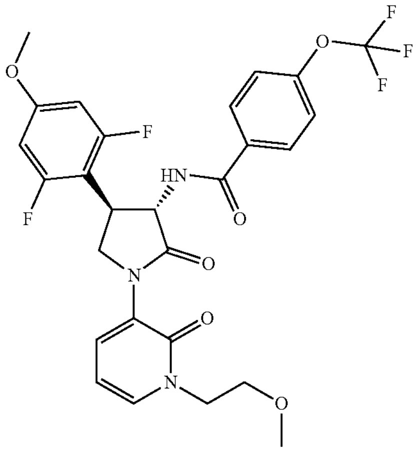 [SMILES: COCCn1cccc(N2C[C@@H](c3c(F)cc(OC)cc3F)[C@H](NC(=O)c3ccc(OC(F)(F)F)cc3)C2=O)c1=O] | 564.3 | Method D, RT = 1.70 min, 94.9% | $^{1}$H NMR (400 MHz, DMSO-$d_6$) δ = 8.64 (d, J = 8.0 Hz, 1H), 7.81-7.55 (m, 4H), 7.50-7.23 (m, 3H), 6.79-6.57 (m, 2H), 6.36 (t, J = 7.0 Hz, 1H), 5.24-5.11 (m, 1H), 4.23-4.04 (m, 5H), 3.72 (s, 3H), 3.66-3.57 (m, 2H), 3.24 (s, 3H). |
| 54 | 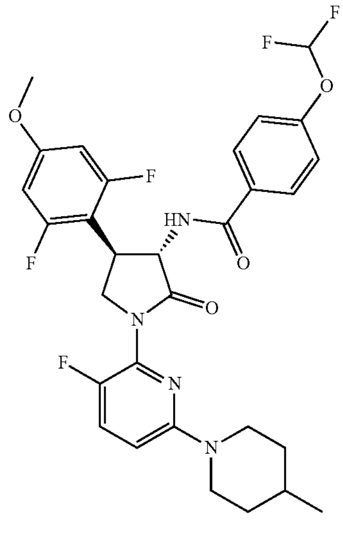 [SMILES: COc1cc(F)c([C@@H]2CN(c3nc(N4CCC(C)CC4)ccc3F)C(=O)[C@H]2NC(=O)c2ccc(OC(F)F)cc2)c(F)c1] | 606.2 | Method D, RT = 1.805 min, 97% | $^{1}$H NMR (400 MHz, DMSO-$d_6$) δ = 9.07 (br d, J = 8.1 Hz, 1H), 7.93-7.82 (m, 2H), 7.63 (t, J = 9.3 Hz, 1H), 7.34 (t, J = 72 Hz, 1H), 7.29-7.6 (m, 2H), 6.86-6.73 (m, 3H), 5.12 (t, J = 9.4 Hz, 1H), 4.25-4.13 (m, 2H), 4.03-3.94 (m, 1H), 3.78 (s, 3H), 3.48-3.42 (m, 4H), 2.48-2.36 (m, 4H), 2.25 (s, 3H). |

TABLE 2-continued

| Ex | Structure | LCMS (M + H)+ | HPLC Method, RT (min.) & Purity | $^1$H NMR |
|---|---|---|---|---|
| 55 | 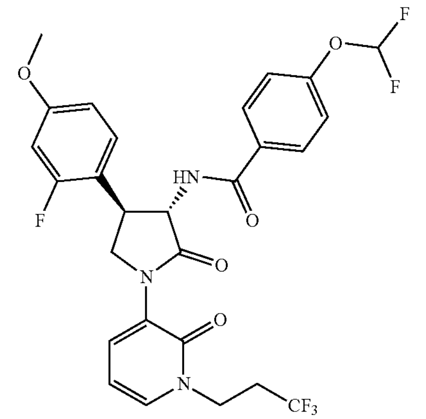 | 584.2 | Method D, RT = 1.81 min, 100% | $^1$H NMR (400 MHz, DMSO-$d_6$) δ = 8.95 (d, J = 8.8 Hz, 1H), 7.96-7.85 (m, 2H), 7.77 (dd, J = 6.8, 2.0 Hz, 1H), 7.63 (dd, J = 7.3, 2.0 Hz, 1H), 7.51 (d, J = 8.1 Hz, 1H), 7.35 (t, J = 72.0 Hz, 1H), 7.32-7.23 (m, 2H), 6.86-6.74 (m, 2H), 6.38 (t, J = 7.1 Hz, 1H), 5.13 (dd, J = 11.5, 8.8 Hz, 1H), 4.30-4.09 (m, 3H), 4.04-3.94 (m, 1H), 3.74 (s, 3H), 3.73-3.64 (m, 1H), 2.84-2.70 (m, 2H). |
| 56 | 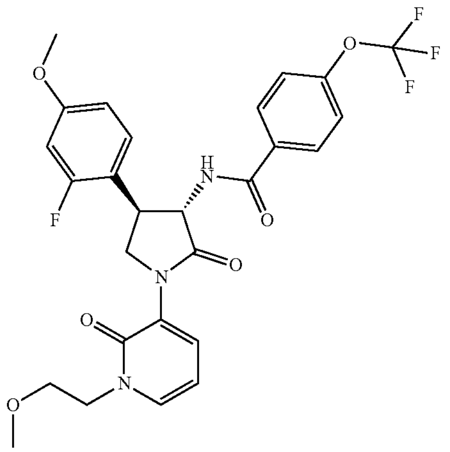 [SMILES: COCCn1cccc(N2C[C@@H](c3ccc(OC)cc3F)[C@H](NC(=O)c3ccc(OC(F)(F)F)cc3)C2=O)c1=O] | 564.2 | Method D, RT = 1.75 min, 98.9% | $^1$H NMR (400 MHz, DMSO-$d_6$) δ = 9.06 (d, J = 8.8 Hz, 1H), 8.04-7.88 (m, 2H), 7.65 (dd, J = 6.7, 2.1 Hz, 1H), 7.59 (dd, J = 7.1, 2.0 Hz, 1H), 7.55-7.37 (m, 3H), 6.90-6.70 (m, 2H), 6.32 (t, J = 7.0 Hz, 1H), 5.14 (dd, J = 11.2, 8.8 Hz, 1H), 4.22-4.06 (m, 3H), 4.05-3.94 (m, 1H), 3.74 (s, 3H), 3.72-3.65 (m, 1H), 3.60 (t, J = 5.3 Hz, 2H), 3.25 (s, 3H). |
| 57 | 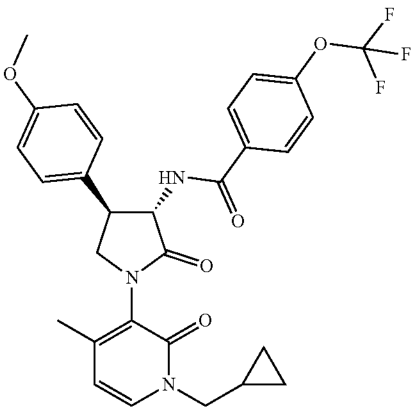 [SMILES: COc1ccc([C@@H]2CN(c3c(C)ccn(CC4CC4)c3=O)C(=O)[C@H]2NC(=O)c2ccc(OC(F)(F)F)cc2)cc1] | 556.3 | Method D, RT = 1.881 min, 100% | $^1$H NMR (400 MHz, DMSO-$d_6$) δ = 9.05 (t, J = 8.6 Hz, 1H), 8.06-7.91 (m, 2H), 7.75-7.60 (m, 1H), 7.57-7.42 (m, 2H), 7.42-7.22 (m, 2H), 6.91 (dd, J = 13.8, 8.7 Hz, 2H), 6.22 (d, J = 6.8 Hz, 1H), 5.28-4.66 (m, 1H), 4.14-3.78 (2s, 3H), 3.77-3.64 (m, 5H), 2.21-2.07 (2s, 3H), 1.27-1.08 (m, 1H), 0.55-0.43 (m, 2H), 0.44-0.32 (m, 2H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 58 | 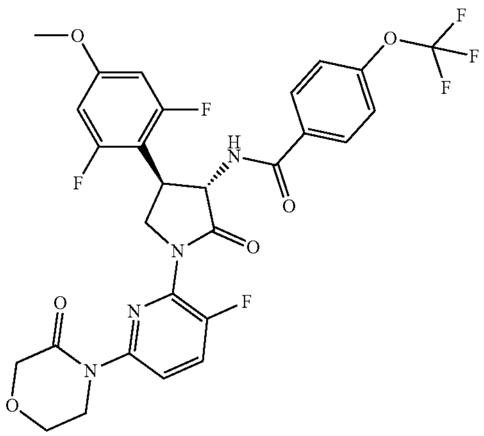 [SMILES: COc1cc(F)c([C@@H]2CN(c3nc(N4CCOCC4=O)ccc3F)C(=O)[C@H]2NC(=O)c2ccc(OC(F)(F)F)cc2)c(F)c1] | 625.2 | Method D, RT = 1.87 min, 100% | $^1$H NMR (400 MHz, DMSO-$d_6$) δ = 9.23 (d, J = 8.5 Hz, 1H), 8.07-8.00 (m, 1H), 7.99-7.87 (m, 3H), 7.55-7.45 (m, 2H), 6.80 (d, J = 10.5 Hz, 2H), 5.15-5.10 (m, 1H), 4.33-4.18 (m, 4H), 4.12-4.04 (m, 1H), 4.02-3.88 (m, 4H), 3.90 (s, 3H). |
| 59 | 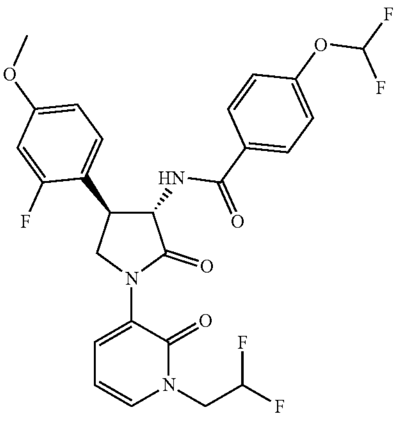 [SMILES: COc1ccc([C@@H]2CN(c3cccn(CC(F)F)c3=O)C(=O)[C@H]2NC(=O)c2ccc(OC(F)F)cc2)c(F)c1] | 552.2 | Method D, RT = 1.75 min, 100% | $^1$H NMR (400 MHz, DMSO-$d_6$) δ = 8.96 (d, J = 8.8 Hz, 1H), 7.96-7.86 (m, 2H), 7.72 (dd, J = 6.8, 2.0 Hz, 1H), 7.66 (dd, J = 7.3, 2.0 Hz, 1H), 7.55-7.49 (m, 1H), 7.35 (t, J = 73.6 Hz, 1H), 7.33-7.25 (m, 2H), 6.85-6.75 (m, 2H), 6.42 (t, J = 7.2 Hz, 1H), 6.35 (t, J = 57.6 Hz, 1H), 5.13 (dd, J = 11.4, 8.7 Hz, 1H), 4.53-4.37 (m, 2H), 4.20-4.10 (m, 1H), 4.05-3.95 (m, 1H), 3.74 (s, 3H), 3.70 (t, J = 9.5 Hz, 1H). |
| 60 | 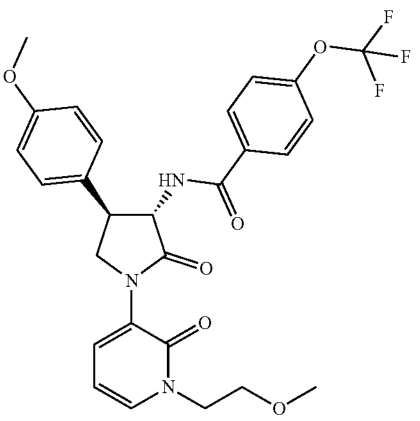 [SMILES: COCCn1cccc(N2C[C@@H](c3ccc(OC)cc3)[C@H](NC(=O)c3ccc(OC(F)(F)F)cc3)C2=O)c1=O] | 546.2 | Method D, RT = 1.69 min, 100% | $^1$H NMR (400 MHz, DMSO-$d_6$) δ = 9.02 (d, J = 8.6 Hz, 1H), 8.08-7.91 (m, 2H), 7.64 (dd, J = 6.8, 2.0 Hz, 1H), 7.59 (dd, J = 7.3, 2.0 Hz, 1H), 7.51-7.43 (m, 2H), 7.41-7.30 (m, 2H), 7.01-6.83 (m, 2H), 6.32 (t, J = 7.0 Hz, 1H), 5.02 (dd, J = 11.1, 8.7 Hz, 1H), 4.19-4.04 (m, 3H), 3.82-3.67 (m, 5H), 3.60 (t, J = 5.3 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 61 | 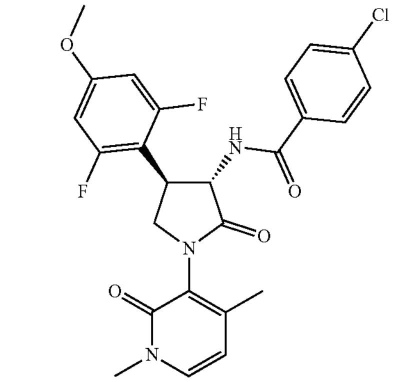 [SMILES: COc1cc(F)c([C@@H]2CN(c3c(C)ccn(C)c3=O)C(=O)[C@H]2NC(=O)c2ccc(Cl)cc2)c(F)c1] | 502.1 | Method D, RT = 1.606 min, 100% | $^1$H NMR (400 MHz, DMSO-$d_6$) δ = 9.19-8.95 (m, 1H), 7.90-7.80 (m, 2H), 7.71-7.62 (m, 1H), 7.60-7.44 (m, 2H), 6.82-6.69 (m, 2H), 6.25-6.16 (m, 1H), 5.34-4.84 (m, 1H), 4.27-4.05 (m, 2H), 3.79-3.70 (2s, 3H), 3.53-3.38 (m, 4H), 2.22-1.98 (2s, 3H). (Mixture of interconvertible atropisomers) |
| 62 | 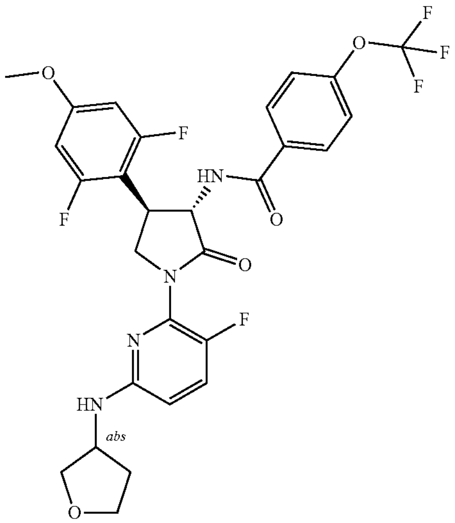 [SMILES: COc1cc(F)c([C@@H]2CN(c3nc(NC4CCOC4)ccc3F)C(=O)[C@H]2NC(=O)c2ccc(OC(F)(F)F)cc2)c(F)c1] | 611.2 | Method D, RT = 1.99 min, 100% | $^1$H NMR (400 MHz, DMSO-$d_6$) δ = 9.18 (d, J = 8.6 Hz, 1H), 8.03-7.87 (m, 2H), 7.54-7.40 (m, 3H), 6.97 (d, J = 5.6 Hz, 1H), 6.79 (d, J = 11.0 Hz, 2H), 6.47 (dd, J = 8.8, 2.7 Hz, 1H), 5.16-5.05 (m, 1H), 4.27-4.09 (m, 3H), 4.04-3.94 (m, 1H), 3.89 (dd, J = 8.8, 5.9 Hz, 1H), 3.85-3.77 (m, 1H), 3.76 (s, 3H), 3.73-3.69 (m, 1H), 3.51-3.47 (m, 1H), 2.23-2.08 (m, 1H), 1.82-1.71 (m, 1H). |
| 63 | 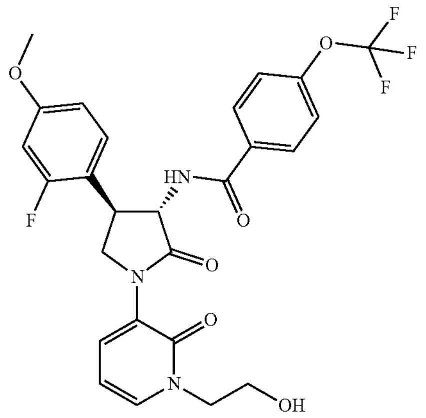 [SMILES: COc1ccc([C@@H]2CN(c3cccn(CCO)c3=O)C(=O)[C@H]2NC(=O)c2ccc(OC(F)(F)F)cc2)c(F)c1] | 550.2 | Method D, RT = 1.62 min, 100% | $^1$H NMR (400 MHz, DMSO-$d_6$) δ = 9.04 (d, J = 8.8 Hz, 1H), 8.05-7.84 (m, 2H), 7.64 (dd, J = 6.8, 2.0 Hz, 1H), 7.59 (dd, J = 7.3, 2.0 Hz, 1H), 7.54-7.43 (m, 3H), 6.89-6.71 (m, 2H), 6.31 (t, J = 7.0 Hz, 1H), 5.13 (dd, J = 11.4, 8.7 Hz, 1H), 4.92 (t, J = 5.4 Hz, 1H), 4.18-4.09 (m, 1H), 4.05-3.92 (m, 1H), 4.07-3.92 (m, 2H), 3.74 (s, 3H), 3.71 (br d, J = 9.5 Hz, 1H), 3.68-3.59 (m, 2H). |

TABLE 2-continued

| Ex | Structure | LCMS (M + H)+ | HPLC Method, RT (min.) & Purity | $^1$H NMR |
|---|---|---|---|---|
| 64 | 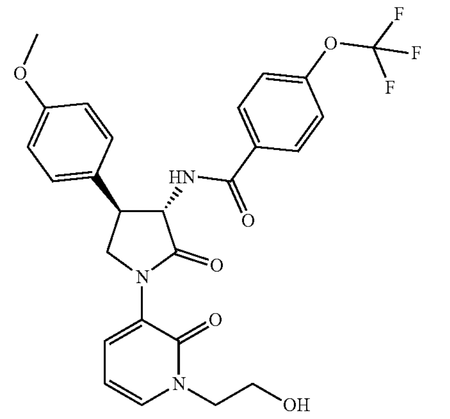 [SMILES: COc1ccc([C@@H]2CN(c3cccn(CCO)c3=O)C(=O)[C@H]2NC(=O)c2ccc(OC(F)(F)F)cc2)cc1] | 532.2 | Method D, RT = 2.147 min, 99% | $^1$H NMR (400 MHz, DMSO-$d_6$) δ = 9.02 (d, J = 8.5 Hz, 1H), 8.06-7.95 (m, 2H), 7.62 (m, 2H), 7.48 (d, J = 8.0 Hz, 2H), 7.40-7.31 (m, 2H), 6.95-6.85 (m, 2H), 6.36-6.28 (m, 1H), 5.06-4.95 (m, 1H), 4.93-4.89 (m, 1H), 4.16-3.98 (m, 3H), 3.78-3.67 (m, 5H), 3.65-3.60 (m, 2H). |
| 65 | 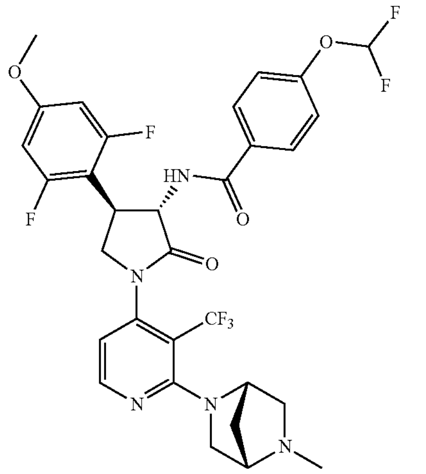 [SMILES: COc1cc(F)c([C@@H]2CN(c3ccnc(N4C[C@@H]5C[C@H]4CN5C)c3C(F)(F)F)C(=O)[C@H]2NC(=O)c2ccc(OC(F)F)cc2)c(F)c1] | 668.2 | Method D, RT = 1.68 min, 98.5% | $^1$H NMR (400 MHz, DMSO-$d_6$) δ = 9.06 (br d, J = 8.1 Hz, 1H), 8.34 (d, J = 4.9 Hz, 1H), 7.89 (d, J = 8.8 Hz, 2H), 7.36 (t, J = 73.6 Hz, 1H), 7.28 (d, J = 8.4 Hz, 2H), 6.86 (br d, J = 4.9 Hz, 1H), 6.80 (br d, J = 10.8 Hz, 2H), 5.09-4.89 (m, 1H), 4.23-4.12 (m, 1H), 4.09-3.98 (m, 1H), 3.98-3.86 (m, 1H), 3.77 (s, 3H), 3.57-3.41 (m, 2H), 3.30-3.20 (m, 2H), 2.85-2.69 (m, 2H), 2.30 (br s, 3H), 1.96-1.84 (m, 1H), 1.80-1.64 (m, 1H). |
| 66 | 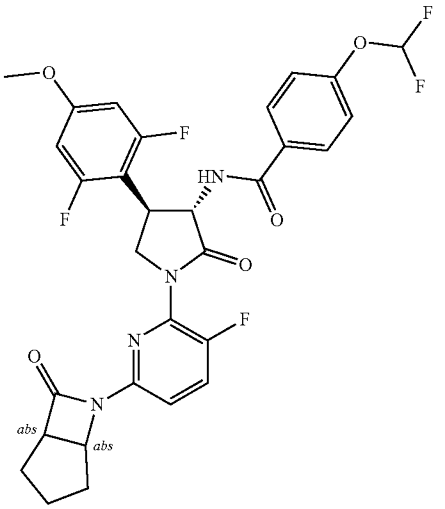 [SMILES: COc1cc(F)c([C@@H]2CN(c3nc(N4C(=O)C5CCCC54)ccc3F)C(=O)[C@H]2NC(=O)c2ccc(OC(F)F)cc2)c(F)c1] | 617.2 | Method D, RT = 2.009 min, 95% | $^1$H NMR (400 MHz, DMSO-$d_6$) δ = 9.11 (d, J = 8.6 Hz, 1H), 7.97-7.81 (m, 3H), 7.58 (dd, J = 2.8, 8.7 Hz, 1H), 7.34 (t, J = 73.6 Hz, 1H), 7.29-7.27 (m, 2H), 6.87-6.68 (m, 2H), 5.17-5.05 (m, 1H), 4.58 (t, J = 3.7 Hz, 1H), 4.28-4.14 (m, 2H), 4.09-4.03 (m, 1H), 3.77 (s, 3H), 3.68-3.62 (m, 1H), 2.27-2.21 (m, 1H), 1.97-1.89 (m, 1H), 1.85-1.78 (m, 1H), 1.72-1.63 (m, 1H), 1.56-1.37 (m, 2H). |

TABLE 2-continued

| Ex | Structure | LCMS (M + H)+ | HPLC Method, RT (min.) & Purity | $^1$H NMR |
|---|---|---|---|---|
| 67 | 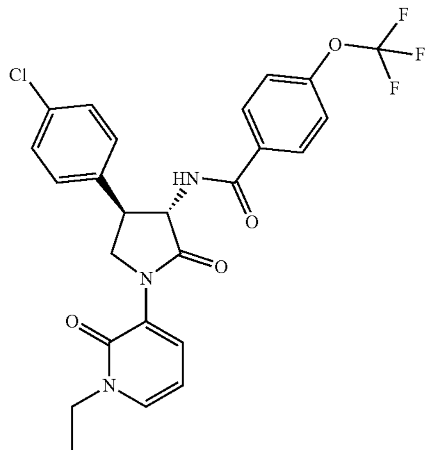 [SMILES: CCn1cccc(N2C[C@@H](c3ccc(Cl)cc3)[C@H](NC(=O)c3ccc(OC(F)(F)F)cc3)C2=O)c1=O] | 520.2 | Method D, RT = 1.899 min, 100% | $^1$H NMR (400 MHz, DMSO-$d_6$) δ = 9.07 (d, J = 8.6 Hz, 1H), 8.03-7.91 (m, 2H), 7.75 (dd, J = 6.6, 2.0 Hz, 1H), 7.58 (dd, J = 7.2, 2.1 Hz, 1H), 7.53-7.44 (m, 4H), 7.44-7.32 (m, 2H), 6.35 (t, J = 7.0 Hz, 1H), 5.05 (dd, J = 10.9, 8.7 Hz, 1H), 4.22-4.11 (m, 1H), 4.04-3.88 (m, 2H), 3.88-3.70 (m, 2H), 1.24 (t, J = 7.1 Hz, 3H). |
| 68 | 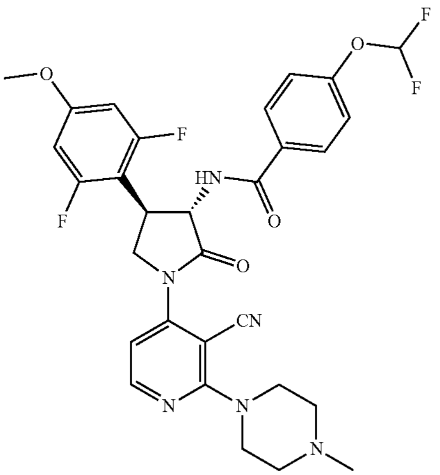 [SMILES: COc1cc(F)c([C@@H]2CN(c3ccnc(N4CCN(C)CC4)c3C#N)C(=O)[C@H]2NC(=O)c2ccc(OC(F)F)cc2)c(F)c1] | 613.2 | Method D, RT = 1.76 min, 99% | $^1$H NMR (400 MHz, DMSO-$d_6$) δ = 9.15 (d, J = 8.3 Hz, 1H), 8.43 (d, J = 5.6 Hz, 1H), 7.89 (d, J = 8.8 Hz, 2H), 7.35 (t, J = 73.2 Hz, 1H), 7.27 (d, J = 8.4 Hz, 2H), 7.12 (d, J = 5.4 Hz, 1H), 6.90-6.72 (m, 2H), 5.14-4.98 (m, 1H), 4.32-4.02 (m, 3H), 3.91 (s, 3H), 3.83-3.72 (m, 4H), 3.72-3.61 (m, 4H), 2.56 (s, 3H). |
| 69 | 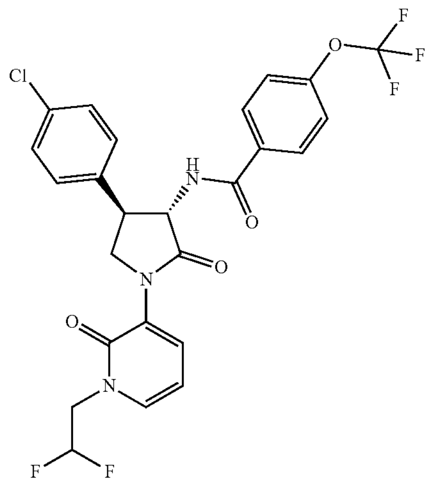 [SMILES: O=C(N[C@@H]1C(=O)N(c2cccn(CC(F)F)c2=O)C[C@H]1c1ccc(Cl)cc1)c1ccc(OC(F)(F)F)cc1] | 556.2 | Method D, RT = 1.970 min, 97.7% | $^1$H NMR (400 MHz, DMSO-$d_6$) δ = 9.07 (d, J = 8.6 Hz, 1H), 8.03-7.91 (m, 2H), 7.72 (d, J = 6.8 Hz, 1H), 7.66 (td, J = 1.1, 7.2 Hz, 1H), 7.48 (d, J = 8.6 Hz, 4H), 7.44-7.29 (m, 2H), 6.42 (m, 1H), 6.34 (t, J = 3.6 Hz, 1 H), 6.40 (t, J = 59.6 Hz, 1H), 5.05 (dd, J = 8.9, 10.9 Hz, 1H), 4.56-4.29 (m, 2H), 4.17 (t, J = 7.7 Hz, 1H), 3.89-3.72 (m, 2H) |

TABLE 2-continued

| Ex | Structure | LCMS (M + H)+ | HPLC Method, RT (min.) & Purity | $^1$H NMR |
|---|---|---|---|---|
| 70 | 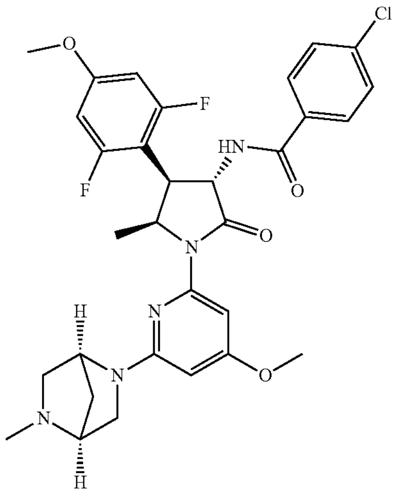 [SMILES: COc1cc(N2C[C@@H]3C[C@H]2CN3C)nc(N2C(=O)[C@@H](NC(=O)c3ccc(Cl)cc3)[C@H](c3c(F)cc(OC)cc3F)[C@@H]2C)c1] | 612.3 | Method D, RT = 1.74 min, 100% | $^1$H NMR (400 MHz, DMSO-$d_6$) δ = 8.92 (d, J = 8.3 Hz, 1H), 7.91-7.74 (m, 2H), 7.63-7.47 (m, 2H), 7.26 (s, , 1H), 6.90-6.68 (m, 2H), 5.78 (d, J = 1.7 Hz, 1H), 5.66-5.63 (m, 1H), 4.96-4.79 (m, 1H), 4.58-4.53 (m, 1H), 4.25-4.20 (m, 1H), 3.77 (s, 3H), 3.76 (s, 3H), 3.42-3.37 (m, 2H), 3.26-3.21 (m, 1H), 2.79-2.77 (m, 1H), 2.41 (d, J = 9.0 Hz, 1H), 2.26 (s, 3H), 1.81-1.79 (m, 1H), 1.72-1.69 (m, 1H), 1.18 (d, J = 6.6 Hz, 3H). |
| 71 | 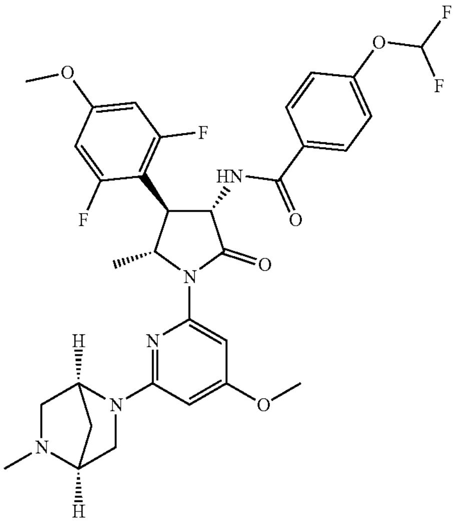 [SMILES: COc1cc(N2C[C@@H]3C[C@H]2CN3C)nc(N2C(=O)[C@@H](NC(=O)c3ccc(OC(F)F)cc3)[C@H](c3c(F)cc(OC)cc3F)[C@H]2C)c1] | 644.2 | Method D, RT = 1.58 min, 100% | $^1$H NMR (400 MHz, DMSO-$d_6$) δ = 9.05 (d, J = 8.6 Hz, 1H), 7.96-7.80 (m, 2H), 7.35 (t, J = 73.6 Hz, 1H), 7.29-7.27 (m, 2H), 6.93-6.66 (m, 3H), 5.85 (s, 1H), 4.99 (dd, J = 10.8, 8.3 Hz, 1H), 4.58-4.39 (m, 2H), 3.78 (s, 3H), 3.76 (s, 3H), 3.64-3.61 (m, 1H), 3.45-3.42 (m, 1H), 3.37-3.29 (m, 1H), 3.23-3.21 (m, 1H), 2.80 (dd, J = 9.0, 1.7 Hz, 1H), 2.44 (br d, J = 9.0 Hz, 1H), 2.25 (s, 3H), 1.90-1.78 (m, 1H), 1.71-1.68 (m, 1H), 1.36 (d, J = 5.9 Hz, 3H). |
| 72 | 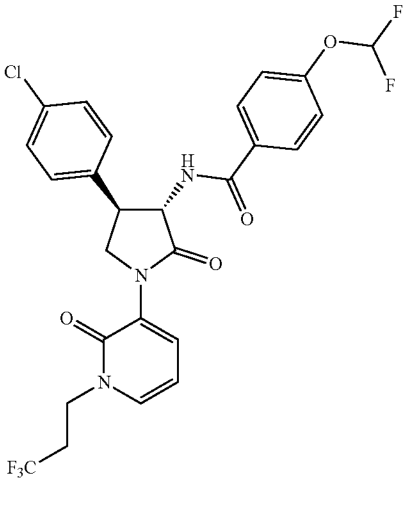 [SMILES: O=C(N[C@@H]1C(=O)N(c2cccn(CCC(F)(F)F)c2=O)C[C@H]1c1ccc(Cl)cc1)c1ccc(OC(F)F)cc1] | 570.2 | Method C, RT = 1.927 min, 100% | $^1$H NMR (400 MHz, DMSO-$d_6$) δ = 8.96 (d, J = 8.6 Hz, 1H), 7.97-7.87 (m, 2H), 7.77 (dd, J = 6.8, 2.0 Hz, 1H), 7.63 (dd, J = 7.2, 1.8 Hz, 1H), 7.51-7.37 (m, 4H), 7.35 (t, J = 73.2 Hz, 1H) , 7.30-7.32 (m, 2H), 6.38 (t, J = 7.0 Hz, 1H), 5.04 (dd, J = 11.1, 8.7 Hz, 1H), 4.26-4.11 (m, 3H), 3.88-3.72 (m, 2H), 2.83-2.70 (m, 2H). |

TABLE 2-continued

| Ex | Structure | LCMS (M + H)+ | HPLC Method, RT (min.) & Purity | $^1$H NMR |
|---|---|---|---|---|
| 73 | 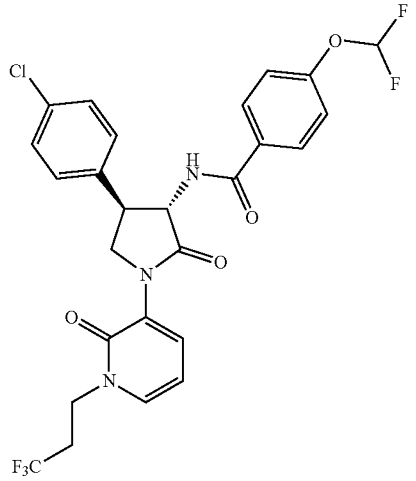 [SMILES: O=C(N[C@@H]1C(=O)N(c2cccn(CCC(F)(F)F)c2=O)C[C@H]1c1ccc(Cl)cc1)c1ccc(OC(F)F)cc1] | 588.2 | Method D, RT = 2.086 min, 98.8% | $^1$H NMR (400 MHz, DMSO-$d_6$) δ = 9.06 (d, J = 8.6 Hz, 1H), 8.02-7.93 (m, 2H), 7.77 (dd, J = 6.8, 2.0 Hz, 1H), 7.63 (dd, J = 7.1, 2.0 Hz, 1H), 7.52-7.46 (m, 4H), 7.44-7.35 (m, 2H), 6.38 (t, J = 7.0 Hz, 1H), 5.05 (dd, J = 11.0, 8.8 Hz, 1H), 4.26-4.15 (m, 3H), 3.89-3.71 (m, 2H), 2.85-2.71 (m, 2H). |
| 74 | 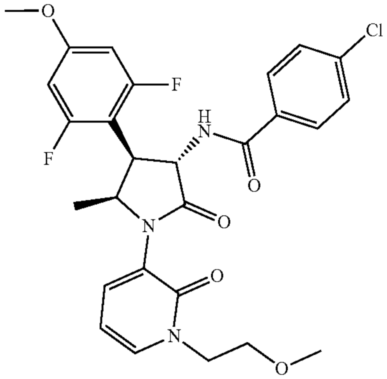 [SMILES: COCCn1cccc(N2C(=O)[C@@H](NC(=O)c3ccc(Cl)cc3)[C@H](c3c(F)cc(OC)cc3F)[C@@H]2C)c1=O] | 546.2 | Method D, RT = 1.69 min, 100% | $^1$H NMR (400 MHz, DMSO-$d_6$) δ = 8.30 (d, J = 5.5 Hz, 1H), 7.68 (dd, J = 7.0, 2.0 Hz, 1H), 7.64-7.56 (m, 2H), 7.49-7.33 (m, 3H), 6.75-6.59 (m, 2H), 6.35 (t, J = 7.0 Hz, 1H), 5.11 (dd, J = 9.0, 5.5 Hz, 1H), 4.90-4.87 (m, 1H), 4.63-4.61 (m, 1H), 4.23-4.06 (m, 2H), 3.72 (s, 3H), 3.61 (t, J = 5.8 Hz, 2H), 3.25 (s, 3H), 0.70 (d, J = 6.5 Hz, 3H). |
| 75 | 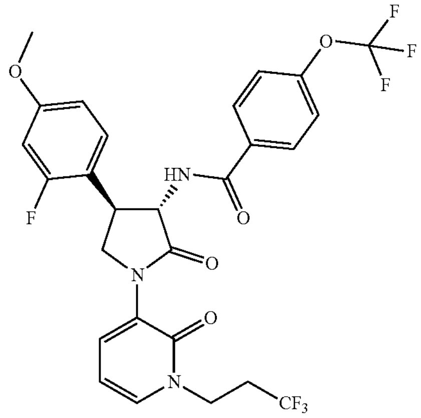 [SMILES: COc1ccc([C@@H]2CN(c3cccn(CCC(F)(F)F)c3=O)C(=O)[C@H]2NC(=O)c2ccc(OC(F)(F)F)cc2)c(F)c1] | 602.2 | Method D, RT = 1.98 min, 100% | $^1$H NMR (400 MHz, DMSO-$d_6$) δ = 9.06 (d, J = 8.8 Hz, 1H), 8.04-7.89 (m, 2H), 7.77 (dd, J = 6.8, 2.0 Hz, 1H), 7.63 (dd, J = 7.3, 2.0 Hz, 1H), 7.57-7.39 (m, 3H), 6.92-6.70 (m, 2H), 6.38 (t, J = 7.0 Hz, 1H), 5.14 (dd, J = 11.4, 8.7 Hz, 1H), 4.29-4.09 (m, 3H), 4.06-3.94 (m, 1H), 3.75 (s, 3H), 3.74-3.61 (m, 1H), 2.87-2.68 (m, 2H) |

TABLE 2-continued

| Ex | Structure | LCMS (M + H)+ | HPLC Method, RT (min.) & Purity | $^1$H NMR |
|---|---|---|---|---|
| 76 | 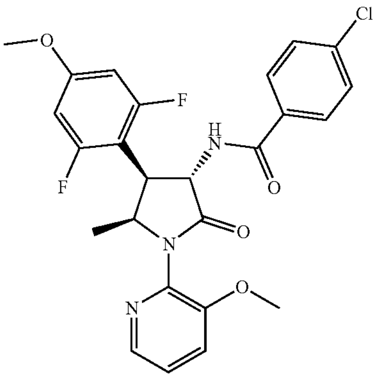 [SMILES: COc1cc(F)c([C@H]2[C@H](NC(=O)c3ccc(Cl)cc3)C(=O)N(c3ncccc3OC)[C@H]2C)c(F)c1] | 502.2 | Method D, RT = 1.78 min, 100% | $^1$H NMR (400 MHz, DMSO-$d_6$) δ = 8.95 (d, J = 9.0 Hz, 1H), 8.11 (dd, J = 4.6, 1.5 Hz, 1H), 7.91-7.76 (m, 2H), 7.64 (dd, J = 8.3, 1.5 Hz, 1H), 7.59-7.49 (m, 2H), 7.42 (dd, J = 4.6, 8.3 Hz, 1H), 6.87-6.70 (m, 2H), 5.67 (dd, J = 12.0, 8.6 Hz, 1H), 4.58-4.46 (m, 1H), 4.40-4.35 (m, 1H), 3.85 (s, 3H), 3.77 (s, 3H), 0.92 (d, J = 6.8 Hz, 3H). |
| 77 | 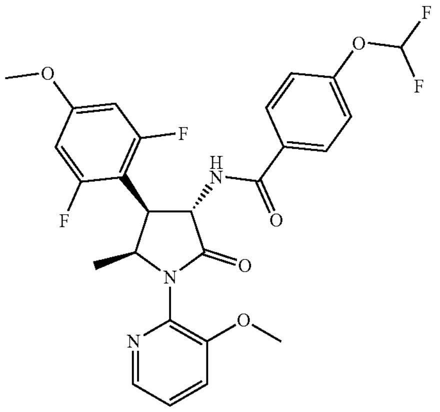 [SMILES: COc1cc(F)c([C@H]2[C@H](NC(=O)c3ccc(OC(F)F)cc3)C(=O)N(c3ncccc3OC)[C@H]2C)c(F)c1] | 534.2 | Method D, RT = 1.76 min, 100% | $^1$H NMR (400 MHz, DMSO-$d_6$) δ = 8.88 (d, J = 8.8 Hz, 1H), 8.11 (dd, J = 4.6, 1.5 Hz, 1H), 7.95-7.83 (m, 2H), 7.64 (dd, J = 8.6, 1.5 Hz, 1H), 7.43-7.40 (m, 1 H), 7.35 (t, J = 73.6 Hz, 1H), 7.26-7.24 (m, 2H), 6.85-6.72 (m, 2H), 5.67 (dd, J = 11.7, 8.6 Hz, 1H), 4.60-4.48 (m, 1H), 4.41-4.36 (m, 1H), 3.86 (s, 3H), 3.77 (s, 3H), 0.92 (d, J = 6.6 Hz, 3H). |
| 78 | 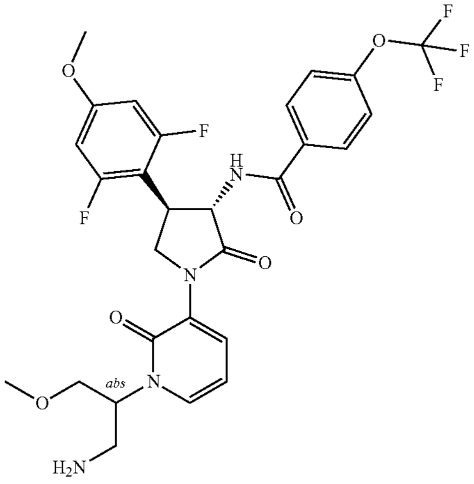 [SMILES: COCC(CN)n1cccc(N2C[C@@H](c3c(F)cc(OC)cc3F)[C@H](NC(=O)c3ccc(OC(F)(F)F)cc3)C2=O)c1=O] | 611.3 | Method C, RT = 1.525 min, 97.1% | $^1$H NMR (400 MHz, DMSO-$d_6$) δ = 9.11 (d, J = 8.6 Hz, 1H), 7.95 (d, J = 8.8 Hz, 2H), 7.68 (dd, J = 7.0, 1.7 Hz, 1H), 7.56 (dd, J = 7.1, 1.7 Hz, 1H), 7.48 (d, J = 8.1 Hz, 2H), 6.77 (d, J = 10.8 Hz, 2H), 6.34 (t, J = 7.1 Hz, 1H), 5.13 (dd, J = 10.8, 8.8 Hz, 1H), 5.02-4.90 (m, 1H), 4.15-3.88 (m, 4H), 3.81-3.70 (m, 4H), 3.61 (dd, J = 10.8, 4.4 Hz, 1H), 3.24-3.18 (m, 4H), 2.96-2.84 (m, 2H). |

TABLE 2-continued

| Ex | Structure | LCMS (M + H)+ | HPLC Method, RT (min.) & Purity | $^1$H NMR |
|---|---|---|---|---|
| 79 | 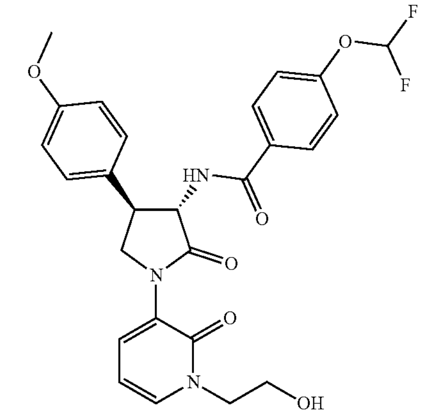 [SMILES: COc1ccc([C@@H]2CN(c3cccn(CCO)c3=O)C(=O)[C@H]2NC(=O)c2ccc(OC(F)F)cc2)cc1] | 514.2 | Method D, RT = 1.36 min, 100% | $^1$H NMR (400 MHz, DMSO-$d_6$) δ = 8.93 (d, J = 8.8 Hz, 1H), 7.99-7.83 (m, 2H), 7.63 (dd, J = 6.7, 2.1 Hz, 1H), 7.58 (dd, J = 7.1, 2.1 Hz, 1H), 7.33 (t, J = 73.6 Hz, 1H), 7.36-7.25 (m, 4H), 6.98-6.77 (m, 2H), 6.35-6.23 (m, 1H), 5.06-4.87 (m, 2H), 4.16-3.96 (m, 3H), 3.82-3.68 (m, 5H), 3.65 (br s, 2H). |
| 80 | 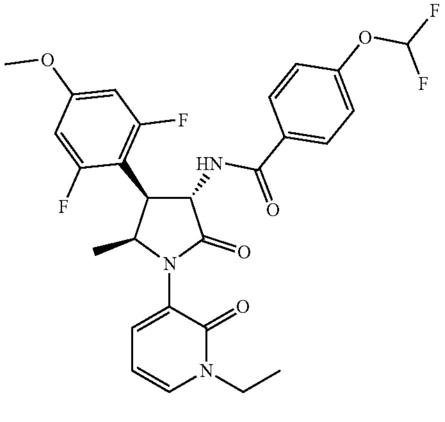 [SMILES: CCn1cccc(N2C(=O)[C@@H](NC(=O)c3ccc(OC(F)F)cc3)[C@H](c3c(F)cc(OC)cc3F)[C@@H]2C)c1=O] | 548.2 | Method D, RT = 1.68 min, 100% | 1H NMR (400 MHz, DMSO-d6) δ = 8.86 (d, J = 8.6 Hz, 1H), 7.90 (d, J = 8.8 Hz, 2H), 7.77 (dd, J = 7.2, 1.8 Hz, 1H), 7.57 (dd, J = 7.2, 1.8 Hz, 1H), 7.35 (t, J = 73.6 Hz, 1H), 7.25-7.23 (m, 2H), 6.77 (d, J = 11.5 Hz, 2H), 6.34 (t, J = 7.0 Hz, 1H), 5.66 (dd, J = 12.0, 8.8 Hz, 1H), 4.69-4.58 (m, 1H), 4.333-4.28 (m, 1H), 4.14-3.98 (m, 1H), 3.98-3.87 (m, 1H), 3.76 (s, 3H), 1.25 (t, J = 7.1 Hz, 3H), 0.91 (d, J = 6.8 Hz, 3H). |
| 81 | 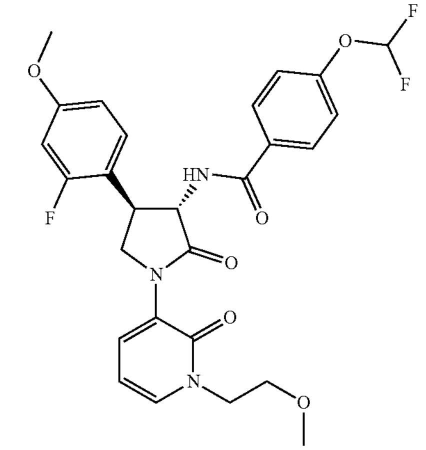 [SMILES: COCCn1cccc(N2C[C@@H](c3ccc(OC)cc3F)[C@H](NC(=O)c3ccc(OC(F)F)cc3)C2=O)c1=O] | 546.2 | Method D, RT = 1.57 min, 95.1% | $^1$H NMR (400 MHz, DMSO-$d_6$) δ = 8.95 (d, J = 8.8 Hz, 1H), 7.97-7.86 (m, 2H), 7.65 (dd, J = 6.6, 2.0 Hz, 1H), 7.59 (dd, J = 7.1, 2.0 Hz, 1H), 7.55-7.46 (m, 1H), 7.35 (t, J = 73.6 Hz, 1H), 7.32-7.23 (m, 2H), 6.87-6.74 (m, 2H), 6.36-6.26 (m, 1H), 5.13 (dd, J = 11.4, 8.9 Hz, 1H), 4.19-4.05 (m, 3H), 4.04-3.95 (m, 1H), 3.74 (s, 3H), 3.73-3.65 (m, 1H), 3.60 (t, J = 5.4 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 82 | 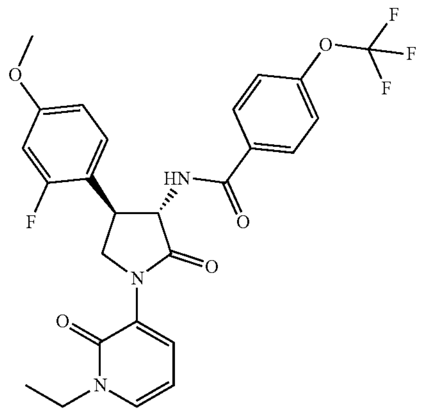 [SMILES: CCn1cccc(N2C[C@@H](c3ccc(OC)cc3F)[C@H](NC(=O)c3ccc(OC(F)(F)F)cc3)C2=O)c1=O] | 534.2 | Method D, RT = 1.77 min, 98.9% | $^1$H NMR (400 MHz, DMSO-d$_6$) δ = 9.05 (d, J = 8.8 Hz, 1H), 8.00-7.92 (m, 2H), 7.75 (dd, J = 6.8, 2.0 Hz, 1H), 7.58 (dd, J = 7.3, 2.0 Hz, 1H), 7.54-7.43 (m,3H), 6.86-6.73 (m, 2H), 6.39-6.29 (m, 1H), 5.13 (dd, J = 11.4, 8.9 Hz, 1H), 4.19-4.09 (m, 1H), 4.04-3.93 (m, 3H), 3.74 (s, 3H), 3.73-3.64 (m, 1H), 1.24 (t, J = 7.1 Hz, 3H). |
| 83 | 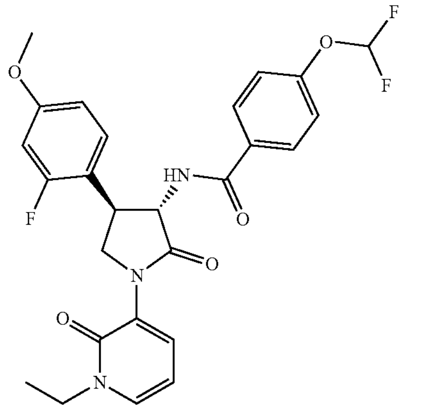 [SMILES: CCn1cccc(N2C[C@@H](c3ccc(OC)cc3F)[C@H](NC(=O)c3ccc(OC(F)F)cc3)C2=O)c1=O] | 516.2 | Method D, RT = 1.58 min, 96.07% | $^1$H NMR (400 MHz, DMSO-d$_6$) δ = 8.95 (d, J = 8.8 Hz, 1H), 7.98-7.84 (m, 2H), 7.75 (dd, J = 6.6, 2.0 Hz, 1H), 7.58-7.51 (m, 1H), 7.35 (t, 72.0 Hz, 1H), 7.28-7.19 (m, 3H), 6.91-6.69 (m, 2H), 6.39-6.31 (m, 1H), 5.13 (dd, J = 11.5, 8.8 Hz, 1H), 4.20-4.08 (m, 1H), 4.06-3.89 (m, 3H), 3.74 (s, 3H), 3.73-3.61 (m, 1H), 1.24 (t, J = 7.1 Hz, 3H). |
| 84 | 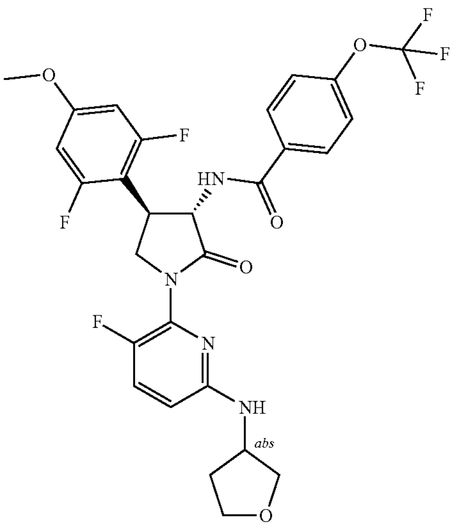 [SMILES: COc1cc(F)c([C@@H]2CN(c3nc(NC4CCOC4)ccc3F)C(=O)[C@H]2NC(=O)c2ccc(OC(F)(F)F)cc2)c(F)c1] | 611.2 | Method D, RT = 1.99 min, 99% | $^1$H NMR (400 MHz, DMSO-d$_6$) δ = 9.18 (d, J = 8.6 Hz, 1H), 7.99-7.86 (m, 2H), 7.54-7.41 (m, 3H), 6.96 (d, J = 5.9 Hz, 1H), 6.79 (d, J = 10.8 Hz, 2H), 6.47 (dd, J = 8.9, 2.6 Hz, 1H), 5.16-5.05 (m, 1H), 4.28-4.18 (m, 1H), 4.18-4.07 (m, 2H), 4.03-3.94 (m, 1H), 3.89-3.86 ( m, 1H), 3.84-3.77 (m, 1H), 3.76 (s, 3H), 3.70 (dt, J = 8.1, 5.7 Hz, 1H), 3.51-3.49 (m, 1H), 2.19-2.16 (m, 1H), 1.83-1.73 (m, 1H). |

TABLE 2-continued

| Ex | Structure | LCMS (M + H)+ | HPLC Method, RT (min.) & Purity | $^1$H NMR |
|---|---|---|---|---|
| 85 | 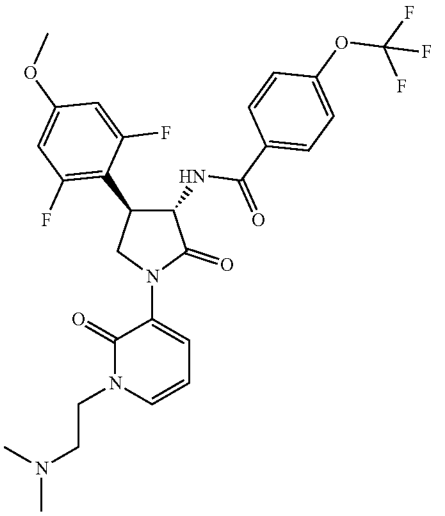 [SMILES: COc1cc(F)c([C@@H]2CN(c3cccn(CCN(C)C)c3=O)C(=O)[C@H]2NC(=O)c2ccc(OC(F)(F)F)cc2)c(F)c1] | 595.3 | Method D, RT = 1.651 min, 100% | $^1$H NMR (400 MHz, DMSO-$d_6$) δ = 9.12 (d, J = 8.6 Hz, 1H), 8.01-7.89 (m, 2H), 7.70 (dd, J = 2.0, 6.8 Hz, 1H), 7.58 (dd, J = 7.3, 2.0 Hz, 1H), 7.49 (dd, J = 8.8, 1.0 Hz, 2H), 6.84-6.72 (m, 2H), 6.32 (t, J = 7.0 Hz, 1H), 5.13 (dd, J = 8.6, 11.0 Hz, 1H), 4.14-3.91 (m, 5H), 3.77 (s, 3H), 2.18 (s, 6H), 2.14-1.73 (m, 2H). |
| 86 | 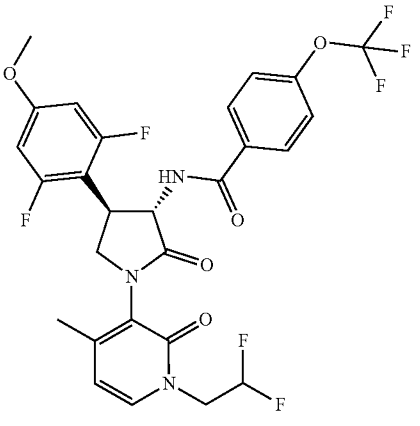 [SMILES: COc1cc(F)c([C@@H]2CN(c3c(C)ccn(CC(F)F)c3=O)C(=O)[C@H]2NC(=O)c2ccc(OC(F)(F)F)cc2)c(F)c1] | 602.2 | Method D, RT = 1.93 min, 97% | $^1$H NMR (400 MHz, DMSO-$d_6$) δ = 9.26-8.96 (m, 1H), 8.04-7.84 (m, 2H), 7.74-7.58 (m, 1H), 7.55-7.37 (m, 2H), 6.90-6.68 (m, 2H), 6.51-6.12 (m, 2H), 5.38-4.83 (m, 1H), 4.52-4.31 (m, 2H), 4.30-4.00 (m, 2H), 3.82-3.73 (m, 3H), 3.59-3.49 (m, 1H), 2.26-1.97 (2s, 3H). (mixture of interconvertible atropisomers) |
| 87 | 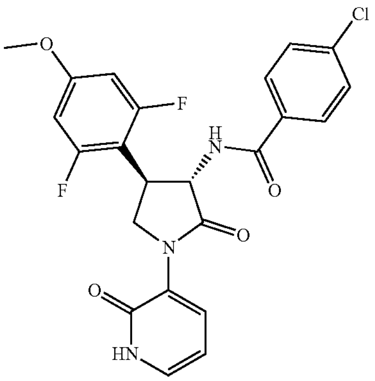 [SMILES: COc1cc(F)c([C@@H]2CN(c3ccc[nH]c3=O)C(=O)[C@H]2NC(=O)c2ccc(Cl)cc2)c(F)c1] | 474.1 | Method D, RT = 1.491 min, 95.5% | $^1$H NMR (400 MHz, DMSO-$d_6$) δ = 12.03 (br dd, J = 3.8, 2.3 Hz, 1H), 9.06 (br d, J = 8.8 Hz, 1H), 7.88-7.80 (m, 2H), 7.61 (dd, J = 7.1, 2.0 Hz, 1H), 7.59-7.51 (m, 2H), 7.40 (dd, J = 1.3, 6.2 Hz, 1H), 6.77 (d, J = 10.8 Hz, 2H), 6.30 (t, J = 6.8 Hz, 1H), 5.12 (dd, J = 10.5, 8.8 Hz, 1H), 4.15-3.87 (m, 3H), 3.77 (s, 3H). |

TABLE 2-continued

| Ex | Structure | LCMS (M + H)+ | HPLC Method, RT (min.) & Purity | $^1$H NMR |
|---|---|---|---|---|
| 88 | 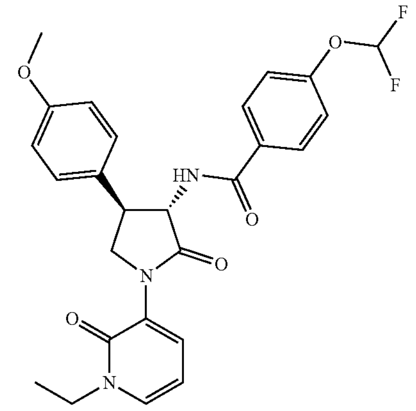 [SMILES: CCn1cccc(N2C[C@@H](c3ccc(OC)cc3)[C@H](NC(=O)c3ccc(OC(F)F)cc3)C2=O)c1=O] | 498.2 | Method D, RT = 1.519 min, 100% | $^1$H NMR (400 MHz, DMSO-$d_6$) δ = 8.92 (d, J = 8.8 Hz, 1H), 7.98-7.86 (m, 2H), 7.74 (dd, J = 6.7,2.1 Hz, 1H), 7.57 (dd, J = 7.3, 2.0 Hz, 1H), 7.34 (t, J = 80.0 Hz, 1H), 7.35-7.27 (m, 4H), 6.97-6.83 (m, 2H), 6.34 (t, J = 7.0 Hz, 1H), 5.01 (dd, J = 11.2, 8.8 Hz, 1H), 4.18-4.08 (m, 1H), 4.04-3.90 (m, 2H), 3.83-3.63 (m, 5H), 1.24 (t, J = 7.2 Hz, 3H). |
| 89 | 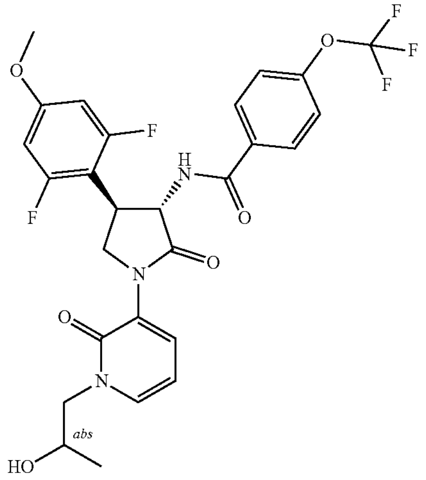 | 582.2 | Method D, RT = 1.693 min, 100% | $^1$H NMR (400 MHz, DMSO-$d_6$) δ = 9.11 (d, J = 8.6 Hz, 1H), 8.00-7.85 (m, 2H), 7.62 (dd, J = 6.8, 2.0 Hz, 1H), 7.58 (dd, J = 7.2, 2.1 Hz, 1H), 7.53-7.39 (m, 2H), 6.76 (d, J = 10.8 Hz, 2H), 6.31 (t, J = 7.1 Hz, 1H), 5.12 (dd, J = 11.0, 8.6 Hz, 1H), 4.94 (br d, J = 5.4 Hz, 1H), 4.16-3.88 (m, 5H), 3.76 (s, 3H), 3.65 (dd, J = 13.0, 8.1 Hz, 1H), 1.09 (d, J = 6.1 Hz, 3H). |
| 90 | 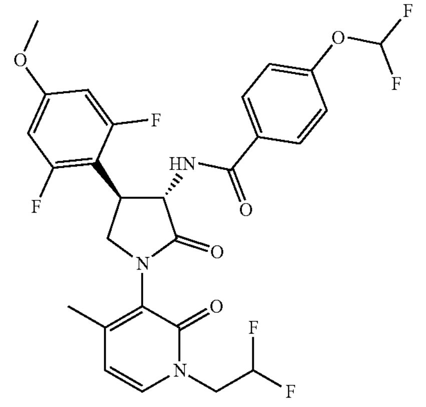 [SMILES: COc1cc(F)c([C@@H]2CN(c3c(C)ccn(CC(F)F)c3=O)C(=O)[C@H]2NC(=O)c2ccc(OC(F)F)cc2)c(F)c1] | 584.2 | Method D, RT = 1.765 min, 100% | $^1$H NMR (400 MHz, DMSO-$d_6$) δ = 9.15-8.90 (m, 1H), 7.99-7.83 (m, 2H), 7.74-7.59 (m, 1H), 7.35 (t, J = 68 Hz, 1 H), 7.56-7.07 (m, 2H), 6.84-6.69 (m, 2H), 6.54-6.11 (m, 2H), 5.39-4.80 (m, 1H), 4.51-4.02 (m, 4H), 3.82-3.71 (m, 3H), 3.58-3.41 (m, 1H), 2.25-1.95 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 91 | 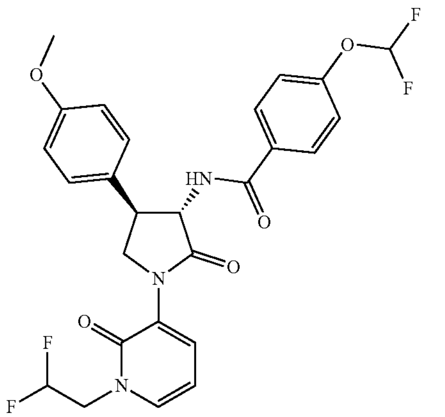 [SMILES: COc1ccc([C@@H]2CN(c3cccn(CC(F)F)c3=O)C(=O)[C@H]2NC(=O)c2ccc(OC(F)F)cc2)cc1] | 534.2 | Method D, RT = 1.597 min, 100% | $^1$H NMR (400 MHz, DMSO-$d_6$) δ = 8.93 (d, J = 8.8 Hz, 1H), 7.99-7.87 (m, 2H), 7.72 (dd, J = 7.0, 2.1 Hz, 1H), 7.66 (dd, J = 7.3, 2.0 Hz, 1H), 7.35 (t, J = 72.4 Hz, 1 H), 7.34-7.25 (m, 4H), 6.94-6.85 (m, 2H), 6.34 (tt, J = 52.2, 4 Hz, 1H), 6.41 (t, J = 8 Hz, 1H), 5.02 (dd, J = 11.1, 8.9 Hz, 1H), 4.54-4.41 (m, 2H), 4.17-4.08 (m, 1H), 3.79-3.70 (m, 5H). |
| 92 | 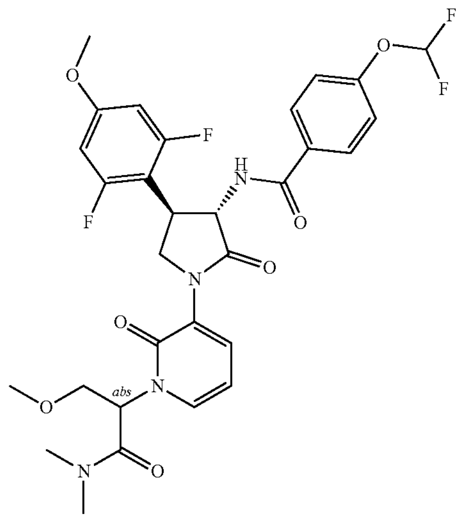 [SMILES: COCC(C(=O)N(C)C)n1cccc(N2C[C@@H](c3c(F)cc(OC)cc3F)[C@H](NC(=O)c3ccc(OC(F)F)cc3)C2=O)c1=O] | 635.2 | Method D, RT = 1.615 min, 100% | $^1$H NMR (400 MHz, DMSO-$d_6$) δ = 9.01 (d, J = 8.6 Hz, 1H), 7.94-7.83 (m, 2H), 7.72 (dd, J = 7.1, 2.0 Hz, 1H), 7.61 (dd, J = 7.2, 1.8 Hz, 1H), 7.34 (t, J = 73.6 Hz, 1H), 7.28 (m, 1H), 6.76 (d, J = 11.0 Hz, 2H), 6.41 (t, J = 7.1 Hz, 1H), 6.07 (dd, J = 8.7, 5.3 Hz, 1H), 5.09 (dd, J = 11.1, 8.7 Hz, 1H), 4.13-4.04 (m, 1H), 4.03-3.79 (m, 5H), 3.76 (s, 3H), 3.26 (s, 3H), 3.11 (s, 3H), 2.84 (s, 3H). |
| 93 | 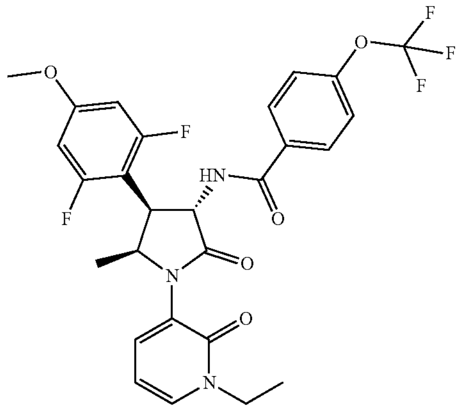 [SMILES: CCn1cccc(N2C(=O)[C@@H](NC(=O)c3ccc(OC(F)(F)F)cc3)[C@H](c3c(F)cc(OC)cc3F)[C@@H]2C)c1=O] | 566.2 | Method D, RT = 1.86 min, 98% | $^1$H NMR (400 MHz, DMSO-$d_6$) δ = 8.97 (d, J = 8.8 Hz, 1H), 8.02-7.88 (m, 2H), 7.78 (dd, J = 6.8, 2.0 Hz, 1H), 7.58 (dd, J = 6.8, 2.0 Hz, 1H), 7.45 (d, J = 8.3 Hz, 2H), 6.81-6.67 (m, 2H), 6.34 (t, J = 7.0 Hz, 1H), 5.67 (dd, J = 12.0, 8.8 Hz, 1H), 4.71-4.56 (m, 1H), 4.33-4.28 (m, 1H), 4.13-3.99 (m, 1H), 3.98-3.89 (m, 1H), 3.76 (s, 3H), 1.25 (t, J = 7.1 Hz, 3H), 0.91 (d, J = 6.6 Hz, 3H). |

TABLE 2-continued

| Ex | Structure | LCMS (M + H)+ | HPLC Method, RT (min.) & Purity | $^1$H NMR |
|---|---|---|---|---|
| 94 | 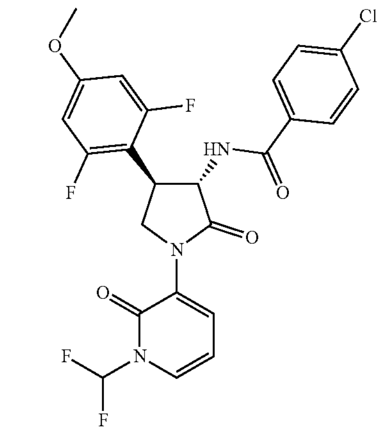 [SMILES: COc1cc(F)c([C@@H]2CN(c3cccn(C(F)F)c3=O)C(=O)[C@H]2NC(=O)c2ccc(Cl)cc2)c(F)c1] | 524.1 | Method D, RT = 1.789 min, 98.8% | $^1$H NMR (400 MHz, DMSO-$d_6$) δ = 9.07 (br d, J = 8.3 Hz, 1H), 7.92 (t, J = 59.6 Hz, 1H), 7.84 (m, 2H), 7.74 (m, 2H), 7.56 (d, J = 8.3 Hz, 2H), 6.77 (d, J = 10.5 Hz, 2H), 6.56 (t, J = 7.1 Hz, 1H), 5.08 (dd, J = 11.0, 8.8 Hz, 1H), 4.20-4.06 (m, 1H), 4.04-3.93 (m, 2H), 3.77 (s, 3H). |
| 95 | 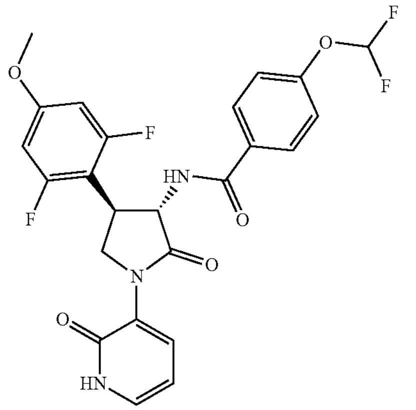 [SMILES: COc1cc(F)c([C@@H]2CN(c3ccc[nH]c3=O)C(=O)[C@H]2NC(=O)c2ccc(OC(F)F)cc2)c(F)c1] | 506.1 | Method D, RT = 1.509 min, 96.5% | $^1$H NMR (400 MHz, DMSO-$d_6$) δ = 12.03 (br s, 1H), 9.00 (br d, J = 7.8 Hz, 1H), 7.94-7.84 (m, 2H), 7.61 (dd, J = 7.2, 2.1 Hz, 1H), 7.40-7.25 (m, 3H), 7.33 (t, J = 73.6 Hz, 1H), 6.77 (d, J = 10.8 Hz, 2H), 6.30 (t, J = 6.7 Hz, 1H), 5.12 (dd, J = 10.8, 8.6 Hz, 1H), 4.15-3.92 (m, 3H), 3.77 (s, 3H). |
| 96 | 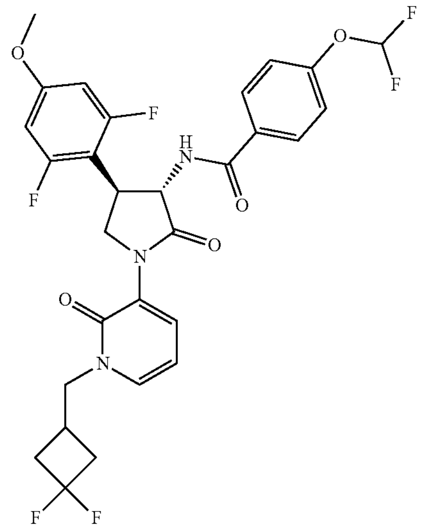 [SMILES: COc1cc(F)c([C@@H]2CN(c3cccn(CC4CC(F)(F)C4)c3=O)C(=O)[C@H]2NC(=O)c2ccc(OC(F)F)cc2)c(F)c1] | 610.2 | Method D, RT = 1.856 min, 100% | $^1$H NMR (400 MHz, DMSO-$d_6$) δ = 9.00 (d, J = 8.8 Hz, 1H), 7.95-7.84 (m, 2H), 7.79 (dd, J = 6.8, 2.0 Hz, 1H), 7.61 (dd, J = 7.3, 2.0 Hz, 1H), 7.33 (t, J = 73.6 Hz, 1H), 7.28 (m, 2H), 6.77 (d, J = 10.5 Hz, 2H), 6.36 (t, J = 7.0 Hz, 1H), 5.11 (dd, J = 10.8, 8.8 Hz, 1H), 4.18-4.03 (m, 3H), 4.03-3.88 (m, 2H), 3.77 (s, 3H), 2.68-2.55 (m, 5H). |

TABLE 2-continued

| Ex | Structure | LCMS (M + H)+ | HPLC Method, RT (min.) & Purity | $^1$H NMR |
|---|---|---|---|---|
| 97 | 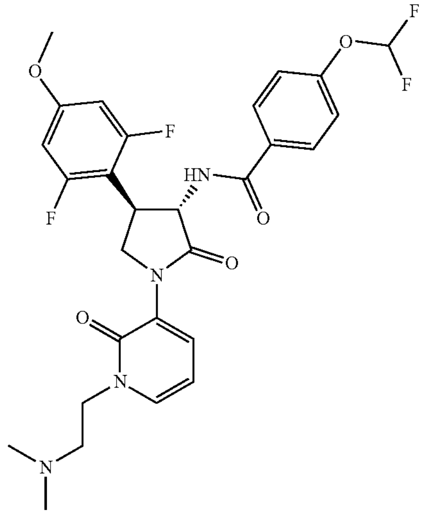 [SMILES: COc1cc(F)c([C@@H]2CN(c3cccn(CCN(C)C)c3=O)C(=O)[C@H]2NC(=O)c2ccc(OC(F)F)cc2)c(F)c1] | 577.3 | Method D, RT = 1.464 min, 98.5% | $^1$H NMR (400 MHz, DMSO-d$_6$) δ = 9.01 (d, J = 8.8 Hz, 1H), 7.92-7.83 (m, 2H), 7.70 (dd, J = 6.7, 2.1 Hz, 1H), 7.58 (dd, J = 7.2, 2.1 Hz, 1H), 7.34 (t, J = 73.6 Hz, 1H), 7.28 (m, 2H), 6.77 (d, J = 10.8 Hz, 2H), 6.32 (t, J = 7.0 Hz, 1H), 5.12 (dd, J = 11.0, 8.6 Hz, 1H), 4.12-3.92 (m, 7H), 3.76 (s, 3H), 2.18 (s, 6H). |
| 98 | 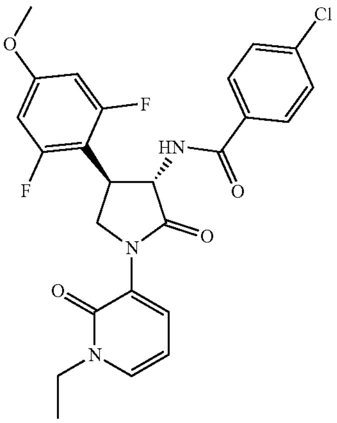 [SMILES: CCn1cccc(N2C[C@@H](c3c(F)cc(OC)cc3F)[C@H](NC(=O)c3ccc(Cl)cc3)C2=O)c1=O] | 502.1 | Method D, RT = 1.680 min, 99.7% | $^1$H NMR (400 MHz, DMSO-d$_6$) δ = 9.06 (br d, J = 8.3 Hz, 1H), 7.94-7.80 (m, 2H), 7.76 (dd, J = 6.8, 1.7 Hz, 1H), 7.64-7.44 (m, 3H), 6.77 (d, J = 10.5 Hz, 2H), 6.35 (t, J = 7.0 Hz, 1H), 5.13 (dd, J = 10.9, 8.7 Hz, 1H), 4.18-4.05 (m, 1H), 4.05-3.92 (m, 4H), 3.78 (s, 3H), 1.25 (t, J = 7.1 Hz, 3H). |
| 99 | 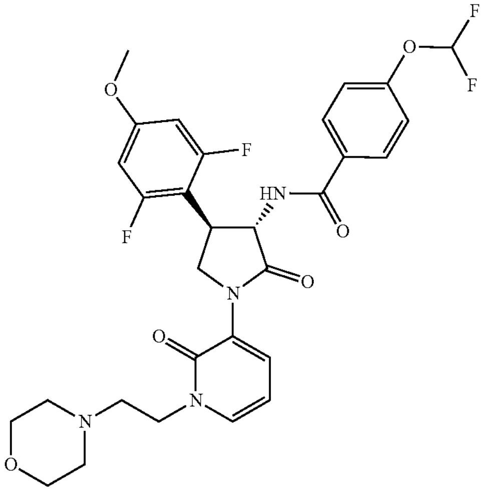 [SMILES: COc1cc(F)c([C@@H]2CN(c3cccn(CCN4CCOCC4)c3=O)C(=O)[C@H]2NC(=O)c2ccc(OC(F)F)cc2)c(F)c1] | 619.2 | Method D, RT = 1.569 min, 100% | $^1$H NMR (400 MHz, DMSO-d$_6$) δ = 9.01 (d, J = 8.6 Hz, 1H), 7.94-7.80 (m, 2H), 7.71 (dd, J = 6.6, 2.0 Hz, 1H), 7.59 (dd, J = 7.1, 2.0 Hz, 1H), 7.34 (t, J = 76.0 Hz, 1 H), 7.27-7.25 (m, 2H), 6.77 (d, J = 10.8 Hz, 2H), 6.33 (t, J = 7.0 Hz, 1H), 5.12 (dd, J = 10.9, 8.7 Hz, 1H), 4.14-3.92 (m, 5H), 3.76 (s, 3H), 3.54 (t, J = 4.5 Hz, 4H), 2.58 (t, J = 6.4 Hz, 2H), 2.43 (m, 4H). |

TABLE 2-continued

| Ex | Structure | LCMS (M + H)+ | HPLC Method, RT (min.) & Purity | $^1$H NMR |
|---|---|---|---|---|
| 100 | 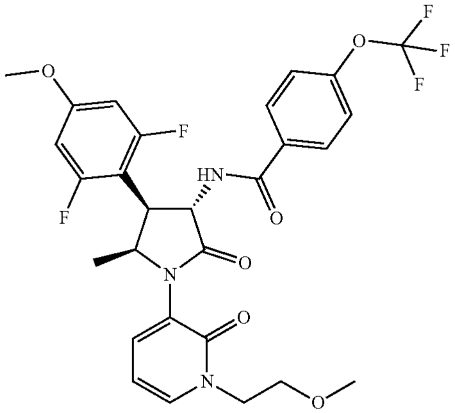 [SMILES: COCCn1cccc(N2C(=O)[C@@H](NC(=O)c3ccc(OC(F)(F)F)cc3)[C@H](c3c(F)cc(OC)cc3F)[C@@H]2C)c1=O] | 596.2 | Method D, RT = 1.84 min, 98% | $^1$H NMR (400 MHz, DMSO-d$_6$) δ = 8.97 (d, J = 8.8 Hz, 1H), 8.01-7.89 (m, 2H), 7.68 (dd, J = 6.7, 2.0 Hz, 1H), 7.60 (dd, J = 6.7, 2.0 Hz, 1H), 7.52-7.38 (m, 2H), 6.84-6.71 (m, 2H), 6.32 (t, J = 7.0 Hz, 1H), 5.67 (dd, J = 12.1, 8.7 Hz, 1H), 4.69-4.57 (m, 1H), 4.32-4.27 (m 1H), 4.23-4.18 (m, 1H), 4.10-3.99 (m, 1H), 3.76 (s, 3H), 3.60 (t, J = 5.3 Hz, 2H), 3.25 (s, 3H), 0.91 (d, J = 6.8 Hz, 3H). |
| 101 | 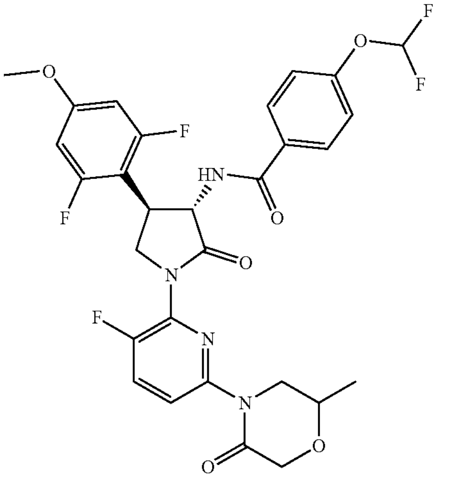 [SMILES: COc1cc(F)c([C@@H]2CN(c3nc(N4CC(C)OCC4=O)ccc3F)C(=O)[C@H]2NC(=O)c2ccc(OC(F)F)cc2)c(F)c1] | 620.1 | Method D, RT = 1.82 min, 100% | $^1$H NMR (400 MHz, DMSO-d$_6$) δ = 9.11 (d, J = 8.3 Hz, 1H), 8.08-7.77 (m, 4H), 7.35 (t, J = 73.6 Hz, 1H), 7.29-7.27 (m, 2H), 6.79 (d, J = 10.8 Hz, 2H), 5.18-5.04 (m, 1H), 4.30 (s, 1H), 4.27-4.20 (m, 3H), 4.11-3.97 (m, 3H), 3.77 (s, 3H), 3.55-3.46 (m, 1H), 1.26 (d, J = 6.1 Hz, 3H). |
| 102 | 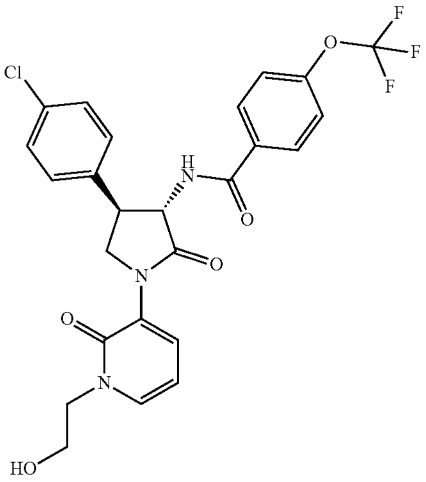 [SMILES: O=C(N[C@@H]1C(=O)N(c2cccn(CCO)c2=O)C[C@H]1c1ccc(Cl)cc1)c1ccc(OC(F)(F)F)cc1] | 536.2 | Method D, RT = 1.730 min, 100% | $^1$H NMR (400 MHz, DMSO-d$_6$) δ = 9.07 (d, J = 8.8 Hz, 1H), 8.04-7.88 (m, 2H), 7.64 (dd, J = 6.8, 2.0 Hz, 1H), 7.59 (dd, J = 7.3, 2.0 Hz, 1H), 7.52-7.44 (m, 4H), 7.43-7.34 (m, 2H), 6.32 (t, J = 7.1 Hz, 1H), 5.04 (dd, J = 10.9, 8.7 Hz, 1H), 4.98-4.88 (m, 1H), 4.16 (t, J = 7.6 Hz, 1H), 4.05-3.95 (m, 2H), 3.88-3.71 (m, 2H), 3.70-3.59 (m, 2H). |

TABLE 2-continued

| Ex | Structure | LCMS (M + H)+ | HPLC Method, RT (min.) & Purity | $^1$H NMR |
|---|---|---|---|---|
| 103 | 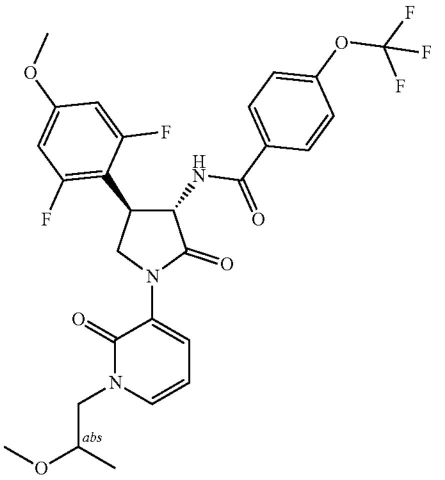 [SMILES: COc1cc(F)c([C@@H]2CN(c3cccn(CC(C)OC)c3=O)C(=O)[C@H]2NC(=O)c2ccc(OC(F)(F)F)cc2)c(F)c1] | 596.2 | Method D, RT = 1.889 min, 100% | $^1$H NMR (400 MHz, DMSO-$d_6$) δ = 9.11 (d, J = 8.6 Hz, 1H), 7.94 (d, J = 8.8 Hz, 2H), 7.67-7.55 (m, 2H), 7.48 (d, J = 8.8 Hz, 2H), 6.77 (d, J = 10.5 Hz, 2H), 6.32 (t, J = 7.0 Hz, 1H), 5.12 (dd, J = 10.8, 8.6 Hz, 1H), 4.15-3.92 (m, 4H), 3.92-3.82 (m, 1H), 3.76 (s, 3H), 3.65 (dt, J = 6.5, 4.6 Hz, 1H), 3.19 (s, 3H), 1.09 (d, J = 6.1 Hz, 3H). |
| 104 | 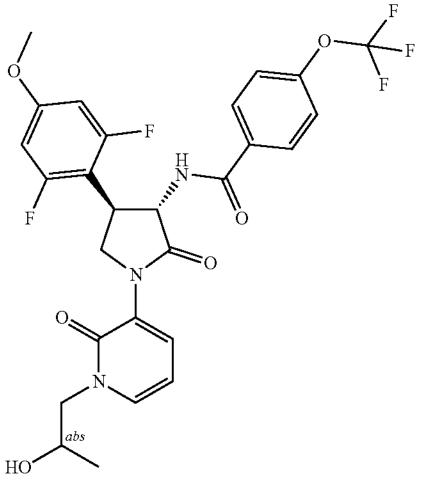 | 564.2 | Method D, RT = 1.512 min, 100% | $^1$H NMR (400 MHz, DMSO-$d_6$) δ = 9.00 (d, J = 8.6 Hz, 1H), 7.94-7.82 (m, 2H), 7.62 (dd, J = 6.8, 2.0 Hz, 1H), 7.58 (dd, J = 7.2, 2.1 Hz, 1H), 7.34 (t, J = 73.6 Hz, 1H), 7.28 (m, 2H), 6.76 (d, J = 10.8 Hz, 2H), 6.30 (t, J = 7.0 Hz, 1H), 5.11 (dd, J = 11.1, 8.7 Hz, 1H), 4.93 (d, J = 5.6 Hz, 1H), 4.17-4.04 (m, 2H), 4.04-3.83 (m, 3H), 3.76 (s, 3H), 3.63 (dd, J = 12.8, 8.2 Hz, 1H), 1.09 (d, J = 6.4 Hz, 3H). |
| 105 | 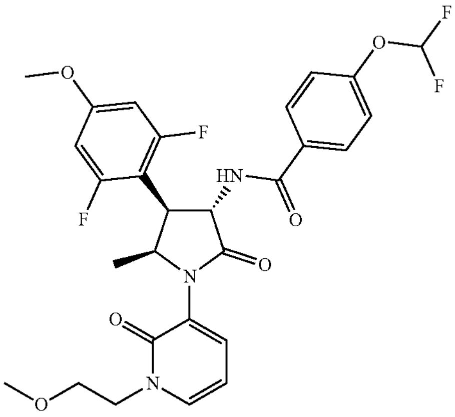 [SMILES: COCCn1cccc(N2C(=O)[C@@H](NC(=O)c3ccc(OC(F)F)cc3)[C@H](c3c(F)cc(OC)cc3F)[C@@H]2C)c1=O] | 578.3 | Method D, RT = 1.66 min, 100% | $^1$H NMR (400 MHz, DMSO-$d_6$) δ = 8.87 (d, J = 8.6 Hz, 1H), 7.90 (d, J = 8.8 Hz, 2H), 7.68 (dd, J = 7.1, 2.0 Hz, 1H), 7.59 (dd, J = 7.1, 2.0 Hz, 1H), 7.35 (t, J = 73.6 Hz, 1H), 7.25-7.35 (m, 2H), 6.84-6.65 (m, 2H), 6.32 (t, J = 7.0 Hz, 1H), 5.66 (dd, J = 12.0, 8.6 Hz, 1H), 4.69-4.58 (m, 1H), 4.33-4.29 (m, 1H), 4.24-4.18 (m, 1H), 4.09-4.03 (m, 1H), 3.76 (s, 3H), 3.60 (t, J = 5.1 Hz, 2H), 3.25 (s, 3H), 0.91 (d, J = 6.6 Hz, 3H). |

TABLE 2-continued

| Ex | Structure | LCMS (M + H)+ | HPLC Method, RT (min.) & Purity | $^{1}$H NMR |
|---|---|---|---|---|
| 106 | 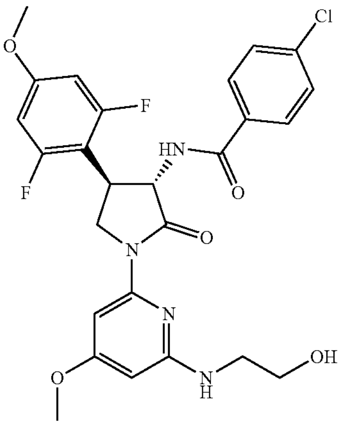 [SMILES: COc1cc(NCCO)nc(N2C[C@@H](c3c(F)cc(OC)cc3F)[C@H](NC(=O)c3ccc(Cl)cc3)C2=O)c1] | 547.2 | Method D, RT = 1.808 min, 97.5% | $^{1}$H NMR (400 MHz, DMSO-$d_6$) δ = 9.10 (br d, J = 8.3 Hz, 1H), 7.91-7.75 (m, 2H), 7.58 (d, J = 8.6 Hz, 2H), 7.16 (d, J = 2.0 Hz, 1H), 6.79 (d, J = 10.8 Hz, 2H), 6.45 (br dd, J = 0.7, 2.4 Hz, 1H), 5.87 (d, J = 1.7 Hz, 1H), 5.08 (dd, J = 10.9, 8.4 Hz, 1H), 4.67-4.56 (m, 1H), 4.40 (t, J = 9.8 Hz, 1H), 4.14-3.98 (m, 1H), 3.94-3.85 (m, 1H), 3.78 (s, 3H), 3.73 (s, 3H), 3.50 (q, J = 5.7 Hz, 2H), 3.31-3.25 (m, 1H), 3.18 (d, J = 5.1 Hz, 1H). |
| 107 | 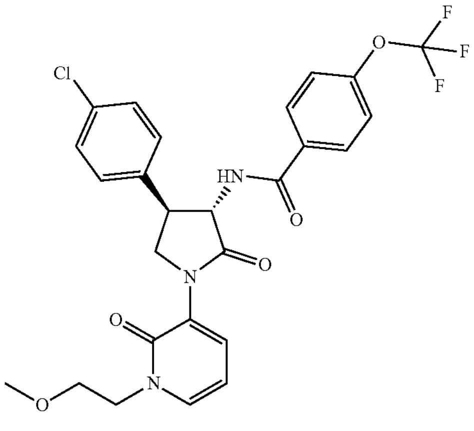 [SMILES: COCCn1cccc(N2C[C@@H](c3ccc(Cl)cc3)[C@H](NC(=O)c3ccc(OC(F)(F)F)cc3)C2=O)c1=O] | 550.2 | Method D, RT = 1.891 min, 100% | $^{1}$H NMR (400 MHz, DMSO-$d_6$) δ = 9.07 (d, J = 8.6 Hz, 1H), 8.04-7.89 (m, 2H), 7.65 (dd, J = 6.8, 2.0 Hz, 1H), 7.60 (dd, J = 7.1, 2.0 Hz, 1H), 7.54-7.44 (m, 4H), 7.44-7.29 (m, 2H), 6.33 (t, J = 7.0 Hz, 1H), 5.05 (dd, J = 10.8, 8.8 Hz, 1H), 4.25-4.04 (m, 3H), 3.88-3.69 (m, 2H), 3.60 (t, J = 5.4 Hz, 2H), 3.25 (s, 3H). |
| 108 | 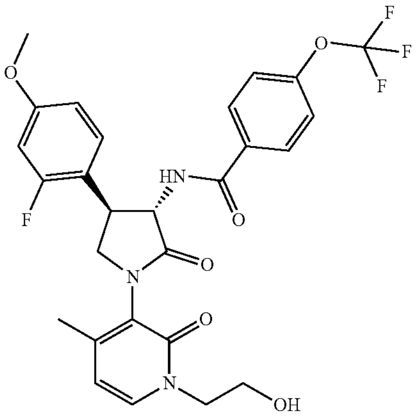 [SMILES: COc1ccc([C@@H]2CN(c3c(C)ccn(CCO)c3=O)C(=O)[C@H]2NC(=O)c2ccc(OC(F)(F)F)cc2)c(F)c1] | 546.2 | Method D, RT = 1.78 min, 100% | $^{1}$H NMR (400 MHz, DMSO-$d_6$) δ = 9.14-8.93 (m, 1H), 8.07-7.91 (m, 3H), 7.57-7.26 (m, 4H), 7.05-6.79 (m, 3H), 5.27-4.71 (m, 2H), 4.54-4.01 (m, 3H), 3.98 3.84 (m, 2H), 3.81-3.67 (m, 5H), 2.31-2.19 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 109 | 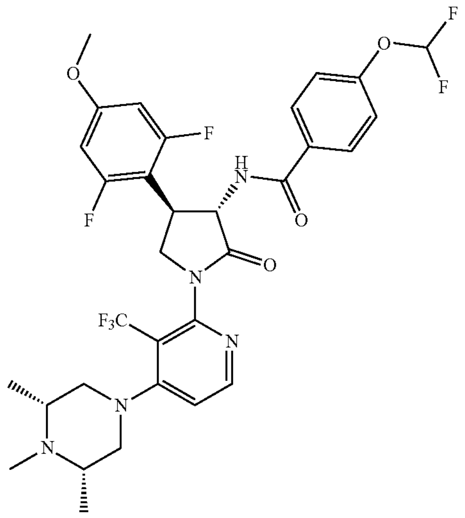 [SMILES: COc1cc(F)c([C@@H]2CN(c3nccc(N4C[C@@H](C)N(C)[C@@H](C)C4)c3C(F)(F)F)C(=O)[C@H]2NC(=O)c2ccc(OC(F)F)cc2)c(F)c1] | 684.3 | Method D, RT = 2.00 min, 100% | $^1$H NMR (400 MHz, DMSO-$d_6$) δ = 9.11-8.90 (m, 1H), 8.46-8.35 (m, 1H), 7.96-7.78 (m, 2H), 7.35 (t, J = 73 Hz, 1H), 7.31-7.25 (m, 3H), 6.79 (d, J =11.0 Hz, 2H), 5.18-4.97 (m, 1H), 4.44-4.35 (m, 1H), 4.28-4.13 (m, 1H), 3.76-3.74 (m, 1H), 3.73 (s, 3H), 3.00-2.70 (m, 3H), 2.35-2.26 (m, 3 H) 2.19 (s, 3H), 1.04 (d, J = 6.4 Hz, 6H). |
| 110 | 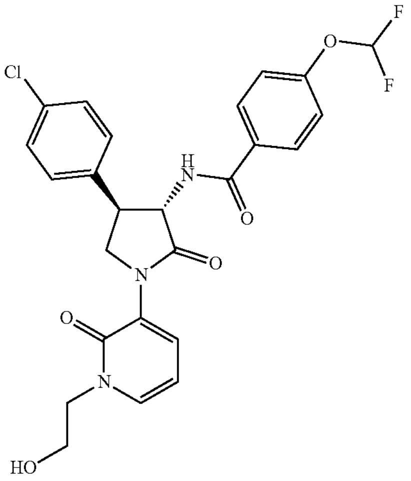 [SMILES: O=C(N[C@@H]1C(=O)N(c2cccn(CCO)c2=O)C[C@H]1c1ccc(Cl)cc1)c1ccc(OC(F)F)cc1] | 518.2 | Method D, RT = 1.547 min, 97.1% | $^1$H NMR (400 MHz, DMSO-$d_6$) δ = 8.96 (d, J = 9.0 Hz, 1H), 7.99-7.84 (m, 2H), 7.64 (dd, J = 7.0, 2.0 Hz, 1H), 7.60 (dd, J = 7.0, 2.0 Hz, 1H), 7.55-7.38 (m, 4H), 7.34 (t, J = 73.6 Hz, 1H), 7.29-7.24 (m, 2H), 6.32 (t, J = 7.0 Hz, 1H), 5.09-5.00 (m, 1H), 4.93 (t, J = 5.3 Hz, 1H), 4.16 (t, J = 7.8 Hz, 1H), 4.05-3.96 (m, 2H), 3.89-3.72 (m, 2H), 3.68-3.60 (m, 2H). |
| 111 | 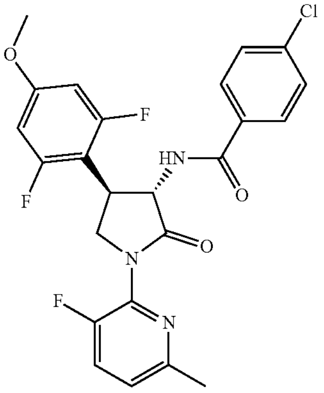 [SMILES: COc1cc(F)c([C@@H]2CN(c3nc(C)ccc3F)C(=O)[C@H]2NC(=O)c2ccc(Cl)cc2)c(F)c1] | 490.1 | Method D, RT = 1.932 min, 95% | $^1$H NMR (400 MHz, DMSO-$d_6$) δ = 9.16 (d, J = 8.8 Hz, 1H), 7.84 (d, J = 8.6 Hz, 2H), 7.80-7.72 (m, 1H), 7.58 (d, J = 8.6 Hz, 2H), 7.31 (dd, J = 8.2, 3.3 Hz, 1H), 6.79 (d, J = 10.8 Hz, 2H), 5.15-5.04 (m, 1H), 4.31-4.16 (m, 2H), 4.12-4.01 (m, 1H), 3.78 (s, 3H), 2.47 (s, 3H). |

TABLE 2-continued

| Ex | Structure | LCMS (M + H)+ | HPLC Method, RT (min.) & Purity | $^1$H NMR |
|---|---|---|---|---|
| 112 | 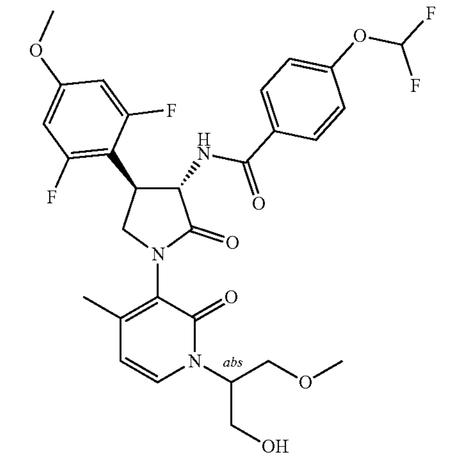 [SMILES: COCC(CO)n1ccc(C)c(N2C[C@@H](c3c(F)cc(OC)cc3F)[C@H](NC(=O)c3ccc(OC(F)F)cc3)C2=O)c1=O] | 608.3 | Method D, RT = 1.602 min, 98.8% | $^1$H NMR (400 MHz, DMSO-$d_6$) δ = 9.15-8.89 (m, 1H), 7.98-7.84 (m, 2H), 7.67-7.56 (m, 1H), 7.55-7.05 (m, 2H), 7.34 (t, J = 73.6 Hz, 1H), 6.76 (dd, J = 5.0, 10.9 Hz, 2H), 6.29-6.12 (m, 1H), 5.36-4.85 (m, 2H), 4.28-4.08 (m, 2H), 3. 76 (s, 3H), 3.74-3.59 (m, 4H), 3.50 (br s, 1H), 3.25-3.21 (2s, 3H), 2.25-2.02 (2s, 3H), 1.98-1.80 (m, 1H). (mixture of interconvertible atropisomers) |
| 113 | 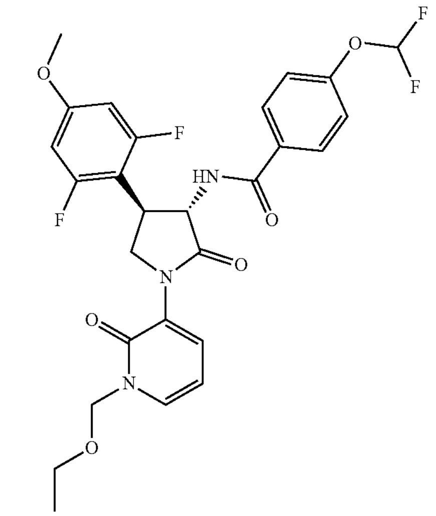 [SMILES: CCOCn1cccc(N2C[C@@H](c3c(F)cc(OC)cc3F)[C@H](NC(=O)c3ccc(OC(F)F)cc3)C2=O)c1=O] | 564.2 | Method D, RT = 2.304 min, 99.9% | $^1$H NMR (400 MHz, DMSO-$d_6$) δ = 9.01 (d, J = 8.5 Hz, 1H), 7.93-7.86 (m, 2H), 7.67 (dd, J = 7.0, 2.0 Hz, 1H), 7.62-7.57 (m, 1H), 7.35 (t, J = 72.6 Hz, 1H), 7.30-7.24 (m, 2H), 6.77 (d, J = 10.5 Hz, 2H), 6.33 (t, J = 7.0 Hz, 1H), 5.12 (dd, J = 11.0, 9.0 Hz, 1H), 4.17-4.04 (m, 3H), 4.02-3.93 (m, 2H), 3.77 (s, 3H), 3.60 (t, J = 5.3 Hz, 2H), 3.25 (s, 3H). |
| 114 | 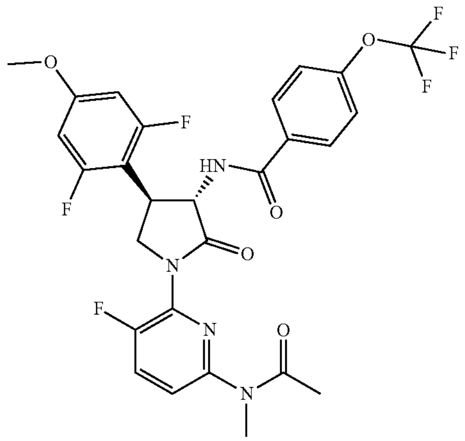 [SMILES: COc1cc(F)c([C@@H]2CN(c3nc(N(C)C(C)=O)ccc3F)C(=O)[C@H]2NC(=O)c2ccc(OC(F)(F)F)cc2)c(F)c1] | 597.2 | Method D, RT = 1.88 min, 97% | $^1$H NMR (400 MHz, DMSO-$d_6$) δ = 9.22 (d, J = 8.8 Hz, 1H), 8.05-7.83 (m, 3H), 7.57 (dd, J = 2.6, 8.9 Hz, 1H), 7.50 (d, J = 8.3 Hz, 2H), 6.79 (d, J = 10.8 Hz, 2H), 5.10 (br dd, J = 8.8, 10.3 Hz, 1H), 4.30-4.16 (m, 2H), 4.09-4.03 (m, 1H), 3.77 (s, 3H), 3.27 (s, 3H), 2.07 (s, 3H). |

TABLE 2-continued

| Ex | Structure | LCMS (M + H)+ | HPLC Method, RT (min.) & Purity | $^1$H NMR |
|---|---|---|---|---|
| 115 | 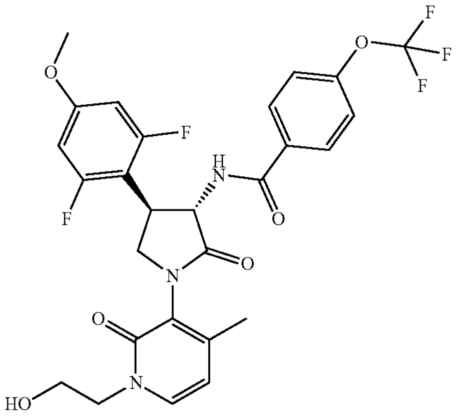 [SMILES: COc1cc(F)c([C@@H]2CN(c3c(C)ccn(CCO)c3=O)C(=O)[C@H]2NC(=O)c2ccc(OC(F)(F)F)cc2)c(F)c1] | 582.3 | Method D, RT = 2.369 min, 99.5% | $^1$H NMR (400 MHz, DMSO-$d_6$) δ = 9.26-9.02 (m, 1H), 8.02-7.89 (m, 2H), 7.61-7.42 (m, 3H), 6.83-6.71 (m, 2H), 6.27-6.14 (m, 1H), 5.41-4.85 (m, 2H), 4.33-3.87 (m, 4H), 3.83-3.72 (m, 3H), 3.70-3.58 (m, 2H), 3.56-3.44 (m, 1H), 2.24-2.02 (2s, 3H). (mixture of interconvertible atropisomers) |
| 116 | 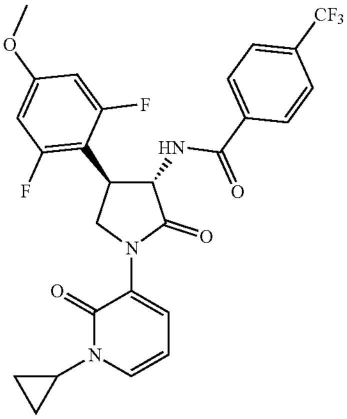 [SMILES: COc1cc(F)c([C@@H]2CN(c3cccn(C4CC4)c3=O)C(=O)[C@H]2NC(=O)c2ccc(C(F)(F)F)cc2)c(F)c1] | 548.2 | Method D, RT = 1.787 min, 99.6% | $^1$H NMR (400 MHz, DMSO-$d_6$) δ = 9.23 (d, J = 8.6 Hz, 1H), 8.02 (d, J = 8.3 Hz, 2H), 7.88 (d, J = 8.3 Hz, 2H), 7.62-7.57 (m, 2H), 6.78 (d, J = 10.8 Hz, 2H), 6.30 (t, J = 7.1 Hz, 1H), 5.14 (dd, J = 11.0, 8.8 Hz, 1H), 4.18-4.06 (m, 1H), 4.04-3.94 (m, 2H), 3.77 (s, 3H), 3.43-3.38 (m, 1H), 1.10-0.98 (m, 2H), 0.93-0.80 (m, 2H). |
| 117 | 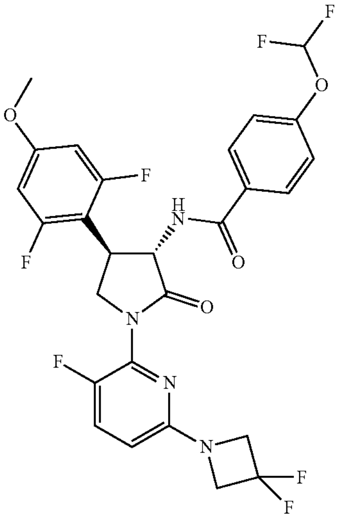 [SMILES: COc1cc(F)c([C@@H]2CN(c3nc(N4CC(F)(F)C4)ccc3F)C(=O)[C@H]2NC(=O)c2ccc(OC(F)F)cc2)c(F)c1] | 599.2 | Method D, RT = 2.095 min, 93% | $^1$H NMR (400 MHz, DMSO-$d_6$) δ = 9.07 (d, J = 8.5 Hz, 1H), 7.88 (d, J = 9.0 Hz, 2H), 7.74 (t, J = 9.0 Hz, 1H), 7.34 (t, J = 76.0 Hz, 1 H), 7.29-7.26 (m, 2H), 6.79 (d, J = 10.5 Hz, 2H), 6.59 (dd, J = 8.5, 2.5 Hz, 1H), 5.16-5.03 (m, 1H), 4.46-4.33 (m, 4H), 4.25-4.14 (m, 2H), 4.02-3.90 (m, 1H), 3.77 (s, 3H). |

TABLE 2-continued

| Ex | Structure | LCMS (M + H)+ | HPLC Method, RT (min.) & Purity | $^1$H NMR |
|---|---|---|---|---|
| 118 | 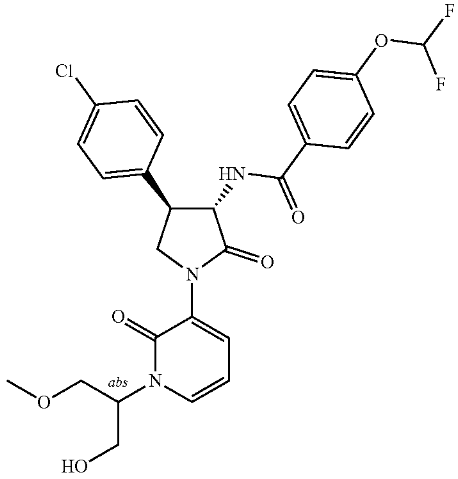 [SMILES: COCC(CO)n1cccc(N2C[C@@H](c3ccc(Cl)cc3)[C@H](NC(=O)c3ccc(OC(F)F)cc3)C2=O)c1=O] | 562.2 | Method D, RT = 1.612 min, 95.8% | $^1$H NMR (400 MHz, DMSO-$d_6$) δ = 8.98 (d, J = 8.8 Hz, 1H), 7.92 (d, J = 9.0 Hz, 2H), 7.69 (dd, J = 7.1, 2.0 Hz, 1H), 7.56 (dd, J = 7.3, 2.0 Hz, 1H), 7.50-7.37 (m, 4H), 7.34 (t, J = 73.6 Hz, 1H), 7.32-7.19 (m, 2H), 6.34 (t, J = 7.1 Hz, 1H), 5.13-5.00 (m, 3H), 4.16 (t, J = 7.9 Hz, 1H), 3.86-3.60 (m, 6H), 3.23 (s, 3H). |
| 119 | 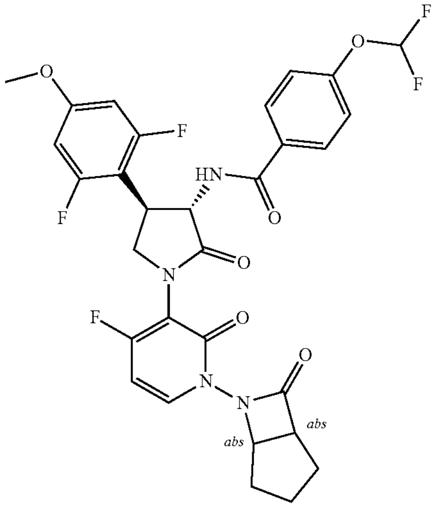 [SMILES: COc1cc(F)c([C@@H]2CN(c3c(F)ccn(N4C(=O)C5CCCC54)c3=O)C(=O)[C@H]2NC(=O)c2ccc(OC(F)F)cc2)c(F)c1] | 617.2 | Method D, RT = 2.014 min, 94% | $^1$H NMR (400 MHz, DMSO-$d_6$) δ = 9.09 (d, J = 8.3 Hz, 1H), 7.97-7.80 (m, 3H), 7.59 (dd, J = 8.7, 2.8 Hz, 1H), 7.34 (t, J = 73.6 Hz, 1H), 7.29-7.27 (m, 2H), 6.79 (d, J = 10.8 Hz, 2H), 5.13-5.09 (m, 1H), 4.60-4.58 (m, 1H), 4.30-4.18 (m, 2H), 4.05-3.98 (m, 1H), 3.77 (s, 3H), 3.67-3.64 (m, 1H), 2.31-2.22 (m, 1H), 1.95-1.88 (m, 1H), 1.85-1.79 (m, 1H), 1.69-1.64 (m, 1H), 1.56-1.35 (m, 2H). |
| 120 | 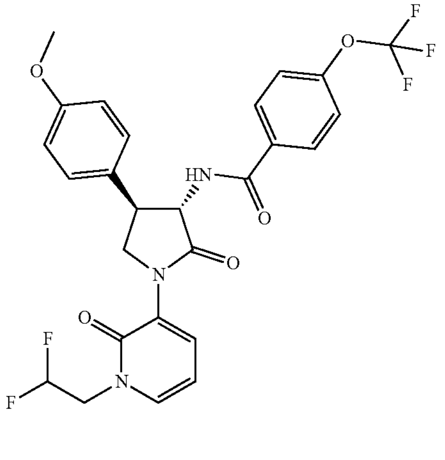 [SMILES: COc1ccc([C@@H]2CN(c3cccn(CC(F)F)c3=O)C(=O)[C@H]2NC(=O)c2ccc(OC(F)(F)F)cc2)cc1] | 552.3 | Method D, RT = 1.777 min, 100% | $^1$H NMR (400 MHz, DMSO-$d_6$) δ = 9.04 (d, J = 8.6 Hz, 1H), 8.03-7.93 (m, 2H), 7.72 (dd, J = 6.8, 2.0 Hz, 1H), 7.66 (dd, J = 7.3, 2.0 Hz, 1H), 7.48 (d, J = 7.8 Hz, 2H), 7.39-7.26 (m, 2H), 6.97-6.82 (m, 2H), 6.42 (t, J = 7 Hz, 1H), 6.35 (tt, J = 56.2, 3.5 Hz, 1H), 5.03 (dd, J = 11.1, 8.7 Hz, 1H), 4.53-4.35 (m, 2H), 4.19-4.09 (m, 1H), 3.81-3.68 (m, 5H). |

TABLE 2-continued

| Ex | Structure | LCMS (M + H)+ | HPLC Method, RT (min.) & Purity | $^1$H NMR |
|---|---|---|---|---|
| 121 | 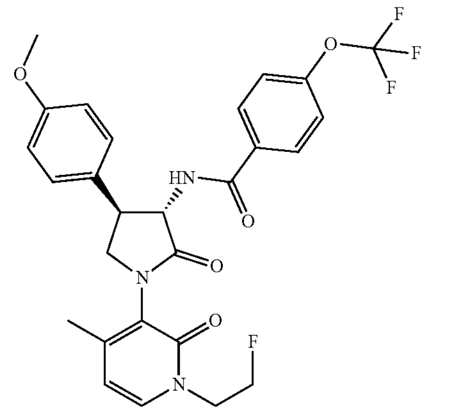 [SMILES: COc1ccc([C@@H]2CN(c3c(C)ccn(CCF)c3=O)C(=O)[C@H]2NC(=O)c2ccc(OC(F)(F)F)cc2)cc1] | 566.2 | Method D, RT = 1.817 min, 99% | $^1$H NMR (400 MHz, DMSO-$d_6$) δ = 9.05 (dd, J = 16.0, 8.7 Hz, 1H), 8.04-7.91 (m, 2H), 7.77-7.18 (m, 5H), 7.01-6.67 (m, 2H), 6.48-6.10 (m, 2H), 5.35-4.62 (m, 1H), 4.53-4.26 (m, 2H), 4.12-3.77 (m, 2H), 3.77-3.62 (m, 4H), 3.57-3.36 (m, 1H), 2.27-1.98 (2s, 3H). (mixture of interconvertible atropisomers) |
| 122 | 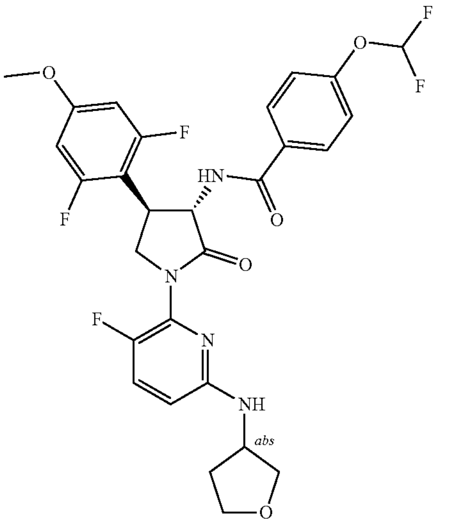 [SMILES: COc1cc(F)c([C@@H]2CN(c3nc(NC4CCOC4)ccc3F)C(=O)[C@H]2NC(=O)c2ccc(OC(F)F)cc2)c(F)c1] | 593.3 | Method D, RT = 1.82 min, 98% | $^1$H NMR (400 MHz, DMSO-$d_6$) δ = 9.07 (d, J = 8.6 Hz, 1H), 7.95-7.81 (m, 2H), 7.53-7.48 (m, 1H), 7.35 (t, J = 73.6 Hz, 1H), 7.28-7.26 (m, 2H) 6.96 (d, J = 5.9 Hz, 1H), 6.78 (d, J = 10.8 Hz, 2H), 6.46 (dd, J = 2.6, 8.9 Hz, 1H), 5.19-5.03 (m, 1H), 4.31-4.19 (m, 1H), 4.19-4.07 (m, 2H), 4.04-3.94 (m, 1H), 3.87-3.86 (m, 1H), 3.84-3.77 (m, 1H), 3.76 (s, 3H), 3.70 (dt, J = 5.7, 8.1 Hz, 1H), 3.50-3.49 (m, 1H), 2.19-2.16 (m, 1H), 1.83-1.70 (m, 1H). |
| 123 | 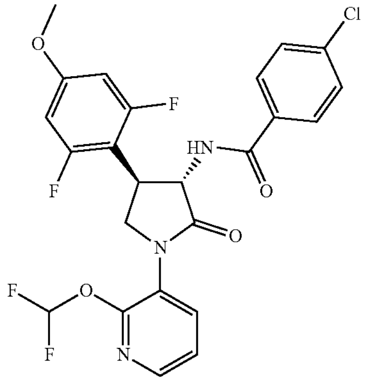 [SMILES: COc1cc(F)c([C@@H]2CN(c3cccnc3OC(F)F)C(=O)[C@H]2NC(=O)c2ccc(Cl)cc2)c(F)c1] | 524.1 | Method D, RT = 1.794 min, 94.4% | $^1$H NMR (400 MHz, DMSO-$d_6$) δ = 9.10 (d, J = 8.6 Hz, 1H), 7.93 (t, J = 59.6 Hz, 1H), 7.86-7.66 (m, 4H), 7.63-7.47 (m, 2H), 6.78 (d, J = 10.8 Hz, 2H), 6.56 (t, J = 7.1 Hz, 1H), 5.09 (dd, J = 10.9, 8.7 Hz, 1H), 4.19-4.06 (m, 1H), 4.03-3.92 (m, 2H), 3.77 (s, 3H). |

TABLE 2-continued

| Ex | Structure | LCMS (M + H)+ | HPLC Method, RT (min.) & Purity | $^1$H NMR |
|---|---|---|---|---|
| 124 | 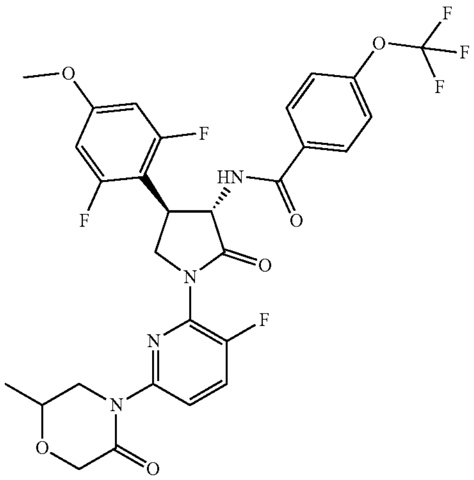 [SMILES: COc1cc(F)c([C@@H]2CN(c3nc(N4CC(C)OCC4=O)ccc3F)C(=O)[C@H]2NC(=O)c2ccc(OC(F)(F)F)cc2)c(F)c1] | 639.2 | Method D, RT = 2.01 min, 100% | $^1$H NMR (400 MHz, DMSO-$d_6$) δ = 9.20 (br d, J = 8.6 Hz, 1H), 8.02-7.87 (m, 4H), 7.49 (d, J = 8.3 Hz, 2H), 6.80 (d, J = 11.0 Hz, 2H), 5.17-5.07 (m, 1H), 4.33-4.20 (m, 4H), 4.12-3.98 (m, 3H), 3.77 (s, 3H), 3.57-3.49 (m, 1H), 1.26 (d, J = 6.1 Hz, 3H). |
| 125 | 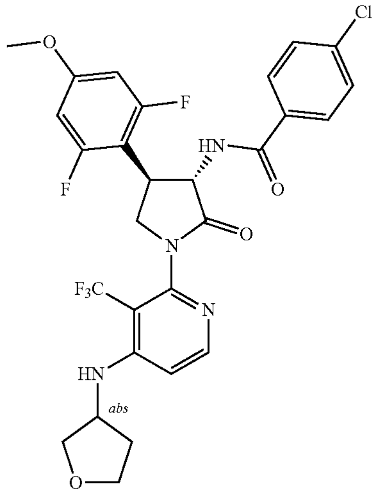 [SMILES: COc1cc(F)c([C@@H]2CN(c3nccc(NC4CCOC4)c3C(F)(F)F)C(=O)[C@H]2NC(=O)c2ccc(Cl)cc2)c(F)c1] | 611.2 | Method D, RT = 1.88 min, 100% | $^1$H NMR (400 MHz, DMSO-$d_6$) δ = 9.09 (br d, J = 8.8 Hz, 1H), 8.32-8.21 (m, 1H), 7.91-7.78 (m, 2H), 7.65-7.51 (m, 2H), 6.97-6.85 (m, 1H), 6.78 (d, J = 10.8 Hz, 2H), 6.13-5.95 (m, 1H), 5.21-5.02 (m, 1H), 4.37-4.11 (m, 3H), 3.95-3.83 (m, 2H), 3.82 (s, 3H), 3.79-3.64 (m, 3H), 2.31-2.19 (m, 1H), 2.04-1.89 (m, 1H). |
| 126 | 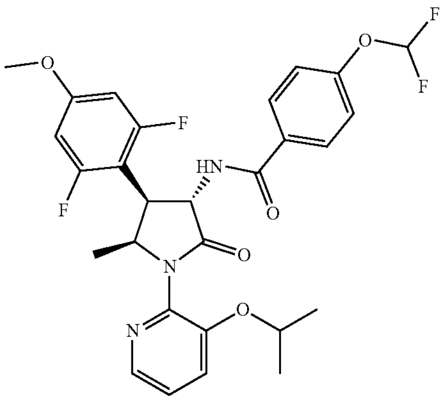 [SMILES: COc1cc(F)c([C@H]2[C@H](NC(=O)c3ccc(OC(F)F)cc3)C(=O)N(c3ncccc3OC(C)C)[C@H]2C)c(F)c1] | 562.2 | Method D, RT = 1.95 min, 100% | $^1$H NMR (400 MHz, DMSO-$d_6$) δ = 8.90 (d, J = 8.6 Hz, 1H), 8.07 (dd, J = 4.6, 1.2 Hz, 1H), 7.99-7.81 (m, 2H), 7.61 (d, J = 7.3 Hz, 1H), 7.39-7.35 (m, 1H), 7.35 (t, J = 73.6 Hz, 1H), 7.27-7.24 (m, 2H), 6.87-6.67 (m, 2H), 5.60 (dd, J = 11.5, 8.6 Hz, 1H), 4.77-4.68 (m, 1H), 4.56-4.43 (m, 1H), 4.40-4.35 (m, 1H), 3.77 (s, 3H), 1.30 (d, J = 5.5 Hz, 3H), 1.26 (d, J = 5.5 Hz, 3H), 0.90 (d, J = 6.4 Hz, 3H). |

TABLE 2-continued

| Ex | Structure | LCMS (M + H)+ | HPLC Method, RT (min.) & Purity | $^1$H NMR |
|---|---|---|---|---|
| 127 | 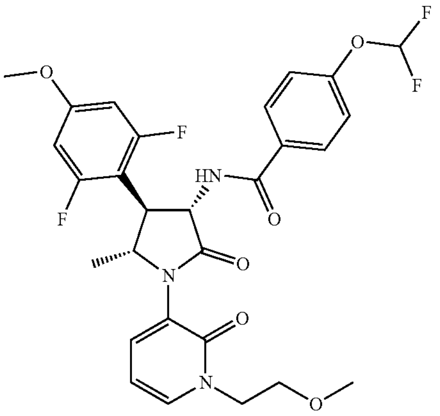 [SMILES: COCCn1cccc(N2C(=O)[C@@H](NC(=O)c3ccc(OC(F)F)cc3)[C@H](c3c(F)cc(OC)cc3F)[C@H]2C)c1=O] | 578.3 | Method D, RT = 1.67 min, 100% | $^1$H NMR (400 MHz, DMSO-$d_6$) δ = 8.98 (d, J = 8.6 Hz, 1H), 7.93-7.82 (m, 2H), 7.69 (dd, J = 6.8, 2.0 Hz, 1H), 7.48-7.45 (m, 1H ), 7.35 (t, J = 73.6 Hz, 1H), 7.28-7.26 (m, 2H), 6.87-6.70 (m, 2H), 6.34 (t, J = 7.0 Hz, 1H), 5.11 (dd, J = 11.1, 8.4 Hz, 1H), 4.53-5.09 (m, 1H), 4.17-4.08 (m, 2H), 3.77 (s, 3H), 3.76-3.74 (m, 1H), 3.63-3.57 (m, 2H), 3.24 (s, 3H), 0.99 (d, J = 6.1 Hz, 3H). |
| 128 | 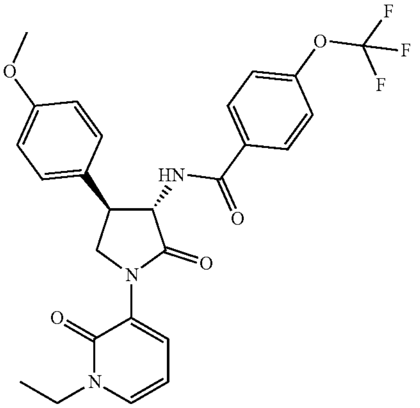 [SMILES: CCn1cccc(N2C[C@@H](c3ccc(OC)cc3)[C@H](NC(=O)c3ccc(OC(F)(F)F)cc3)C2=O)c1=O] | 516.2 | Method D, RT = 1.7 min, 100% | $^1$H NMR (400 MHz, DMSO-$d_6$) δ = 9.03 (d, J = 8.8 Hz, 1H), 8.05-7.92 (m, 2H), 7.75 (dd, J = 6.6, 2.0 Hz, 1H), 7.58 (dd, J = 7.3, 2.0 Hz, 1H), 7.48 (d, J = 8.1 Hz, 2H), 7.39-7.28 (m, 2H), 7.00-6.83 (m, 2H), 6.35 (t, J = 7.0 Hz, 1H), 5.02 (dd, J = 11.1, 8.7 Hz, 1H), 4.18-4.08 (m, 1H), 4.05-3.92 (m, 2H), 3.83-3.68 (m, 5H), 1.25 (t, J = 7.1 Hz, 3H). |
| 129 | 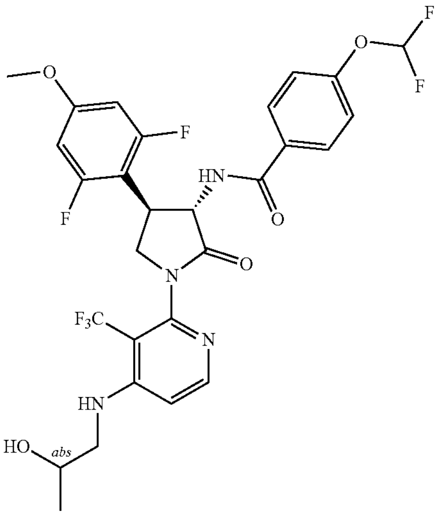 [SMILES: COc1cc(F)c([C@@H]2CN(c3nccc(NCC(C)O)c3C(F)(F)F)C(=O)[C@H]2NC(=O)c2ccc(OC(F)F)cc2)c(F)c1] | 631.2 | Method D, RT = 1.75 min, 98.77% | $^1$H NMR (400 MHz, DMSO-$d_6$) δ = 9.06-8.99 (m, 1H), 8.24-8.14 (m, 1H), 7.94-7.81 (m, 2H), 7.33 (t, J = 73.6 Hz, 1H), 7.28-7.24 (m, 2H), 6.93-6.81 (m, 1H), 6.77 (d, J = 10.5 Hz, 2H), 6.28 (br d, J = 4.9 Hz, 1H), 5.16-4.93 (m, 2H), 4.32-4.10 (m, 2H), 3.92-3.82 (m, 1H), 3.76 (s, 3H), 3.75-3.68 (m, 1H), 3.47-3.39 (m, 2H), 1.18-1.04 (m, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 130 | 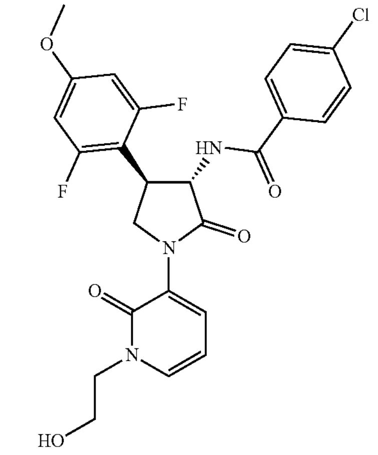 [SMILES: COc1cc(F)c([C@@H]2CN(c3cccn(CCO)c3=O)C(=O)[C@H]2NC(=O)c2ccc(Cl)cc2)c(F)c1] | 518.2 | Method D, RT = 1.467 min, 100% | $^1$H NMR (400 MHz, DMSO-$d_6$) δ = 9.07 (d, J = 8.6 Hz, 1H), 7.83 (d, J = 8.6 Hz, 2H), 7.65 (dd, J = 6.8, 2.0 Hz, 1H), 7.62-7.43 (m, 3H), 6.77 (d, J = 10.8 Hz, 2H), 6.31 (t, J = 7.0 Hz, 1H), 5.12 (dd, J = 11.0, 8.8 Hz, 1H), 5.02-4.88 (m, 1H), 4.19-3.88 (m, 5H), 3.76 (s, 3H), 3.69-3.60 (m, 2H). |
| 131 | 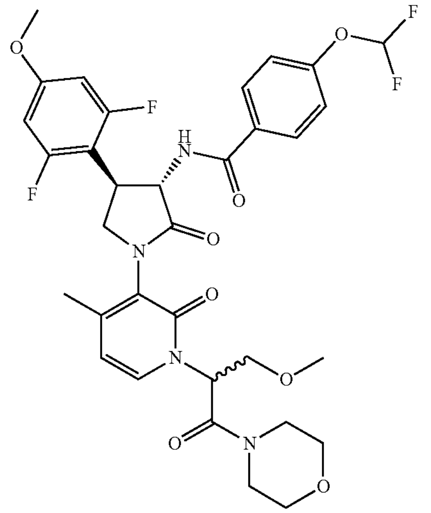 [SMILES: COCC(C(=O)N1CCOCC1)n1ccc(C)c(N2C[C@@H](c3c(F)cc(OC)cc3F)[C@H](NC(=O)c3ccc(OC(F)F)cc3)C2=O)c1=O] | 691.2 | Method D, RT = 1.732 min, 99% | $^1$H NMR (400 MHz, DMSO-$d_6$) δ = 9.14-8.91 (m, 1H), 7.97-7.80 (m, 2H), 7.69-7.55 (m, 1H), 7.35 (t, J = 73.6 Hz, 1H), 7.28 (m, 1H), 6.86-6.69 (m, 2H), 6.40-6.25 (m, 1H), 6.08-5.99 (m, 1H), 5.37-4.87 (m, 2H), 3.91-3.77 (m, 4H), 3.77-3.73 (m, 3H), 3.63-3.37 (m, 4H), 3.30-3.22 (m, 3H), 2.83-2.58 (m, 3H), 2.26-2.03 (m, 3H), 1.81 (br s, 2H). (mixture of interconvertible atropisomers) |
| 132 | 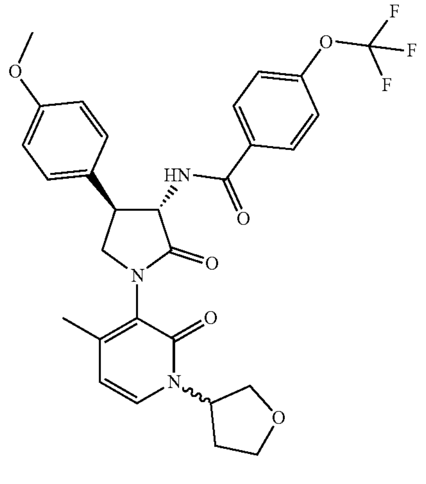 [SMILES: COc1ccc([C@@H]2CN(c3c(C)ccn(C4CCOC4)c3=O)C(=O)[C@H]2NC(=O)c2ccc(OC(F)(F)F)cc2)cc1] | 572.3 | Method D, RT = 1.72 min, 100% | $^1$H NMR (400 MHz, DMSO-$d_6$) δ = 9.14-8.91 (m, 1H), 8.06-7.96 (m, 2H), 7.53 (td, J = 3.5, 7.1 Hz, 1H), 7.50-7.43 (m, 2H), 7.43-7.34 (m, 1H), 7.32 (d, J = 8.8 Hz, 1H), 7.01-6.79 (m, 2H), 6.28 (dd, J = 3.1, 7.2 Hz, 1H), 5.43-5.31 (m, 1H), 5.28-4.61 (m, 1H), 4.16-4.02 (m, 1H), 3.97-3.64 (m, 5H), 3.47 (t, J = 9.4 Hz, 1H), 2.98-2.83 (m, 2H), 2.19-2.05 (2s, 3H), 2.03-1.83 (m, 1H), 1.19-1.13 (m, 2H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 133 | 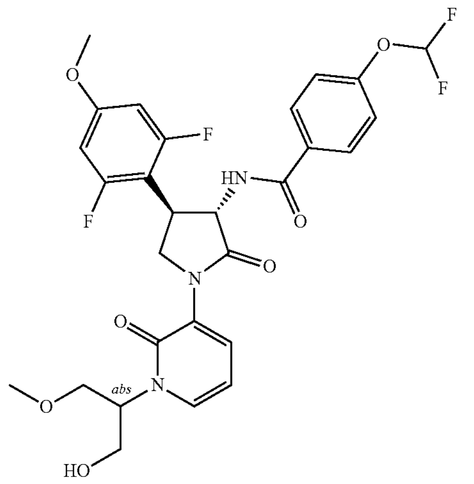 [SMILES: COCC(CO)n1cccc(N2C[C@@H](c3c(F)cc(OC)cc3F)[C@H](NC(=O)c3ccc(OC(F)F)cc3)C2=O)c1=O] | 594.2 | Method D, RT = 1.526 min, 100% | $^1$H NMR (400 MHz, DMSO-$d_6$) δ = 9.01 (d, J = 8.6 Hz, 1H), 7.95-7.83 (m, 2H), 7.70 (dd, J = 6.8, 2.0 Hz, 1H), 7.56 (dd, J = 7.2, 1.8 Hz, 1H), 7.34 (t, J = 73.6 Hz, 1H), 7.28 (m, 2H), 6.76 (d, J = 10.5 Hz, 2H), 6.34 (t, J = 7.0 Hz, 1H), 5.17-5.04 (m, 3H), 4.14-4.03 (m, 1H), 4.03-3.92 (m, 2H), 3.81-3.65 (m, 6H), 3.65-3.56 (m, 1H), 3.23 (s, 3H). |
| 134 | 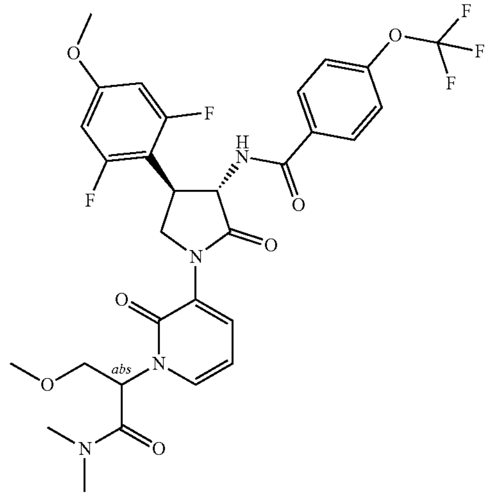 [SMILES: COCC(C(=O)N(C)C)n1cccc(N2C[C@@H](c3c(F)cc(OC)cc3F)[C@H](NC(=O)c3ccc(OC(F)(F)F)cc3)C2=O)c1=O] | 653.3 | Method D, RT = 1.790 min, 98.6% | $^1$H NMR (400 MHz, DMSO-$d_6$) δ = 9.12 (d, J = 8.3 Hz, 1H), 8.00-7.88 (m, 2H), 7.72 (dd, J = 7.0, 1.8 Hz, 1H), 7.61 (dd, J = 7.2, 1.8 Hz, 1H), 7.48 (dd, J = 1.0, 8.8 Hz, 2H), 6.77 (d, J = 10.8 Hz, 2H), 6.41 (t, J = 7.2 Hz, 1H), 6.08 (dd, J = 8.8, 5.1 Hz, 1H), 5.10 (dd, J = 11.0, 8.6 Hz, 1H), 4.16-4.04 (m, 1H), 4.02-3.91 (m, 2H), 3.89-3.80 (m, 2H), 3.76 (s, 3H), 3.27 (s, 3H), 3.11 (s, 3H), 2.85 (s, 3H). |
| 135 | 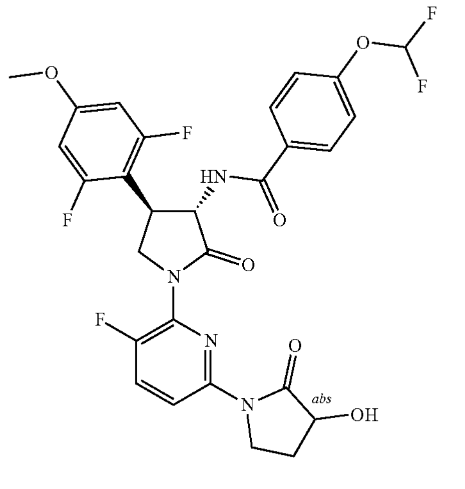 [SMILES: COc1cc(F)c([C@@H]2CN(c3nc(N4CCC(O)C4=O)ccc3F)C(=O)[C@H]2NC(=O)c2ccc(OC(F)F)cc2)c(F)c1] | 607.2 | Method D, RT = 1.66 min, 100% | $^1$H NMR (400 MHz, DMSO-$d_6$) δ = 9.12 (d, J = 8.6 Hz, 1H), 8.28 (dd, J = 9.0, 3.2 Hz, 1H), 7.94 (t, J = 9.0 Hz, 1H), 7.91-7.83 (m, 2H), 7.35 (t, J = 73.6 Hz, 1H), 7.28-7.26 (m, 2H), 6.80 (d, J = 10.8 Hz, 2H), 5.86 (br d, J = 6.1 Hz, 1H), 5.17-5.05 (m, 1H), 4.46-4.35 (m, 1H), 4.30-4.17 (m, 2H), 4.12-3.90 (m, 2H), 3.77 (s, 3H), 3.75-3.60 (m, 1H), 2.43-2.34 (m, 1H), 1.88-1.75 (m, 1H). |

TABLE 2-continued

| Ex | Structure | LCMS (M + H)+ | HPLC Method, RT (min.) & Purity | $^1$H NMR |
|---|---|---|---|---|
| 136 | 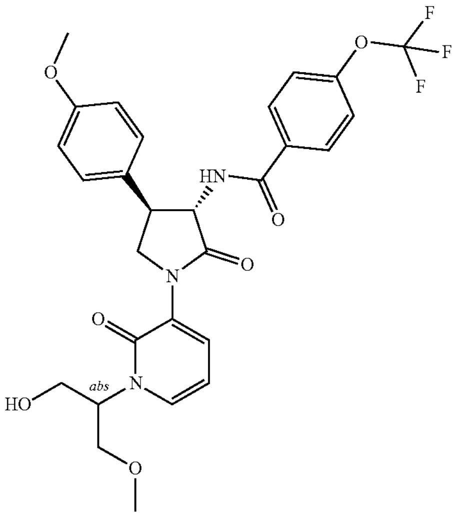 [SMILES: COCC(CO)n1cccc(N2C[C@@H](c3ccc(OC)cc3)[C@H](NC(=O)c3ccc(OC(F)(F)F)cc3)C2=O)c1=O] | 576.3 | Method D, RT = 1.606 min, 98% | $^1$H NMR (400 MHz, DMSO-$d_6$) δ = 9.05-8.98 (m, 1H), 7.98 (d, J = 8.3 Hz, 2H), 7.70-7.65 (m, 1H), 7.61-7.52 (m, 1H), 7.51-7.39 (m, 2H), 7.34 (d, J = 8.3 Hz, 2H), 6.90 (d, J = 8.3 Hz, 2H), 6.34 (t, J = 6.8 Hz, 1H), 5.12-4.96 (m, 3H), 4.15-4.06 (m, 1H), 3.79-3.60 (m, 9H), 3.23 (s, 3H). (NMR not clean) |
| 137 | 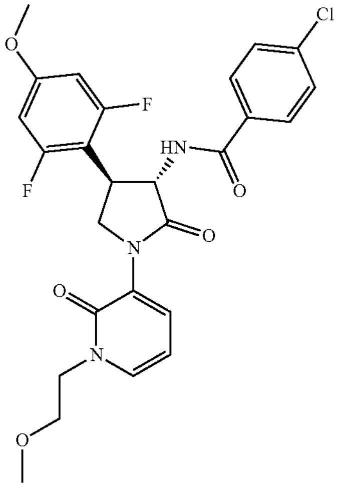 [SMILES: COCCn1cccc(N2C[C@@H](c3c(F)cc(OC)cc3F)[C@H](NC(=O)c3ccc(Cl)cc3)C2=O)c1=O] | 532.1 | Method D, RT = 1.666 min, 99.6% | $^1$H NMR (400 MHz, DMSO-$d_6$) δ = 9.06 (d, J = 8.8 Hz, 1H), 7.93-7.76 (m, 2H), 7.66 (dd, J = 6.8, 2.0 Hz, 1H), 7.63-7.48 (m, 3H), 6.77 (d, J = 10.5 Hz, 2H), 6.33 (t, J = 7.0 Hz, 1H), 5.12 (dd, J = 11.0, 8.6 Hz, 1H), 4.23-4.04 (m, 2H), 4.02-3.94 (m, 2H), 3.93-3.89 (m, 1H), 3.77 (s, 3H), 3.61 (t, J = 5.3 Hz, 2H), 3.26 (s, 3H). |
| 138 | 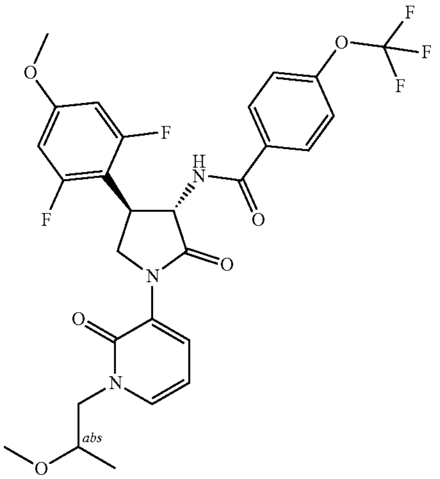 [SMILES: COc1cc(F)c([C@@H]2CN(c3cccn(CC(C)OC)c3=O)C(=O)[C@H]2NC(=O)c2ccc(OC(F)(F)F)cc2)c(F)c1] | 596.2 | Method D, RT = 1.869 min, 100% | $^1$H NMR (400 MHz, DMSO-$d_6$) δ = 9.11 (d, J = 8.6 Hz, 1H), 8.00-7.83 (m, 2H), 7.61 (dt, J = 2.0, 7.1 Hz, 2H), 7.48 (d, J = 8.1 Hz, 2H), 6.77 (d, J = 10.8 Hz, 2H), 6.32 (t, J = 7.0 Hz, 1H), 5.13 (dd, J = 10.6, 8.7 Hz, 1H), 4.15-3.97 (m, 3H), 3.97-3.81 (m, 2H), 3.76 (s, 3H), 3.68-3.59 (m, 1H), 3.18 (s, 3H), 1.09 (d, J = 6.1 Hz, 3H). |

TABLE 2-continued

| Ex | Structure | LCMS (M + H)+ | HPLC Method, RT (min.) & Purity | $^{1}$H NMR |
|---|---|---|---|---|
| 139 | 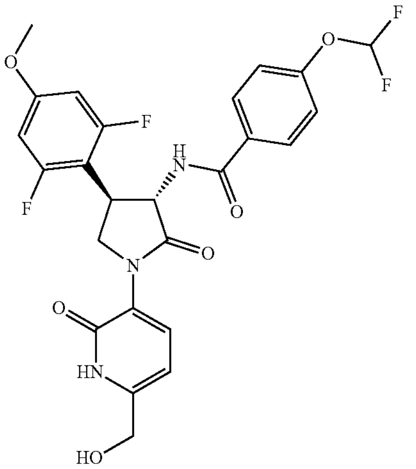 [SMILES: COc1cc(F)c([C@@H]2CN(c3ccc(CO)[nH]c3=O)C(=O)[C@H]2NC(=O)c2ccc(OC(F)F)cc2)c(F)c1] | 536.3 | Method D, RT = 1.386 min, 97.2% | $^{1}$H NMR (400 MHz, DMSO-d$_6$) δ = 11.94-11.70 (m, 1H), 9.00 (d, J = 8.6 Hz, 1H), 7.95-7.84 (m, 2H), 7.63-7.55 (m, 1H), 7.34 (t, J = 73.6 Hz, 1H), 7.28 (m, 2H), 6.77 (d, J = 10.8 Hz, 2H), 6.26 (dt, J = 1.1, 2.9 Hz, 1H), 5.56-5.43 (m, 1H), 5.17-5.03 (m, 1H), 4.41-4.23 (m, 2H), 4.12-3.88 (m, 3H), 3.76 (s, 3H). |
| 140 | 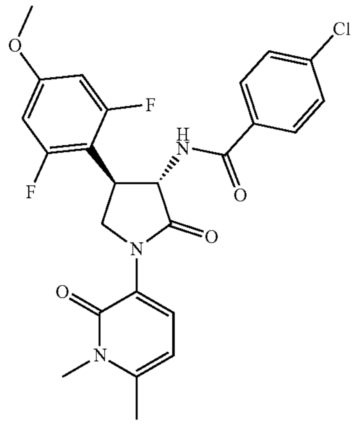 [SMILES: COc1cc(F)c([C@@H]2CN(c3ccc(C)n(C)c3=O)C(=O)[C@H]2NC(=O)c2ccc(Cl)cc2)c(F)c1] | 502.2 | Method D, RT = 1.605 min, 98.6% | $^{1}$H NMR (400 MHz, DMSO-d$_6$) δ = 9.07 (d, J = 8.6 Hz, 1H), 7.89-7.78 (m, 2H), 7.62-7.52 (m, 2H), 7.46 (d, J = 7.3 Hz, 1H), 6.77 (d, J = 10.5 Hz, 2H), 6.28-6.18 (m, 1H), 5.12 (dd, J = 11.1, 8.7 Hz, 1H), 4.16-4.02 (m, 1H), 3.99-3.86 (m, 2H), 3.76 (s, 3H), 3.49 (s, 3H), 2.39 (s, 3H) |
| 141 | 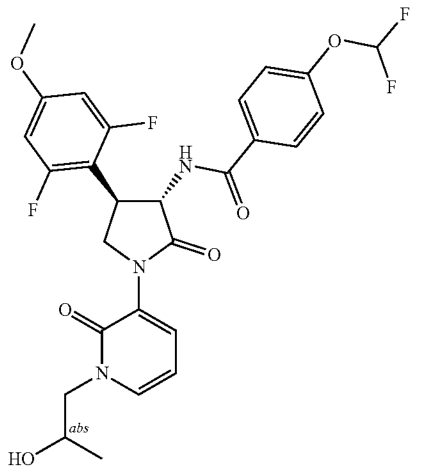 [SMILES: COc1cc(F)c([C@@H]2CN(c3cccn(CC(C)O)c3=O)C(=O)[C@H]2NC(=O)c2ccc(OC(F)F)cc2)c(F)c1] | 564.2 | Method D, RT = 1.508 min, 100% | $^{1}$H NMR (400 MHz, DMSO-d$_6$) δ = 9.00 (d, J = 8.6 Hz, 1H), 7.97-7.81 (m, 2H), 7.62 (dd, J = 6.7, 2.1 Hz, 1H), 7.58 (dd, J = 7.1, 2.0 Hz, 1H), 7.34 (t, J = 73.6 Hz, 1H), 7.28 (m, 2H), 6.76 (d, J = 10.8 Hz, 2H), 6.31 (t, J = 7.1 Hz, 1H), 5.11 (dd, J = 10.9, 8.7 Hz, 1H), 4.94 (d, J = 5.4 Hz, 1H), 4.15-3.85 (m, 5H), 3.76 (s, 3H), 3.64 (dd, J = 12.8, 8.2 Hz, 1H), 1.09 (d, J = 6.4 Hz, 3H). |

TABLE 2-continued

| Ex | Structure | LCMS (M + H)+ | HPLC Method, RT (min.) & Purity | $^1$H NMR |
|---|---|---|---|---|
| 142 | 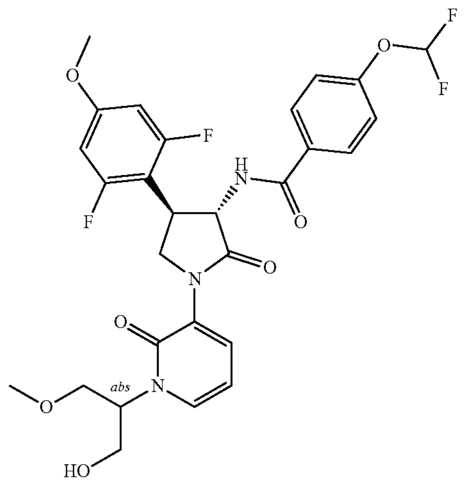 [SMILES: COCC(CO)n1cccc(N2C[C@@H](c3c(F)cc(OC)cc3F)[C@H](NC(=O)c3ccc(OC(F)F)cc3)C2=O)c1=O] | 594.3 | Method D, RT = 1.528 min, 100% | $^1$H NMR (400 MHz, DMSO-$d_6$) δ = 9.00 (d, J = 8.8 Hz, 1H), 7.94-7.82 (m, 2H), 7.70 (dd, J = 2.0, 7.1 Hz, 1H), 7.56 (dd, J = 2.0, 7.1 Hz, 1H), 7.34 (t, J = 73.6 Hz, 1H), 7.28 (m, 2H), 6.76 (d, J = 10.8 Hz, 2H), 6.34 (t, J = 7.0 Hz, 1H), 5.17-4.98 (m, 3H), 4.15-4.04 (m, 1H), 4.01-3.91 (m, 2H), 3.77(s, 3H), 3.77-3.58 (m, 4H), 3.23 (s, 3H). |
| 143 | 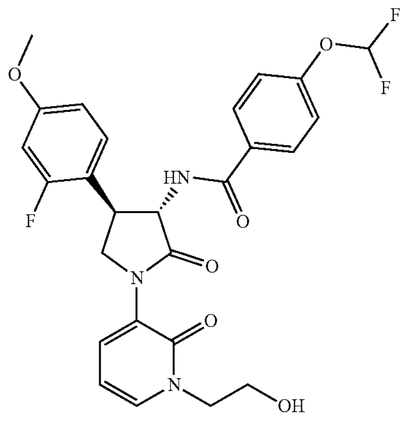 [SMILES: COc1ccc([C@@H]2CN(c3cccn(CCO)c3=O)C(=O)[C@H]2NC(=O)c2ccc(OC(F)F)cc2)c(F)c1] | 532.2 | Method D, RT = 1.44 min, 100% | $^1$H NMR (400 MHz, DMSO-$d_6$) δ = 8.95 (d, J = 9.0 Hz, 1H), 7.99-7.87 (m, 2H), 7.63 (dd, J = 6.8, 2.0 Hz, 1H), 7.59 (dd, J = 7.1, 2.0 Hz, 1H), 7.51 (d, J = 9.3 Hz, 1H), 7.35 (t, J = 73.6 Hz, 1H), 7.26 (d, J = 8.8 Hz, 2H), 6.88-6.75 (m, 2H), 6.31 (t, J = 7.0 Hz, 1H), 5.12 (dd, J = 11.2, 8.8 Hz, 1H), 4.93 (t, J = 5.4 Hz, 1H), 4.17-4.09 (m, 1H), 4.06-3.93 (m, 3H), 3.74 (s, 3H), 3.72-3.58 (m, 3H). |
| 144 | 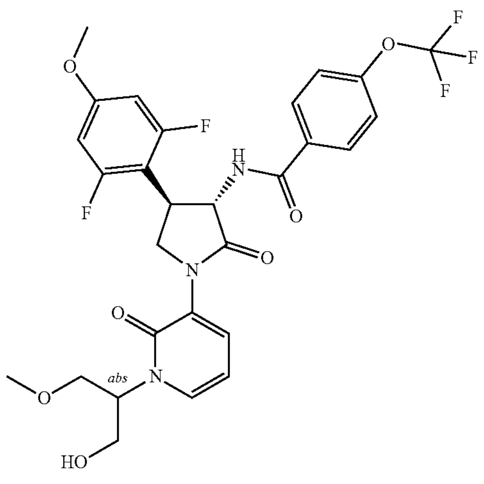 [SMILES: COCC(CO)n1cccc(N2C[C@@H](c3c(F)cc(OC)cc3F)[C@H](NC(=O)c3ccc(OC(F)(F)F)cc3)C2=O)c1=O] | 612.3 | Method D, RT = 1.698 min, 100% | $^1$H NMR (400 MHz, DMSO-$d_6$) δ = 9.11 (d, J = 8.6 Hz, 1H), 8.07-7.89 (m, 2H), 7.70 (dd, J = 6.8, 2.0 Hz, 1H), 7.56 (dd, J = 7.1, 2.0 Hz, 1H), 7.52-7.41 (m, 2H), 6.77 (d, J = 10.8 Hz, 2H), 6.34 (t, J = 7.1 Hz, 1H), 5.22-4.95 (m, 3H), 4.20-4.03 (m, 1H), 4.03-3.90 (m, 2H), 3.83-3.61 (m, 4H), 3.76 (s, 3H), 3.23 (s, 3H). |

TABLE 2-continued

| Ex | Structure | LCMS (M + H)+ | HPLC Method, RT (min.) & Purity | $^1$H NMR |
|---|---|---|---|---|
| 145 | 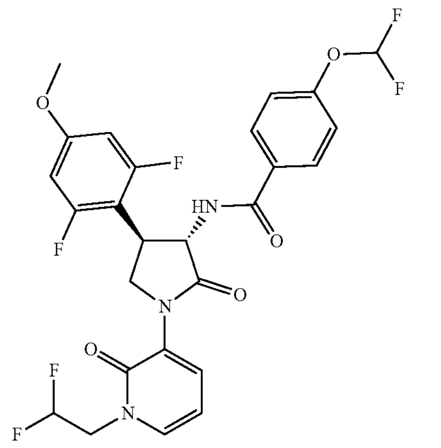 [SMILES: COc1cc(F)c([C@@H]2CN(c3cccn(CC(F)F)c3=O)C(=O)[C@H]2NC(=O)c2ccc(OC(F)F)cc2)c(F)c1] | 570.2 | Method D, RT = 1.708 min, 97% | $^1$H NMR (400 MHz, DMSO-$d_6$) δ = 9.02 (d, J = 8.6 Hz, 1H), 7.89 (d, J = 8.8 Hz, 2H), 7.74 (dd, J = 6.8, 1.7 Hz, 1H), 7.66 (dd, J = 7.2, 1.7 Hz, 1H), 7.34 (t, J = 76.0 Hz, 1 H), 7.28-7.25 (m, 2H), 6.77 (d, J = 10.8 Hz, 2H), 6.53-6.18 (m, 2H), 6.42 (t, J = 7 Hz, 1H), 6.35 (tt, J = 56.2, 3.5 Hz, 1H), 5.11 (dd, J = 10.6, 8.7 Hz, 1H), 4.56-4.34 (m, 2H), 4.16-4.06 (m, 1H), 4.03-3.92 (m, 2H), 3.77 (s, 3H). |
| 146 | 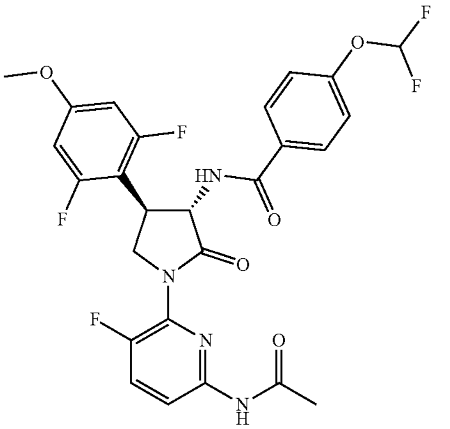 [SMILES: COc1cc(F)c([C@@H]2CN(c3nc(NC(C)=O)ccc3F)C(=O)[C@H]2NC(=O)c2ccc(OC(F)F)cc2)c(F)c1] | 565.2 | Method D, RT = 1.70 min, 98% | $^1$H NMR (400 MHz, DMSO-$d_6$) δ = 10.61 (s, 1H), 9.11 (d, J = 8.6 Hz, 1H), 8.04 (br d, J = 3.4 Hz, 1H), 7.93-7.70 (m, 3H), 7.35 (t, J = 73.6 Hz, 1H), 7.29-7.27 (m, 2H), 6.80 (d, J = 10.8 Hz, 2H), 5.06 (dd, J = 10.5, 8.6 Hz, 1H), 4.27-4.04 (m, 3H), 3.77 (s, 3H), 2.09 (s, 3H). |
| 147 | 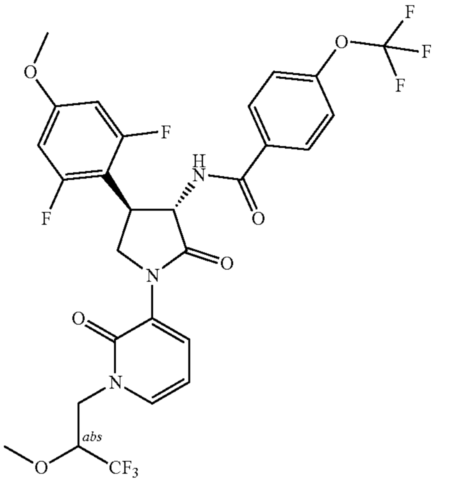 [SMILES: COc1cc(F)c([C@@H]2CN(c3cccn(CC(OC)C(F)(F)F)c3=O)C(=O)[C@H]2NC(=O)c2ccc(OC(F)(F)F)cc2)c(F)c1] | 650.2 | Method D, RT = 2.091 min, 100% | $^1$H NMR (400 MHz, DMSO-$d_6$) δ = 9.14 (d, J = 8.6 Hz, 1H), 7.95 (d, J = 8.8 Hz, 2H), 7.73-6.67 (m, 2H), 7.48 (d, J = 8.8 Hz, 2H), 6.77 (d, J = 10.8 Hz, 2H), 6.39 (t, J = 7.1 Hz, 1H), 5.13 (dd, J = 10.5, 8.8 Hz, 1H), 4.42 (dd, J = 13.2, 3.4 Hz, 1H), 4.33-4.19 (m, 1H), 4.16-3.87 (m, 4H), 3.76 (s, 3H), 3.34 (s, 3H). |

TABLE 2-continued

| Ex | Structure | LCMS (M + H)+ | HPLC Method, RT (min.) & Purity | $^1$H NMR |
|---|---|---|---|---|
| 148 | 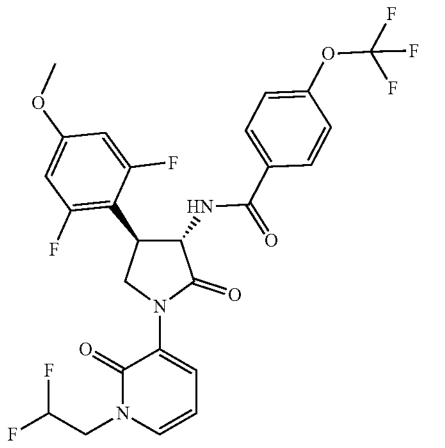 [SMILES: COc1cc(F)c([C@@H]2CN(c3cccn(CC(F)F)c3=O)C(=O)[C@H]2NC(=O)c2ccc(OC(F)(F)F)cc2)c(F)c1] | 588.2 | Method D, RT = 1.883 min, 96% | $^1$H NMR (400 MHz, DMSO-$d_6$) δ = 9.13 (d, J = 8.6 Hz, 1H), 7.95 (d, J = 8.8 Hz, 2H), 7.74 (dd, J = 7.0, 1.6 Hz, 1H), 7.67 (dd, J = 7.2, 1.8 Hz, 1H), 7.49 (d, J = 8.3 Hz, 2H), 6.78 (d, J = 10.8 Hz, 2H), 6.42 (t, J = 7 Hz, 1H), 6.35 (tt, J = 56.2, 3.5 Hz, 1H), 5.12 (dd, J = 8.6, 11.0 Hz, 1H), 4.54-4.36 (m, 2H), 4.18-4.05 (m, 1H), 4.03-3.93 (m, 2H), 3.77 (s, 3H). |
| 149 | 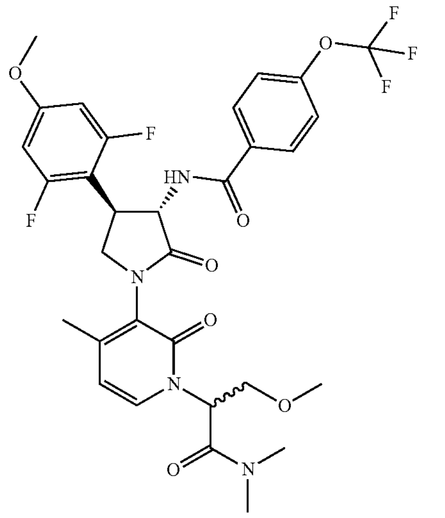 [SMILES: COCC(C(=O)N(C)C)n1ccc(C)c(N2C[C@@H](c3c(F)cc(OC)cc3F)[C@H](NC(=O)c3ccc(OC(F)(F)F)cc3)C2=O)c1=O] | 631.3 | Method D, RT = 1.716 min, 100% | $^1$H NMR (400 MHz, DMSO-$d_6$) δ = 9.08-8.96 (m, 1H), 8.03-7.89 (m, 2H), 7.54-7.44 (m, 2H), 7.40-7.20 (m, 2H), 6.90 (m, 2H), 6.28 (d, J = 7.3 Hz, 1H), 6.09-6.03 (m, 1H), 5.23-4.73 (m, 1H), 4.13-4.03 (m, 1H), 3.94-3.78 (m, 4H), 3.74-3.61 (2s, 3H), 3.60-3.52 (m, 1H), 3.27-3.24 (2s, 3H), 3.14-3.07 (m, 3H), 2.82-2. 37 (2s, 3H), 2.86-2.81 (2s, 3H). (mixture of interconvertible atropisomers) |
| 150 | 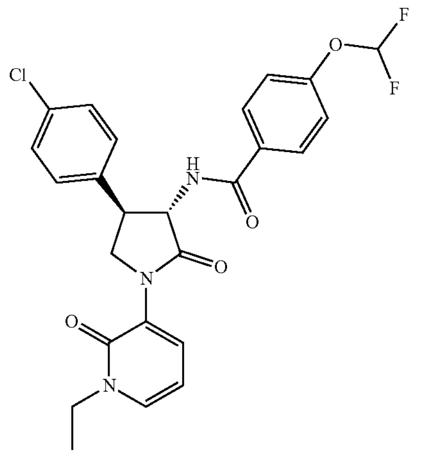 [SMILES: CCn1cccc(N2C[C@@H](c3ccc(Cl)cc3)[C@H](NC(=O)c3ccc(OC(F)F)cc3)C2=O)c1=O] | 502.2 | Method D, RT = 1.715 min, 98.1% | $^1$H NMR (400 MHz, DMSO-$d_6$) δ = 8.96 (d, J = 8.5 Hz, 1H), 8.00-7.84 (m, 2H), 7.75 (dd, J = 6.8, 1.8 Hz, 1H), 7.59 (dd, J = 7.5, 1.8 Hz, 1H), 7.51-7.39 (m, 4H), 7.34 (t, J = 73.6 Hz, 1H), 7.27 (d, J = 8.2 HZ, 2H), 6.35 (t, J = 6.8 Hz, 1H), 5.04 (dd, J = 8.8, 10.8 Hz, 1H), 4.17 (t, J = 7.8 Hz, 1H), 4.07-3.93 (m, 2H), 3.90-3.64 (m, 2H), 1.25 (t, J = 7.3 Hz, 3H). |

TABLE 2-continued

| Ex | Structure | LCMS (M + H)+ | HPLC Method, RT (min.) & Purity | $^1$H NMR |
|---|---|---|---|---|
| 151 | 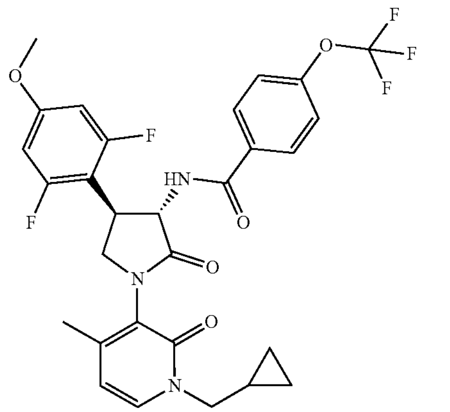 [SMILES: COc1cc(F)c([C@@H]2CN(c3c(C)ccn(CC4CC4)c3=O)C(=O)[C@H]2NC(=O)c2ccc(OC(F)(F)F)cc2)c(F)c1] | 592.3 | Method D, RT = 2.017 min, 100% | $^1$H NMR (400 MHz, DMSO-d$_6$) δ = 9.25-8.95 (m, 1H), 8.05-7.86 (m, 2H), 7.76-7.62 (m, 1H), 7.53-7.38 (m, 2H), 6.77 (dd, J = 10.8, 5.9 Hz, 2H), 6.30-6.15 (m, 1H), 5.40-4.84 (m, 1H), 4.29-4.08 (m, 2H), 3.90-3.65 (m, 5H), 3.53-3.49(m, 1H), 2.19-1.06 (2s, 3H), 1.23-1.18 (m, 1H), 0.53-0.43 (m, 2H), 0.42-0.30 (m, 2H). (mixture of interconvertible atropisomers) |
| 152 | 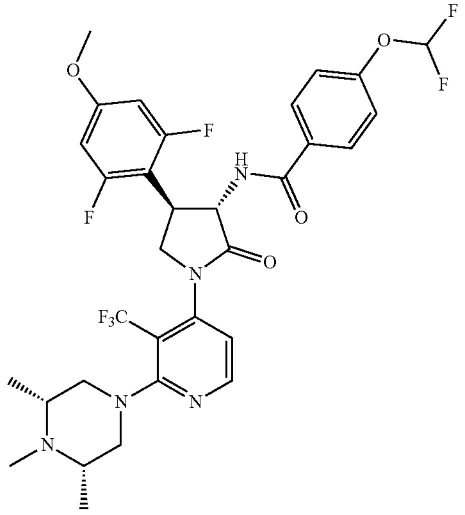 | 684.3 | Method D, RT = 1.97 min, 100% | $^1$H NMR (400 MHz, DMSO-d$_6$) δ = 9.06 (d, J = 8.3 Hz, 1H), 8.49 (br d, J = 4.6 Hz, 1H), 7.88 (d, J = 8.8 Hz, 2H), 7.35 (t, J = 73.6 Hz, 1H), 7.28 (d, J = 8.8 Hz, 2H), 7.13-7.08 (m, 1H), 6.79 (d, J = 10.8 Hz, 2H), 5.08-4.94 (m, 1H), 4.22 (q, J = 10.0 Hz, 1H), 4.14-4.01 (m, 1H), 3.97-3.87 (m, 1H), 3.76 (s, 3H), 3.53 (br d, J = 12.5 Hz, 2H), 2.88-2.69 (m, 2H), 2.31-2.16 (m, 2H), 2.15 (s, 3H), 1.05 (s, 3H), 1.03 (s, 3H). |
| 153 | 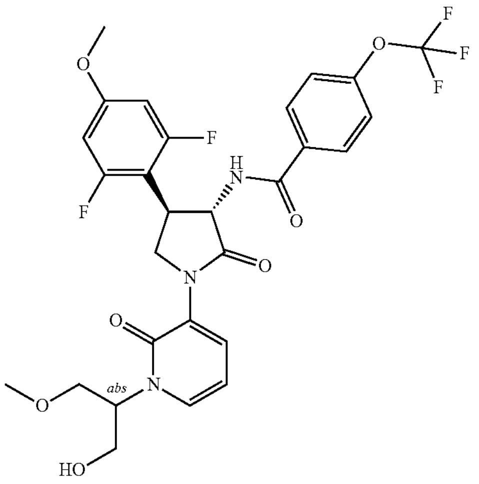 [SMILES: COCC(CO)n1cccc(N2C[C@@H](c3c(F)cc(OC)cc3F)[C@H](NC(=O)c3ccc(OC(F)(F)F)cc3)C2=O)c1=O] | 612.2 | Method D, RT = 1.702 min, 100% | $^1$H NMR (400 MHz, DMSO-d$_6$) δ = 9.12 (d, J = 8.6 Hz, 1H), 8.02-7.86 (m, 2H), 7.70 (dd, J = 7.1, 2.0 Hz, 1H), 7.57 (dd, J = 7.3, 2.0 Hz, 1H), 7.52-7.41 (m, 2H), 6.77 (d, J = 10.8 Hz, 2H), 6.34 (t, J = 7.1 Hz, 1H), 5.22-4.97 (m, 3H), 4.19-4.03 (m, 1H), 4.03-3.88 (m, 2H), 3.83-3.57 (m, 4H), 3.76 (s, 3H), 3.23 (s, 3H). |

TABLE 2-continued

| Ex | Structure | LCMS (M + H)+ | HPLC Method, RT (min.) & Purity | $^1$H NMR |
|---|---|---|---|---|
| 154 | 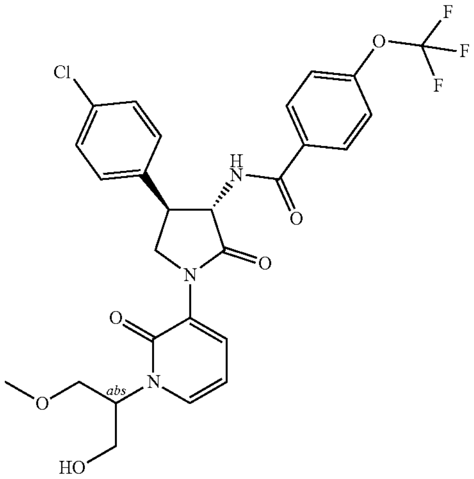 [SMILES: COCC(CO)n1cccc(N2C[C@@H](c3ccc(Cl)cc3)[C@H](NC(=O)c3ccc(OC(F)(F)F)cc3)C2=O)c1=O] | 580.2 | Method D, RT = 1.794 min, 100% | $^1$H NMR (400 MHz, DMSO-$d_6$) δ = 9.07 (d, J = 8.6 Hz, 1H), 7.98 (d, J = 8.8 Hz, 2H), 7.69 (dd, J = 6.8, 2.0 Hz, 1H), 7.57 (dd, J = 7.1, 2.0 Hz, 1H), 7.48 (d, J = 8.3 Hz, 4H), 7.43-7.35 (m, 2H), 6.34 (t, J = 7.0 Hz, 1H), 5.11-4.95 (m, 3H), 4.17 (t, J = 8.1 Hz, 1H), 3.85-3.62 (m, 6H), 3.23 (s, 3H). |
| 155 | 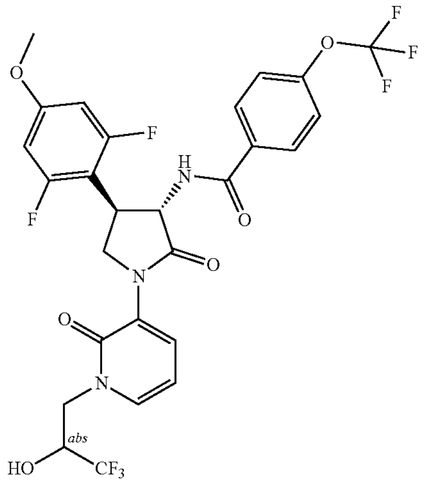 [SMILES: COc1cc(F)c([C@@H]2CN(c3cccn(CC(O)C(F)(F)F)c3=O)C(=O)[C@H]2NC(=O)c2ccc(OC(F)(F)F)cc2)c(F)c1] | 636.2 | Method D, RT = 1.887 min, 96.2% | $^1$H NMR (400 MHz, DMSO-$d_6$) δ = 9.12 (d, J = 8.6 Hz, 1H), 8.00-7.88 (m, 2H), 7.70 (dd, J = 6.8, 2.0 Hz, 1H), 7.64 (dd, J = 7.2, 2.0 Hz, 1H), 7.48 (d, J = 8.1 Hz, 2H), 6.77 (d, J = 10.8 Hz, 2H), 6.37 (t, J = 7.0 Hz, 1H), 5.10 (dd, J = 10.4, 8.9 Hz, 1H), 4.44 (dd, J = 2.8, 13.1 Hz, 1H), 4.39-4.27 (m, 1H), 4.16-3.99 (m, 2H), 3.97-3.89 (m, 2H), 3.85 (dd, J = 13.1, 9.4 Hz, 1H), 3.76 (s, 3H). |
| 156 | 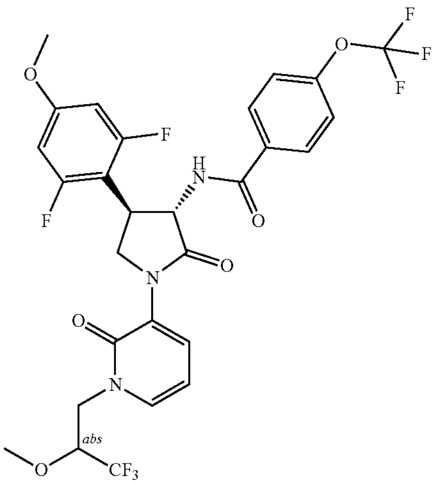 [SMILES: COc1cc(F)c([C@@H]2CN(c3cccn(CC(OC)C(F)(F)F)c3=O)C(=O)[C@H]2NC(=O)c2ccc(OC(F)(F)F)cc2)c(F)c1] | 650.2 | Method D, RT = 2.067 min, 100% | $^1$H NMR (400 MHz, DMSO-$d_6$) δ = 9.14 (d, J = 8.6 Hz, 1H), 8.01-7.86 (m, 2H), 7.71 (dd, J = 6.8, 2.0 Hz, 1H), 7.67 (dd, J = 7.3, 2.0 Hz, 1H), 7.48 (d, J = 8.1 Hz, 2H), 6.77 (d, J = 10.8 Hz, 2H), 6.39 (t, J = 7.1 Hz, 1H), 5.12 (dd, J = 10.9, 8.7 Hz, 1H), 4.42 (dd, J = 13.4, 3.4 Hz, 1H), 4.38-4.26 (m, 1H), 4.15-3.93 (m, 4H), 3.76 (s, 3H), 3.34 (S, 3H). |

TABLE 2-continued

| Ex | Structure | LCMS (M + H)+ | HPLC Method, RT (min.) & Purity | $^1$H NMR |
|---|---|---|---|---|
| 157 | 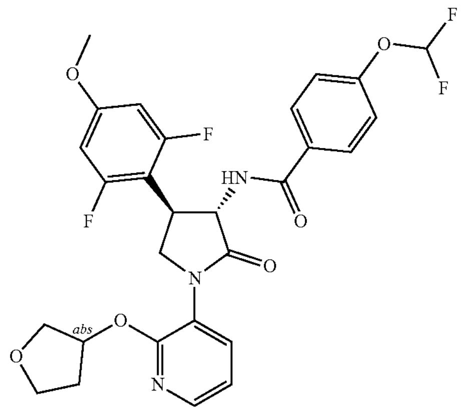 [SMILES: COc1cc(F)c([C@@H]2CN(c3cccnc3OC3CCOC3)C(=O)[C@H]2NC(=O)c2ccc(OC(F)F)cc2)c(F)c1] | 576.2 | Method D, RT = 1.815 min, 99% | $^1$H NMR (400 MHz, DMSO-$d_6$) δ = 9.05 (d, J = 8.5 Hz, 1H), 8.15 (dd, J = 5.0, 2.0 Hz, 1H), 7.97-7.87 (m, 2H), 7.79 (dd, J = 7.5, 2.0 Hz, 1H), 7.35 (t, J = 72.0 Hz, 1H), 7.28-7.26 (m, 2H), 7.12 (dd, J = 7.8, 4.8 Hz, 1H), 6.80 (d, J = 10.5 Hz, 2H), 5.60 (dt, J = 4.4, 2.3 Hz, 1H), 5.05 (dd, J = 8.5, 11.0 Hz, 1H), 4.19-4.12 (m, 1H), 4.05-3.94 (m, 2H), 3.94-3.81 (m, 3H), 3.80-3.72 (m, 4H), 2.31-2.20 (m, 1H), 2.11-2.01 (m, 1H). |
| 158 | 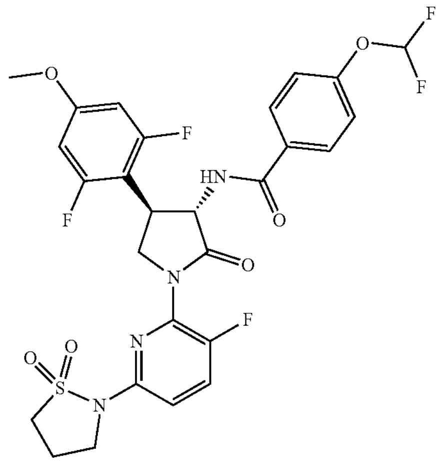 [SMILES: COc1cc(F)c([C@@H]2CN(c3nc(N4CCCS4(=O)=O)ccc3F)C(=O)[C@H]2NC(=O)c2ccc(OC(F)F)cc2)c(F)c1] | 626.2 | Method D, RT = 1.81 min, 98% | $^1$H NMR (400 MHz, DMSO-$d_6$) δ = 9.11 (d, J = 8.6 Hz, 1H), 7.97-7.78 (m, 3H), 7.35 (t, J = 73.6 Hz, 1H), 7.29-7.27 (m, 2H), 7.13 (dd, J = 8.9, 2.6 Hz, 1H), 6.80 (d, J = 10.8 Hz, 2H), 5.19-5.04 (m, 1H), 4.29-4.14 (m, 2H), 4.09-3.97 (m, 1H), 3.92 m 3.85 (m, 2H), 3.77 (s, 3H), 3.59 (t, J = 7.2 Hz, 2H), 2.41-2.37 (m, 2H). |
| 159 | 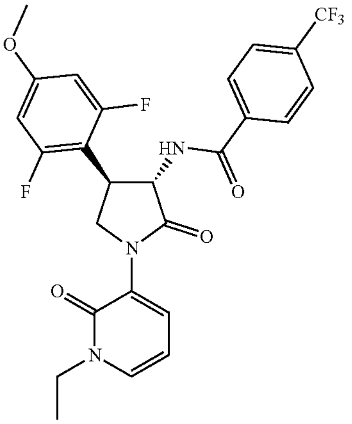 [SMILES: CCn1cccc(N2C[C@@H](c3c(F)cc(OC)cc3F)[C@H](NC(=O)c3ccc(C(F)(F)F)cc3)C2=O)c1=O] | 536.2 | Method D, RT = 1.791 min, 97.8% | $^1$H NMR (400 MHz, DMSO-$d_6$) δ = 9.24 (d, J = 8.8 Hz, 1H), 8.02 (d, J = 8.3 Hz, 2H), 7.88 (d, J = 8.3 Hz, 2H), 7.77 (dd, J = 6.7, 2.1 Hz, 1H), 7.59 (dd, J = 7.1, 2.1 Hz, 1H), 6.78 (d, J = 10.5 Hz, 2H), 6.36 (t, J = 7.0 Hz, 1H), 5.15 (dd, J = 11.1, 8.7 Hz, 1H), 4.17-4.06 (m, 1H), 4.04-3.94 (m, 4H), 3.77 (s, 3H), 1.25 (t, J = 7.2 Hz, 3H). |

TABLE 2-continued

| Ex | Structure | LCMS (M + H)+ | HPLC Method, RT (min.) & Purity | $^1$H NMR |
|---|---|---|---|---|
| 160 | 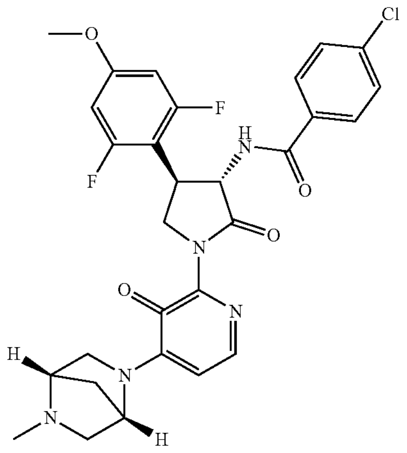 | 593.2 | Method D, RT = 1.61 min, 98% | $^1$H NMR (400 MHz, DMSO-$d_6$) δ = 9.19 (d, J = 8.8 Hz, 1H), 8.12 (d, J = 6.4 Hz, 1H), 7.84 (d, J = 8.6 Hz, 2H), 7.58 (d, J = 8.6 Hz, 2H), 6.84-6.69 (m, 3H), 5.16 (dd, J = 8.8, 10.5 Hz, 1H), 4.77 (br s, 1H), 4.24-4.04 (m, 3H), 3.76 (s, 3H), 3.72-3.70 (m, 1H), 3.56-3.51 (m, 2H), 2.85 (d, J = 9.0 Hz, 1H), 2.58 (d, J = 9.0, Hz, 1H), 2.30 (s, 3H), 1.94 (br d, J = 9.5 Hz, 1H), 1.83 (br d, J = 9.5 Hz, 1H). |
| 161 | 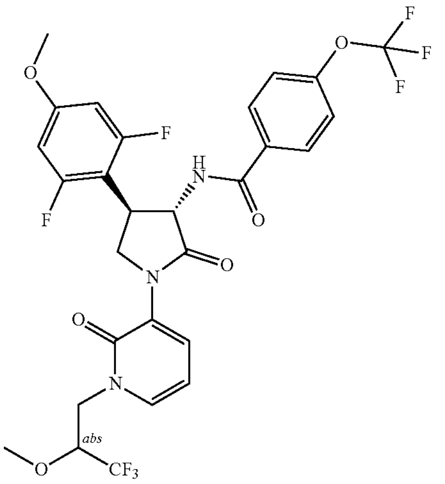 [SMILES: COc1cc(F)c([C@@H]2CN(c3cccn(CC(OC)C(F)(F)F)c3=O)C(=O)[C@H]2NC(=O)c2ccc(OC(F)(F)F)cc2)c(F)c1] | 632.2 | Method D, RT = 1.930 min, 100% | $^1$H NMR (400 MHz, DMSO-$d_6$) δ = 9.02 (d, J = 8.3 Hz, 1H), 7.88 (d, J = 8.8 Hz, 2H), 7.73-7.68 (m, 2H), 7.34 (t, J = 73.6 Hz, 1H), 7.29-7.26 (m, 2H), 6.77 (d, J = 10.8 Hz, 2H), 6.39 (t, J = 7.0 Hz, 1H), 5.12 (dd, J = 10.5, 8.8 Hz, 1H), 4.42 (dd, J = 13.4, 3.4 Hz, 1H), 4.35-4.22 (m, 1H), 4.15-3.92 (m, 4H), 3.76 (s, 3H), 3.36 (s, 3H). |
| 162 | 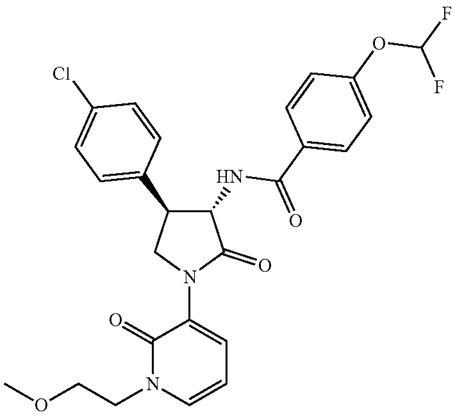 [SMILES: COCCn1cccc(N2C[C@@H](c3ccc(Cl)cc3)[C@H](NC(=O)c3ccc(OC(F)F)cc3)C2=O)c1=O] | 532.2 | Method D, RT = 1.711 min, 100% | $^1$H NMR (400 MHz, DMSO-$d_6$) δ = 8.97 (d, J = 8.6 Hz, 1H), 7.97-7.87 (m, 2H), 7.65 (dd, J = 6.8, 2.0 Hz, 1H), 7.59 (dd, J = 7.3, 2.0 Hz, 1H), 7.52-7.39 (m, 4H), 7.34 (t, J = 73.6 Hz, 1H), 7.26 (d, J = 8.0 Hz, 2H), 6.33 (t, J = 7.0 Hz, 1H), 5.10-4.95 (m, 1H), 4.20-4.08 (m, 3H), 3.86-3.71 (m, 2H), 3.60 (t, J = 5.3 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 163 | 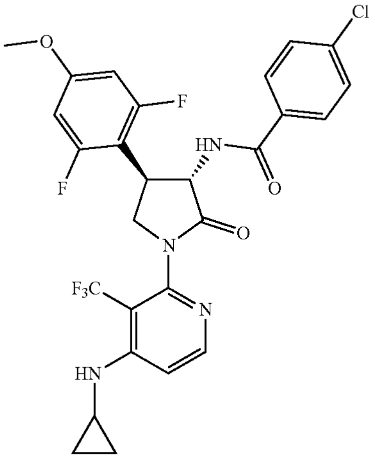 [SMILES: COc1cc(F)c([C@@H]2CN(c3nccc(NC4CC4)c3C(F)(F)F)C(=O)[C@H]2NC(=O)c2ccc(Cl)cc2)c(F)c1] | 581.2 | Method D, RT = 2.03 min, 98.4% | $^1$H NMR (400 MHz, DMSO-$d_6$) δ = 9.09 (br d, J = 8.8 Hz, 1H), 8.32-8.21 (m, 1H), 7.91-7.78 (m, 2H), 7.65-7.51 (m, 2H), 7.14 (t, J = 5.6 Hz, 1H), 6.93-6.84 (m, 1H), 6.78 (d, J = 10.8 Hz, 2H), 5.21-5.02 (m, 1H), 4.34-4.26 (m, 1H), 4.22-4.09 (m, 1H), 3.78 (s, 3H), 3.77-3.66 (m, 1H), 2.27-2.23 (m, 1H), 0.85-0.76 (m, 2H), 0.62-0.55 (m, 2H). |
| 164 | 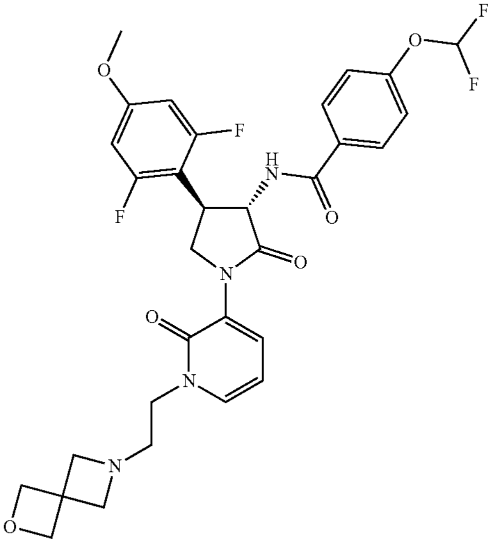 [SMILES: COc1cc(F)c([C@@H]2CN(c3cccn(CCN4CC5(COC5)C4)c3=O)C(=O)[C@H]2NC(=O)c2ccc(OC(F)F)cc2)c(F)c1] | 631.3 | Method D, RT = 1.459 min, 98.3% | $^1$H NMR (400 MHz, DMSO-$d_6$) δ = 9.01 (d, J = 8.8 Hz, 1H), 7.89 (d, J = 8.8 Hz, 2H), 7.69-7.55 (m, 2H), 7.34 (t, J = 73.6 Hz, 1H), 7.28 (m, 2H), 6.77 (d, J = 10.8 Hz, 2H), 6.31 (t, J = 7.1 Hz, 1H), 5.11 (dd, J = 10.9, 8.7 Hz, 1H), 4.57 (s, 4H), 4.15-4.05 (m, 1H), 4.00-3.92 (m, 2H), 3.90-3.82 (m, 2H), 3.76 (s, 3H), 3.29 (s, 4H), 2.65-2.57 (m, 2H). |
| 165 | 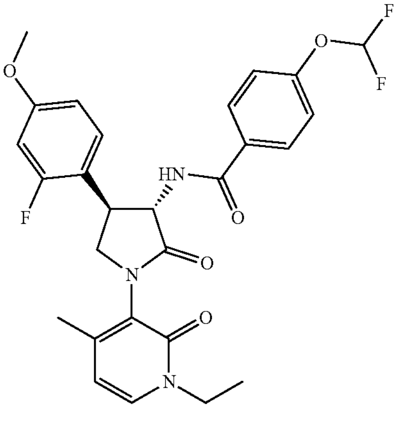 [SMILES: CCn1ccc(C)c(N2C[C@@H](c3ccc(OC)cc3F)[C@H](NC(=O)c3ccc(OC(F)F)cc3)C2=O)c1=O] | 530.2 | Method D, RT = 1.67 min, 98.58% | $^1$H NMR (400 MHz, DMSO-$d_6$) δ = 8.99-8.94 (m, 1H), 8.00-7.83 (m, 2H), 7.68-7.74 (tm, 1H), 7.37-7.52 (m, 1H), 7.27-7.22 (m, 1H), 7.57-7.10 (m, 2H), 6.90-6.71 (m, 2H), 6.22 (d, J = 6.8 Hz, 1H), 5.43-4.74 (m, 1H), 4.21-3.85 (m, 5H), 3.74 (2s, 3H), 2.21-2.05 (2s, 3H), 1.31-1.11 (m, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 166 | 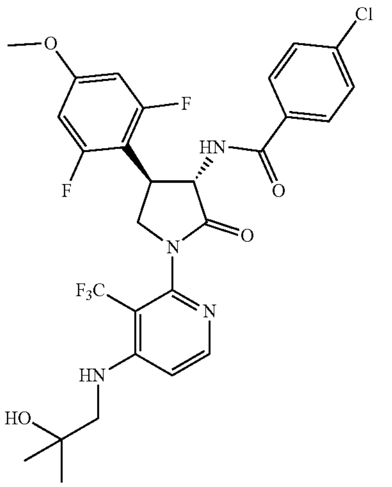 [SMILES: COc1cc(F)c([C@@H]2CN(c3nccc(NCC(C)(C)O)c3C(F)(F)F)C(=O)[C@H]2NC(=O)c2ccc(Cl)cc2)c(F)c1] | 613.2 | Method D, RT = 1.87 min, 98.43% | $^1$H NMR (400 MHz, DMSO-$d_6$) δ = 9.09 (d, J = 8.8 Hz, 1H), 8.25-8.13 (m, 1H), 7.90-7.75 (m, 2H), 7.56 (d, J = 8.6 Hz, 2H), 6.96-6.84 (m, 1H), 6.78 (d, J = 10.8 Hz, 2H), 5.95 (br s, 1H), 5.14 (br dd, J = 11.0, 8.8 Hz, 1H), 4.35-4.28 (m, 1H), 4.26-4.14 (m, 2H), 3.77 (s, 3H), 3.76-3.71 (m, 1H), 3.25-3.13 (m, 2H), 1.17 (s, 3H), 1.15 (s, 3H). |
| 167 | 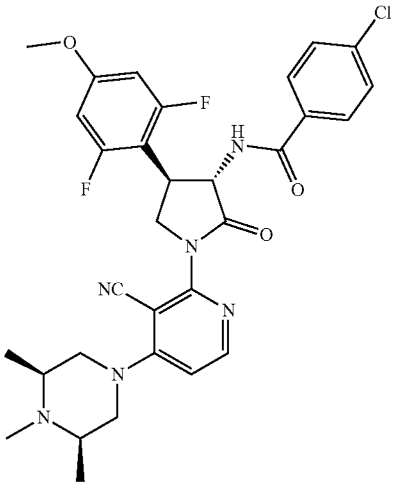 [SMILES: COc1cc(F)c([C@@H]2CN(c3nccc(N4C[C@@H](C)N(C)[C@@H](C)C4)c3C#N)C(=O)[C@H]2NC(=O)c2ccc(Cl)cc2)c(F)c1] | 609.3 | Method D, RT = 1.88 min, 98% | $^1$H NMR (400 MHz, DMSO-$d_6$) δ = 10.08 (br s, 1H), 9.20 (d, J = 8.6 Hz, 1H), 8.43 (d, J = 5.9 Hz, 1H), 7.84 (d, J = 8.6 Hz, 2H), 7.58 (d, J = 8.6 Hz, 2H), 6.80 (d, J = 10.8 Hz, 2H), 5.10 (dd, J = 10.8, 8.8 Hz, 1H), 4.40-4.28 (m, 1H), 4.26-4.18 (m, 1H), 4.13-4.01 (m, 3H), 3.77 (s, 3H), 3.55-3.50 (m, 2H), 3.33-3.23 (m, 2H), 2.78 (s, 3H), 1.45-1.21 (m, 6H). |
| 168 | 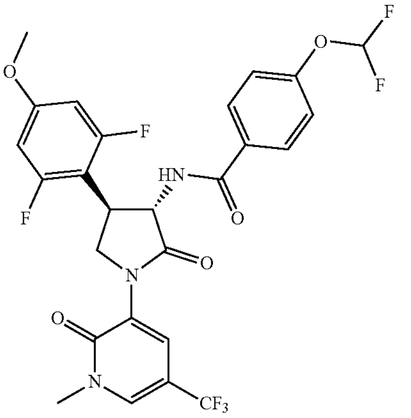 [SMILES: COc1cc(F)c([C@@H]2CN(c3cc(C(F)(F)F)cn(C)c3=O)C(=O)[C@H]2NC(=O)c2ccc(OC(F)F)cc2)c(F)c1] | 588.2 | Method D, RT = 1.850 min, 100% | $^1$H NMR (400 MHz, DMSO-$d_6$) δ = 8.99 (br d, J = 8.6 Hz, 1H), 8.46 (s, 1H), 7.95-7.73 (m, 3H), 7.34 (t, J = 73.6 Hz, 1H), 7.30-7.24 (m, 2H), 6.77 (d, J = 10.8 Hz, 2H), 5.10 (dd, J = 10.8, 8.6 Hz, 1H), 4.22-3.95 (m, 3H), 3.77 (s, 3H), 3.58 (s, 3H). |

TABLE 2-continued

| Ex | Structure | LCMS (M + H)+ | HPLC Method, RT (min.) & Purity | $^1$H NMR |
|---|---|---|---|---|
| 169 | 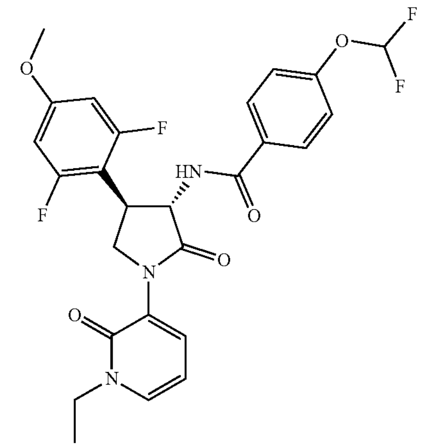 [SMILES: CCn1cccc(N2C[C@@H](c3c(F)cc(OC)cc3F)[C@H](NC(=O)c3ccc(OC(F)F)cc3)C2=O)c1=O] | | Method D, RT = 1.424 min, 100% | $^1$H NMR (400 MHz, DMSO-$d_6$) δ = 9.00 (d, J = 8.5 Hz, 1H), 7.93-7.85 (m, 2H), 7.76 (dd, J = 6.5, 2.0 Hz, 1H), 7.58 (dd, J = 7.5, 2.0 Hz, 1H), 7.35 (t, J = 73.6 Hz, 1H), 7.29-7.27 (m, 2H), 6.77 (d, J = 11.0 Hz, 2H), 6.35 (t, J-7.0 Hz, 1H), 5.11 (dd, J = 10.8, 8.8 Hz, 1H), 4.14-4.05 (m, 1H), 4.03-3.94 (m, 4H), 3.77 (s, 3H), 1.25 (t, J = 7.3 Hz, 3H). |
| 170 | 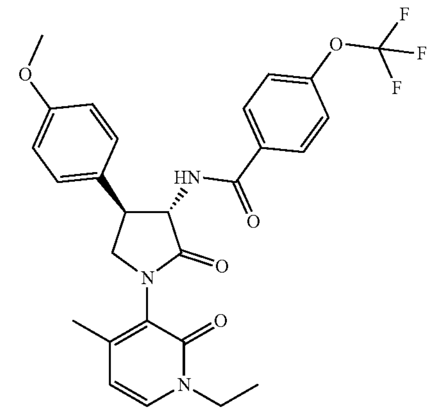 [SMILES: CCn1ccc(C)c(N2C[C@@H](c3ccc(OC)cc3)[C@H](NC(=O)c3ccc(OC(F)(F)F)cc3)C2=O)c1=O] | 530.2 | Method D, RT = 1.749 min, 100% | $^1$H NMR (400 MHz, DMSO-$d_6$) δ = 9.12-9.89 (m, 1H), 8.12-7.89 (m, 2H), 7.75-7.52 (m, 1H), 7.52-7.42 (m, 2H), 7.42-7.16 (m, 2H), 6.99-6.65 (m, 2H), 6.31-6.09 (m, 1H), 5.32-4.68 (m, 1H), 4.16-3.77 (m, 4H), 3.76-3.51 (m, 4H), 2.23-1.94 (2s, 3H), 1.34-1.15 (m, 3H). (mixture of interconvertible atropisomers) |
| 171 | 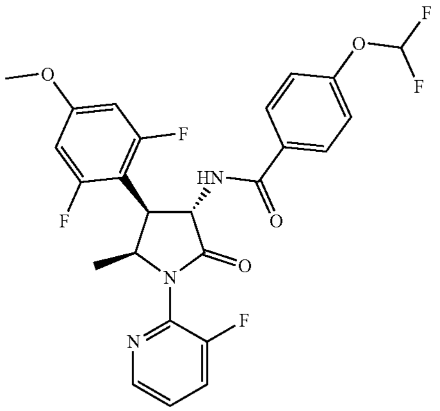 [SMILES: COc1cc(F)c([C@H]2[C@H](NC(=O)c3ccc(OC(F)F)cc3)C(=O)N(c3ncccc3F)[C@H]2C)c(F)c1] | 522.1 | Method D, RT = 1.88 min, 99% | $^1$H NMR (400 MHz, DMSO-$d_6$) δ = 9.05-8.92 (m, 1H), 8.41 (br d, J = 4.9 Hz, 1H), 7.98-7.78 (m, 3H), 7.52-7.49 (m, 1H), 7.35 (t, J = 73.6 Hz, 1H), 7.27-7.25 (m, 2H), 6.86-6.72 (m, 2H), 5.61-5.48 (m, 1H), 4.86-4.77 (m, 1H), 4.40-4.35 (m, 1H), 3.78 (s, 3H), 0.99 (d, J = 6.8 Hz, 3H). |

TABLE 2-continued

| Ex | Structure | LCMS (M + H)+ | HPLC Method, RT (min.) & Purity | $^1$H NMR |
|---|---|---|---|---|
| 172 | 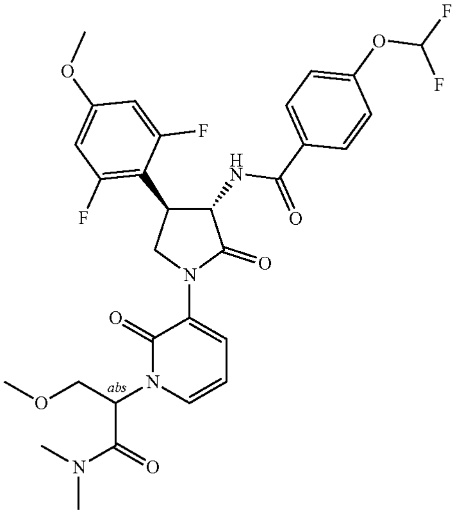 [SMILES: COCC(C(=O)N(C)C)n1cccc(N2C[C@@H](c3c(F)cc(OC)cc3F)[C@H](NC(=O)c3ccc(OC(F)F)cc3)C2=O)c1=O] | 635.3 | Method D, RT = 1.614 min, 100% | $^1$H NMR (400 MHz, DMSO-$d_6$) δ = 9.01 (d, J = 8.6 Hz, 1H), 7.94-7.83 (m, 2H), 7.72 (dd, J = 7.1, 2.0 Hz, 1H), 7.61 (dd, J = 7.2, 2.0 Hz, 1H), 7.34 (t, J = 73.6 Hz, 1H), 7.29-7.24 (m, 1H), 6.76 (d, J = 11.0 Hz, 2H), 6.41 (t, J = 7.1 Hz, 1H), 6.07 (dd, J = 8.7, 5.3 Hz, 1H), 5.09 (dd, J = 11.1, 8.7 Hz, 1H), 4.13-4.04 (m, 1H), 4.03-3.79 (m, 5H), 3.76 (s, 3H), 3.26 (s, 3H), 3.11 (s, 3H), 2.84 (s, 3H). |
| 173 | 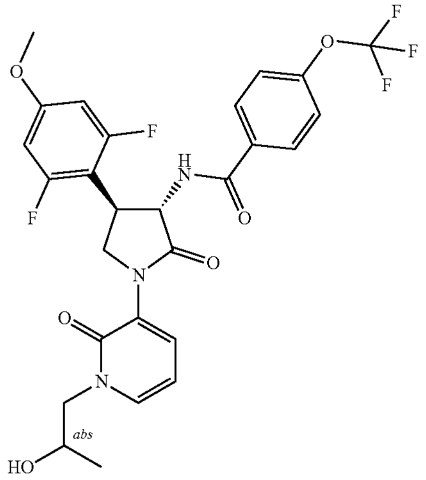 [SMILES: COc1cc(F)c([C@@H]2CN(c3cccn(CC(C)O)c3=O)C(=O)[C@H]2NC(=O)c2ccc(OC(F)(F)F)cc2)c(F)c1] | 582.2 | Method D, RT = 1.690 min, 98.6% | $^1$H NMR (400 MHz, DMSO-$d_6$) δ = 9.11 (d, J = 8.6 Hz, 1H), 7.99-7.86 (m, 2H), 7.63-7.58 (m, 2H), 7.53-7.37 (m, 2H), 6.76 (d, J = 10.8 Hz, 2H), 6.31 (t, J = 7.1 Hz, 1H), 5.12 (dd, J = 11.0, 8.6 Hz, 1H), 4.94 (br d, J = 5.1 Hz, 1H), 4.17-4.03 (m, 2H), 4.03-3.83 (m, 3H), 3.76 (s, 3H), 3.63 (dd, J = 12.8, 8.2 Hz, 1H), 1.09 (d, J = 6.4 Hz, 3H). |
| 174 | 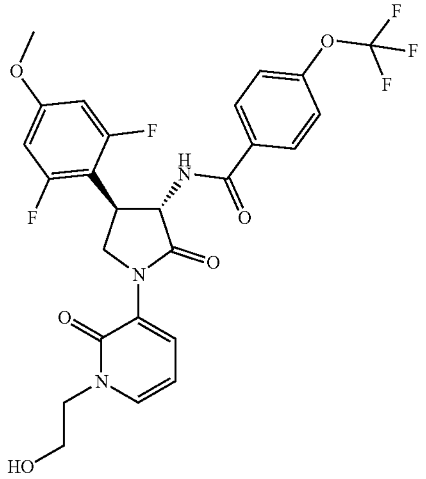 [SMILES: COc1cc(F)c([C@@H]2CN(c3cccn(CCO)c3=O)C(=O)[C@H]2NC(=O)c2ccc(OC(F)(F)F)cc2)c(F)c1] | 568.1 | Method D, RT = 2.171 min, 100% | $^1$H NMR (400 MHz, DMSO-$d_6$) δ = 9.12 (d, J = 8.5 Hz, 1H), 7.99-7.90 (m, 2H), 7.65 (dd, J = 6.5, 2.0 Hz, 1H), 7.59 (dd, J = 7.3, 2.0 Hz, 1H), 7.49 (d, J = 8.0 Hz, 2H), 6.77 (d, J = 10.5 Hz, 2H), 6.35-6.29 (m, 1H), 5.12 (dd, J = 11.3, 8.8 Hz, 1H), 4.97-4.92 (m, 1H), 4.14-4.05 (m, 1H), 4.03-3.95 (m, 4H), 3.77 (s, 3H), 3.67-3.62 (m, 2H). |

TABLE 2-continued

| Ex | Structure | LCMS (M + H)+ | HPLC Method, RT (min.) & Purity | $^1$H NMR |
|---|---|---|---|---|
| 175 | 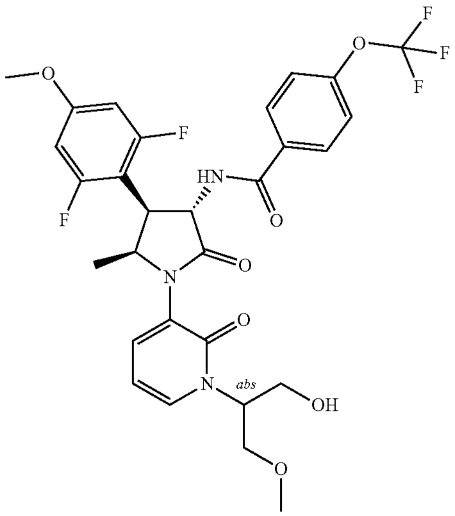 [SMILES: COCC(CO)n1cccc(N2C(=O)[C@@H](NC(=O)c3ccc(OC(F)(F)F)cc3)[C@H](c3c(F)cc(OC)cc3F)[C@@H]2C)c1=O] | 626.2 | Method D, RT = 1.72 min, 99% | $^1$H NMR (400 MHz, DMSO-$d_6$) δ = 8.97 (br d, J = 8.1 Hz, 1H), 7.96 (d, J = 8.6 Hz, 2H), 7.74-7.66 (m, 1H), 7.56 (dd, J = 7.0, 1.3 Hz, 1H), 7.45 (d, J = 8.6 Hz, 2H), 6.77 (d, J = 11.5 Hz, 2H), 6.33 (t, J = 7.0 Hz, 1H), 5.71-5.61 (m, 1H), 5.14-4.97 (m, 2H), 4.67-4.56 (m, 1H), 4.29 (dd, J = 8.3, 11.7 Hz, 1H), 3.83-3.69, (m, 5H), 3.65 (td, J = 5.4, 10.9 Hz, 2H), 3.23 (s, 3H), 0.91 (br d, J = 6.8 Hz, 3H). |
| 176 | 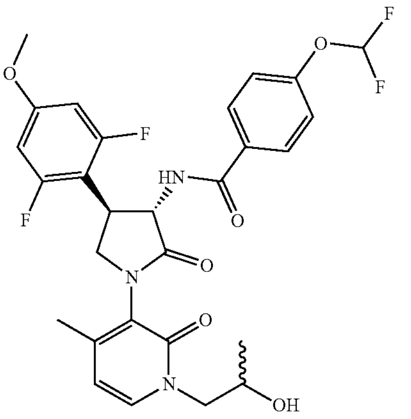 [SMILES: COc1cc(F)c([C@@H]2CN(c3c(C)ccn(CC(C)O)c3=O)C(=O)[C@H]2NC(=O)c2ccc(OC(F)F)cc2)c(F)c1] | 578.2 | Method D, RT = 1.584 min, 100% | $^1$H NMR (400 MHz, DMSO-$d_6$) δ = 9.11-8.92 (m, 1H), 7.88 (d, J = 9.0 Hz, 2H), 7.52 (s, 1H), 7.34 (t, J = 72 Hz, 1H), 7.28-7.11 (m, 1H), 6.77 (br d, J = 10.8 Hz, 2H), 6.24-6.14 (m, 1H), 5.40-5.28 (m, 1H), 4.97-4.84 (m, 2H), 4.30-3.98 (m, 3H), 3.93-3.84 (m, 1H), 3.80-3.71 (2s, 3H), 3.62-3.43 (m, 2H), 2.23-2.01 (2s, 3H), 1.08 (d, J = 6.4 Hz, 3H). (mixture of interconvertible atropisomers) |
| 177 | 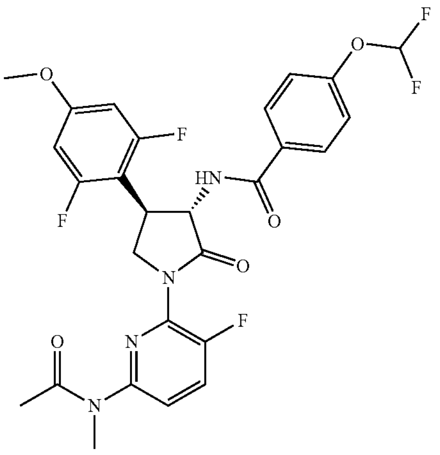 [SMILES: COc1cc(F)c([C@@H]2CN(c3nc(N(C)C(C)=O)ccc3F)C(=O)[C@H]2NC(=O)c2ccc(OC(F)F)cc2)c(F)c1] | 579.3 | Method D, RT = 1.69 min, 94% | $^1$H NMR (400 MHz, DMSO-$d_6$) δ = 9.10 (d, J = 8.6 Hz, 1H), 7.96 (t, J = 8.9 Hz, 1H), 7.92-7.84 (m, 2H), 7.56 (dd, J = 8.4, 2.6 Hz, 1H), 7.34 (t, J = 73.6 Hz, 1H), 7.27-7.25 (m, 2H), 6.79 (d, J = 10.8 Hz, 2H), 5.14-5.04 (m, 1H), 4.29-4.13 (m, 2H), 4.11-4.01 (m, 1H), 3.77 (s, 3H), 3.27 (s, 3H), 2.07 (s, 3H). |

TABLE 2-continued

| Ex | Structure | LCMS (M + H)+ | HPLC Method, RT (min.) & Purity | $^1$H NMR |
|---|---|---|---|---|
| 178 | 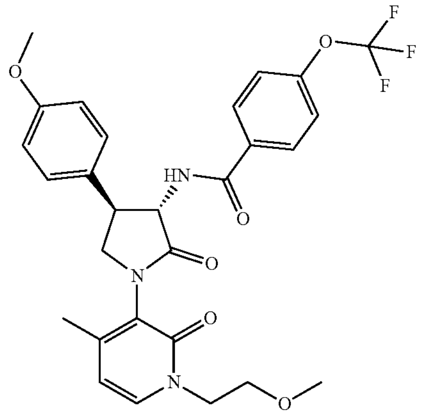 [SMILES: COCCn1ccc(C)c(N2C[C@@H](c3ccc(OC)cc3)[C@H](NC(=O)c3ccc(OC(F)(F)F)cc3)C2=O)c1=O] | 560.3 | Method D, RT = 1.738 min, 100% | $^1$H NMR (400 MHz, DMSO-$d_6$) δ = 9.09-8.98 (m, 1H), 8.06-7.91 (m, 2H), 7.59-7.52 (m, 1H), 7.51-7.48 (m, 2H), 7.41-7.35 (m, 1H), 7.32 (d, J = 8.6 Hz, 1H), 6.93-6.89 (m, 2H), 6.20 (d, J = 7.1 Hz, 1H), 5.27-4.66 (m, 1H), 4.19-3.99 (m, 2H), 3.95-3.80 (m, 2H), 3.74-3.68 (2s, 3H), 3.66-3.45 (m, 3H), 3.24 (s, 3H), 2.23-2.03 (2s, 3H). (mixture of interconvertible atropisomers) |
| 179 | 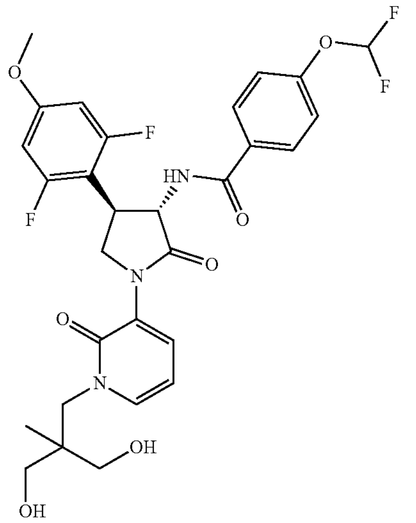 [SMILES: COc1cc(F)c([C@@H]2CN(c3cccn(CC(C)(CO)CO)c3=O)C(=O)[C@H]2NC(=O)c2ccc(OC(F)F)cc2)c(F)c1] | 608.2 | Method D, RT = 1.506 min, 100% | $^1$H NMR (400 MHz, DMSO-$d_6$) δ = 9.06-8.98 (m, 1H), 7.93-7.85 (m, 2H), 7.69-7.61 (m, 2H), 7.34 (t, J = 73.6 Hz, 1H), 7.28 (m, 2H), 6.77 (d, J = 10.8 Hz, 2H), 6.40 (t, J = 7.0 Hz, 1H), 5.14 (dd, J = 11.1, 8.4 Hz, 1H), 4.74 (t, J = 5.4 Hz, 2H), 4.15-4.04 (m, 1H), 4.03-3.89 (m, 4H), 3.76 (s, 3H), 3.24-3.11 (m, 4H), 0.78 (s, 3H) |
| 180 | 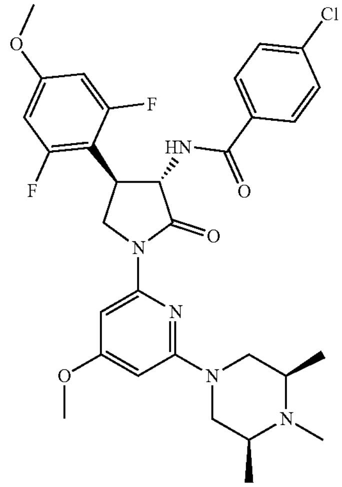 [SMILES: COc1cc(N2C[C@@H](C)N(C)[C@@H](C)C2)nc(N2C[C@@H](c3c(F)cc(OC)cc3F)[C@H](NC(=O)c3ccc(Cl)cc3)C2=O)c1] | 614.2 | Method C, RT = 1.75 min, 89.7% | $^1$H NMR (400 MHz, DMSO-$d_6$) δ = 9.12 (br d, J = 8.3 Hz, 1H), 7.91-7.75 (m, 2H), 7.58 (br d, J = 8.6 Hz, 2H), 7.43 (s, 1H), 6.90-6.71 (m, 2H), 6.34 (s, 1H), 5.08-4.97 (m, 1H), 4.55-4.38 (m, 1H), 4.15-4.00 (m, 1H), 3.94-3.83 (m, 1H), 3.82 (s, 3H), 3.78 (s, 3H), 3.45-3.37 (m, 2H), 3.33-3.28 (m, 2H), 2.93-2.82 (m, 2H), 2.79 (s, 3H) 1.34 (d, J = 6.4 H, 6H). |

TABLE 2-continued

| Ex | Structure | LCMS (M + H)+ | HPLC Method, RT (min.) & Purity | $^1$H NMR |
|---|---|---|---|---|
| 181 | 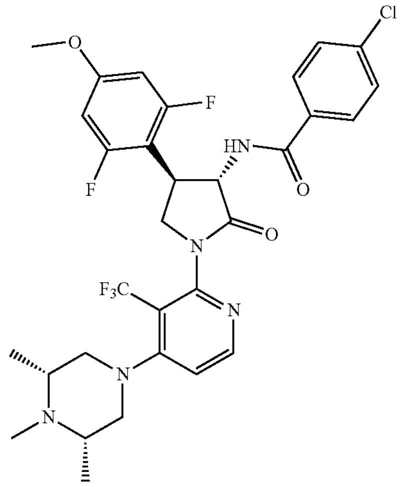 [SMILES: COc1cc(F)c([C@@H]2CN(c3nccc(N4C[C@@H](C)N(C)[C@@H](C)C4)c3C(F)(F)F)C(=O)[C@H]2NC(=O)c2ccc(Cl)cc2)c(F)c1] | 652.2 | Method D, RT = 2.04 min, 100% | $^1$H NMR (400 MHz, DMSO-$d_6$) δ = 9.09 (br d, J = 8.6 Hz, 1H), 8.49-8.35 (m, 1H), 7.81 (br d, J = 6.8 Hz, 2H), 7.60-7.51 (m, 2H), 7.18 (br d, J = 5.9 Hz, 1H), 6.78 (d, J = 10.8 Hz, 2H), 5.18-5.00 (m, 1H), 4.44-4.05 (m, 2H), 3.88-3.75 (m, 1H) 3.74 (s, 3H), 3.44-3.37 (m, 2H), 2.92-2.69 (m, 2H), 2.37-2.22 (m, 2H), 2.21 (s, 3H), 1.05 (d, J = 6.4 Hz, 6H). |
| 182 | 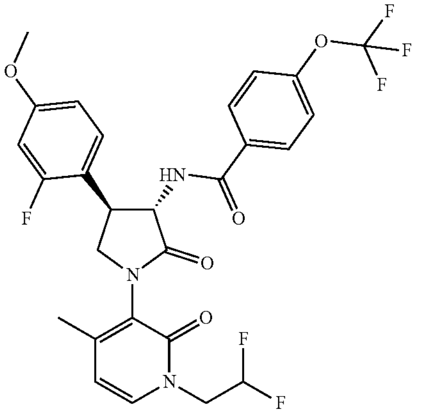 [SMILES: COc1ccc([C@@H]2CN(c3c(C)ccn(CC(F)F)c3=O)C(=O)[C@H]2NC(=O)c2ccc(OC(F)(F)F)cc2)c(F)c1] | 584.2 | Method D, RT = 1.91 min, 100% | $^1$H NMR (400 MHz, DMSO-$d_6$) δ = 9.12-9.89 (m, 1H), 8.06-7.89 (m, 2H), 7.69-3.61 (m, 1H), 7.58-7.40 (m, 3H), 6.91-6.71 (m, 2H), 6.38-6.35 (m, 1H), 6.32 (t, J = 57.2 Hz, 1H), 5.40-4.78 (m, 1H), 4.54-4.33 (m, 2H), 4.17-3.98 (m, 1H), 3.74-3.70 (2s, 3H), 3.65-3.56 (m, 1H), 3.47-3.38 (m, 1H), 2.24-2.08 (2s, 3H). (mixture of interconvertible atropisomers) |
| 183 | 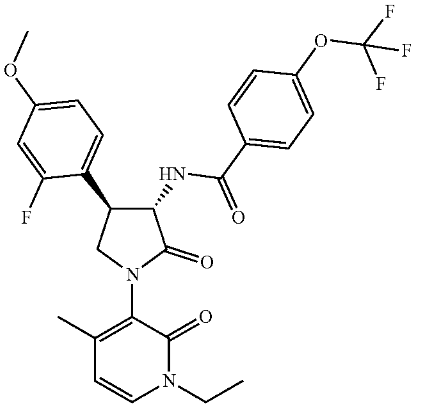 [SMILES: CCn1ccc(C)c(N2C[C@@H](c3ccc(OC)cc3F)[C@H](NC(=O)c3ccc(OC(F)(F)F)cc3)C2=O)c1=O] | 548.2 | Method D, RT = 1.81 min, 94.5% | $^1$H NMR (400 MHz, DMSO-$d_6$) δ = 9.12-9.02 (m, 1H), 8.02-7.88 (m, 2H), 7.69-7.62 (m, 1H), 7.57-7.39 (m, 3H), 6.88-6.70 (m, 2H), 6.26-6.21 (m, 1H), 5.40-4.78 (m, 1H), 4.17-3.89 (m, 3H), 3.74-3.70 (2s, 3H), 3.61-3.58 (m, 1H), 3.42-3.37 (m, 1H), 2.22-2.02 (2s, 3H), 1.28-1.18 (m, 3H). (mixture of interconvertible atropisomers) |

TABLE 2-continued

| Ex | Structure | LCMS (M + H)+ | HPLC Method, RT (min.) & Purity | $^1$H NMR |
| --- | --- | --- | --- | --- |
| 184 | 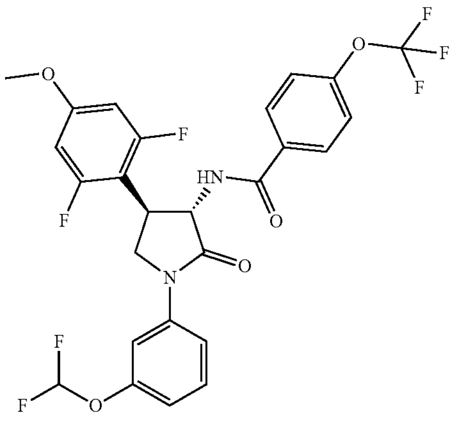 [SMILES: COc1cc(F)c([C@@H]2CN(c3cccc(OC(F)F)c3)C(=O)[C@H]2NC(=O)c2ccc(OC(F)(F)F)cc2)c(F)c1] | 573.1 | Method D, RT = 2.24 min, 100% | $^1$H NMR (400 MHz, DMSO-$d_6$) δ = 9.17 (d, J = 8.6 Hz, 1H), 7.95 (d, J = 8.6 Hz, 2H), 7.71 (s, 1H), 7.62-7.55 (m, 1H), 7.51-7.46 (m, 3H), 7.26 (t, J = 76.2 Hz, 1H), 7.02-6.96 (m, 1H), 6.80 (d, J = 10.8 Hz, 2H), 5.11-4.98 (m, 1H), 4.24-4.07 (m, 2H), 4.05-3.96 (m, 1H), 3.78 (s, 3H). |
| 185 | 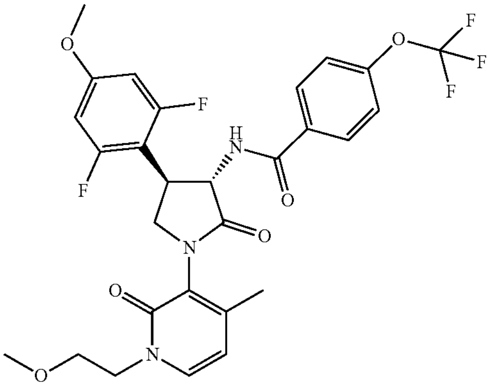 [SMILES: COCCn1ccc(C)c(N2C[C@@H](c3c(F)cc(OC)cc3F)[C@H](NC(=O)c3ccc(OC(F)(F)F)cc3)C2=O)c1=O] | 596.2 | Method D, RT = 1.850 min, 98.6% | $^1$H NMR (400 MHz, DMSO-$d_6$) δ = 9.25-9.01 (m, 1H), 8.06-7.89 (m, 2H), 7.64-7.52 (m, 1H), 7.52-7.38 (m, 2H), 6.77 (dd, J = 10.8, 5.9 Hz, 2H), 6.26-6.12 (m, 1H), 5.39-4.84 (m, 1H), 4.30-3.99 (m, 4H), 3.79-3.71 (m, 3H), 3.62-3.54 (m, 2H), 3.54-3.44 (m, 1H), 3.26-3.21 (2s, 3H), 2.23-1.99 (m, 3H). (mixture of interconvertible atropisomers) |
| 186 | 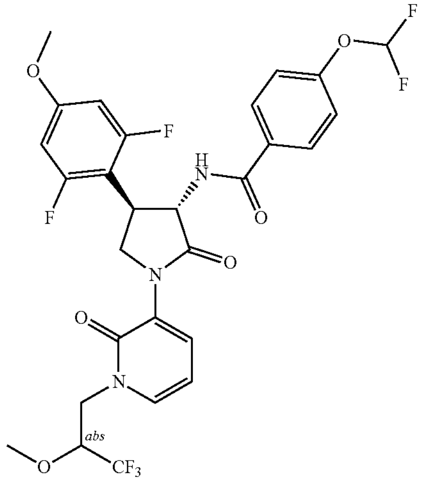 [SMILES: COc1cc(F)c([C@@H]2CN(c3cccn(CC(OC)C(F)(F)F)c3=O)C(=O)[C@H]2NC(=O)c2ccc(OC(F)F)cc2)c(F)c1] | 632.3 | Method C, RT = 1.911 min, 100% | $^1$H NMR (400 MHz, DMSO-$d_6$) δ = 9.02 (d, J = 8.3 Hz, 1H), 7.89 (d, J = 8.8 Hz, 2H), 7.76-7.61 (m, 2H), 7.34 (t, J = 73.6 Hz, 1H), 7.28 (m, 2H), 6.77 (d, J = 10.8 Hz, 2H), 6.39 (t, J = 7.1 Hz, 1H), 5.17-5.03 (m, 1H), 4.42 (dd, J = 13.4, 3.4 Hz, 1H), 4.38-4.26 (m, 1H), 4.16-3.92 (m, 4H), 3.76 (s, 3H), 3.36 (s, 3H). |

TABLE 2-continued
| Ex | Structure | LCMS (M + H)+ | HPLC Method, RT (min.) & Purity | $^1$H NMR |
|---|---|---|---|---|
| 187 | 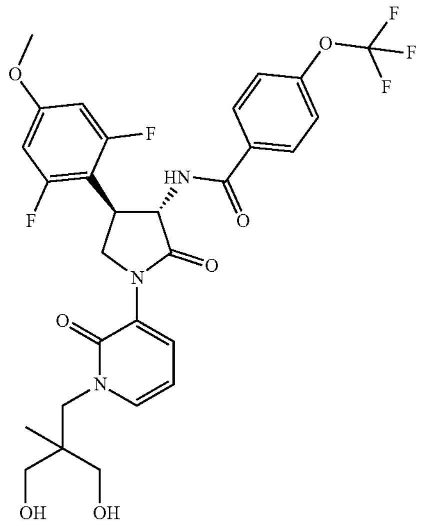 [SMILES: COc1cc(F)c([C@@H]2CN(c3cccn(CC(C)(CO)CO)c3=O)C(=O)[C@H]2NC(=O)c2ccc(OC(F)(F)F)cc2)c(F)c1] | 626.2 | Method D, RT = 1.788 min, 100% | $^1$H NMR (400 MHz, DMSO-$d_6$) δ = 9.17-9.09 (m, 1H), 8.00-7.92 (m, 2H), 7.71-7.62 (m, 2H), 7.53-7.46 (m, 2H), 6.77 (d, J = 10.8 Hz, 2H), 6.40 (t, J = 7.1 Hz, 1H), 5.15 (dd, J = 11.1, 8.4 Hz, 1H), 4.74 (br t, J = 5.4 Hz, 2H), 4.17-4.04 (m, 1H), 4.02-3.88 (m, 4H), 3.76 (s, 3H), 3.23-3.10 (m, 4H), 0.78 (s, 3H). |
| 188 | 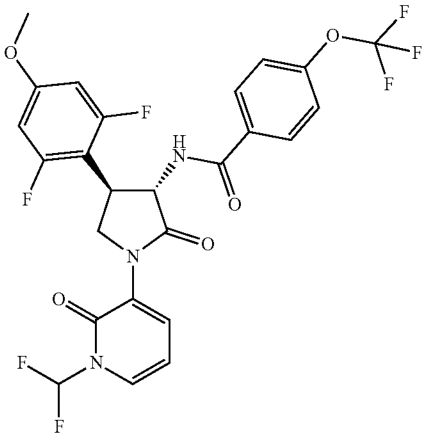 [SMILES: COc1cc(F)c([C@@H]2CN(c3cccn(C(F)F)c3=O)C(=O)[C@H]2NC(=O)c2ccc(OC(F)(F)F)cc2)c(F)c1] | 574.2 | Method D, RT = 1.940 min, 98.8% | $^1$H NMR (400 MHz, DMSO-$d_6$) δ = 9.12 (d, J = 8.6 Hz, 1H), 7.95-7.70 (m, 4H), 7.92 (t, J = 59.6 Hz, 1H), 7.49 (d, J = 8.3 Hz, 2H), 6.78 (d, J = 10.8 Hz, 2H), 6.56 (t, J = 7.2 Hz, 1H), 5.09 (dd, J = 11.0, 8.6 Hz, 1H), 4.18-4.08 (m, 1H), 4.06-3.94 (m, 2H), 3.77 (s, 3H). |
| 189 | 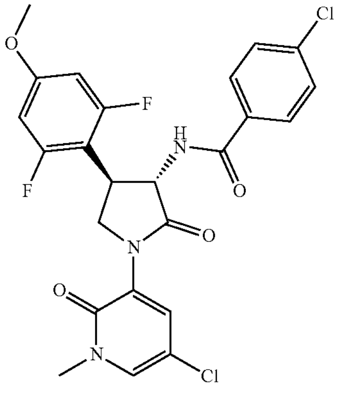 [SMILES: COc1cc(F)c([C@@H]2CN(c3cc(Cl)cn(C)c3=O)C(=O)[C@H]2NC(=O)c2ccc(Cl)cc2)c(F)c1] | 522 | Method D, RT = 1.730 min, 99.3% | $^1$H NMR (400 MHz, DMSO-$d_6$) δ = 9.07 (d, J = 8.3 Hz, 1H), 8.07 (d, J = 2.9 Hz, 1H), 7.88-7.78 (m, 2H), 7.70 (d, J = 2.9 Hz, 1H), 7.63-7.50 (m, 2H), 6.78 (d, J = 10.8 Hz, 2H), 5.10 (dd, J = 10.5, 8.8 Hz, 1H), 4.15-3.92 (m, 3H), 3.76 (s, 3H), 3.49 (s, 3H). |

TABLE 2-continued

| Ex | Structure | LCMS (M + H)+ | HPLC Method, RT (min.) & Purity | $^1$H NMR |
|---|---|---|---|---|
| 190 | 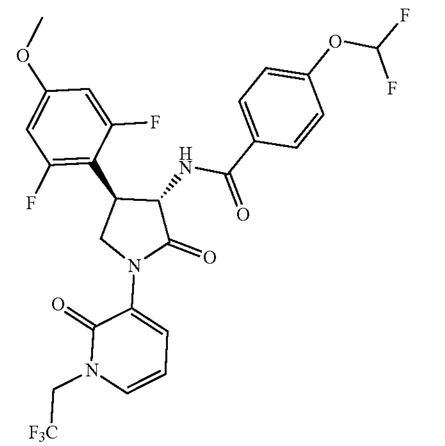 [SMILES: COc1cc(F)c([C@@H]2CN(c3cccn(CC(F)(F)F)c3=O)C(=O)[C@H]2NC(=O)c2ccc(OC(F)F)cc2)c(F)c1] | 588.2 | Method D, RT = 1.803 min, 100% | $^1$H NMR (400 MHz, DMSO-$d_6$) δ = 9.03 (d, J = 8.6 Hz, 1H), 7.94-7.83 (m, 2H), 7.78-7.72 (m, 1H), 7.68 (dd, J = 7.2, 1.8 Hz, 1H), 7.34 (t, J = 73.6 Hz, 1H), 7.28 (m, 2H), 6.77 (d, J = 10.8 Hz, 2H), 6.46 (t, J = 7.1 Hz, 1H), 5.12 (dd, J = 11.2, 8.6 Hz, 1H), 5.03-4.86 (m, 2H), 4.17-4.06 (m, 1H), 4.03-3.90 (m, 2H), 3.76 (s, 3H). |
| 191 | 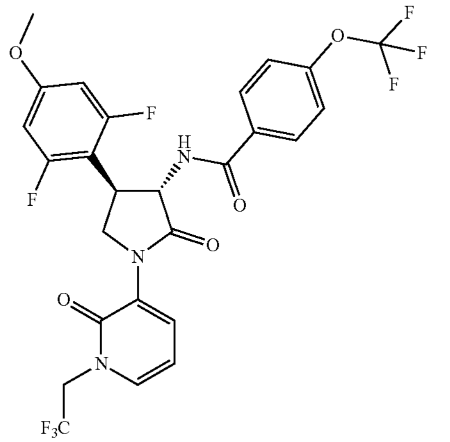 [SMILES: COc1cc(F)c([C@@H]2CN(c3cccn(CC(F)(F)F)c3=O)C(=O)[C@H]2NC(=O)c2ccc(OC(F)(F)F)cc2)c(F)c1] | 606.2 | Method D, RT = 1.972 min, 100% | $^1$H NMR (400 MHz, DMSO-$d_6$) δ = 9.13 (d, J = 8.6 Hz, 1H), 7.99-7.84 (m, 2H), 7.80-7.71 (m, 1H), 7.68 (dd, J = 7.1, 2.0 Hz, 1H), 7.55-7.36 (m, 2H), 6.78 (d, J = 10.8 Hz, 2H), 6.46 (t, J = 7.1 Hz, 1H), 5.13 (dd, J = 11.1, 8.7 Hz, 1H), 5.03-4.84 (m, 2H), 4.17-4.05 (m, 1H), 4.04-3.88 (m, 2H), 3.77 (s, 3H). |
| 192 | 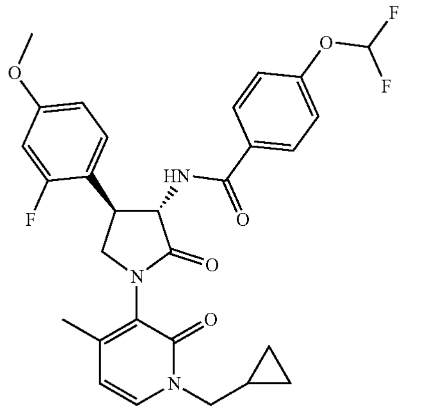 [SMILES: COc1ccc([C@@H]2CN(c3c(C)ccn(CC4CC4)c3=O)C(=O)[C@H]2NC(=O)c2ccc(OC(F)F)cc2)c(F)c1] | 556.3 | Method D, RT = 1.81 min, 100% | $^1$H NMR (400 MHz, DMSO-$d_6$) δ = 9.03-9.86 (m, 1H), 8.01-7.84 (m, 2H), 7.72-8.65 (m, 1H), 7.60-7.39 (m, 1H), 7.35 (t, J = 73 Hz, 1H), 7.26-7.19 (m, 2H), 6.90-6.72 (m, 2H), 6.22 (d, J = 6.8 Hz, 1H), 5.43-4.76 (m, 1H), 4.20-3.93 (m, 2H), 3.90-3.74 (m, 2H), 3.72-3.66 (2s, 3H), 3.42-3.37 (m, 1H), 2.23-1.99 (2s, 3H), 1.31-1.15 (m, 1H), 0.55-0.45 (m, 2H), 0.41-0.30 (m, 2H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 193 | 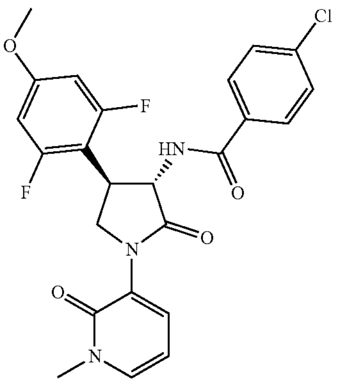 [SMILES: COc1cc(F)c([C@@H]2CN(c3cccn(C)c3=O)C(=O)[C@H]2NC(=O)c2ccc(Cl)cc2)c(F)c1] | 488.2 | Method D, RT = 2.126 min, 100% | $^1$H NMR (400 MHz, DMSO-$d_6$) δ = 9.09 (br d, J = 8.0 Hz, 1H), 7.92-7.71 (m, 3H), 7.61-3.52 (m, 3H), 6.78 (br d, J = 11.0 Hz, 2H), 6.33 (br t, J = 6.8 Hz, 1H), 5.12 (br t, J = 9.3 Hz, 1H), 4.09 (br d, J = 8.5 Hz, 1H), 3.97 (br d, J = 8.5 Hz, 2H), 3.77 (s, 3H), 3.51 (br s, 3H). |
| 194 | 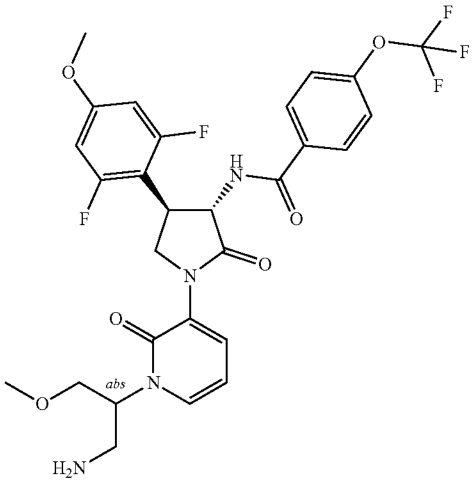 [SMILES: COCC(CN)n1cccc(N2C[C@@H](c3c(F)cc(OC)cc3F)[C@H](NC(=O)c3ccc(OC(F)(F)F)cc3)C2=O)c1=O] | 611.3 | Method C, RT = 1.510 min, 96.6% | $^1$H NMR (400 MHz, DMSO-$d_6$) δ = 9.11 (br d, J = 7.6 Hz, 1H), 7.98-7.91 (m, 2H), 7.68 (br d, J = 7.1 Hz, 1H), 7.56 (dt, J = 1.1, 6.9 Hz, 1H), 7.51-7.41 (m, 2H), 6.81-6.70 (m, 2H), 6.40-6.31 (m, 1H), 5.12-4.97 (m, 2H), 4.12-4.07 (m, 2H), 4.02-3.92 (m, 2H), 3.76 (s, 3H), 3.65-3.61 (m, 1H), 3.34-3.31 (m, 1H), 3.25-3.16 (m, 4H), 3.06-3.01 (m, 2H). |
| 195 | 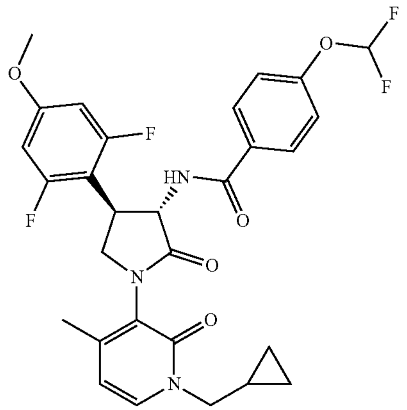 [SMILES: COc1cc(F)c([C@@H]2CN(c3c(C)ccn(CC4CC4)c3=O)C(=O)[C@H]2NC(=O)c2ccc(OC(F)F)cc2)c(F)c1] | 574.3 | Method D, RT = 1.86 min, 100% | $^1$H NMR (400 MHz, DMSO-$d_6$) δ = 9.18-8.77 (m, 1H), 8.02-7.63 (m, 3H), 7.33 (t, J = 76 Hz, 1H), 7.28-7.24 (m, 2H), 6.81-6.72 (m, 2H), 6.32-6.10 (m, 1H), 5.42-4.80 (m, 1H), 4.32-4.04 (m, 2H), 3.93-3.66 (m, 5H), 3.55-3.43 (m, 1H), 2.24-1.99 (2s, 3H), 1.29-1.11 (m, 1H), 0.55-0.42 (m, 2H), 0.42-0.30 (m, 2H). (mixture of atrop isomsers) |

TABLE 2-continued

| Ex | Structure | LCMS (M + H)+ | HPLC Method, RT (min.) & Purity | ¹H NMR |
|---|---|---|---|---|
| 196 | 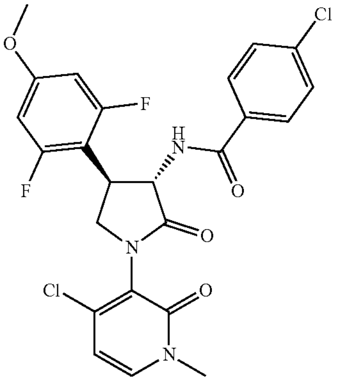 [SMILES: COc1cc(F)c([C@@H]2CN(c3c(Cl)ccn(C)c3=O)C(=O)[C@H]2NC(=O)c2ccc(Cl)cc2)c(F)c1] | 522.2 | Method D, RT = 1.680 min, 100% | ¹H NMR (400 MHz, DMSO-$d_6$) δ = 9.19-9.00 (m, 1H), 7.92-7.75 (m, 3H), 7.64-7.47 (m, 2H), 6.77 (d, J = 10.8 Hz, 2H), 6.53 (dd, J = 7.3, 8.6 Hz, 1H), 5.37-5.09 (m, 1H), 4.25-4.11 (m, 1H), 4.04-3.89 (m, 1H), 3.76 (s, 3H), 3.64-3.56 (m, 1H), 3.52-3.47 (2s, 3H). (mixture of interconvertible atropisomers) |
| 197 | 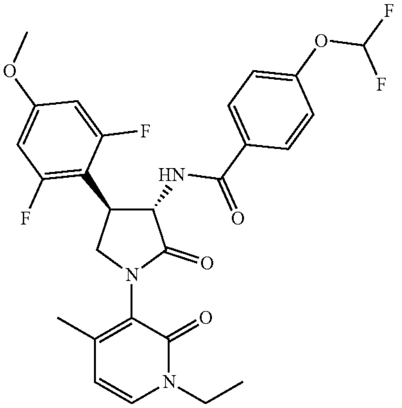 [SMILES: CCn1ccc(C)c(N2C[C@@H](c3c(F)cc(OC)cc3F)[C@H](NC(=O)c3ccc(OC(F)F)cc3)C2=O)c1=O] | 548.2 | Method D, RT = 1.695 min, 98% | ¹H NMR (400 MHz, DMSO-$d_6$) δ = 9.13-8.88 (m, 1H), 7.96-7.76 (m, 2H), 7.71-7.64 (m, 1H), 7.34 (t, J = 76 Hz, 1H), 7.28-7.24 (m, 2H), 6.84-6.66 (m, 2H), 6.31-6.16 (m, 1H), 5.36-4.82 (m, 1H), 4.29-4.07 (m, 2H), 4.02-3.83 (m, 2H), 3.80-3.72 (2s, 3H), 3.53-3.45 (m, 1H), 2.23-1.99 (2s, 3H), 1.26-1.17 (m, 3H). (mixture of interconvertible atropisomers) |
| 198 | 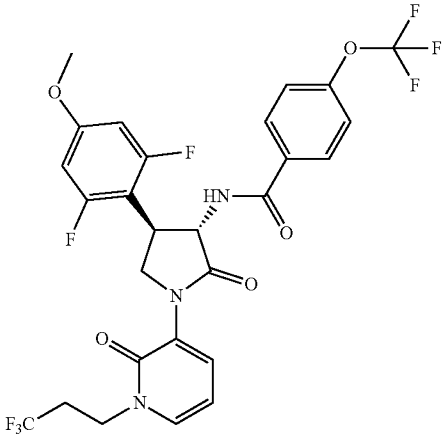 [SMILES: COc1cc(F)c([C@@H]2CN(c3cccn(CCC(F)(F)F)c3=O)C(=O)[C@H]2NC(=O)c2ccc(OC(F)(F)F)cc2)c(F)c1] | 529.3 | Method D, RT = 2.851 min, 99% | ¹H NMR (400 MHz, DMSO-$d_6$) δ = 9.16-9.03 (m, 1H), 8.02-7.87 (m, 2H), 7.83-7.73 (m, 1H), 7.68-7.57 (m, 1H), 7.52-7.42 (m, 2H), 6.83-6.71 (m, 2H), 6.46-6.30 (m, 1H), 5.15-5.06 (m, 1H), 4.26-4.17 (m, 2H), 4.14-4.05 (m, 1H), 4.02-3.94 (m, 2H), 3.76 (s, 3H), 2.84-2.69 (m, 2H). |

TABLE 2-continued

| Ex | Structure | LCMS (M + H)+ | HPLC Method, RT (min.) & Purity | $^1$H NMR |
|---|---|---|---|---|
| 199 | 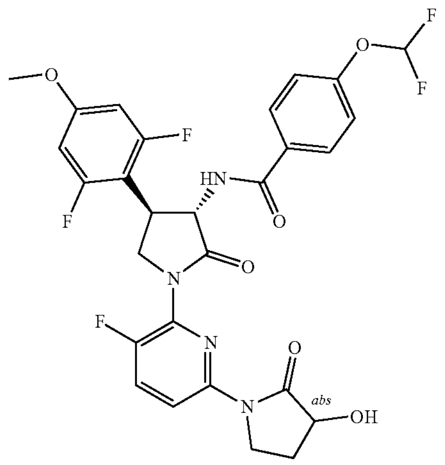 [SMILES: COc1cc(F)c([C@@H]2CN(c3nc(N4CCC(O)C4=O)ccc3F)C(=O)[C@H]2NC(=O)c2ccc(OC(F)F)cc2)c(F)c1] | 607.2 | Method D, RT = 1.66 min, 100% | $^1$H NMR (400 MHz, DMSO-$d_6$) δ = 9.11 (d, J = 8.3 Hz, 1H), 8.29 (dd, J = 8.9, 3.1 Hz, 1H), 7.94 (t, J = 9.2 Hz, 1H), 7.91-7.83 (m, 2H), 7.35 (t, J = 73.6 Hz, 1H), 7.28-7.26 (m, 2H), 6.80 (d, J = 10.8 Hz, 2H), 5.94-5.77 (m, 1H), 5.10 (dd, J = 10.5, 8.6 Hz, 1H), 4.39 (br t, J = 8.4 Hz, 1H), 4.30-4.17 (m, 2H), 4.12-3.96 (m, 2H), 3.77 (s, 3H), 3.68-3.66 (m, 1H), 2.44-2.34 (m, 1H), 1.89-1.74 (m, 1H). |
| 200 | 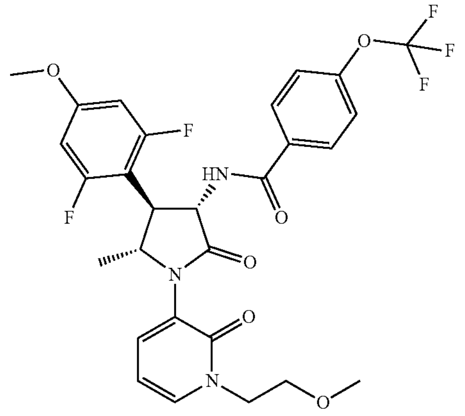 [SMILES: COCCn1cccc(N2C(=O)[C@@H](NC(=O)c3ccc(OC(F)(F)F)cc3)[C@H](c3c(F)cc(OC)cc3F)[C@H]2C)c1=O] | 596.3 | Method D, RT = 1.86 min, 100% | $^1$H NMR (400 MHz, DMSO-$d_6$) δ = 9.08 (d, J = 8.6 Hz, 1H), 8.01-7.85 (m, 2H), 7.69 (dd, J = 6.8, 2.0 Hz, 1H), 7.53-7.39 (m, 3H), 6.87-6.71 (m, 2H), 6.34 (t, J = 7.0 Hz, 1H), 5.12 (dd, J = 11.2, 8.6 Hz, 1H), 4.53-4.49 (m, 1H), 4.19-4.04 (m, 2H), 3.77 (s, 3H), 3.67-3.54 (m, 3H), 3.24 (s, 3H), 0.99 (d, J = 6.1 Hz, 3H). |
| 201 | 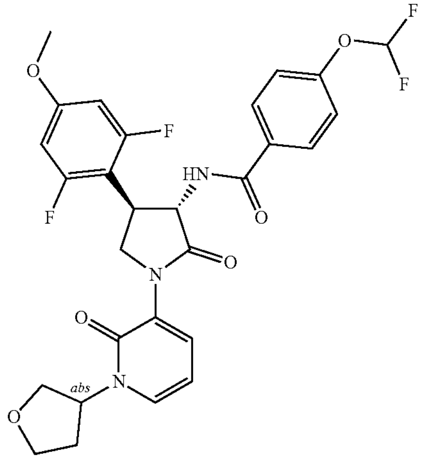 [SMILES: COc1cc(F)c([C@@H]2CN(c3cccn(C4CCOC4)c3=O)C(=O)[C@H]2NC(=O)c2ccc(OC(F)F)cc2)c(F)c1] | 576.2 | Method D, RT = 1.591 min, 100% | $^1$H NMR (400 MHz, DMSO-$d_6$) δ = 7.94-7.85 (m, 2H), 7.64 (dd, J = 6.8, 2.0 Hz, 1H), 7.59 (dd, J = 7.2, 2.0 Hz, 1H), 7.36 (t, J = 72.2 Hz, 1H), 7.27-7.25 (m, 3H), 6.77 (d, J = 10.8 Hz, 2H), 6.41 (t, J = 7.1 Hz, 1H), 5.47-5.38 (m, 1H), 5.10 (d, J = 11.2 Hz, 1H), 4.18-3.92 (m, 4H), 3.90-3.82 (m, 2H), 3.81-3.73 (m, 4H), 2.47-2.42 (m, 1H), 2.04-1.92 (m, 1H). |

TABLE 2-continued

| Ex | Structure | LCMS (M + H)+ | HPLC Method, RT (min.) & Purity | $^1$H NMR |
|---|---|---|---|---|
| 202 | 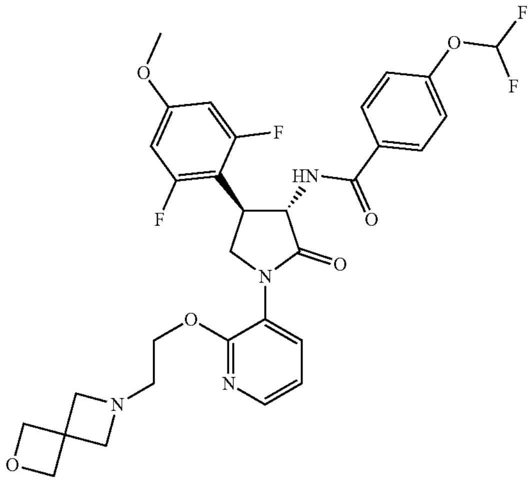 [SMILES: COc1cc(F)c([C@@H]2CN(c3cccnc3OCCN3CC4(COC4)C3)C(=O)[C@H]2NC(=O)c2ccc(OC(F)F)cc2)c(F)c1] | 631.3 | Method D, RT = 1.580 min, 100% | $^1$H NMR (400 MHz, DMSO-$d_6$) δ = 9.05 (d, J = 8.6 Hz, 1H), 8.13 (dd, J = 5.0, 2.0 Hz, 1H), 7.95-7.86 (m, 2H), 7.79 (dd, J = 7.6, 2.0 Hz, 1H), 7.34 (t, J = 73.6 Hz, 1H), 7.28 (m, 2H), 7.10 (dd, J = 7.6, 5.1 Hz, 1H), 6.80 (d, J = 10.8 Hz, 2H), 5.12 (dd, J = 11.2, 8.6 Hz, 1H), 4.58 (s, 4H), 4.33-4.12 (m, 4H), 3.99 (br d, J = 10.0 Hz, 2H), 3.77 (s, 3H), 3.36 (m, 3H), 2.71 (t, J = 5.5 Hz, 2H). |
| 203 | 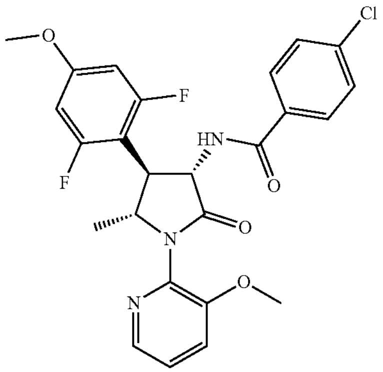 [SMILES: COc1cc(F)c([C@H]2[C@H](NC(=O)c3ccc(Cl)cc3)C(=O)N(c3ncccc3OC)[C@@H]2C)c(F)c1] | 502.2 | Method D, RT = 1.79 min, 100% | $^1$H NMR (400 MHz, DMSO-$d_6$) δ = 9.16 (d, J = 9.0 Hz, 1H), 8.12 (dd, J = 4.6, 1.2 Hz, 1H), 7.92-7.79 (m, 2H), 7.65 (dd, J = 8.3, 4.6 Hz, 1H), 7.60-7.52 (m, 2H), 7.44 (dd, J = 8.3, 4.6 Hz, 1H), 6.88-6.68 (m, 2H), 5.29 (dd, J = 11.5, 8.8 Hz, 1H), 4.37-4.24 (m, 1H), 3.87 (s, 3H), 3.77 (s, 3H), 3.70 (t, J = 10.6 Hz, 1H), 1.01 (d, J = 6.1 Hz, 3H). |
| 204 | 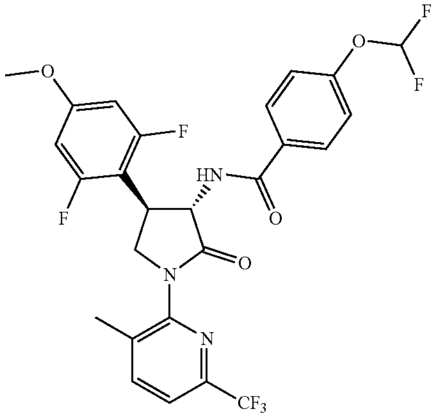 [SMILES: COc1cc(F)c([C@@H]2CN(c3nc(C(F)(F)F)ccc3C)C(=O)[C@H]2NC(=O)c2ccc(OC(F)F)cc2)c(F)c1] | 572.1 | Method D, RT = 2.12 min, 100% | $^1$H NMR (400 MHz, DMSO-$d_6$) δ = 9.02-8.87 (m, 1H), 8.10-7.99 (m, 1H), 7.80 (br d, J = 8.1 Hz, 1H), 7.66 (br d, J = 8.6 Hz, 2H), 7.35 (t, J = 72.0 Hz, 1H), 7.17 (d, J = 8.4 Hz, 2H), 6.71-6.57 (m, 2H), 5.28-5.18 (m, 1H), 4.44-4.26 (m, 3H), 3.70 (s, 3H), 2.39 (s, 3H). |

TABLE 2-continued

| Ex | Structure | LCMS (M + H)+ | HPLC Method, RT (min.) & Purity | $^1$H NMR |
|---|---|---|---|---|
| 205 | 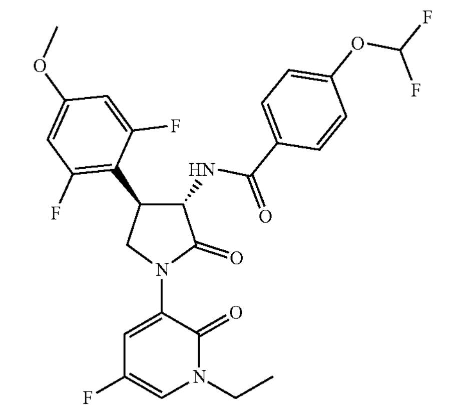 [SMILES: CCn1cc(F)cc(N2C[C@@H](c3c(F)cc(OC)cc3F)[C@H](NC(=O)c3ccc(OC(F)F)cc3)C2=O)c1=O] | 552.2 | Method D, RT = 1.708 min, 100% | $^1$H NMR (400 MHz, DMSO-$d_6$) δ = 9.01 (d, J = 8.6 Hz, 1H), 8.05 (dd, J = 4.4, 3.3 Hz, 1H), 7.93-7.83 (m, 2H), 7.78 (dd, J = 8.4, 3.3 Hz, 1H), 7.34 (t, J = 76 Hz, 1H), 7.28-7.25 (m, 2H), 6.77 (d, J = 10.8 Hz, 2H), 5.12 (dd, J = 10.6, 8.7 Hz, 1H), 4.18-4.04 (m, 2H), 4.03-3.88 (m, 3H), 3.77 (s, 3H), 1.25 (t, J = 7.1 Hz, 3H). |
| 206 | 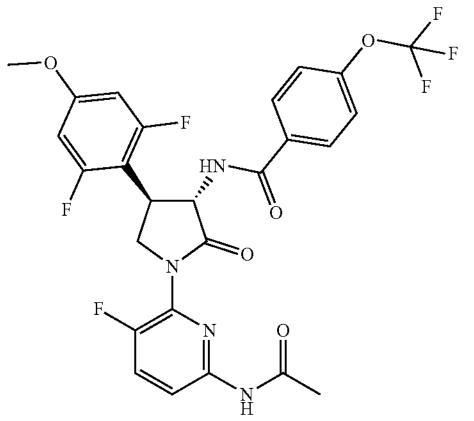 [SMILES: COc1cc(F)c([C@@H]2CN(c3nc(NC(C)=O)ccc3F)C(=O)[C@H]2NC(=O)c2ccc(OC(F)(F)F)cc2)c(F)c1] | 583.2 | Method C, RT = 1.87 min, 100% | $^1$H NMR (400 MHz, DMSO-$d_6$) δ = 10.61 (s, 1H), 9.21 (d, J = 8.3 Hz, 1H), 8.11-7.98 (m, 1H), 7.97-7.90 (m, 2H), 7.86 (t, J = 8.9 Hz, 1H), 7.50 (d, J = 8.6 Hz, 2H), 6.80 (d, J = 11.0 Hz, 2H), 5.07 (dd, J = 10.3, 8.6 Hz, 1H), 4.29-4.03 (m, 3H), 3.77 (s, 3H), 2.09 (s, 3H). |
| 207 | 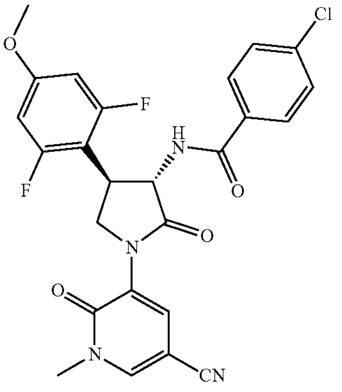 [SMILES: COc1cc(F)c([C@@H]2CN(c3cc(C#N)cn(C)c3=O)C(=O)[C@H]2NC(=O)c2ccc(Cl)cc2)c(F)c1] | 513.1 | Method D, RT = 1.650 min, 99.4% | $^1$H NMR (400 MHz, DMSO-$d_6$) δ = 9.08 (d, J = 8.3 Hz, 1H), 8.66 (d, J = 2.4 Hz, 1H), 7.88 (d, J = 2.4 Hz, 1H), 7.86-7.75 (m, 2H), 7.62-7.53 (m, 2H), 6.82-6.68 (m, 2H), 5.10 (dd, J = 11.1, 8.7 Hz, 1H), 4.16-4.06 (m, 1H), 4.03-3.97 (m, 1H), 3.96-3.89 (m, 1H), 3.77 (s, 3H), 3.53 (s, 3H) |

TABLE 2-continued

| Ex | Structure | LCMS (M + H)+ | HPLC Method, RT (min.) & Purity | $^1$H NMR |
|---|---|---|---|---|
| 208 | 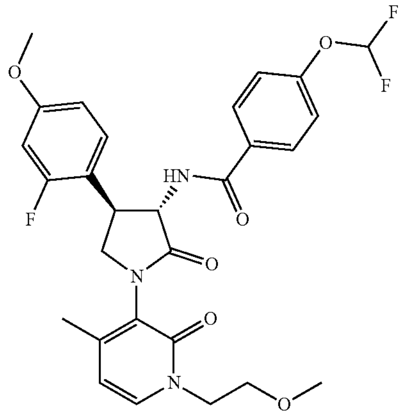 [SMILES: COCCn1ccc(C)c(N2C[C@@H](c3ccc(OC)cc3F)[C@H](NC(=O)c3ccc(OC(F)F)cc3)C2=O)c1=O] | 560.2 | Method D, RT = 1.65 min, 100% | $^1$H NMR (400 MHz, DMSO-$d_6$) δ = 9.04-8.93 (t, J = 8.4 Hz, 1H), 8.00-7.81 (m, 2H), 7.61-7.50 (m, 2H), 7.35 (t, J = 72 Hz, 1H), 7.28-7.23 (m, 2H), 6.90-6.73 (m, 2H), 6.20 (d, J = 6.8 Hz, 1H), 5.42-4.74 (m, 1H), 4.21-3.92 (m, 4H), 3.74-3.70 (2S, 3H), 3.61-3.55 (m, 3H), 3.24 (s, 3H), 2.22-2.03 (2s, 3H). (mixture of interconvertible atropisomers) |
| 209 | 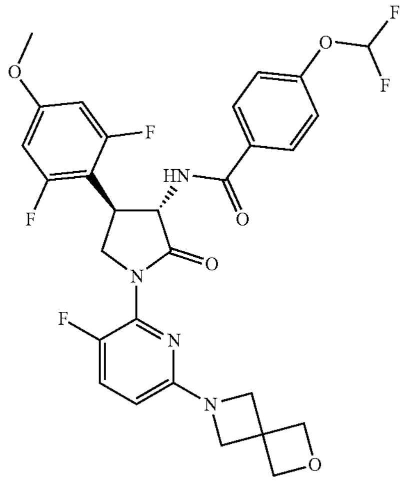 [SMILES: COc1cc(F)c([C@@H]2CN(c3nc(N4CC5(COC5)C4)ccc3F)C(=O)[C@H]2NC(=O)c2ccc(OC(F)F)cc2)c(F)c1] | 605.2 | Method D, RT = 1.845 min, 97% | $^1$H NMR (400 MHz, DMSO-$d_6$) δ = 9.09 (d, J = 8.3 Hz, 1H), 7.89 (d, J = 8.8 Hz, 2H), 7.64 (t, J = 9.2 Hz, 1H), 7.35 (t, J = 76 Hz, 1H), 7.29-7.27 (m, 2H), 6.80 (br d, J = 10.8 Hz, 2H), 6.40 (dd, J = 9.0, 2.2 Hz, 1H), 5.17-5.05 (m, 1H), 4.71 (s, 4H), 4.24-4.02 (m, 6H), 4.00-3.94 (m, 1H), 3.78 (s, 3H). |
| 210 | 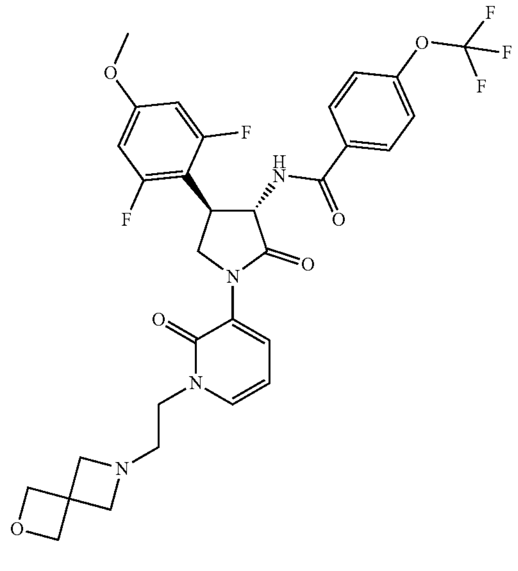 [SMILES: COc1cc(F)c([C@@H]2CN(c3cccn(CCN4CC5(COC5)C4)c3=O)C(=O)[C@H]2NC(=O)c2ccc(OC(F)(F)F)cc2)c(F)c1] | 649.3 | Method D, RT = 1.626 min, 95.6% | $^1$H NMR (400 MHz, DMSO-$d_6$) δ = 9.10 (d, J = 8.6 Hz, 1H), 8.00-7.88 (m, 2H), 7.64 (dd, J = 6.8, 2.0 Hz, 1H), 7.58 (dd, J = 7.1, 2.0 Hz, 1H), 7.49 (d, J = 8.1 Hz, 2H), 6.77 (d, J = 10.8 Hz, 2H), 6.31 (t, J = 7.0 Hz, 1H), 5.12 (dd, J = 11.1, 8.7 Hz, 1H), 4.57 (s, 4H), 4.15-4.04 (m, 1H), 4.01-3.92 (m, 2H), 3.88-3.84 (m, 2H), 3.77 (s, 3H), 3.29 (s, 4H), 2.61 (t, J = 6.0 Hz, 2H). |

TABLE 2-continued

| Ex | Structure | LCMS (M + H)+ | HPLC Method, RT (min.) & Purity | $^1$H NMR |
| --- | --- | --- | --- | --- |
| 211 | 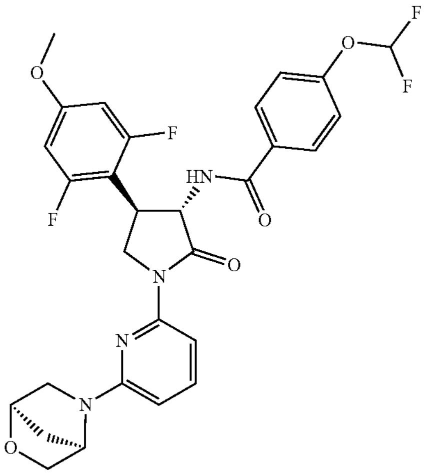 [SMILES: COc1cc(F)c([C@@H]2CN(c3cccc(N4C[C@H]5C[C@@H]4CO5)n3)C(=O)[C@H]2NC(=O)c2ccc(OC(F)F)cc2)c(F)c1] | 587.2 | Method D, RT = 1.964 min, 94% | $^1$H NMR (400 MHz, DMSO-$d_6$) δ = 8.75 (d, J = 7.8 Hz, 1H), 7.71 (d, J = 8.3 Hz, 2H), 7.68-7.61 (m, 1H), 7.61-7.54 (m, 1H), 7.33 (t, J = 72.6 Hz, 1H), 7.19-7.15 (m, 2H), 6.62 (d, J = 11.0 Hz, 2H), 6.31 (d, J = 7.8 Hz, 1H), 5.28 (t, J = 8.4 Hz, 1H), 4.85-4.81 (m, 1H), 4.67-4.62 (m, 1H), 4.40-4.19 (m, 3H), 3.82-3.68 (m, 4H), 3.65 (d, J = 7.6 Hz, 1H), 3.44 (br d, J = 9.8 Hz, 1H), 3.24 (m, 1H), 1.94-1.76 (m, 2H). |
| 212 | 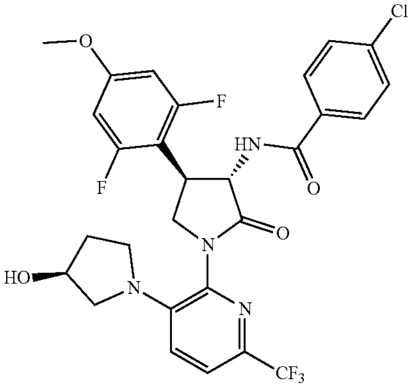 [SMILES: COc1cc(F)c([C@@H]2CN(c3nc(C(F)(F)F)ccc3N3CC[C@H](O)C3)C(=O)[C@H]2NC(=O)c2ccc(Cl)cc2)c(F)c1] | 611.2 | Method D, RT = 2.05 min, 95.7% | $^1$H NMR (400 MHz, DMSO-$d_6$) δ = 9.09 (d, J = 8.1 Hz, 1H), 7.83-7.77 (m, 3H), 7.59-7.55 (m, 2H), 7.13 (d, J = 8 Hz, 1H), 6.79 (d, J = 10.8 Hz, 2H), 5.39-5.25 (m, 1H), 5.11-5.06 (m, 1H), 4.97 (d, J = 3.2 Hz, 1H), 4.39 (br d, J = 2.7 Hz, 1H), 4.30-4.20 (m, 1H), 3.90-3.79 (m, 1H), 3.76 (s, 3H), 3.65-3.50 (m, 4H), 2.02-1.83 (m, 2H). |
| 213 | 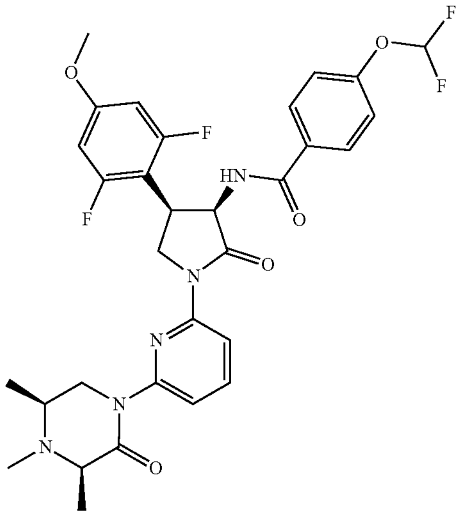 [SMILES: COc1cc(F)c([C@@H]2CN(c3cccc(N4C[C@H](C)N(C)[C@H](C)C4=O)n3)C(=O)[C@@H]2NC(=O)c2ccc(OC(F)F)cc2)c(F)c1] | 616.2 | Method D, RT = 1.903 min, 100% | $^1$H NMR (400 MHz, DMSO-$d_6$) δ = 8.74 (d, J = 7.8 Hz, 1H), 7.78-7.63 (m, 3H), 7.63-7.55 (m, 1H), 7.33 (t, J = 76 Hz, 1H), 7.18-7.14 (m, 2H), 6.70-6.54 (m, 3H), 5.29 (t, J = 8.4 Hz, 1H), 4.42-4.24 (m, 4H), 4.12-3.98 (m, 2H), 3.70 (s, 3H), 2.17 (s, 3H), 2.16-2.08 (m, 3H), 1.07 (d, J = 6.1 Hz, 6H). |

TABLE 2-continued

| Ex | Structure | LCMS (M + H)+ | HPLC Method, RT (min.) & Purity | $^1$H NMR |
|---|---|---|---|---|
| 214 | 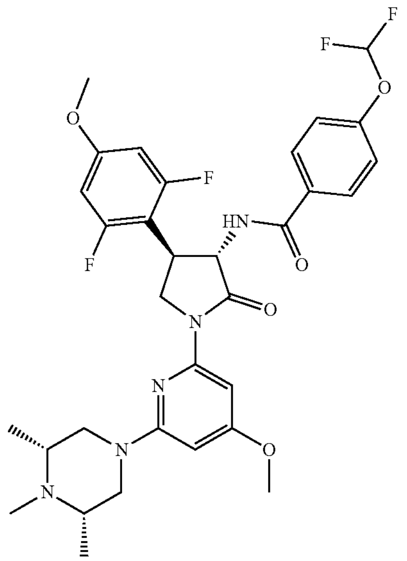 [SMILES: COc1cc(N2C[C@@H](C)N(C)[C@@H](C)C2)nc(N2C[C@@H](c3c(F)cc(OC)cc3F)[C@H](NC(=O)c3ccc(OC(F)F)cc3)C2=O)c1] | 646.3 | Method D, RT = 1.97 min, 100% | $^1$H NMR (400 MHz, DMSO-$d_6$) δ = 9.05 (d, J = 8.3 Hz, 1H), 7.88 (d, J = 9.2 Hz, 2H), 7.35 (t, J = 73.6 Hz, 1H), 7.33-7.27 (m, 4H), 6.79 (d, J = 10.8 Hz, 2H), 5.08-5.03 (m, 1H), 4.49-4.38 (m, 1H), 4.17-3.98 (m, 3H), 3.93-3.84 (m, 1H), 3.80 (s, 3H), 3.78 (s, 3H), 2.48 (s, 3H), 2.30-2.01 (m, 4H), 1.15-1.02 (m, 6H). |
| 215 | 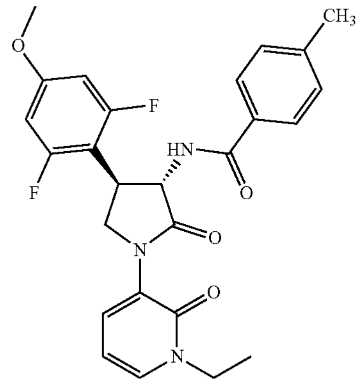 [SMILES: CCn1cccc(N2C[C@@H](c3c(F)cc(OC)cc3F)[C@H](NC(=O)c3ccc(C)cc3)C2=O)c1=O] | 482.2 | Method D, RT = 1.557 min, 100% | $^1$H NMR (400 MHz, DMSO-$d_6$) δ = 8.89 (d, J = 8.8 Hz, 1H), 7.76 (dd, J = 6.7, 2.1 Hz, 1H), 7.73 (d, J = 8.3 Hz, 2H), 7.57 (dd, J = 7.2, 2.1 Hz, 1H), 7.28 (d, J = 8.1 Hz, 2H), 6.77 (d, J = 10.8 Hz, 2H), 6.35 (t, J = 7.0 Hz, 1H), 5.12 (dd, J = 11.1, 8.7 Hz, 1H), 4.18-4.04 (m, 1H), 4.04-3.89 (m, 4H), 3.76 (s, 3H), 2.35 (s, 3H), 1.25 (t, J = 7.1 Hz, 3H). |
| 216 | 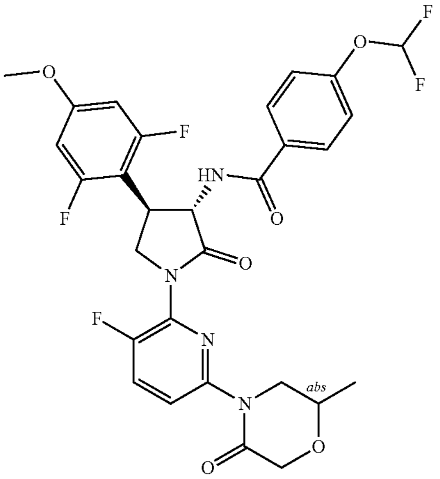 [SMILES: COc1cc(F)c([C@@H]2CN(c3nc(N4CC(C)OCC4=O)ccc3F)C(=O)[C@H]2NC(=O)c2ccc(OC(F)F)cc2)c(F)c1] | 621.2 | Method D, RT = 2.24 min, 100% | $^1$H NMR (400 MHz, DMSO-$d_6$) δ = 9.10 (d, J = 8.6 Hz, 1H), 8.02-7.81 (m, 4H), 7.34 (t, J = 73.6 Hz, 1H), 7.29-7.27 (m, 2H), 6.80 (d, J = 10.8 Hz, 2H), 5.16-5.03 (m, 1H), 4.33-4.19 (m, 4H), 4.10-3.96 (m, 3H), 3.77 (s, 3H), 3.60-3.48 (m, 1H), 1.26 (d, J = 6.1 Hz, 3H). |

TABLE 2-continued

| Ex | Structure | LCMS (M + H)+ | HPLC Method, RT (min.) & Purity | $^1$H NMR |
|---|---|---|---|---|
| 217 | 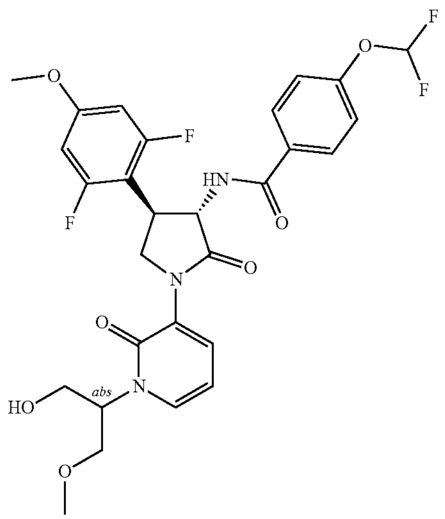 [SMILES: COCC(CO)n1cccc(N2C[C@@H](c3c(F)cc(OC)cc3F)[C@H](NC(=O)c3ccc(OC(F)F)cc3)C2=O)c1=O] | 608.3 | Method D, RT = 1.54 min, 97% | $^1$H NMR (400 MHz, DMSO-$d_6$) δ = 8.87 (br d, J = 8.3 Hz, 1H), 7.96-7.84 (m, 2H), 7.71 (dd, J = 7.1, 2.0 Hz, 1H), 7.56 (dd, J = 7.1, 2.0 Hz, 1H), 7.33 (t, J = 73.6 Hz, 1H), 7.25-7.23 (m, 2H), 6.77 (d, J = 11.5 Hz, 2H), 6.33 (t, J = 7.1 Hz, 1H), 5.65 (dd, J = 11.7, 8.6 Hz, 1H), 5.14-4.93 (m, 2H), 4.70-4.52 (m, 1H), 4.32-4.27 (m, 1H), 3.76 (s, 3H), 3.75-3.69 (m, 4H), 3.23 (s, 3H), 0.91 (br d, J = 6.6 Hz, 3H). |
| 218 | 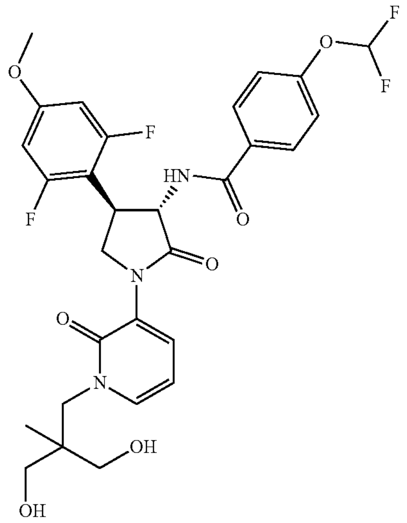 [SMILES: COc1cc(F)c([C@@H]2CN(c3cccn(CC(C)(CO)CO)c3=O)C(=O)[C@H]2NC(=O)c2ccc(OC(F)F)cc2)c(F)c1] | 608.3 | Method D, RT = 1.522 min, 97.4% | $^1$H NMR (400 MHz, DMSO-$d_6$) δ = 9.06-8.98 (m, 1H), 7.93-7.85 (m, 2H), 7.69-7.61 (m, 2H), 7.34 (t, J = 73.6 Hz, 1H), 7.28 (m, 2H), 6.77 (d, J = 10.8 Hz, 2H), 6.40 (t, J = 7.0 Hz, 1H), 5.14 (dd, J = 11.1, 8.4 Hz, 1H), 4.74 (t, J = 5.4 Hz, 2H), 4.15-4.04 (m, 1H), 4.03-3.89 (m, 4H), 3.76 (s, 3H), 3.24-3.11 (m, 4H), 0.78 (s, 3H). |
| 219 | 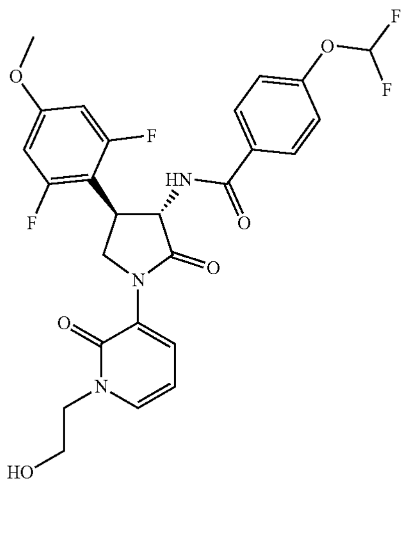 [SMILES: COc1cc(F)c([C@@H]2CN(c3cccn(CCO)c3=O)C(=O)[C@H]2NC(=O)c2ccc(OC(F)F)cc2)c(F)c1] | 550.2 | Method D, RT = 1.700 min, 98.8% | $^1$H NMR (400 MHz, DMSO-$d_6$) δ = 8.99 (br d, J = 8.6 Hz, 1H), 8.02-7.83 (m, 2H), 7.65 (dd, J = 6.6, 2.0 Hz, 1H), 7.59 (dd, J = 7.1, 2.0 Hz, 1H), 7.34 (t, J = 73.6 Hz, 1H), 7.28 (m, 2H), 6.77 (d, J = 10.8 Hz, 2H), 6.32 (t, J = 7.0 Hz, 1H), 5.12 (dd, J = 10.9, 8.7 Hz, 1H), 4.93 (t, J = 5.3 Hz, 1H), 4.17-4.05 (m, 1H), 4.05-3.90 (m, 4H), 3.77 (s, 3H), 3.70-3.59 (m, 2H). |

TABLE 2-continued

| Ex | Structure | LCMS (M + H)+ | HPLC Method, RT (min.) & Purity | $^1$H NMR |
|---|---|---|---|---|
| 220 | 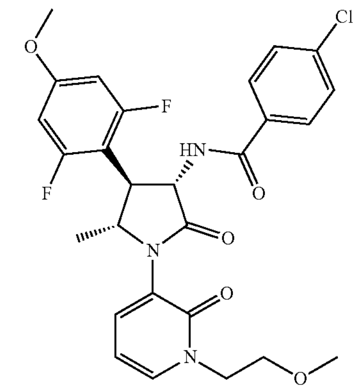 [SMILES: COCCn1cccc(N2C(=O)[C@@H](NC(=O)c3ccc(Cl)cc3)[C@H](c3c(F)cc(OC)cc3F)[C@H]2C)c1=O] | 546.2 | Method D, RT = 1.71 min, 95% | $^1$H NMR (400 MHz, DMSO-$d_6$) δ = 9.03 (d, J = 8.6 Hz, 1H), 7.88-7.77 (m, 2H), 7.68 (dd, J = 6.7, 1.8 Hz, 1H), 7.58-7.49 (m, 2H), 7.46 (dd, J = 6.7, 1.8 Hz, 1H), 6.87-6.72 (m, 2H), 6.34 (t, J = 7.1 Hz, 1H), 5.18-5.00 (m, 1H), 4.57-4.42 (m, 1H), 4.23-4.05 (m, 2H), 3.78 (s, 3H), 3.67-3.56 (m, 3H), 3.25 (m, 3H), 0.99 (d, J = 6.4 Hz, 3H). |
| 221 | 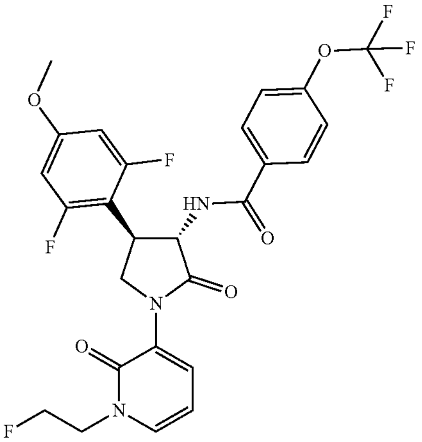 [SMILES: COc1cc(F)c([C@@H]2CN(c3cccn(CCF)c3=O)C(=O)[C@H]2NC(=O)c2ccc(OC(F)(F)F)cc2)c(F)c1] | 570.2 | Method D, RT = 1.801 min, 100% | $^1$H NMR (400 MHz, DMSO-$d_6$) δ = 9.12 (d, J = 8.6 Hz, 1H), 8.03-7.87 (m, 2H), 7.72 (dd, J = 6.7, 1.8 Hz, 1H), 7.64 (dd, J = 7.3, 1.8 Hz, 1H), 7.49 (d, J = 8.3 Hz, 2H), 6.77 (d, J = 10.8 Hz, 2H), 6.37 (t, J = 7.0 Hz, 1H), 5.13 (dd, J = 10.9, 8.7 Hz, 1H), 4.71 (dt, J = 48.6, 4.6 Hz, 2H), 4.38-4.29 (m, 1H), 4.29-4.20 (m, 1H), 4.16-4.05 (m, 1H), 4.04-3.94 (m, 2H), 3.77 (s, 3H). |
| 222 | 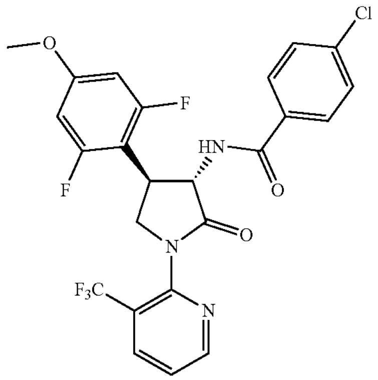 [SMILES: COc1cc(F)c([C@@H]2CN(c3ncccc3C(F)(F)F)C(=O)[C@H]2NC(=O)c2ccc(Cl)cc2)c(F)c1] | 526.1 | Method D, RT = 1.94 min, 95.6% | $^1$H NMR (400 MHz, DMSO-$d_6$) δ = 9.14 (br d, J = 8.1 Hz, 1H), 8.90 (dd, J = 4.6, 1.2 Hz, 1H), 8.39 (dd, J = 7.8, 1.2 Hz, 1H), 7.91-7.79 (m, 2H), 7.73 (dd, J = 7.7, 4.8 Hz, 1H), 7.62-7.51 (m, 2H), 6.80 (d, J = 10.8 Hz, 2H), 5.14 (dd, J = 11.1, 8.7 Hz, 1H), 4.29-4.23 (m, 1H), 4.18-4.06 (m, 1H), 4.02-3.94 (m, 1H), 3.78 (s, 3H). |

TABLE 2-continued

| Ex | Structure | LCMS (M + H)+ | HPLC Method, RT (min.) & Purity | $^1$H NMR |
|---|---|---|---|---|
| 223 | 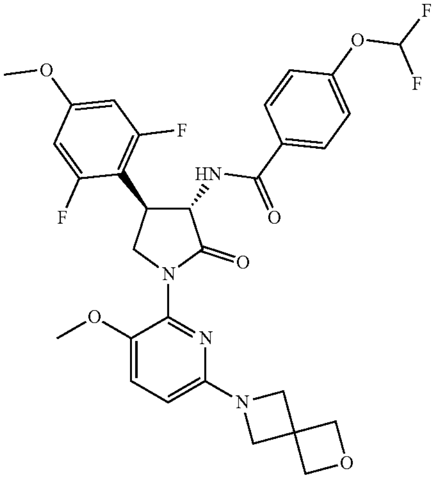 [SMILES: COc1cc(F)c([C@@H]2CN(c3nc(N4CC5(COC5)C4)ccc3OC)C(=O)[C@H]2NC(=O)c2ccc(OC(F)F)cc2)c(F)c1] | 617.2 | Method D, RT = 1.75 min, 93% | $^1$H NMR (400 MHz, DMSO-$d_6$) δ = 9.04 (d, J = 8.6 Hz, 1H), 7.95-7.84 (m, 2H), 7.57-7.52 (m, 1H), 7.34 (t, J = 76 Hz, 1H), 7.28-7.25 (m, 2H), 6.77 (d, J = 10.8 Hz, 2H), 6.44 (d, J = 8.8 Hz, 1H), 5.22 (dd, J = 11.1, 8.9 Hz, 1H), 4.71 (s, 4H), 4.18-3.91 (m, 6H), 3.88-3.81 (m, 1H), 3.76 (s, 3H), 3.75 (s, 3H). |
| 224 | 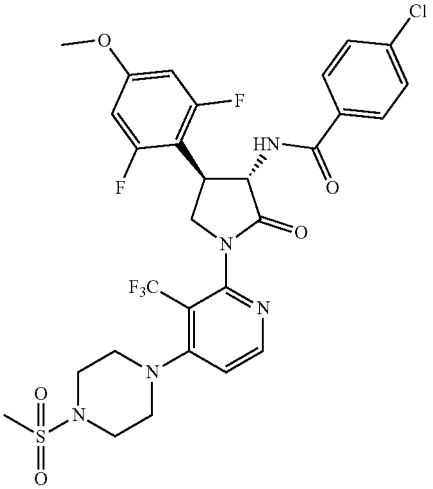 [SMILES: COc1cc(F)c([C@@H]2CN(c3nccc(N4CCN(S(C)(=O)=O)CC4)c3C(F)(F)F)C(=O)[C@H]2NC(=O)c2ccc(Cl)cc2)c(F)c1] | 688.2 | Method D, RT = 1.94 min, 100% | $^1$H NMR (400 MHz, DMSO-$d_6$) δ = 9.10 (br d, J = 8.1 Hz, 1H), 8.53 (br d, J = 6.6 Hz, 1H), 7.94-7.75 (m, 2H), 7.62-7.50 (m, 2H), 7.29 (br d, J = 5.4 Hz, 1H), 6.79 (d, J = 10.8 Hz, 2H), 5.20-5.03 (m, 1H), 4.46-4.12 (m, 2H), 3.90-3.74 (m, 1H), 3.72 (s, 3H), 3.32-3.18 (m, 6H), 2.95 (s, 3H), 2.64-2.53 (m, 2H). |
| 225 | 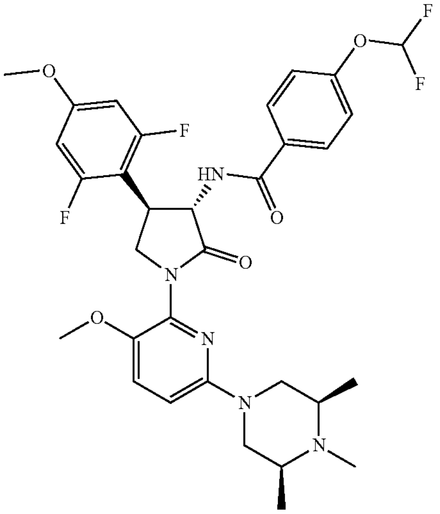 [SMILES: COc1cc(F)c([C@@H]2CN(c3nc(N4C[C@@H](C)N(C)[C@@H](C)C4)ccc3OC)C(=O)[C@H]2NC(=O)c2ccc(OC(F)F)cc2)c(F)c1] | 646.3 | Method D, RT = 1.81 min, 97% | $^1$H NMR (400 MHz, DMSO-$d_6$) δ = 9.03 (br d, J = 9.0 Hz, 1H), 7.96-7.82 (m, 2H), 7.54-7.52 (m, 1H), 7.34 (t, J = 76.0 Hz, 1H), 7. 28-7.26 (m, 2H), 6.88 (d, J = 8.8 Hz, 1H), 6.77 (d, J = 10.8 Hz, 2H), 5.21 (dd, J = 11.1, 8.9 Hz, 1H), 4.23-4.10 (m, 1H), 4.10-3.93 (m, 3H), 3.89-3.82 (m, 1H), 3.77 (s, 3H), 3.76 (s, 3H), 2.49-2.43 (m, 1H), 2.39-2.06 (m, 6H), 1.11 (br d, J = 6.4 Hz, 6H). |

TABLE 2-continued

| Ex | Structure | LCMS (M + H)+ | HPLC Method, RT (min.) & Purity | $^1$H NMR |
|---|---|---|---|---|
| 226 | 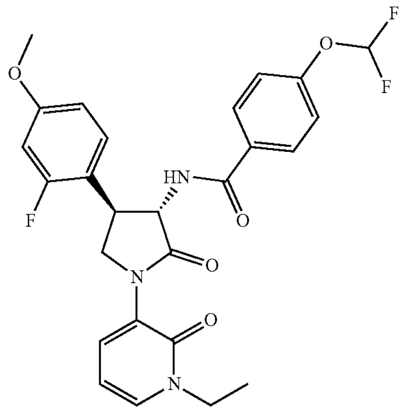 [SMILES: CCn1cccc(N2C[C@@H](c3ccc(OC)cc3F)[C@H](NC(=O)c3ccc(OC(F)F)cc3)C2=O)c1=O] | 516.2 | Method D, RT = 1.53 min, 95.1% | $^1$H NMR (400 MHz, DMSO-d$_6$) δ = 8.51 (d, J = 8.5 Hz, 1H), 7.93 (d, J = 9.0 Hz, 1H), 7.78 (dd, J = 6.5, 2.0 Hz, 1H), 7.76-7.66 (m, 2H), 7.64 (dd, J = 7.0, 2.0 Hz, 1H), 7.35 (t, J = 72.0 Hz, 1H), 7.23-7.16 (m, 2H), 6.82-6.63 (m, 2H), 6.38 (t, J = 7.0 Hz, 1H), 5.15-5.05 (m, 1H), 4.17-4.06 (m, 1H), 4.04-3.94 (m, 3H), 3.82-3.74 (m, 1H), 3.72 (s, 3H), 1.25 (t, J = 7.1 Hz, 3H). |
| 227 | 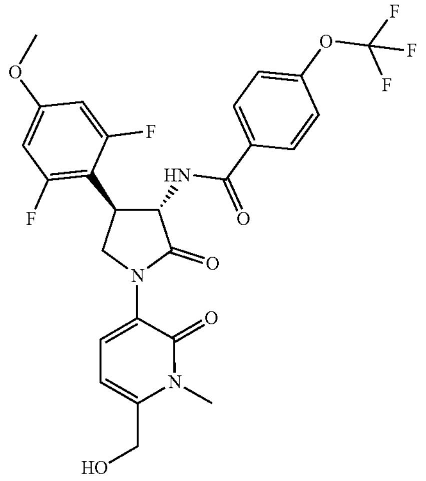 [SMILES: COc1cc(F)c([C@@H]2CN(c3ccc(CO)n(C)c3=O)C(=O)[C@H]2NC(=O)c2ccc(OC(F)(F)F)cc2)c(F)c1] | 568.2 | Method D, RT = 1.64 min, 96% | $^1$H NMR (400 MHz, DMSO-d$_6$) δ = 9.11 (d, J = 8.6 Hz, 1H), 8.02-7.86 (m, 2H), 7.56 (d, J = 7.6 Hz, 1H), 7.52-7.36 (m, 2H), 6.85-6.68 (m, 2H), 6.40 (d, J = 7.6 Hz, 1H), 5.67 (t, J = 5.6 Hz, 1H), 5.12 (dd, J = 11.1, 8.7, Hz, 1H), 4.49 (d, J = 5.4 Hz, 2H), 4.18-4.04 (m, 1H), 4.02-3.89 (m, 2H), 3.76 (s, 3H), 3.49 (s, 3H). |
| 228 | 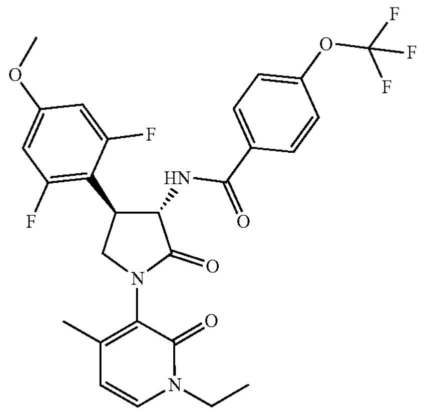 [SMILES: CCn1ccc(C)c(N2C[C@@H](c3c(F)cc(OC)cc3F)[C@H](NC(=O)c3ccc(OC(F)(F)F)cc3)C2=O)c1=O] | 566.2 | Method D, RT = 1.886 min, 100% | $^1$H NMR (400 MHz, DMSO-d$_6$) δ = 9.26-8.95 (m, 1H), 8.02-7.83 (m, 2H), 7.76-7.60 (m, 1H), 7.56-7.33 (m, 2H), 6.79-6.72 (m, 2H), 6.30-6.14 (m, 1H), 5.38-4.79 (m, 1H), 4.30-4.06 (m, 2H), 4.04-3.84 (m, 2H), 3.80-3.69 (2s, 3H), 3.53-3.44 (m, 1H), 2.22-1.97 (2s, 3H), 1.29-1.15 (m, 3H). (mixture of interconvertible atropisomers). |

TABLE 2-continued

| Ex | Structure | LCMS (M + H)+ | HPLC Method, RT (min.) & Purity | $^1$H NMR |
|---|---|---|---|---|
| 229 | 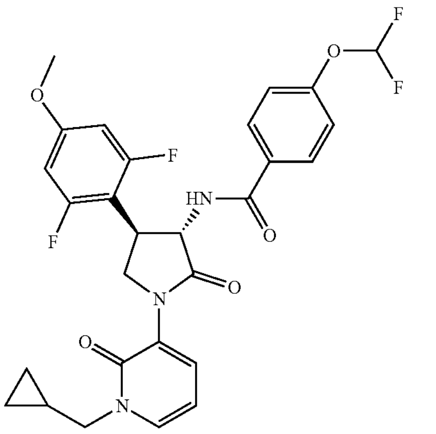 [SMILES: COc1cc(F)c([C@@H]2CN(c3cccn(CC4CC4)c3=O)C(=O)[C@H]2NC(=O)c2ccc(OC(F)F)cc2)c(F)c1] | 560.2 | Method D, RT = 1.78 min, 100% | $^1$H NMR (400 MHz, DMSO-$d_6$) δ = 9.00 (d, J = 8.6 Hz, 1H), 7.96-7.85 (m, 2H), 7.79 (dd, J = 6.6, 2.0 Hz, 1H), 7.59 (dd, J = 7.3, 2.0 Hz, 1H), 7.34 (t, J = 72 Hz, 1H), 7.27-7.25 (m, 2H), 6.77 (d, J = 10.8 Hz, 2H), 6.35 (t, J = 7.0 Hz, 1H), 5.12 (dd, J = 10.9, 8.7 Hz, 1H), 4.17-4.04 (m, 1H), 4.04-3.91 (m, 2H), 3.87-3.78 (m, 2H), 3.77 (s, 3H), 1.31-1.16 (m, 1H), 0.55-0.43 (m, 2H), 0.43-0.33 (m, 2H). |
| 230 | 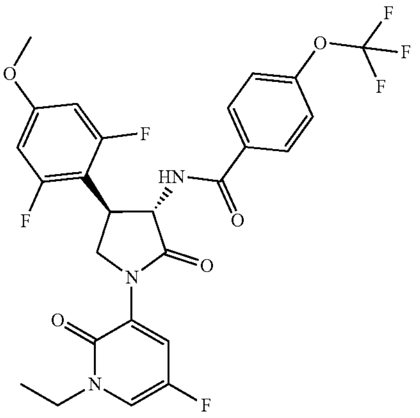 [SMILES: CCn1cc(F)cc(N2C[C@@H](c3c(F)cc(OC)cc3F)[C@H](NC(=O)c3ccc(OC(F)(F)F)cc3)C2=O)c1=O] | 570.2 | Method D, RT = 1.89 min, 100% | $^1$H NMR (400 MHz, DMSO-$d_6$) δ = 9.12 (d, J = 8.6 Hz, 1H), 8.05 (dd, J = 4.5, 3.3 Hz, 1H), 7.98-7.90 (m, 2H), 7.78 (dd, J = 8.4, 3.3 Hz, 1H), 7.49 (d, J = 8.9 Hz, 2H), 6.78 (d, J = 10.8 Hz, 2H), 5.14 (m, 1H), 4.19-4.04 (m, 2H), 4.03-3.88 (m, 3H), 3.77 (s, 3H), 1.25 (t, J = 7.1 Hz, 3H) |
| 231 | 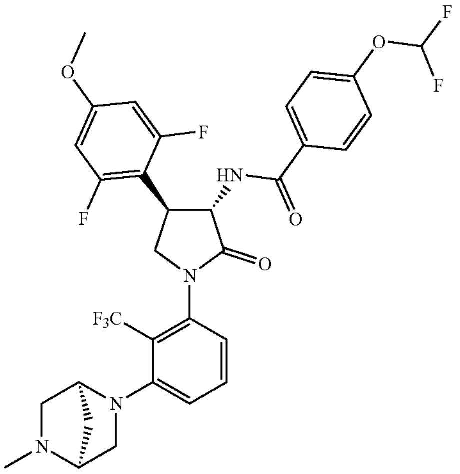 [SMILES: COc1cc(F)c([C@@H]2CN(c3cccc(N4C[C@@H]5C[C@H]4CN5C)c3C(F)(F)F)C(=O)[C@H]2NC(=O)c2ccc(OC(F)F)cc2)c(F)c1] | 668.2 | Method D, RT = 1.69 min, 100% | $^1$H NMR (400 MHz, DMSO-$d_6$) δ = 9.11-9.00 (m, 1H), 8.24-8.06 (m, 1H), 7.95-7.78 (m, 2H), 7.35 (t, J = 72 Hz, 1H), 7.31-7.25 (m, 2H), 7.01-6.83 (m, 1H), 6.82-6.68 (m, 2H), 5.16-5.01 (m, 1H), 4.58-4.43 (m, 1H), 4.38-4.27 (m, 1H), 4.25-4.08 (m, 1H), 3.86-3.77 (m, 1H), 3.76 (s, 3H), 3.64-3.55 (m, 1H), 3.50-3.40 (m, 1H), 3.28-3.21 (m, 1H), 2.83-2.63 (m, 2H), 2.27 (s, 3H), 2.00-1.87 (m, 1H), 1.81 (m, 1H). |

TABLE 2-continued

| Ex | Structure | LCMS (M + H)+ | HPLC Method, RT (min.) & Purity | $^1$H NMR |
|---|---|---|---|---|
| 232 | 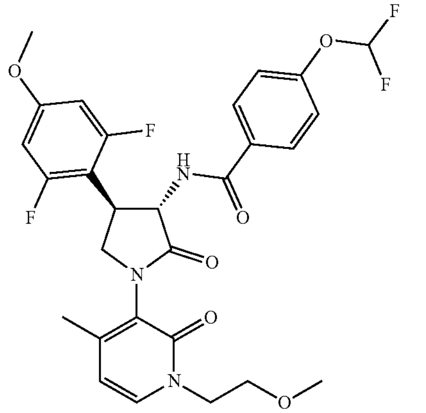 [SMILES: COCCn1ccc(C)c(N2C[C@@H](c3c(F)cc(OC)cc3F)[C@H](NC(=O)c3ccc(OC(F)F)cc3)C2=O)c1=O] | 578.2 | Method D, RT = 1.686 min, 99.4% | $^1$H NMR (400 MHz, DMSO-$d_6$) δ = 9.18-8.82 (m, 1H), 8.02-7.83 (m, 2H), 7.66-7.48 (m, 1H), 7.34 (t, J = 73.6 Hz, 1H), 7.28 (m, 2H), 6.88-6.61 (m, 2H), 6.28-6.12 (m, 1H), 5.38-4.81 (m, 1H), 4.32-3.94 (m, 4H), 3.82-3.72 (2s, 3H), 3.62-3.44 (m, 3H), 3.27-3.19 (2s, 3H), 2.25-2.02 (m, 3H). (mixture of interconvertible atropisomers) |
| 233 | 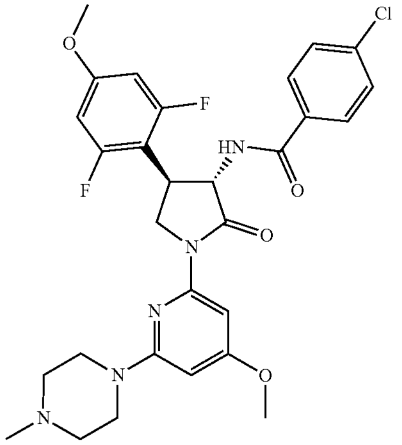 [SMILES: COc1cc(N2CCN(C)CC2)nc(N2C[C@@H](c3c(F)cc(OC)cc3F)[C@H](NC(=O)c3ccc(Cl)cc3)C2=O)c1] | 586.2 | Method D, RT = 1.92 min, 97.4% | $^1$H NMR (400 MHz, DMSO-$d_6$) δ = 9.13 (br d, J = 8.1 Hz, 1H), 7.83 (br d, J = 8.6 Hz, 2H), 7.58 (br d, J = 8.3 Hz, 2H), 7.41 (s, 1H), 6.80 (br d, J = 10.8 Hz, 2H), 6.28 (s, 1H), 5.10-4.98 (m, 1H), 4.50-4.23 (m, 3H), 4.13-4.04 (m, 1H), 3.93-3.85 (m, 2H), 3.82 (s, 3H), 3.75 (s, 3H), 3.15-2.95 (m, 5H), 2.83 (s, 3H). |
| 234 | 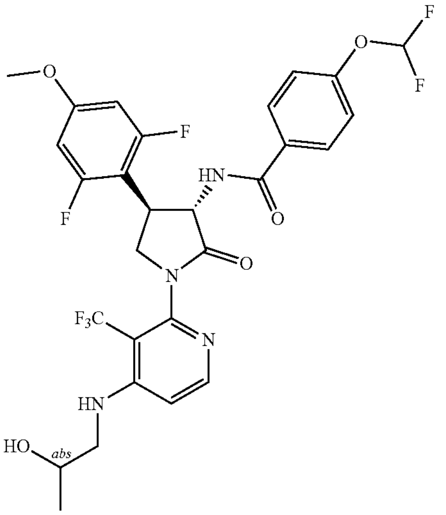 [SMILES: COc1cc(F)c([C@@H]2CN(c3nccc(NCC(C)O)c3C(F)(F)F)C(=O)[C@H]2NC(=O)c2ccc(OC(F)F)cc2)c(F)c1] | 631.3 | Method D, RT = 1.74 min, 98.5% | $^1$H NMR (400 MHz, DMSO-$d_6$) δ = 9.06-8.99 (m, 1H), 8.24-8.14 (m, 1H), 7.94-7.81 (m, 2H), 7.33 (t, J = 73.6 Hz, 1H), 7.28-7.24 (m, 2H), 6.93-6.81 (m, 1H), 6.77 (d, J = 10.5 Hz, 2H), 6.28 (br d, J = 4.9 Hz, 1H), 5.16-4.93 (m, 2H), 4.32-4.10 (m, 2H), 3.92-3.82 (m, 1H), 3.76 (s, 3H), 3.75-3.68 (m, 1H), 3.47-3.39 (m, 2H), 1.18-1.04 (m, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 235 | 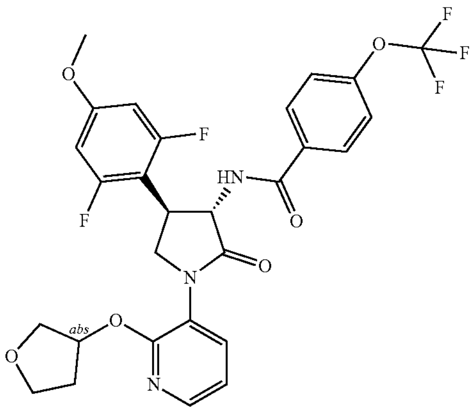 [SMILES: COc1cc(F)c([C@@H]2CN(c3cccnc3OC3CCOC3)C(=O)[C@H]2NC(=O)c2ccc(OC(F)(F)F)cc2)c(F)c1] | 594.2 | Method D, RT = 1.972 min, 95% | $^1$H NMR (400 MHz, DMSO-d$_6$) δ = 9.15 (d, J = 8.6 Hz, 1H), 8.15 (dd, J = 5.0, 1.8 Hz, 1H), 8.02-7.88 (m, 2H), 7.79 (dd, J = 7.7, 1.8 Hz, 1H), 7.56-7.42 (m, 2H), 7.12 (dd, J = 7.6, 4.9 Hz, 1H), 6.80 (d, J = 10.8 Hz, 2H), 5.60 (br dd, J = 6.2, 4.5 Hz, 1H), 5.07 (dd, J = 11.0, 8.3 Hz, 1H), 4.16 (br d, J = 10.0 Hz, 1H), 4.05-3.88 (m, 3H), 3.87-3.80 (m, 2H), 3.77 (s, 3H), 3.76-3.73 (m, 1H), 2.30-2.21 (m, 1H), 2.12-2.03 (m, 1H). |
| 236 | 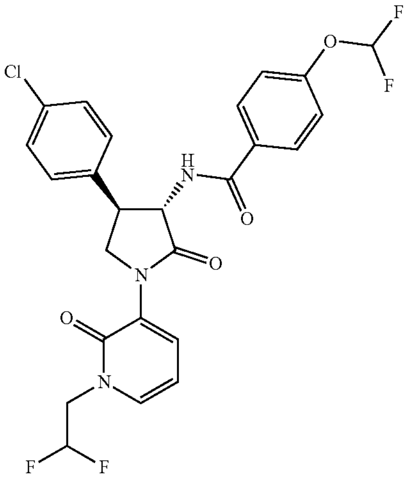 [SMILES: O=C(N[C@@H]1C(=O)N(c2cccn(CC(F)F)c2=O)C[C@H]1c1ccc(Cl)cc1)c1ccc(OC(F)F)cc1] | 538.2 | Method D, RT = 1.793 min, 96.3% | $^1$H NMR (400 MHz, DMSO-d$_6$) δ = 8.96 (d, J = 8.5 Hz, 1H), 7.98-7.85 (m, 2H), 7.72 (dd, J = 2.0, 7.0 Hz, 1H), 7.67 (dd, J = 2.0, 7.5 Hz, 1H), 7.59-7.07 (m, 5H), 7.38 (t, J = 58.4 Hz, 1H), 7.34 (t, J = 73.6 Hz, 1H), 6.42 (t, J = 8.0 Hz, 1H), 6.35 (tt, J = 56.2 Hz, 1H), 5.05 (dd, J = 8.8, 10.8 Hz, 1H), 4.54-4.36 (m, 2H), 4.18 (t, J = 7.8 Hz, 1H), 3.91-3.65 (m, 2H). |
| 237 | 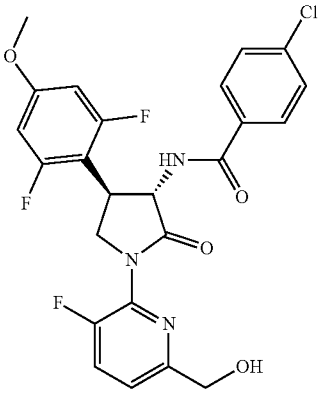 [SMILES: COc1cc(F)c([C@@H]2CN(c3nc(CO)ccc3F)C(=O)[C@H]2NC(=O)c2ccc(Cl)cc2)c(F)c1] | 506.2 | Method D, RT = 1.655 min, 96% | $^1$H NMR (400 MHz, DMSO-d$_6$) δ = 9.17 (d, J = 8.3 Hz, 1H), 7.95-7.75 (m, 3H), 7.65-7.55 (m, 2H), 7.50 (dd, J = 8.3, 3.4 Hz, 1H), 6.80 (d, J = 10.8 Hz, 2H), 5.55 (t, J = 5.9 Hz, 1H), 5.19-4.98 (m, 1H), 4.54 (d, J = 5.9 Hz, 2H), 4.27-4.13 (m, 2H), 4.11-4.00 (m, 1H), 3.77 (s, 3H). |

TABLE 2-continued
| Ex | Structure | LCMS (M + H)+ | HPLC Method, RT (min.) & Purity | $^1$H NMR |
|---|---|---|---|---|
| 238 | 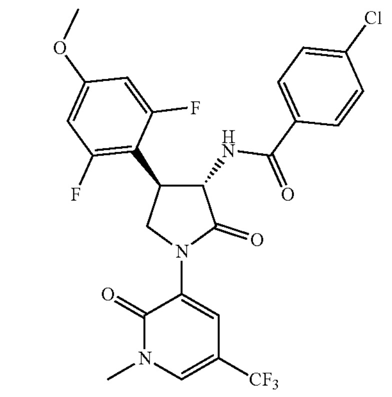 [SMILES: COc1cc(F)c([C@@H]2CN(c3cc(C(F)(F)F)cn(C)c3=O)C(=O)[C@H]2NC(=O)c2ccc(Cl)cc2)c(F)c1] | 556.2 | Method D, RT = 2.691 min, 100% | $^1$H NMR (400 MHz, DMSO-$d_6$) δ = 9.06 (d, J = 8.3 Hz, 1H), 8.47 (d, J = 1.2 Hz, 1H), 7.92-7.80 (m, 3H), 7.65-7.53 (m, 2H), 6.78 (d, J = 10.8 Hz, 2H), 5.11 (dd, J = 8.6, 10.8 Hz, 1H), 4.19-3.96 (m, 3H), 3.77 (s, 3H), 3.57 (s, 3H). |
| 239 | 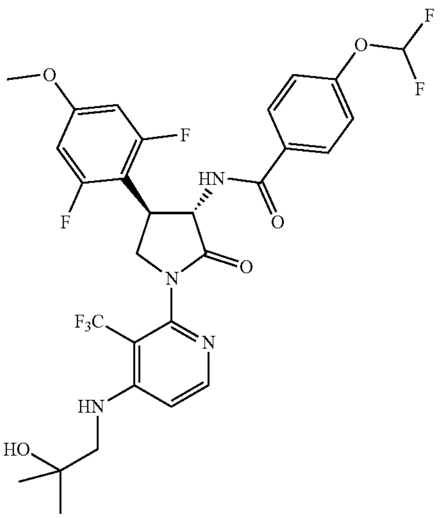 [SMILES: COc1cc(F)c([C@@H]2CN(c3nccc(NCC(C)(C)O)c3C(F)(F)F)C(=O)[C@H]2NC(=O)c2ccc(OC(F)F)cc2)c(F)c1] | 645.2 | Method D, RT = 1.84 min, 100% | $^1$H NMR (400 MHz, DMSO-$d_6$) δ = 9.02 (d, J = 8.8 Hz, 1H), 8.26-8.14 (m, 1H), 7.94-7.81 (m, 2H), 7.35 (t, J = 72.2 Hz, 1H), 7.34-7.25 (m, 2H), 6.94-6.83 (m, 1H), 6.78 (d, J = 10.5 Hz, 2H), 5.98-5.91 (m, 1H), 5.16-5.05 (m, 1H), 4.87 (s, 1H), 4.36-4.14 (m, 2H), 3.76 (s, 3H), 3.75-3.67 (m, 1H) 3.22-3.13 (m, 2H), 1.17 (s, 3H), 1.15 (s, 3H). |
| 240 | 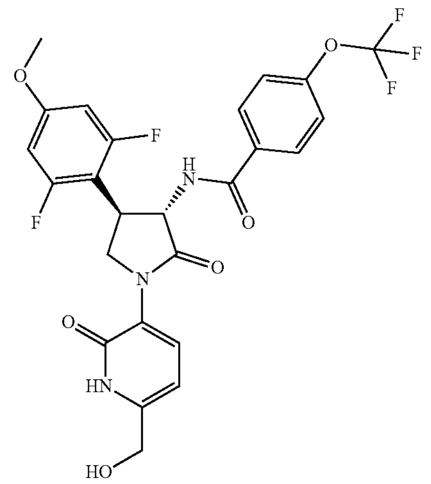 [SMILES: COc1cc(F)c([C@@H]2CN(c3ccc(CO)[nH]c3=O)C(=O)[C@H]2NC(=O)c2ccc(OC(F)(F)F)cc2)c(F)c1] | 554.2 | Method D, RT = 1.572 min, 98.7% | $^1$H NMR (400 MHz, DMSO-$d_6$) δ = 11.91-11.48 (m, 1H), 9.11 (d, J = 8.8 Hz, 1H), 8.03-7.84 (m, 2H), 7.57 (d, J = 7.3 Hz, 1H), 7.48 (dd, J = 9.0, 1.0 Hz, 2H), 6.77 (d, J = 10.8 Hz, 2H), 6.26 (d, J = 7.3 Hz, 1H), 5.56-550 (brs, 1H), 5.13 (dd, J = 11.0, 8.6 Hz, 1H), 4.31 (s, 2H), 4.15-3.87 (m, 3H), 3.76 (s, 3H). |

TABLE 2-continued

| Ex | Structure | LCMS (M + H)+ | HPLC Method, RT (min.) & Purity | $^1$H NMR |
|---|---|---|---|---|
| 241 | 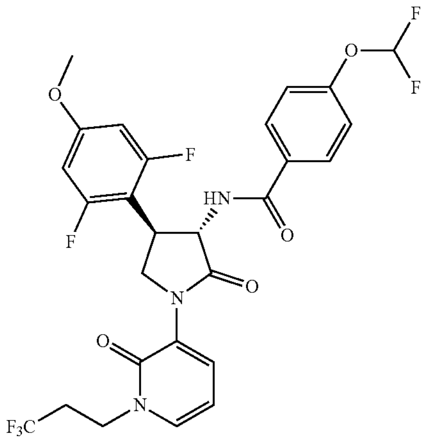 [SMILES: COc1cc(F)c([C@@H]2CN(c3cccn(CCC(F)(F)F)c3=O)C(=O)[C@H]2NC(=O)c2ccc(OC(F)F)cc2)c(F)c1] | 602.2 | Method D, RT = 1.838 min, 100% | $^1$H NMR (400 MHz, DMSO-d$_6$) δ = 9.08-8.95 (m, 1H), 7.89 (d, J = 8.8 Hz, 2H), 7.82-7.59 (m, 2H), 7.34 (t, J = 76.0 Hz, 1H), 7.28-7.26 (m, 2H), 6.77 (d, J = 10.8 Hz, 2H), 6.38 (t, J = 8.2 Hz, 1H), 5.19-5.05 (m, 1H), 4.27-4.17 (m, 2H), 4.14-4.03 (m, 1H), 4.03-3.92 (m, 2H), 3.77 (s, 3H), 2.85-2.69 (m, 2H). |
| 242 | 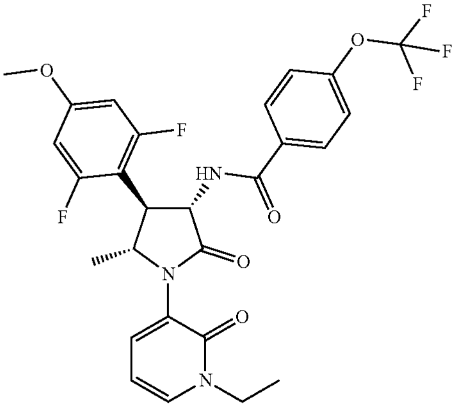 [SMILES: CCn1cccc(N2C(=O)[C@@H](NC(=O)c3ccc(OC(F)(F)F)cc3)[C@H](c3c(F)cc(OC)cc3F)[C@H]2C)c1=O] | 566.2 | Method D, RT = 1.87 min, 100% | $^1$H NMR (400 MHz, DMSO-d$_6$) δ = 9.08 (d, J = 8.6 Hz, 1H), 7.99-7.87 (m, 2H), 7.79 (dd, J = 6.8, 2.0 Hz, 1H), 7.53-7.37 (m, 3H), 6.84-6.71 (m, 2H), 6.36 (t, J = 7.0 Hz, 1H), 5.13 (dd, J = 11.2, 8.6 Hz, 1H), 4.54-4.44 (m, 1H), 4.04-3.90 (m, 2H), 3.77 (s, 3H), 3.62 (t, J = 10.5 Hz, 1H), 1.24 (t, J = 7.1 Hz, 3H), 0.99 (d, J = 6.1 Hz, 3H). |
| 243 | 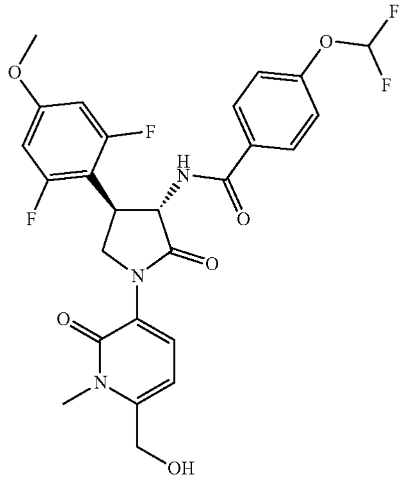 [SMILES: COc1cc(F)c([C@@H]2CN(c3ccc(CO)n(C)c3=O)C(=O)[C@H]2NC(=O)c2ccc(OC(F)F)cc2)c(F)c1] | 550.2 | Method D, RT = 1.455 min, 94% | $^1$H NMR (400 MHz, DMSO-d$_6$) δ = 9.00 (d, J = 8.6 Hz, 1H), 7.96-7.81 (m, 2H), 7.55 (d, J = 7.6 Hz, 1H), 7.34 (t, J = 76 Hz, 1H), 7.27-7.16 (m, 2H), 6.77 (d, J = 10.8 Hz, 2H), 6.40 (d, J = 7.6 Hz, 1H), 5.67 (br s, 1H), 5.11 (dd, J = 11.0, 8.6 Hz, 1H), 4.49 (s, 2H), 4.15-3.90 (m, 3H), 3.76 (s, 3H), 3.49 (s, 3H). |

TABLE 2-continued

| Ex | Structure | LCMS (M + H)+ | HPLC Method, RT (min.) & Purity | $^1$H NMR |
|---|---|---|---|---|
| 244 | 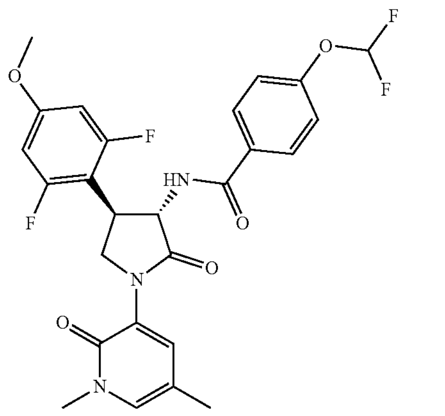 [SMILES: COc1cc(F)c([C@@H]2CN(c3cc(C)cn(C)c3=O)C(=O)[C@H]2NC(=O)c2ccc(OC(F)F)cc2)c(F)c1] | 534.2 | Method D, RT = 1.669 min, 100% | $^1$H NMR (400 MHz, DMSO-$d_6$) δ = 8.99 (br d, J = 8.3 Hz, 1H), 7.97-7.78 (m, 2H), 7.56 (s, 1H), 7.54-7.03 (m, 3H), 7.34 (t, J = 73.6 Hz, 1H), 6.77 (d, J = 10.5 Hz, 2H), 5.09 (dd, J = 11.0, 8.6 Hz, 1H), 4.11 (q, J = 10.3 Hz, 1H), 3.97 (br d, J = 9.5 Hz, 2H), 3.77 (s, 3H), 3.46 (s, 3H), 2.08 (s, 3H). |
| 245 | 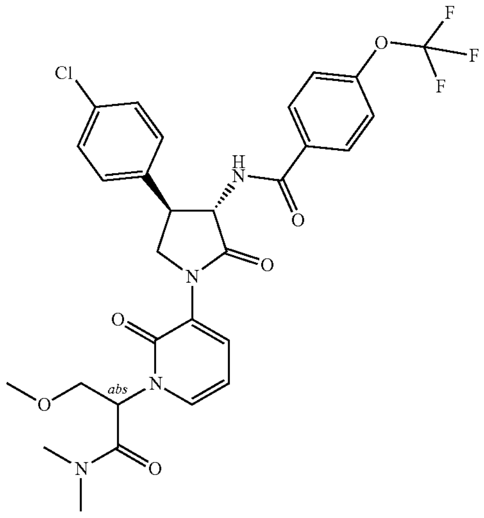 [SMILES: COCC(C(=O)N(C)C)n1cccc(N2C[C@@H](c3ccc(Cl)cc3)[C@H](NC(=O)c3ccc(OC(F)(F)F)cc3)C2=O)c1=O] | 621.2 | Method D, RT = 1.876 min, 97.5% | $^1$H NMR (400 MHz, DMSO-$d_6$) δ = 9.08 (br d, J = 8.3 Hz, 1H), 8.06-7.89 (m, 2H), 7.75-7.66 (m, 1H), 7.61 (dd, J = 7.2, 1.8 Hz, 1H), 7.52-7.44 (m, 3H), 7.43-7.34 (m, 2H), 6.41 (t, J = 7.2 Hz, 1H), 6.07 (dd, J = 8.8, 5.1 Hz, 1H), 5.08-4.94 (m, 1H), 4.14-4.05 (m, 2H), 3.91-3.75 (m, 4H), 3.26 (s, 3H), 3.10 (s, 3H), 2.84 (s, 3H). |
| 246 | 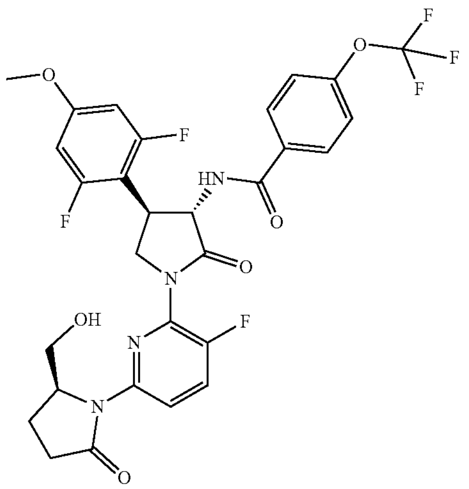 [SMILES: COc1cc(F)c([C@@H]2CN(c3nc(N4C(=O)CC[C@H]4CO)ccc3F)C(=O)[C@H]2NC(=O)c2ccc(OC(F)(F)F)cc2)c(F)c1] | 639.2 | Method D, RT = 1.86 min, 96% | $^1$H NMR (400 MHz, DMSO-$d_6$) δ = 9.21 (d, J = 8.6 Hz, 1H), 8.25 (dd, J = 9.0, 3.2 Hz, 1H), 8.00-7.82 (m, 3H), 7.50 (d, J = 8.1 Hz, 2H), 6.80 (d, J = 10.8 Hz, 2H), 5.09 (dd, J = 10.3, 8.6 Hz, 1H), 4.86 (t, J = 5.6 Hz, 1H), 4.63-4.61 (m, 1H), 4.27-4.20 (m, 2H), 4.08-3.97 (m, 1H), 3.77 (s, 3H), 3.73-3.71 (m, 1H), 3.61-3.59 (m, 1H), 2.80-2.67 (m, 1H), 2.46-2.35 (m, 1H), 2.24-2.09 (m, 1H), 2.09-1.96 (m, 1H). |

TABLE 2-continued

| Ex | Structure | LCMS (M + H)+ | HPLC Method, RT (min.) & Purity | $^1$H NMR |
|---|---|---|---|---|
| 247 | 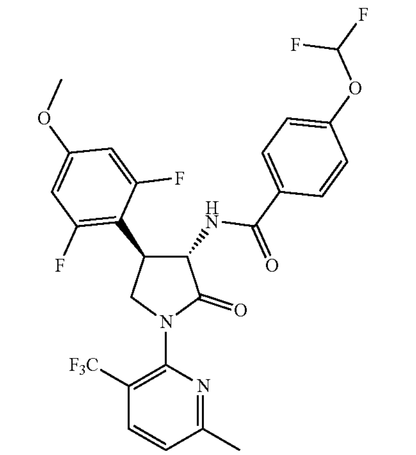 [SMILES: COc1cc(F)c([C@@H]2CN(c3nc(C)ccc3C(F)(F)F)C(=O)[C@H]2NC(=O)c2ccc(OC(F)F)cc2)c(F)c1] | 572.2 | Method D, RT = 1.99 min, 94.3% | $^1$H NMR (400 MHz, DMSO-$d_6$) δ = 9.09 (d, J = 8.6 Hz, 1H), 8.25 (d, J = 8.3 Hz, 1H), 7.94-7.84 (m, 2H), 7.69 (d, J = 8.8 Hz, 1H), 7.35 (t, J = 76.2 Hz, 1H), 7.28 (d, J = 8.2 Hz, 2H), 6.80 (d, J = 10.8 Hz, 2H), 5.16 (dd, J = 11.0, 8.8 Hz, 1H), 4.26 (q, J = 9.9 Hz, 1H), 4.10 (br t, J = 8.6 Hz, 1H), 3.99-3.88 (m, 1H), 3.77 (s, 3H), 2.61 (s, 3H). |
| 248 | 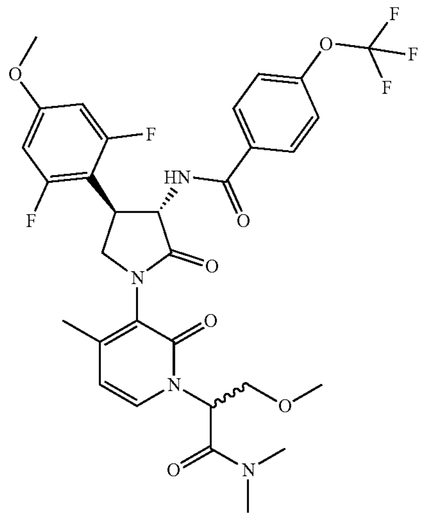 [SMILES: COCC(C(=O)N(C)C)n1ccc(C)c(N2C[C@@H](c3c(F)cc(OC)cc3F)[C@H](NC(=O)c3ccc(OC(F)(F)F)cc3)C2=O)c1=O] | 667.3 | Method D, RT = 1.839 min, 100% | $^1$H NMR (400 MHz, DMSO-$d_6$) δ = 9.25-8.87 (m, 1H), 8.05-7.84 (m, 2H), 7.75-7.57 (m, 1H), 7.54-7.34 (m, 2H), 6.77 (dd, J = 5.6, 10.8 Hz, 1H), 6.35-6.19 (m, 1H), 6.11-5.92 (m, 1H), 5.39-4.82 (m, 1H), 4.30-3.96 (m, 3H), 3.92-3.68 (m, 5H), 3.59-3.45 (m, 1H), 3.29-3.23 (2s, 3H), 3.16-3.06 (m, 3H), 2.86-2.80 (2s, 3H), 2.22-1.95 (2s, 3H). (Mixture of interconvertible atropisomers) |
| 249 | 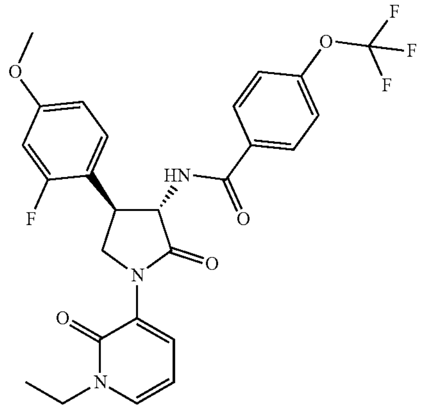 [SMILES: CCn1cccc(N2C[C@@H](c3ccc(OC)cc3F)[C@H](NC(=O)c3ccc(OC(F)(F)F)cc3)C2=O)c1=O] | 534.2 | Method D, RT = 1.77 min, 98.9% | $^1$H NMR (400 MHz, DMSO-$d_6$) δ = 9.05 (d, J = 8.8 Hz, 1H), 8.00-7.92 (m, 2H), 7.75 (dd, J = 6.8, 2.0 Hz, 1H), 7.58 (dd, J = 7.3, 2.0 Hz, 1H), 7.54-7.43 (m, 3H), 6.86-6.78 (m, 2H), 6.39-6.29 (m, 1H), 5.13 (dd, J = 11.4, 8.9 Hz, 1H), 4.19-4.11 (m, 1H), 4.04-3.93 (m, 3H), 3.75 (s, 3H), 3.73-3.64 (m, 1H), 1.24 (t, J = 7.1 Hz, 3H). |

TABLE 2-continued

| Ex | Structure | LCMS (M + H)+ | HPLC Method, RT (min.) & Purity | $^1$H NMR |
|---|---|---|---|---|
| 250 | 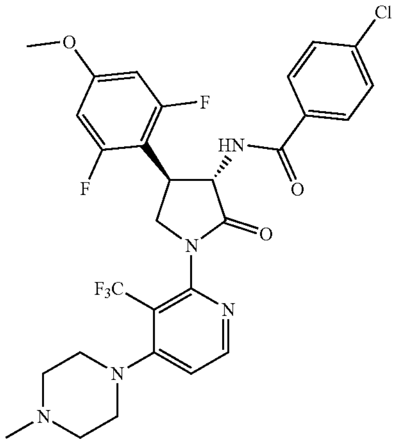 [SMILES: COc1cc(F)c([C@@H]2CN(c3nccc(N4CCN(C)CC4)c3C(F)(F)F)C(=O)[C@H]2NC(=O)c2ccc(Cl)cc2)c(F)c1] | 624.2 | Method D, RT = 1.89 min, 96.4% | $^1$H NMR (400 MHz, DMSO-$d_6$) δ = 9.11 (br d, J = 7.8 Hz, 1H), 8.45-8.41 (m, 1H), 7.89-7.79 (m, 2H), 7.59-7.54 (m, 2H), 7.20 (br d, J = 5.9 Hz, 1H), 6.79 (br d, J = 10.8 Hz, 2H), 5.18-5.02 (m, 1H), 4.41-4.15 (m, 2H), 3.78 (s, 3H), 3.77-3.71 (m, 1H), 3.27-3.01 (m, 4H), 2.49-2.37 (m, 4H), 2.22 (s, 3H). |
| 251 | 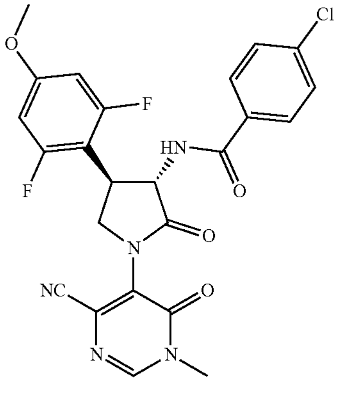 [SMILES: COc1cc(F)c([C@@H]2CN(c3c(C#N)ncn(C)c3=O)C(=O)[C@H]2NC(=O)c2ccc(Cl)cc2)c(F)c1] | 513.2 | Method D, RT = 1.653 min, 100% | $^1$H NMR (400 MHz, DMSO-$d_6$) δ = 9.17 (d, J = 8.8 Hz, 1H), 8.02 (d, J = 7.1 Hz, 1H), 7.92-7.81 (m, 2H), 7.65-7.48 (m, 2H), 6.79 (d, J = 11.0 Hz, 2H), 6.70 (d, J = 7.1 Hz, 1H), 5.23 (dd, J = 11.5, 8.6 Hz, 1H), 4.26-4.11 (m, 2H), 3.77 (s, 3H), 3.75-3.70 (m, 1H), 3.56 (s, 3H). |
| 252 | 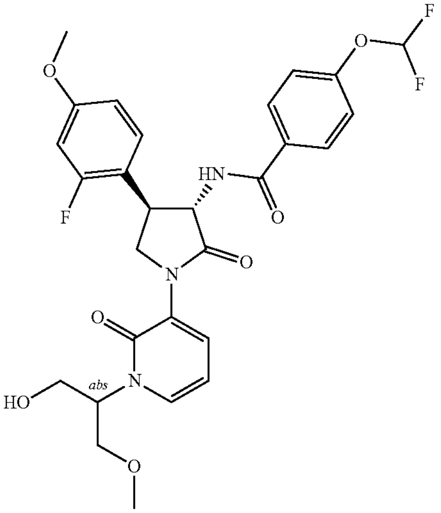 [SMILES: COCC(CO)n1cccc(N2C[C@@H](c3ccc(OC)cc3F)[C@H](NC(=O)c3ccc(OC(F)F)cc3)C2=O)c1=O] | 558.3 | Method D, RT = 1.421 min, 100% | $^1$H NMR (400 MHz, DMSO-$d_6$) δ = 8.96-8.87 (m, 1H), 7.93 (d, J = 8.6 Hz, 2H), 7.68 (dd, J = 6.7, 1.8 Hz, 1H), 7.56 (dd, J = 7.5, 1.8 Hz, 1H), 7.34 (t, J = 76 Hz, 1H), 7.33-7.27 (m, 2H), 7.29-7.22 (m, 2H), 6.90 (d, J = 8.6 Hz, 2H), 6.34 (t, J = 7.1 Hz, 1H), 5.10-4.99 (m, 3H), 4.13-4.06 (m, 2H), 3.79-3.64 (m, 7H), 3.23 (s, 3H), 3.17 (d, J = 4.9 Hz, 1H). |

TABLE 2-continued

| Ex | Structure | LCMS (M + H)+ | HPLC Method, RT (min.) & Purity | $^1$H NMR |
|---|---|---|---|---|
| 253 | 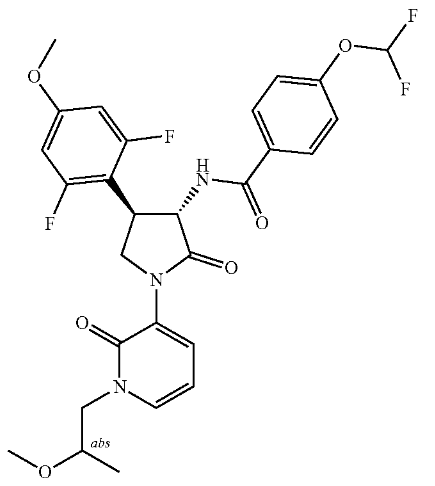 [SMILES: COc1cc(F)c([C@@H]2CN(c3cccn(CC(C)OC)c3=O)C(=O)[C@H]2NC(=O)c2ccc(OC(F)F)cc2)c(F)c1] | 578.3 | Method D, RT = 1.692 min, 93.2% | $^1$H NMR (400 MHz, DMSO-$d_6$) δ = 9.01 (d, J = 8.6 Hz, 1H), 7.93-7.81 (m, 2H), 7.61 (dt, J = 7.2, 1.7 Hz, 2H), 7.34 (t, J = 73.6 Hz, 1H), 7.28 (m, 2H), 6.76 (d, J = 10.8 Hz, 2H), 6.32 (t, J = 7.0 Hz, 1H), 5.12 (dd, J = 11.0, 8.6 Hz, 1H), 4.14-3.79 (m, 5H), 3.76 (s, 3H), 3.68-3.61 (m, 1H), 3.18 (s, 3H), 1.09 (d, J = 6.1 Hz, 3H). |
| 254 | 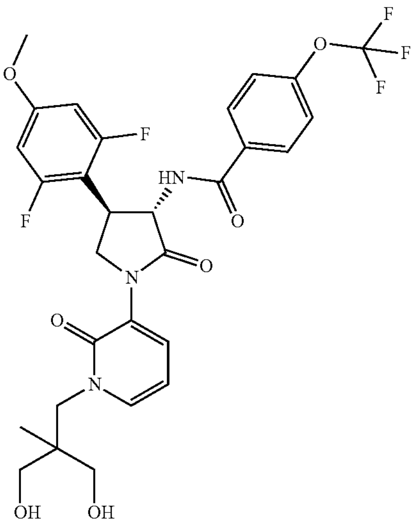 [SMILES: COc1cc(F)c([C@@H]2CN(c3cccn(CC(C)(CO)CO)c3=O)C(=O)[C@H]2NC(=O)c2ccc(OC(F)(F)F)cc2)c(F)c1] | 626.2 | Method D, RT = 1.700 min, 98.8% | $^1$H NMR (400 MHz, DMSO-$d_6$) δ = 9.06-8.98 (m, 1H), 7.93-7.85 (m, 2H), 7.69-7.61 (m, 2H), 7.56-7.13 (m, 2H), 6.77 (d, J = 10.8 Hz, 2H), 6.40 (t, J = 7.0 Hz, 1H), 5.14 (dd, J = 11.1, 8.4 Hz, 1H), 4.74 (t, J = 5.4 Hz, 2H), 4.15-4.04 (m, 1H), 4.03-3.89 (m, 4H), 3.76 (s, 3H), 3.24-3.11 (m, 4H), 0.78 (s, 3H). |
| 255 | 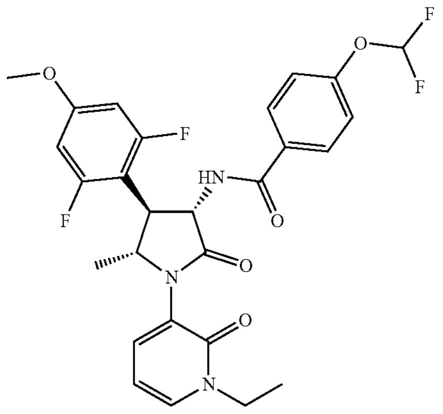 [SMILES: CCn1cccc(N2C(=O)[C@@H](NC(=O)c3ccc(OC(F)F)cc3)[C@H](c3c(F)cc(OC)cc3F)[C@H]2C)c1=O] | 548.2 | Method D, RT = 1.70 min, 96% | $^1$H NMR (400 MHz, DMSO-$d_6$) δ = 9.01 (d, J = 8.6 Hz, 1H), 7.88 (d, J = 8.8 Hz, 2H), 7.78 (dd, J = 6.6, 2.0 Hz, 1H), 7.46-7.44 (m, 1H) 7.34 (t, J = 73.6 Hz, 1H), 7.27-7.25 (m, 2H), 6.78 (d, J = 11.0 Hz, 2H), 6.36 (t, J = 7.0 Hz, 1H), 5.14-5.09 (m, 1H), 4.54-4.47 (m, 1H), 4.04-3.91 (m, 2H), 3.77 (s, 3H), 3.67-3.60 (m, 1H), 1.24 (t, J = 7.1 Hz, 3H), 0.98 (d, J = 6.1 Hz, 3H). |

TABLE 2-continued

| Ex | Structure | LCMS (M + H)+ | HPLC Method, RT (min.) & Purity | $^1$H NMR |
|---|---|---|---|---|
| 256 | 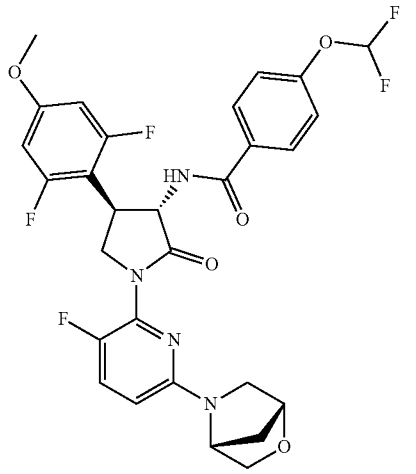 [SMILES: COc1cc(F)c([C@@H]2CN(c3nc(N4C[C@H]5C[C@@H]4CO5)ccc3F)C(=O)[C@H]2NC(=O)c2ccc(OC(F)F)cc2)c(F)c1] | 605.2 | Method D, RT = 1.904 min, 95% | $^1$H NMR (400 MHz, DMSO-$d_6$) δ = 9.06 (d, J = 8.6 Hz, 1H), 7.96-7.81 (m, 2H), 7.61 (t, J = 9.2 Hz, 1H), 7.34 (t, J = 72 Hz, 1 H), 7.29-7.26 (m, 2H), 6.79 (d, J = 10.8 Hz, 2H), 6.53 (dd, J = 2.2, 9.0 Hz, 1H), 5.20-5.08 (m, 1H), 4.83-4.78 (m, 1H), 4.68-4.62 (m, 1H), 4.25-4.13 (m, 2H), 4.04-3.92 (m, 1H), 3.78 (s, 4H), 3.64 (d, J = 7.3 Hz, 1H), 3.44 (d, J = 9.5 Hz, 1H), 3.23 (d, J = 10.3 Hz, 1H), 1.95-1.78 (m, 2H). |
| 257 | 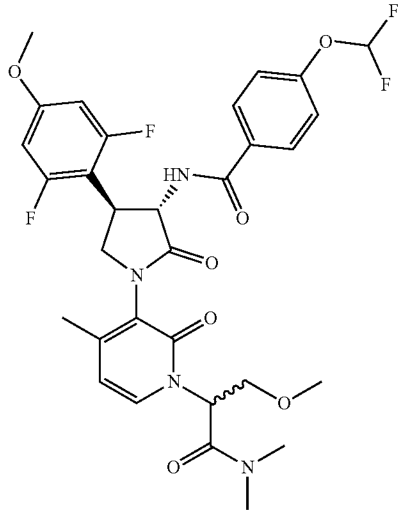 [SMILES: COCC(C(=O)N(C)C)n1ccc(C)c(N2C[C@@H](c3c(F)cc(OC)cc3F)[C@H](NC(=O)c3ccc(OC(F)F)cc3)C2=O)c1=O] | 649.3 | Method D, RT = 1.672 min, 97.1% | $^1$H NMR (400 MHz, DMSO-$d_6$) δ = 9.18-8.91 (m, 1H), 7.98-7.80 (m, 2H), 7.69-7.56 (m, 1H), 7.55-6.92 (m, 2H), 7.34 (t, J = 73.6 Hz, 1H), 6.78-6.70 (m, 1H), 6.38-6.25 (m, 1H), 6.10-5.92 (m, 1H), 5.39-4.81 (m, 1H), 4.31-4.04 (m, 2H), 3.90-3.73 (m, 5H), 3.56-3.49 (m, 1H), 3.28-3.24 (2s, 3H), 3.19-3.03 (m, 3H), 2.99-2.89 (m, 1H), 2.86-2.81 (2s, 3H), 2.23-2.04 (2s, 3H). (mixture of interconvertible atropisomers) |
| 258 | 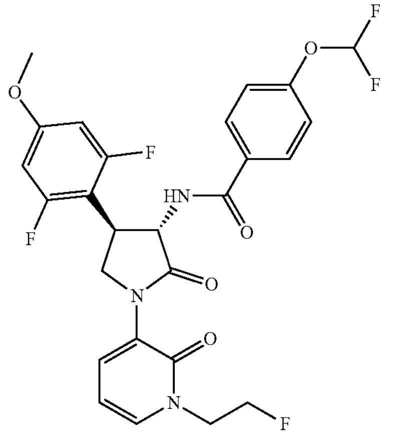 [SMILES: COc1cc(F)c([C@@H]2CN(c3cccn(CCF)c3=O)C(=O)[C@H]2NC(=O)c2ccc(OC(F)F)cc2)c(F)c1] | 552.2 | Method D, RT = 1.625 min, 100% | $^1$H NMR (400 MHz, DMSO-$d_6$) δ = 9.02 (d, J = 8.6 Hz, 1H), 7.83-7.95 (m, 2H), 7.72 (dd, J = 6.8, 2.0 Hz, 1H), 7.63 (dd, J = 7.1, 2.0 Hz, 1H), 7.35 (t, J = 72 Hz, 1 H), 7.28-7.26 (m, 2H), 6.77 (d, J = 10.8 Hz, 2H), 6.37 (t, J = 7.0 Hz, 1H), 5.12 (dd, J = 11.0, 8.6 Hz, 1H), 4.71 (dt, J = 48.6, 4.6 Hz, 2H), 4.29-4.37 (m, 1H), 4.26 (dt, J = 4.6, 2.2 Hz, 1H), 4.04-4.14 (m, 1H), 3.94-4.02 (m, 2H), 3.76 (s, 3H). |

TABLE 2-continued

| Ex | Structure | LCMS (M + H)+ | HPLC Method, RT (min.) & Purity | $^1$H NMR |
|---|---|---|---|---|
| 259 | 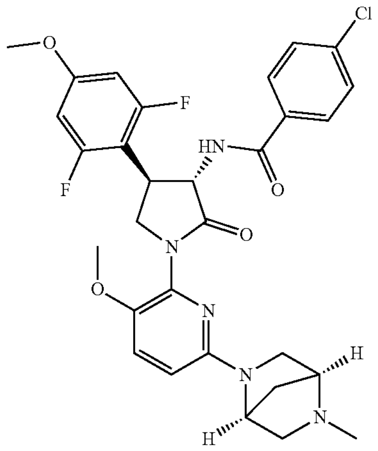 [SMILES: COc1cc(F)c([C@@H]2CN(c3nc(N4C[C@@H]5C[C@H]4CN5C)ccc3OC)C(=O)[C@H]2NC(=O)c2ccc(Cl)cc2)c(F)c1] | 598.3 | Method D, RT = 1.48 min, 97% | $^1$H NMR (400 MHz, DMSO-$d_6$) δ = 9.12 (d, J = 8.8 Hz, 1H), 7.84 (d, J = 8.8 Hz, 2H), 7.62 (d, J = 8.8 Hz, 2H), 7.49 (d, J = 9.0 Hz, 1H), 6.84-6.70 (m, 2H), 6.51 (d, J = 9.0 Hz, 1H), 5.22 (dd, J = 11.4, 8.9 Hz, 1H), 4.48-7.43 (m, 1H), 4.17-4.05 (m, 1H), 4.01 (br t, J = 8.8 Hz, 1H), 3.90-3.83 (m, 1H), 3.76 (s, 3H), 3.74 (s, 3H), 3.44-3.33 (m, 2H), 3.25-3.24 (m, 1H), 2.83-2.78 (m, 1H), 2.46-2.43 (m, 1H), 2.25 (s, 3H), 1.87-1.82 (m, 1H), 1.71-1.69 (m, 1H). |
| 260 | 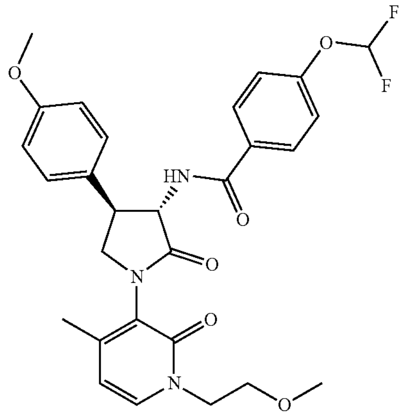 [SMILES: COCCn1ccc(C)c(N2C[C@@H](c3ccc(OC)cc3)[C@H](NC(=O)c3ccc(OC(F)F)cc3)C2=O)c1=O] | 542.3 | Method D, RT = 1.56 min, 94% | $^1$H NMR (400 MHz, DMSO-$d_6$) δ = 8.98-8.90 (m, 1H), 8.00-7.85 (m, 2H), 7.58-7.51 (m, 1H), 7.41-7.16 (m, 5H), 6.97-6.85 (m, 2H), 6.24-6.18 (m, 1H), 5.27-4.60 (m, 1H), 4.20-3.97 (m, 3H), 3.93-3.79 (m, 2H), 3.75-3.71 (2s, 3H), 3.61-3.53 (m, 2H), 3.24 (s, 3H), 2.20-2.07 (2s, 3H). (mixture of interconvertible atropisomers isomsers) |
| 261 | 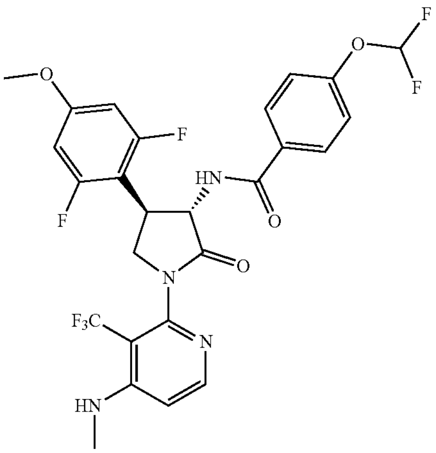 [SMILES: CNc1ccnc(N2C[C@@H](c3c(F)cc(OC)cc3F)[C@H](NC(=O)c3ccc(OC(F)F)cc3)C2=O)c1C(F)(F)F] | 587.2 | Method D, RT = 1.83 min, 100% | $^1$H NMR (400 MHz, DMSO-$d_6$) δ = 9.03 (br d, J = 8.8 Hz, 1H), 8.29-8.13 (m, 1H), 7.99-7.78 (m, 2H), 7.35 (t, J = 72 Hz, 1H), 7.31-7.25 (m, 2H), 6.85-6.65 (m, 4H), 5.22-5.02 (m, 1H), 4.34-4.05 (m, 2H), 3.82 (s, 3H), 3.80-3.68 (s, 1H), 2.85 (d, J = 4.4 Hz, 3H). |

TABLE 2-continued

| Ex | Structure | LCMS (M + H)+ | HPLC Method, RT (min.) & Purity | $^1$H NMR |
|---|---|---|---|---|
| 262 | 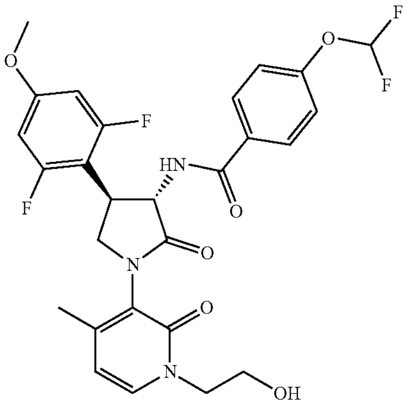 [SMILES: COc1cc(F)c([C@@H]2CN(c3c(C)ccn(CCO)c3=O)C(=O)[C@H]2NC(=O)c2ccc(OC(F)F)cc2)c(F)c1] | 564.3 | Method D, RT = 1.508 min, 100% | $^1$H NMR (400 MHz, DMSO-d$_6$) δ = 9.18-8.88 (m, 1H), 7.96-7.91 (m, 2H), 7.64-7.07 (m, 4H), 6.77 (dd, J = 10.8, 4.9 Hz, 2H), 6.29-6.13 (m, 1H), 5.38-4.79 (m, 2H), 4.31-3.87 (m, 3H), 3.81-3.58 (m, 5H), 3.55-3.44 (m, 2H), 2.27-1.93 (2s, 3H). (mixture of interconvertible atropisomers) |
| 263 | 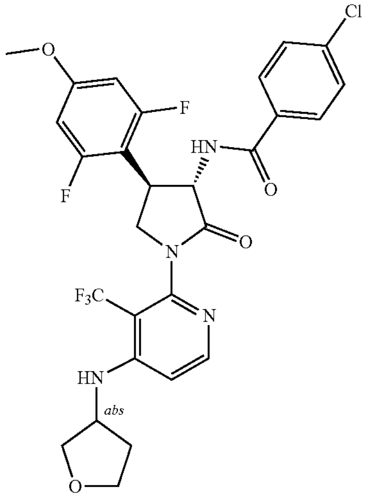 [SMILES: COc1cc(F)c([C@@H]2CN(c3nccc(NC4CCOC4)c3C(F)(F)F)C(=O)[C@H]2NC(=O)c2ccc(Cl)cc2)c(F)c1] | 611.2 | Method D, RT = 1.88 min, 100% | $^1$H NMR (400 MHz, DMSO-d$_6$) δ = 9.09 (br d, J = 8.8 Hz, 1H), 8.32-8.21 (m, 1H), 7.91-7.78 (m, 2H), 7.65-7.51 (m, 2H), 6.97-6.85 (m, 1H), 6.78 (d, J = 10.8 Hz, 2H), 6.13-5.95 (m, 1H), 5.21-5.02 (m, 1H), 4.37-4.11 (m, 3H), 3.95-3.83 (m, 2H), 3.82 (s, 3H), 3.79-3.64 (m, 3H), 2.31-2.19 (m, 1H), 2.04-1.89 (m, 1H). (mixture of interconvertible atropisomers). |
| 264 | 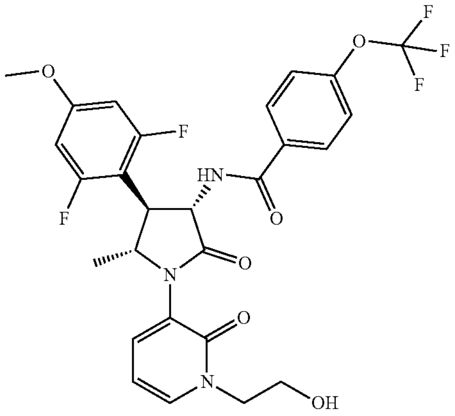 [SMILES: COc1cc(F)c([C@H]2[C@H](NC(=O)c3ccc(OC(F)(F)F)cc3)C(=O)N(c3cccn(CCO)c3=O)[C@@H]2C)c(F)c1] | 582.3 | Method D, RT = 1.80 min, 94% | $^1$H NMR (400 MHz, DMSO-d$_6$) δ = 9.09 (d, J = 8.8 Hz, 1H), 7.94 (d, J = 8.8 Hz, 2H), 7.68 (dd, J = 6.6, 2.0 Hz, 1H), 7.53-7.39 (m, 3H), 6.79 (d, J = 11.0 Hz, 2H), 6.33 (t, J = 7.0 Hz, 1H), 5.13 (dd, J = 11.4, 8.4 Hz, 1H), 4.99-4.90 (m, 1H), 4.55-4.44 (m, 1H), 4.06-3.98 (m, 2H), 3.77 (s, 3H), 3.68-3.56 (m, 3H), 0.99 (d, J = 5.9 Hz, 3H). |

TABLE 2-continued

| Ex | Structure | LCMS (M + H)+ | HPLC Method, RT (min.) & Purity | $^1$H NMR |
|---|---|---|---|---|
| 265 | 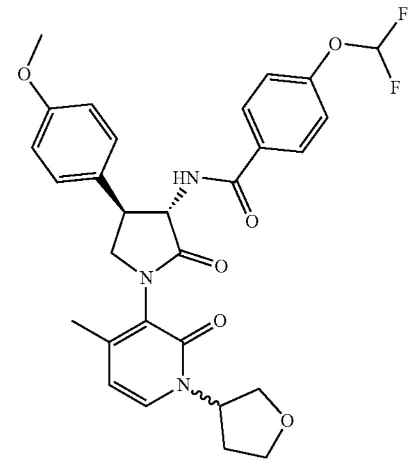 [SMILES: COc1ccc([C@@H]2CN(c3c(C)ccn(C4CCOC4)c3=O)C(=O)[C@H]2NC(=O)c2ccc(OC(F)F)cc2)cc1] | 554.3 | Method D, RT = 1.541 min, 96% | $^1$H NMR (400 MHz, DMSO-d$_6$) δ = 9.02-8.81 (m, 1H), 7.98-7.83 (m, 2H), 7.58-7.48 (m, 1H), 7.42-7.07 (m, 5H), 6.99-6.80 (m, 2H), 6.32-6.24 (m, 1H), 5.43-5.30 (m, 1H), 5.26-4.63 (m, 1H), 4.14-3.99 (m, 2H), 3.94-3.63 (m, 7H), 3.46 (t, J = 9.7 Hz, 1H), 2.47-2.38 (m, 1H), 2.22-2.07 (2s, 3H), 2.02-1.88 (m, 1H). (mixture of interconvertible atropisomers). |
| 266 | 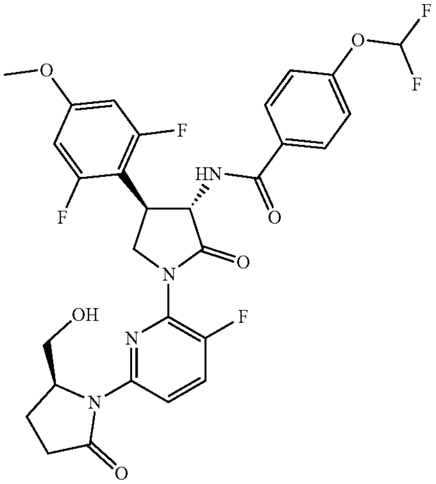 [SMILES: COc1cc(F)c([C@@H]2CN(c3nc(N4C(=O)CC[C@H]4CO)ccc3F)C(=O)[C@H]2NC(=O)c2ccc(OC(F)F)cc2)c(F)c1] | 621.1 | Method D, RT = 1.80 min, 98% | $^1$H NMR (400 MHz, DMSO-d$_6$) δ = 9.10 (d, J = 8.0 Hz, 1H), 8.25 (dd, J = 9.0, 3.0 Hz, 1H), 7.92-7.87 (m, 3H), 7.35 (t, J = 73.6 Hz, 1H), 7.29-7.27 (m, 2H), 6.79 (d, J = 11.0 Hz, 2H), 5.08 (dd, J = 10.0, 8.5 Hz, 1H), 4.85 (t, J = 5.8 Hz, 1H), 4.61-4.58 (m, 1H), 4.32-4.14 (m, 2H), 4.05-3.96 (m, 1H), 3.77 (s, 3H), 3.75-3.66 (m, 1H), 3.64-3.60 (m, 1H), 2.74-2.67 (m, 1H), 2.42-2.40 (m, 1H), 2.33-2.30 (m, 1H), 2.10-2.04 (m, 1H). |
| 267 | 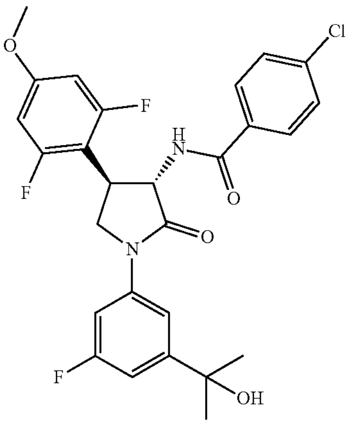 [SMILES: COc1cc(F)c([C@@H]2CN(c3cc(F)cc(C(C)(C)O)c3)C(=O)[C@H]2NC(=O)c2ccc(Cl)cc2)c(F)c1] | 533.2 | Method D, RT = 1.989 min, 93.4% | $^1$H NMR (400 MHz, DMSO-d$_6$) δ = 9.17-9.08 (m, 1H), 7.85 (d, J = 8.8 Hz, 2H), 7.63-7.48 (m, 4H), 7.11 (dd, J = 10.4, 1.3 Hz, 1H), 6.81 (d, J = 10.8 Hz, 2H), 5.18 (d, J = 1.5 Hz, 1H), 5.06 (dd, J = 8.1, 10.0 Hz, 1H), 4.24-4.05 (m, 2H), 4.04-3.99 (m, 1H), 3.79 (s, 3H), 1.44 (s, 6H). |

TABLE 2-continued

| Ex | Structure | LCMS (M + H)+ | HPLC Method, RT (min.) & Purity | $^1$H NMR |
|---|---|---|---|---|
| 268 | 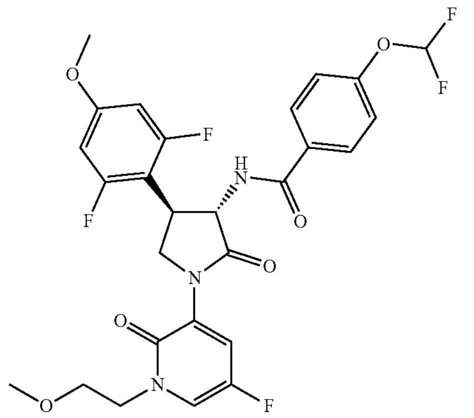 [SMILES: COCCn1cc(F)cc(N2C[C@@H](c3c(F)cc(OC)cc3F)[C@H](NC(=O)c3ccc(OC(F)F)cc3)C2=O)c1=O] | 582.2 | Method D, RT = 1.640 min, 100% | $^1$H NMR (400 MHz, DMSO-$d_6$) δ = 9.01 (d, J = 8.6 Hz, 1H), 7.93 (dd, J = 4.5, 3.3 Hz, 1H), 7.91-7.85 (m, 2H), 7.80 (dd, J = 8.4, 3.3 Hz, 1H), 7.34 (t, J = 73.6 Hz, 1H), 7.28 (m, 2H), 6.77 (d, J = 10.8 Hz, 2H), 5.12 (dd, J = 10.8, 8.6 Hz, 1H), 4.18-4.03 (m, 4H), 3.97 (s, 1H), 3.77 (s, 3H), 3.61 (t, J = 5.4 Hz, 2H), 3.26 (s, 3H). |
| 269 | 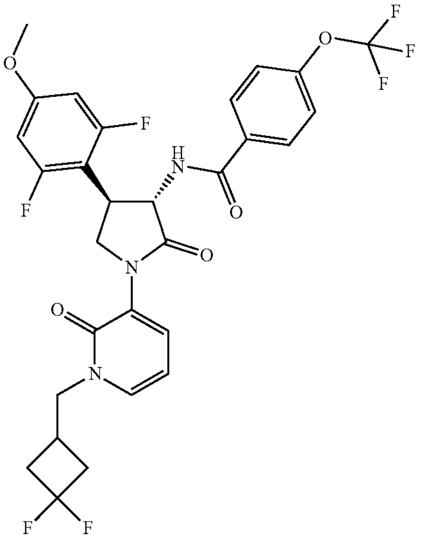 [SMILES: COc1cc(F)c([C@@H]2CN(c3cccn(CC4CC(F)(F)C4)c3=O)C(=O)[C@H]2NC(=O)c2ccc(OC(F)(F)F)cc2)c(F)c1] | 628.2 | Method D, RT = 2.016 min, 100% | $^1$H NMR (400 MHz, DMSO-$d_6$) δ = 9.11 (d, J = 8.6 Hz, 1H), 8.01-7.89 (m, 2H), 7.79 (dd, J = 6.6, 2.0 Hz, 1H), 7.61 (dd, J = 7.1, 2.0 Hz, 1H), 7.49 (d, J = 8.1 Hz, 2H), 6.77 (d, J = 10.8 Hz, 2H), 6.36 (t, J = 7.0 Hz, 1H), 5.13 (dd, J = 10.8, 8.6 Hz, 1H), 4.20-4.05 (m, 3H), 4.05-3.91 (m, 2H), 3.77 (s, 3H), 2.69-2.55 (m, 4H), 2.48-2.41 (m, 1H). |
| 270 | 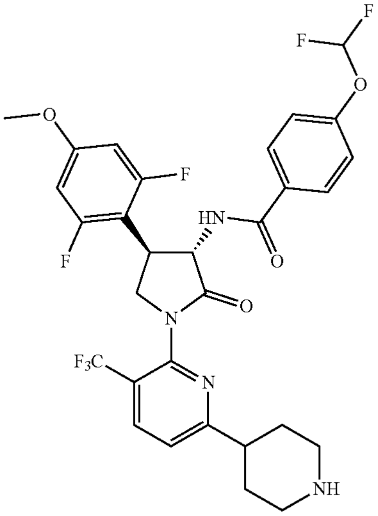 [SMILES: COc1cc(F)c([C@@H]2CN(c3nc(C4CCNCC4)ccc3C(F)(F)F)C(=O)[C@H]2NC(=O)c2ccc(OC(F)F)cc2)c(F)c1] | 641.2 | Method D, RT = 1.698 min, 94.4% | $^1$H NMR (400 MHz, DMSO-$d_6$) δ = 9.08 (d, J = 8.8 Hz, 1H), 8.27 (d, J = 8.3 Hz, 1H), 7.89 (d, J = 8.8 Hz, 2H), 7.57 (d, J = 8.1 Hz, 1H), 7.54-7.11 (m, 3H), 7.34 (t, J = 73.6 Hz, 1H), 6.79 (d, J = 10.8 Hz, 2H), 5.23-5.12 (m, 1H), 4.31-4.19 (m, 1H), 4.13 (br t, J = 9.8 Hz, 1H), 3.96 (br t, J = 9.8 Hz, 1H), 3.77 (s, 3H), 3.08 (br d, J = 12.0 Hz, 2H), 2.95-3.90 (m, 1H), 2.68-2.61 (m, 2H), 1.85-2.80 (m, 2H), 1.72-1.60 (m, 2H). |

TABLE 2-continued

| Ex | Structure | LCMS (M + H)+ | HPLC Method, RT (min.) & Purity | $^1$H NMR |
|---|---|---|---|---|
| 271 | 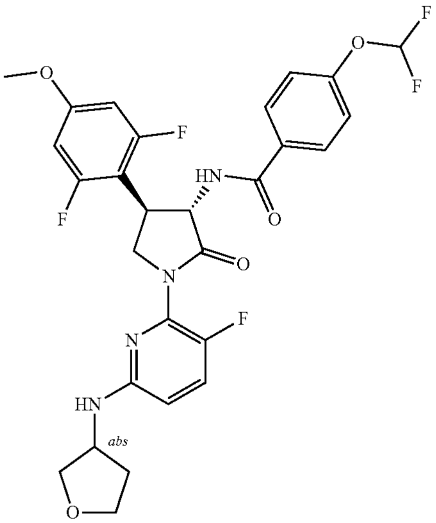 [SMILES: COc1cc(F)c([C@@H]2CN(c3nc(NC4CCOC4)ccc3F)C(=O)[C@H]2NC(=O)c2ccc(OC(F)F)cc2)c(F)c1] | 593.3 | Method D, RT = 1.83 min, 98% | $^1$H NMR (400 MHz, DMSO-$d_6$) δ = 9.07 (d, J = 8.8 Hz, 1H), 7.93-7.83 (m, 2H), 77.53-7.48 (m, 1H), 7.35 (t, J = 73.6 Hz, 1H), 7.28-7.26 (m, 2H), 6.96 (d, J = 5.9 Hz, 1H), 6.87-6.64 (m, 2H), 6.46 (dd, J = 8.9, 2.6 Hz, 1H), 5.17-5.05 (m, 1H), 4.29-4.19 (m, 1H), 4.19-4.08 (m, 2H), 4.02-3.93 (m, 1H), 3.90-3.88 (m, 1H), 3.85-3.77 (m, 1H), 3.76 (s, 3H), 3.73-3.71 (m, 1H), 3.51-3.49 (m, 1H), 2.18-2.13 (m, 1H), 1.86-1.70 (m, 1H). |
| 272 | 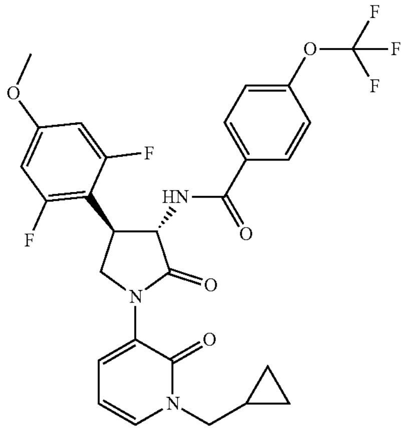 [SMILES: COc1cc(F)c([C@@H]2CN(c3cccn(CC4CC4)c3=O)C(=O)[C@H]2NC(=O)c2ccc(OC(F)(F)F)cc2)c(F)c1] | 578.2 | Method D, RT = 1.946 min, 100% | $^1$H NMR (400 MHz, DMSO-$d_6$) δ = 9.11 (d, J = 8.8 Hz, 1H), 8.03-7.87 (m, 2H), 7.79 (dd, J = 6.6, 2.0 Hz, 1H), 7.59 (dd, J = 7.1, 2.0 Hz, 1H), 7.49 (d, J = 8.1 Hz, 2H), 6.77 (d, J = 10.5 Hz, 2H), 6.35 (t, J = 7.0 Hz, 1H), 5.14 (dd, J = 11.0, 8.6 Hz, 1H), 4.17-4.05 (m, 1H), 4.05-3.92 (m, 2H), 3.89-3.73 (m, 2H), 3.72 (s, 3H), 1.31-1.18 (m, 1H), 0.55-0.45 (m, 2H), 0.43-0.34 (m, 2H). |
| 273 | 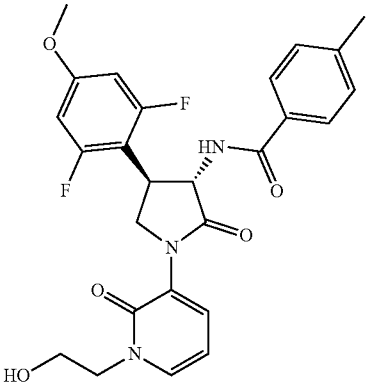 [SMILES: COc1cc(F)c([C@@H]2CN(c3cccn(CCO)c3=O)C(=O)[C@H]2NC(=O)c2ccc(C)cc2)c(F)c1] | 498.3 | Method D, RT = 1.692 min, 93.2% | $^1$H NMR (400 MHz, DMSO-$d_6$) δ = 8.87 (d, J = 8.5 Hz, 1H), 7.79-7.69 (m, 2H), 7.65 (dd, J =6.8, 1.8 Hz, 1H), 7.58 (dd, J = 7.5, 2.0 Hz, 1H), 7.28 (d, J = 8.5 Hz, 2H), 6.76 (d, J = 10.5 Hz, 2H), 6.35-6.27 (m, 1H), 5.11 (dd, J = 11.0, 8.5 Hz, 1H), 4.98-4.89 (m, 1H), 4.14-4.06 (m, 1H), 4.03-3.94 (m, 4H), 3.76 (s, 3H), 3.65 (d, J = 5.5 Hz, 2H), 2.35 (s, 3H). |

TABLE 2-continued

| Ex | Structure | LCMS (M + H)+ | HPLC Method, RT (min.) & Purity | $^1$H NMR |
|---|---|---|---|---|
| 274 | 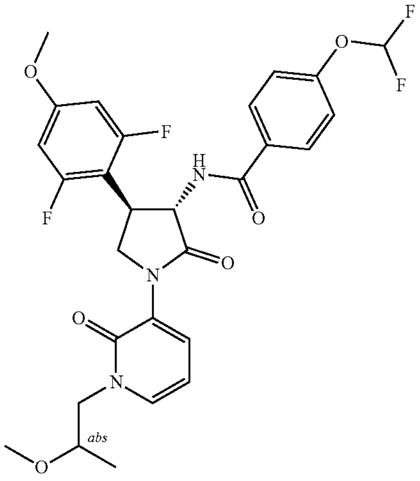 [SMILES: COc1cc(F)c([C@@H]2CN(c3cccn(CC(C)OC)c3=O)C(=O)[C@H]2NC(=O)c2ccc(OC(F)F)cc2)c(F)c1] | 626.2 | Method D, RT = 1.700 min, 98.8% | $^1$H NMR (400 MHz, DMSO-$d_6$) δ = 9.01 (d, J = 8.6 Hz, 1H), 7.88 (d, J = 8.8 Hz, 2H), 7.63-7.58 (m, 2H), 7.34 (t, J = 73.6 Hz, 1H), 7.28 (m, 2H), 6.76 (d, J = 10.8 Hz, 2H), 6.32 (t, J = 7.0 Hz, 1H), 5.10 (dd, J = 10.9, 8.9 Hz, 1H), 4.15-3.82 (m, 5H), 3.76 (s, 3H), 3.67-3.63 (m, 1H), 3.19 (s, 3H), 1.09 (d, J = 6.1 Hz, 3H). |
| 275 | 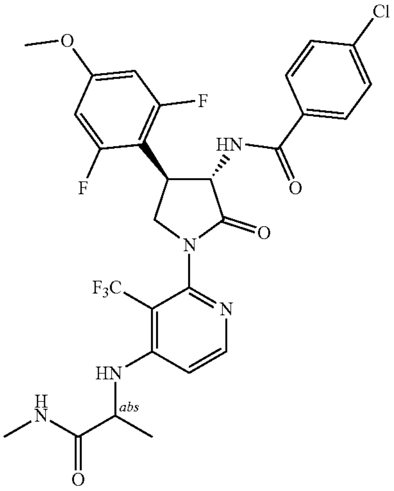 [SMILES: CNC(=O)C(C)Nc1ccnc(N2C[C@@H](c3c(F)cc(OC)cc3F)[C@H](NC(=O)c3ccc(Cl)cc3)C2=O)c1C(F)(F)F] | 626.2 | Method D, RT = 1.77 min, 97.5% | $^1$H NMR (400 MHz, DMSO-$d_6$) δ = 9.10 (d, J = 8.5 Hz, 1H), 8.39-8.25 (m, 1H), 8.23-8.13 (m, 1H), 7.90-7.75 (m, 2H), 7.62-7.49 (m, 2H), 6.79 (d, J = 10.5 Hz, 2H), 6.73-6.61 (m, 1H), 6.43-6.27 (m, 1H), 5.21-5.02 (m, 1H), 4.38-4.05 (m, 3H), 3.85-3.79 (m, 1H), 3.77 (s, 3H), 2.66 (d, J = 8 Hz, 3H), 1.32 (d, J = 4.2 Hz, 3H). |
| 276 | 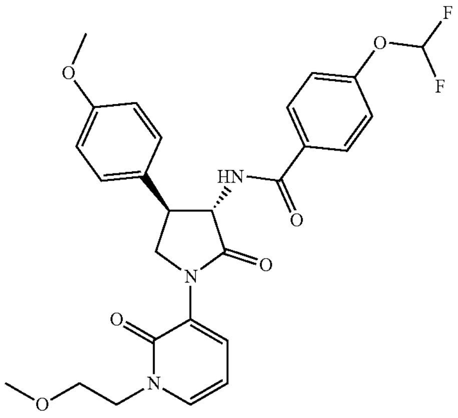 [SMILES: COCCn1cccc(N2C[C@@H](c3ccc(OC)cc3)[C@H](NC(=O)c3ccc(OC(F)F)cc3)C2=O)c1=O] | 528.3 | Method D, RT = 1.509 min, 100% | $^1$H NMR (400 MHz, DMSO-$d_6$) δ = 8.92 (d, J = 8.6 Hz, 1H), 7.99-7.90 (m, 2H), 7.64 (dd, J = 6.8, 2.0 Hz, 1H), 7.59 (dd, J = 7.2, 2.0 Hz, 1H), 7.33 (t, J = 80.0 Hz, 1H), 7.36-7.27 (m, 4H), 6.96-6.80 (m, 2H), 6.32 (t, J = 7.0 Hz, 1H), 5.01 (dd, J = 10.9, 8.9 Hz, 1H), 4.18-4.06 (m, 3H), 3.81-3.68 (m, 5H), 3.60 (t, J = 5.4 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 277 | 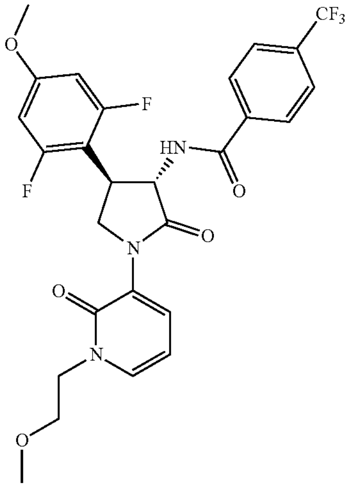 [SMILES: COCCn1cccc(N2C[C@@H](c3c(F)cc(OC)cc3F)[C@H](NC(=O)c3ccc(C(F)(F)F)cc3)C2=O)c1=O] | 566.2 | Method D, RT = 1.782 min, 99.6% | $^1$H NMR (400 MHz, DMSO-$d_6$) δ = 9.23 (d, J = 8.3 Hz, 1H), 8.02 (d, J = 8.1 Hz, 2H), 7.88 (d, J = 8.1 Hz, 2H), 7.67 (dd, J = 6.8, 2.0 Hz, 1H), 7.61 (dd, J = 7.3, 2.0 Hz, 1H), 6.77 (d, J = 10.8 Hz, 2H), 6.33 (t, J = 7.0 Hz, 1H), 5.15 (dd, J = 11.0, 8.6 Hz, 1H), 4.22-4.06 (m, 3H), 4.04-3.94 (m, 2H), 3.77 (s, 3H), 3.61 (t, J = 5.3 Hz, 2H), 3.26 (s, 3H). |
| 278 | 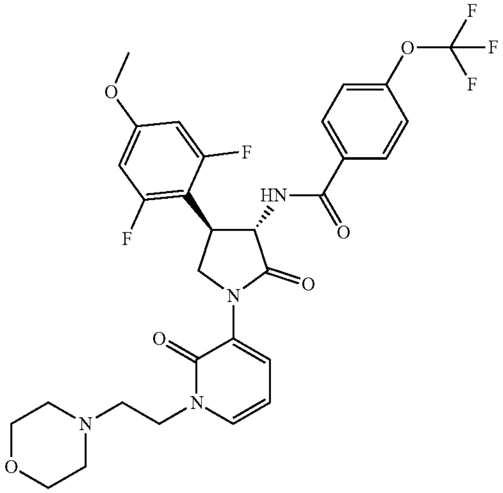 [SMILES: COc1cc(F)c([C@@H]2CN(c3cccn(CCN4CCOCC4)c3=O)C(=O)[C@H]2NC(=O)c2ccc(OC(F)(F)F)cc2)c(F)c1] | 637.3 | Method D, RT = 1.504 min, 100% | $^1$H NMR (400 MHz, DMSO-$d_6$) δ = 9.12 (d, J = 8.6 Hz, 1H), 7.86-8.00 (m, 2H), 7.72 (dd, J = 6.8, 2.0 Hz, 1H), 7.59 (dd, J = 7.3, 2.0 Hz, 1H), 7.49 (dd, J = 8.9, 0.9 Hz, 2H), 6.69-6.84 (m, 2H), 6.33 (t, J = 7.0 Hz, 1H), 5.13 (dd, J = 11.1, 8.7 Hz, 1H), 3.91-4.15 (m, 5H), 3.76 (s, 3H), 3.54 (t, J = 4.5 Hz, 4H), 2.57 (s, 2H), 2.36-2.48 (m, 4H). |
| 279 | 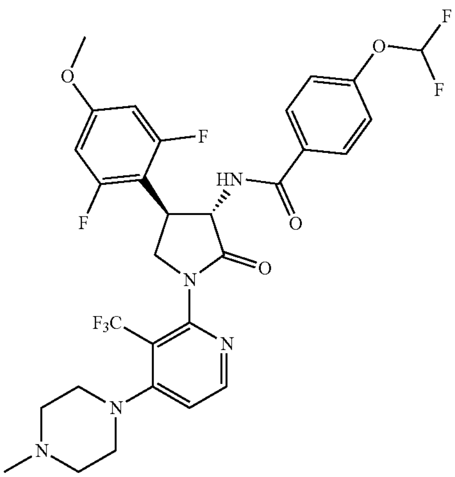 [SMILES: COc1cc(F)c([C@@H]2CN(c3nccc(N4CCN(C)CC4)c3C(F)(F)F)C(=O)[C@H]2NC(=O)c2ccc(OC(F)F)cc2)c(F)c1] | 656.3 | Method D, RT = 1.71 min, 97.5% | $^1$H NMR (400 MHz, DMSO-$d_6$) δ = 9.06 (br d, J = 8.8 Hz, 1H), 8.62-8.51 (m, 1H), 7.92-7.80 (m, 2H), 7.35 (t, J = 72 Hz, 1H), 7.34-7.23 (m, 3H), 6.80 (d, J = 10.8 Hz, 2H), 5.15-4.99 (m, 1H), 4.46-4.38 (m, 1H), 4.32-4.16 (m, 1H), 3.90-3.78 (m, 1H), 3.77 (s, 3H), 3.49-3.37 (m, 4H), 3.30-3.05 (m, 4H), 2.89 (s, 3H). |

TABLE 2-continued
| Ex | Structure | LCMS (M + H)+ | HPLC Method, RT (min.) & Purity | $^1$H NMR |
|---|---|---|---|---|
| 280 | 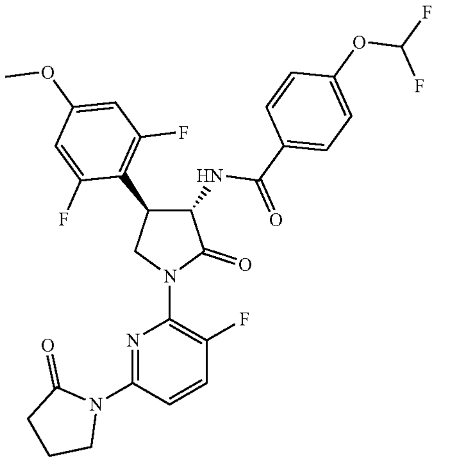 [SMILES: COc1cc(F)c([C@@H]2CN(c3nc(N4CCCC4=O)ccc3F)C(=O)[C@H]2NC(=O)c2ccc(OC(F)F)cc2)c(F)c1] | 591.2 | Method D, RT = 1.82 min, 98% | $^1$H NMR (400 MHz, DMSO-$d_6$) δ = 9.12 (d, J = 8.6 Hz, 1H), 8.27 (dd, J = 9.2, 3.1 Hz, 1H), 7.95-7.85 (m, 3H), 7.35 (t, J = 73.6 Hz, 1H), 7.29-7.27 (m, 2H), 6.80 (d, J = 10.8 Hz, 2H), 5.11 (br dd, J = 10.4, 8.2 Hz, 1H), 4.31-4.17 (m, 2H), 4.10-3.91 (m, 3H), 3.78 (s, 3H), 2.59 (t, J = 8.1 Hz, 2H), 2.09-1.98 (m, 2H). |
| 281 | 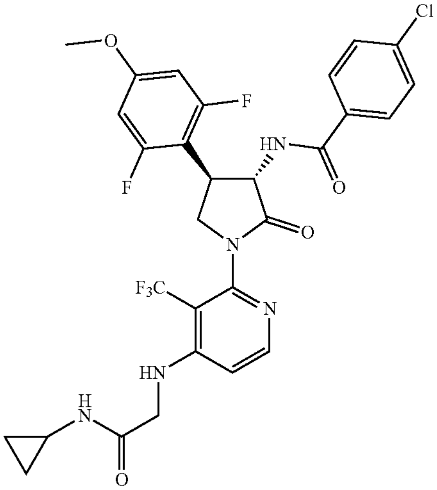 [SMILES: COc1cc(F)c([C@@H]2CN(c3nccc(NCC(=O)NC4CC4)c3C(F)(F)F)C(=O)[C@H]2NC(=O)c2ccc(Cl)cc2)c(F)c1] | 638.3 | Method C, RT = 1.71 min, 98.5% | $^1$H NMR (400 MHz, DMSO-$d_6$) δ = 9.13-8.95 (m, 1H), 8.29-8.20 (m, 2H), 7.91-7.75 (m, 2H), 7.61-7.56 (m, 2H), 6.81-6.76 (m, 2H), 6.75-6.68 (m, 1H), 6.58-6.51 (m, 1H), 5.19-4.98 (m, 1H), 4.35-4.26 (m, 1H), 4.25-4.10 (m, 1H), 3.89-3.75 (m, 2H), 3.80 (s, 3H), 3.78-3.74 (m, 1H), 2.64-2.68 (m, 1H), 0.68-0.62 (m, 2H), 0.46-0.42 (m, 2H). |
| 282 | 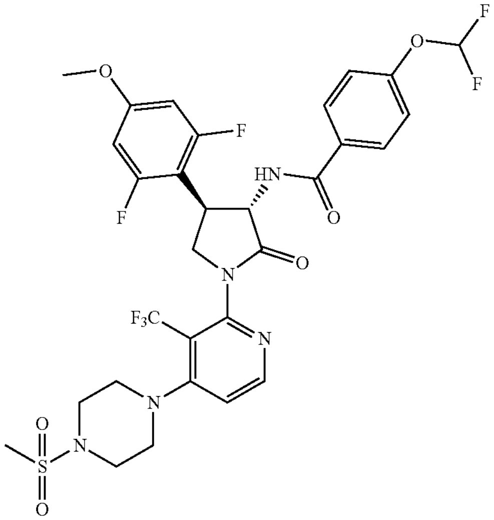 [SMILES: COc1cc(F)c([C@@H]2CN(c3nccc(N4CCN(S(C)(=O)=O)CC4)c3C(F)(F)F)C(=O)[C@H]2NC(=O)c2ccc(OC(F)F)cc2)c(F)c1] | 720.2 | Method D, RT = 1.88 min, 97.8% | $^1$H NMR (400 MHz, DMSO-$d_6$) δ = 9.09-8.98 (m, 1H), 8.57-8.49 (m, 1H), 7.87 (td, J = 7.4, 0.9 Hz, 2H), 7.35 (t, J = 72 Hz, 1H), 7.32-7.25 (m, 3H), 6.79 (d, J = 10.8 Hz, 2H), 5.17-5.06 (m, 1H), 4.45-4.35 (m, 1H), 4.29-4.18 (m, 1H), 3.90-3.80 (m, 1H), 3.77 (s, 3H), 3.41-3.25 (m, 8H), 2.96 (s, 3H). |

TABLE 2-continued

| Ex | Structure | LCMS (M + H)+ | HPLC Method, RT (min.) & Purity | $^1$H NMR |
|---|---|---|---|---|
| 283 | 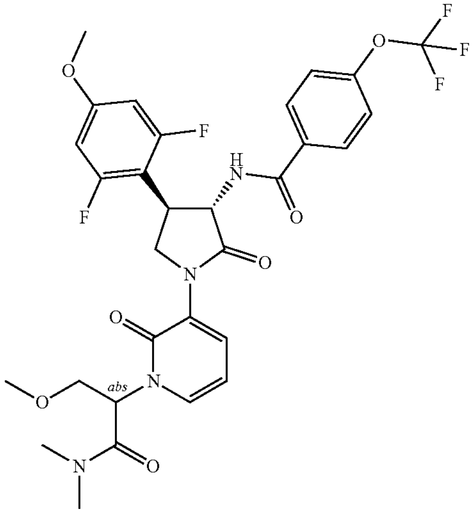 [SMILES: COCC(C(=O)N(C)C)n1cccc(N2C[C@@H](c3c(F)cc(OC)cc3F)[C@H](NC(=O)c3ccc(OC(F)(F)F)cc3)C2=O)c1=O] | 653.3 | Method D, RT = 1.790 min, 100% | $^1$H NMR (400 MHz, DMSO-$d_6$) δ = 9.11 (d, J = 8.8 Hz, 1H), 8.00-7.87 (m, 2H), 7.72 (dd, J = 7.1, 2.0 Hz, 1H), 7.62 (dd, J = 7.2, 2.0 Hz, 1H), 7.54-7.40 (m, 2H), 6.77 (d, J = 10.8 Hz, 2H), 6.4 (t, J = 7.1 Hz, 1H), 6.06 (dd, J = 8.6, 5.1 Hz, 1H), 5.13 (dd, J = 11.1, 8.7 Hz, 1H), 4.15-3.96 (m, 2H), 3.96-3.79 (m, 3H), 3.76 (s, 3H), 3.27 (s, 3H), 3.12 (s, 3H), 2.85 (s, 3H). |
| 284 | 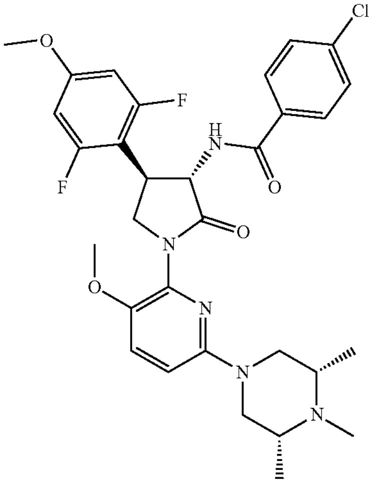 [SMILES: COc1cc(F)c([C@@H]2CN(c3nc(N4C[C@@H](C)N(C)[C@@H](C)C4)ccc3OC)C(=O)[C@H]2NC(=O)c2ccc(Cl)cc2)c(F)c1] | 614.3 | Method D, RT = 1.53 min, 99% | $^1$H NMR (400 MHz, DMSO-$d_6$) δ = 9.11 (d, J = 9.0 Hz, 1H), 7.84 (d, J = 8.6 Hz, 2H), 7.61-7.54 (m, 2H), 7.52 (d, J = 8.8 Hz, 1H), 6.86 (d, J = 8.8 Hz, 1H), 6.82-6.71 (m, 2H), 5.21 (dd, J = 9.2, 10.9 Hz, 1H), 4.18-4.01 (m, 2H), 3.99-3.90 (m, 2H), 3.88-3.82 (m, 1H), 3.76 (s, 6H), 2.47-2.39 (m, 2H), 2.23-2.11 (m, 5H), 1.12-1.01 (m, 6H). |
| 285 | 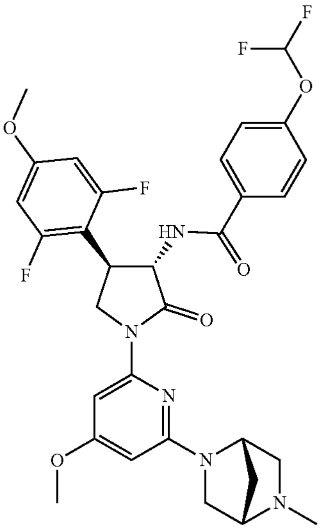 [SMILES: COc1cc(N2C[C@@H](c3c(F)cc(OC)cc3F)[C@H](NC(=O)c3ccc(OC(F)F)cc3)C2=O)nc(N2C[C@@H]3C[C@H]2CN3C)c1] | 630.2 | Method D, RT = 1.73 min, 96.8% | $^1$H NMR (400 MHz, DMSO-$d_6$) δ = 9.06 (d, J = 8.8 Hz, 1H), 7.88 (d, J = 8.8 Hz, 2H), 7.36 (t, J = 73.6 Hz, 1H), 7.30-7.26 (m, 3H), 6.80 (d, J = 10.8 Hz, 2H), 5.84 (s, 1H), 5.08 (dd, J = 11.1, 8.4 Hz, 1H), 4.70-4.60 (m, 1H), 4.52-4.40 (m, 1H), 4.12-4.01 (m, 1H), 3.91-3.83 (m, 2H), 3.81 (s, 3H) 3.78 (s, 3H), 3.67-3.56 (m, 1H), 3.46 (m, 1H), 2.92-2.85 (m, 1H), 2.46-(s, 3H), 1.97-1.85 (m, 2H), 1.79-1.75 (m, 1H). |

TABLE 2-continued

| Ex | Structure | LCMS (M + H)+ | HPLC Method, RT (min.) & Purity | $^1$H NMR |
|---|---|---|---|---|
| 286 | 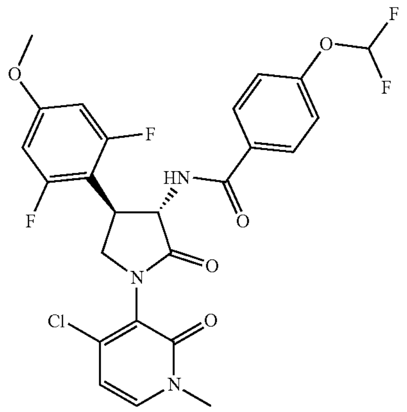 [SMILES: COc1cc(F)c([C@@H]2CN(c3c(Cl)ccn(C)c3=O)C(=O)[C@H]2NC(=O)c2ccc(OC(F)F)cc2)c(F)c1] | 554.1 | Method D, RT = 1.659 min, 97.8% | $^1$H NMR (400 MHz, DMSO-$d_6$) δ = 9.13-8.93 (m, 1H), 7.97-7.78 (m, 3H), 7.34 (t, J = 73.6 Hz, 1H), 7.28 (m, 2H), 6.77 (d, J = 10.8 Hz, 2H), 6.53 (dd, J = 7.3, 8.6 Hz, 1H), 5.35-5.07 (m, 1H), 4.24-4.09 (m, 1H), 4.05-3.89 (m, 1H), 3.76 (s, 3H), 3.64-3.53 (m, 1H), 3.50 (d, J = 5.6 Hz, 3H). (mixture of interconvertible atropisomers) |
| 287 | 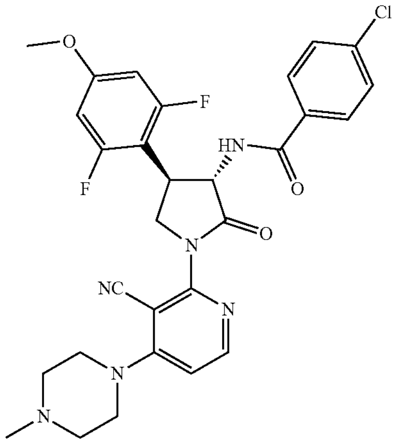 [SMILES: COc1cc(F)c([C@@H]2CN(c3nccc(N4CCN(C)CC4)c3C#N)C(=O)[C@H]2NC(=O)c2ccc(Cl)cc2)c(F)c1] | 581.3 | Method D, RT = 1.76 min, 94% | $^1$H NMR (400 MHz, DMSO-$d_6$) δ = 9.19 (d, J = 8.6 Hz, 1H), 8.33 (d, J = 5.9 Hz, 1H), 7.87-7.78 (m, 2H), 7.61-7.53 (m, 2H), 7.00 (d, J = 6.4 Hz, 1H), 6.80 (d, J = 10.8 Hz, 2H), 5.10 (dd, J = 10.8, 8.6 Hz, 1H), 4.38-4.30 (m, 1H), 4.20 (q, J = 9.9 Hz, 1H), 4.06-3.96 (m, 1H), 3.77 (s, 3H), 3.57-3.45 (m, 4H), 2.51-2.44 (m, 4H), 2.26 (s, 3H). |
| 288 | 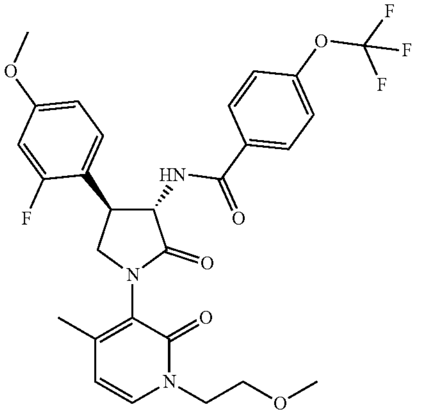 [SMILES: COCCn1ccc(C)c(N2C[C@@H](c3ccc(OC)cc3F)[C@H](NC(=O)c3ccc(OC(F)(F)F)cc3)C2=O)c1=O] | 578.2 | Method D, RT = 1.83 min, 100% | $^1$H NMR (400 MHz, DMSO-$d_6$) δ = 9.17-9.00 (m, 1H), 8.09-7.87 (m, 2H), 7.66-7.35 (m, 4H), 6.94-6.66 (m, 2H), 6.20 (d, J = 6.8 Hz, 1H), 5.41-4.78 (m, 1H), 4.22-3.89 (m, 4H), 3.78-3.72 (2s, 3H), 3.63-3.37 (2s, 3H), 3.24 (s, 3H), 2.21-2.06 (2s, 3H). (mixture of interconvertible atropisomers isomers) |

TABLE 2-continued

| Ex | Structure | LCMS (M + H)+ | HPLC Method, RT (min.) & Purity | $^1$H NMR |
|---|---|---|---|---|
| 289 | 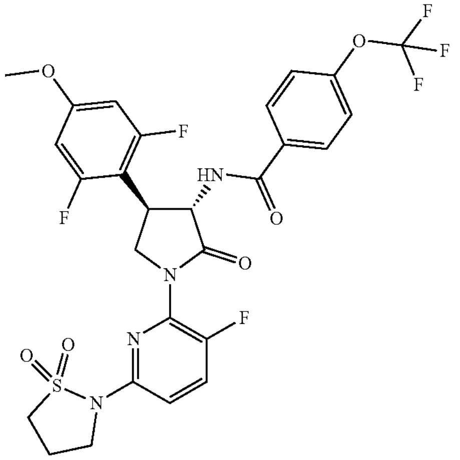 [SMILES: COc1cc(F)c([C@@H]2CN(c3nc(N4CCCS4(=O)=O)ccc3F)C(=O)[C@H]2NC(=O)c2ccc(OC(F)(F)F)cc2)c(F)c1] | 644.1 | Method D, RT = 1.99 min, 94% | $^1$H NMR (400 MHz, DMSO-$d_6$) δ = 9.21 (d, J = 8.3 Hz, 1H), 7.99-7.82 (m, 3H), 7.50 (d, J = 8.8 Hz, 2H), 7.13 (dd, J = 9.3, 2.4 Hz, 1H), 6.80 (d, J = 10.8 Hz, 2H), 5.17-5.07 (m, 1H), 4.28-4.16 (m, 2H), 4.09-3.99 (m, 1H), 3.94-3.82 (m, 2H), 3.77 (s, 3H), 3.59 (t, J = 7.2 Hz, 2H), 2.43-2.38 (m, 2H). |
| 290 | 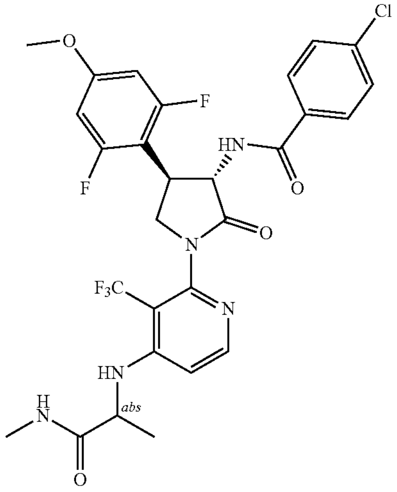 [SMILES: CNC(=O)C(C)Nc1ccnc(N2C[C@@H](c3c(F)cc(OC)cc3F)[C@H](NC(=O)c3ccc(Cl)cc3)C2=O)c1C(F)(F)F] | 626.2 | Method D, RT = 1.77 min, 100% | $^1$H NMR (400 MHz, DMSO-$d_6$) δ = 9.10 (d, J = 8.5 Hz, 1H), 8.39-8.25 (m, 1H), 8.23-8.13 (m, 1H), 7.90-7.75 (m, 2H), 7.62-7.49 (m, 2H), 6.79 (d, J = 10.5 Hz, 2H), 6.73-6.61 (m, 1H), 6.43-6.27 (m, 1H), 5.21-5.02 (m, 1H), 4.38-4.05 (m, 3H), 3.85-3.79 (m, 1H), 3.77 (s, 3H), 2.69-2.64 (2s, 3H), 1.43-1.32 (m, 3H). (mixture of interconvertible atropisomers) |
| 291 | 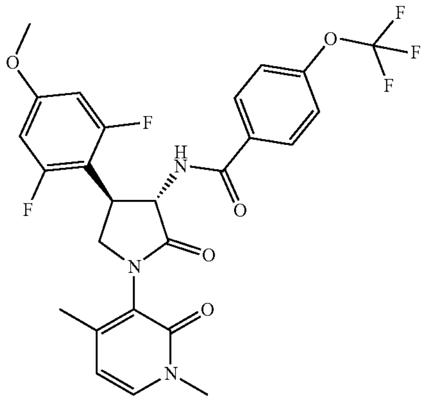 [SMILES: COc1cc(F)c([C@@H]2CN(c3c(C)ccn(C)c3=O)C(=O)[C@H]2NC(=O)c2ccc(OC(F)(F)F)cc2)c(F)c1] | 552.2 | Method D, RT = 1.761 min, 100% | $^1$H NMR (400 MHz, DMSO-$d_6$) δ = 9.25-8.95 (m, 1H), 8.01-7.86 (m, 2H), 7.73-7.57 (m, 1H), 7.54-7.36 (m, 2H), 6.88-6.66 (m, 2H), 6.28-6.15 (m, 1H), 5.38-4.84 (m, 1H), 4.30-4.05 (m, 2H), 3.80-3.72 (2s, 3H), 3.55-3.40 (m, 4H), 2.23-2.01 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 292 | 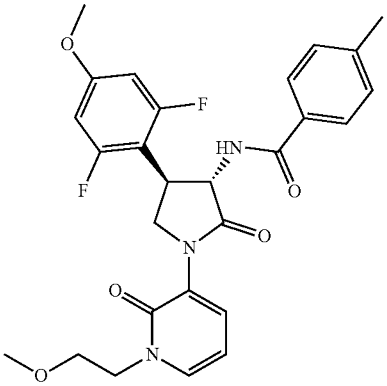 | 512.3 | Method D, RT = 1.560 min, 100% | $^1$H NMR (400 MHz, DMSO-$d_6$) δ = 8.89 (d, J = 8.8 Hz, 1H), 7.77-7.69 (m, 2H), 7.66 (dd, J = 6.8, 2.0 Hz, 1H), 7.59 (dd, J = 7.3, 2.0 Hz, 1H), 7.28 (d, J = 8.1 Hz, 2H), 6.77 (d, J = 10.8 Hz, 2H), 6.32 (t, J = 7.0 Hz, 1H), 5.12 (dd, J = 8.7, 11.1 Hz, 1H), 4.20-4.04 (m, 3H), 3.97 (br d, J = 9.5 Hz, 2H), 3.76 (s, 3H), 3.60 (t, J = 5.3 Hz, 2H), 3.25 (s, 3H), 2.35 (s, 3H). |
| 293 | 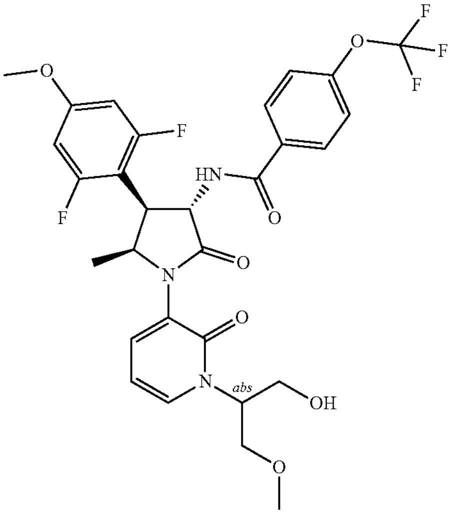 [SMILES: COCC(CO)n1cccc(N2C(=O)[C@@H](NC(=O)c3ccc(OC(F)(F)F)cc3)[C@H](c3c(F)cc(OC)cc3F)[C@@H]2C)c1=O] | 626.2 | Method D, RT = 1.72 min, 94% | $^1$H NMR (400 MHz, DMSO-$d_6$) δ = 8.97 (br d, J = 8.1 Hz, 1H), 7.96 (d, J = 8.6 Hz, 2H), 7.74-7.66 (m, 1H), 7.56 (dd, J = 7.0, 1.3 Hz, 1H), 7.45 (d, J = 8.6 Hz, 2H), 6.77 (d, J = 11.5 Hz, 2H), 6.33 (t, J = 7.0 Hz, 1H), 5.71-5.61 (m, 1H), 5.14-4.97 (m, 2H), 4.67-4.56 (m, 1H), 4.29 (dd, J = 11.7, 8.3 Hz, 1H), 3.83-3.69, (m, 4H), 3.65 (td, J = 5.4, 10.9 Hz, 2H), 3.34-3.32 (m, 1H), 3.23 (s, 3H), 0.91 (br d, J = 6.8 Hz, 3H). |
| 294 | 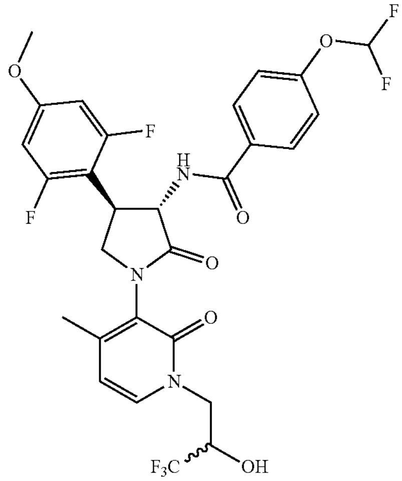 [SMILES: COc1cc(F)c([C@@H]2CN(c3c(C)ccn(CC(O)C(F)(F)F)c3=O)C(=O)[C@H]2NC(=O)c2ccc(OC(F)F)cc2)c(F)c1] | 632.2 | Method D, RT = 1.808 min, 98.1% | $^1$H NMR (400 MHz, DMSO-$d_6$) δ = 9.18-8.84 (m, 1H), 8.00-7.82 (m, 2H), 7.73-7.06 (m, 3H), 7.34 (t, J = 73.6 Hz, 1H), 6.79-6.73 (m, 2H), 6.35-6.11 (m, 1H), 5.37-4.75 (m, 1H), 4.49-4.03 (m, 5H), 3.88-3.74 (m, 4H), 3.55-3.48 (m, 1H), 2.25-2.01 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 295 | 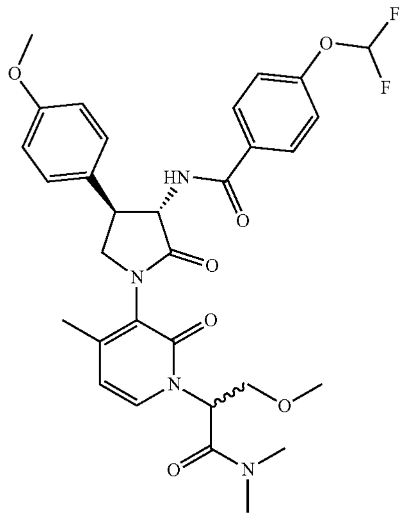 [SMILES: COCC(C(=O)N(C)C)n1ccc(C)c(N2C[C@@H](c3ccc(OC)cc3)[C@H](NC(=O)c3ccc(OC(F)F)cc3)C2=O)c1=O] | 613.3 | Method D, RT = 1.563 min, 100% | $^1$H NMR (400 MHz, DMSO-$d_6$) δ = 8.94 (d, J = 9.0 Hz, 1H), 7.97-7.87 (m, 2H), 7.65-7.56 (m, 1H), 7.52-7.15 (m, 4H), 6.95-6.80 (m, 2H), 6.28 (d, J = 7.6 Hz, 1H), 6.02 (s, 1H), 5.21-4.73 (m, 1H), 4.11-4.03 (m, 1H), 3.93-3.75 (m, 5H), 3.74-3.67 (2s, 3H), 3.28-3.22 (2s, 3H), 3.16-3.05 (m, 3H), 2.90-2.80 (2s, 3H), 2.24-2.06 (2s, 3H). (mixture of interconvertible atropisomers) |
| 296 | 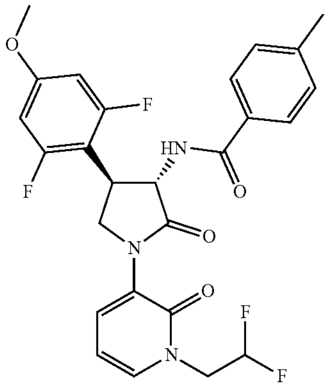 [SMILES: COc1cc(F)c([C@@H]2CN(c3cccn(CC(F)F)c3=O)C(=O)[C@H]2NC(=O)c2ccc(C)cc2)c(F)c1] | 518.2 | Method D, RT = 1.656 min, 100% | $^1$H NMR (400 MHz, DMSO-$d_6$) δ = 8.90 (d, J = 8.6 Hz, 1H), 7.78-7.70 (m, 3H), 7.66 (dd, J = 7.3, 2.0 Hz, 1H), 7.28 (d, J = 8.1 Hz, 2H), 6.77 (d, J = 10.8 Hz, 2H), 6.42 (t, J = 8.0 Hz, 1H), 6.35 (tt, J = 56.2 Hz, 1H), 5.11 (dd, J = 8.6, 11.0 Hz, 1H), 4.55-4.35 (m, 2H), 4.16-4.05 (m, 1H), 3.98 (br d, J = 9.3 Hz, 2H), 3.76 (s, 3H), 2.35 (s, 3H). |
| 297 | 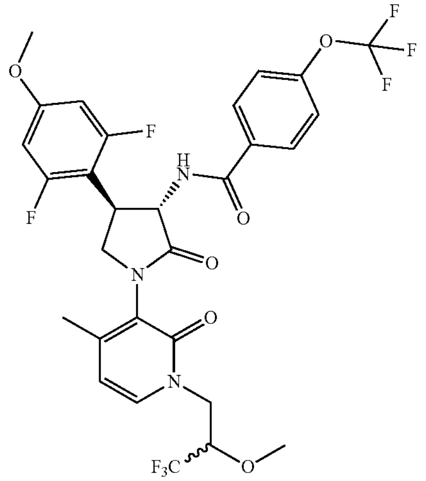 [SMILES: COc1cc(F)c([C@@H]2CN(c3c(C)ccn(CC(OC)C(F)(F)F)c3=O)C(=O)[C@H]2NC(=O)c2ccc(OC(F)(F)F)cc2)c(F)c1] | 664.2 | Method D, RT = 2.100 min, 100% | $^1$H NMR (400 MHz, DMSO-$d_6$) δ = 9.27-8.88 (m, 1H), 8.04-7.82 (m, 2H), 7.71-7.54 (m, 1H), 7.54-7.26 (m, 2H), 6.77 (dd, J = 10.6, 5.5 Hz, 2H), 6.44-6.10 (m, 1H), 5.40-4.80 (m, 1H), 4.43-3.89 (m, 5H), 3.83-3.69 (m, 3H), 3.61-3.46 (m, 1H), 3.38-3.33 (m, 3H), 2.26-2.03 (m, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 298 | 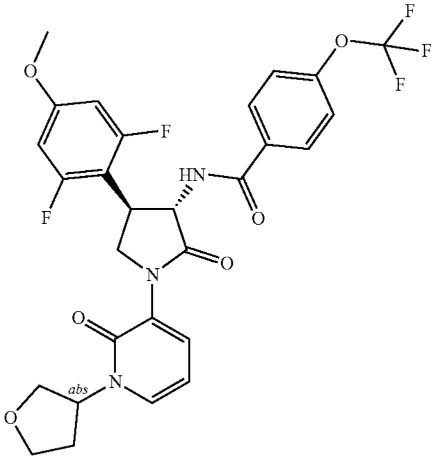 [SMILES: COc1cc(F)c([C@@H]2CN(c3cccn(C4CCOC4)c3=O)C(=O)[C@H]2NC(=O)c2ccc(OC(F)(F)F)cc2)c(F)c1] | 594.2 | Method D, RT = 1.773 min, 100% | $^1$H NMR (400 MHz, DMSO-$d_6$) δ = 9.12 (d, J = 8.6 Hz, 1H), 7.98-7.89 (m, 2H), 7.64 (dd, J = 7.1, 2.0 Hz, 1H), 7.59 (dd, J = 7.2, 2.0 Hz, 1H), 7.49 (dd, J = 1.0, 8.8 Hz, 2H), 6.78 (d, J = 10.8 Hz, 2H), 6.41 (t, J = 7.1 Hz, 1H), 5.45-5.39 (m, 1H), 5.12 (dd, J = 11.1, 8.7 Hz, 1H), 4.17-4.02 (m, 2H), 3.98 (br d, J = 8.8 Hz, 2H), 3.87 (d, J = 4.4 Hz, 2H), 3.82-3.69 (m, 4H), 2.48-2.40 (m, 1H), 1.98 (m, 1H). |
| 299 | 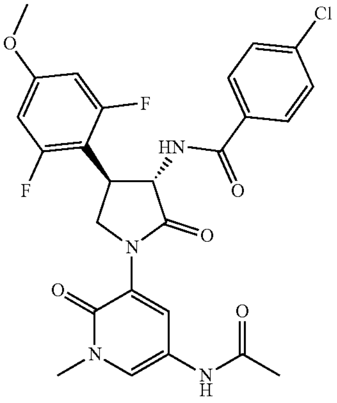 [SMILES: COc1cc(F)c([C@@H]2CN(c3cc(NC(C)=O)cn(C)c3=O)C(=O)[C@H]2NC(=O)c2ccc(Cl)cc2)c(F)c1] | 545.2 | Method D, RT = 1.397 min, 94.9% | $^1$H NMR (400 MHz, DMSO-$d_6$) δ = 9.83 (s, 1H), 9.07 (d, J = 8.6 Hz, 1H), 8.14 (d, J = 2.7 Hz, 1H), 7.84 (d, J = 8.6 Hz, 2H), 7.66 (d, J = 2.7 Hz, 1H), 7.58-7.52 (m, 3H), 6.78 (d, J = 10.8 Hz, 2H), 5.01 (br dd, J = 8.2, 9.9 Hz, 1H), 4.16-3.94 (m, 3H), 3.74 (s, 3H), 3.49 (s, 3H), 2.00 (s, 3H). |
| 300 | 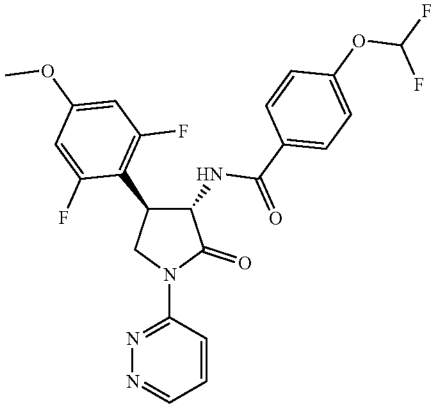 [SMILES: COc1cc(F)c([C@@H]2CN(c3cccnn3)C(=O)[C@H]2NC(=O)c2ccc(OC(F)F)cc2)c(F)c1] | 491.1 | Method D, RT = 1.65 min, 99% | $^1$H NMR (400 MHz, DMSO-$d_6$) δ = 9.19-9.01 (m, 2H), 8.66-8.51 (m, 1H), 7.89 (d, J = 8.6 Hz, 2H), 7.78 (dd, J = 9.3, 4.6 Hz, 1H), 7.35 (t, J = 76 Hz, 1H), 7.30-7.29 (m, 2H), 6.80 (br d, J = 10.5 Hz, 2H), 5.06 (br t, J = 9.4 Hz, 1H), 4.58 (br t, J = 8.8 Hz, 1H), 4.30-4.05 (m, 2H), 3.78 (s, 3H). |

TABLE 2-continued

| Ex | Structure | LCMS (M + H)+ | HPLC Method, RT (min.) & Purity | $^{1}$H NMR |
|---|---|---|---|---|
| 301 | 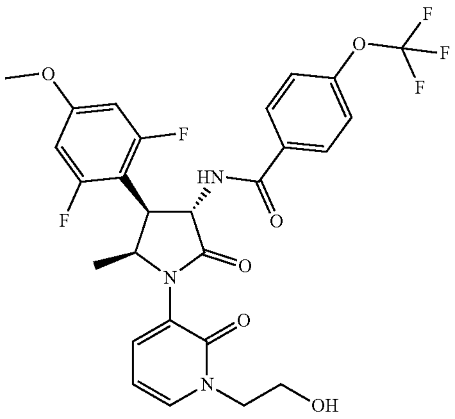 [SMILES: COc1cc(F)c([C@H]2[C@H](NC(=O)c3ccc(OC(F)(F)F)cc3)C(=O)N(c3cccn(CCO)c3=O)[C@H]2C)c(F)c1] | 582.1 | Method D, RT = 1.73 min, 100% | $^{1}$H NMR (400 MHz, DMSO-$d_6$) δ = 8.97 (d, J = 8.8 Hz, 1H), 8.02-7.91 (m, 2H), 7.67 (dd, J = 6.6, 2.0 Hz, 1H), 7.59 (dd, J = 6.6, 2.0 Hz, 1H), 7.45 (d, J = 8.1 Hz, 2H), 6.82-6.70 (m, 2H), 6.31 (t, J = 7.0 Hz, 1H), 5.67 (dd, J = 12.0, 8.6 Hz, 1H), 4.65-4.59 (m, 1H), 4.32-4.27 (m, 1H), 4.12-4.06 (m, 2H), 3.97-3.92 (m, 2H), 3.76 (s, 3H), 3.34-3.30 (m, 1H), 0.92 (d, J = 6.8 Hz, 3H). |
| 302 | 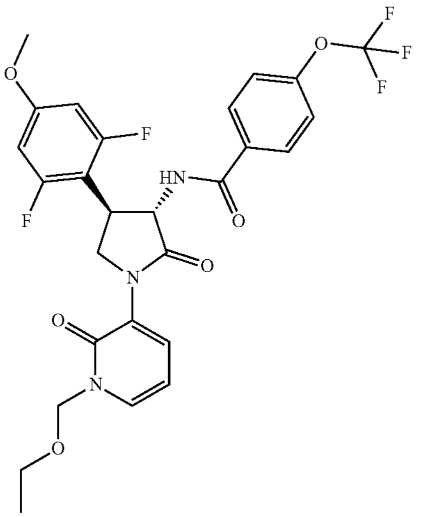 [SMILES: CCOCn1cccc(N2C[C@@H](c3c(F)cc(OC)cc3F)[C@H](NC(=O)c3ccc(OC(F)(F)F)cc3)C2=O)c1=O] | 582.2 | Method D, RT = 1.808 min, 100% | $^{1}$H NMR (400 MHz, DMSO-$d_6$) δ = 9.12 (d, J = 8.5 Hz, 1H), 7.99-7.90 (m, 2H), 7.67 (dd, J = 6.8, 1.8 Hz, 1H), 7.60 (dd, J = 7.0, 2.0 Hz, 1H), 7.49 (d, J = 8.0 Hz, 2H), 6.77 (d, J = 10.5 Hz, 2H), 6.33 (t, J = 7.0 Hz, 1H), 5.13 (dd, J = 10.8, 8.8 Hz, 1H), 4.17-4.04 (m, 3H), 4.03-3.93 (m, 2H), 3.77 (s, 3H), 3.60 (t, J = 5.3 Hz, 2H), 3.25 (s, 3H). |
| 303 | 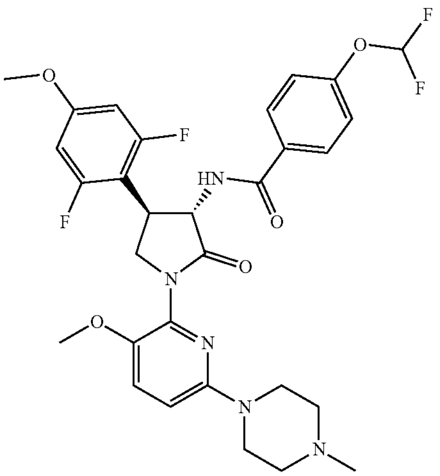 [SMILES: COc1cc(F)c([C@@H]2CN(c3nc(N4CCN(C)CC4)ccc3OC)C(=O)[C@H]2NC(=O)c2ccc(OC(F)F)cc2)c(F)c1] | 618.2 | Method D, RT = 1.76 min, 100% | $^{1}$H NMR (400 MHz, DMSO-$d_6$) δ = 9.03 (br d, J = 9.0 Hz, 1H), 7.95-7.83 (m, 2H), 7.62 (d, J = 9.0 Hz, 1H), 7.34 (t, J = 76 Hz, 1H), 7.28-7.26 (m, 2H), 6.97 (d, J = 9.0 Hz, 1H), 6.78 (d, J = 10.8 Hz, 2H), 5.21-5.16 (m, 1H), 4.34-4.12 (m, 3H), 4.11-4.05 (m, 1H), 3.93-3.83 (m, 1H), 3.79 (s, 3H), 3.77 (s, 3H), 3.58-3.47 (m, 2H), 3.18-2.96 (m, 4H), 2.86 (s, 3H). |

TABLE 2-continued

| Ex | Structure | LCMS (M + H)+ | HPLC Method, RT (min.) & Purity | $^1$H NMR |
|---|---|---|---|---|
| 304 | 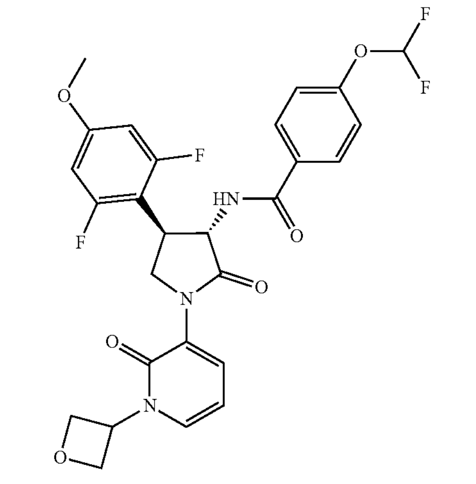 [SMILES: COc1cc(F)c([C@@H]2CN(c3cccn(C4COC4)c3=O)C(=O)[C@H]2NC(=O)c2ccc(OC(F)F)cc2)c(F)c1] | 562.2 | Method D, RT = 1.527 min, 96% | $^1$H NMR (400 MHz, DMSO-d$_6$) δ = 9.01 (d, J = 8.6 Hz, 1H), 7.89 (d, J = 8.8 Hz, 2H), 7.82 (dd, J = 7.0, 1.6 Hz, 1H), 7.64 (dd, J = 7.2, 1.6 Hz, 1H), 7.34 (t, J = 76.0 Hz, 1H), 7.27-7.25 (m, 2H), 6.77 (d, J = 10.8 Hz, 2H), 6.45 (t, J = 7.1 Hz, 1H), 5.54 (m, 1H), 5.09 (dd, J = 10.6, 8.7 Hz, 1H), 4.89 (t, J = 7.2 Hz, 2H), 4.77 (q, J = 7.2 Hz, 2H), 4.15-4.03 (m, 1H), 3.99-3.95 (m, 2H), 3.76 (s, 3H). |
| 305 | 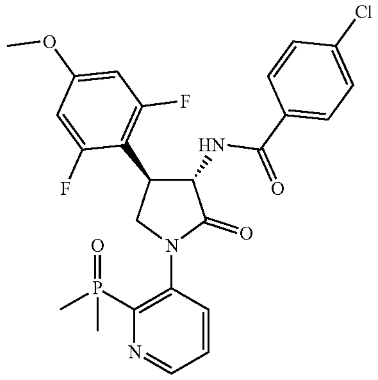 [SMILES: COc1cc(F)c([C@@H]2CN(c3cccnc3P(C)(C)=O)C(=O)[C@H]2NC(=O)c2ccc(Cl)cc2)c(F)c1] | 534.1 | Method D, RT = 1.55 min, 95.6% | $^1$H NMR (400 MHz, DMSO-d$_6$) δ = 9.10-9.07 (m, 1H), 8.76-8.75 (d, J = 4.4 Hz, 1H), 7.98-7.97 (m, 1H), 7.84 (d, J = 8.6 Hz, 2H), 7.78-7.74 (m, 1H), 7.57-7.51 (m, 2H), 6.76-6.74 (d, J = 10.8 Hz, 1 H), 6.63-6.60 (d, J = 11.2 Hz, 1H), 5.17-5.13 (m, 1H), 4.22-4.19 (m, 1H), 4.1-4.03 (m, 2H), 3.77 (s, 3H), 1.85-1.65 (m, 6H). |
| 306 | 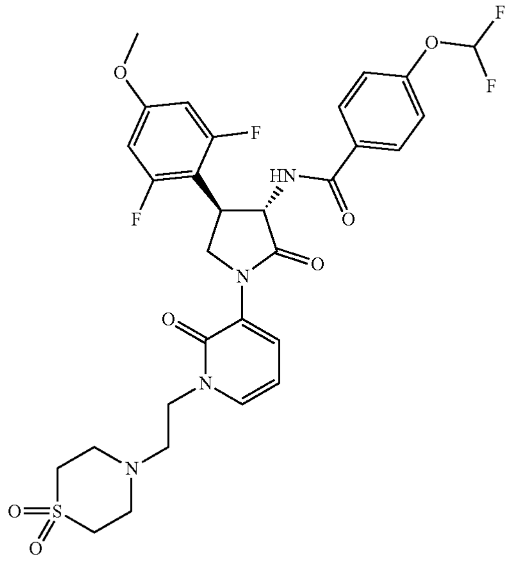 [SMILES: COc1cc(F)c([C@@H]2CN(c3cccn(CCN4CCS(=O)(=O)CC4)c3=O)C(=O)[C@H]2NC(=O)c2ccc(OC(F)F)cc2)c(F)c1] | 667.2 | Method D, RT = 1.524 min, 98.4% | $^1$H NMR (400 MHz, DMSO-d$_6$) δ = 9.01 (d, J = 8.8 Hz, 1H), 7.94-7.84 (m, 2H), 7.75 (dd, J = 6.7, 2.0 Hz, 1H), 7.60 (dd, J = 7.1, 2.0 Hz, 1H), 7.34 (t, J = 73.6 Hz, 1H), 7.28 (m, 2H), 6.77 (d, J = 10.8 Hz, 2H), 6.35 (t, J = 7.0 Hz, 1H), 5.11 (dd, J = 10.9, 8.4 Hz, 1H), 4.14-4.01 (m, 3H), 3.98 (br d, J = 8.6 Hz, 2H), 3.76 (s, 3H), 3.14-3.05 (m, 4H), 3.04-2.90 (m, 4H), 2.85-2.77 (m, 2H). |

TABLE 2-continued

| Ex | Structure | LCMS (M + H)+ | HPLC Method, RT (min.) & Purity | $^1$H NMR |
| --- | --- | --- | --- | --- |
| 307 | 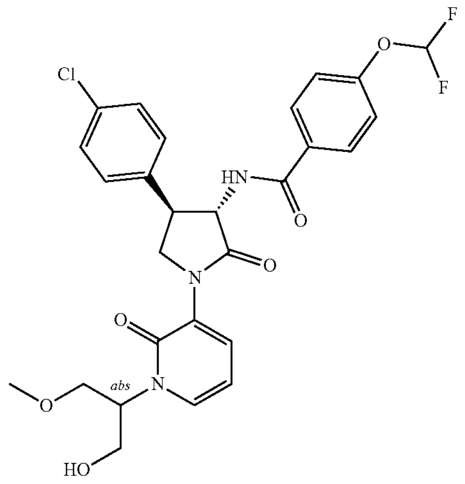 [SMILES: COCC(CO)n1cccc(N2C[C@@H](c3ccc(Cl)cc3)[C@H](NC(=O)c3ccc(OC(F)F)cc3)C2=O)c1=O] | 562.2 | Method D, RT = 1.618 min, 100% | $^1$H NMR (400 MHz, DMSO-$d_6$) δ = 8.97 (d, J = 8.8 Hz, 1H), 7.92 (d, J = 9.0 Hz, 2H), 7.68 (dd, J = 7.2, 1.8 Hz, 1H), 7.58-7.54 (m, 1H), 7.53-7.32 (m, 5H), 7.34 (t, J = 73.6 Hz, 1H), 7.28-7.22 (m, 1H), 6.34 (t, J = 7.1 Hz, 1H), 5.12-4.99 (m, 3H), 4.20-4.13 (m, 1H), 3.88-3.59 (m, 6H), 3.22 (s, 3H). |
| 308 | 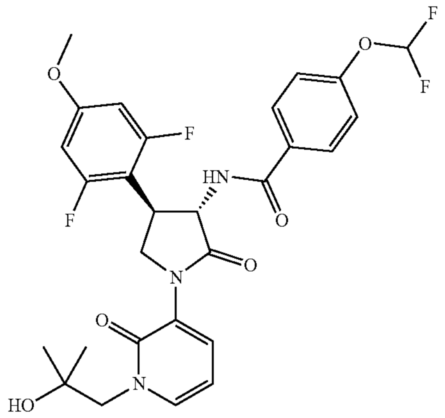 [SMILES: COc1cc(F)c([C@@H]2CN(c3cccn(CC(C)(C)O)c3=O)C(=O)[C@H]2NC(=O)c2ccc(OC(F)F)cc2)c(F)c1] | 578.2 | Method D, RT = 1.575 min, 100% | $^1$H NMR (400 MHz, DMSO-$d_6$) δ = 9.02 (d, J = 8.8 Hz, 1H), 7.95-7.81 (m, 2H), 7.65 (dd, J = 6.8, 2.0 Hz, 1H), 7.60 (dd, J = 7.3, 2.0 Hz, 1H), 7.34 (t, J = 76 Hz, 1H), 7.27-7.25 (m, 2H), 6.77 (d, J = 10.8 Hz, 2H), 6.32 (t, J = 7.1 Hz, 1H), 5.15 (dd, J = 10.9, 8.7 Hz, 1H), 4.79 (br s, 1H), 4.12-4.03 (m, 1H), 4.02-3.88 (m, 4H), 3.76 (s, 3H), 1.09 (d, J = 5.1 Hz, 6H). |
| 309 | 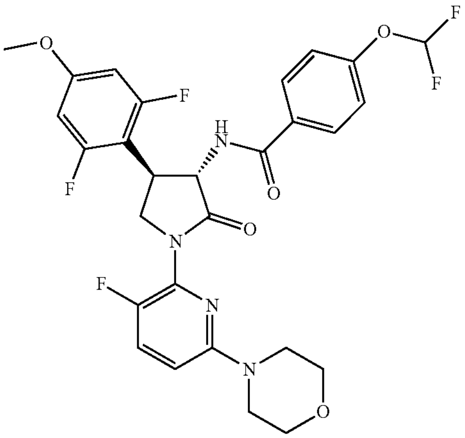 [SMILES: COc1cc(F)c([C@@H]2CN(c3nc(N4CCOCC4)ccc3F)C(=O)[C@H]2NC(=O)c2ccc(OC(F)F)cc2)c(F)c1] | 592.2 | Method D, RT = 1.86 min, 94% | $^1$H NMR (400 MHz, DMSO-$d_6$) δ = 9.08 (d, J = 8.5 Hz, 1H), 7.95-7.84 (m, 2H), 7.73-7.60 (m, 1H), 7.35 (t, J = 73.6 Hz, 1H), 7.32-7.29 (m, 2H), 6.89-6.73 (m, 3H), 5.12 (dd, J = 8.5, 10.5 Hz, 1H), 4.25-4.14 (m, 2H), 4.03-3.95 (m, 1H), 3.77 (s, 3H), 3.74-3.66 (m, 4H), 3.43-3.41 (m, 4H). |

TABLE 2-continued

| Ex | Structure | LCMS (M + H)+ | HPLC Method, RT (min.) & Purity | $^1$H NMR |
|---|---|---|---|---|
| 310 | 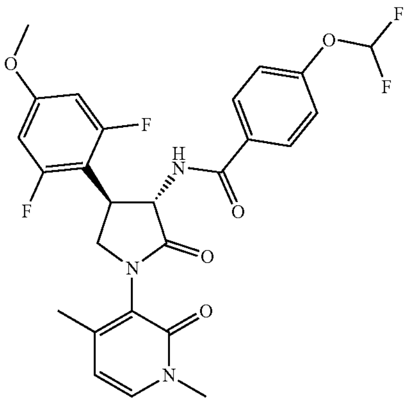 [SMILES: COc1cc(F)c([C@@H]2CN(c3c(C)ccn(C)c3=O)C(=O)[C@H]2NC(=O)c2ccc(OC(F)F)cc2)c(F)c1] | 534.2 | Method D, RT = 1.575 min, 99.1% | $^1$H NMR (400 MHz, DMSO-$d_6$) δ = 9.14-8.90 (m, 1H), 7.98-7.79 (m, 2H), 7.74-7.58 (m, 1H), 7.53-7.16 (m, 3H), 6.85-6.70 (m, 2H), 6.26-6.16 (m, 1H), 5.38-4.83 (m, 1H), 4.31-4.06 (m, 2H), 3.81-3.71 (2s, 3H), 3.53-3.41 (m, 4H), 2.23-1.97 (2s, 3H). (mixture of interconvertible atropisomers) |
| 311 | 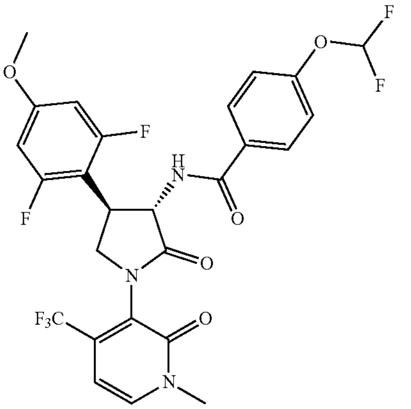 [SMILES: COc1cc(F)c([C@@H]2CN(c3c(C(F)(F)F)ccn(C)c3=O)C(=O)[C@H]2NC(=O)c2ccc(OC(F)F)cc2)c(F)c1] | 588.2 | Method D, RT = 1.792 min, 98.8% | $^1$H NMR (400 MHz, DMSO-$d_6$) δ = 9.19-8.89 (m, 1H), 8.15-8.01 (m, 1H), 7.89 (dd, J = 8.7, 5.0 Hz, 2H), 7.34-7.16 (m, 3H), 6.80-6.68 (m, 2H), 6.57 (dd, J = 7.0, 5.3 Hz, 1H), 5.36-5.10 (m, 1H), 4.26-4.12 (m, 1H), 4.03-3.86 (m, 1H), 3.75 (s, 3H), 3.61-3.40 (m, 4H). (mixture of interconvertible atropisomers). |
| 312 | 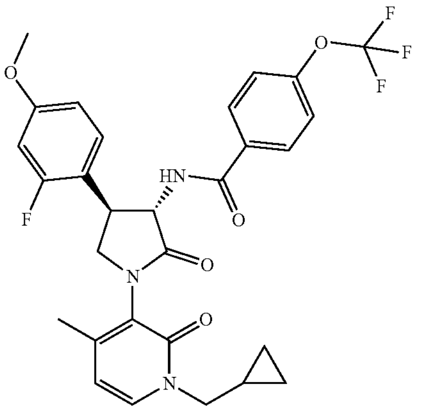 [SMILES: COc1ccc([C@@H]2CN(c3c(C)ccn(CC4CC4)c3=O)C(=O)[C@H]2NC(=O)c2ccc(OC(F)(F)F)cc2)c(F)c1] | 574.3 | Method C, RT = 1.94 min, 98.3% | $^1$H NMR (400 MHz, DMSO-$d_6$) δ = 9.11-9.89 (m, 1H), 8.02-7.89 (m, 2H), 7.72-7.66 (m, 1H), 7.57-7.41 (m, 3H), 6.87-6.74 (m, 2H), 6.22 (d, J =6.8 Hz, 1H), 5.42-4.75 (m, 1H), 4.18-3.95 (m, 1H), 3.86-3.81 (m, 1H), 3.78-3.74 (2s, 3H) 3.76-3.65 (m, 1H), 3.42-3.35 (m, 2H), 2.20-2.10 (2s, 3H), 1.27-1.18 (m, 1H), 0.53-0.44 (m, 2H), 0.42-0.34 (m, 2H) (mixture of interconvertible atropisomers isomers) |

TABLE 2-continued

| Ex | Structure | LCMS (M + H)+ | HPLC Method, RT (min.) & Purity | $^1$H NMR |
|---|---|---|---|---|
| 313 | 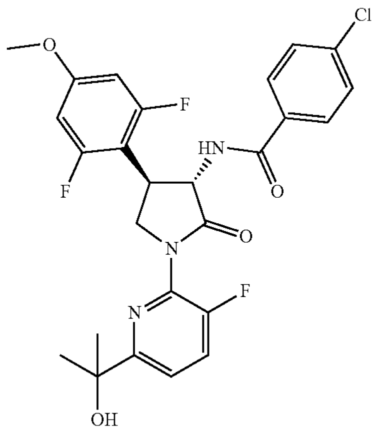 [SMILES: COc1cc(F)c([C@@H]2CN(c3nc(C(C)(C)O)ccc3F)C(=O)[C@H]2NC(=O)c2ccc(Cl)cc2)c(F)c1] | 534.2 | Method D, RT = 1.85 min, 99% | $^1$H NMR (400 MHz, DMSO-$d_6$) δ = 9.17 (d, J = 8.6 Hz, 1H), 7.91-7.75 (m, 3H), 7.65 (dd, J = 8.4, 3.5 Hz, 1H), 7.61-7.49 (m, 2H), 6.80 (d, J = 10.8 Hz, 2H), 5.34 (br s, 1H), 5.16 (dd, J = 10.6, 8.7 Hz, 1H), 4.32-4.15 (m, 2H), 4.11-4.02 (m, 1H), 3.77 (s, 3H), 1.43 (s, 3H), 1.42 (s, 3H). |
| 314 | 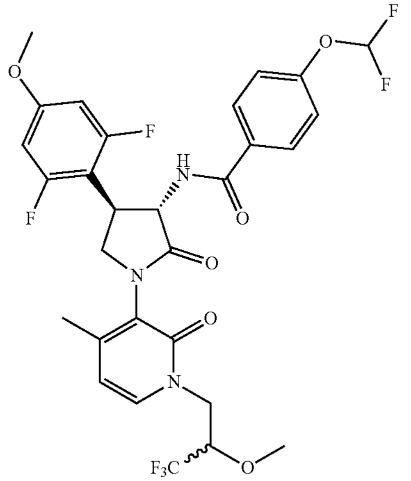 [SMILES: COc1cc(F)c([C@@H]2CN(c3c(C)ccn(CC(OC)C(F)(F)F)c3=O)C(=O)[C@H]2NC(=O)c2ccc(OC(F)F)cc2)c(F)c1] | 646.3 | Method D, RT = 1.943 min, 98.6% | $^1$H NMR (400 MHz, DMSO-$d_6$) δ = 9.19-8.87 (m, 1H), 8.04-7.81 (m, 2H), 7.73-7.57 (m, 1H), 7.36-7.16 (m, 3H), 6.82-6.63 (m, 2H), 6.36-6.16 (m, 1H), 5.42-4.81 (m, 1H), 4.46-3.90 (m, 5H), 3.84-3.72 (2s, 3H), 3.61-3.50 (m, 1H), 3.37-3.34 (2s, 3H), 2.24-2.08 (2s, 3H). (mixtrue of interconvertible atropisomers) |
| 315 | 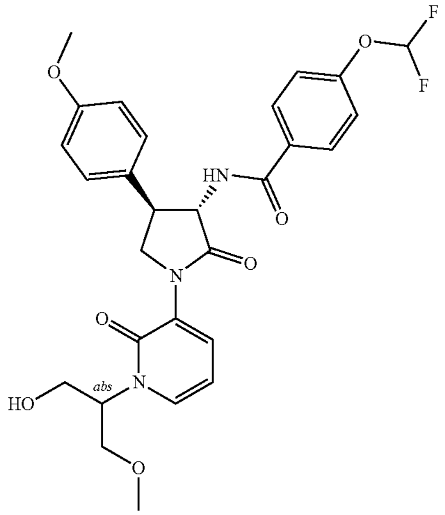 [SMILES: COCC(CO)n1cccc(N2C[C@@H](c3ccc(OC)cc3)[C@H](NC(=O)c3ccc(OC(F)F)cc3)C2=O)c1=O] | 558.3 | Method D, RT = 1.424 min, 100% | $^1$H NMR (400 MHz, DMSO-$d_6$) δ = 8.94-8.88 (m, 1H), 7.92 (d, J = 8.8 Hz, 2H), 7.71-7.64 (m, 1H), 7.56 (d, J = 7.3 Hz, 1H), 7.33 (t, J = 80 Hz, 1H), 7.54-7.13 (m, 4H), 6.90 (d, J = 8.3 Hz, 2H), 6.34 (t, J = 6.8 Hz, 1H), 5.11-4.97 (m, 3H), 4.16-4.08 (m, 2H), 3.80-3.62 (m, 8H), 3.23 (s, 3H). |

TABLE 2-continued

| Ex | Structure | LCMS (M + H)+ | HPLC Method, RT (min.) & Purity | $^1$H NMR |
|---|---|---|---|---|
| 316 | 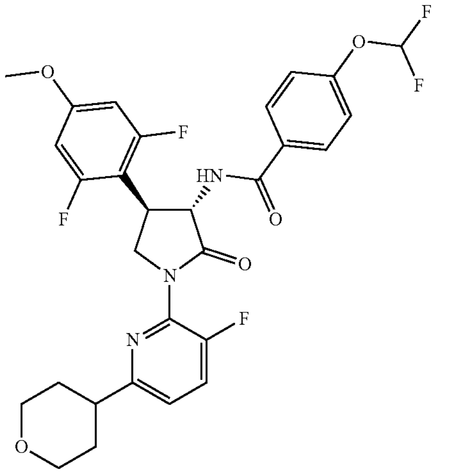 [SMILES: COc1cc(F)c([C@@H]2CN(c3nc(C4CCOCC4)ccc3F)C(=O)[C@H]2NC(=O)c2ccc(OC(F)F)cc2)c(F)c1] | 592.2 | Method D, RT = 1.95 min, 98% | $^1$H NMR (400 MHz, DMSO-$d_6$) δ = 9.10 (br d, J = 8.6 Hz, 1H), 7.90 (d, J = 8.6 Hz, 2H), 7.86-7.72 (m, 1H), 7.35 (t, J = 70 Hz, 1H), 7.37-7.29 (m, 3H), 6.79 (d, J = 10.8 Hz, 2H), 5.14-5.11 (m, 1H), 4.32-4.17 (m, 2H), 4.16-4.03 (m, 1H), 3.99-3.88 (m, 2H), 3.78 (s, 3H), 3.45-3.42 (m, 2H), 3.02-2.91 (m, 1H), 1.86-1.61 (m, 4H) |
| 317 | 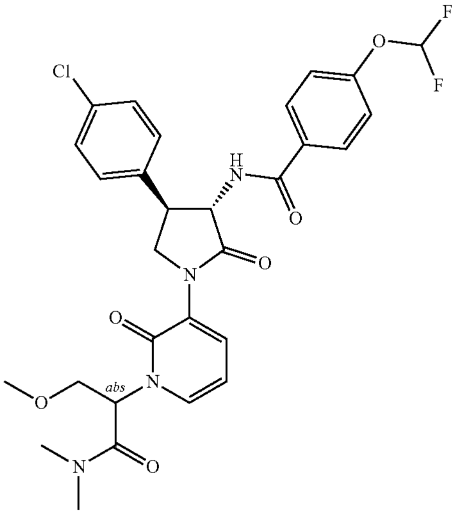 [SMILES: COCC(C(=O)N(C)C)n1cccc(N2C[C@@H](c3ccc(Cl)cc3)[C@H](NC(=O)c3ccc(OC(F)F)cc3)C2=O)c1=O] | 603.2 | Method D, RT = 1.696 min, 96.6% | $^1$H NMR (400 MHz, DMSO-$d_6$) δ = 9.02-8.90 (m, 1H), 7.97-7.86 (m, 2H), 7.70 (dd, J = 7.0, 1.8 Hz, 1H), 7.61 (dd, J = 7.2, 1.8 Hz, 1H), 7.50-7.37 (m, 4H), 7.34 (t, J = 73.6 Hz, 1H), 7.27 (d, J = 8.2 Hz, 2H), 6.41 (t, J = 7.1 Hz, 1H), 6.07 (dd, J = 8.4, 5.0 Hz, 1H), 5.07-4.95 (m, 1H), 4.13-4.08 (m, 1H), 3.91-3.77 (m, 4H), 3.26 (s, 3H), 3.10 (s, 3H), 2.84 (s, 3H). |
| 318 | 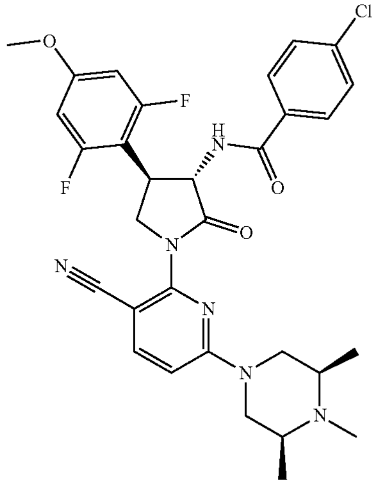 [SMILES: COc1cc(F)c([C@@H]2CN(c3nc(N4C[C@@H](C)N(C)[C@@H](C)C4)ccc3C#N)C(=O)[C@H]2NC(=O)c2ccc(Cl)cc2)c(F)c1] | 609.3 | Method D, RT = 1.95 min, 100% | $^1$H NMR (400 MHz, DMSO-$d_6$) δ = 9.21 (d, J = 8.3 Hz, 1H), 8.08 (d, J = 8.2 Hz, 1H), 7.84 (d, J = 8.8 Hz, 2H), 7.52 (d, J = 8.4 Hz, 2H), 7.06 (d, J = 9.0 Hz, 1H), 6.82 (d, J = 10.8 Hz, 2H), 5.05 (dd, J = 10.9, 8.4 Hz, 1H), 4.67-4.52 (m, 2H), 4.49-4.40 (m, 1H), 4.27-4.16 (m, 1H), 4.05-3.96 (m, 1H), 3.78 (s, 3H), 3.40-3.28 (m, 2H), 3.16-3.02 (m, 2H), 2.85 (s, 3H), 1.37 (d, J = 6.8 Hz, 6H). |

TABLE 2-continued

| Ex | Structure | LCMS (M + H)+ | HPLC Method, RT (min.) & Purity | $^1$H NMR |
|---|---|---|---|---|
| 319 | 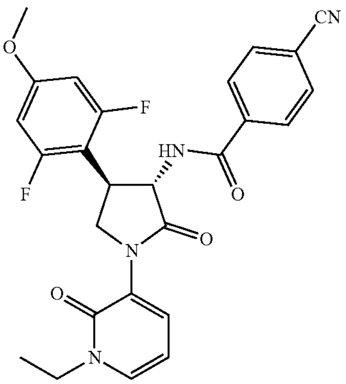 [SMILES: CCn1cccc(N2C[C@@H](c3c(F)cc(OC)cc3F)[C@H](NC(=O)c3ccc(C#N)cc3)C2=O)c1=O] | 493.2 | Method D, RT = 1.458 min, 100% | $^1$H NMR (400 MHz, DMSO-$d_6$) δ = 9.27 (d, J = 8.8 Hz, 1H), 7.98 (d, J = 1.2 Hz, 4H), 7.77 (dd, J = 6.6, 2.0 Hz, 1H), 7.58 (dd, J = 7.1, 2.0 Hz, 1H), 6.78 (d, J = 10.8 Hz, 2H), 6.35 (t, J = 7.0 Hz, 1H), 5.14 (dd, J = 11.0, 8.6 Hz, 1H), 4.17-4.04 (m, 1H), 4.04-3.86 (m, 4H), 3.76 (s, 3H), 1.25 (t, J = 7.2 Hz, 3H). |
| 320 | 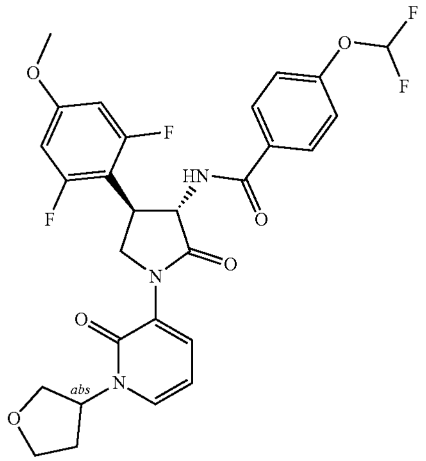 [SMILES: COc1cc(F)c([C@@H]2CN(c3cccn(C4CCOC4)c3=O)C(=O)[C@H]2NC(=O)c2ccc(OC(F)F)cc2)c(F)c1] | 576.2 | Method D, RT = 1.591 min, 98% | $^1$H NMR (400 MHz, DMSO-d6) δ = 7.93-7.84 (m, 2H), 7.64 (dd, J = 1.8, 7.0 Hz, 1H), 7.59 (dd, J = 2.0, 7.1 Hz, 1H), 7.34 (t, J = 76 Hz, 1H), 7.27-7.28 (m, 3H), 6.77 (d, J = 11.0 Hz, 2H), 6.41 (t, J = 7.1 Hz, 1H), 5.44-5.40 (m, 1H), 5.13-5.09 (m, 1H), 4.16-3.91 (m, 4H), 3.87 (d, J = 4.4 Hz, 2H), 3.80-3.72 (m, 4H), 2.47-2.40 (m, 1H), 2.06-1.93 (m, 1H). |
| 321 | 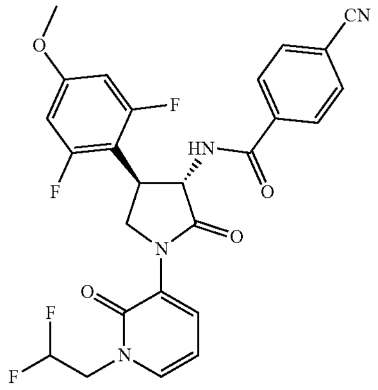 [SMILES: COc1cc(F)c([C@@H]2CN(c3cccn(CC(F)F)c3=O)C(=O)[C@H]2NC(=O)c2ccc(C#N)cc2)c(F)c1] | 529.2 | Method D, RT = 1.542 min, 100% | $^1$H NMR (400 MHz, DMSO-$d_6$) δ = 9.27 (d, J = 8.6 Hz, 1H), 8.05-7.90 (m, 4H), 7.74 (dd, J = 6.8, 2.0 Hz, 1H), 7.67 (dd, J = 7.3, 2.0 Hz, 1H), 6.78 (d, J = 10.8 Hz, 2H), 6.35 (t, J = 56.2 Hz, 1H), 6.43-6.4 (m, 1H), 5.13 (dd, J = 11.0, 8.6 Hz, 1H), 4.56-4.34 (m, 2H), 4.16-4.05 (m, 1H), 4.05-3.90 (m, 2H), 3.77 (s, 3H). |

TABLE 2-continued
| Ex | Structure | LCMS (M + H)+ | HPLC Method, RT (min.) & Purity | $^1$H NMR |
|---|---|---|---|---|
| 322 | 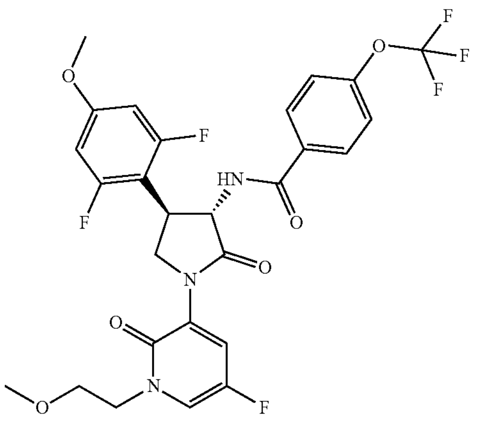 [SMILES: COCCn1cc(F)cc(N2C[C@@H](c3c(F)cc(OC)cc3F)[C@H](NC(=O)c3ccc(OC(F)(F)F)cc3)C2=O)c1=O] | 600.2 | Method D, RT = 1.824 min, 97.6% | $^1$H NMR (400 MHz, DMSO-$d_6$) δ = 9.12 (d, J = 8.8 Hz, 1H), 7.99-7.88 (m, 3H), 7.81 (dd, J = 8.4, 3.3 Hz, 1H), 7.54-7.40 (m, 2H), 6.78 (d, J = 10.8 Hz, 2H), 5.14 (dd, J = 8.6, 10.8 Hz, 1H), 4.20-4.03 (m, 4H), 4.02-3.91 (m, 1H), 3.77 (s, 3H), 3.61 (t, J = 5.4 Hz, 2H), 3.26 (s, 3H). |
| 323 | 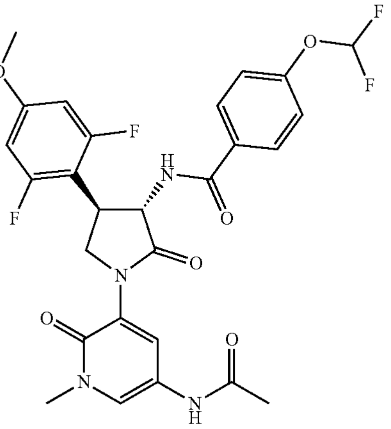 | 577.2 | Method D, RT = 1.382 min, 99.03% | $^1$H NMR (400 MHz, DMSO-$d_6$) δ = 9.83 (s, 1H), 9.01 (d, J = 8.1 Hz, 1H), 8.14 (d, J = 2.7 Hz, 1H), 7.89 (d, J = 8.8 Hz, 2H), 7.66 (d, J = 2.7 Hz, 1H), 7.34 (t, J = 73.6 Hz, 1H), 7.28 (m, 2H), 6.77 (d, J = 10.8 Hz, 2H), 5.07-4.94 (m, 1H), 4.19-3.91 (m, 3H), 3.77 (s, 3H), 3.49 (s, 3H), 2.01 (s, 3H). |
| 324 | 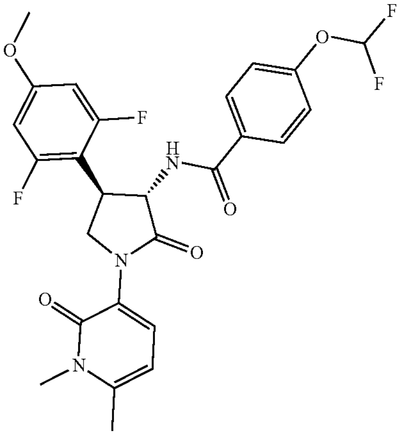 [SMILES: COc1cc(F)c([C@@H]2CN(c3ccc(C)n(C)c3=O)C(=O)[C@H]2NC(=O)c2ccc(OC(F)F)cc2)c(F)c1] | 534.2 | Method D, RT = 1.589 min, 99.7% | $^1$H NMR (400 MHz, DMSO-$d_6$) δ = 9.00 (d, J = 9.0 Hz, 1H), 7.92-7.83 (m, 2H), 7.55-7.14 (m, 3H), 7.34 (t, J = 73.6 Hz, 1H), 6.77 (d, J = 11.0 Hz, 2H), 6.28-6.20 (m, 1H), 5.11 (dd, J = 10.8, 8.6 Hz, 1H), 4.12-4.03 (m, 1H), 3.97-3.92 (m, 2H), 3.76 (s, 3H), 3.49 (s, 3H), 2.40 (s, 3H). |

TABLE 2-continued

| Ex | Structure | LCMS (M + H)+ | HPLC Method, RT (min.) & Purity | $^1$H NMR |
|---|---|---|---|---|
| 325 | 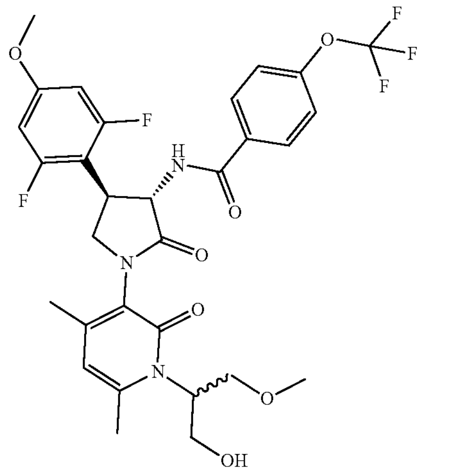 [SMILES: COCC(CO)n1c(C)cc(C)c(N2C[C@@H](c3c(F)cc(OC)cc3F)[C@H](NC(=O)c3ccc(OC(F)(F)F)cc3)C2=O)c1=O] | 626.3 | Method D, RT = 1.762 min, 98.6% | $^1$H NMR (400 MHz, DMSO-$d_6$) δ = 9.27-8.91 (m, 1H), 8.02-7.84 (m, 2H), 7.70-7.54 (m, 1H), 7.54-7.34 (m, 2H), 6.79-3.72 (m, 2H), 6.31-6.13 (m, 1H), 5.38-4.83 (m, 3H), 4.27-4.05 (m, 2H), 3.81-3.55 (m, 7H), 3.55-3.45 (m, 1H), 3.24-3.16 (2s, 3H), 2.23-1.94 (2s, 3H). (mixture of interconvertible atropisomers) |
| 326 | 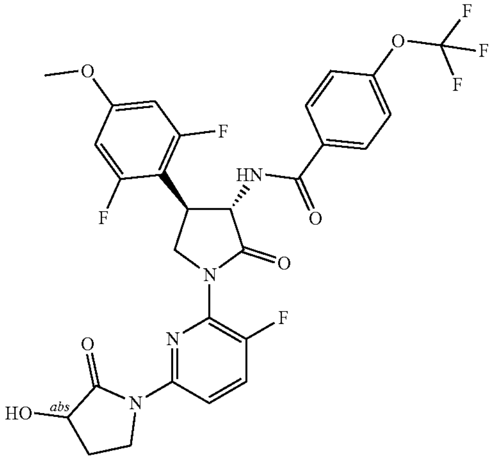 [SMILES: COc1cc(F)c([C@@H]2CN(c3nc(N4CCC(O)C4=O)ccc3F)C(=O)[C@H]2NC(=O)c2ccc(OC(F)(F)F)cc2)c(F)c1] | 625.2 | Method D, RT = 1.85 min, 98% | $^1$H NMR (400 MHz, DMSO-$d_6$) δ = 9.22 (d, J = 8.3 Hz, 1H), 8.29 (dd, J = 9.0, 2.9 Hz, 1H), 8.03-7.88 (m, 3H), 7.55-7.41 (m, 2H), 6.80 (d, J = 10.8 Hz, 2H), 5.86 (d, J = 6.1 Hz, 1H), 5.12 (dd, J = 10.5, 8.3 Hz, 1H), 4.44-4.38 (m, 1H), 4.29-4.16 (m, 2H), 4.13-3.93 (m, 2H), 3.77 (s, 3H), 3.73-3.69 (m, 1H), 2.44-2.33 (m, 1H), 1.88-1.75 (m, 1H). |
| 327 | 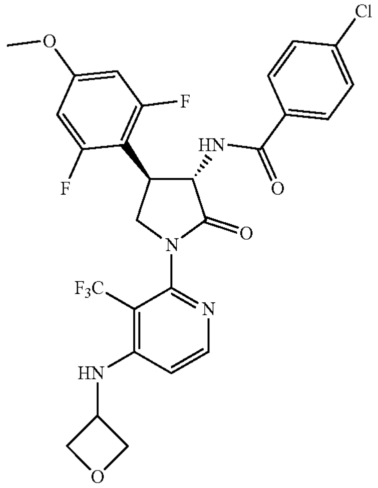 [SMILES: COc1cc(F)c([C@@H]2CN(c3nccc(NC4COC4)c3C(F)(F)F)C(=O)[C@H]2NC(=O)c2ccc(Cl)cc2)c(F)c1] | 597.2 | Method C, RT = 1.73 min, 100% | $^1$H NMR (400 MHz, DMSO-$d_6$) δ = 9.10 (d, J = 8.8 Hz, 1H), 8.26-8.21 (m, 1H), 7.89-7.80 (m, 2H), 7.63-7.55 (m, 2H), 6.98-6.89 (m, 1H), 6.79 (d, J = 10.8 Hz, 2H), 6.51-6.45 (m, 1H), 5.19-5.11 (m, 1H), 4.86-4.81(m, 2H), 4.77-4.69 (m, 1H), 4.65-4.60 (m, 2H), 4.35-4.26 (m, 1H), 4.22-4.15 (m, 1H), 3.76 (s, 3H), 3.75-3.63 (m, 1H). |

TABLE 2-continued

| Ex | Structure | LCMS (M + H)+ | HPLC Method, RT (min.) & Purity | $^1$H NMR |
|---|---|---|---|---|
| 328 | 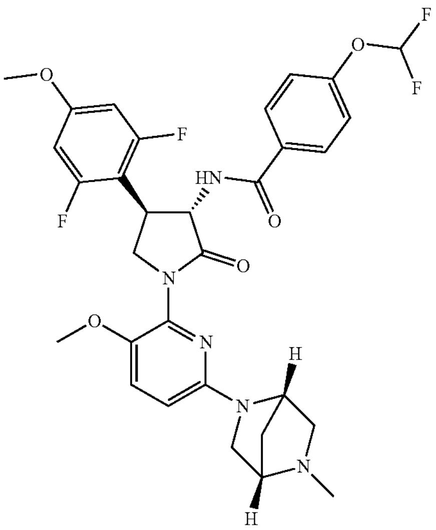 [SMILES: COc1cc(F)c([C@@H]2CN(c3nc(N4C[C@@H]5C[C@H]4CN5C)ccc3OC)C(=O)[C@H]2NC(=O)c2ccc(OC(F)F)cc2)c(F)c1] | 630.3 | Method C, RT = 1.47 min, 97% | $^1$H NMR (400 MHz, DMSO-$d_6$) δ = 9.05 (d, J = 8.8 Hz, 1H), 7.96-7.82 (m, 2H), 7.50-7.48 (m, 1H), 7.35 (t, J = 73.6 Hz, 1H), 7.29-7.27 (m, 2H), 6.84-6.69 (m, 2H), 6.52 (d, J = 9.0 Hz, 1H), 5.22-5.198 (m, 1H), 4.48-4.42 (m, 1H), 4.18-4.08 (m, 1H), 4.04-3.96 (m, 1H), 3.91-3.82 (m, 1H), 3.76 (s, 3H), 3.74 (s, 3H), 3.47-3.40 (br s, 2H), 3.25-3.230 (m, 1H), 2.89-2.74 (m, 1H), 2.47-2.43 (m, 1H), 2.30 (s, 3H), 1.88-1.81 (m, 1H), 1.71-1.68 (m, 1H). |
| 329 | 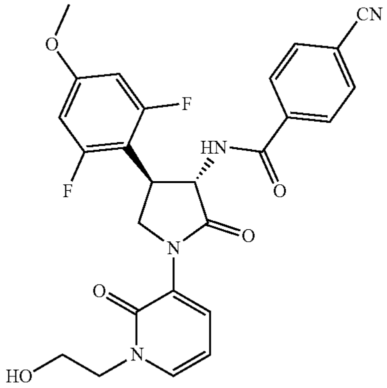 [SMILES: COc1cc(F)c([C@@H]2CN(c3cccn(CCO)c3=O)C(=O)[C@H]2NC(=O)c2ccc(C#N)cc2)c(F)c1] | 509.2 | Method D, RT = 1.268 min, 97.5% | $^1$H NMR (400 MHz, DMSO-$d_6$) δ = 9.28 (br d, J = 8.8 Hz, 1H), 8.07-7.87 (m, 4H), 7.65 (dd, J = 6.8, 2.0 Hz, 1H), 7.59 (dd, J = 7.3, 2.0 Hz, 1H), 6.77 (d, J = 10.8 Hz, 2H), 6.31 (t, J = 7.0 Hz, 1H), 5.16-5.11 (m, 2H), 4.14-3.93 (m, 5H), 3.76 (s, 3H), 3.64 (t, J = 5.5 Hz, 2H). |
| 330 | 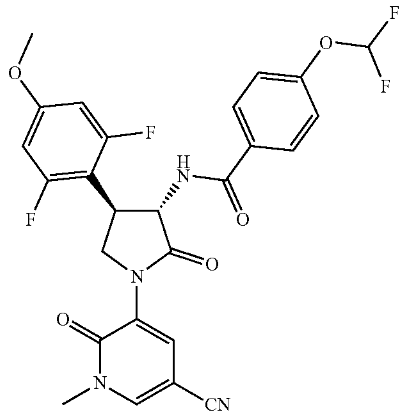 [SMILES: COc1cc(F)c([C@@H]2CN(c3cc(C#N)cn(C)c3=O)C(=O)[C@H]2NC(=O)c2ccc(OC(F)F)cc2)c(F)c1] | 545.2 | Method D, RT = 1.621 min, 100% | $^1$H NMR (400 MHz, DMSO-$d_6$) δ = 9.02 (d, J = 8.3 Hz, 1H), 8.65 (d, J = 2.2 Hz, 1H), 7.98-7.79 (m, 3H), 7.34 (t, J = 73.6 Hz, 1H), 7.28 (m, 2H), 6.77 (d, J = 10.8 Hz, 2H), 5.10 (dd, J = 8.6, 11.0 Hz, 1H), 4.17-4.07 (m, 1H), 4.01 (br t, J = 8.8 Hz, 2H), 3.76 (s, 3H), 3.53 (s, 3H). |

TABLE 2-continued

| Ex | Structure | LCMS (M + H)+ | HPLC Method, RT (min.) & Purity | $^1$H NMR |
|---|---|---|---|---|
| 331 | 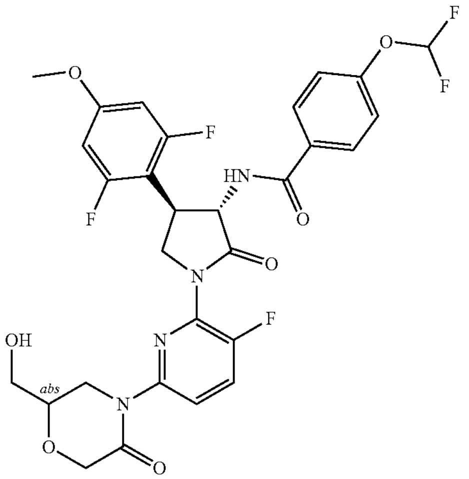 [SMILES: COc1cc(F)c([C@@H]2CN(c3nc(N4CC(CO)OCC4=O)ccc3F)C(=O)[C@H]2NC(=O)c2ccc(OC(F)F)cc2)c(F)c1] | 636.1 | Method D, RT = 1.555 min, 100% | $^1$H NMR (400 MHz, DMSO-$d_6$) δ = 9.12 (d, J = 8.1 Hz, 1H), 8.01-7.93 (m, 2H), 7.89 (d, J = 8.8 Hz, 2H), 7.34 (t, J = 72.6 Hz, 1H), 7.28 (d, J = 8.6 Hz, 2H), 6.83-6.75 (m, 2H), 5.14-5.06 (m, 2H), 4.35-4.19 (m, 4H), 4.13-3.91 (m, 3H), 3.77 (s, 3H), 3.68-3.47 (m, 3H). |
| 332 | 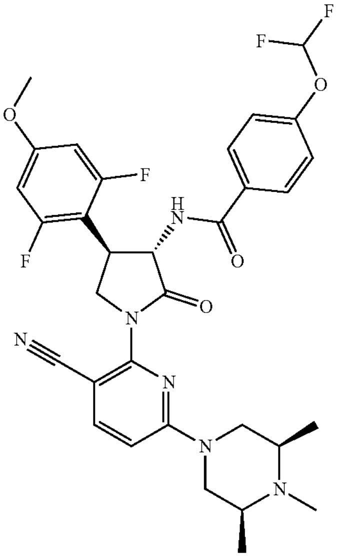 [SMILES: COc1cc(F)c([C@@H]2CN(c3nc(N4C[C@@H](C)N(C)[C@@H](C)C4)ccc3C#N)C(=O)[C@H]2NC(=O)c2ccc(OC(F)F)cc2)c(F)c1] | 641.3 | Method D, RT = 1.94 min, 100% | $^1$H NMR (400 MHz, DMSO-$d_6$) δ = 9.13 (d, J = 9.0 Hz, 1H), 8.07 (d, J = 8.6 Hz, 1H), 7.90-7.87 (d, J = 8.8 Hz, 2H), 7.35 (t, J = 73.6 Hz, 1H), 7.30-7.28 (m, 2H), 7.06-7.04 (m, 1H), 6.81 (d, J = 10.8 Hz, 2H), 5.04 (dd, J = 10.8, 8.3 Hz, 1H), 4.66-4.54 (m, 2H), 4.49-4.43 (m, 1H), 4.24-4.21 (m, 1H), 4.03-4.01 (m, 1H), 3.78 (s, 3H), 3.13-3.02 (m, 2H), 2.91-2.79 (m, 2H), 2.48 (s, 3H) 1.39-1.30 (m, 6H). |
| 333 | 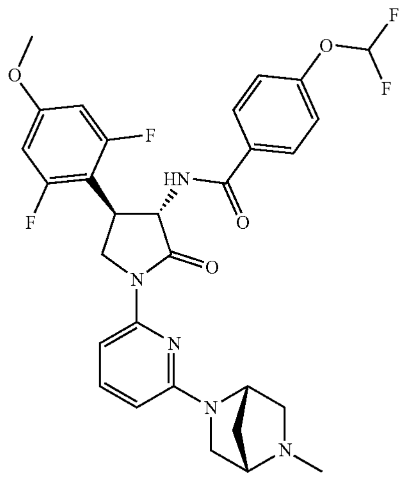 [SMILES: COc1cc(F)c([C@@H]2CN(c3cccc(N4C[C@@H]5C[C@H]4CN5C)n3)C(=O)[C@H]2NC(=O)c2ccc(OC(F)F)cc2)c(F)c1] | 606.2 | Method C, RT = 1.88 min, 90.3% | $^1$H NMR (400 MHz, DMSO-$d_6$) δ = 9.09 (br d, J = 8.1 Hz, 1H), 8.50-8.37 (m, 1H), 7.91-7.72 (m, 2H), 7.56 (d, J = 8.6 Hz, 2H), 7.47 (t, J = 64.2 Hz, 1H), 7.19 (br d, J = 5.6 Hz, 1H), 6.78 (br d, J = 10.8 Hz, 2H), 5.17-5.04 (m, 1H), 4.42-4.10 (m, 2H), 3.88-3.78 (m, 1H), 3.77 (s, 3H), 3.47-3.36 (m, 2H), 3.21-3.09 (m, 2H), 2.47-2.34 (m, 4H), 2.22 (s, 3H). |

TABLE 2-continued

| Ex | Structure | LCMS (M + H)+ | HPLC Method, RT (min.) & Purity | $^1$H NMR |
|---|---|---|---|---|
| 334 | 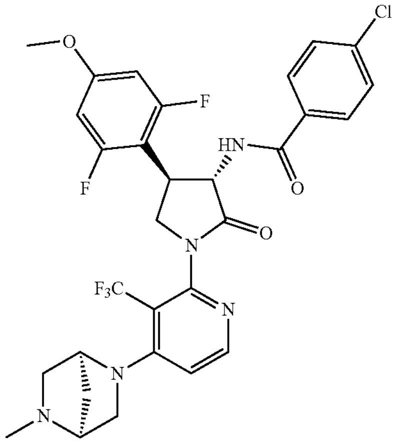 [SMILES: COc1cc(F)c([C@@H]2CN(c3nccc(N4C[C@@H]5C[C@H]4CN5C)c3C(F)(F)F)C(=O)[C@H]2NC(=O)c2ccc(Cl)cc2)c(F)c1] | 636.2 | Method D, RT = 1.72 min, 100% | $^1$H NMR (400 MHz, DMSO-$d_6$) δ = 9.12 (d, J = 8.8 Hz, 1H), 8.18-8.07 (m, 1H), 7.85 (br d, J = 7.6 Hz, 2H), 7.57 (d, J = 8.6 Hz, 2H), 7.02-6.84 (m, 1H), 6.79 (d, J = 10.8 Hz, 2H), 5.15-5.04 (m, 1H), 4.46 (br s, 1H), 4.39-4.26 (m, 1H), 4.21-4.06 (m, 1H), 3.88-3.75 (m, 1H), 3.71 (s, 3H), 3.62-3.53 (m, 1H), 3.26-3.21 (m, 2H), 3.49-3.41 (m, 1H), 2.81-2.73 (m, 1H), 2.25 (s, 3H), 1.98-1.87 (m, 1H), 1.83-1.66 (m, 1H). |
| 335 | 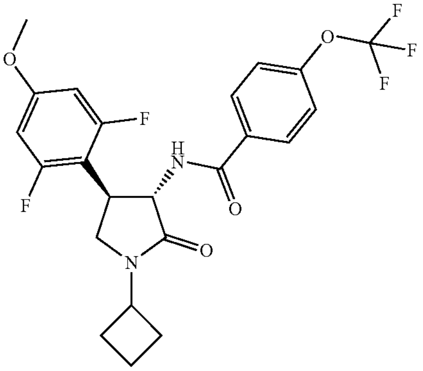 [SMILES: COc1cc(F)c([C@@H]2CN(C3CCC3)C(=O)[C@H]2NC(=O)c2ccc(OC(F)(F)F)cc2)c(F)c1] | 485.2 | Method D, RT = 2.003 min, 100% | $^1$H NMR (400 MHz, DMSO-$d_6$) δ = 9.01 (d, J = 8.8 Hz, 1H), 8.00-7.89 (m, 2H), 7.48 (d, J = 8.3 Hz, 2H), 6.76 (d, J = 10.8 Hz, 2H), 4.92 (dd, J = 10.4, 8.7 Hz, 1H), 3.93-3.89 (m, 1H), 3.76 (s,3H), 3.75-3.68 (m, 1H), 3.66-3.54 (m, 1H), 3.29-3.24 (m, 1H), 3.06 (dd, J = 13.9, 7.1 Hz, 1H), 1.01-0.89 (m, 1H), 0.50 (d, J = 8.1 Hz, 2H), 0.29-0.11 (m, 2H). |
| 336 | 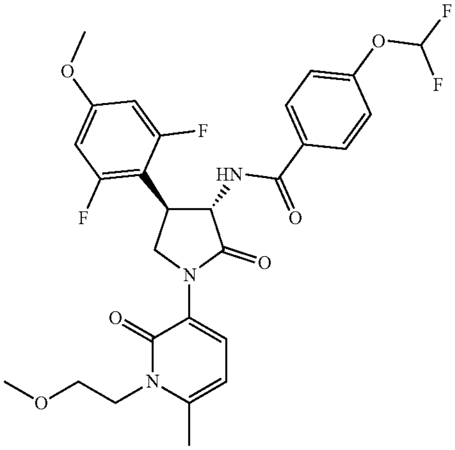 [SMILES: COCCn1c(C)ccc(N2C[C@@H](c3c(F)cc(OC)cc3F)[C@H](NC(=O)c3ccc(OC(F)F)cc3)C2=O)c1=O] | 578.2 | Method D, RT = 1.709 min, 100% | $^1$H NMR (400 MHz, DMSO-$d_6$) δ = 9.01 (d, J = 8.6 Hz, 1H), 7.94-7.81 (m, 2H), 7.34 (t, J = 76 Hz, 1H), 7.48-7.25 (m, 3H), 6.77 (d, J = 10.5 Hz, 2H), 6.26-6.17 (m, 1H), 5.12 (dd, J = 11.1, 8.7 Hz, 1H), 4.17 (t, J = 5.5 Hz, 2H), 4.13-4.01 (m, 1H), 3.94 (br d, J = 9.8 Hz, 2H), 3.76 (s, 3H), 3.59 (t, J = 5.6 Hz, 2H), 3.24 (s, 3H), 2.44 (s, 3H). |

TABLE 2-continued
| Ex | Structure | LCMS (M + H)+ | HPLC Method, RT (min.) & Purity | $^1$H NMR |
|---|---|---|---|---|
| 337 | 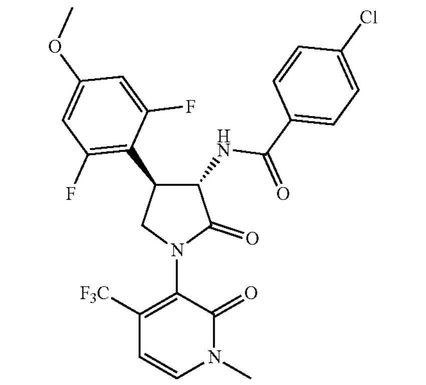 [SMILES: COc1cc(F)c([C@@H]2CN(c3c(C(F)(F)F)ccn(C)c3=O)C(=O)[C@H]2NC(=O)c2ccc(Cl)cc2)c(F)c1] | 556.2 | Method D, RT = 1.832 min, 100% | $^1$H NMR (400 MHz, DMSO-$d_6$) δ = 9.22-8.90 (m, 1H), 8.13-7.98 (m, 1H), 7.91-7.72 (m, 2H), 7.61-7.45 (m, 2H), 6.77 (dd, J = 2.1, 10.6 Hz, 2H), 6.62-6.48 (m, 1H), 5.33-5.12 (m, 1H), 4.27-4.07 (m, 1H), 4.03-3.89 (m, 2H), 3.75 (s, 3H), 3.59-3.54 (2s, 3H). (mixture of interconvertible atropisomers) |
| 338 | 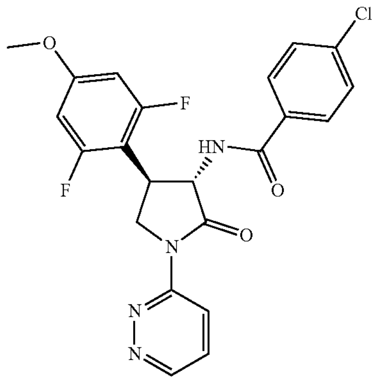 [SMILES: COc1cc(F)c([C@@H]2CN(c3cccnn3)C(=O)[C@H]2NC(=O)c2ccc(Cl)cc2)c(F)c1] | 459.1 | Method D, RT = 1.65 min, 96% | $^1$H NMR (400 MHz, DMSO-$d_6$) δ = 9.19 (d, J = 8.1 Hz, 1H), 9.08 (dd, J = 4.6, 1.5 Hz, 1H), 8.59 (dd, J = 9.0, 1.5 Hz, 1H), 7.91-7.74 (m, 3H), 7.64-7.51 (m, 2H), 6.81 (d, J = 10.8 Hz, 2H), 5.07 (dd, J = 10.8, 8.2 Hz, 1H), 4.59 (t, J = 9.0 Hz, 1H), 4.27-4.05 (m, 2H), 3.78 (s, 3H). |
| 339 | 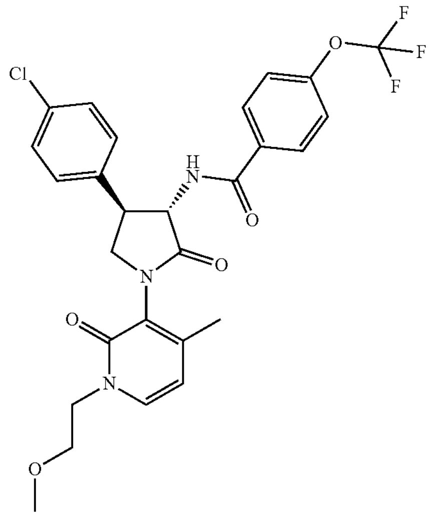 [SMILES: COCCn1ccc(C)c(N2C[C@@H](c3ccc(Cl)cc3)[C@H](NC(=O)c3ccc(OC(F)(F)F)cc3)C2=O)c1=O] | 564.2 | Method D, RT = 1.961 min, 98.7% | $^1$H NMR (400 MHz, DMSO-$d_6$) δ = 9.21-8.98 (m, 1H), 8.05-7.89 (m, 2H), 7.56 (dd, J = 7.0, 4.3 Hz, 1H), 7.54-7.42 (m, 5H), 7.42-7.32 (m, 1H), 6.23-6.19 (m, 1H), 5.31-5.28 (m, 1H), 4.17-3.85 (m, 5H), 3.73-3.52 (m, 2H), 3.24 (s, 3H), 2.22-2.09 (2s, 3H). |

TABLE 2-continued

| Ex | Structure | LCMS (M + H)+ | HPLC Method, RT (min.) & Purity | $^{1}$H NMR |
|---|---|---|---|---|
| 340 | 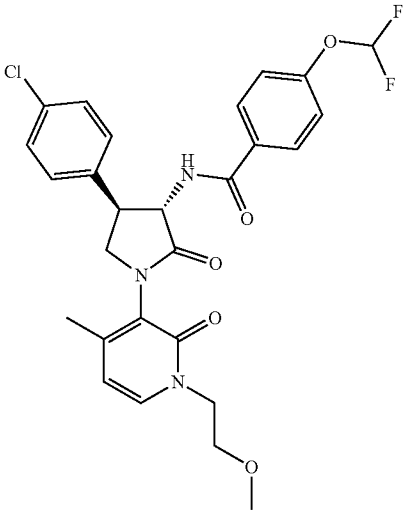 [SMILES: COCCn1ccc(C)c(N2C[C@@H](c3ccc(Cl)cc3)[C@H](NC(=O)c3ccc(OC(F)F)cc3)C2=O)c1=O] | 546.2 | Method D, RT = 1.776 min, 100% | $^{1}$H NMR (400 MHz, DMSO-$d_6$) δ = 9.03-8.88 (m, 1H), 7.95-7.90 (m, 2H), 7.60-7.48 (m, 2H), 7.45-7.16 (m, 5H), 6.24-6.14 (m, 1H), 5.27-4.67 (m, 1H), 4.06 (br s, 3H), 3.96-3.89 (m, 2H), 3.72-3.70 (m, 2H), 3.24 (s, 3H), 2.22-2.09 (2s, 3H). (mixture of interconvertible atropisomers) |
| 341 | 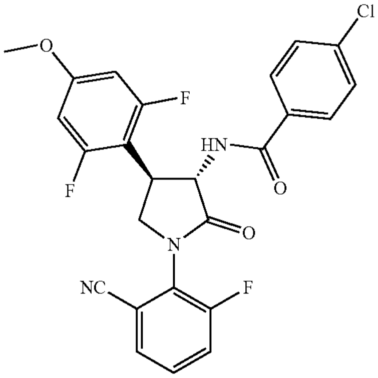 [SMILES: COc1cc(F)c([C@@H]2CN(c3c(F)cccc3C#N)C(=O)[C@H]2NC(=O)c2ccc(Cl)cc2)c(F)c1] | 500.1 | Method D, RT = 1.91 min, 100% | $^{1}$H NMR (400 MHz, DMSO-$d_6$) δ = 9.27-9.17 (m, 1H), 7.93-7.78 (m, 4H), 7.73-7.63 (m, 1H), 7.62-7.53 (m, 2H), 6.81 (d, J = 10.8 Hz, 2H), 5.26-5.06 (m, 1H), 4.34-4.24 (m, 1H), 4.13-4.04 (m, 1H), 4.00-3.90 (m, 1H), 3.78 (s, 3H). |
| 342 | 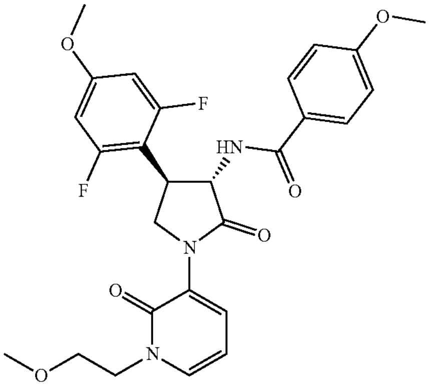 | 528.2 | Method D, RT = 1.468 min, 100% | $^{1}$H NMR (400 MHz, DMSO-$d_6$) δ = 8.82 (d, J = 8.8 Hz, 1H), 7.88-7.75 (m, 2H), 7.66 (dd, J = 6.8, 2.0 Hz, 1H), 7.59 (dd, J = 7.3, 2.0 Hz, 1H), 7.08-6.93 (m, 2H), 6.77 (d, J = 10.8 Hz, 2H), 6.32 (t, J = 7.0 Hz, 1H), 5.11 (dd, J = 11.0, 8.8 Hz, 1H), 4.22-4.01 (m, 3H), 4.01-3.88 (m, 2H), 3.81 (s, 3H), 3.76 (s, 3H), 3.60 (t, J = 5.3 Hz, 2H), 3.25 (s, 3H). |

TABLE 2-continued

| Ex | Structure | LCMS (M + H)+ | HPLC Method, RT (min.) & Purity | $^1$H NMR |
|---|---|---|---|---|
| 343 | 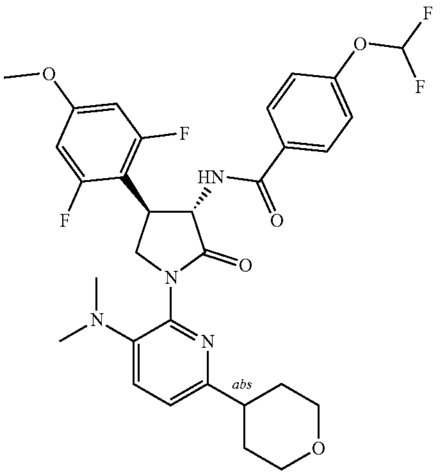 [SMILES: COc1cc(F)c([C@@H]2CN(c3nc(C4CCOCC4)ccc3N(C)C)C(=O)[C@H]2NC(=O)c2ccc(OC(F)F)cc2)c(F)c1] | 617.2 | Method D, RT = 1.65 min, 96% | $^1$H NMR (400 MHz, DMSO-d$_6$) δ = 9.05 (d, J = 8.6 Hz, 1H), 7.89 (d, J = 8.8 Hz, 2H), 7.45-7.43 (m, 1H), 7.44 (d, J = 8.2 Hz, 1H), 7.35 (t, J = 73.6 Hz, 1H), 7.28-7.16 (m, 2H), 6.78 (d, J = 10.8 Hz, 2H), 5.19 (dd, J = 11.4, 8.9 Hz, 1H), 4.28-4.15 (m, 1H), 4.13-4.03 (m, 1H), 4.01-3.90 (m, 3H), 3.76 (s, 3H), 3.43-3.39 (m, 2H), 2.85-2.84 (m, 1H), 2.75 (s, 6H), 1.80-1.63 (m, 4H). |
| 344 | 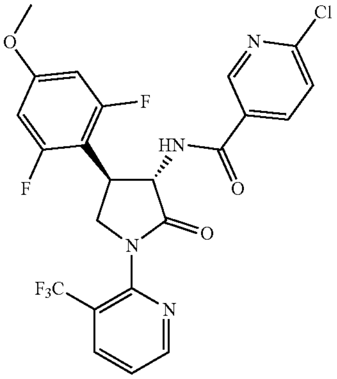 [SMILES: COc1cc(F)c([C@@H]2CN(c3ncccc3C(F)(F)F)C(=O)[C@H]2NC(=O)c2ccc(Cl)nc2)c(F)c1] | 527.1 | Method C, RT = 1.67 min, 94.1% | $^1$H NMR (400 MHz, DMSO-d$_6$) δ = 9.36 (d, J = 8.6 Hz, 1H), 8.90 (dd, J = 4.8, 1.3 Hz, 1H), 8.84-8.78 (m, 1H), 8.40 (dd, J = 7.9, 1.3 Hz, 1H), 8.22 (dd, J = 8.3, 2.4 Hz, 1H), 7.80-7.61 (m, 2H), 6.90-6.71 (m, 2H), 5.15 (dd, J = 11.0, 8.6 Hz, 1H), 4.29-4.21 (m, 1H), 4.17-4.14 (m, 1H), 4.01-3.99 (m, 1H), 3.78 (s, 3H). |
| 345 | 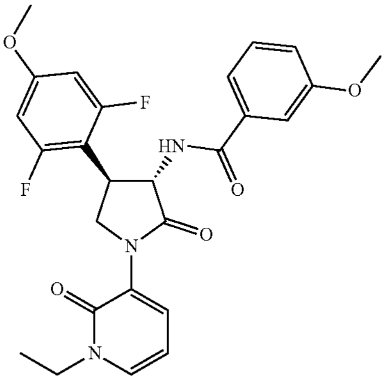 [SMILES: CCn1cccc(N2C[C@@H](c3c(F)cc(OC)cc3F)[C@H](NC(=O)c3cccc(OC)c3)C2=O)c1=O] | 498.2 | Method D, RT = 1.502 min, 100% | $^1$H NMR (400 MHz, DMSO-d$_6$) δ = 8.96 (d, J = 8.6 Hz, 1H), 7.76 (dd, J = 6.8, 1.5 Hz, 1H), 7.58 (dd, J = 7.3, 1.5 Hz, 1H), 7.48-7.30 (m, 3H), 7.19-7.03 (m, 1H), 6.77 (d, J = 10.8 Hz, 2H), 6.35 (t, J = 7.0 Hz, 1H), 5.12 (dd, J = 10.8, 9.0 Hz, 1H), 4.19-4.04 (m, 1H), 4.04-3.89 (m, 4H), 3.79 (s, 3H), 3.77 (s, 3H), 1.25 (t, J = 7.1 Hz, 3H). |

TABLE 2-continued

| Ex | Structure | LCMS (M + H)+ | HPLC Method, RT (min.) & Purity | $^1$H NMR |
|---|---|---|---|---|
| 346 | 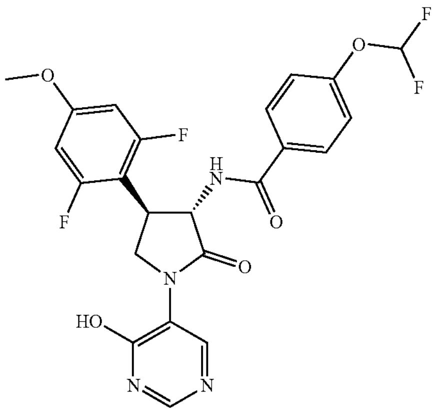 [SMILES: COc1cc(F)c([C@@H]2CN(c3cncnc3O)C(=O)[C@H]2NC(=O)c2ccc(OC(F)F)cc2)c(F)c1] | 507.1 | Method D, RT = 1.41 min, 95% | $^1$H NMR (400 MHz, DMSO-$d_6$) δ = 13.11-12.82 (m, 1H), 9.08-8.96 (m, 1H), 8.30-8.01 (m, 2H), 7.97-7.81 (m, 2H), 7.35 (t, J = 70 Hz, 1H), 7.31-7.26 (m, 2H), 6.78 (d, J = 11.0 Hz, 2H), 5.15-5.11 (m, 1H), 4.15-3.89 (m, 3H), 3.77 (s, 3H). |
| 347 | 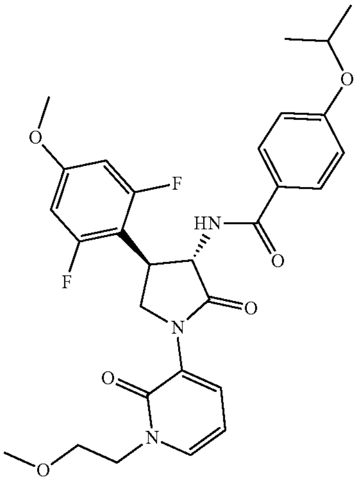 [SMILES: COCCn1cccc(N2C[C@@H](c3c(F)cc(OC)cc3F)[C@H](NC(=O)c3ccc(OC(C)C)cc3)C2=O)c1=O] | 556.3 | Method D, RT = 1.639 min, 98% | $^1$H NMR (400 MHz, DMSO-$d_6$) δ = 8.79 (d, J = 8.6 Hz, 1H), 7.84-7.72 (m, 2H), 7.65 (dd, J = 6.8, 2.0 Hz, 1H), 7.58 (dd, J = 7.3, 2.0 Hz, 1H), 7.04-6.90 (m, 2H), 6.76 (d, J = 10.5 Hz, 2H), 6.32 (t, J = 7.0 Hz, 1H), 5.10 (dd, J = 11.0, 8.6 Hz, 1H), 4.70 (m, 1H), 4.21-4.03 (m, 3H), 4.02-3.89 (m, 2H), 3.76 (s, 3H), 3.60 (t, J = 5.3 Hz, 2H), 3.25 (s, 3H), 1.27 (d, J = 5.9 Hz, 6H). |
| 348 | 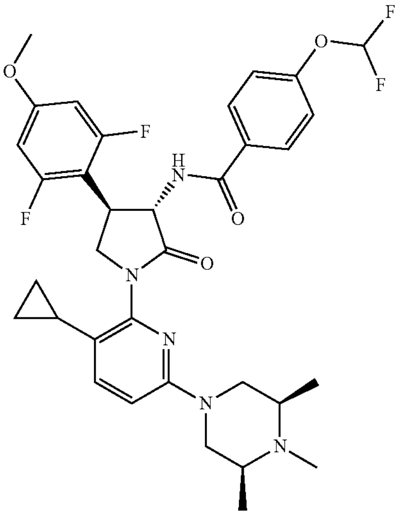 [SMILES: COc1cc(F)c([C@@H]2CN(c3nc(N4C[C@@H](C)N(C)[C@@H](C)C4)ccc3C3CC3)C(=O)[C@H]2NC(=O)c2ccc(OC(F)F)cc2)c(F)c1] | 656.3 | Method C, RT = 1.66 min, 95.3% | $^1$H NMR (400 MHz, DMSO-$d_6$) δ = 9.04 (d, J = 8.4 Hz, 1H), 7.89-7.87 (m, 2H), 7.42 (d, J = 8.4 Hz, 1H), 7.35 (t, J = 73.6 Hz, 1H), 7.28 (d, J = 8.2 Hz, 2H), 6.95-6.92 (m, 1H), 6.80 (d, J = 10.8 Hz, 2H), 5.11 (dd, J = 10.8, 8.6 Hz, 1H), 4.46-4.35 (m, 3H), 4.26-4.05 (m, 2H), 4.01-3.92 (m, 1H), 3.77 (s, 3H), 3.08-2.71 (m, 6H), 1.97-1.87 (m, 1H), 1.36 (d, J = 6.8 Hz, 6 H), 0.96-0.76 (m, 2H), 0.62-0.43 (m, 2H). |

TABLE 2-continued

| Ex | Structure | LCMS (M + H)+ | HPLC Method, RT (min.) & Purity | $^1$H NMR |
|---|---|---|---|---|
| 349 | 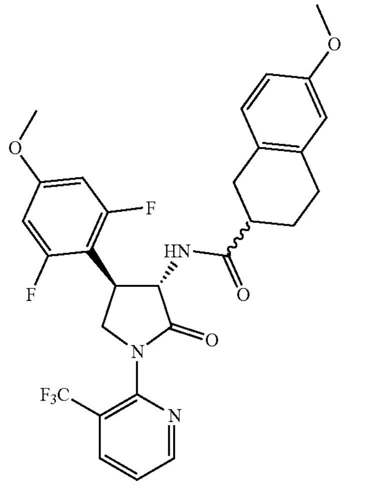 [SMILES: COc1cc(F)c([C@@H]2CN(c3ncccc3C(F)(F)F)C(=O)[C@H]2NC(=O)C2CCc3cc(OC)ccc3C2)c(F)c1] | 576.3 | Method D, RT = 1.95 min, 100% | $^1$H NMR (400 MHz, DMSO-d$_6$) δ = 8.89-8.82 (m, 1H), 8.50 (t, J = 7.9 Hz, 1H), 8.38 (d, J = 8.1 Hz, 1H), 7.73-7.70 (m, 1H), 6.94-6.84 (m, 1H), 6.84-6.80 (m, 2H), 6.67-6.59 (m, 2H), 4.98-4.81 (m, 1H), 4.18-4.02 (m, 2H), 4.01-3.89 (m, 1H), 3.78 (s, 3H), 3.69 (s, 3H), 2.78-2.56 (m, 4H), 2.51-2.54 (m, 1H), 1.93-1.77 (m, 1H), 1.66-1.48 (m, 1H). |
| 350 | 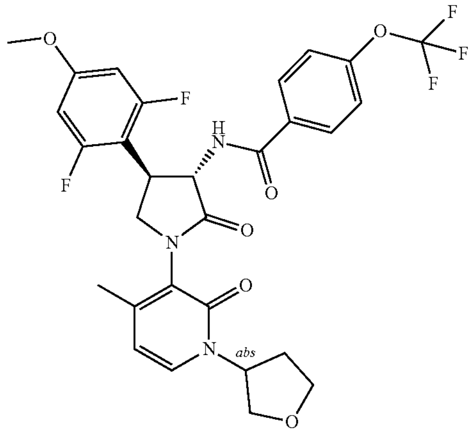 [SMILES: COc1cc(F)c([C@@H]2CN(c3c(C)ccn(C4CCOC4)c3=O)C(=O)[C@H]2NC(=O)c2ccc(OC(F)(F)F)cc2)c(F)c1] | 608.3 | Method F, RT = 1.84 min, 98% | $^1$H NMR (400 MHz, DMSO-d$_6$) δ = 9.23-9.01 (m, 1H), 8.01-7.85 (m, 2H), 7.60-7.51 (m, 1H), 7.51-7.38 (m, 2H), 6.79-6.75 (m, 2H), 6.36-6.21 (m, 1H), 5.43-4.87 (m, 2H), 4.31-4.00 (m, 3H), 3.90-3.81 (m, 2H), 3.81-3.69 (m, 4H), 3.54-3.48 (m, 1H), 2.47-2.39 (m, 1H), 2.22-2.04 (2s, 3H), 2.00-1.86 (m, 1H). (mixture of interconvertible atropisomers) |
| 351 | 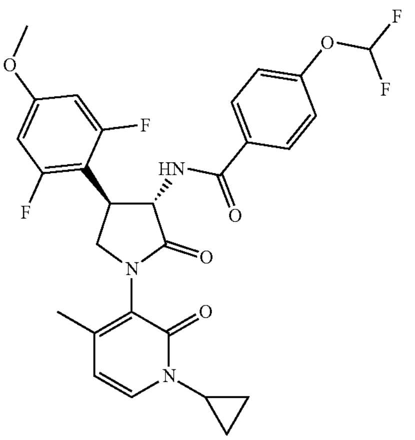 [SMILES: COc1cc(F)c([C@@H]2CN(c3c(C)ccn(C4CC4)c3=O)C(=O)[C@H]2NC(=O)c2ccc(OC(F)F)cc2)c(F)c1] | 560.2 | Method D, RT = 1.7 min, 100% | $^1$H NMR (400 MHz, DMSO-d$_6$) δ = 9.17-8.82 (m, 1H), 8.01-7.81 (m, 2H), 7.59-7.09 (m, 4H), 6.86-6.77 (m, 2H), 6.26-6.07 (m, 1H), 5.38-4.82 (m, 2H), 4.32-4.05 (m, 2H), 3.79-3.74 (2s, 3H), 3.51-3.46 (m, 1H), 2.22-2.00 (2s, 3H), 1.07-0.92 (m, 2H), 0.92-0.72 (m, 2H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 352 | 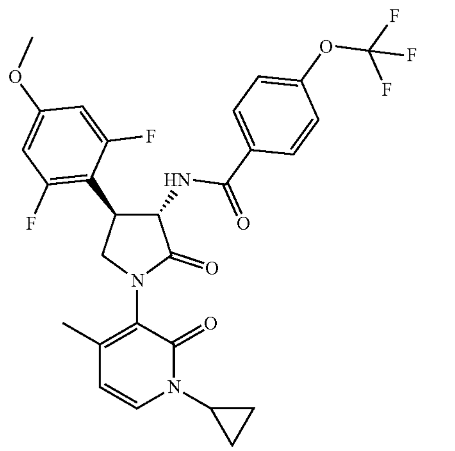 [SMILES: COc1cc(F)c([C@@H]2CN(c3c(C)ccn(C4CC4)c3=O)C(=O)[C@H]2NC(=O)c2ccc(OC(F)(F)F)cc2)c(F)c1] | 578.2 | Method D, RT = 1.87 min, 100% | $^1$H NMR (400 MHz, DMSO-$d_6$) δ = 9.26-8.88 (m, 1H), 8.03-7.83 (m, 2H), 7.58-7.35 (m, 3H), 6.81-6.73 (m, 2H), 6.25-6.08 (m, 1H), 5.35-4.85 (m, 2H), 4.27-4.05 (m, 2H), 3.78-3.74 (2s, 3H), 3.54-3.47 (m, 1H), 2.22-1.99 (2s, 3H), 1.06-0.92 (m, 2H), 0.92-0.70 (m, 2H). (mixture of interconvertible atropisomers) |
| 353 | 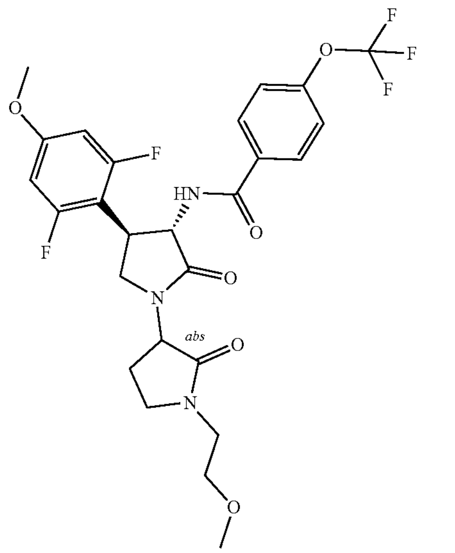 [SMILES: COCCN1CCC(N2C[C@@H](c3c(F)cc(OC)cc3F)[C@H](NC(=O)c3ccc(OC(F)(F)F)cc3)C2=O)C1=O] | 572.2 | Method D, RT = 1.732 min, 100% | $^1$H NMR (400 MHz, DMSO-$d_6$) δ = 9.03 (d, J = 8.3 Hz, 1H), 7.92 (d, J = 8.6 Hz, 2H), 7.47 (d, J = 8.6 Hz, 2H), 6.75 (d, J = 10.8 Hz, 2H), 4.96 (dd, J = 10.8, 8.8 Hz, 1H), 4.84 (t, J = 9.3 Hz, 1H), 3.97-3.89 (m, 1H), 3.75 (s, 3H), 3.67-3.61 (m, 1H), 3.46-3.39 (m, 7H), 3.22 (s, 3H), 2.28-2.19 (m, 1H), 2.13-2.04 (m, 1H). |
| 354 | 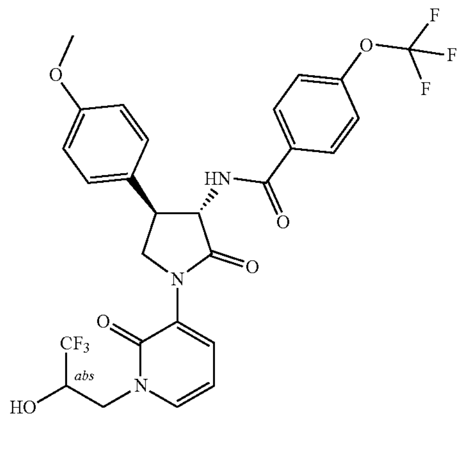 [SMILES: COc1ccc([C@@H]2CN(c3cccn(CC(O)C(F)(F)F)c3=O)C(=O)[C@H]2NC(=O)c2ccc(OC(F)(F)F)cc2)cc1] | 600.2 | Method D, RT = 1.813 min, 100% | $^1$H NMR (400 MHz, DMSO-$d_6$) δ = 9.03 (d, J = 8.6 Hz, 1H), 8.03-7.90 (m, 2H), 7.66 (m, 2H), 7.47 (d, J = 8.3 Hz, 2H), 7.35 (d, J = 8.6 Hz, 2H), 6.91 (d, J = 8.6 Hz, 2H), 6.37 (t, J = 7.0 Hz, 1H), 5.05-4.94 (m, 1H), 4.44 (dd, J = 13.2, 2.7 Hz, 1H), 4.38-4.29 (m, 1H), 4.14-4.04 (m, 1H), 3.92-3.74 (m, 3H), 3.72 (s, 3H), 3.34-3.30 (m, 1H). |

TABLE 2-continued

| Ex | Structure | LCMS (M + H)+ | HPLC Method, RT (min.) & Purity | $^1$H NMR |
|---|---|---|---|---|
| 355 | 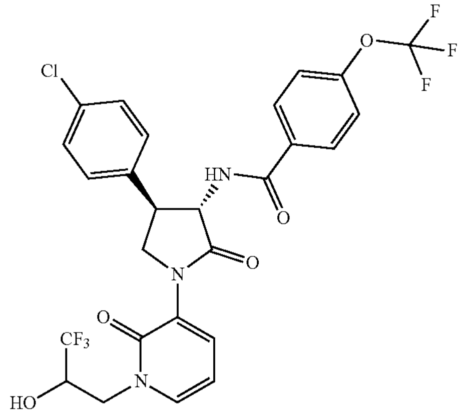 [SMILES: O=C(N[C@@H]1C(=O)N(c2cccn(CC(O)C(F)(F)F)c2=O)C[C@H]1c1ccc(Cl)cc1)c1ccc(OC(F)(F)F)cc1] | 604.2 | Method D, RT = 2.015 min, 100% | $^1$H NMR (400 MHz, DMSO-$d_6$) δ = 9.07 (br d, J = 8.6 Hz, 1H), 8.04-7.90 (m, 2H), 7.73-7.57 (m, 2H), 7.51-4.45 (m, 4H), 7.44-7.32 (m, 2H), 6.81-6.73 (brs, 1H), 6.41-6.31 (m, 1H), 5.08-5.01 (m, 1H), 4.48-4.42 (m, 1H), 4.37-4.30 (m, 1H), 4.14-4.04 (m, 1H), 3.90-3.79 (m, 3H). |
| 356 | 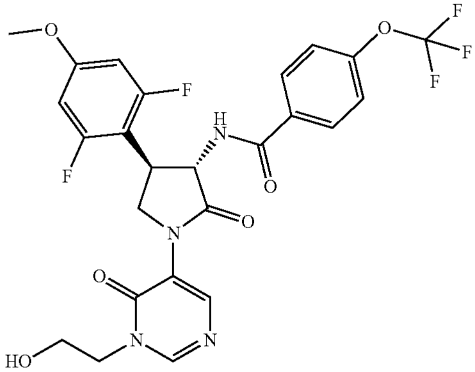 [SMILES: COc1cc(F)c([C@@H]2CN(c3cncn(CCO)c3=O)C(=O)[C@H]2NC(=O)c2ccc(OC(F)(F)F)cc2)c(F)c1] | 569.2 | Method D, RT = 1.69 min, 100% | $^1$H NMR (400 MHz, DMSO-$d_6$) δ = 9.14 (br d, J = 8.1 Hz, 1H), 8.00 (d, J = 4.6 Hz, 1H), 7.94 (d, J = 9.0 Hz, 2H), 7.69 (d, J = 4.6 Hz, 1H), 7.49 (d, J = 8.3 Hz, 2H), 6.78 (d, J = 10.8 Hz, 2H), 5.07-5.05 (m, 1H), 4.84 (t, J = 5.9 Hz, 1H), 4.36-4.27 (m, 1H), 4.22-4.01 (m, 4H), 3.77 (s, 3H), 3.73 (ABq, J = 5.9 Hz, 2H). |
| 357 | 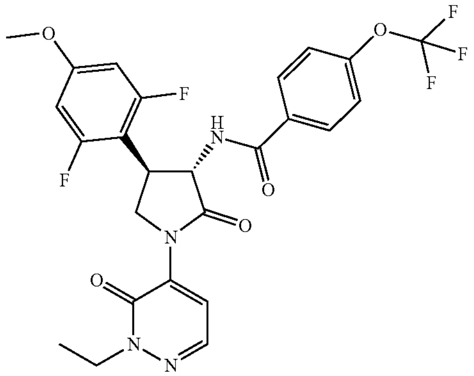 [SMILES: CCn1nccc(N2C[C@@H](c3c(F)cc(OC)cc3F)[C@H](NC(=O)c3ccc(OC(F)(F)F)cc3)C2=O)c1=O] | 553.2 | Method D, RT = 1.95 min, 100% | $^1$H NMR (400 MHz, DMSO-$d_6$) δ = 9.13 (d, J = 8.1 Hz, 1H), 8.01 (d, J = 4.6 Hz, 1H), 7.99-7.82 (m, 2H), 7.70 (d, J = 4.4 Hz, 1H), 7.49 (d, J = 8.1 Hz, 2H), 6.78 (d, J = 10.8 Hz, 2H), 5.01-5.05 (m, 1H), 4.42-4.27 (m, 1H), 4.25-4.05 (m, 4H), 3.77 (s, 3H), 1.28 (t, J = 7.2 Hz, 3H). |
| 358 | 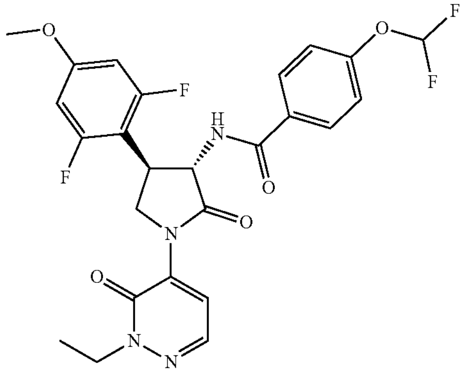 [SMILES: CCn1nccc(N2C[C@@H](c3c(F)cc(OC)cc3F)[C@H](NC(=O)c3ccc(OC(F)F)cc3)C2=O)c1=O] | 535.3 | Method D, RT = 1.77 min, 100% | $^1$H NMR (400 MHz, DMSO-$d_6$) δ = 9.02 (d, J = 8.3 Hz, 1H), 8.01 (d, J = 4.4 Hz, 1H), 7.88 (d, J = 8.8 Hz, 2H), 7.70 (d, J = 4.4 Hz, 1H), 7.34 (t, J = 73.6 Hz, 1H), 7.28-7.26 (m, 2H), 6.78 (d, J = 10.8 Hz, 2H), 5.05 (dd, J = 10.8, 8.6 Hz, 1H), 4.37-4.26 (m, 1H), 4.23-4.05 (m, 4H), 3.77 (s, 3H), 1.28 (t, J = 7.1 Hz, 3H). |

TABLE 2-continued

| Ex | Structure | LCMS (M + H)+ | HPLC Method, RT (min.) & Purity | $^1$H NMR |
|---|---|---|---|---|
| 359 | 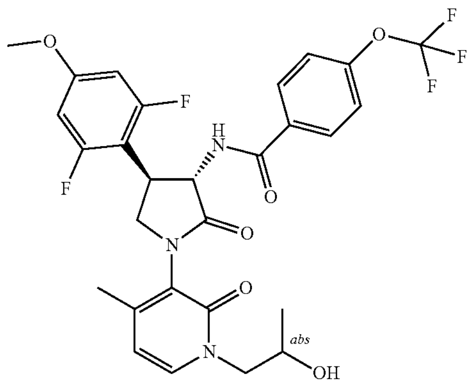 [SMILES: COc1cc(F)c([C@@H]2CN(c3c(C)ccn(CC(C)O)c3=O)C(=O)[C@H]2NC(=O)c2ccc(OC(F)(F)F)cc2)c(F)c1] | 596.2 | Method D, RT = 1.75 min, 98% | $^1$H NMR (400 MHz, DMSO-d$_6$) δ = 9.28-8.97 (m, 1H), 8.07-7.82 (m, 2H), 7.61-7.34 (m, 3H), 6.79-6.75 (m, 2H), 6.28-6.09 (m, 1H), 5.41-4.80 (m, 2H), 4.31-3.97 (m, 3H), 3.95-3.85 (m, 1H), 3.82-3.73 (2s, 3H), 3.63-3.45 (m, 2H), 2.23-2.01 (2s, 3H), 1.09 (d, J = 6.4 Hz, 3H). (mixture of interconvertible atropisomers) |
| 360 | 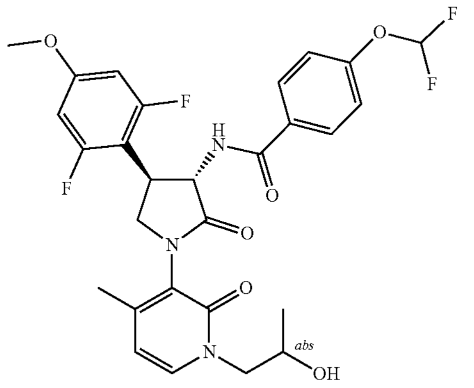 [SMILES: COc1cc(F)c([C@@H]2CN(c3c(C)ccn(CC(C)O)c3=O)C(=O)[C@H]2NC(=O)c2ccc(OC(F)F)cc2)c(F)c1] | 578.3 | Method C, RT = 1.57 min, 99% | $^1$H NMR (400 MHz, DMSO-d$_6$) δ = 9.15-8.81 (m, 1H), 7.99-7.77 (m, 2H), 7.63-7.09 (m, 4H), 6.79-6.72 (m, 2H), 6.30-6.09 (m, 1H), 5.40-4.82 (m, 2H), 4.35-3.98 (m, 3H), 3.94-3.84 (m, 1H), 3.81-3.72 (2s, 3H), 3.63-3.45 (m, 2H), 2.23-2.02 (2s, 3H), 1.09 (d, J = 6.1 Hz, 3H). (mixture of interconvertible atropisomers) |
| 361 | 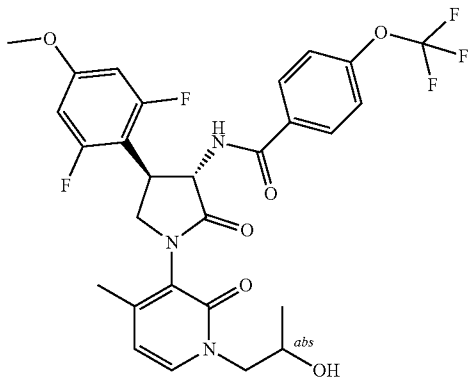 [SMILES: COc1cc(F)c([C@@H]2CN(c3c(C)ccn(CC(C)O)c3=O)C(=O)[C@H]2NC(=O)c2ccc(OC(F)(F)F)cc2)c(F)c1] | 596.2 | Method C, RT = 1.80 min, 93% | $^1$H NMR (400 MHz, DMSO-d$_6$) δ = 9.18-9.05 (m, 1H), 7.97-7.91 (m, 2H), 7.57-7.46 (m, 3H), 6.77-6.73 (m, 2H), 6.30-6.17 (m, 1H), 5.40-4.88 (m, 2H), 4.35-3.98 (m, 3H), 3.94-3.84 (m, 1H), 3.81-3.72 (2s, 3H), 3.63-3.45 (m, 2H), 2.19-2.02 (2s, 3H), 1.11-1.06 (m, 3H). (mixture of interconvertible atropisomers) |
| 362 | 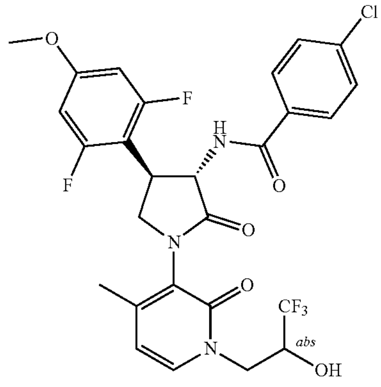 [SMILES: COc1cc(F)c([C@@H]2CN(c3c(C)ccn(CC(O)C(F)(F)F)c3=O)C(=O)[C@H]2NC(=O)c2ccc(Cl)cc2)c(F)c1] | 546.2 | Method D, RT = 1.61 min, 97% | $^1$H NMR (400 MHz, DMSO-d$_6$) δ = 9.20-8.90 (m, 1H), 7.91-7.74 (m, 2H), 7.64-7.36 (m, 3H), 6.82-6.64 (m, 2H), 6.27-6.07 (m, 1H), 5.36-4.81 (m, 2H), 4.28-3.82 (m, 4H), 3.80-3.73 (2s, 3H), 3.69-3.46 (m, 2H), 2.23-2.04 (2s, 3H), 1.09-1.06 (m, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 363 | 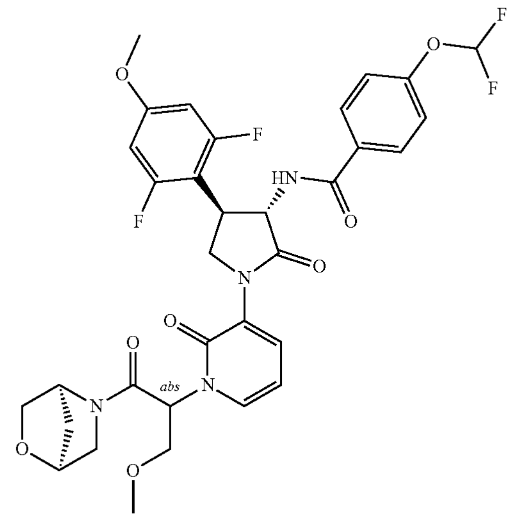 [SMILES: COCC(C(=O)N1C[C@@H]2C[C@H]1CO2)n1cccc(N2C[C@@H](c3c(F)cc(OC)cc3F)[C@H](NC(=O)c3ccc(OC(F)F)cc3)C2=O)c1=O] | 707.3 | Method D, RT = 1.78 min, 100% | $^1$H NMR (400 MHz, DMSO-$d_6$) δ = 9.11 (d, J = 8.8 Hz, 1H), 7.94 (d, J = 8.3 Hz, 2H), 7.78-3.73 (m, 1H), 7.67-7.57 (m, 1H), 7.52-7.41 (m, 2H), 6.76 (d, J = 10.8 Hz, 2H), 6.41 (t, J = 7.2 Hz, 1H), 6.05-5.64 (m, 1H), 5.16-5.00 (m, 1H), 4.74-4.54 (m, 2H), 4.15-3.78 (m, 6H), 3.76 (s, 3H), 3.68-3.51 (m, 3H), 3.27 (s, 3H), 1.90-1.69 (m, 2H). |
| 364 | 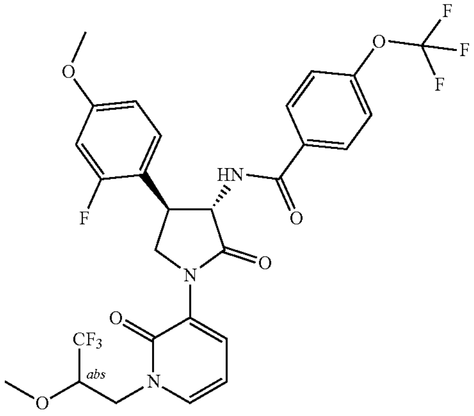 [SMILES: COc1ccc([C@@H]2CN(c3cccn(CC(OC)C(F)(F)F)c3=O)C(=O)[C@H]2NC(=O)c2ccc(OC(F)(F)F)cc2)c(F)c1] | 632.2 | Method D, RT = 2.06 min, 100% | $^1$H NMR (400 MHz, DMSO-$d_6$) δ = 9.07 (d, J = 8.8 Hz, 1H), 7.97 (d, J = 8.8 Hz, 2H), 7.74-7.63 (m, 2H), 7.54-7.41 (m, 3H), 6.87-6.73 (m, 2H), 6.39 (t, J = 7.0 Hz, 1H), 5.13 (dd, J = 11.1, 9.2 Hz, 1H), 4.41 (dd, J = 13.0, 3.4 Hz, 1H), 4.35-4.26 (m, 1H), 4.16-4.08 (m, 1H), 4.06-3.95 (m, 1H), 3.78-3.72 (m, 4H) 3.77-3.69 (m, 1H), 3.36 (s, 3H). |
| 365 | 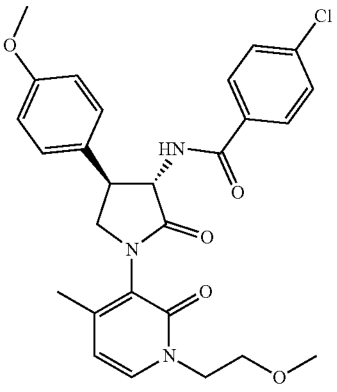 [SMILES: COCCn1ccc(C)c(N2C[C@@H](c3ccc(OC)cc3)[C@H](NC(=O)c3ccc(Cl)cc3)C2=O)c1=O] | 510.2 | Method D, RT = 1.588 min, 89% | $^1$H NMR (400 MHz, DMSO-$d_6$) δ = 9.02-8.97 (m, 1H), 7.92-8.86 (m, 2H), 7.60-7.49 (m, 3H), 7.43-7.24 (m, 2H), 6.97-6.80 (m, 2H), 6.22-6.18 (m, 1H), 5.27-4.64 (m, 1H), 4.18-3.96 (m, 3H), 3.93-3.80 (m, 2H), 3.75-3.70 (2s, 3H), 3.66-3.53 (m, 2H), 3.24 (s, 3H), 2.21-2.04-(2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 366 | 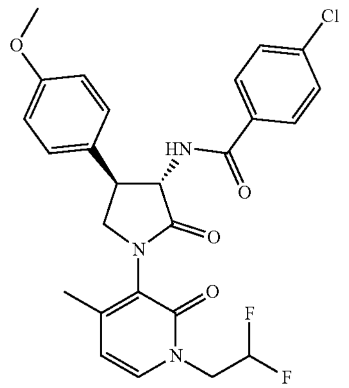 [SMILES: COc1ccc([C@@H]2CN(c3c(C)ccn(CC(F)F)c3=O)C(=O)[C@H]2NC(=O)c2ccc(Cl)cc2)cc1] | 516.2 | Method D, RT = 1.67 min, 100% | $^1$H NMR (400 MHz, DMSO-$d_6$) δ = 9.03-8.98 (m, 1H), 7.91-7.76 (m, 2H), 7.65-7.61 (m, 1H), 7.57-7.51 (m, 2H), 7.44-7.25 (m, 2H), 6.94-6.98 (m, 2H), 6.48-6.12 (m, 2H), 5.31-4.61 (m, 1H), 4.51-4.31 (m, 2H), 4.10-3.78 (m, 2H), 3.74-3.70 (2s, 3H), 3.71-3.64 (m, 1H), 2.23-2.09 (2s, 3H). (mixture of interconvertible atropisomers) |
| 367 | 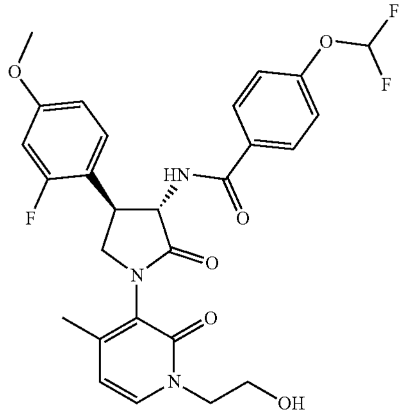 [SMILES: COc1ccc([C@@H]2CN(c3c(C)ccn(CCO)c3=O)C(=O)[C@H]2NC(=O)c2ccc(OC(F)F)cc2)c(F)c1] | 546.2 | Method D, RT = 1.51 min, 100% | $^1$H NMR (400 MHz, DMSO-$d_6$) δ = 8.99-8.94 (m, 1H), 7.99-7.84 (m, 2H), 7.61-7.52 (m, 2H), 7.37-7.33 (m, 1H), 7.31-7.22 (m, 2H), 6.90-6.70 (m, 2H), 6.22-6.17 (m, 1H), 5.41-4.73 (m, 1H), 4.15-3.87 (m, 5H), 3.74-3.71(2s, 3H), 3.64-3.54 (m, 3H), 2.25-2.02 (2s, 3H). (mixture of interconvertible atropisomers) |
| 368 | 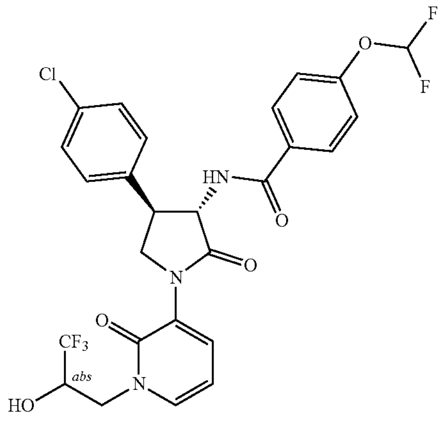 [SMILES: O=C(N[C@@H]1C(=O)N(c2cccn(CC(O)C(F)(F)F)c2=O)C[C@H]1c1ccc(Cl)cc1)c1ccc(OC(F)F)cc1] | 586.1 | Method D, RT = 1.852 min, 98.6% | $^1$H NMR (400 MHz, DMSO-$d_6$) δ = 8.95 (d, J = 8.8 Hz, 1H), 7.96-7.85 (m, 2H), 7.69 (dd, J = 6.8, 2.0 Hz, 1H), 7.65 (dd, J = 7.3, 2.0 Hz, 1H), 7.49-7.39 (m, 4H), 7.34 (t, J = 73.6 Hz, 1H), 7.28-7.24 (m, 2H), 6.79-6.70 (m, 1H), 6.37 (t, J = 7.0 Hz, 1H), 5.03 (dd, J = 11.0, 8.8 Hz, 1H), 4.45 (dd, J = 13.1, 2.8 Hz, 1H), 4.37-4.29 (m, 1H), 4.20 (t, J = 8.8 Hz, 1H), 3.89-3.79 (m, 2H), 3.75-3.67 (m, 1H). |

TABLE 2-continued

| Ex | Structure | LCMS (M + H)+ | HPLC Method, RT (min.) & Purity | $^1$H NMR |
|---|---|---|---|---|
| 369 | 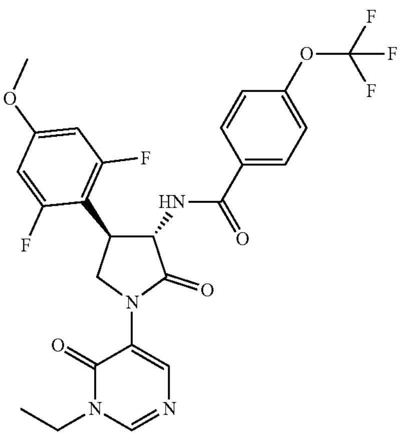 [SMILES: CCn1cncc(N2C[C@@H](c3c(F)cc(OC)cc3F)[C@H](NC(=O)c3ccc(OC(F)(F)F)cc3)C2=O)c1=O] | 535.2 | Method D, RT = 1.60 min, 98.7% | $^1$H NMR (400 MHz, DMSO-$d_6$) δ = 9.01 (d, J = 8.6 Hz, 1H), 8.54 (s, 1H), 8.13 (s, 1H), 7.97-7.84 (m, 2H), 7.34 (t, J = 73.0 Hz, 1H), 7.28-7.25 (m, 2H), 6.77 (d, J = 10.8 Hz, 2H), 5.12 (dd, J = 11.1, 8.7 Hz, 1H), 4.19-4.05 (m, 1H), 4.05-3.90 (m, 4H), 3.76 (s, 3H), 1.28 (t, J = 7.1 Hz, 3H). |
| 370 | 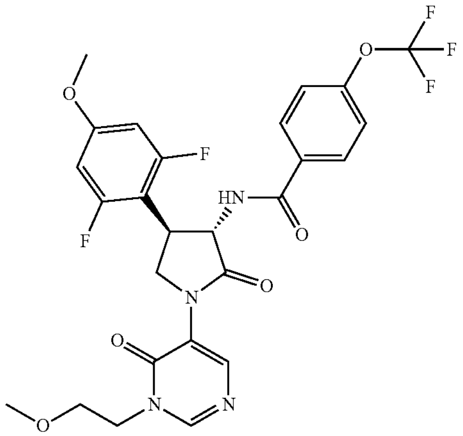 [SMILES: COCCn1cncc(N2C[C@@H](c3c(F)cc(OC)cc3F)[C@H](NC(=O)c3ccc(OC(F)(F)F)cc3)C2=O)c1=O] | 565.2 | Method D, RT = 1.61 min, 98.7% | $^1$H NMR (400 MHz, DMSO-$d_6$) δ = 9.01 (d, J = 8.8 Hz, 1H), 8.40 (s, 1H), 8.14 (s, 1H), 7.88 (d, J = 8.6 Hz, 2H), 7.34 (t, J = 73.0 Hz, 1H), 7.28-7.25 (m, 2H), 6.77 (d, J = 10.8 Hz, 2H), 5.12 (dd, J = 10.9, 8.9 Hz, 1H), 4.23-4.03 (m, 3H), 4.03-3.88 (m, 2H), 3.76 (s, 3H), 3.60 (t, J = 5.1 Hz, 2H), 3.26 (s, 3H). |
| 371 | 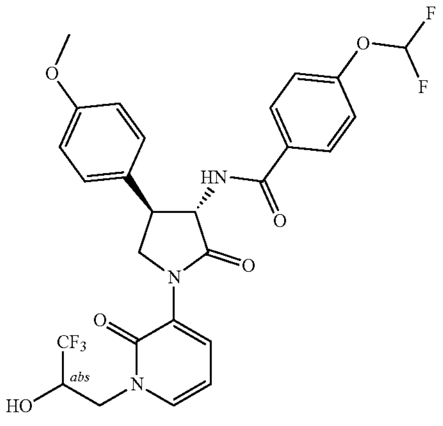 [SMILES: COc1ccc([C@@H]2CN(c3cccn(CC(O)C(F)(F)F)c3=O)C(=O)[C@H]2NC(=O)c2ccc(OC(F)F)cc2)cc1] | 582.2 | Method D, RT = 1.644 min, 100% | $^1$H NMR (400 MHz, DMSO-$d_6$) δ = 8.93 (d, J = 8.6 Hz, 1H), 7.94-7.92 (m, 2H), 7.68 (dd, J = 6.7, 1.8 Hz, 1H), 7.63 (dd, J = 7.2, 1.8 Hz, 1H), 7.33 (t, J = 72.0 Hz, 1H), 7.35-7.10 (m, 4H), 6.97-6.87 (m, 2H), 6.84-6.61 (m, 1H), 6.37 (t, J = 7.0 Hz, 1H), 4.99 (dd, J = 10.9, 8.9 Hz, 1H), 4.44 (dd, J = 13.2, 2.9 Hz, 1H), 4.38-4.29 (m, 1H), 4.12-4.05 (m, 1H), 3.85 (dd, J = 13.1, 9.2 Hz, 1H), 3.82-3.73 (m, 2H), 3.72 (s, 3H). |

TABLE 2-continued

| Ex | Structure | LCMS (M + H)+ | HPLC Method, RT (min.) & Purity | $^1$H NMR |
|---|---|---|---|---|
| 372 | 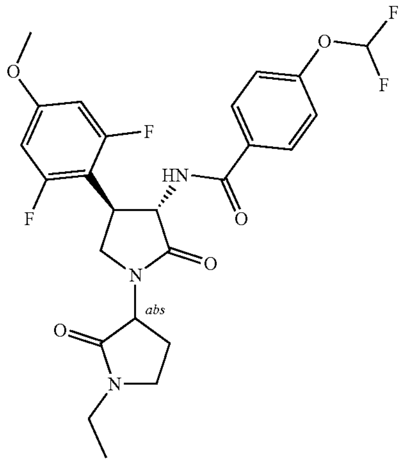 [SMILES: CCN1CCC(N2C[C@@H](c3c(F)cc(OC)cc3F)[C@H](NC(=O)c3ccc(OC(F)F)cc3)C2=O)C1=O] | 542.2 | Method D, RT = 1.77 min, 100% | $^1$H NMR (400 MHz, DMSO-$d_6$) δ = 9.03 (d, J = 8.8 Hz, 1H), 8.00-7.86 (m, 2H), 7.47 (d, J = 8.1 Hz, 2H), 6.75 (d, J = 10.8 Hz, 2H), 4.97 (dd, J = 10.8, 8.6 Hz, 1H), 4.84 (t, J = 9.4 Hz, 1H), 4.01-3.85 (m, 1H), 3.75 (s, 3H), 3.64 (br t, J = 8.7 Hz, 1H), 3.36 (m, 3H), 3.23 (dt, J = 13.7, 6.6 Hz, 2H), 2.28-2.18 (m, 1H), 2.15-2.03 (m, 1H), 1.03 (t, J = 7.2 Hz, 3H). |
| 373 | 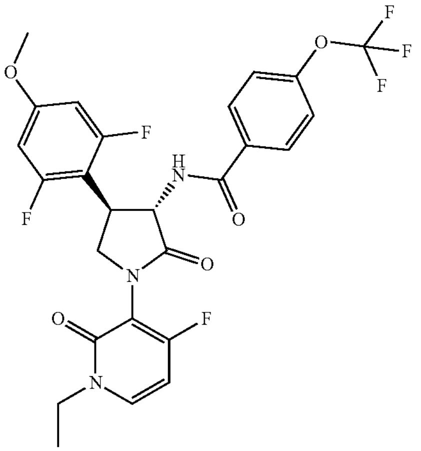 [SMILES: CCn1ccc(F)c(N2C[C@@H](c3c(F)cc(OC)cc3F)[C@H](NC(=O)c3ccc(OC(F)(F)F)cc3)C2=O)c1=O] | 552.2 | Method D, RT = 1.717 min, 94.7% | $^1$H NMR (400 MHz, DMSO-$d_6$) δ = 9.09-9.01 (m, 1H), 8.01-7.85 (m, 3H), 7.53-7.23 (m, 3H), 6.84-6.72 (m, 2H), 6.50-6.46 (m, 1H), 5.07-4.99 (m, 1H), 4.27-4.10 (m, 1H), 4.06-3.92 (m, 4H), 3.79-3.75 (2s, 3H), 1.31-1.19 (m, 3H). (mixture of interconvertible atropisomers) |
| 374 | 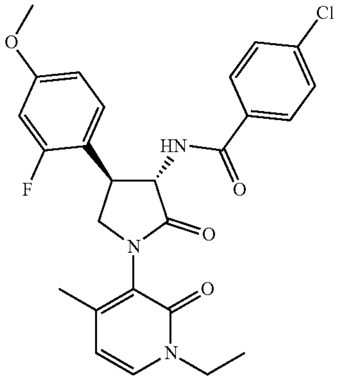 [SMILES: CCn1ccc(C)c(N2C[C@@H](c3ccc(OC)cc3F)[C@H](NC(=O)c3ccc(Cl)cc3)C2=O)c1=O] | 498.2 | Method D, RT = 1.68 min, 100% | $^1$H NMR (400 MHz, DMSO-$d_6$) δ = 9.05-9.0 (m, 1H), 7.92-7.79 (m, 2H), 7.68-7.61 (m, 1H), 7.59-7.35 (m, 3H), 6.89-6.72 (m, 2H), 6.25-6.20 (m, 1H), 5.41-4.74 (m, 1H), 4.18-3.85 (m, 4H), 3.76-3.72 (2s, 3H), 3.62-3.36 (m, 1H), 2.22-2.04 (2s, 3H), 1.22 (m, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 375 | 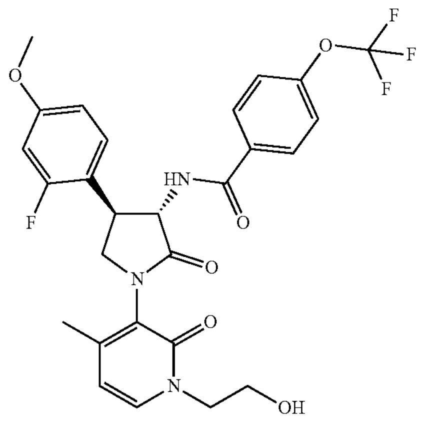 [SMILES: COc1ccc([C@@H]2CN(c3c(C)ccn(CCO)c3=O)C(=O)[C@H]2NC(=O)c2ccc(OC(F)(F)F)cc2)c(F)c1] | 564.2 | Method D, RT = 1.61 min, 100% | $^1$H NMR (400 MHz, DMSO-$d_6$) δ = 9.09-9.06 (m, 1H), 8.03-7.87 (m, 2H), 7.62-7.37 (m, 4H), 6.89-6.68 (m, 2H), 6.22-6.18 (m, 1H), 5.41-4.78 (m, 2H), 4.16-3.89 (m, 4H), 3.78-3.74 (2s, 3H), 3.64-3.60 (m, 3H), 2.21-2.03 (2s, 3H). (Mixture of interconvertible atropisomers) |
| 376 | 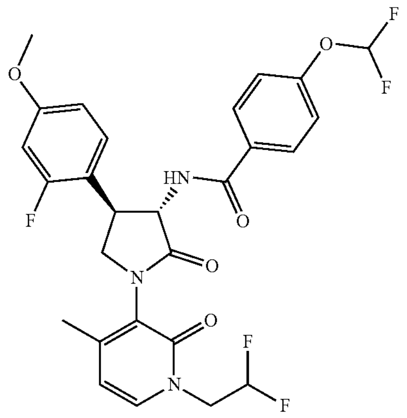 [SMILES: COc1ccc([C@@H]2CN(c3c(C)ccn(CC(F)F)c3=O)C(=O)[C@H]2NC(=O)c2ccc(OC(F)F)cc2)c(F)c1] | 566.2 | Method D, RT = 1.74 min, 94.2% | $^1$H NMR (400 MHz, DMSO-$d_6$) δ = 9.02-8.93 (m, 1H), 7.99-7.83 (m, 2H), 7.69-7.61 (m, 1H), 7.56-7.45 (m, 1H), 7.51-7.21 (m, 3H), 6.88-6.69 (m, 2H), 6.36-6.13 (m, 2H), 5.41-4.74 (m, 1H), 4.50-4.32 (m, 2H), 4.18-3.89 (m, 2H), 3.74-(2s, 3H), 3.62-3.36 (m, 1H), 2.22-2.10 (2s, 3H). (mixture of interconvertible atropisomers) |
| 377 | 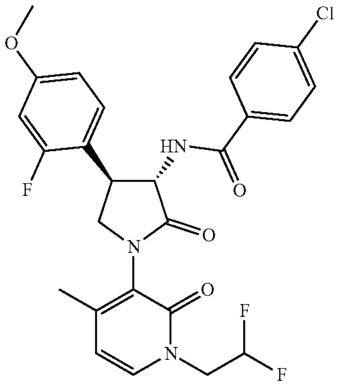 [SMILES: COc1ccc([C@@H]2CN(c3c(C)ccn(CC(F)F)c3=O)C(=O)[C@H]2NC(=O)c2ccc(Cl)cc2)c(F)c1] | 534.2 | Method D, RT = 1.76 min, 100% | $^1$H NMR (400 MHz, DMSO-$d_6$) δ = 9.12-8.96 (m, 1H), 7.99-7.83 (m, 2H), 7.66-7.61 (m, 1H), 7.59-7.35 (m, 3H), 6.89-6.71 (m, 2H), 6. 51-6.26 (m, 2H), 5.41-4.74 (m, 1H), 4.50-4.32 (m, 2H), 4.18-3.89 (m, 2H), 3.74 (2s, 3H), 3.62-3.36 (m, 1H), 2.23-2.03 (2s, 3H). (mixture of interconvertible atropisomers) |

TABLE 2-continued

| Ex | Structure | LCMS (M + H)+ | HPLC Method, RT (min.) & Purity | $^{1}$H NMR |
|---|---|---|---|---|
| 378 | 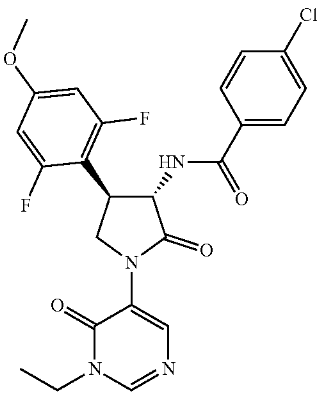 [SMILES: CCn1cncc(N2C[C@@H](c3c(F)cc(OC)cc3F)[C@H](NC(=O)c3ccc(Cl)cc3)C2=O)c1=O] | 503.2 | Method D, RT = 1.62 min, 97.9% | $^{1}$H NMR (400 MHz, DMSO-$d_6$) δ = 9.07 (d, J = 8.6 Hz, 1H), 8.54 (s, 1H), 8.13 (s, 1H), 7.88-7.77 (m, 2H), 7.60-7.50 (m, 2H), 6.77 (d, J = 10.8 Hz, 2H), 5.12 (dd, J = 11.0, 8.6 Hz, 1H), 4.16-4.05 (m, 1H), 4.03-3.90 (m, 4H), 3.76 (s, 3H), 1.28 (t, J = 7.1 Hz, 3H). |
| 379 | 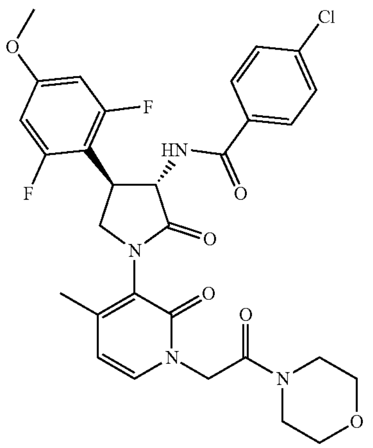 [SMILES: COc1cc(F)c([C@@H]2CN(c3c(C)ccn(CC(=O)N4CCOCC4)c3=O)C(=O)[C@H]2NC(=O)c2ccc(Cl)cc2)c(F)c1] | 615.2 | Method F, RT = 1.63 min, 96.0% | $^{1}$H NMR (400 MHz, DMSO-$d_6$) δ = 9.20-8.89 (m, 1H), 7.91-7.71 (m, 2H), 7.66-7.34 (m, 3H), 6.84-6.64 (m, 2H), 6.31-6.12 (m, 1H), 5.33-4.73 (m, 3H), 4.30-4.01 (m, 2H), 3.76 (s, 3H), 3.70-3.62 (m, 2H), 3.61-3.36 (m, 7H), 2.25-1.99 (2s, 3H). (mixture of interconvertible atropisomers) |
| 380 | 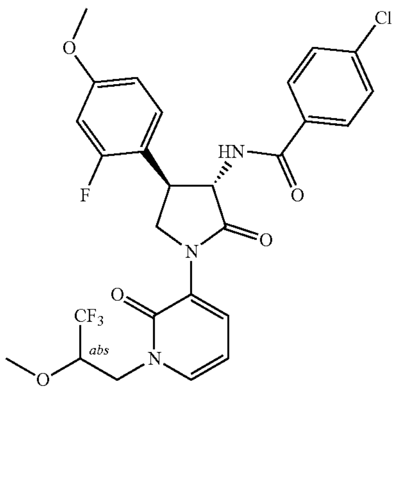 [SMILES: COc1ccc([C@@H]2CN(c3cccn(CC(OC)C(F)(F)F)c3=O)C(=O)[C@H]2NC(=O)c2ccc(Cl)cc2)c(F)c1] | 582.2 | Method D, RT = 1.92 min, 95.7% | $^{1}$H NMR (400 MHz, DMSO-$d_6$) δ = 9.03 (d, J = 8.6 Hz, 1H), 7.93-7.78 (m, 2H), 7.72-7.65 (m, 2H), 7.61-7.43 (m, 3H), 6.89-6.75 (m, 2H), 6.39 (t, J = 7.1 Hz, 1H), 5.14 (dd, J = 11.2, 8.8 Hz, 1H), 4.42 (dd, J = 13.6, 3.5 Hz, 1H), 4.36-4.25 (m, 1H), 4.18-4.09 (m, 1H), 4.08-3.95 (m, 2H), 3.78 (s, 3H), 3.77-3.71 (m, 1H), 3.25 (s, 3H). |

TABLE 2-continued

| Ex | Structure | LCMS (M + H)+ | HPLC Method, RT (min.) & Purity | $^1$H NMR |
|---|---|---|---|---|
| 381 | 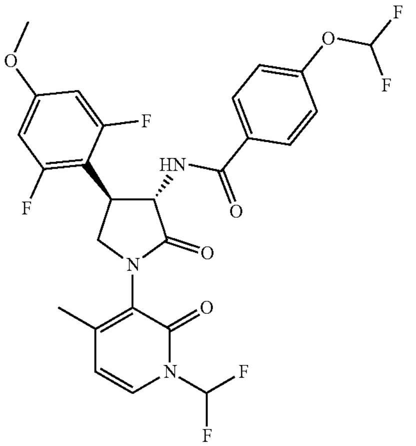 [SMILES: COc1cc(F)c([C@@H]2CN(c3c(C)ccn(C(F)F)c3=O)C(=O)[C@H]2NC(=O)c2ccc(OC(F)F)cc2)c(F)c1] | 570.2 | Method D, RT = 1.812 min, 96% | $^1$H NMR (400 MHz, DMSO-$d_6$) δ = 9.12-8.94 (m, 1H), 8.05-7.68 (m, 4H), 7.51-7.24 (m, 3H), 6.87-6.69 (m, 2H), 6.52-6.39 (m, 1H), 5.33-4.74 (m, 1H), 4.35-4.00 (m, 2H), 3.79-3.74 (2s, 3H), 3.62-3.51 (m, 1H), 2.28-2.00 (2s, 3H). (mixture of interconvertible atropisomers) |
| 382 | 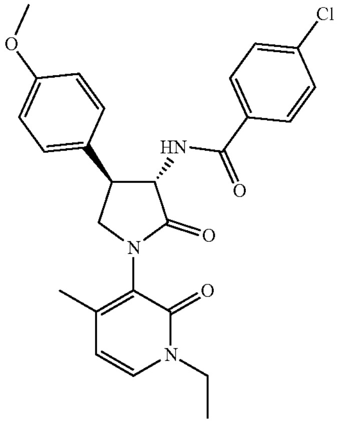 [SMILES: CCn1ccc(C)c(N2C[C@@H](c3ccc(OC)cc3)[C@H](NC(=O)c3ccc(Cl)cc3)C2=O)c1=O] | 480.2 | Method D, RT = 1.685 min, 96% | $^1$H NMR (400 MHz, DMSO-$d_6$) δ = 9.02-8.97 (m, 1H), 7.90-7.86 (m, 2H), 7.68-7.63 (m, 1H), 7.60-7.47 (m, 2H), 7.41-7.18 (m, 2H), 6.93-6.89 (m, 2H), 6.24-6.17 (m, 1H), 5.29-4.64 (m, 1H), 4.13-3.80 (m, 4H), 3.74-3.71 (2s, 3H), 3.47-3.42 (m, 1H), 2.24-2.02 (2s, 3H), 1.32-1.13 (m, 3H). (mixture of interconvertible atropisomers) |
| 383 | 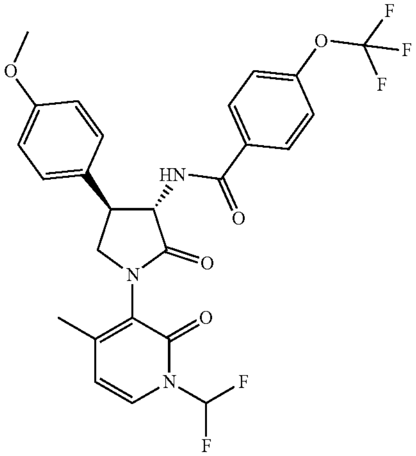 [SMILES: COc1ccc([C@@H]2CN(c3c(C)ccn(C(F)F)c3=O)C(=O)[C@H]2NC(=O)c2ccc(OC(F)(F)F)cc2)cc1] | 552.2 | Method D, RT = 1.884 min, 97% | $^1$H NMR (400 MHz, DMSO-$d_6$) δ = 9.14-8.94 (m, 1H), 8.05-7.67 (m, 4H), 7.57-7.42 (m, 2H), 7.42-7.25 (m, 2H), 7.04-6.79 (m, 2H), 6.47-6.41 (m, 1H), 5.32-4.54 (m, 1H), 4.08-3.79 (m, 2H), 3.79-3.51 (m, 4H), 2.28-2.10 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 384 | 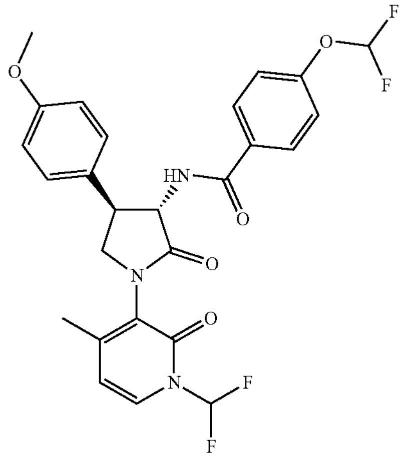 [SMILES: COc1ccc([C@@H]2CN(c3c(C)ccn(C(F)F)c3=O)C(=O)[C@H]2NC(=O)c2ccc(OC(F)F)cc2)cc1] | 534.2 | Method D, RT = 1.726 min, 93% | $^1$H NMR (400 MHz, DMSO-$d_6$) δ = 9.06-8.82 (m, 1H), 8.08-7.68 (m, 4H), 7.57-7.06 (m, 5H), 6.97-6.76 (m, 2H), 6.47-6.42 (m, 1H), 5.31-4.56 (m, 1H), 4.07-3.78 (m, 2H), 3.76-3.49 (m, 4H), 2.30-2.10 (2s, 3H). (mixture of interconvertible atropisomers) |
| 385 | 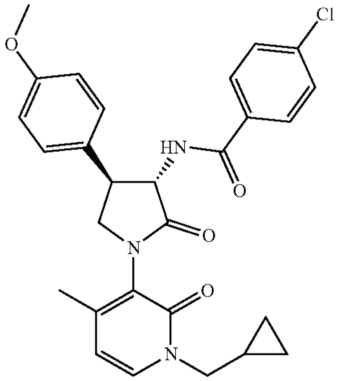 [SMILES: COc1ccc([C@@H]2CN(c3c(C)ccn(CC4CC4)c3=O)C(=O)[C@H]2NC(=O)c2ccc(Cl)cc2)cc1] | 506.2 | Method D, RT = 1.758 min, 100% | $^1$H NMR (400 MHz, DMSO-$d_6$) δ = 9.02-8.98 (m, 1H), 7.94-7.79 (m, 2H), 7.70-7.66 (m, 1H), 7.60-7.47 (m, 2H), 7.42-7.23 (m, 2H), 7.00-6.80 (m, 2H), 6.24-6.20 (m, 1H), 5.28-4.62 (m, 1H), 4.15-3.78 (m, 3H), 3.75-3.70 (m, 4H), 3.51-3.40 (m, 1H), 2.23-2.02 (2s, 3H), 1.28-1.08 (m, 1H), 0.55-0.44 (m, 2H), 0.42-0.30 (m, 2H). (mixture of interconvertible atropisomers) |
| 386 | 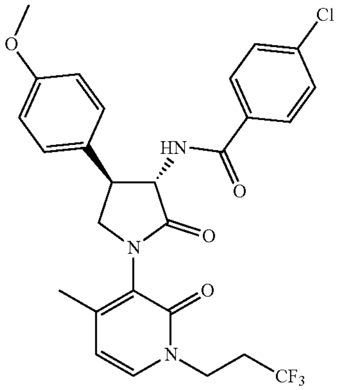 [SMILES: COc1ccc([C@@H]2CN(c3c(C)ccn(CCC(F)(F)F)c3=O)C(=O)[C@H]2NC(=O)c2ccc(Cl)cc2)cc1] | 548.2 | Method D, RT = 1.794 min, 97% | $^1$H NMR (400 MHz, DMSO-$d_6$) δ = 9.03-8.98 (m, 1H), 7.90-7.86 (m, 2H), 7.70-7.66 (m, 1H), 7.63-7.50 (m, 2H), 7.46-7.21 (m, 2H), 6.94-6.88 (m, 2H), 6.28-6.23 (m, 1H), 5.32-4.58 (m, 1H), 4.27-3.77 (m, 4H), 3.74-3.70 (2s, 3H) 3.48-3.46 (m, 1H), 2.85-2.66 (m, 2H), 2.24-2.02 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 387 | 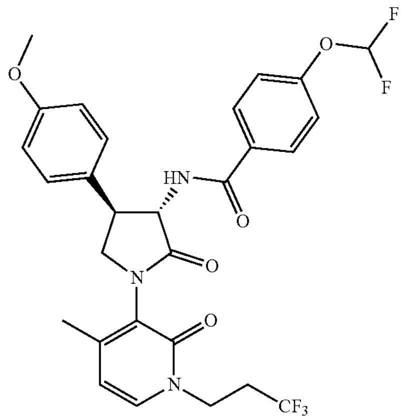 [SMILES: COc1ccc([C@@H]2CN(c3c(C)ccn(CCC(F)(F)F)c3=O)C(=O)[C@H]2NC(=O)c2ccc(OC(F)F)cc2)cc1] | 580.2 | Method D, RT = 1.766 min, 100% | $^1$H NMR (400 MHz, DMSO-$d_6$) δ = 8.96-8.92 (m, 1H), 7.95-7.91 (m, 2H), 7.70-7.65 (m, 1H), 7.55-7.07 (m, 5H), 6.93-6.87 (m, 2H), 6.28-6.23 (m, 1H), 5.30-4.64 (m, 1H), 4.29-3.78 (m, 4H), 3.74-3.70 (2s, 3H) 3.48-3.46 (m, 1H), 2.86-2.64 (m, 2H), 2.23-2.06 (2s, 3H). (mixture of interconvertible atropisomers) |
| 388 | 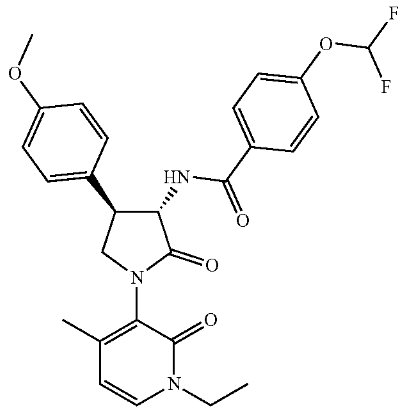 [SMILES: CCn1ccc(C)c(N2C[C@@H](c3ccc(OC)cc3)[C@H](NC(=O)c3ccc(OC(F)F)cc3)C2=O)c1=O] | 512.3 | Method D, RT = 1.572 min, 100% | $^1$H NMR (400 MHz, DMSO-$d_6$) δ = 8.96-8.92 (m, 1H), 8.00-7.88 (m, 2H), 7.67-7.62 (m, 1H), 7.55-7.05 (m, 5H), 6.93-6.88 (m, 2H), 6.24-6.18 (m, 1H), 5.32-4.63 (m, 1H), 4.14-3.77 (m, 4H), 3.74-3.70 (2s, 3H), 3.47-3.42 (m, 1H), 2.25-2.04 (2s, 3H), 1.25-1.19 (m, 3H). (mixture of interconvertible atropisomers) |
| 389 | 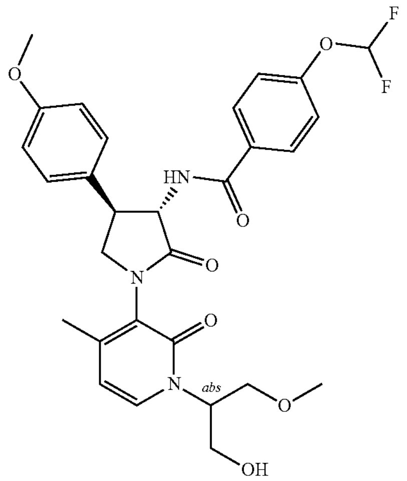 [SMILES: COCC(CO)n1ccc(C)c(N2C[C@@H](c3ccc(OC)cc3)[C@H](NC(=O)c3ccc(OC(F)F)cc3)C2=O)c1=O] | 572.3 | Method D, RT = 1.517 min, 100% | $^1$H NMR (400 MHz, DMSO-$d_6$) δ = 9.00-8.88 (m, 1H), 7.96-7.90 (m, 2H), 7.62-7.56 (m, 1H), 7.53-7.12 (m, 5H), 6.93-6.95 (m, 2H), 6.26-6.18 (m, 1H), 5.27-5.16 (m, 1H), 5.10-4.94 (m, 2H), 4.75-4.65 (m, 1H), 4.14-4.05 (m, 1H), 3.95-3.82 (m, 2H), 3.77-3.57 (m, 6H), 3.24-3.20 (2s, 3H), 2.20-2.08 (2s, 3H). (mixture of atrop and diastereomers) |

TABLE 2-continued

| Ex | Structure | LCMS (M + H)+ | HPLC Method, RT (min.) & Purity | $^1$H NMR |
|---|---|---|---|---|
| 390 | 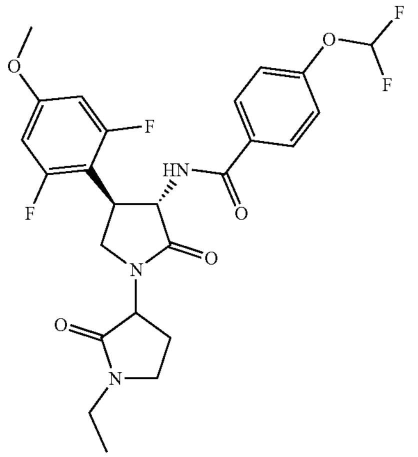 [SMILES: CCN1CCC(N2C[C@@H](c3c(F)cc(OC)cc3F)[C@H](NC(=O)c3ccc(OC(F)F)cc3)C2=O)C1=O] | 524.2 | Method D, RT = 1.603 min, 98% | $^1$H NMR (400 MHz, DMSO-$d_6$) δ = 8.92 (d, J = 8.6 Hz, 1H), 7.91-7.75 (m, 2H), 7.33 (t, J = 73.6 Hz, 1H), 7.27-7.24 (m, 2H), 6.74 (d, J = 10.8 Hz, 2H), 4.96 (dd, J = 10.9, 8.9 Hz, 1H), 4.84 (t, J = 9.4 Hz, 1H), 3.97-3.86 (m, 1H), 3.75 (s, 3H), 3.64 (br t, J = 8.7 Hz, 1H), 3.37-3.31 (m, 3H), 3.26-3.20 (m, 2H), 2.26-2.17 (m, 1H), 2.13-2.03 (m, 1H), 1.03 (t, J = 7.2 Hz, 3H). |
| 391 | 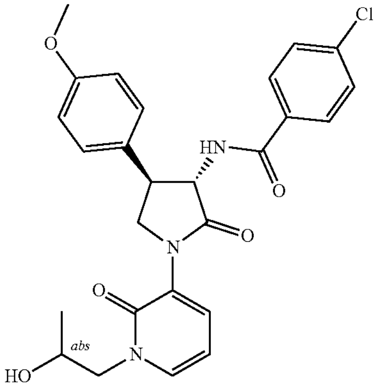 [SMILES: COc1ccc([C@@H]2CN(c3cccn(CC(C)O)c3=O)C(=O)[C@H]2NC(=O)c2ccc(Cl)cc2)cc1] | 496.1 | Method D, RT = 1.467 min, 100% | $^1$H NMR (400 MHz, DMSO-$d_6$) δ = 8.98 (d, J = 8.6 Hz, 1H), 7.92-7.81 (m, 2H), 7.64-7.49 (m, 4H), 7.38-7.27 (m, 2H), 6.90 (d, J = 8.6 Hz, 2H), 6.30 (t, J = 7.0 Hz, 1H), 5.05-4.96 (m, 1H), 4.96-4.88 (m, 1H), 4.12-4.04 (m, 2H), 3.96-3.90 (m, 1H), 3.79-3.70 (m, 2H), 3.72 (s, 3H), 3.70-3.61 (m, 1H), 1.08 (d, J = 6.1 Hz, 3H). |
| 392 | 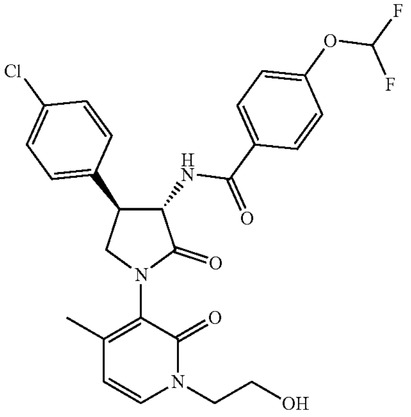 [SMILES: Cc1ccn(CCO)c(=O)c1N1C[C@@H](c2ccc(Cl)cc2)[C@H](NC(=O)c2ccc(OC(F)F)cc2)C1=O] | 532.2 | Method D, RT = 1.606 min, 97.2% | $^1$H NMR (400 MHz, DMSO-$d_6$) δ = 9.02-8.95 (m, 1H), 7.98-7.90 (m, 2H), 7.58-7.49 (m, 2H), 7.46-7.15 (m, 6H), 6.23-6.18 (m, 1H), 5.33-4.97 (m, 1H), 5.05-4.97 (m, 1H), 4.94-4.90 (m, 1H), 4.06-3.86 (m, 4H), 3.67-3.58 (m, 2H), 2.22-2.10 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 393 | 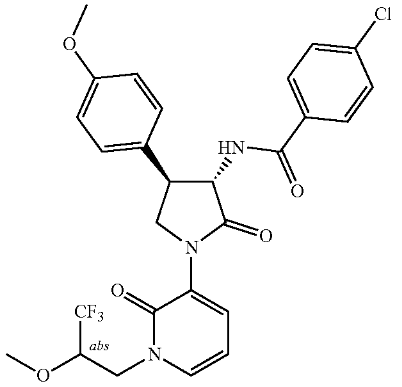 [SMILES: COc1ccc([C@@H]2CN(c3cccn(CC(OC)C(F)(F)F)c3=O)C(=O)[C@H]2NC(=O)c2ccc(Cl)cc2)cc1] | 564.2 | Method D, RT = 1.848 min, 100% | $^1$H NMR (400 MHz, DMSO-d$_6$) δ = 8.98 (d, J = 9.3 Hz, 1H), 7.89-7.81 (m, 2H), 7.73-7.63 (m, 2H), 7.59-7.51 (m, 2H), 7.34 (d, J = 8.6 Hz, 2H), 6.90 (d, J = 8.6 Hz, 2H), 6.38 (t, J = 7.0 Hz, 1H), 5.05-4.98 (m, 1H), 4.44-4.37 (m, 1H), 4.32-4.26 (m, 1H), 4.13-4.02 (m, 3H), 3.80-3.74 (m, 1H), 3.72 (s, 3H), 3.36 (s, 3H). |
| 394 | 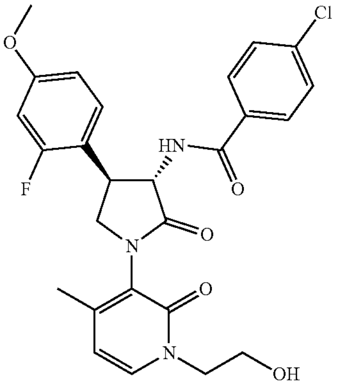 [SMILES: COc1ccc([C@@H]2CN(c3c(C)ccn(CCO)c3=O)C(=O)[C@H]2NC(=O)c2ccc(Cl)cc2)c(F)c1] | 514.2 | Method D, RT = 1.52 min, 100% | $^1$H NMR (400 MHz, DMSO-d$_6$) δ = 9.05-8.98 (m, 1H), 7.88-7.75 (m, 2H), 7.59-7.43 (m, 4H), 6.86-6.74 (m, 2H), 6.21-6.18 (m, 1H), 5.42-4.74 (m, 2H), 4.15-3.92 (m, 4H), 3.76-3.72 (2s, 3H), 3.66-3.56 (m, 3H), 2.22-2.05 (2s, 3H). (mixture of interconvertible atropisomers) |
| 395 | 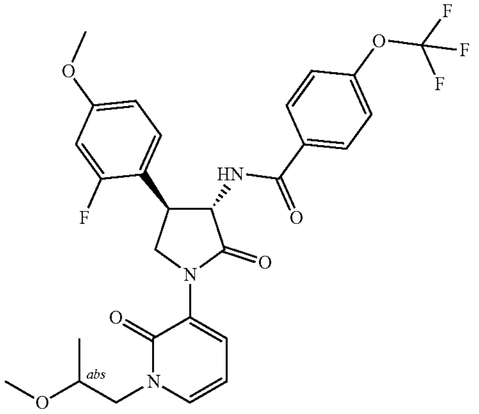 [SMILES: COc1ccc([C@@H]2CN(c3cccn(CC(C)OC)c3=O)C(=O)[C@H]2NC(=O)c2ccc(OC(F)(F)F)cc2)c(F)c1] | 578.2 | Method D, RT = 1.85 min, 100% | $^1$H NMR (400 MHz, DMSO-d$_6$) δ = 9.05 (d, J = 8.3 Hz, 1H), 7.96 (d, J = 8.8 Hz, 2H), 7.63-7.56 (m, 2H), 7.53-7.43 (m, 3H), 6.85-6.76 (m, 2H), 6.32 (t, J = 7.0 Hz, 1H), 5.15-5.10 (m, 1H), 4.13-3.93 (m, 3H), 3.91 (br d, J = 7.1 Hz, 2H), 3.76 (s, 3H), 3.74-3.64 (m, 1H), 3.25 (s, 3H), 1.08 (d, J = 6.1 Hz, 3H). |

TABLE 2-continued

| Ex | Structure | LCMS (M + H)+ | HPLC Method, RT (min.) & Purity | $^1$H NMR |
| --- | --- | --- | --- | --- |
| 396 | 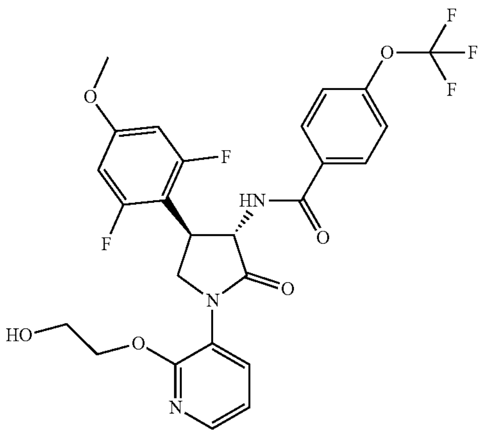 [SMILES: COc1cc(F)c([C@@H]2CN(c3cccnc3OCCO)C(=O)[C@H]2NC(=O)c2ccc(OC(F)(F)F)cc2)c(F)c1] | 568.2 | Method D, RT = 1.84 min, 94.9% | $^1$H NMR (400 MHz, DMSO-$d_6$) δ = 9.14 (d, J = 8.6 Hz, 1H), 8.13 (dd, J = 4.9, 2.0 Hz, 1H), 7.98-7.90 (m, 2H), 7.79 (dd, J = 7.6, 1.7 Hz, 1H), 7.49 (d, J = 8.6 Hz, 2H), 7.09 (dd, J = 7.6, 4.9 Hz, 1H), 6.78 (d, J = 10.8 Hz, 2H), 5.08 (dd, J = 10.9, 8.4 Hz, 1H), 4.74 (t, J = 5.5 Hz, 1H), 4.38 (td, J = 5.5, 2.6 Hz, 2H), 4.15 (q, J = 9.8 Hz, 1H), 4.05-4.96 (m, 2H), 3.76 (s, 3H), 3.75-3.69 (m, 2H). |
| 397 | 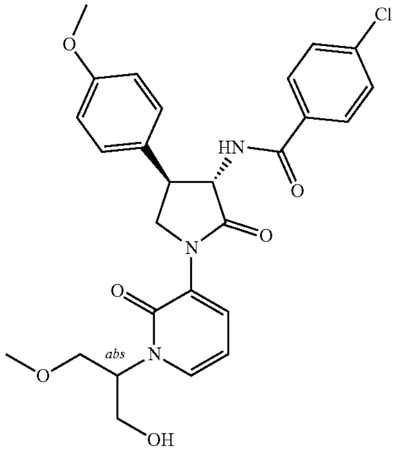 [SMILES: COCC(CO)n1cccc(N2C[C@@H](c3ccc(OC)cc3)[C@H](NC(=O)c3ccc(Cl)cc3)C2=O)c1=O] | 526.2 | Method D, RT = 1.471 min, 91% | $^1$H NMR (400 MHz, DMSO-$d_6$) δ = 9.01-8.94 (m, 1H), 7.91-7.83 (m, 2H), 7.68 (dd, J = 6.8, 2.0 Hz, 1H), 7.58-7.49 (m, 3H), 7.34 (d, J = 8.6 Hz, 2H), 6.90 (d, J = 8.6 Hz, 2H), 6.33 (t, J = 7.1 Hz, 1H), 5.11-4.97 (m, 3H), 4.13-4.10 (m, 1H), 3.78-3.65 (m, 8H), 3.65-3.60 (m, 1H), 3.23 (s, 3H). |
| 398 | 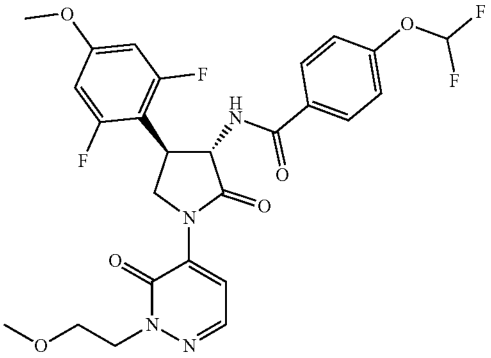 [SMILES: COCCn1nccc(N2C[C@@H](c3c(F)cc(OC)cc3F)[C@H](NC(=O)c3ccc(OC(F)F)cc3)C2=O)c1=O] | 565.2 | Method D, RT = 1.73 min, 97% | $^1$H NMR (400 MHz, DMSO-$d_6$) δ = 9.02 (d, J = 8.3 Hz, 1H), 8.01 (d, J = 4.6 Hz, 1H), 7.90-7.80 (m, 2H), 7.69 (d, J = 4.6 Hz, 1H), 7.34 (t, J = 73.6 Hz, 1H), 7.28-7.26 (m, 2H), 6.78 (d, J = 10.8 Hz, 2H), 5.05 (dd, J = 10.9, 8.4 Hz, 1H), 4.37-4.22 (m, 3H), 4.21-4.05 (m, 2H), 3.77 (s, 3H), 3.70 (t, J = 5.5 Hz, 2H), 3.24 (s, 3H). |

TABLE 2-continued

| Ex | Structure | LCMS (M + H)+ | HPLC Method, RT (min.) & Purity | $^1$H NMR |
|---|---|---|---|---|
| 399 | 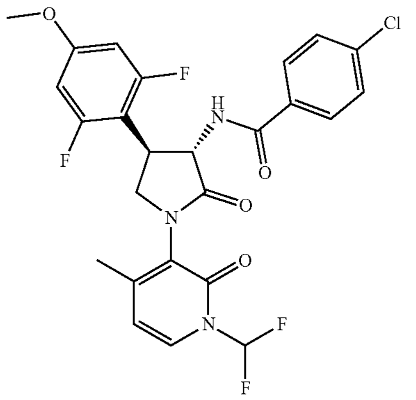 [SMILES: COc1cc(F)c([C@@H]2CN(c3c(C)ccn(C(F)F)c3=O)C(=O)[C@H]2NC(=O)c2ccc(Cl)cc2)c(F)c1] | 538.1 | Method D, RT = 1.88 min, 94% | $^1$H NMR (400 MHz, DMSO-d$_6$) δ = 9.15-9.04 (m, 1H), 8.07-7.68 (m, 4H), 7.64-7.45 (m, 2H), 6.87-6.65 (m, 2H), 6.51-6.36 (m, 1H), 5.36-4.78 (m, 1H), 4.35-3.99 (m, 2H), 3.83-3.73 (2s, 3H), 3.66-3.52 (m, 1H), 2.29-2.05 (2s, 3H). (mixture of interconvertible atropisomers) |
| 400 | 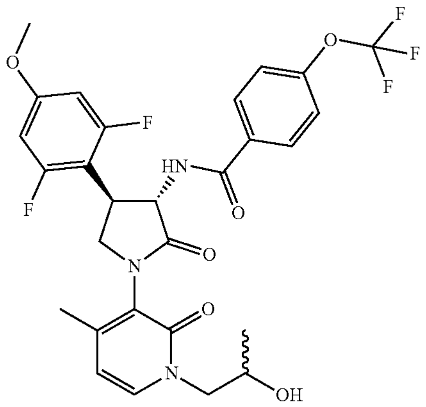 [SMILES: COc1cc(F)c([C@@H]2CN(c3c(C)ccn(CC(C)O)c3=O)C(=O)[C@H]2NC(=O)c2ccc(OC(F)(F)F)cc2)c(F)c1] | 596.3 | Method D, RT = 1.721 min, 100% | $^1$H NMR (400 MHz, DMSO-d$_6$) δ = 9.24-8.92 (m, 1H), 7.99-7.86 (m, 1H), 7.96-7.91 (m, 1H), 7.60-7.42 (m, 3H), 6.83-6.69 (m, 2H), 6.26-6.16 (m, 1H), 5.00-4.84 (m, 2H), 4.30-3.96 (m, 4H), 3.80-3.74 (2s, 3H), 3.62-3.47 (m, 2H), 2.24-2.02 (2s, 3H), 1.14-1.03 (m, 3H). (mixture of interconvertible atropisomers) |
| 401 | 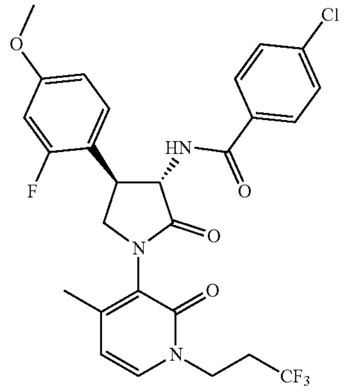 [SMILES: COc1ccc([C@@H]2CN(c3c(C)ccn(CCC(F)(F)F)c3=O)C(=O)[C@H]2NC(=O)c2ccc(Cl)cc2)c(F)c1] | 566.2 | Method D, RT = 1.87 min, 94.4% | $^1$H NMR (400 MHz, DMSO-d$_6$) δ = 9.05-9.00 (m, 1H), 7.99-7.81 (m, 2H), 7.70-7.65 (m, 1H), 7.62-7.50 (m, 2H), 7.45-7.40 (m, 1H), 6.90-6.72 (m, 2H), 6.28-6.24 (m, 1H), 5.42-4.74 (m, 1H), 4.30-3.94 (m, 3H), 3.76-3.70 (2s, 3H), 3.49-3.34 (m, 2H), 2.81-2.68 (m, 2H), 2.22-2.06 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 402 | 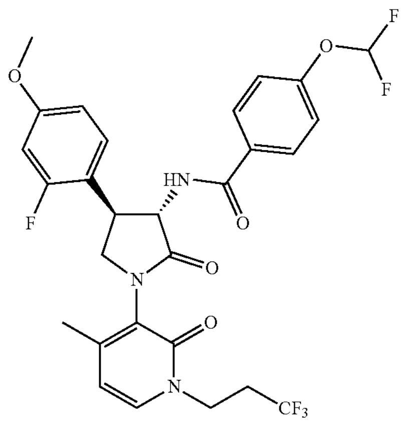 [SMILES: COc1ccc([C@@H]2CN(c3c(C)ccn(CCC(F)(F)F)c3=O)C(=O)[C@H]2NC(=O)c2ccc(OC(F)F)cc2)c(F)c1] | 598.2 | Method D, RT = 1.83 min, 100% | $^1$H NMR (400 MHz, DMSO-$d_6$) δ = 8.99-8.95 (m, 1H), 7.99-7.84 (m, 2H), 7.61-7.52 (m, 1H), 7.58-7.12 (m, 4H), 6.90-6.70 (m, 2H), 6.21-6.17 (m, 1H), 5.42-4.74 (m, 1H), 4.30-3.94 (m, 3H), 3.76-3.70 (2s, 3H), 3.49-3.34 (m, 2H), 2.81-2.68 (m, 2H), 2.22-2.06 (2s, 3H). (mixture of interconvertible atropisomers) |
| 403 | 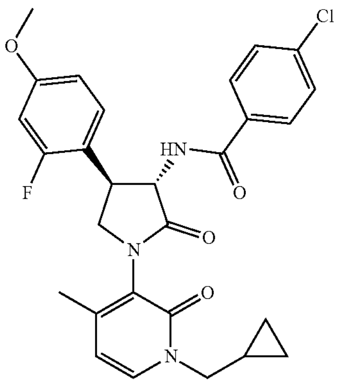 [SMILES: COc1ccc([C@@H]2CN(c3c(C)ccn(CC4CC4)c3=O)C(=O)[C@H]2NC(=O)c2ccc(Cl)cc2)c(F)c1] | 566.2 | Method D, RT = 1.87 min, 94.4% | $^1$H NMR (400 MHz, DMSO-$d_6$) δ = 9.06-9.01 (m, 1H), 7.99-7.82 (m, 2H), 7.71-7.67 (m, 1H), 7.63-7.52 (m, 2H), 7.49-7.37 (m, 1H), 6.90-6.73 (m, 2H), 6.25-6.21 (m, 1H), 5.42-4.74 (m, 1H), 4.22-3.95 (m, 2H), 3.95-3.82 (m, 1H), 3.79-3.75 (2s, 3H), 3.74-3.54 (m, 2H), 2.23-2.03 (2s, 3H), 1.32-1.09 (m, 1H), 0.58-0.45 (m, 2H), 0.42-0.26 (m, 2H) (mixture of interconvertible atropisomers) |
| 404 | 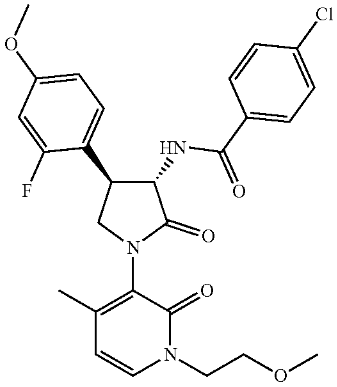 [SMILES: COCCn1ccc(C)c(N2C[C@@H](c3ccc(OC)cc3F)[C@H](NC(=O)c3ccc(Cl)cc3)C2=O)c1=O] | 598.2 | Method D, RT = 1.83 min, 100% | $^1$H NMR (400 MHz, DMSO-$d_6$) δ = 9.06-9.01 (m, 1H), 7.99-7.82 (m, 2H), 7. 71-7.67 (m, 1H), 7.63-7.52 (m, 2H), 7.49-7.37 (m, 1H), 6.90-6.73 (m, 2H), 6.25-6.21 (m, 1H)), 5.42-4.69 (m, 1H), 4.19-3.90 (m, 4H), 3.78-3.72 (2s, 3H), 3.63-3.35 (m, 3H), 3.24 (s, 3H), 2.23-2.02 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 405 | 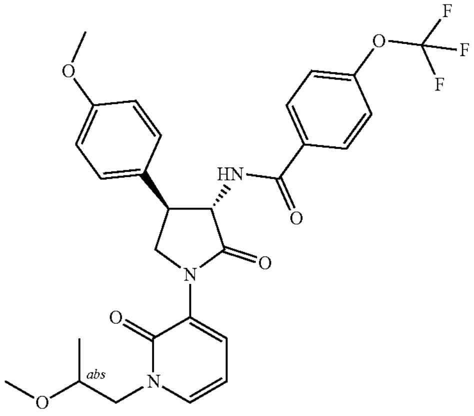 [SMILES: COc1ccc([C@@H]2CN(c3cccn(CC(C)OC)c3=O)C(=O)[C@H]2NC(=O)c2ccc(OC(F)(F)F)cc2)cc1] | 560.3 | Method D, RT = 1.885 min, 100% | $^1$H NMR (400 MHz, DMSO-$d_6$) δ = 9.05-8.99 (m, 1H), 7.99 (d, J = 8.8 Hz, 2H), 7.60 (d, J = 7.1 Hz, 2H), 7.49 (d, J = 8.8 Hz, 2H), 7.35 (d, J = 8.8 Hz, 2H), 6.91 (d, J = 8.8 Hz, 2H), 6.32 (d, J = 7.1 Hz, 1H), 5.05-4.97 (m, 1H), 4.12-4.08 (m, 1H), 4.08-4.02 (m, 1H), 3.93-3.86 (m, 1H), 3.78-3.73 (m, 2H), 3.72 (s, 3H), 3.68-3.62 (m, 1H), 3.2 (s, 3H), 1.09 (d, J = 6.4 Hz, 3H). |
| 406 | 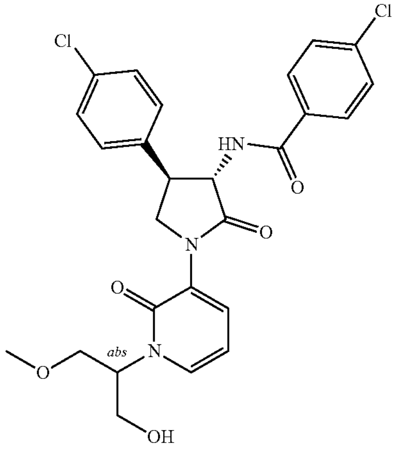 [SMILES: COCC(CO)n1cccc(N2C[C@@H](c3ccc(Cl)cc3)[C@H](NC(=O)c3ccc(Cl)cc3)C2=O)c1=O] | 530.2 | Method D, RT = 1.681 min, 97.2% | $^1$H NMR (400 MHz, DMSO-$d_6$) δ = 9.07-8.96 (m, 1H), 7.90-7.84 (m, 2H), 7.68 (dd, J = 7.0, 1.8 Hz, 1H), 7.59-7.52 (m, 3H), 7.50-7.44 (m, 2H), 7.43-7.38 (m, 2H), 6.37-6.31 (m, 1H), 5.13-4.98 (m, 2H), 4.20-4.12 (m, 1H), 3.88-3.58 (m, 7H), 3.23 (s, 3H). |
| 407 | 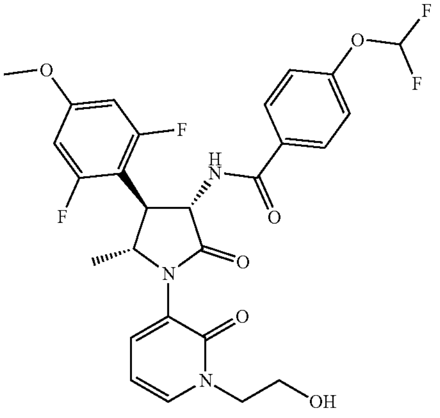 [SMILES: COc1cc(F)c([C@H]2[C@H](NC(=O)c3ccc(OC(F)F)cc3)C(=O)N(c3cccn(CCO)c3=O)[C@@H]2C)c(F)c1] | 564.2 | Method D, RT = 1.59 min, 100% | $^1$H NMR (400 MHz, DMSO-$d_6$) δ = 8.98 (d, J = 8.6 Hz, 1H), 7.94-7.81 (m, 2H), 7.67 (dd, J = 6.6 , 2.2 Hz, 1H), 7.47-7.45 (m, 1H), 7.35 (t, J = 73.6 Hz, 1H), 7.28-7.26 (m, 2H), 6.85-6.67 (m, 2H), 6.33 (t, J = 7.0 Hz, 1H), 5.11 (dd, J = 11.4, 8.7 Hz, 1H), 4.55-4.47 (m, 1H), 4.03-3.97 (m, 3H), 3.77 (s, 3H), 3.67-3.61 (m, 3H), 0.99 (d, J = 5.9 Hz, 3H). |

TABLE 2-continued

| Ex | Structure | LCMS (M + H)+ | HPLC Method, RT (min.) & Purity | $^1$H NMR |
|---|---|---|---|---|
| 408 | 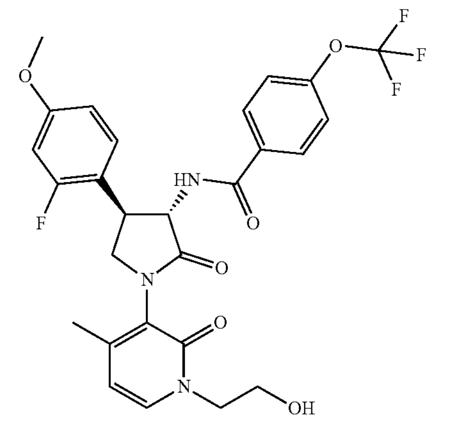 [SMILES: COc1ccc([C@@H]2CN(c3c(C)ccn(CCO)c3=O)C(=O)[C@H]2NC(=O)c2ccc(OC(F)(F)F)cc2)c(F)c1] | 582.2 | Method D, RT = 2.052 min, 95.7% | $^1$H NMR (400 MHz, DMSO-$d_6$) δ = 9.14 (d, J = 8.3 Hz, 1H), 8.13 (dd, J = 4.9, 2.0 Hz, 1H), 8.01-7.88 (m, 2H), 7.79 (dd, J = 7.6, 1.7 Hz, 1H), 7.49 (d, J = 8.3 Hz, 2H), 7.11 (dd, J = 7.6, 4.9 Hz, 1H), 6.78 (d, J = 10.5 Hz, 2H), 5.11 (dd, J = 11.0, 8.6 Hz, 1H), 4.47-4.40 (m, 2H), 4.19-4.09 (m, 1H), 4.03 (t, J = 9.7 Hz, 1H), 3.97-3.91 (m, 1H), 3.77 (s, 3H), 3.72-3.67 (m, 2H), 3.30 (s, 3H). |
| 409 | 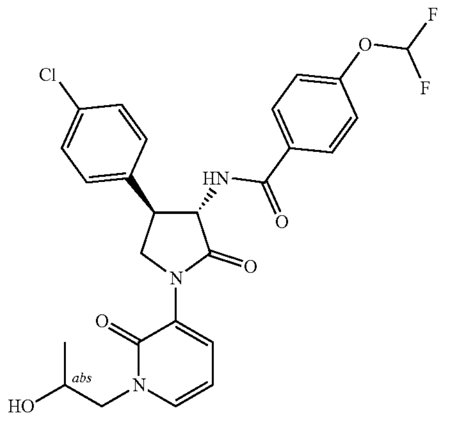 [SMILES: CC(O)Cn1cccc(N2C[C@@H](c3ccc(Cl)cc3)[C@H](NC(=O)c3ccc(OC(F)F)cc3)C2=O)c1=O] | 532.2 | Method D, RT = 1.618 min, 98.4% | $^1$H NMR (400 MHz, DMSO-$d_6$) δ = 8.96 (br d, J = 8.6 Hz, 1H), 7.96-7.83 (m, 2H), 7.62-7.57 (m, 2H), 7.50-7.37 (m, 4H), 7.34 (t, J = 73.6 Hz, 1H), 7.29-7.25 (m, 2H), 6.31 (t, J = 7.0 Hz, 1H), 5.08-4.98 (m, 2H), 4.98-4.86 (m, 1H), 4.17 (t, J = 8.3 Hz, 1H), 4.08 (dd, J = 12.7, 3.7 Hz, 1H), 3.96-3.88 (m, 1H), 3.81 (dd, J = 10.5, 8.3 Hz, 1H), 3.76-3.69 (m, 1H), 1.09 (d, J = 6.4 Hz, 3H). |
| 410 | 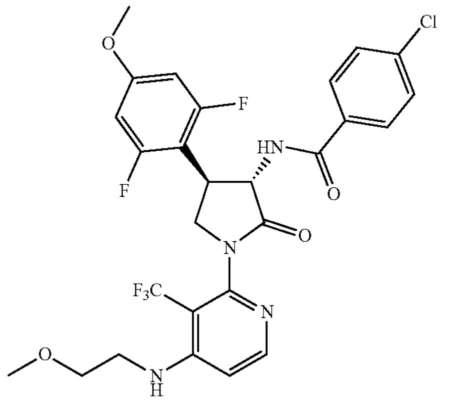 [SMILES: COCCNc1ccnc(N2C[C@@H](c3c(F)cc(OC)cc3F)[C@H](NC(=O)c3ccc(Cl)cc3)C2=O)c1C(F)(F)F] | 599.2 | Method D, RT = 1.94 min, 95.8% | $^1$H NMR (400 MHz, DMSO-$d_6$) δ = 8.85 (d, J = 7.6 Hz, 1H), 8.25-8.13 (m, 1H), 7.61 (d, J = 8.6 Hz, 2H), 7.45 (d, J = 8.6 Hz, 2H), 6.85 (d, J = 6.1 Hz, 1H), 6.69-6.56 (m, 2H), 6.40-6.30 (m, 1H), 4.99 (dd, J = 9.2, 7.7 Hz, 1H), 4.59-4.53 (m, 1H), 4.32-4.23 (m, 1H), 3.99 (br t, J = 8.9 Hz, 1H), 3.70 (s, 3H), 3.53-3.44 (m, 4H), 3.28 (s, 3H). |

TABLE 2-continued

| Ex | Structure | LCMS (M + H)+ | HPLC Method, RT (min.) & Purity | $^1$H NMR |
| --- | --- | --- | --- | --- |
| 411 | 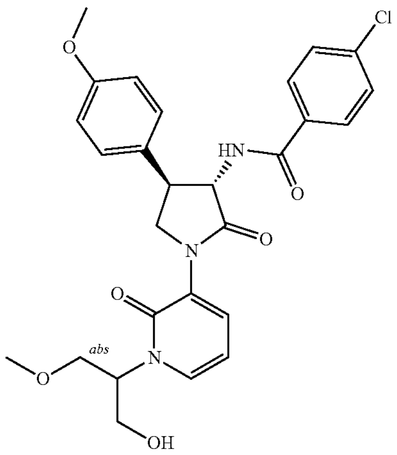 [SMILES: COCC(CO)n1cccc(N2C[C@@H](c3ccc(OC)cc3)[C@H](NC(=O)c3ccc(Cl)cc3)C2=O)c1=O] | 526.2 | Method D, RT = 1.465 min, 93% | $^1$H NMR (400 MHz, DMSO-d$_6$) δ = 8.98 (d, J = 8.6 Hz, 1H), 7.93-7.81 (m, 2H), 7.67 (dd, J = 6.8, 1.7 Hz, 1H), 7.59-7.48 (m, 3H), 7.34 (d, J = 8.8 Hz, 2H), 6.90 (d, J = 8.6 Hz, 2H), 6.33 (t, J = 7.0 Hz, 1H), 5.12-4.93 (m, 3H), 4.13-4.05 (m, 1H), 3.80-3.73 (m, 4H), 3.72 (s, 3H), 3.69-3.58 (m, 2H), 3.23 (s, 3H). |
| 412 | 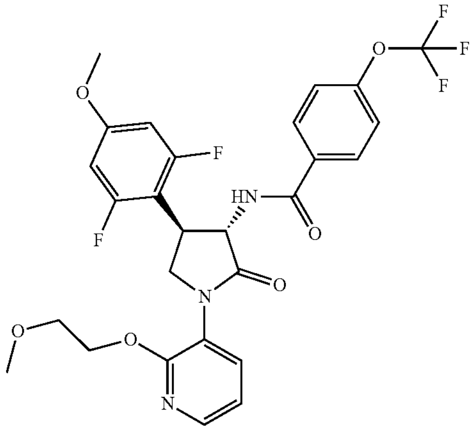 [SMILES: COCCOc1ncccc1N1C[C@@H](c2c(F)cc(OC)cc2F)[C@H](NC(=O)c2ccc(OC(F)(F)F)cc2)C1=O] | 564.2 | Method D, RT = 1.78 min, 99.3% | $^1$H NMR (400 MHz, DMSO-d$_6$) δ = 9.03 (d, J = 8.6 Hz, 1H), 8.13 (dd, J = 4.9, 1.7 Hz, 1H), 7.94-7.83 (m, 2H), 7.79 (dd, J = 7.6, 1.7 Hz, 1H), 7.34 (t, J = 73.0 Hz, 1H), 7.28-7.26 (m, 2H), 7.14-7.14 (m, 1H), 6.78 (d, J = 10.8 Hz, 2H), 5.09 (dd, J = 10.9, 8.7 Hz, 1H), 4.44 (dd, J = 5.4, 3.9 Hz, 2H), 4.20-4.09 (m, 1H), 4.03 (t, J = 9.5 Hz, 1H), 3.97-3.90 (m, 1H), 3.77 (s, 3H), 3.73-3.65 (m, 2H), 3.30 (s, 3H). |
| 413 | 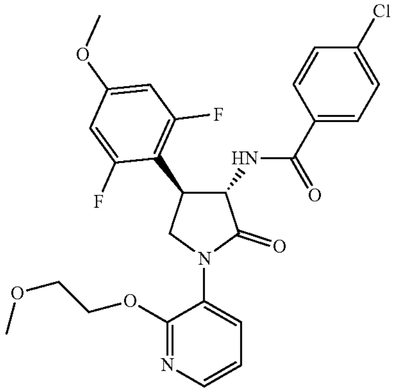 [SMILES: COCCOc1ncccc1N1C[C@@H](c2c(F)cc(OC)cc2F)[C@H](NC(=O)c2ccc(Cl)cc2)C1=O] | 532.2 | Method D, RT = 1.87 min, 98.2% | $^1$H NMR (400 MHz, DMSO-d$_6$) δ = 9.10 (d, J = 8.8 Hz, 1H), 8.13 (dd, J = 5.0, 1.8 Hz, 1H), 7.89-7.81 (m, 2H), 7.79 (dd, J = 7.6, 2.0 Hz, 1H), 7.61-7.50 (m, 2H), 7.11 (dd, J = 7.6, 5.1 Hz, 1H), 6.78 (d, J = 10.8 Hz, 2H), 5.10 (dd, J = 11.0, 8.8 Hz, 1H), 4.51-4.40 (m, 2H), 4.19-4.08 (m, 1H), 4.02 (t, J = 9.7 Hz, 1H), 3.97-3.91 (m, 1H), 3.77 (s, 3H), 3.73-3.67 (m, 2H), 3.30 (s, 3H). |

TABLE 2-continued

| Ex | Structure | LCMS (M + H)+ | HPLC Method, RT (min.) & Purity | $^1$H NMR |
|---|---|---|---|---|
| 414 | 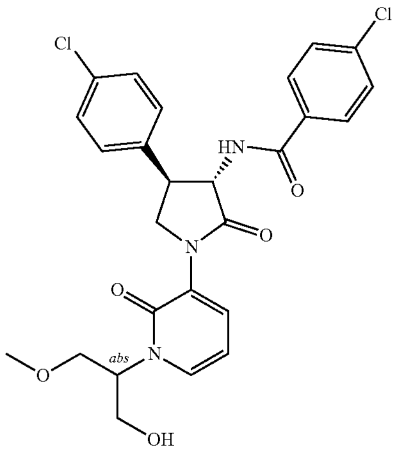 [SMILES: COCC(CO)n1cccc(N2C[C@@H](c3ccc(Cl)cc3)[C@H](NC(=O)c3ccc(Cl)cc3)C2=O)c1=O] | 530.2 | Method D, RT = 1.670 min, 97.1% | $^1$H NMR (400 MHz, DMSO-$d_6$) δ = 9.02 (d, J = 8.3 Hz, 1H), 7.87 (d, J = 8.8 Hz, 2H), 7.68 (dd, J = 1.6, 7.0 Hz, 1H), 7.61-7.52 (m, 3H), 7.51-7.44 (m, 2H), 7.44-7.30 (m, 2H), 6.34 (t, J = 7.1 Hz, 1H), 5.11-4.97 (m, 3H), 4.14 (t, J = 7.3 Hz, 1H), 3.86-3.61 (m, 6H), 3.23 (s, 3H). |
| 415 | 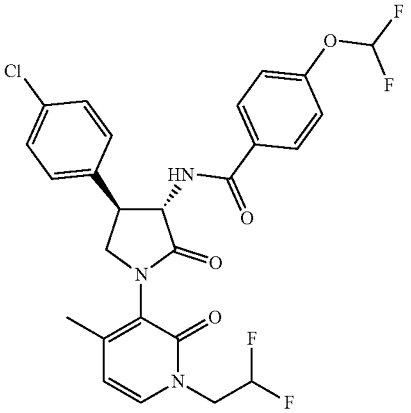 [SMILES: Cc1ccn(CC(F)F)c(=O)c1N1C[C@@H](c2ccc(Cl)cc2)[C@H](NC(=O)c2ccc(OC(F)F)cc2)C1=O] | 552.2 | Method D, RT = 1.838 min, 97.2% | $^1$H NMR (400 MHz, DMSO-$d_6$) δ = 9.09-8.88 (m, 1H), 8.01-7.87 (m, 2H), 7.71-7.57 (m, 1H), 7.55-7.10 (m, 7H), 6.48-6.12 (m, 2H), 5.32-4.71 (m, 1H), 4.45-4.31 (m, 2H), 4.15-3.69 (m, 3H), 2.23 2.11 (2s, 3H). (mixture of interconvertible atropisomers) |
| 416 | 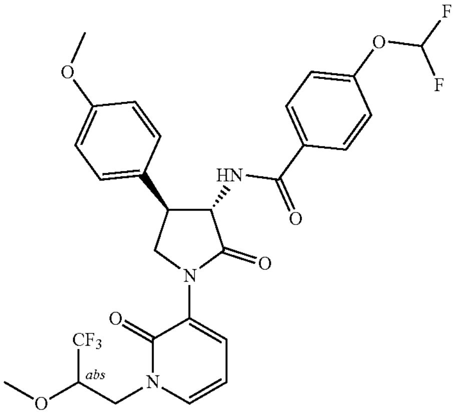 [SMILES: COc1ccc([C@@H]2CN(c3cccn(CC(OC)C(F)(F)F)c3=O)C(=O)[C@H]2NC(=O)c2ccc(OC(F)F)cc2)cc1] | 596.2 | Method D, RT = 1.824 min, 100% | $^1$H NMR (400 MHz, DMSO-$d_6$) δ = 8.92 (d, J = 8.3 Hz, 1H), 7.92 (d, J = 8.8 Hz, 2H), 7.69 (dd, J = 6.7, 1.8 Hz, 1H), 7.66 (dd, J = 7.3, 1.8 Hz, 1H), 7.37-7.22 (m, 4H), 7.33 (t, J = 76.0 Hz, 1H), 6.90 (d, J = 8.8 Hz, 2H), 6.38 (t, J = 7.0 Hz, 1H), 5.07-4.94 (m, 1H), 4.41 (dd, J = 13.3, 3.5 Hz, 1H), 4.36-4.26 (m, 1H), 4.16-3.95 (m, 2H), 3.82-3.73 (m, 2H), 3.72 (s, 3H), 3.36 (s, 3H). |

TABLE 2-continued

| Ex | Structure | LCMS (M + H)+ | HPLC Method, RT (min.) & Purity | $^1$H NMR |
|---|---|---|---|---|
| 417 | 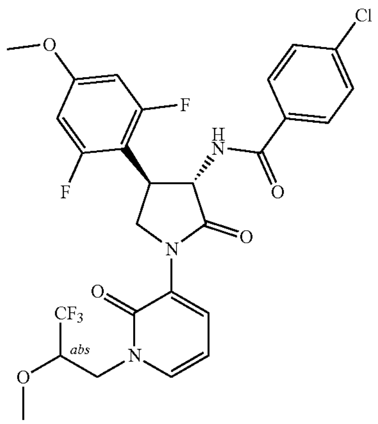 [SMILES: COc1cc(F)c([C@@H]2CN(c3cccn(CC(OC)C(F)(F)F)c3=O)C(=O)[C@H]2NC(=O)c2ccc(Cl)cc2)c(F)c1] | 600.2 | Method D, RT = 1.95 min, 100% | $^1$H NMR (400 MHz, DMSO-$d_6$) δ = 9.07 (d, J = 8.8 Hz, 1H), 7.89-7.77 (m, 2H), 7.71 (dd, J = 6.8, 2.0 Hz, 1H), 7.68 (dd, J = 2.0, 7.1 Hz, 1H), 7.60-7.48 (m, 2H), 6.77 (d, J = 10.8 Hz, 2H), 6.39 (t, J = 7.0 Hz, 1H), 5.12 (dd, J = 10.8, 8.8 Hz, 1H), 4.42 (dd, J = 13.3, 3.3 Hz, 1H), 4.33-4.24 (m, 1H), 4.15-3.92 (m, 4H), 3.76 (s, 3H), 3.36 (s, 3H). |
| 418 | 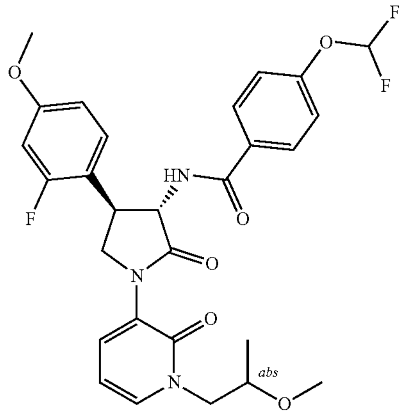 [SMILES: COc1ccc([C@@H]2CN(c3cccn(CC(C)OC)c3=O)C(=O)[C@H]2NC(=O)c2ccc(OC(F)F)cc2)c(F)c1] | 560.3 | Method D, RT = 1.67 min, 100% | $^1$H NMR (400 MHz, DMSO-$d_6$) δ = 8.95 (d, J = 8.8 Hz, 1H), 7.97-7.83 (m, 2H), 7.66-7.56 (m, 2H), 7.54-7.48 (m, 1H), 7.35 (t, J = 76.0 Hz, 1H), 7.31-7.24 (m, 2H), 6.87-6.73 (m, 2H), 6.31 (t, J = 7.0 Hz, 1H), 5.13 (dd, J = 11.5, 8.8 Hz, 1H), 4.22-4.12 (m, 1H), 4.08 (dd, J = 13.2, 3.7 Hz, 1H), 4.04-3.94 (m, 1H), 3.84 (dd, J = 13.3, 7.7 Hz, 1H), 3.74 (s, 3H), 3.70-3.60 (m, 2H), 3.18 (s, 3H), 1.09 (d, J = 6.4 Hz, 3H). |
| 419 | 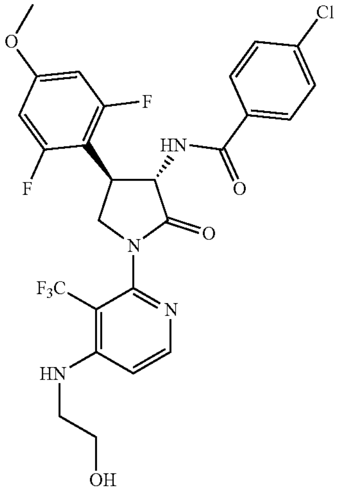 [SMILES: COc1cc(F)c([C@@H]2CN(c3nccc(NCCO)c3C(F)(F)F)C(=O)[C@H]2NC(=O)c2ccc(Cl)cc2)c(F)c1] | 585.2 | Method D, RT = 1.79 min, 92.4% | $^1$H NMR (400 MHz, DMSO-$d_6$) δ = 9.15-8.96 (m, 1H), 8.34 (d, J = 5.1 Hz, 1H), 7.83 (d, J = 8.6 Hz, 2H), 7.61-7.50 (m, 2H), 6.87-6.73 (m, 2H), 6.71 (d, J = 5.1 Hz, 1H), 6.43 (br t, J = 6.1 Hz, 1H), 5.08-4.91 (m, 1H), 4.81-4.71 (m, 1H), 4.27-4.00 (m, 2H), 3.81-3.77 (m, 1H), 3.76 (s, 3H), 3.61-3.47 (m, 4H). |

TABLE 2-continued

| Ex | Structure | LCMS (M + H)+ | HPLC Method, RT (min.) & Purity | $^1$H NMR |
|---|---|---|---|---|
| 420 | 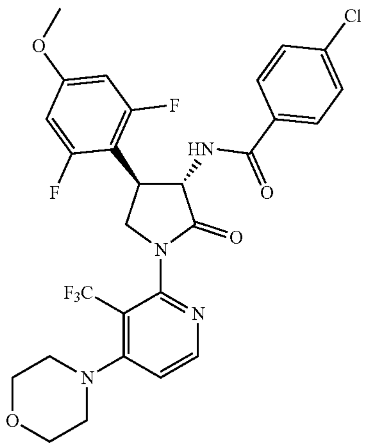 [SMILES: COc1cc(F)c([C@@H]2CN(c3nccc(N4CCOCC4)c3C(F)(F)F)C(=O)[C@H]2NC(=O)c2ccc(Cl)cc2)c(F)c1] | 611.2 | Method D, RT = 1.94 min, 97.4% | $^1$H NMR (400 MHz, DMSO-$d_6$) δ = 9.10 (br d, J = 8.1 Hz, 1H), 8.55-8.41 (m, 1H), 7.82 (br d, J = 8.1 Hz, 2H), 7.66-7.39 (m, 2H), 7.22 (d, J = 5.6 Hz, 1H), 6.87-6.59 (m, 2H), 5.19-5.01 (m, 1H), 4.42-4.11 (m, 2H), 3.80 (s, 3H), 3.79-3.56 (m, 5H), 3.28-3.19 (m, 2H), 3.17-3.05 (m, 2H). |
| 421 | 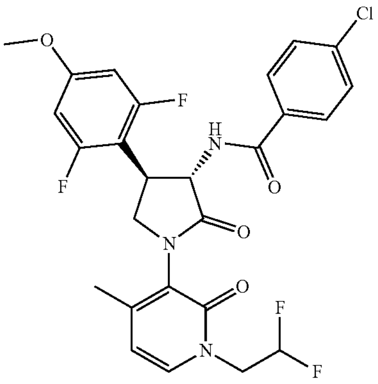 [SMILES: COc1cc(F)c([C@@H]2CN(c3c(C)ccn(CC(F)F)c3=O)C(=O)[C@H]2NC(=O)c2ccc(Cl)cc2)c(F)c1] | 552.2 | Method D, RT = 1.77 min, 100% | $^1$H NMR (400 MHz, DMSO-$d_6$) δ = 9.22-8.91 (m, 1H), 7.91-7.76 (m, 2H), 7.72-7.44 (m, 3H), 6.87-6.68 (m, 2H), 6.51-6.03 (m, 2H), 5.38-4.75 (m, 1H), 4.51-4.32 (m, 2H), 4.30-4.02 (m, 2H), 3.79-3.73 (2s, 3H), 3.60-3.44 (m, 1H), 2.25-2.02 (2s, 3H). (mixture of interconvertible atropisomers) |
| 422 | 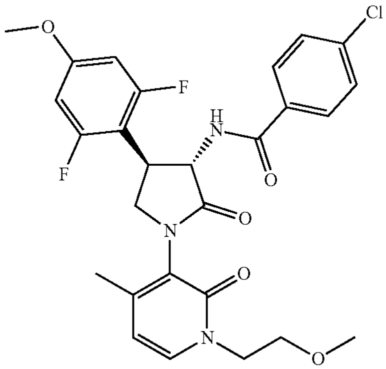 [SMILES: COCCn1ccc(C)c(N2C[C@@H](c3c(F)cc(OC)cc3F)[C@H](NC(=O)c3ccc(Cl)cc3)C2=O)c1=O] | 546.3 | Method D, RT = 1.69 min, 100% | $^1$H NMR (400 MHz, DMSO-$d_6$) δ = 9.23-8.89 (m, 1H), 7.98-7.74 (m, 2H), 7.68-7.41 (m, 3H), 6.79-6.74 (m, 2H), 6.28-6.09 (m, 1H), 5.44-4.77 (m, 1H), 4.29-3.96 (m, 4H), 3.77-3.74 (2s, 3H), 3.63-3.42 (m, 3H), 3.27-3.23 (2s, 3H), 2.23-1.99 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 423 | 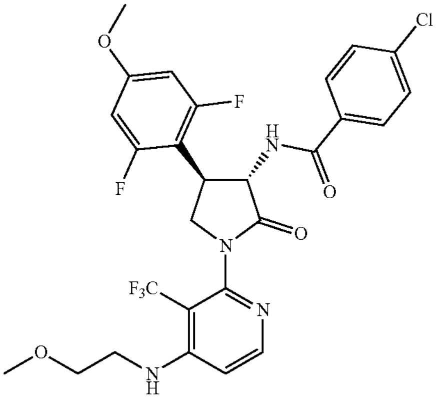 [SMILES: COCCNc1ccnc(N2C[C@@H](c3c(F)cc(OC)cc3F)[C@H](NC(=O)c3ccc(Cl)cc3)C2=O)c1C(F)(F)F] | 599.2 | Method D, RT = 1.94 min, 100% | $^1$H NMR (400 MHz, DMSO-d$_6$) δ = 9.11-9.07 (m, 1H), 8.25-8.13 (m, 1H), 7.88-7.82 (m, 2H), 7.56 (d, J = 8.6 Hz, 2H), 6.91-6.85 (m, 1H), 6.69-6.56 (d, J = 10.8 Hz, 2H), 6.46-6.33 (m, 1H), 5.16-5.11 (m, 1H), 4.35-4.13 (m, 2H), 3.79 (s, 3H), 3.78-3.71 (m ,1H), 3.53-3.44 (m, 4H), 3.28 (s, 3H). (mixture of interconvertible atropisomers) |
| 424 | 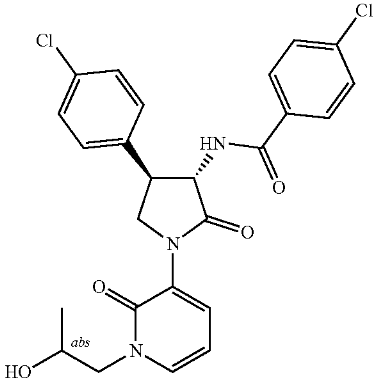 [SMILES: CC(O)Cn1cccc(N2C[C@@H](c3ccc(Cl)cc3)[C@H](NC(=O)c3ccc(Cl)cc3)C2=O)c1=O] | 500.2 | Method D, RT = 1.635 min, 100% | $^1$H NMR (400 MHz, DMSO-d$_6$) δ = 9.03 (d, J = 8.8 Hz, 1H), 7.90-7.82 (m, 2H), 7.65-7.52 (m, 4H), 7.50-7.44 (m, 2H), 7.43-7.36 (m, 2H), 6.31 (t, J = 7.0 Hz, 1H), 5.07-5.00 (m, 1H), 4.98-4.88 (m, 1H), 4.17-4.10 (m, 1H), 4.06 (dd, J = 12.7, 3.7 Hz, 1H), 3.96-3.88 (m, 1H), 3.84-3.74 (m, 2H), 3.68-3.64 (m, 1H), 1.08 (d, J = 6.4 Hz, 3H). |
| 425 | 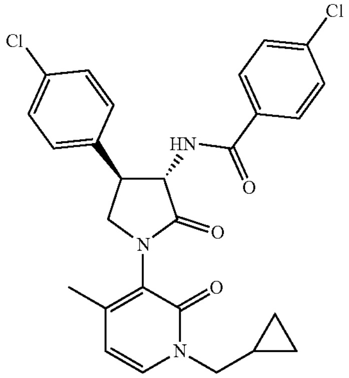 [SMILES: Cc1ccn(CC2CC2)c(=O)c1N1C[C@@H](c2ccc(Cl)cc2)[C@H](NC(=O)c2ccc(Cl)cc2)C1=O] | 510.2 | Method D, RT = 1.937 min, 97.2% | $^1$H NMR (400 MHz, DMSO-d$_6$) δ = 9.08-9.02 (m, 1H), 7.90-7.86 (m, 2H), 7.71-7.67 (m, 1H), 7.60-7.47 (m, 3H), 7.46-7.31 (m, 3H), 6.24-6.20 (m, 1H), 5.36-4.62 (m, 1H), 4.15-3.82 (m, 3H), 3.81-3.47 (m, 2H), 2.22-2.07 (2s, 3H), 1.31-1.16 (m, 1H), 0.54-0.41 (m, 2H), 0.41-0.28 (m, 2H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 426 | 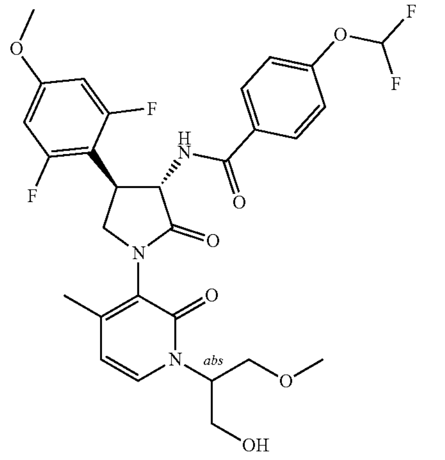 [SMILES: COCC(CO)n1ccc(C)c(N2C[C@@H](c3c(F)cc(OC)cc3F)[C@H](NC(=O)c3ccc(OC(F)F)cc3)C2=O)c1=O] | 608.3 | Method D, RT = 1.539 min, 97.8% | $^1$H NMR (400 MHz, DMSO-d$_6$) δ = 9.17-8.79 (m, 1H), 8.01-7.80 (m, 2H), 7.68-7.56 (m, 1H), 7.56-7.05 (m, 3H), 6.79-6.74 (m, 2H), 6.30-6.10 (m, 1H), 5.39-4.78 (m, 3H), 4.32-4.00 (m, 2H), 3.78-3.75 (2s, 3H), 3.74-3.58 (m, 3H), 3.51-3.48 (m, 1H), 3.53-3.44 (m, 1H), 3.25-3.18 (2s, 3H), 2.26-1.91 (2s, 3H). (mixture of interconvertible atropisomers) |
| 427 | 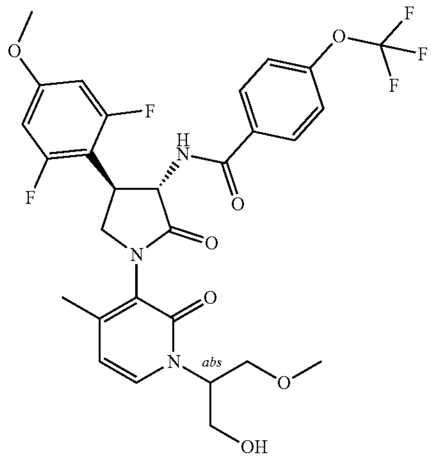 [SMILES: COCC(CO)n1ccc(C)c(N2C[C@@H](c3c(F)cc(OC)cc3F)[C@H](NC(=O)c3ccc(OC(F)(F)F)cc3)C2=O)c1=O] | 626.2 | Method D, RT = 1.759 min, 98.3% | $^1$H NMR (400 MHz, DMSO-d$_6$) δ = 9.23-8.88 (m, 1H), 8.04-7.87 (m, 2H), 7.71-7.55 (m, 1H), 7.55-7.35 (m, 2H), 6.85-6.62 (m, 2H), 6.29-6.12 (m, 1H), 5.39-4.82 (m, 3H), 4.32-4.02 (m, 2H), 3.77-3.74 (2s, 3H), 3.74-3.57 (m, 4H), 3.53-3.50 (m, 1H), 3.23-3.19 (2s, 3H), 2.23-2.00 (2s, 3H). (mixture of interconvertible atropisomers) |
| 428 | 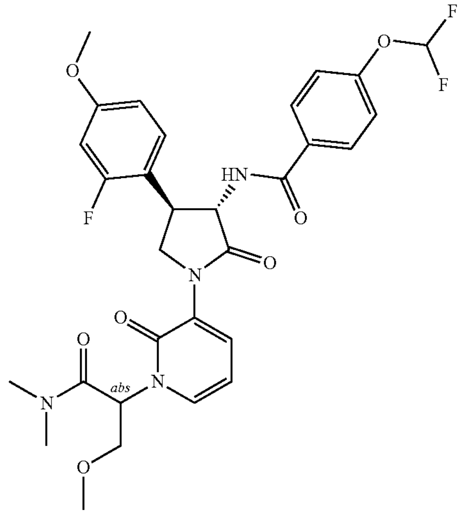 [SMILES: COCC(C(=O)N(C)C)n1cccc(N2C[C@@H](c3ccc(OC)cc3F)[C@H](NC(=O)c3ccc(OC(F)F)cc3)C2=O)c1=O] | 617.7 | Method D, RT = 1.58 min, 100% | $^1$H NMR (400 MHz, DMSO-d$_6$) δ = 8.95 (d, J = 8.8 Hz, 1H), 7.97-7.83 (m, 2H), 7.66-7.56 (m, 2H), 7.54-7.48 (m, 1H), 7.35 (t, J = 76.0 Hz, 1H), 7.31-7.24 (m, 2H), 6.87-6.73 (m, 2H), 6.31 (t, J = 7.0 Hz, 1H), 5.16-5.04 (m, 1H), 4.15-3.98 (m, 2H), 3.93-3.80 (m, 2H), 3.78 (s, 3H), 3.68-3.51 (m, 2H), 3.27 (s, 3H), 3.01 (s, 3H), 2.99 (s, 3H). |

TABLE 2-continued

| Ex | Structure | LCMS (M + H)+ | HPLC Method, RT (min.) & Purity | $^1$H NMR |
|---|---|---|---|---|
| 429 | 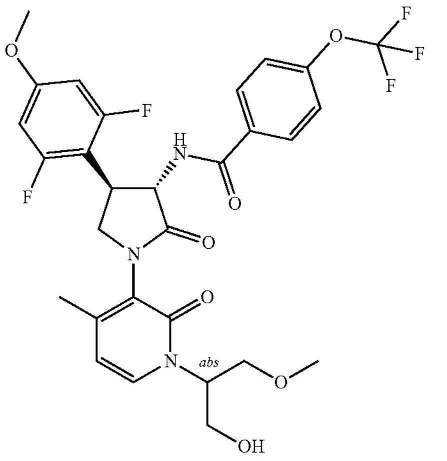 [SMILES: COCC(CO)n1ccc(C)c(N2C[C@@H](c3c(F)cc(OC)cc3F)[C@H](NC(=O)c3ccc(OC(F)(F)F)cc3)C2=O)c1=O] | 626.3 | Method D, RT = 1.775 min, 100% | $^1$H NMR (400 MHz, DMSO-d$_6$) δ = 9.27-9.01 (m, 1H), 8.05-7.81 (m, 2H), 7.69-7.53 (m, 1H), 7.53-7.32 (m, 2H), 6.79-6.75 (m, 2H), 6.32-6.13 (m, 1H), 5.40-4.81 (m, 3H), 4.32-4.01 (m, 2H), 3.76-3.74 (2s, 3H), 3.74-3.57 (m, 3H), 3.51-3.49 (m, 1H), 3.55-3.46 (m, 1H), 3.22 (s, 3H), 2.24-1.96 (2s, 3H). (mixture of interconvertible atropisomers) |
| 430 | 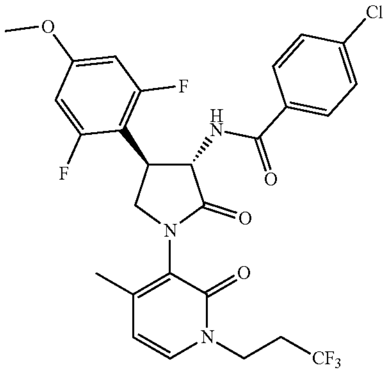 [SMILES: COc1cc(F)c([C@@H]2CN(c3c(C)ccn(CCC(F)(F)F)c3=O)C(=O)[C@H]2NC(=O)c2ccc(Cl)cc2)c(F)c1] | 584.2 | Method D, RT = 1.89 min, 99% | $^1$H NMR (400 MHz, DMSO-d$_6$) δ = 9.21-8.84 (m, 1H), 7.92-7.78 (m, 2H), 7.76-7.64 (m, 1H), 7.61-7.43 (m, 2H), 6.79-6.75 (m, 2H), 6.34-6.17 (m, 1H), 5.37-4.78 (m, 1H), 4.31-4.00 (m, 4H), 3.78-3.75 (2s, 3H), 3.55-3.40 (m, 1H), 2.83-2.66 (m, 2H), 2.24-1.98 (2s, 3H). (mixture of interconvertible atropisomers) |
| 431 | 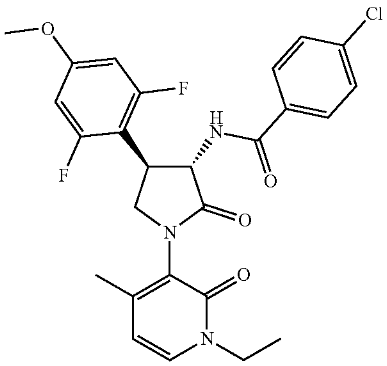 [SMILES: CCn1ccc(C)c(N2C[C@@H](c3c(F)cc(OC)cc3F)[C@H](NC(=O)c3ccc(Cl)cc3)C2=O)c1=O] | 516.2 | Method D, RT = 1.69 min, 94% | $^1$H NMR (400 MHz, DMSO-d$_6$) δ = 9.21-8.89 (m, 1H), 7.91-7.76 (m, 2H), 7.73-7.61 (m, 1H), 7.61-7.39 (m, 2H), 6.79-6.75 (m, 2H), 6.29-6.13 (m, 1H), 5.38-4.77 (m, 1H), 4.30-3.82 (m, 4H), 3.77-3.75 (2s, 3H), 3.55-3.44 (m, 1H), 2.21-2.01 (2s, 3H), 1.30-1.13 (m, 3H). (mixture of interconvertible atropisomers) |

TABLE 2-continued
| Ex | Structure | LCMS (M + H)+ | HPLC Method, RT (min.) & Purity | $^1$H NMR |
|---|---|---|---|---|
| 432 | 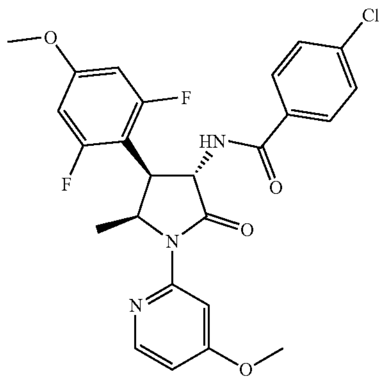 [SMILES: COc1ccnc(N2C(=O)[C@@H](NC(=O)c3ccc(Cl)cc3)[C@H](c3c(F)cc(OC)cc3F)[C@@H]2C)c1] | 502.2 | Method D, RT = 2.02 min, 100% | $^1$H NMR (400 MHz, DMSO-d$_6$) δ = 8.90 (d, J = 8.6 Hz, 1H), 8.26 (d, J = 5.9 Hz, 1H), 7.97 (d, J = 2.2 Hz, 1H), 7.93-7.80 (m, 2H), 7.58-7.08 (m, 2H), 6.93-6.71 (m, 3H), 5.72-5.67 (m, 1H), 5.02-4.88 (m, 1H), 4.32-4.27 (m, 1H), 3.84 (s, 3H), 3.78 (s, 3H), 1.17 (d, J = 6.6 Hz, 3H). |
| 433 | 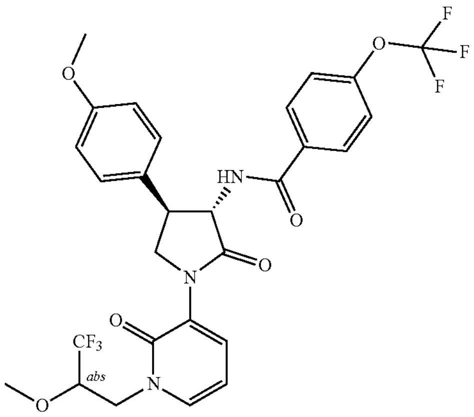 [SMILES: COc1ccc([C@@H]2CN(c3cccn(CC(OC)C(F)(F)F)c3=O)C(=O)[C@H]2NC(=O)c2ccc(OC(F)(F)F)cc2)cc1] | 614.2 | Method D, RT = 1.97 min, 100% | $^1$H NMR (400 MHz, DMSO-d$_6$) δ = 9.02 (d, J = 8.3 Hz, 1H), 8.05-7.86 (m, 2H), 7.72-7.59 (m, 2H), 7.47 (d, J = 8.3 Hz, 2H), 7.35 (d, J = 8.6 Hz, 2H), 6.91 (d, J = 8.6 Hz, 2H), 6.39 (t, J = 7.1 Hz, 1H), 5.08-4.97 (m, 1H), 4.46-4.38 (m, 1H), 4.33-4.24 (m, 1H), 4.16 (t, J = 7.8 Hz, 1H), 4.02 (dd, J = 13.3, 8.7 Hz, 1H), 3.81-3.72 (m, 2H), 3.72 (s, 3H), 3.36 (s, 3H). |
| 434 | 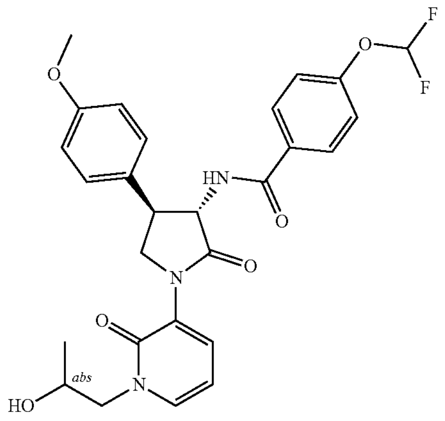 [SMILES: COc1ccc([C@@H]2CN(c3cccn(CC(C)O)c3=O)C(=O)[C@H]2NC(=O)c2ccc(OC(F)F)cc2)cc1] | 528.3 | Method D, RT = 1.412 min, 98% | $^1$H NMR (400 MHz, DMSO-d$_6$) δ = 8.96-8.89 (m, 1H), 7.96-7.89 (m, 2H), 7.64-7.55 (m, 2H), 7.35-7.33 (m, 2H), 7.33 (t, J = 76.0 Hz, 1H), 7.25-7.20 (m, 2H), 6.95-6.88 (m, 2H), 6.34-6.26 (m, 1H), 5.05-4.91 (m, 2H), 4.12-4.01 (m, 2H), 3.95-3.88 (m, 1H), 3.80-3.62 (m, 6H), 1.09 (d, J = 6.4 Hz, 3H). |

TABLE 2-continued
| Ex | Structure | LCMS (M + H)+ | HPLC Method, RT (min.) & Purity | $^1$H NMR |
|---|---|---|---|---|
| 435 | 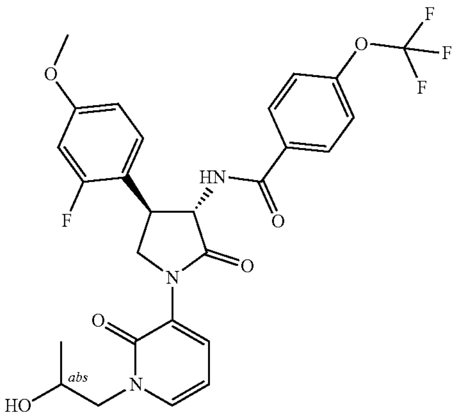 [SMILES: COc1ccc([C@@H]2CN(c3cccn(CC(C)O)c3=O)C(=O)[C@H]2NC(=O)c2ccc(OC(F)(F)F)cc2)c(F)c1] | 564.2 | Method D, RT = 1.66 min, 100% | $^1$H NMR (400 MHz, DMSO-$d_6$) δ = 9.06 (d, J = 8.8 Hz, 1H), 8.03-7.86 (m, 2H), 7.62-7.57 (m, 2H), 7.55-7.38 (m, 3H), 6.88-6.71 (m, 2H), 6.31 (t, J = 7.1 Hz, 1H), 5.12 (dd, J = 11.2, 8.8 Hz, 1H), 4.95-4.91 (m, 1H), 4.16-3.87 (m, 4H), 3.78 (s, 3H), 3.77-3.61 (m, 2H), 1.08 (d, J = 6.4 Hz, 3H). |
| 436 | 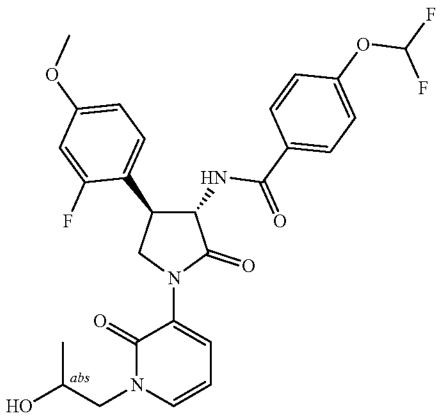 [SMILES: COc1ccc([C@@H]2CN(c3cccn(CC(C)O)c3=O)C(=O)[C@H]2NC(=O)c2ccc(OC(F)F)cc2)c(F)c1] | 546.2 | Method D, RT = 1.48 min, 100% | $^1$H NMR (400 MHz, DMSO-$d_6$) δ = 9.02-8.87 (m, 1H), 7.91 (d, J = 7.8 Hz, 2H), 7.66-7.55 (m, 2H), 7.53-7.46 (m, 1H), 7.35 (t, J = 72.0 Hz, 1H), 7.28-7.24 (m, 2H), 6.89-6.70 (m, 2H), 6.31 (t, J = 7.1 Hz, 1H), 5.17-5.02 (m, 1H), 4.95-4.91 (m, 1H), 4.14-3.86 (m, 4H), 3.77(s, 3H), 3.76-3.63 (m, 2H), 1.09 (d, J = 6.1 Hz, 3H). |
| 437 | 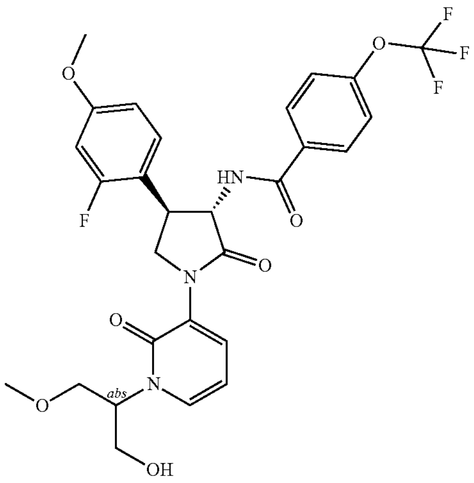 [SMILES: COCC(CO)n1cccc(N2C[C@@H](c3ccc(OC)cc3F)[C@H](NC(=O)c3ccc(OC(F)(F)F)cc3)C2=O)c1=O] | 594.3 | Method D, RT = 1.68 min, 100% | $^1$H NMR (400 MHz, DMSO-$d_6$) δ = 9.06 (br d, J = 8.8 Hz, 1H), 7.97 (d, J = 8.8 Hz, 2H), 7.69 (br d, J = 7.1 Hz, 1H), 7.57 (br d, J = 7.3 Hz, 1H), 7.54-7.38 (m, 3H), 6.90-6.73 (m, 2H), 6.41-6.26 (m, 1H), 5.19-4.98 (m, 3H), 4.18-4.10 (m, 1H), 4.04-3.94 (m, 1H), 3.79 (s, 3H) 3.77-3.59 (m, 5H), 3.23 (s, 3H). |

TABLE 2-continued

| Ex | Structure | LCMS (M + H)+ | HPLC Method, RT (min.) & Purity | $^1$H NMR |
|---|---|---|---|---|
| 438 | 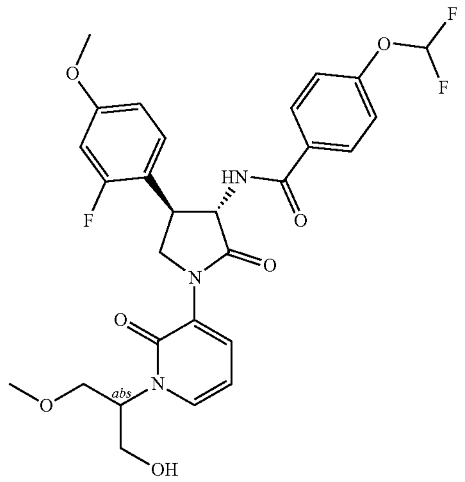 [SMILES: COCC(CO)n1cccc(N2C[C@@H](c3ccc(OC)cc3F)[C@H](NC(=O)c3ccc(OC(F)F)cc3)C2=O)c1=O] | 576.2 | Method D, RT = 1.50 min, 98.8% | $^1$H NMR (400 MHz, DMSO-$d_6$) δ = 8.94 (d, J = 8.6 Hz, 1H), 7.96-7.86 (m, 2H), 7.68 (dd, J = 7.0, 1.8 Hz, 1H), 7.56 (dd, J = 7.2, 1.8 Hz, 1H), 7.53-7.48 (m, 1H), 7.33 (t, J = 74.0 Hz, 1H), 7.28-7.24 (m, 2H), 6.86-6.70 (m, 2H), 6.34 (t, J = 7.1 Hz, 1H), 5.19-4.98 (m, 3H), 4.18-4.10 (m, 1H), 4.04-3.94 (m, 1H), 3.79 (s, 3H) 3.78-3.59 (m, 5H), 3.23 (s, 3H). |
| 439 | 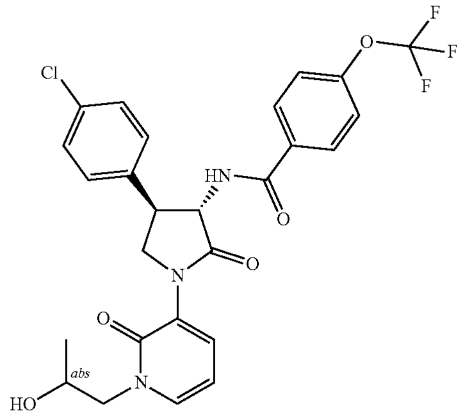 [SMILES: CC(O)Cn1cccc(N2C[C@@H](c3ccc(Cl)cc3)[C@H](NC(=O)c3ccc(OC(F)(F)F)cc3)C2=O)c1=O] | 550.2 | Method D, RT = 1.788 min, 100% | $^1$H NMR (400 MHz, DMSO-$d_6$) δ = 9.13-8.99 (m, 1H), 7.98 (d, J = 8.6 Hz, 2H), 7.68-7.55 (m, 2H), 7.51-7.45 (m, 4H), 7.44-7.34 (m, 2H), 6.31 (t, J = 7.1 Hz, 1H), 5.10-4.99 (m, 1H), 4.99-4.84 (m, 1H), 4.18-4.01 (m, 2H), 3.96-3.86 (m, 1H), 3.84-3.75 (m, 2H), 3.71-3.61 (m, 1H), 1.08 (d, J = 6.4 Hz, 3H). |
| 440 | 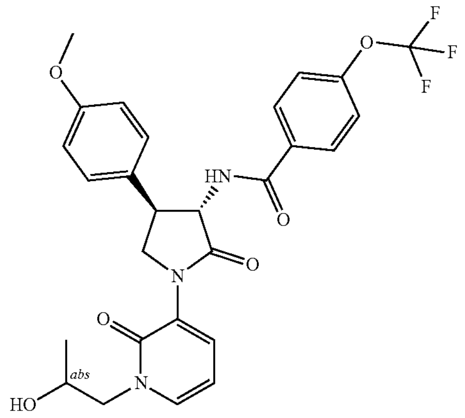 [SMILES: COc1ccc([C@@H]2CN(c3cccn(CC(C)O)c3=O)C(=O)[C@H]2NC(=O)c2ccc(OC(F)(F)F)cc2)cc1] | 546.2 | Method D, RT = 1.596 min, 100% | $^1$H NMR (400 MHz, DMSO-$d_6$) δ = 9.02 (d, J = 8.8 Hz, 1H), 8.05-7.85 (m, 2H), 7.67-7.55 (m, 2H), 7.47 (d, J = 7.8 Hz, 2H), 7.40-7.25 (m, 2H), 6.90 (d, J = 8.8 Hz, 2H), 6.30 (t, J = 7.0 Hz, 1H), 5.01 (dd, J = 11.0, 8.8 Hz, 1H), 4.97-4.86 (m, 1H), 4.20-4.03 (m, 2H), 3.98-3.86 (m, 1H), 3.72 (s, 3H), 3.82-3.56 (m, 3H), 1.09 (d, J = 6.4 Hz, 3H). |

TABLE 2-continued

| Ex | Structure | LCMS (M + H)+ | HPLC Method, RT (min.) & Purity | $^1$H NMR |
|---|---|---|---|---|
| 441 | 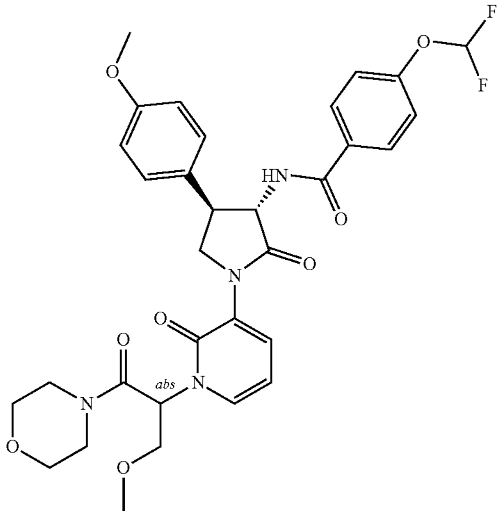 [SMILES: COCC(C(=O)N1CCOCC1)n1cccc(N2C[C@@H](c3ccc(OC)cc3)[C@H](NC(=O)c3ccc(OC(F)F)cc3)C2=O)c1=O] | 641.3 | Method D, RT = 1.505 min, 100% | $^1$H NMR (400 MHz, DMSO-d6) δ = 8.97-8.84 (m, 1H), 7.93 (d, J = 8.1 Hz, 2H), 7.72-7.59 (m, 2H), 7.36-7.34 (m, 2H), 7.33 (t, J = 74.0 Hz, 1H), 7.27-7.25 (m, 2H), 6.90 (d, J = 8.8 Hz, 2H), 6.47-6.33 (m, 1H), 6.07-6.04 (m, 1H), 5.05-4.93 (m, 1H), 4.12-4.04 (m, 1H), 3.93-3.74 (m, 3H), 3.72 (s, 3H), 3.64-3.44 (m, 6H), 3.28 (s, 3H), 3.38-3.19 (m, 3H). |
| 442 | 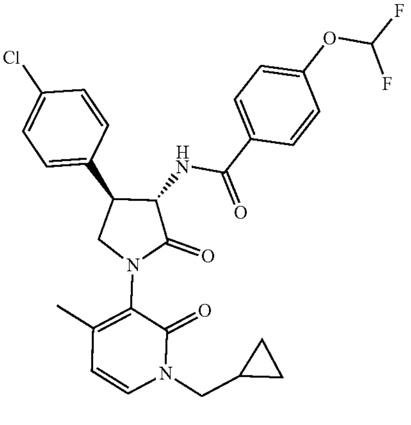 [SMILES: Cc1ccn(CC2CC2)c(=O)c1N1C[C@@H](c2ccc(Cl)cc2)[C@H](NC(=O)c2ccc(OC(F)F)cc2)C1=O] | 542.2 | Method D, RT = 1.901 min, 97.7% | $^1$H NMR (400 MHz, DMSO-$d_6$) δ = 9.02-8.97 (m, 1H), 7.99-7.85 (m, 2H), 7.71-7.67 (m, 1H), 7.56-7.47 (m, 1H), 7.45-7.12 (m, 6H), 6.25-6.21 (m, 1H), 5.33-4.62 (m, 1H), 4.17-3.94 (m, 1H), 4.17-3.82 (m, 2H), 3.81-3.47 (m, 2H), 2.21-2.07 (2s, 3H), 1.28-1.16 (m, 1H), 0.52-0.45 (m, 2H), 0.42-0.34 (m, 2H). (mixture of interconvertible atropisomers) |
| 443 | 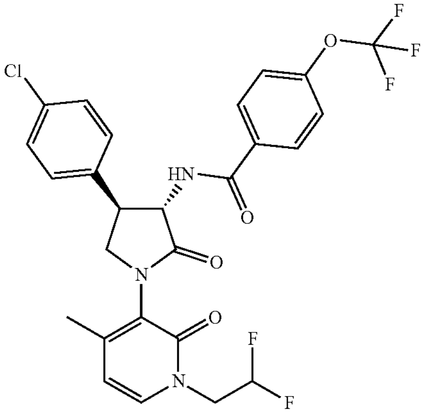 [SMILES: Cc1ccn(CC(F)F)c(=O)c1N1C[C@@H](c2ccc(Cl)cc2)[C@H](NC(=O)c2ccc(OC(F)(F)F)cc2)C1=O] | 570.2 | Method D, RT = 2.006 min, 100% | $^1$H NMR (400 MHz, DMSO-$d_6$) δ = 9.15-9.03 (m, 1H), 8.03-7.94 (m, 2H), 7.67-7.63 (m, 1H), 7.55-7.37 (m, 6H), 6.50-6.15 (m, 1H), 6.33-6.29 (m, 1H) 5.36-4.67 (m, 1H), 4.51-4.35 (m, 2H), 4.16-3.50 (m, 3H), 2.26-2.12 (2s, 3H). (mixture of interconvertible atropisomers) |

TABLE 2-continued

| Ex | Structure | LCMS (M + H)+ | HPLC Method, RT (min.) & Purity | $^{1}H$ NMR |
|---|---|---|---|---|
| 444 | 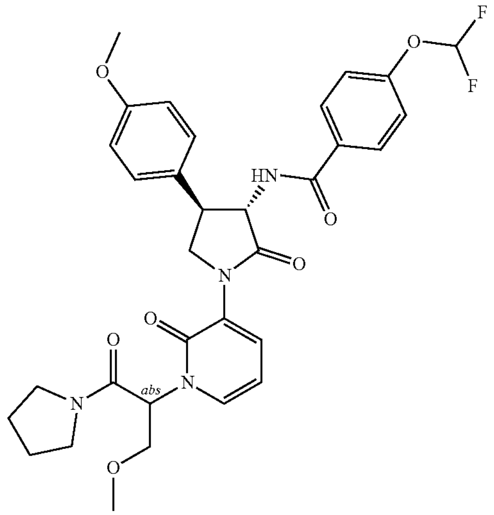 [SMILES: COCC(C(=O)N1CCCC1)n1cccc(N2C[C@@H](c3ccc(OC)cc3)[C@H](NC(=O)c3ccc(OC(F)F)cc3)C2=O)c1=O] | 625.3 | Method D, RT = 1.594 min, 100% | $^{1}H$ NMR (400 MHz, DMSO-$d_6$) δ = 8.91 (d, J = 9.0 Hz, 1H), 7.95-7.88 (m, 2H), 7.76-7.72 (m, 1H), 7.64-7.59 (m, 1H), 7.35-7.33 (m, 2H), 7.33 (t, J = 72.0 Hz, 1H), 7.28-7.24 (m, 2H), 6.94-6.83 (m, 2H), 6.43-6.35 (m, 1H), 5.95-5.87 (m, 1H), 5.03-4.94 (m, 1H), 4.05 (br d, J = 1.2 Hz, 1H), 3.92-3.84 (m, 1H), 3.80-3.75 (m, 2H), 3.72 (s, 3H), 3.66-3.59 (m, 2H), 3.57-3.49 (m, 2H), 3.35-3.29 (m, 1H), 3.27 (s, 3H), 1.96-1.84 (m, 2H), 1.82-1.70 (m, 2H). |
| 445 | 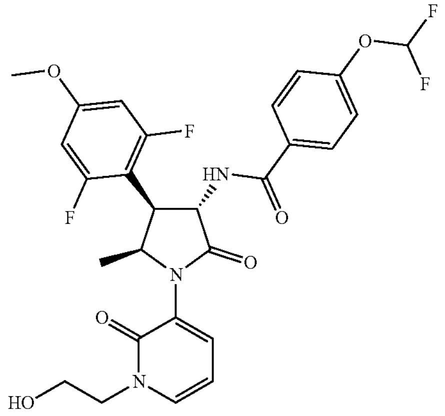 [SMILES: COc1cc(F)c([C@H]2[C@H](NC(=O)c3ccc(OC(F)F)cc3)C(=O)N(c3cccn(CCO)c3=O)[C@H]2C)c(F)c1] | 564.2 | Method D, RT = 1.49 min, 100% | $^{1}H$ NMR (400 MHz, DMSO-$d_6$) δ = 8.86 (d, J = 8.6 Hz, 1H), 7.95-7.82 (m, 2H), 7.66 (dd, J = 6.6 Hz, 2.0, 1H), 7.58 (dd, J = 6.6, 2.0, Hz, 1H), 7.35 (t, J = 73.6 Hz, 1H), 7.28-7.26 (m, 2H), 6.85-6.65 (m, 2H), 6.31 (t, J = 7.0 Hz, 1H), 5.66 (dd, J = 11.9, 8.7 Hz, 1H), 4.94 (t, J = 5.3 Hz, 1H), 4.69-4.56 (m, 1H), 4.30 (dd, J = 12.0, 8.1 Hz, 1H), 4.16-4.03 (m, 1H), 3.99-3.89 (m, 1H), 3.76 (s, 3H), 3.71-3.57 (m, 2H), 0.91 (d, J = 6.6 Hz, 3H). |
| 446 | 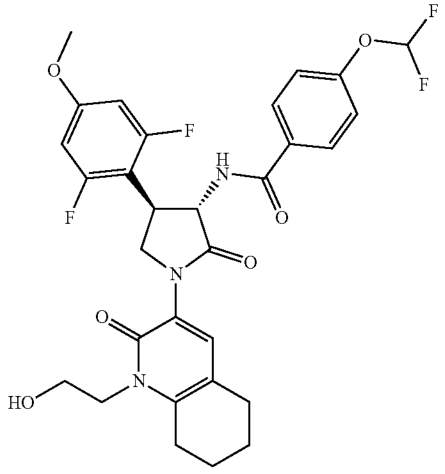 [SMILES: COc1cc(F)c([C@@H]2CN(c3cc4c(n(CCO)c3=O)CCCC4)C(=O)[C@H]2NC(=O)c2ccc(OC(F)F)cc2)c(F)c1] | 604.3 | Method D, RT = 1.792 min, 100% | $^{1}H$ NMR (400 MHz, DMSO-$d_6$) δ = 9.01-8.96 (m, 1H), 7.91-7.85 (m, 2H), 7.34 (t, J = 73.2 Hz, 1H), 7.34 (s, 1H), 7.29-7.21 (m, 2H), 6.80-6.72 (m, 2H), 5.14-5.06 (m, 1H), 5.00-4.92 (m, 1H), 4.14-4.01 (m, 3H), 3.98-3.90 (m, 2H), 3.76 (s, 3H), 3.66-3.58 (m, 2H), 2.86-2.79 (m, 2H), 2.56-2.47 (m, 2H), 1.81-1.71 (m, 2H), 1.70-1.60 (m, 2H). |

TABLE 2-continued

| Ex | Structure | LCMS (M + H)+ | HPLC Method, RT (min.) & Purity | $^1$H NMR |
|---|---|---|---|---|
| 447 | 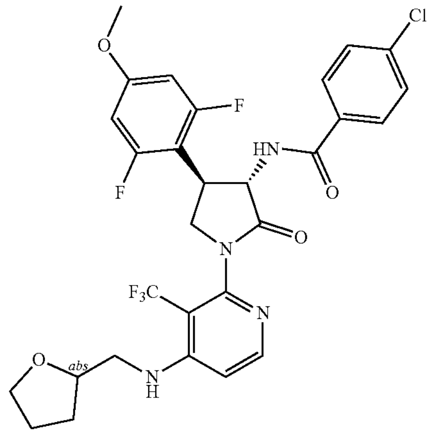 [SMILES: COc1cc(F)c([C@@H]2CN(c3nccc(NCC4CCCO4)c3C(F)(F)F)C(=O)[C@H]2NC(=O)c2ccc(Cl)cc2)c(F)c1] | 625.2 | Method D, RT = 2.1 min, 100% | $^1$H NMR (400 MHz, DMSO-$d_6$) δ = 9.14-8.95 (m, 1H), 8.33-8.14 (m, 1H), 7.89-7.76 (m, 2H), 7.56 (d, J = 8.6 Hz, 2H), 6.96-6.86 (m, 1H), 6.78 (d, J = 11.0 Hz, 2H), 6.44-6.29 (m, 1H), 5.17-5.05 (m, 1H), 4.33-4.02 (m, 3H), 3.80 (s, 3H), 3.79-3.68 (m, 1H), 3.68-3.57 (m, 1H), 3.46-3.36 (m, 2H), 1.98-1.76 (m, 2H), 1.68-1.54 (m, 1H), 1.21-1.04 (m, 2H). |
| 448 | 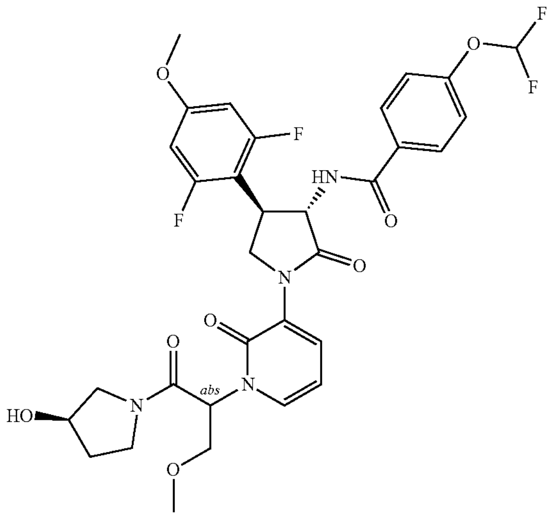 [SMILES: COCC(C(=O)N1CC[C@@H](O)C1)n1cccc(N2C[C@@H](c3c(F)cc(OC)cc3F)[C@H](NC(=O)c3ccc(OC(F)F)cc3)C2=O)c1=O] | 677.2 | Method D, RT = 1.71 min, 100% | $^1$H NMR (400 MHz, DMSO-$d_6$) δ = 9.02-8.98 (m, 1H), 7.88 (d, J = 8.1 Hz, 2H), 7.83-7.73 (m, 1H), 7.63-7.59 (m, 1H), 7.33 (t, J = 74.0 Hz, 1H), 7.28-7.24 (m, 2H), 6.84-6.67 (m, 2H), 6.40 (dt, J = 7.2, 1.6 Hz, 1H), 5.89-5.81 (m, 1H), 5.14-4.91 (m, 2H), 4.39-4.20 (m, 1H), 4.15-4.05 (m, 1H), 4.02-3.81 (m, 4H), 3.78 (s, 3H), 3.76-3.68 (m, 1H), 3.51-3.38 (m, 3H), 3.27 (2s, 3H), 2.02-1.66 (m, 2H). |
| 449 | 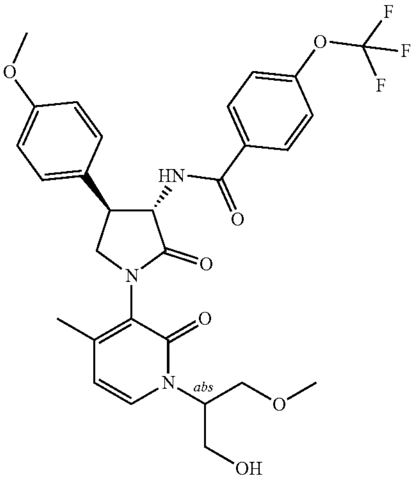 [SMILES: COCC(CO)n1ccc(C)c(N2C[C@@H](c3ccc(OC)cc3)[C@H](NC(=O)c3ccc(OC(F)(F)F)cc3)C2=O)c1=O] | 590.3 | Method D, RT = 1.72 min, 100% | $^1$H NMR (400 MHz, DMSO-$d_6$) δ = 9.08-7.02 (m, 1H), 8.07-7.90 (m, 2H), 7.67-7.54 (m, 1H), 7.54-7.41 (m, 2H), 7.38 (d, J = 8.5 Hz, 1H), 7.32 (d, J = 8.5 Hz, 1H), 6.98-6.78 (m, 2H), 6.21 (d, J = 7.5 Hz, 1H), 5.23-4.64 (m, 3H), 4.14-3.81 (m, 2H), 3.78-3.70 (m, 4H), 3.64-3.42 (m, 4H), 3.23-3.20 (2s, 3H), 2.20-2.08 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 450 | 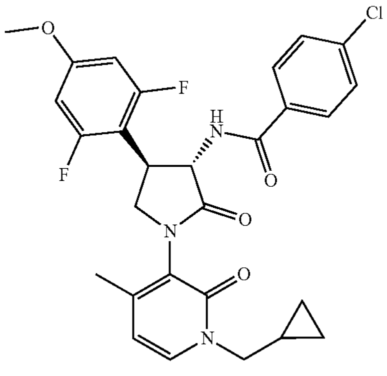 [SMILES: COc1cc(F)c([C@@H]2CN(c3c(C)ccn(CC4CC4)c3=O)C(=O)[C@H]2NC(=O)c2ccc(Cl)cc2)c(F)c1] | 542.2 | Method D, RT = 1.87 min, 97% | $^1$H NMR (400 MHz, DMSO-$d_6$) δ = 9.23-8.96 (m, 1H), 7.91-7.78 (m, 2H), 7.73-7.65 (m, 1H), 7.59-7.52 (m, 2H), 6.79-6.75 (m, 2H), 6.27-6.19 (m, 1H), 5.36-4.89 (m, 1H), 4.28-4.03 (m, 3H), 3.86-3.80 (m, 1H), 3.77-3.74 (2s, 3H), 3.58-3.45 (m, 1H), 2.26-1.96 (2s, 3H), 1.28-1.15 (m, 1H), 0.50-0.46 (m, 2H), 0.40-0.37 (m, 2H). (mixture of interconvertible atropisomers) |
| 451 | 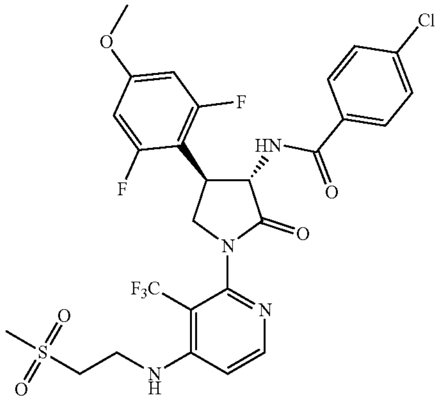 [SMILES: COc1cc(F)c([C@@H]2CN(c3nccc(NCCS(C)(=O)=O)c3C(F)(F)F)C(=O)[C@H]2NC(=O)c2ccc(Cl)cc2)c(F)c1] | 647.2 | Method C, RT = 1.88 min, 100% | $^1$H NMR (400 MHz, DMSO-$d_6$) δ = 9.09 (d, J = 8.8 Hz, 1H), 8.33-8.22 (m, 1H), 7.90-7.75 (m, 2H), 7.58-7.54 (m, 2H), 6.94-6.85 (m, 1H), 6.85-6.68 (m, 3H), 5.17-5.06 (m, 1H), 4.32-4.18 (m, 2H), 3.82-3.67 (m, 6H), 3.45 (t, J = 6.7 Hz, 2H), 3.07 (s, 3H). |
| 452 | 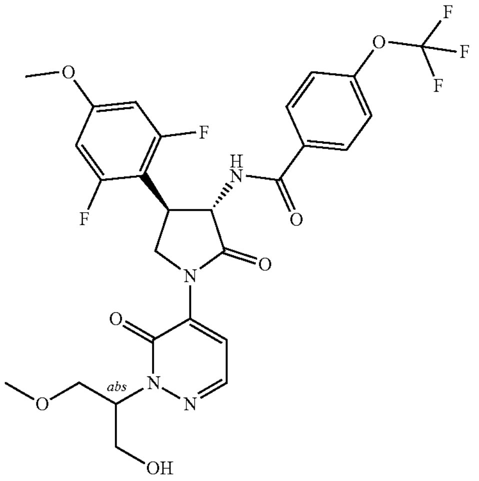 [SMILES: COCC(CO)n1nccc(N2C[C@@H](c3c(F)cc(OC)cc3F)[C@H](NC(=O)c3ccc(OC(F)(F)F)cc3)C2=O)c1=O] | 613.2 | Method D, RT = 2.002 min, 96% | $^1$H NMR (400 MHz, DMSO-$d_6$) δ = 9.16 (br s, 1H), 8.05 (d, J = 4.6 Hz, 1H), 7.94 (d, J = 8.8 Hz, 2H), 7.66 (d, J = 4.4 Hz, 1H), 7.49 (d, J = 8.8 Hz, 2H), 6.78 (d, J = 10.8 Hz, 2H), 5.34-5.22 (m, 1H), 5.08 (br d, J = 10.8 Hz, 1H), 4.98-4.81 (br s, 1H), 4.37-4.28 (m, 1H), 4.21-4.04 (m, 2H), 3.77 (s, 3H), 3.72-3.56 (m, 4H), 3.21 (s, 3H). |

TABLE 2-continued

| Ex | Structure | LCMS (M + H)+ | HPLC Method, RT (min.) & Purity | $^1$H NMR |
|---|---|---|---|---|
| 453 | 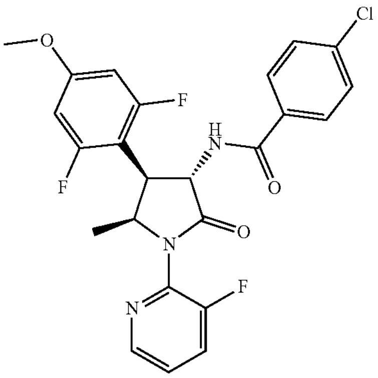 [SMILES: COc1cc(F)c([C@H]2[C@H](NC(=O)c3ccc(Cl)cc3)C(=O)N(c3ncccc3F)[C@H]2C)c(F)c1] | 490.2 | Method D, RT = 1.84 min, 96% | $^1$H NMR (400 MHz, DMSO-$d_6$) δ = 9.05 (d, J = 8.3 Hz, 1H), 8.41 (d, J = 4.6 Hz, 1H), 7.94-7.84 (m, 3H), 7.57-7.48 (m, 3H), 6.89-6.73 (m, 2H), 5.53 (dd, J = 10.8, 8.6 Hz, 1H), 4.84-4.70 (m, 1H), 4.37 (dd, J = 10.8, 8.6 Hz, 1H), 3.78 (s, 3H), 1.03 (d, J = 6.6 Hz, 3H). |
| 454 | 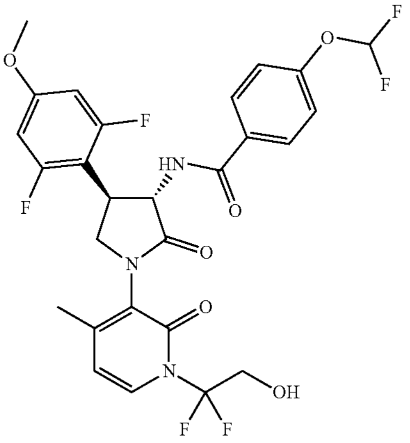 [SMILES: COc1cc(F)c([C@@H]2CN(c3c(C)ccn(C(F)(F)CO)c3=O)C(=O)[C@H]2NC(=O)c2ccc(OC(F)F)cc2)c(F)c1] | 600.2 | Method D, RT = 1.846 min, 96% | $^1$H NMR (400 MHz, DMSO-$d_6$) δ = 9.13-8.94 (m, 1H), 7.97-7.78 (m, 2H), 7.72-7.61 (m, 1H), 7.54-7.11 (m, 3H), 6.85-6.66 (m, 2H), 6.42-6.30 (m, 1H), 6.02-5.89 (m, 1H), 5.36-4.84 (m, 1H), 4.32-3.99 (m, 4H), 3.76 (2s, 3H), 3.59-3.52 (m, 1H), 2.26-2.08 (2s, 3H). (mixture of interconvertible atropisomers) |
| 455 | 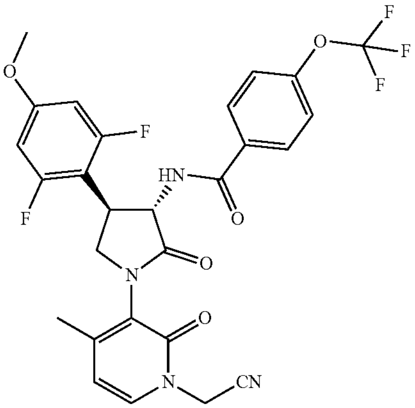 [SMILES: COc1cc(F)c([C@@H]2CN(c3c(C)ccn(CC#N)c3=O)C(=O)[C@H]2NC(=O)c2ccc(OC(F)(F)F)cc2)c(F)c1] | 577.2 | Method D, RT = 2.02 min, 98% | $^1$H NMR (400 MHz, DMSO-$d_6$) δ = 9.26-9.01 (m, 1H), 8.04-7.86 (m, 2H), 7.81-7.65 (m, 1H), 7.57-7.40 (m, 2H), 6.90-6.66 (m, 2H), 6.44-6.27 (m, 1H), 5.39-4.81 (m, 3H), 4.30-4.05 (m, 2H), 3.77 (s, 3H), 3.62-3.47 (m, 1H), 2.25-2.02 (2s, 3H). (mixture of interconvertible atropisomers) |

TABLE 2-continued

| Ex | Structure | LCMS (M + H)+ | HPLC Method, RT (min.) & Purity | $^{1}$H NMR |
|---|---|---|---|---|
| 456 | 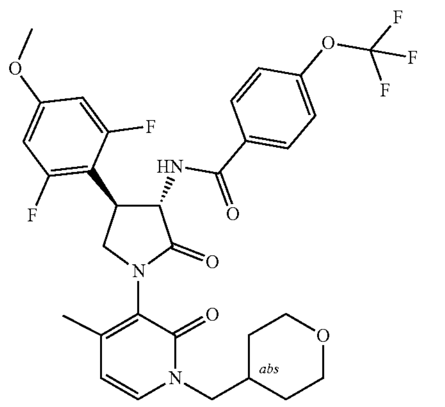 [SMILES: COc1cc(F)c([C@@H]2CN(c3c(C)ccn(CC4CCOCC4)c3=O)C(=O)[C@H]2NC(=O)c2ccc(OC(F)(F)F)cc2)c(F)c1] | 636.3 | Method D, RT = 1.904 min, 100% | $^{1}$H NMR (400 MHz, DMSO-$d_6$) δ = 9.30-8.92 (m, 1H), 8.10-7.83 (m, 2H), 7.73-7.53 (m, 1H), 7.53-7.23 (m, 2H), 6.84-6.60 (m, 2H), 6.30-6.13 (m, 1H), 5.43-4.78 (m, 1H), 4.34-4.02 (m, 2H), 3.95-3.69 (m, 4H), 3.70 (s, 3H), 3.56-3.43 (m, 1H), 3.27-3.13 (m, 2H), 2.22-2.04 (2s, 3H), 2.04-1.83 (m, 1H), 1.44-1.38 (m, 2H), 1.35-1.11 (m, 2H). (mixture of interconvertible atropisomers) |
| 457 | 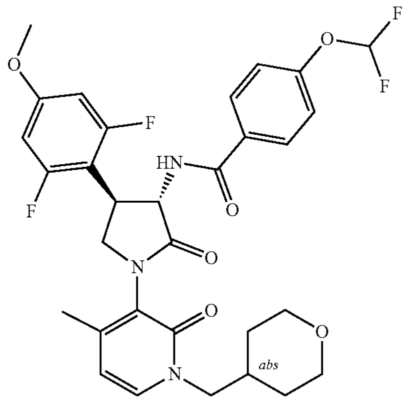 [SMILES: COc1cc(F)c([C@@H]2CN(c3c(C)ccn(CC4CCOCC4)c3=O)C(=O)[C@H]2NC(=O)c2ccc(OC(F)F)cc2)c(F)c1] | 618.3 | Method D, RT = 1.732 min, 100% | $^{1}$H NMR (400 MHz, DMSO-$d_6$) δ = 9.20-8.79 (m, 1H), 8.01-7.76 (m, 2H), 7.71-7.55 (m, 1H), 7.55-7.00 (m, 3H), 6.78-6.73 (m, 2H), 6.30-6.06 (m, 1H), 5.42-4.82 (m, 1H), 4.33-4.01 (m, 2H), 3.93-3.78 (m, 4H), 3.78-3.76 (2s, 3H), 3.55-3.43 (m, 1H), 3.27-3.15 (m, 2H), 2.23-2.03 (2s, 3H), 2.03-1.88 (m, 1H), 1.43 (m, 2H), 1.36-1.13 (m, 2H). (mixture of interconvertible atropisomers) |
| 458 | 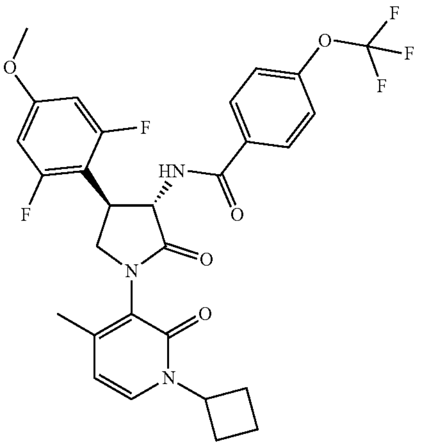 [SMILES: COc1cc(F)c([C@@H]2CN(c3c(C)ccn(C4CCC4)c3=O)C(=O)[C@H]2NC(=O)c2ccc(OC(F)(F)F)cc2)c(F)c1] | 592.2 | Method D, RT = 2.021 min, 100% | $^{1}$H NMR (400 MHz, DMSO-$d_6$) δ = 9.28-8.95 (m, 1H), 8.05-7.90 (m, 2H), 7.84-7.64 (m, 1H), 7.57-7.38 (m, 2H), 6.78-6.73 (m, 2H), 6.35-6.15 (m, 1H), 5.37-4.79 (m, 2H), 4.33-3.91 (m, 2H), 3.78-3.77 (2s, 3H), 3.74-3.63 (m, 1H), 3.59-3.37 (m, 1H), 2.40-2.20 (m, 3H), 2.20-1.97 (2s, 3H), 1.83-1.13 (m, 1H), 0.59-0.27 (m, 1H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 459 | 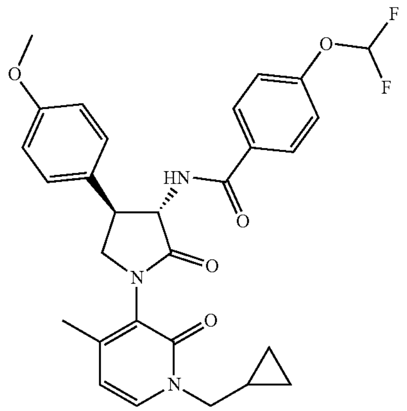 [SMILES: COc1ccc([C@@H]2CN(c3c(C)ccn(CC4CC4)c3=O)C(=O)[C@H]2NC(=O)c2ccc(OC(F)F)cc2)cc1] | 538.3 | Method D, RT = 1.714 min, 94% | $^1$H NMR (400 MHz, DMSO-$d_6$) δ = 9.03-8.82 (m, 1H), 7.99-7.89 (m, 2H), 7.70-7.66 (m, 1H), 7.55-7.06 (m, 5H), 6.92-6.89 (m, 2H), 6.24-6.21 (m, 1H), 5.29-4.62 (m, 1H), 4.13-3.81 (m, 2H), 3.79-3.59 (m, 5H), 3.48-3.44 (m, 1H), 2.25-2.04 (2s, 3H), 1.25-1.20 (m, 1H), 0.56-0.27 (m, 4H). (mixture of interconvertible atropisomers) |
| 460 | 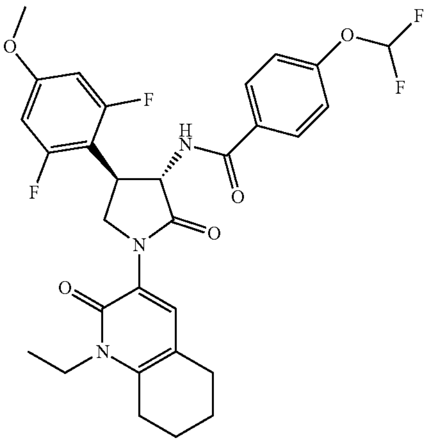 [SMILES: CCn1c2c(cc(N3C[C@@H](c4c(F)cc(OC)cc4F)[C@H](NC(=O)c4ccc(OC(F)F)cc4)C3=O)c1=O)CCCC2] | 588.3 | Method D, RT = 2.136 min, 100% | 1H NMR (400 MHz, DMSO-d6) δ = 8.99 (d, J = 8.8 Hz, 1H), 7.93-7.81 (m, 2H), 7.34 (t, J = 73.6 Hz, 1H), 7.34 (s, 1H), 7.27-7.25 (m, 2H), 6.76 (d, J = 10.8 Hz, 2H), 5.11 (dd, J = 11.1, 8.7 Hz, 1H), 4.16-3.99 (m, 3H), 3.94 (br d, J = 9.3 Hz, 2H), 3.76 (s, 3H), 2.75 (br t, J = 6.0 Hz, 2H), 2.52-2.47 (m, 2H), 1.85-1.72 (m, 2H), 1.70-1.54 (m, 2H), 1.18 (t, J = 7.0 Hz, 3H). |
| 461 | 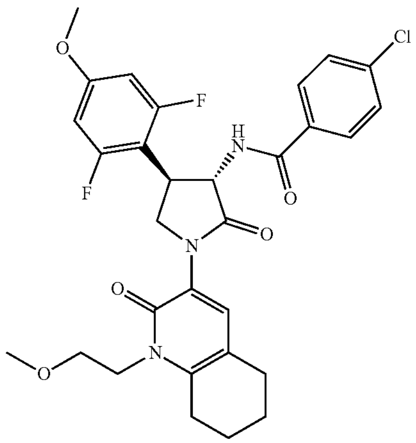 [SMILES: COCCn1c2c(cc(N3C[C@@H](c4c(F)cc(OC)cc4F)[C@H](NC(=O)c4ccc(Cl)cc4)C3=O)c1=O)CCCC2] | 586.2 | Method D, RT = 2.146 min, 95% | $^1$H NMR (400 MHz, DMSO-$d_6$) δ = 9.06 (d, J = 8.6 Hz, 1H), 7.91-7.73 (m, 2H), 7.62-7.44 (m, 2H), 7.34 (s, 1H), 6.76 (d, J = 10.8 Hz, 2H), 5.12 (dd, J = 11.1, 8.7 Hz, 1H), 4.22-4.03 (m, 3H), 3.98-3.90 (m, 2H), 3.76 (s, 3H), 3.55 (t, J = 5.6 Hz, 2H), 3.23 (s, 3H), 2.86-2.70 (m, 2H), 2.52-2.47 (m, 2H), 1.87-1.69 (m, 2H), 1.69-1.49 (m, 2H). |

TABLE 2-continued

| Ex | Structure | LCMS (M + H)+ | HPLC Method, RT (min.) & Purity | ¹H NMR |
|---|---|---|---|---|
| 462 | 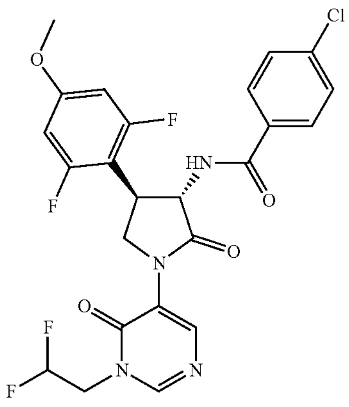 [SMILES: COc1cc(F)c([C@@H]2CN(c3cncn(CC(F)F)c3=O)C(=O)[C@H]2NC(=O)c2ccc(Cl)cc2)c(F)c1] | 639.2 | Method D, RT = 1.707 min, 98.7% | ¹H NMR (400 MHz, DMSO-$d_6$) δ = 9.08 (d, J = 8.6 Hz, 1H), 8.50 (s, 1H), 8.18 (s, 1H), 7.89-7.76 (m, 2H), 7.61-7.48 (m, 2H), 6.77 (d, J = 10.8 Hz, 2H), 6.40 (tt, J = 52.0, 4.2 Hz, 1H), 5.12 (dd, J = 11.1, 8.7 Hz, 1H), 4.62-4.36 (m, 2H), 4.18-4.04 (m, 1H), 4.04-3.86 (m, 2H), 3.76 (s, 3H). |
| 463 | 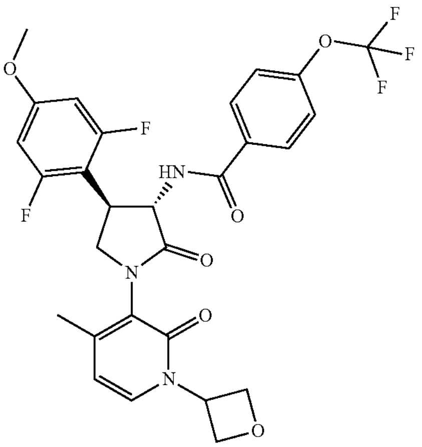 [SMILES: COc1cc(F)c([C@@H]2CN(c3c(C)ccn(C4COC4)c3=O)C(=O)[C@H]2NC(=O)c2ccc(OC(F)(F)F)cc2)c(F)c1] | 594.2 | Method D, RT = 1.777 min, 95% | ¹H NMR (400 MHz, DMSO-$d_6$) δ = 9.24-9.01 (m, 1H), 8.02-7.85 (m, 2H), 7.78-7.74 (m, 1H), 7.54-7.39 (m, 2H), 6.86-6.65 (m, 2H), 6.41-6.26 (m, 1H), 5.58-5.41 (m, 1H), 5.37-4.65 (m, 5H), 4.30-4.00 (m, 2H), 3.77-3.74 (2s, 3H), 3.53-3.50 (m, 1H), 2.25-2.02 (2s, 3H). (mixture of interconvertible atropisomers) |
| 464 | 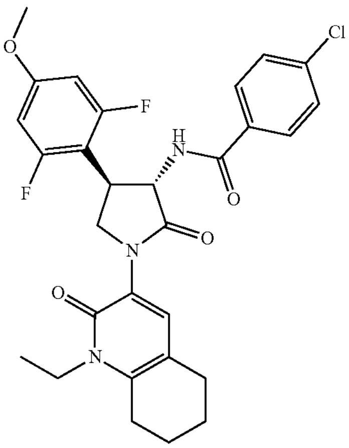 [SMILES: CCn1c2c(cc(N3C[C@@H](c4c(F)cc(OC)cc4F)[C@H](NC(=O)c4ccc(Cl)cc4)C3=O)c1=O)CCCC2] | 556.2 | Method D, RT = 2.145 min, 94% | ¹H NMR (400 MHz, DMSO-$d_6$) δ = 9.06 (d, J = 8.6 Hz, 1H), 7.83 (d, J = 8.6 Hz, 2H), 7.56 (d, J = 8.6 Hz, 2H), 7.32 (s, 1H), 6.76 (d, J = 10.8 Hz, 2H), 5.12 (dd, J = 11.1, 8.7 Hz, 1H), 4.15-3.98 (m, 3H), 3.94 (br d, J = 9.0 Hz, 2H), 3.76 (s, 3H), 2.81-2.66 (m, 2H), 2.52-2.47 (m, 2H), 1.87-1.70 (m, 2H), 1.70-1.56 (m, 2H), 1.18 (t, J = 7.0 Hz, 3H). |

TABLE 2-continued

| Ex | Structure | LCMS (M + H)+ | HPLC Method, RT (min.) & Purity | $^1$H NMR |
|---|---|---|---|---|
| 465 | 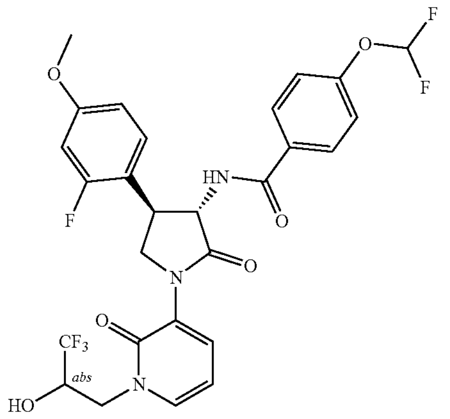 [SMILES: COc1ccc([C@@H]2CN(c3cccn(CC(O)C(F)(F)F)c3=O)C(=O)[C@H]2NC(=O)c2ccc(OC(F)F)cc2)c(F)c1] | 600.2 | Method D, RT = 1.85 min, 100% | $^1$H NMR (400 MHz, DMSO-d$_6$) δ = 8.96 (d, J = 8.3 Hz, 1H), 7.97-7.85 (m, 2H), 7.69 (dd, J = 6.8, 2.0 Hz, 1H), 7.65 (dd, J = 7.3, 2.0 Hz, 1H), 7.52 (d, J = 9.8 Hz, 1H), 7.35 (t, J = 73.6 Hz, 1H), 7.29-7.2 (m, 2H), 6.88-6.76 (m, 2H), 6.38 (t, J = 7.0 Hz, 1H), 5.12 (dd, J = 11.2, 8.8 Hz, 1H), 4.45 (dd, J = 13.0, 2.7 Hz, 1H), 4.39-4.30 (m, 1H), 4.13-4.06 (m, 1H), 4.05-3.97 (m, 1H), 3.90-3.82 (m, 1H), 3.77-3.72 (m, 4H). |
| 466 | 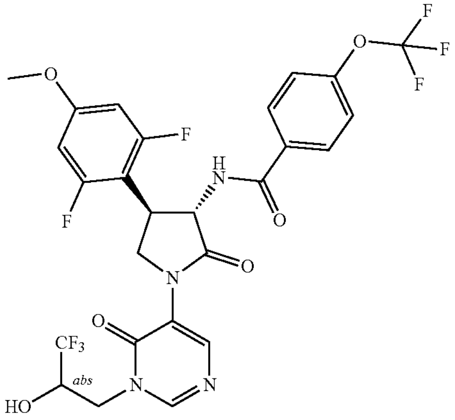 [SMILES: COc1cc(F)c([C@@H]2CN(c3cncn(CC(O)C(F)(F)F)c3=O)C(=O)[C@H]2NC(=O)c2ccc(OC(F)(F)F)cc2)c(F)c1] | 637.2 | Method D, RT = 2.07 min, 97% | $^1$H NMR (400 MHz, DMSO-d$_6$) δ = 9.16 (d, J = 8.6 Hz, 1H), 8.05 (d, J = 4.6 Hz, 1H), 7.99-7.85 (m, 2H), 7.74 (d, J = 4.6 Hz, 1H), 7.49 (d, J = 8.6 Hz, 2H), 6.79 (d, J = 10.8 Hz, 2H), 5.06 (br dd, J = 4.6, 1.7 Hz, 1H), 5.10-4.98 (m, 1H), 4.55-4.45 (m, 1H), 4.42-4.23 (m, 3H), 4.23-4.02 (m, 2H), 3.77 (s, 3H). |
| 467 | 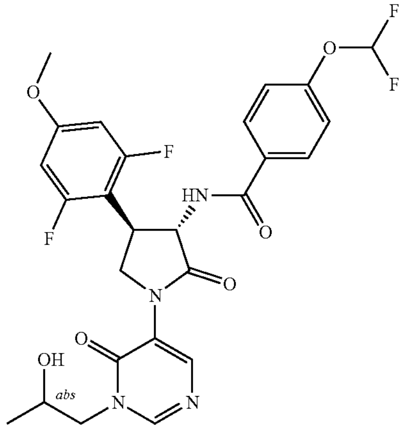 [SMILES: COc1cc(F)c([C@@H]2CN(c3cncn(CC(C)O)c3=O)C(=O)[C@H]2NC(=O)c2ccc(OC(F)F)cc2)c(F)c1] | 565.2 | Method D, RT = 1.619 min, 100% | $^1$H NMR (400 MHz, DMSO-d$_6$) δ = 9.02 (d, J = 8.6 Hz, 1H), 8.34 (s, 1H), 8.12 (s, 1H), 7.96-7.80 (m, 2H), 7.34 (t, J = 72.6 Hz, 1H), 7.30-7.24 (m, 2H), 6.77 (d, J = 10.8 Hz, 2H), 5.13-5.02 (m, 2H), 4.17-4.04 (m, 2H), 4.04-3.83 (m, 3H), 3.76 (s, 3H), 3.66 (dd, J = 13.1, 8.7 Hz, 1H), 1.11 (d, J = 6.4 Hz, 3H). |

TABLE 2-continued

| Ex | Structure | LCMS (M + H)+ | HPLC Method, RT (min.) & Purity | $^{1}$H NMR |
|---|---|---|---|---|
| 468 | 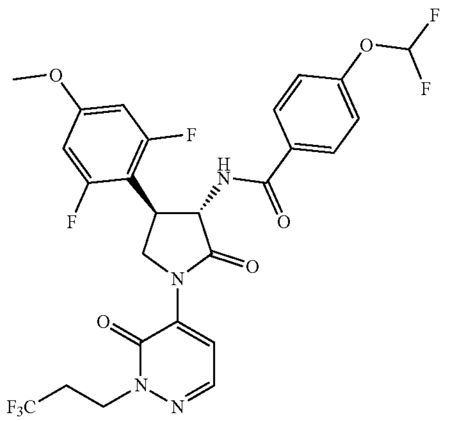 [SMILES: COc1cc(F)c([C@@H]2CN(c3ccnn(CCC(F)(F)F)c3=O)C(=O)[C@H]2NC(=O)c2ccc(OC(F)F)cc2)c(F)c1] | 603.1 | Method D, RT = 1.97 min, 100% | $^{1}$H NMR (400 MHz, DMSO-$d_6$) δ = 9.04 (d, J = 8.3 Hz, 1H), 8.04 (d, J = 4.6 Hz, 1H), 7.92-7.83 (m, 2H), 7.74 (d, J = 4.6 Hz, 1H), 7.35 (t, J = 73.6 Hz, 1H), 7.29-7.27 (m, 2H), 6.78 (d, J = 10.8 Hz, 2H), 5.05 (dd, J = 11.0, 8.3 Hz, 1H), 4.40-4.28 (m, 3H), 4.25-4.15 (m, 1H), 4.15-4.04 (m, 1H), 3.77 (s, 3H), 2.86-2.74 (m, 2H). |
| 469 | 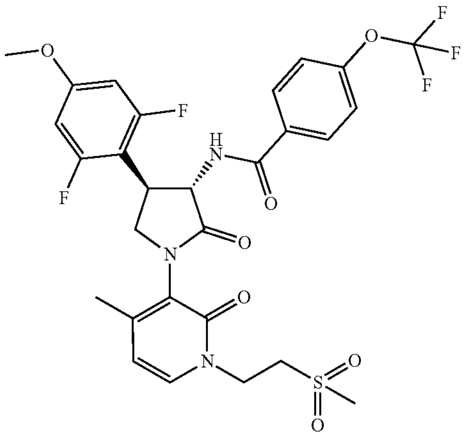 [SMILES: COc1cc(F)c([C@@H]2CN(c3c(C)ccn(CCS(C)(=O)=O)c3=O)C(=O)[C@H]2NC(=O)c2ccc(OC(F)(F)F)cc2)c(F)c1] | 644.2 | Method D, RT = 2.00 min, 100% | $^{1}$H NMR (400 MHz, DMSO-$d_6$) δ = 9.26-8.90 (m, 1H), 8.06-7.85 (m, 2H), 7.76-7.61 (m, 1H), 7.55-7.35 (m, 2H), 6.86-6.63 (m, 2H), 6.36-6.19 (m, 1H), 5.39-4.81 (m, 1H), 4.38-4.06 (m, 4H), 3.82-3.69 (2s, 3H), 3.61-3.46 (m, 3H), 3.10-2.97 (2s, 3H), 2.25-1.96 (2s, 3H). (mixture of interconvertible atropisomers) |
| 470 | 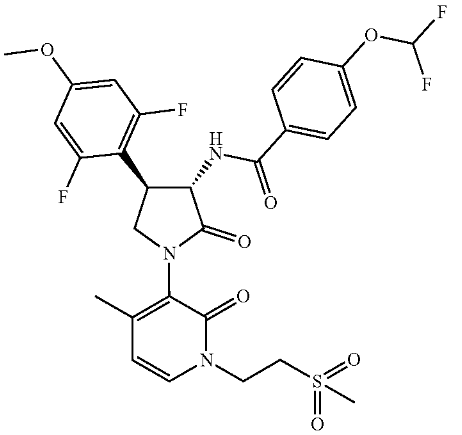 [SMILES: COc1cc(F)c([C@@H]2CN(c3c(C)ccn(CCS(C)(=O)=O)c3=O)C(=O)[C@H]2NC(=O)c2ccc(OC(F)F)cc2)c(F)c1] | 626.2 | Method D, RT = 1.84 min, 100% | $^{1}$H NMR (400 MHz, DMSO-$d_6$) δ = 9.19-8.87 (m, 1H), 7.99-7.80 (m, 2H), 7.73-7.63 (m, 1H), 7.56-7.05 (m, 3H), 6.87-6.56 (m, 2H), 6.34-6.17 (m, 1H), 5.39-4.84 (m, 1H), 4.44-4.05 (m, 4H), 3.84-3.73 (2s, 3H), 3.64-3.42 (m, 3H), 3.10-2.98 (2s, 3H), 2.24-1.98 (2s, 3H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 471 | 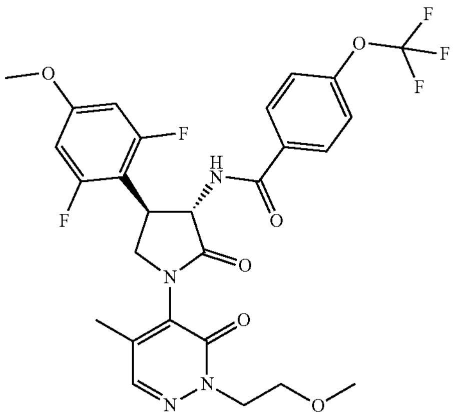 [SMILES: COCCn1ncc(C)c(N2C[C@@H](c3c(F)cc(OC)cc3F)[C@H](NC(=O)c3ccc(OC(F)(F)F)cc3)C2=O)c1=O] | 597.2 | Method D, RT = 2.12 min, 98% | $^1$H NMR (400 MHz, DMSO-d$_6$) δ = 9.25-9.00 (m, 1H), 8.08-7.76 (m, 3H), 7.59-7.35 (m, 2H), 6.90-6.64 (m, 2H), 5.38-4.75 (m, 1H), 4.42-4.10 (m, 4H), 3.81-3.74 (2s, 3H), 3.74-3.50 (m, 3H), 3.23 (s, 3H), 2.28-2.03 (2s, 3H). (mixture of interconvertible atropisomers) |
| 472 | 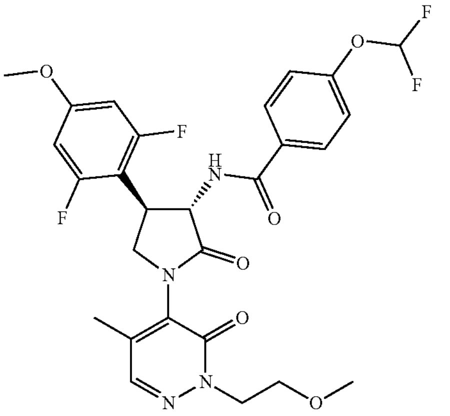 [SMILES: COCCn1ncc(C)c(N2C[C@@H](c3c(F)cc(OC)cc3F)[C@H](NC(=O)c3ccc(OC(F)F)cc3)C2=O)c1=O] | 579.2 | Method D, RT = 1.89 min, 100% | $^1$H NMR (400 MHz, DMSO-d$_6$) δ = 9.16-8.93 (m, 1H), 8.05-7.93 (m, 1H), 7.93-7.77 (m, 2H), 7.56-7.09 (m, 3H), 6.88-6.66 (m, 2H), 5.36-4.74 (m, 1H), 4.45-4.12 (m, 4H), 3.82-3.72 (2s, 3H), 3.72-3.51 (m, 3H), 3.23 (s, 3H), 2.26-2.02 (2s, 3H). (mixture of interconvertible atropisomers) |
| 473 | 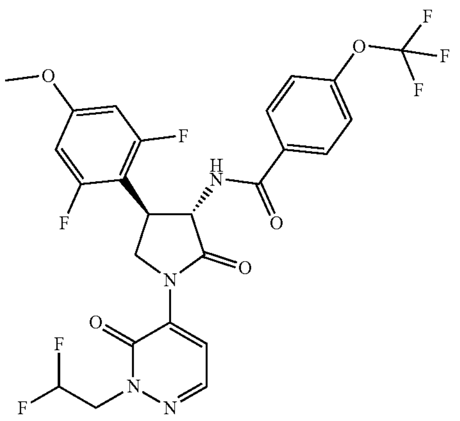 [SMILES: COc1cc(F)c([C@@H]2CN(c3ccnn(CC(F)F)c3=O)C(=O)[C@H]2NC(=O)c2ccc(OC(F)(F)F)cc2)c(F)c1] | 589.2 | Method D, RT = 2.17 min, 100% | $^1$H NMR (400 MHz, DMSO-d$_6$) δ = 9.16 (d, J = 8.3 Hz, 1H), 8.07 (d, J = 4.6 Hz, 1H), 7.94 (d, J = 8.8 Hz, 2H), 7.77 (d, J = 4.6 Hz, 1H), 7.50 (d, J = 8.6 Hz, 2H), 6.79 (d, J = 10.8 Hz, 2H), 6.40 (tt, J = 56.0, 4.0 Hz, 1H), 5.07 (dd, J = 11.0, 8.3 Hz, 1H), 4.56 (td, J = 14.4, 4.0 Hz, 2H), 4.42-4.30 (m, 1H), 4.27-4.16 (m, 1H), 4.16-4.03 (m, 1H), 3.77 (s, 3H). |

TABLE 2-continued

| Ex | Structure | LCMS (M + H)+ | HPLC Method, RT (min.) & Purity | ¹H NMR |
|---|---|---|---|---|
| 474 | 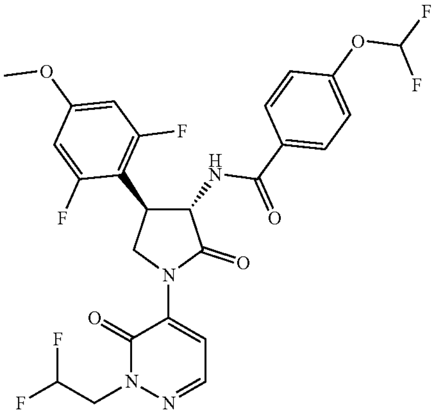 [SMILES: COc1cc(F)c([C@@H]2CN(c3ccnn(CC(F)F)c3=O)C(=O)[C@H]2NC(=O)c2ccc(OC(F)F)cc2)c(F)c1] | 571.3 | Method D, RT = 2.00 min, 97% | ¹H NMR (400 MHz, DMSO-$d_6$) δ = 9.05 (d, J = 8.1 Hz, 1H), 8.06 (d, J = 4.6 Hz, 1H), 7.87 (d, J = 8.8 Hz, 2H), 7.76 (d, J = 4.6 Hz, 1H), 7.34 (t, J = 73.6 Hz, 1H), 7.29-7.26 (m, 2H), 6.78 (d, J = 10.8 Hz, 2H), 6.40 (tt, J = 56.0, 4.0 Hz, 1H), 5.05 (dd, J = 11.0, 8.3 Hz, 1H), 4.55 (td, J = 14.3, 4.2 Hz, 2H), 4.39-4.29 (m, 1H), 4.26-4.15 (m, 1H), 4.15-4.02 (m, 1H), 3.76 (s, 3H). |
| 475 | 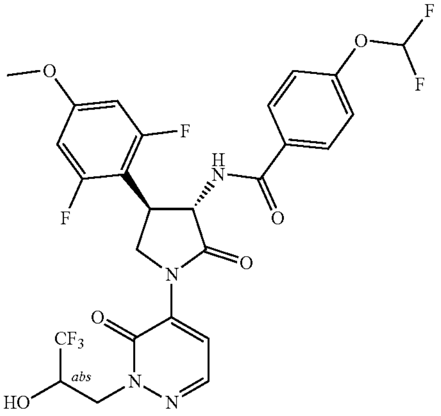 [SMILES: COc1cc(F)c([C@@H]2CN(c3ccnn(CC(O)C(F)(F)F)c3=O)C(=O)[C@H]2NC(=O)c2ccc(OC(F)F)cc2)c(F)c1] | 619.2 | Method D, RT = 1.95 min, 95% | ¹H NMR (400 MHz, DMSO-$d_6$) δ = 9.05 (d, J = 8.1 Hz, 1H), 8.04 (d, J = 4.4 Hz, 1H), 7.87 (d, J = 8.6 Hz, 2H), 7.74 (d, J = 4.6 Hz, 1H), 7.34 (t, J = 73.6 Hz, 1H), 7.29-7.26 (m, 2H), 6.78 (d, J = 11.0 Hz, 2H), 6.70-6.50 (brs, 1H), 5.04 (dd, J = 11.2, 7.8 Hz, 1H), 4.56-4.46 (m, 1H), 4.39-4.06 (m, 5H), 3.77 (s, 3H). |
| 476 | 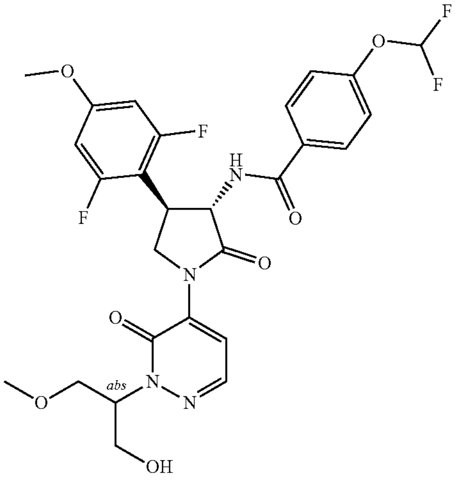 [SMILES: COCC(CO)n1nccc(N2C[C@@H](c3c(F)cc(OC)cc3F)[C@H](NC(=O)c3ccc(OC(F)F)cc3)C2=O)c1=O] | 595.2 | Method D, RT = 1.74 min, 100% | ¹H NMR (400 MHz, DMSO-$d_6$) δ = 9.04 (d, J = 8.3 Hz, 1H), 8.05 (d, J = 4.4 Hz, 1H), 7.93-7.83 (m, 2H), 7.65 (d, J = 4.6 Hz, 1H), 7.35 (t, J = 73.6 Hz, 1H), 7.29-7.26 (m, 2H), 6.78 (d, J = 10.8 Hz, 2H), 5.32-5.22 (m, 1H), 5.05 (dd, J = 11.2, 8.6 Hz, 1H), 4.91 (t, J = 5.9 Hz, 1H), 4.33-4.25 (m, 1H), 4.19-4.12 (m, 1H), 4.15-4.06 (m, 1H), 3.77 (s, 3H), 3.71-3.57 (m, 4H), 3.20 (s, 3H). |

TABLE 2-continued

| Ex | Structure | LCMS (M + H)+ | HPLC Method, RT (min.) & Purity | $^1$H NMR |
|---|---|---|---|---|
| 477 | 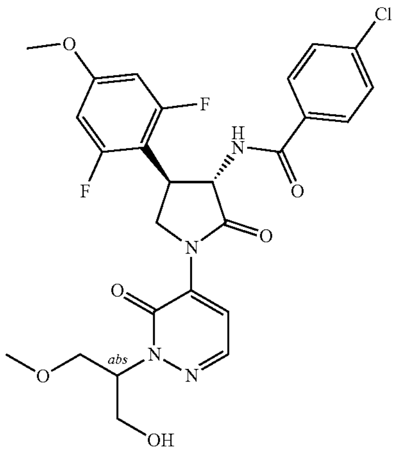 [SMILES: COCC(CO)n1nccc(N2C[C@@H](c3c(F)cc(OC)cc3F)[C@H](NC(=O)c3ccc(Cl)cc3)C2=O)c1=O] | 563.2 | Method C, RT = 1.76 min, 100% | $^1$H NMR (400 MHz, DMSO-$d_6$) δ = 9.09 (d, J = 8.6 Hz, 1H), 8.04 (d, J = 4.6 Hz, 1H), 7.86-7.75 (m, 2H), 7.65 (d, J = 4.4 Hz, 1H), 7.57 (d, J = 8.6 Hz, 2H), 6.78 (d, J = 10.8 Hz, 2H), 5.35-5.24 (m, 1H), 5.07 (dd, J = 10.9, 8.4 Hz, 1H), 4.89 (t, J = 5.7 Hz, 1H), 4.37-4.27 (m, 1H), 4.22-4.04 (m, 2H), 3.77 (s, 3H), 3.72-3.57 (m, 4H), 3.21 (s, 3H). |
| 478 | 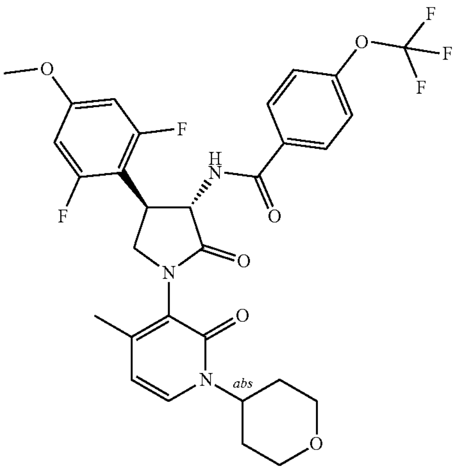 [SMILES: COc1cc(F)c([C@@H]2CN(c3c(C)ccn(C4CCOCC4)c3=O)C(=O)[C@H]2NC(=O)c2ccc(OC(F)(F)F)cc2)c(F)c1] | 622.3 | Method D, RT = 1.86 min, 98% | $^1$H NMR (400 MHz, DMSO-$d_6$) δ = 9.22-8.93 (m, 1H), 8.05-7.84 (m, 2H), 7.80-7.65 (m, 1H), 7.56-7.35 (m, 2H), 6.87-6.63 (m, 2H), 6.37-6.16 (m, 1H), 5.38-4.80 (m, 2H), 4.31-4.07 (m, 2H), 4.04-3.93 (m, 2H), 3.77-3.69 (2 s, 3H), 3.55-3.39 (m, 3H), 2.25-2.05 (2s, 3H), 1.99-1.84 (m, 2H), 1.77-1.60 (m, 2H). (mixture of interconvertible atropisomers) |
| 479 | 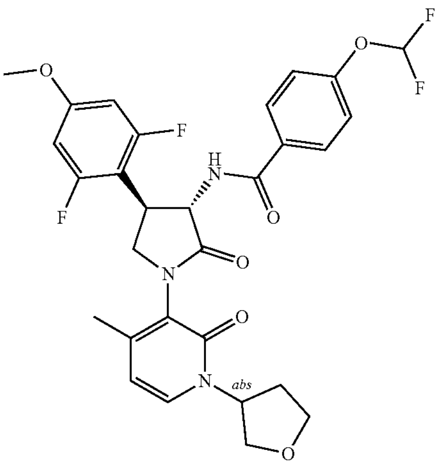 [SMILES: COc1cc(F)c([C@@H]2CN(c3c(C)ccn(C4CCOC4)c3=O)C(=O)[C@H]2NC(=O)c2ccc(OC(F)F)cc2)c(F)c1] | 590.2 | Method D, RT = 1.66 min, 98% | $^1$H NMR (400 MHz, DMSO-$d_6$) δ = 9.11-8.87 (m, 1H), 7.94-7.79 (m, 2H), 7.61-7.47 (m, 1H), 7.46-7.05 (m, 3H), 6.78-6.75 (m, 2H), 6.35-6.20 (m, 1H), 5.41-5.24 (m, 1H), 4.88-4.86 (m, 1H), 4.28-4.00 (m, 3H), 3.89-3.82 (m, 3H), 3.79-3.76 (2s, 3H) 3.50-3.47 (m, 1H), 2.47-2.37 (m, 1H), 2.24-2.04 (2s, 3H), 2.02-1.88 (m, 1H). (mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 480 | 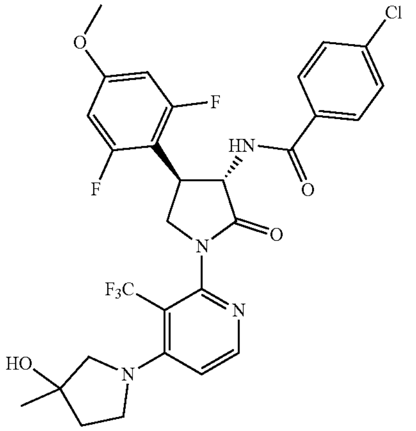 [SMILES: COc1cc(F)c([C@@H]2CN(c3nccc(N4CCC(C)(O)C4)c3C(F)(F)F)C(=O)[C@H]2NC(=O)c2ccc(Cl)cc2)c(F)c1] | 625.3 | Method D, RT = 2.03 min, 100% | $^1$H NMR (400 MHz, DMSO-d$_6$) δ = 9.07 (br d, J = 8.6 Hz, 1H), 8.13 (d, J = 6.1 Hz, 1H), 7.81 (br d, J = 8.6 Hz, 2H), 7.56 (d, J = 8.6 Hz, 2H), 6.89-6.67 (m, 3H), 5.20-5.11 (m, 1H), 4.88 (br s, 1H), 4.51-4.41 (m, 1H), 4.24-4.16 (m, 1H), 3.77 (s, 3H), 3.76-3.66 (m, 2H), 3.48-3.43 (m, 1H), 3.39-3.09 (m, 2H), 1.94-1.83 (m, 2H), 1.36 (s, 3H). |
| 481 | 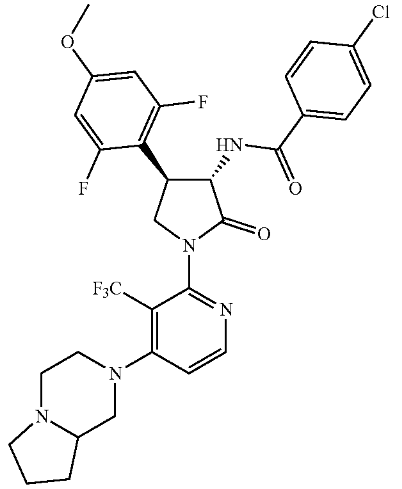 [SMILES: COc1cc(F)c([C@@H]2CN(c3nccc(N4CCN5CCCC5C4)c3C(F)(F)F)C(=O)[C@H]2NC(=O)c2ccc(Cl)cc2)c(F)c1] | 650.3 | Method D, RT = 2.15 min, 100% | $^1$H NMR (400 MHz, DMSO-d$_6$) δ = 9.16-9.00 (m, 1H), 8.40 (d, J = 5.6 Hz, 1H), 7.82 (br d, J = 6.8 Hz, 2H), 7.56 (d, J = 8.3 Hz, 2H), 7.20 (d, J = 5.6 Hz, 1H), 6.78 (d, J = 11.0 Hz, 2H), 5.18-5.02 (m, 1H), 4.42-4.31 (m, 1H), 4.28-4.14 (m, 1H), 3.83-3.70 (m, 4H), 3.67-3.41 (m, 2H), 3.13-2.96 (m, 3H), 2.89-2.70 (m, 1H), 2.18-1.94 (m, 3H), 1.83-1.62 (m, 3H), 1.40-1.25 (m, 1H). |
| 482 | 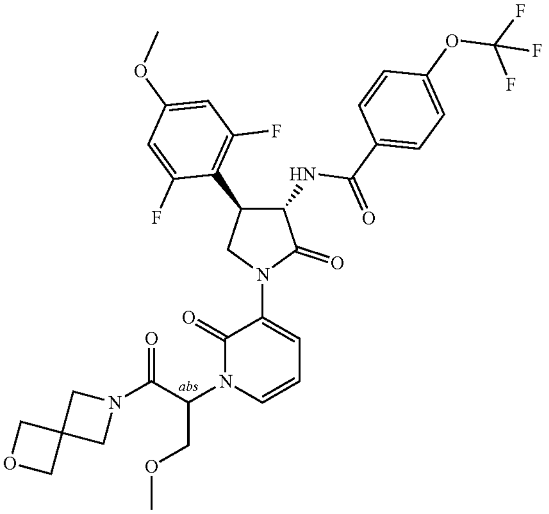 [SMILES: COCC(C(=O)N1CC2(COC2)C1)n1cccc(N2C[C@@H](c3c(F)cc(OC)cc3F)[C@H](NC(=O)c3ccc(OC(F)(F)F)cc3)C2=O)c1=O] | 707.2 | Method D, RT = 1.83 min, 100% | $^1$H NMR (400 MHz, DMSO-d$_6$) δ = 9.18 (d, J = 8.0 Hz, 1H), 8.11 (dd, J = 4.8, 1.8 Hz, 1H), 8.01-7.94 (m, 2H), 7.84 (dd, J = 7.8, 1.8 Hz, 1H), 7.53-7.44 (m, 2H), 7.16 (dd, J = 7.5, 5.0 Hz, 1H), 6.80 (d, J = 10.5 Hz, 2H), 5.41 (dd, J = 6.0, 3.5 Hz, 1H), 5.12-5.05 (m, 1H), 4.70-4.59 (m, 4H), 4.29-4.14 (m, 2H), 4.10-3.98 (m, 4H), 3.80-3.74 (m, 5H), 3.51-3.69 (m, 1H), 3.30 (s, 3H). |

TABLE 2-continued

| Ex | Structure | LCMS (M + H)+ | HPLC Method, RT (min.) & Purity | $^1$H NMR |
|---|---|---|---|---|
| 483 | 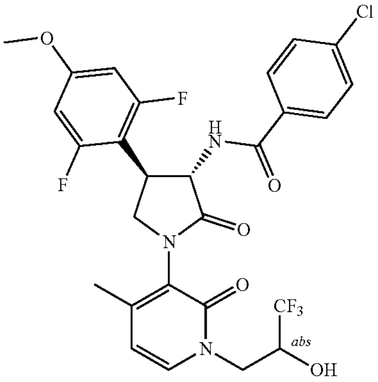 [SMILES: COc1cc(F)c([C@@H]2CN(c3c(C)ccn(CC(O)C(F)(F)F)c3=O)C(=O)[C@H]2NC(=O)c2ccc(Cl)cc2)c(F)c1] | 600.2 | Method D, RT = 1.84 min, 97% | $^1$H NMR (400 MHz, DMSO-$d_6$) δ = 9.23-8.89 (m, 1H), 7.94-7.75 (m, 2H), 7.67-7.42 (m, 3H), 6.87-6.60 (m, 3H), 6.38-6.16 (m, 1H), 5.39-4.80 (m, 1H), 4.48-4.03 (m, 4H), 3.86-3.78 (m, 1H), 3.77-3.74 (2s, 3H), 3.58-3.45 (m, 1H), 2.26-1.96 (2s, 3H). (mixture of interconvertible atropisomers) |
| 484 | 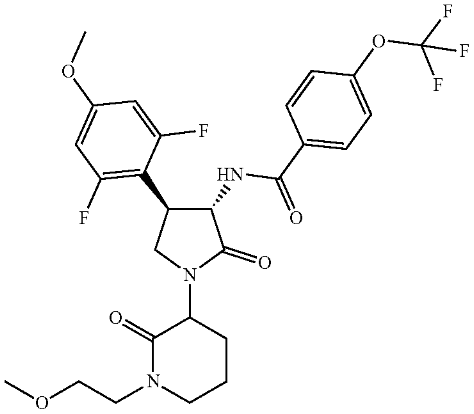 [SMILES: COCCN1CCCC(N2C[C@@H](c3c(F)cc(OC)cc3F)[C@H](NC(=O)c3ccc(OC(F)(F)F)cc3)C2=O)C1=O] | 586.2 | Method D, RT = 2.007 min, 100% | $^1$H NMR (400 MHz, DMSO-$d_6$) δ = 9.05-8.97 (m, 1H), 7.92 (d, J = 8.8 Hz, 2H), 7.47 (d, J = 8.6 Hz, 2H), 6.78-6.70 (m, 2H), 5.02-4.94 (m, 1H), 4.66-4.57 (m, 1H), 3.96-3.85 (m, 1H), 3.75 (s, 3H), 3.59-3.52 (m, 1H), 3.46-3.41 (m, 4H), 3.41-3.35 (m, 3H), 3.23 (s, 3H), 2.04-1.82 (m, 4H). |
| 485 | 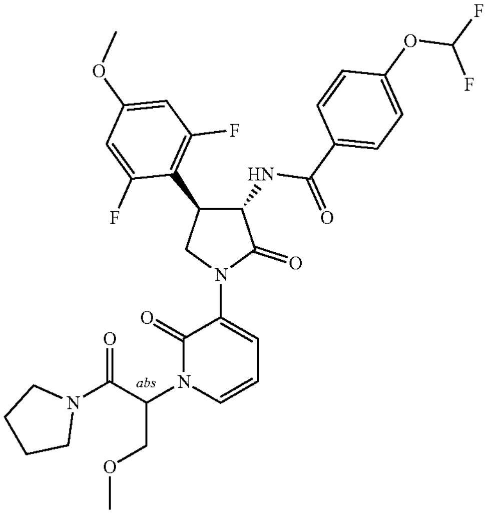 [SMILES: COCC(C(=O)N1CCCC1)n1cccc(N2C[C@@H](c3c(F)cc(OC)cc3F)[C@H](NC(=O)c3ccc(OC(F)F)cc3)C2=O)c1=O] | 661.3 | Method D, RT = 1.93 min, 100% | $^1$H NMR (400 MHz, DMSO-$d_6$) δ = 9.01 (d, J = 8.3 Hz, 1H), 7.88 (d, J = 8.8 Hz, 2H), 7.77 (dd, J = 6.8, 1.7 Hz, 1H), 7.60 (dd, J = 7.2, 1.7 Hz, 1H), 7.35 (t, J = 73.6 Hz, 1H), 7.30-7.23 (m, 2H), 6.80-6.74 (m, 2H), 6.40 (t, J = 7.0 Hz, 1H), 5.92 (dd, J = 8.6, 5.1 Hz, 1H), 5.09 (dd, J = 10.9, 8.4 Hz, 1H), 4.13-4.05 (m, 1H), 4.03-3.95 (m, 1H), 3.95-3.83 (m, 3H), 3.76 (s, 3H), 3.65-3.53 (m, 2H), 3.34-3.28 (m, 2H), 3.27 (s, 3H), 1.96-1.85 (m, 2H), 1.82-1.68 (m, 2H). |

TABLE 2-continued

| Ex | Structure | LCMS (M + H)+ | HPLC Method, RT (min.) & Purity | $^1$H NMR |
|---|---|---|---|---|
| 486 | 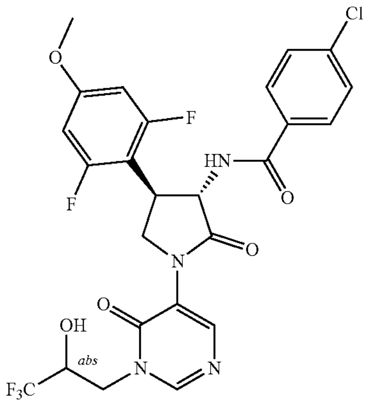 [SMILES: COc1cc(F)c([C@@H]2CN(c3cncn(CC(O)C(F)(F)F)c3=O)C(=O)[C@H]2NC(=O)c2ccc(Cl)cc2)c(F)c1] | 587.2 | Method D, RT = 1.862 min, 98.9% | $^1$H NMR (400 MHz, DMSO-$d_6$) δ = 9.06 (br s, 1H), 8.45 (s, 1H), 8.19 (s, 1H), 7.83 (d, J = 8.6 Hz, 2H), 7.56 (d, J = 8.6 Hz, 2H), 6.78 (d, J = 10.5 Hz, 2H), 5.10 (d, J = 11.2 Hz, 1H), 4.43-4.29 (m, 2H), 4.12 (br dd, J = 10.3, 9.5 Hz, 1H), 4.05-3.87 (m, 3H), 3.76 (s, 3H), 3.35-3.32 (m, 1H). |
| 487 | 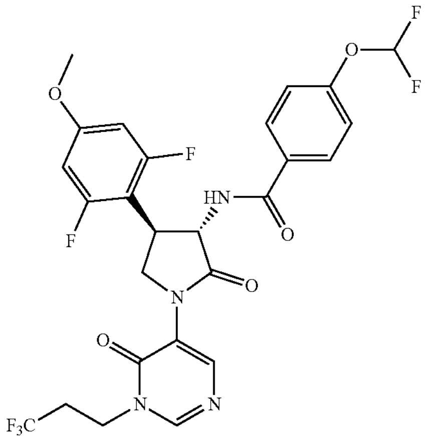 [SMILES: COc1cc(F)c([C@@H]2CN(c3cncn(CCC(F)(F)F)c3=O)C(=O)[C@H]2NC(=O)c2ccc(OC(F)F)cc2)c(F)c1] | 603.2 | Method D, RT = 1.791 min, 100% | $^1$H NMR (400 MHz, DMSO-$d_6$) δ = 9.03 (d, J = 8.6 Hz, 1H), 8.56 (s, 1H), 8.17 (s, 1H), 7.96-7.79 (m, 2H), 7.34 (t, J = 74.0 Hz, 1H), 7.29-7.24 (m, 2H), 6.77 (d, J = 10.8 Hz, 2H), 5.12 (dd, J = 11.2, 8.6 Hz, 1H), 4.23 (t, J = 7.2 Hz, 2H), 4.17-4.05 (m, 1H), 4.05-3.87 (m, 2H), 3.76 (s, 3H), 2.92-2.72 (m, 2H). |
| 488 | 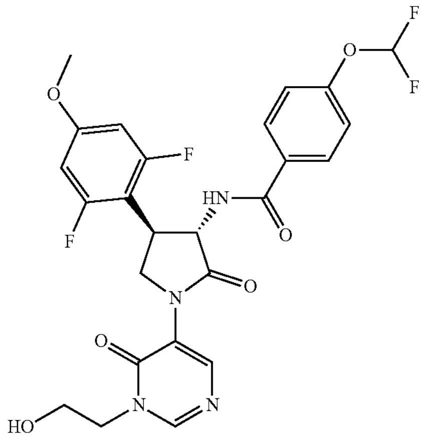 [SMILES: COc1cc(F)c([C@@H]2CN(c3cncn(CCO)c3=O)C(=O)[C@H]2NC(=O)c2ccc(OC(F)F)cc2)c(F)c1] | 551.2 | Method D, RT = 1.441 min, 100% | $^1$H NMR (400 MHz, DMSO-$d_6$) δ = 9.01 (d, J = 8.6 Hz, 1H), 8.37 (s, 1H), 8.13 (s, 1H), 7.95-7.83 (m, 2H), 7.34 (t, J = 73.0 Hz, 1H), 7.28-7.25 (m, 2H), 6.76 (d, J = 10.8 Hz, 2H), 5.11 (dd, J = 11.0, 8.6 Hz, 1H), 4.17-4.06 (m, 1H), 4.02 (t, J = 5.1 Hz, 2H), 3.99-3.91 (m, 3H), 3.76 (s, 3H), 3.68-3.60 (m, 2H). |

TABLE 2-continued

| Ex | Structure | LCMS (M + H)+ | HPLC Method, RT (min.) & Purity | $^1$H NMR |
|---|---|---|---|---|
| 489 | 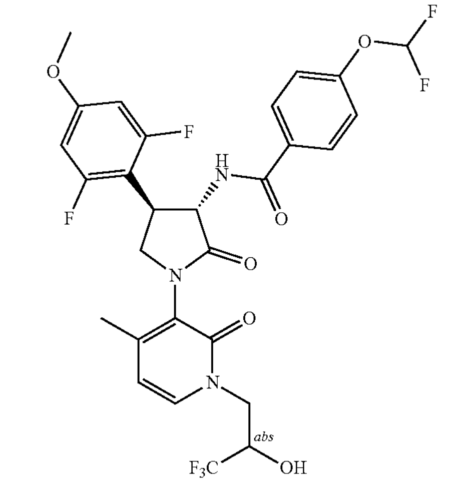 [SMILES: COc1cc(F)c([C@@H]2CN(c3c(C)ccn(CC(O)C(F)(F)F)c3=O)C(=O)[C@H]2NC(=O)c2ccc(OC(F)F)cc2)c(F)c1] | 632.3 | Method D, RT = 1.77 min, 98% | $^1$H NMR (400 MHz, DMSO-$d_6$) δ = 9.12-8.89 (m, 1H), 7.99-7.79 (m, 2H), 7.61-7.52 (m, 1H), 7.55-7.09 (m, 3H), 6.86-6.55 (m, 3H), 6.235-6.25 (m, 1H), 5.34-4.77 (m, 1H), 4.47-4.23 (m, 3H), 4.19-4.10 (m, 1H), 3.82-3.79(m, 1H), 3.77-3.73 (2s, 3H), 3.57-3.47 (m, 1H), 2.24-2.00 (2s, 3H). (mixture of interconvertible atropisomers) |
| 490 | 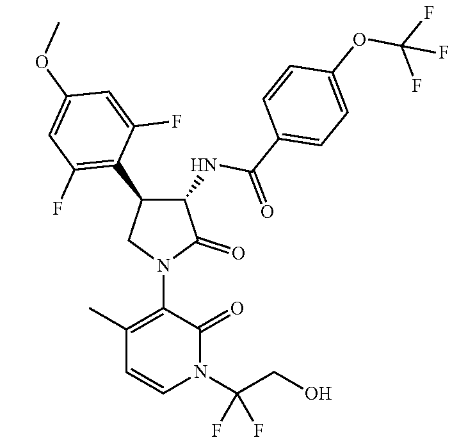 [SMILES: COc1cc(F)c([C@@H]2CN(c3c(C)ccn(C(F)(F)CO)c3=O)C(=O)[C@H]2NC(=O)c2ccc(OC(F)(F)F)cc2)c(F)c1] | 618.2 | Method F, RT = 1.999 min, 93% | $^1$H NMR (400 MHz, DMSO-$d_6$) δ = 9.23-9.03 (m, 1H), 8.01-7.87 (m, 2H), 7.71-7.62 (m, 1H), 7.54-7.41 (m, 2H), 6.85-6.68 (m, 2H), 6.42-6.28 (m, 1H), 6.01-5.86 (m, 1H), 5.33-4.77 (m, 1H), 4.32-4.17 (m, 3H), 4.14-4.02 (m, 1H), 3.78-3.76 (2s, 3H), 3.61-3.54 (m, 1H), 2.26-2.08 (2s, 3H). (mixture of interconvertible atropisomers) |
| 491 | 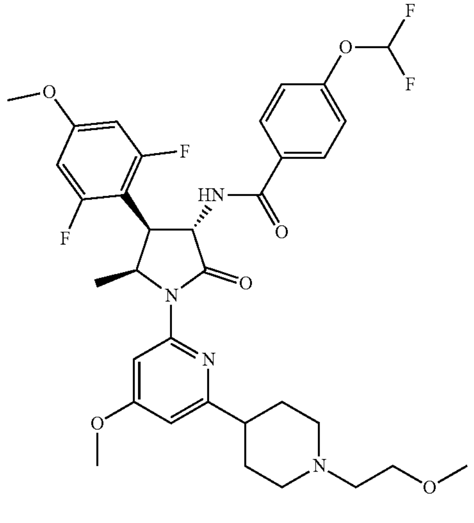 | 675.2 | Method-D, RT = 1.742 min, 97.5% | $^1$H NMR (400 MHz, DMSO-$d_6$) δ = 8.89 (d, J = 8.5 Hz, 1H), 7.89 (d, J = 8.8 Hz, 2H), 7.82 (d, J = 2.0 Hz, 1H), 7.34 (t, J = 76.0 Hz, 1H), 7.27 (d, J = 8.5 Hz, 2H), 6.80 (d, J = 11.5 Hz, 2H), 6.75 (d, J = 2.0 Hz, 1H), 5.66 (dd, J = 12.6, 8.4 Hz, 1H), 4.97 (quin, J = 7.1 Hz, 1H), 4.31 (dd, J = 12.6 , 7.9 Hz, 1H), 3.82 (s, 3H), 3.79 (s, 3H), 3.53-3.40 (m, 2H), 3.25 (s, 3H), 3.09-2.87 (m, 2H), 2.65-2.54 (m, 2H), 2.47-2.38 (m, 1H), 2.16-1.95 (m, 2H), 1.88-1.67 (m, 4H), 1.20 (br d, J = 6.3 Hz, 3H). |

TABLE 2-continued

| Ex | Structure | LCMS (M + H)+ | HPLC Method, RT (min.) & Purity | $^1$H NMR |
|---|---|---|---|---|
| 492 | 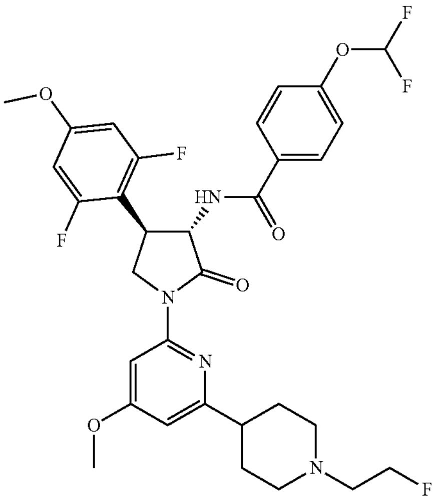 [SMILES: COc1cc(C2CCN(CCF)CC2)nc(N2C[C@@H](c3c(F)cc(OC)cc3F)[C@H](NC(=O)c3ccc(OC(F)F)cc3)C2=O)c1] | 649.2 | Method-D, RT = 1.963 min, 94.7% | $^1$H NMR (400 MHz, DMSO-$d_6$) δ = 9.11 (d, J = 8.3 Hz, 1H), 7.92-7.86 (m, 2H), 7.84 (d, J = 2.0 Hz, 1H), 7.34 (t, J = 76.0 Hz, 1H), 7.29 (d, J = 8.3 Hz, 2H), 6.81 (d, J = 10.8 Hz, 2H), 6.75 (d, J = 2.0 Hz, 1H), 5.06 (dd, J = 10.5, 8.3 Hz, 1H), 4.86 (dt, J = 47.2, 4.5 Hz, 2H), 4.44-4.43 (m, 1H), 4.47 (br t, J = 9.9 Hz, 1H), 4.15 (q, J = 9.9 Hz, 1H), 3.97 (br t, J = 10.5 Hz, 1H), 3.85 (s, 3H), 3.79 (s, 3H), 3.67-3.51 (m, 4H), 3.20-3.04 (m, 1H), 2.96-2.83 (m, 1H), 2.15-1.96 (m, 4H). |
| 493 | 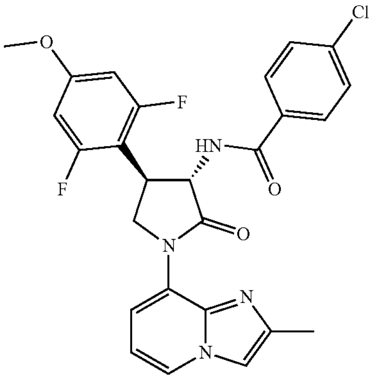 [SMILES: COc1cc(F)c([C@@H]2CN(c3cccn4cc(C)nc34)C(=O)[C@H]2NC(=O)c2ccc(Cl)cc2)c(F)c1] | 511.2 | Method C, RT = 1.465 min, 98.3%. | $^1$H NMR (400 MHz, DMSO-$d_6$) δ = 9.14 (d, J = 8.5 Hz, 1H), 8.43 (d, J = 6.8 Hz, 1H), 7.86 (d, J = 8.5 Hz, 2H), 7.77 (s, 1H), 7.58 (d, J = 8.5 Hz, 2H), 7.42 (d, J = 7.5 Hz, 1H), 6.90 (t, J = 7.1 Hz, 1H), 6.80 (d, J = 10.8 Hz, 2H), 5.20 (dd, J = 11.0, 8.5 Hz, 1H), 4.55-4.46 (m, 1H), 4.33 (br t, J = 9.9 Hz, 1H), 4.25-4.13 (m, 1H), 3.78 (s, 3H), 2.36 (s, 3H). |
| 494 | 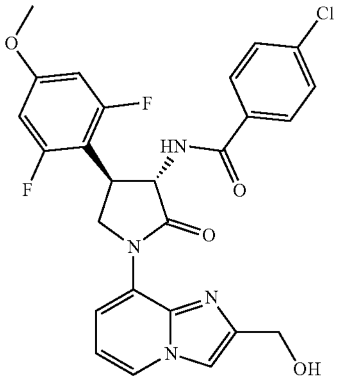 [SMILES: COc1cc(F)c([C@@H]2CN(c3cccn4cc(CO)nc34)C(=O)[C@H]2NC(=O)c2ccc(Cl)cc2)c(F)c1] | 527.12 | Method C, RT = 1.387 min, 95.6%. | $^1$H NMR (400 MHz, DMSO-$d_6$) δ = 9.13 (d, J = 8.5 Hz, 1 H), 8.49 (d, J = 6.5 Hz, 1 H), 7.92-7.82 (m, 3H), 7.58 (d, J = 8.5 Hz, 2H), 7.47 (d, J = 7.25 Hz, 1H), 6.93 (t, J = 7.1 Hz, 1H), 6.85-6.75 (m, 2H), 5.26-5.17 (m, 2H), 4.62 (d, J = 4.7 Hz, 2H), 4.59-4.48 (m, 1H), 4.37-4.17 (m, 2H), 3.78 (s, 3 H). |

TABLE 2-continued

| Ex | Structure | LCMS (M + H)+ | HPLC Method, RT (min.) & Purity | $^1$H NMR |
|---|---|---|---|---|
| 495 | 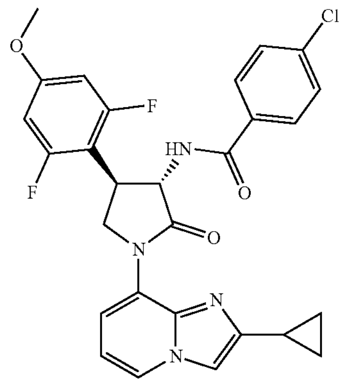 [SMILES: COc1cc(F)c([C@@H]2CN(c3cccn4cc(C5CC5)nc34)C(=O)[C@H]2NC(=O)c2ccc(Cl)cc2)c(F)c1] | 537.14 | Method C, RT = 1.635 min, 100%. | $^1$H NMR (400 MHz, DMSO-$d_6$) δ = 9.12 (d, J = 8.8 Hz, 1H), 8.38 (dd, J = 6.8, 1.0 Hz, 1H), 7.90-7.81 (m, 2H), 7.77 (s, 1H), 7.62-7.49 (m, 2H), 7.39 (dd, J = 7.3, 1.0 Hz, 1H), 6.92-6.86 (m, 1H), 6.80 (d, J = 10.8 Hz, 2H), 5.17 (dd, J = 11.0, 8.8 Hz, 1H), 4.51-4.42 (m, 1H), 4.35 (t, J = 11.0 Hz, 1H), 4.25-4.13 (m, 1H), 3.78 (s, 3H), 2.08-1.96 (m, 1H), 0.96-0.89 (m, 2H), 0.84-0.76 (m, 2H). |
| 496 | 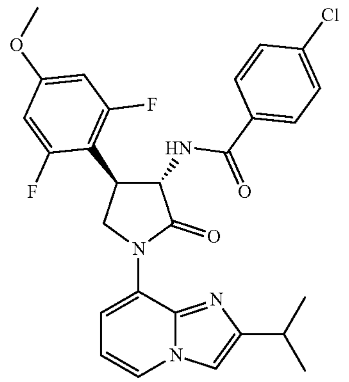 [SMILES: COc1cc(F)c([C@@H]2CN(c3cccn4cc(C(C)C)nc34)C(=O)[C@H]2NC(=O)c2ccc(Cl)cc2)c(F)c1] | 539 | Method C, RT = 1.685 min, 100%. | $^1$H NMR (400 MHz, DMSO-$d_6$) δ = 9.13 (d, J = 8.8 Hz, 1H), 8.42 (dd, J = 6.6, 1.1 Hz, 1H), 7.92-7.80 (m, 2H), 7.76 (s, 1H), 7.62-7.51 (m, 2H), 7.42 (dd, J = 7.5, 1.1 Hz, 1H), 6.90 (t, J = 7.0 Hz, 1H), 6.80 (d, J = 10.8 Hz, 2H), 5.20 (dd, J = 11.1, 8.6 Hz, 1H), 4.60-4.48 (m, 1H), 4.37 (t, J = 10.3 Hz, 1H), 4.21 (q, J = 10.3 Hz, 1H), 3.77 (s, 3H), 3.04-2.97 (m, 1H), 1.29 (d, J = 6.8 Hz, 6H). |
| 497 | 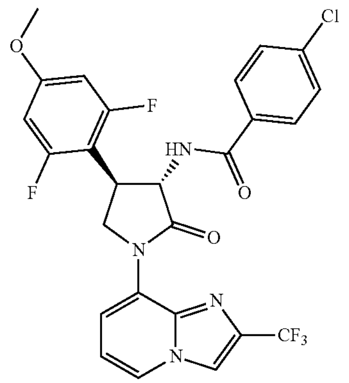 [SMILES: COc1cc(F)c([C@@H]2CN(c3cccn4cc(C(F)(F)F)nc34)C(=O)[C@H]2NC(=O)c2ccc(Cl)cc2)c(F)c1] | 565 | Method C, RT = 2.034 min, 94.3%. | $^1$H NMR (400 MHz, DMSO-$d_6$) δ = 9.14 (d, J = 8.5 Hz, 1H), 8.65 (d, J = 1.0 Hz, 1H), 8.57 (dd, J = 6.8, 1.0 Hz, 1H), 7.93-7.80 (m, 2H), 7.70 (dd, J = 7.5, 1.0 Hz, 1H), 7.62-7.51 (m, 2H), 7.21-7.09 (m, 1H), 6.80 (d, J = 10.8 Hz, 2H), 5.19 (dd, J = 10.8, 8.6 Hz, 1H), 4.54-4.45 (m, 1H), 4.37-4.29 (m, 1H), 4.29-4.19 (m, 1H), 3.77 (s, 3H). |

TABLE 2-continued

| Ex | Structure | LCMS (M + H)+ | HPLC Method, RT (min.) & Purity | $^1$H NMR |
|---|---|---|---|---|
| 498 | 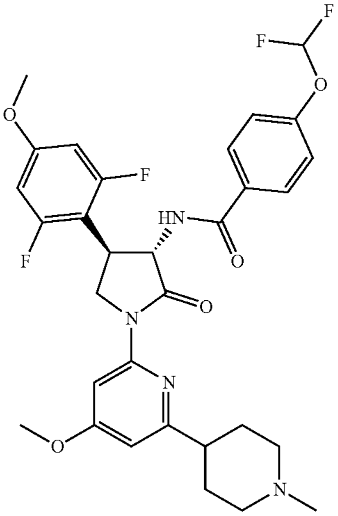 [SMILES: COc1cc(C2CCN(C)CC2)nc(N2C[C@@H](c3c(F)cc(OC)cc3F)[C@H](NC(=O)c3ccc(OC(F)F)cc3)C2=O)c1] | 617.2 | Method D, RT = 1.564 min, 98.7% | $^1$H NMR (400 MHz, DMSO-$d_6$) δ = 9.09 (d, J = 8.3 Hz, 1H), 7.95-7.84 (m, 2H), 7.80 (d, J = 2.2 Hz, 1H), 7.36 (t, J = 74.1 Hz, 1H), 7.29 (d, J = 8.3 Hz, 2H), 6.80 (d, J = 11.0 Hz, 2H), 6.70 (d, J = 2.2 Hz, 1H), 5.07 (dd, J = 11.0, 8.3 Hz, 1H), 4.47 (t, J = 9.8 Hz, 1H), 4.16-4.05 (m, 1H), 4.00-3.90 (m, 1H), 3.83 (s, 3H), 3.78 (s, 3H), 2.84-2.80 (m, 2H), 2.16 (s, 3H), 1.98-1.86 (m, 3H), 1.83-1.71 (m, 4H). |
| 499 | 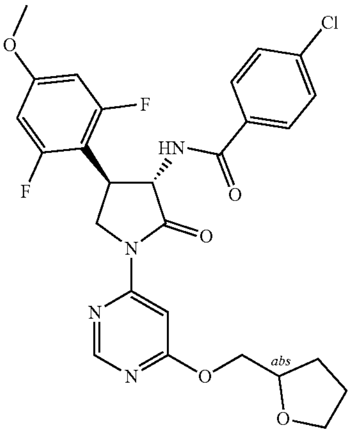 [SMILES: COc1cc(F)c([C@@H]2CN(c3cc(OCC4CCCO4)ncn3)C(=O)[C@H]2NC(=O)c2ccc(Cl)cc2)c(F)c1] | 559.15 | Method C, RT = 2.043 min, 100%. | $^1$H NMR (400 MHz, DMSO-$d_6$) δ = 9.17 (d, J = 8.0 Hz, 1H), 8.65 (d, J = 0.8 Hz, 1H), 7.88-7.74 (m, 2H), 7.66 (d, J = 0.8 Hz, 1H), 7.62-7.52 (m, 2H), 6.78 (d, J = 10.8 Hz, 2H), 5.05 (dd, J = 11.1, 8.1 Hz, 1H), 4.45 (t, J = 9.8 Hz, 1H), 4.38-4.24 (m, 2H), 4.21-4.07 (m, 2H), 4.00-3.89 (m, 1H), 3.82-3.72 (m, 4H), 3.70-3.59 (m, 1H), 2.04-1.93 (m, 1H), 1.92-1.75 (m, 2H), 1.71-1.59 (m, 1H). |
| 500 | 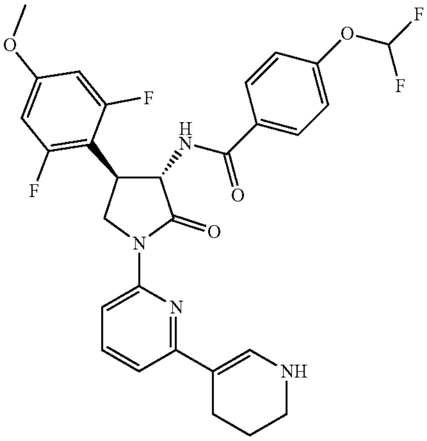 [SMILES: COc1cc(F)c([C@@H]2CN(c3cccc(C4=CNCCC4)n3)C(=O)[C@H]2NC(=O)c2ccc(OC(F)F)cc2)c(F)c1] | 571.2 | Method D, RT = 1.489 min, 98%. | $^1$H NMR (400 MHz, DMSO-$d_6$) δ = 9.09 (d, J = 8.3 Hz, 1H), 8.19 (d, J = 8.3 Hz, 1H), 7.89 (d, J = 8.8 Hz, 2H), 7.84 (t, J = 8.0 Hz, 1H), 7.35 (t, J = 72.5 Hz, 1H), 7.36-7.23 (m, 3H), 6.88-6.72 (m, 3H), 5.08 (dd, J = 10.8, 8.3 Hz, 1H), 4.49 (t, J = 9.9 Hz, 1H), 4.13 (q, J = 9.9 Hz, 1H), 4.02-3.96 (m, 1H), 3.78 (s, 3H), 3.77-3.72 (m, 2H), 3.54-3.49 (brs, 1H), 2.92-1.89 (m, 2H), 2.28-2.24 (m, 2H). |

TABLE 2-continued

| Ex | Structure | LCMS (M + H)+ | HPLC Method, RT (min.) & Purity | $^1$H NMR |
|---|---|---|---|---|
| 501 | 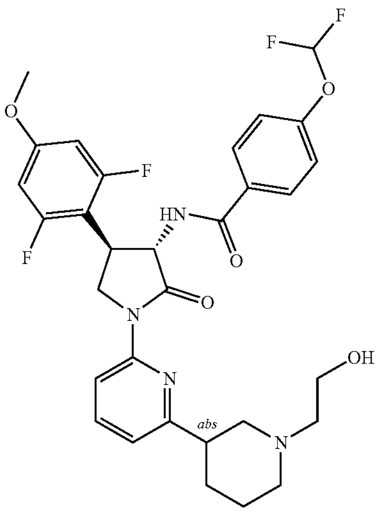 [SMILES: COc1cc(F)c([C@@H]2CN(c3cccc(C4CCCN(CCO)C4)n3)C(=O)[C@H]2NC(=O)c2ccc(OC(F)F)cc2)c(F)c1] | 617.3 | Method D, RT = 1.473 min, 100%. | $^1$H NMR (400 MHz, DMSO-$d_6$) δ = 9.09 (d, J = 8.5 Hz, 1H), 8.17 (d, J = 8.5 Hz, 1H), 7.89 (d, J = 9.0 Hz, 2H), 7.80 (t, J = 7.8 Hz, 1H), 7.35 (t, J = 73.6 Hz, 1H), 7.29 (d, J = 8.5 Hz, 2H), 7.12 (d, J = 7.5 Hz, 1H), 6.80 (m, 2H), 5.08 (dd, J = 10.8, 8.3 Hz, 1H), 4.49 (t, J = 9.8 Hz, 1H), 4.34-4.30 (m, 1H), 4.12 (q, J = 9.8 Hz, 1H), 4.00-3.89 (m, 1H), 3.79 (s, 3H), 3.51-3.47 (m, 2H), 3.04-3.00 (m, 1H), 2.88-2.84 (m, 2H), 2.43-2.39 (m, 2H), 2.17-2.12 (m, 1H), 2.02-1.92 (m, 1H), 1.90-1.86 (m, 1H), 1.74-1.45 (m, 3H). |
| 502 | 577* | 617.2 | Method D, RT = 1.494 min, 95%. | $^1$H NMR (400 MHz, DMSO-$d_6$) δ = 9.09 (d, J = 8.5 Hz, 1H), 8.18 (d, J = 8.0 Hz, 1H), 7.90 (d, J = 8.5 Hz, 2H), 7.80 (t, J = 8.0 Hz, 1H), 7.29 (d, J = 8.5 Hz, 2H), 7.35 (t, J = 73.6 Hz, 1H), 7.13 (d, J = 7.5 Hz, 1H), 6.80 (d, J = 11.0 Hz, 2H), 5.08 (dd, J = 10.8, 8.3 Hz, 1H), 4.48 (t, J = 9.5 Hz, 2H), 4.13 (q, J = 10.0 Hz, 1H), 4.03-3.92 (m, 1H), 3.79 (s, 3H), 3.52 (s, 2H), 3.06-3.02 (m, 1H), 2.96-2.82 (m, 2H), 2.65-2.55 (m, 1H), 2.48-2.41 (m, 1H), 2.31-2.00 (m, 2H), 1.92-1.83 (m, 1H), 1.78-1.50 (m, 3H). |
| 503 | 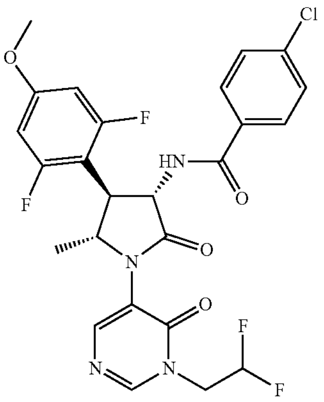 [SMILES: COc1cc(F)c([C@H]2[C@H](NC(=O)c3ccc(Cl)cc3)C(=O)N(c3cncn(CC(F)F)c3=O)[C@@H]2C)c(F)c1] | 553.2 | Method D, RT = 2.977 min, 99%. | $^1$H NMR (400 MHz, DMSO-$d_6$) δ = 9.09-9.07 (d, J = 8.4 Hz, 1H), 8.48 (s, 1H), 8.05 (s, 1H), 7.79 (d, J = 8.5 Hz, 2H), 7.54 (d, J = 8.5 Hz, 2H), 6.76 (d, J = 11.0 Hz, 2H), 6.36 (t, J = 48.0 Hz, 1H), 5.10 (d, J = 11.5 Hz, 1H), 4.57-4.31 (m, 3H), 3.74 (s, 3H), 3.64 (t, J = 10.5 Hz, 1H), 1.03 (d, J = 6.0 Hz, 3H). |

TABLE 2-continued

| Ex | Structure | LCMS (M + H)+ | HPLC Method, RT (min.) & Purity | $^1$H NMR |
|---|---|---|---|---|
| 504 | 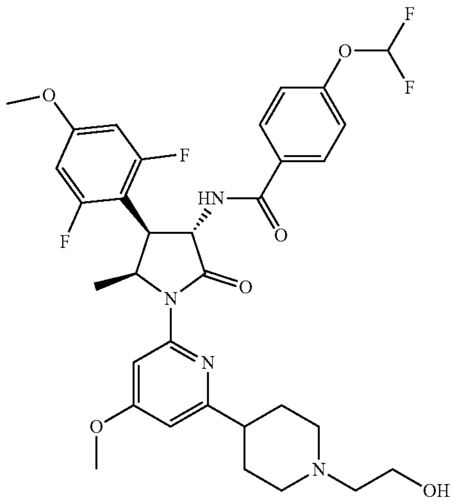 [SMILES: COc1cc(C2CCN(CCO)CC2)nc(N2C(=O)[C@@H](NC(=O)c3ccc(OC(F)F)cc3)[C@H](c3c(F)cc(OC)cc3F)[C@@H]2C)c1] | 661.35 | Method-D, RT = 1.605 min, 100% | $^1$H NMR (400 MHz, DMSO-$d_6$) δ = 8.92-8.86 (m, 1H), 7.93-7.86 (m, 2H), 7.84-7.79 (m, 1H), 7.34 (t, J = 76.0 Hz, 1H), 7.31-7.22 (m, 2H), 6.84-6.76 (m, 2H), 6.69 (d, J = 2.0 Hz, 1H), 5.67 (dd, J = 12.8, 8.3 Hz, 1H), 5.02-4.92 (m, 1H), 4.39-4.26 (m, 2H), 3.82 (s, 3H), 3.79 (s, 3H), 3.55-3.47 (m, 2H), 2.99-2.92 (m, 2H), 2.63-2.55 (m, 2H), 2.42-2.36 (m, 2H), 2.09-1.97 (m, 1H), 1.82-1.66 (m, 4H), 1.19 (d, J = 6.6 Hz, 3H). |
| 505 | 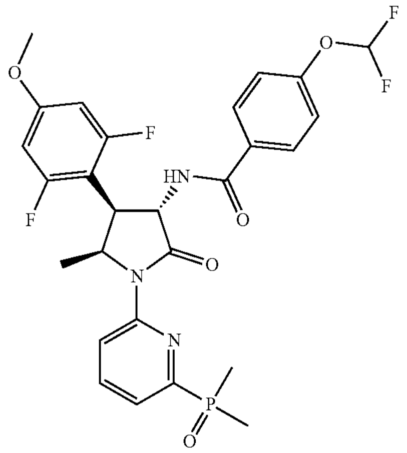 [SMILES: COc1cc(F)c([C@H]2[C@H](NC(=O)c3ccc(OC(F)F)cc3)C(=O)N(c3cccc(P(C)(C)=O)n3)[C@H]2C)c(F)c1] | 580.2 | Method D, RT = 1.636 min, 98%. | $^1$H NMR (400 MHz, DMSO-$d_6$) δ = 8.94 (d, J = 8.5 Hz, 1H), 8.49 (dd, J = 8.5, 1.3 Hz, 1H), 8.05 (m, 1H), 7.95-7.82 (m, 2H), 7.77-7.65 (m, 1H), 7.33 (t, J = 74.6 Hz, 1H), 7.26 (d, J = 8.8 Hz, 2H), 6.86-6.69 (m, 2H), 5.66 (dd, J = 12.5, 8.3 Hz, 1H), 5.04-4.91 (m, 1H), 4.35 (dd, J = 12.5, 7.8 Hz, 1H), 3.78 (s, 3H), 1.68 (d, J = 13.6 Hz, 3H), 1.57 (d, J = 13.6 Hz, 3H), 1.22 (d, J = 6.8 Hz, 3H). |
| 506 | 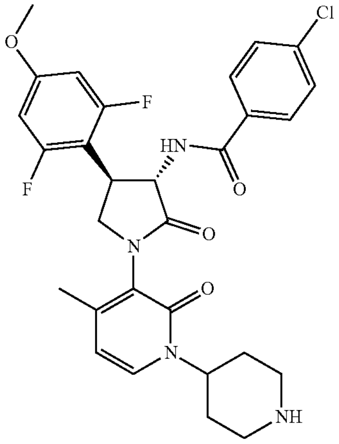 [SMILES: COc1cc(F)c([C@@H]2CN(c3c(C)ccn(C4CCNCC4)c3=O)C(=O)[C@H]2NC(=O)c2ccc(Cl)cc2)c(F)c1] | 571.2 | Method C, RT = 1.427 min, 92%. | $^1$H NMR (400 MHz, DMSO-$d_6$) δ = 9.22-8.93 (m, 1H), 7.91-7.77 (m, 2H), 7.70-7.60 (m, 1H), 7.60-7.43 (m, 2H), 6.85-6.67 (m, 2H), 6.35-6.14 (m, 1H), 5.36-4.85 (m, 1H), 4.81-4.65 (m, 1H), 4.29-4.05 (m, 2H), 3.81-3.72 (2s, 3H), 3.52-3.48 (m, 2H), 3.15-3.06 (m, 2H), 2.66-2.56 (m, 2H), 2.48-2.44 (m, 1H), 2.24-2.01 (2s, 3H), 1.77-1.65 (m, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 507 | 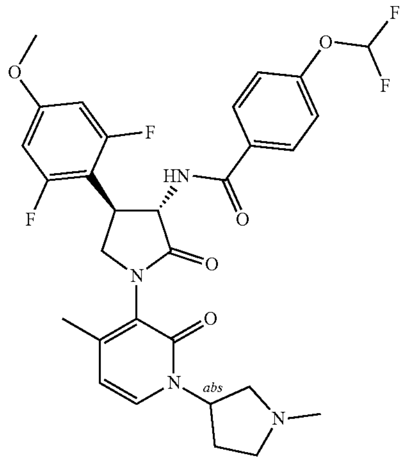 [SMILES: COc1cc(F)c([C@@H]2CN(c3c(C)ccn(C4CCN(C)C4)c3=O)C(=O)[C@H]2NC(=O)c2ccc(OC(F)F)cc2)c(F)c1] | 603.2 | Method D, RT = 1.531 min, 100%. | $^1$H NMR (400 MHz, DMSO-$d_6$) δ = 9.11-8.90 (m, 1H), 7.95-7.83 (m, 2H), 7.38-7.22 (m, 4H), 6.83-6.73 (m, 2H), 6.44-6.32 (m, 1H), 5.30-4.96 (m, 2H), 4.35-4.03 (m, 2H), 3.98-3.80 (m, 2H), 3.77 (s, 3H), 3.63-3.49 (m, 2H), 3.15-3.06 (m, 1H), 2.93-2.88 (2s, 3H), 2.24-2.09 (2s, 3H), 1.26-1.15 (m, 2H). (Mixture of interconvertible atropisomers) |
| 508 | 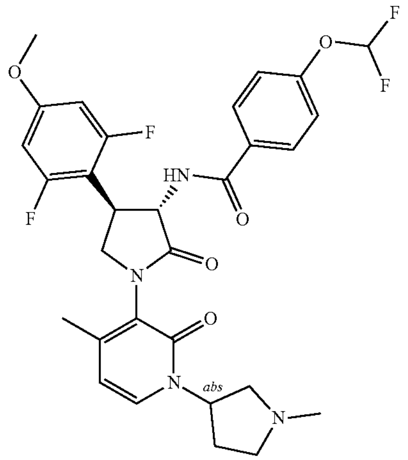 [SMILES: COc1cc(F)c([C@@H]2CN(c3c(C)ccn(C4CCN(C)C4)c3=O)C(=O)[C@H]2NC(=O)c2ccc(OC(F)F)cc2)c(F)c1] | 603.2 | Method D, RT = 1.503 min, 96%. | $^1$H NMR (400 MHz, DMSO-$d_6$) δ = 9.10-8.93 (m, 1H), 7.91-7.86 (m, 2H), 7.76-7.63 (m, 1H), 7.37-7.24 (m, 3H), 6.78 (m, 2H), 6.43-6.30 (m, 1H), 5.33-4.93 (m, 2H), 4.34-4.11 (m, 2H), 3.94-3.80 (m, 2H), 3.77 (s, 3H), 3.63-3.49 (m, 2H), 3.19-3.05 (m, 1H), 2.93-2.88 (2s, 3H), 2.25-2.07 (2s, 3H), 1.27-1.14 (m, 2H). (Mixture of interconvertible atropisomers) |
| 509 | 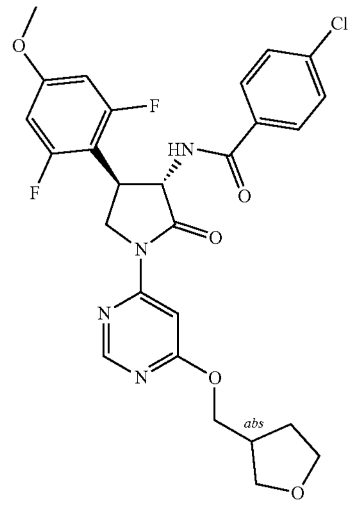 [SMILES: COc1cc(F)c([C@@H]2CN(c3cc(OCC4CCOC4)ncn3)C(=O)[C@H]2NC(=O)c2ccc(Cl)cc2)c(F)c1] | 559.15 | Method C, RT = 2.012 min, 100%. | $^1$H NMR (400 MHz, DMSO-$d_6$) δ = 9.18 (br d, J = 7.8 Hz, 1H), 8.65 (s, 1H), 7.83 (d, J = 8.5 Hz, 2H), 7.66 (s, 1H), 7.57 (d, J = 8.5 Hz, 2H), 6.78 (d, J = 10.8 Hz, 2H), 5.08-4.97 (m, 1H), 4.45 (t, J = 9.8 Hz, 1H), 4.39-4.31 (m, 1H), 4.29-4.22 (m, 1H), 4.14 (q, J = 9.8 Hz, 1H), 3.99-3.91 (m, 1H), 3.81-3.71 (m, 5H), 3.64 (q, J = 7.8 Hz, 1H), 3.53 (dd, J = 8.6, 5.6 Hz, 1H), 2.72-2.64 (m, 1H), 2.07-1.95 (m, 1H), 1.71-1.59 (m, 1H). |

TABLE 2-continued

| Ex | Structure | LCMS (M + H)+ | HPLC Method, RT (min.) & Purity | $^1$H NMR |
|---|---|---|---|---|
| 510 | 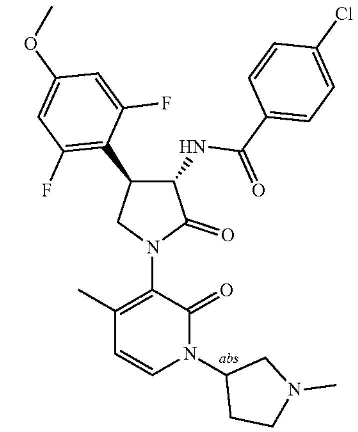 [SMILES: COc1cc(F)c([C@@H]2CN(c3c(C)ccn(C4CCN(C)C4)c3=O)C(=O)[C@H]2NC(=O)c2ccc(Cl)cc2)c(F)c1] | 572.2 | Method D, RT = 1.564 min, 94%. | $^1$H NMR (400 MHz, DMSO-$d_6$) δ = 9.20-8.94 (m, 1H), 7.91-7.78 (m, 2H), 7.76-7.64 (m, 1H), 7.62-7.50 (m, 2H), 6.85-6.66 (m, 2H), 6.46-6.29 (m, 1H), 5.28-4.87 (m, 2H), 4.31-4.06 (m, 2H), 3.94-3.75 (m, 2H), 3.77 (s, 3H), 3.61-3.43 (m, 2H), 3.17-3.13 (m, 1H), 2.89 (s, 3H), 2.55-2.49 (m, 2H), 2.28-1.99 (2s, 3H). (Mixture of interconvertible atropisomers) |
| 511 | 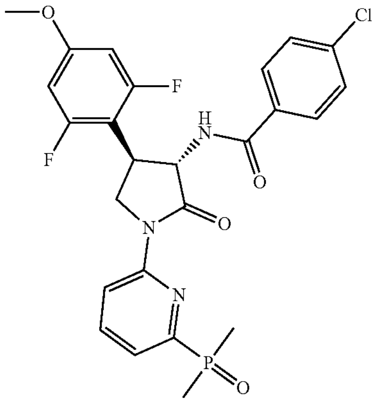 [SMILES: COc1cc(F)c([C@@H]2CN(c3cccc(P(C)(C)=O)n3)C(=O)[C@H]2NC(=O)c2ccc(Cl)cc2)c(F)c1] | 534.1 | Method D, RT = 1.671 min, 100%. | $^1$H NMR (400 MHz, DMSO-$d_6$) δ = 9.17 (d, J = 8.0 Hz, 1H), 8.47 (dd, J = 8.5, 1.3 Hz, 1H), 8.05 (m, 1H), 7.91-7.80 (m, 2H), 7.73 (dd, J = 6.9, 5.9 Hz, 1H), 7.62-7.49 (m, 2H), 6.80 (d, J = 10.5 Hz, 2H), 5.09 (dd, J = 10.9, 8.1 Hz, 1H), 4.54 (t, J = 9.5 Hz, 1H), 4.15 (q, J = 9.9 Hz, 1H), 4.03-3.89 (m, 1H), 3.78 (s, 3H), 1.68 (d, J = 13.6 Hz, 3H), 1.57 (d, J = 13.6 Hz, 3H). |
| 512 | 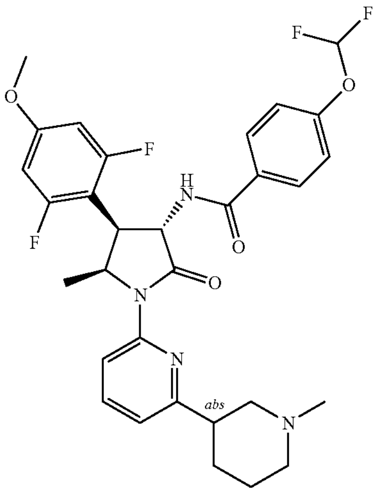 [SMILES: COc1cc(F)c([C@H]2[C@H](NC(=O)c3ccc(OC(F)F)cc3)C(=O)N(c3cccc(C4CCCN(C)C4)n3)[C@H]2C)c(F)c1] | 601.2 | Method D, RT = 1.661 min, 94%. | $^1$H NMR (400 MHz, DMSO-$d_6$) δ = 8.91 (d, J = 8.5 Hz, 1H), 8.18 (d, J = 8.3 Hz, 1H), 7.94-7.85 (m, 2H), 7.80 (t, J = 7.9 Hz, 1H), 7.34 (t, J = 75.4 Hz, 1H), 7.78-7.15 (m, 2H), 7.12 (d, J = 7.5 Hz, 1H), 6.80 (d, J = 11.5 Hz, 2H), 5.65 (dd, J = 12.6, 8.4 Hz, 1H), 5.01-4.91 (m, 1H), 4.32 (dd, J = 12.5, 8.3 Hz, 1H), 3.78 (s, 3H), 3.09-2.79 (m, 3H), 2.36-2.28 (m, 4H), 2.11-2.01 (m, 1H), 1.91-1.87 (m, 1H), 1.78-1.71 (m, 1H), 1.68-1.44 (m, 2H), 1.21 (d, J = 6.5 Hz, 3H). |

TABLE 2-continued

| Ex | Structure | LCMS (M + H)+ | HPLC Method, RT (min.) & Purity | $^1$H NMR |
|---|---|---|---|---|
| 513 | 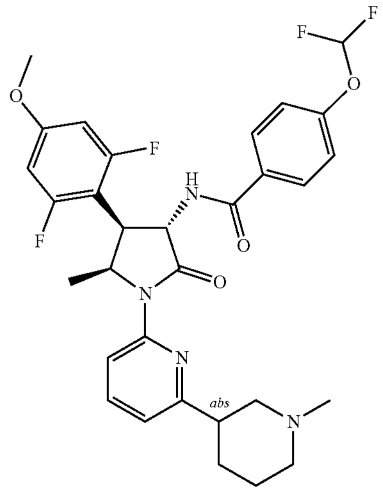 [SMILES: COc1cc(F)c([C@H]2[C@H](NC(=O)c3ccc(OC(F)F)cc3)C(=O)N(c3cccc(C4CCCN(C)C4)n3)[C@H]2C)c(F)c1] | 601.3 | Method D, RT = 1.657 min, 100%. | $^1$H NMR (400 MHz, DMSO-$d_6$) δ = 8.91 (d, J = 8.3 Hz, 1H), 8.19 (d, J = 8.3 Hz, 1H), 7.94-7.85 (m, 2H), 7.81 (t, J = 8.0 Hz, 1H), 7.28-7.21 (m, 2H), 7.42 (t, J = 73.8 Hz, 1H), 7.17-7.07 (m, 1H), 6.89-6.71 (m, 2H), 5.64 (dd, J = 12.4, 8.1 Hz, 1H), 5.02-4.88 (m, 1H), 4.32 (dd, J = 12.6, 7.9 Hz, 1H), 3.78 (s, 3H), 3.08-2.86 (m, 3H), 2.41-2.27 (m, 4H), 2.23-2.08 (m, 1H), 1.97-1.85 (m, 1H), 1.81-1.42 (m, 3H), 1.22 (d, J = 6.5 Hz, 3H). |
| 514 | 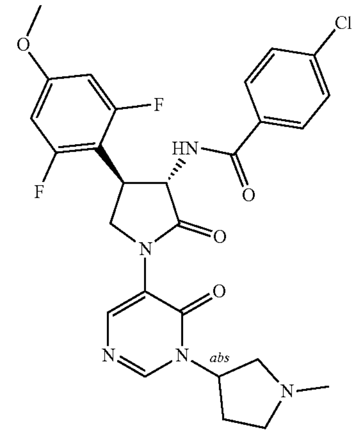 [SMILES: COc1cc(F)c([C@@H]2CN(c3cncn(C4CCN(C)C4)c3=O)C(=O)[C@H]2NC(=O)c2ccc(Cl)cc2)c(F)c1] | 558.1 | Method D, RT = 1.464 min, 100%. | $^1$H NMR (400 MHz, DMSO-$d_6$) δ = 9.07 (d, J = 8.8 Hz, 1H), 8.63 (s, 1H), 8.12 (s, 1H), 7.88-7.75 (m, 2H), 7.63-7.48 (m, 2H), 6.77 (d, J = 10.8 Hz, 2H), 5.25-5.17 (m, 1H), 5.11 (dd, J = 11.1, 8.4 Hz, 1H), 4.16-4.05 (m, 1H), 3.96 (d, J = 9.5 Hz, 2H), 3.76 (s, 3H), 3.13-3.03 (m, 1H), 3.00-2.88 (m, 1H), 2.63-2.50 (m, 2H), 2.47-2.38 (m, 1H), 2.33 (s, 3H), 1.93-1.89 (m, 1H). |
| 515 | 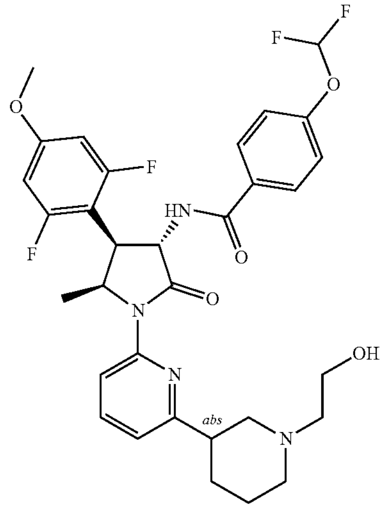 [SMILES: COc1cc(F)c([C@H]2[C@H](NC(=O)c3ccc(OC(F)F)cc3)C(=O)N(c3cccc(C4CCCN(CCO)C4)n3)[C@H]2C)c(F)c1] | 631.3 | Method C, RT = 1.553 min, 94%. | $^1$H NMR (400 MHz, DMSO-$d_6$) = 8.91 (d, J = 7.8 Hz, 1H), 8.18 (d, J = 8.5 Hz, 1H), 7.90 (d, J = 8.8 Hz, 2H), 7.79 (t, J = 7.9 Hz, 1H), 7.34 (t, J = 73.5 Hz, 1H), 7.27 (d, J = 8.8 Hz, 2H), 7.12 (d, J = 7.8 Hz, 1H), 6.86-6.74 (m, 2H), 5.66 (dd, J = 12.5, 8.3 Hz, 1H), 5.00-4.90 (m, 1H), 4.42-4.39 (m, 1H), 4.32 (dd, J = 12.6, 8.4 Hz, 1H), 3.79 (s, 3H), 3.52-3.49 (m, 2H), 3.07 (d, J = 10.8 Hz, 1H), 2.94-2.83 (m, 2H), 2.47-2.44 (m, 2H), 2.21-2.13 (m, 1H), 2.06-1.98 (m, 1H), 1.92-1.85 (m, 1H), 1.72-1.68 (m, 1H), 1.64-1.46 (m, 2H), 1.22 (d, J = 6.8 Hz, 3H). |

TABLE 2-continued
| Ex | Structure | LCMS (M + H)+ | HPLC Method, RT (min.) & Purity | $^1$H NMR |
|---|---|---|---|---|
| 516 | 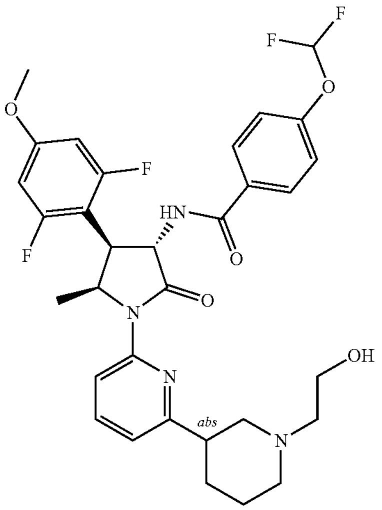 [SMILES: COc1cc(F)c([C@H]2[C@H](NC(=O)c3ccc(OC(F)F)cc3)C(=O)N(c3cccc(C4CCCN(CCO)C4)n3)[C@H]2C)c(F)c1] | 631.2 | Method D, RT = 1.642 min, 98%. | $^1$H NMR (400 MHz, DMSO-$d_6$) δ = 9.34 (s, 1H), 8.93 (s, 1H), 8.32-8.23 (m, 1H), 7.89 (d, J = 9.0 Hz, 3H), 7.34 (t, J = 72.5 Hz, 1H), 7.27 (d, J = 8.8 Hz, 2H), 6.82 (d, J = 11.5 Hz, 2H), 5.65-5.60 (m, 1H), 5.33-5.29 (m, 1H), 5.01-4.95 (m, 1H), 4.37-4.33 (m, 1H), 3.79 (s, 3H), 3.76-3.71 (m, 2H), 3.52-3.49 (m, 1H), 3.24-3.19 (m, 4H), 2.97-2.91 (m, 2H), 2.04-1.84 (m, 4H), 1.22 (d, J = 6.8 Hz, 3H). |
| 517 | 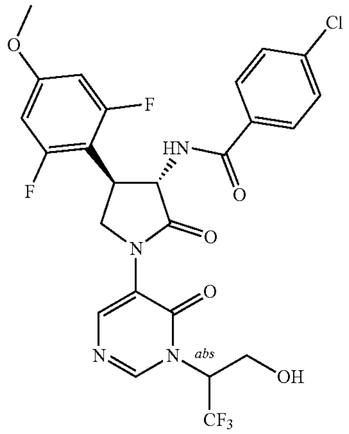 [SMILES: COc1cc(F)c([C@@H]2CN(c3cncn(C(CO)C(F)(F)F)c3=O)C(=O)[C@H]2NC(=O)c2ccc(Cl)cc2)c(F)c1] | 587.1 | Method D, RT = 1.683 min, 100%. | $^1$H NMR (400 MHz, DMSO-$d_6$) δ = 9.09 (d, J = 8.6 Hz, 1H), 8.45 (s, 1H), 8.18 (s, 1H), 7.89-7.76 (m, 2H), 7.63-7.46 (m, 2H), 7.15-6.85 (br s, 1H), 6.78 (d, J = 10.8 Hz, 2H), 5.11 (dd, J = 10.6, 8.7 Hz, 1H), 4.45-4.27 (m, 2H), 4.18-4.07 (m, 1H), 4.07-3.89 (m, 3H), 3.77 (s, 3H). |
| 518 | 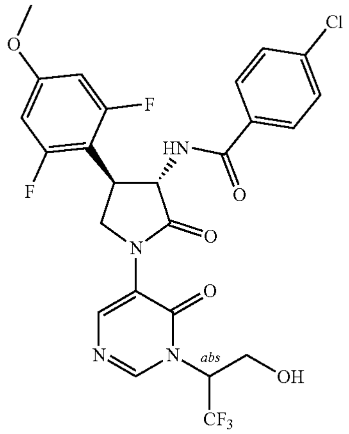 [SMILES: COc1cc(F)c([C@@H]2CN(c3cncn(C(CO)C(F)(F)F)c3=O)C(=O)[C@H]2NC(=O)c2ccc(Cl)cc2)c(F)c1] | 587.1 | Method D, RT = 1.684 min, 100%. | $^1$H NMR (400 MHz, DMSO-$d_6$) δ = 9.09 (d, J = 8.3 Hz, 1H), 8.46 (s, 1H), 8.20 (s, 1H), 7.84 (d, J = 8.6 Hz, 2H), 7.63-7.48 (m, 2H), 7.15-6.85 (br s, 1H), 6.78 (d, J = 10.8 Hz, 2H), 5.11 (dd, J = 10.8, 8.8 Hz, 1H), 4.45-4.25 (m, 2H), 4.19-4.08 (m, 1H), 4.08-3.87 (m, 3H), 3.77 (s, 3H). |

TABLE 2-continued

| Ex | Structure | LCMS (M + H)+ | HPLC Method, RT (min.) & Purity | $^1$H NMR |
|---|---|---|---|---|
| 519 | 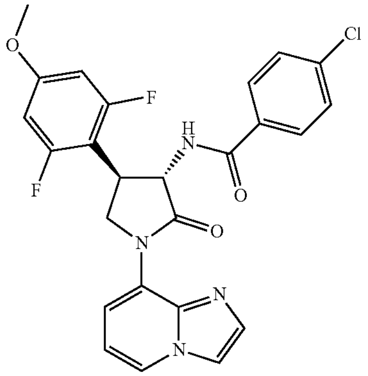 [SMILES: COc1cc(F)c([C@@H]2CN(c3cccn4ccnc34)C(=O)[C@H]2NC(=O)c2ccc(Cl)cc2)c(F)c1] | 497.11 | Method C, RT = 1.449 min, 98%. | $^1$H NMR (400 MHz, DMSO-d$_6$) δ = 9.14 (d, J = 8.5 Hz, 1H), 8.53 (dd, J = 6.8, 1.0 Hz, 1H), 8.04 (d, J = 1.3 Hz, 1H), 7.90-7.79 (m, 2H), 7.61 (d, J = 1.0 Hz, 1H), 7.60-7.52 (m, 2H), 7.48 (dd, J = 7.4, 1.0 Hz, 1H), 6.97 (t, J = 7.0 Hz, 1H), 6.79 (d, J = 10.8 Hz, 2H), 5.20 (dd, J = 11.3, 8.5 Hz, 1H), 4.54-4.46 (m, 1H), 4.41 (t, J = 9.9 Hz, 1H), 4.21 (q, J = 10.1 Hz, 1H), 3.77 (s, 3H). |
| 520 | 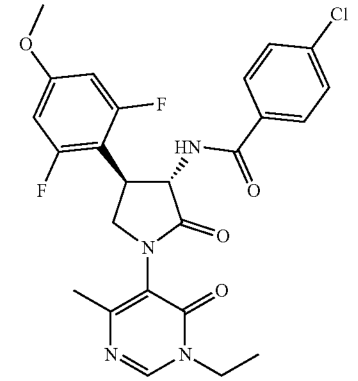 [SMILES: CCn1cnc(C)c(N2C[C@@H](c3c(F)cc(OC)cc3F)[C@H](NC(=O)c3ccc(Cl)cc3)C2=O)c1=O] | 517.1 | Method D, RT = 1.681 min, 100%. | $^1$H NMR (400 MHz, DMSO-d$_6$) δ = 9.20-8.97 (m, 1H), 8.52-8.39 (m, 1H), 7.88-7.77 (m, 2H), 7.60-7.50 (m, 2H), 6.81-6.71 (m, 2H), 5.30-4.85 (m, 1H), 4.29-4.02 (m, 2H), 3.99-3.87 (m, 2H), 3.80-3.74 (2s, 3H), 3.64-3.55 (m, 1H), 2.54-2.48 (m, 1H), 2.29-2.14 (2s, 3H), 1.30-1.21 (m, 3H). (Mixture of interconvertible atrop isomers) |
| 521 | 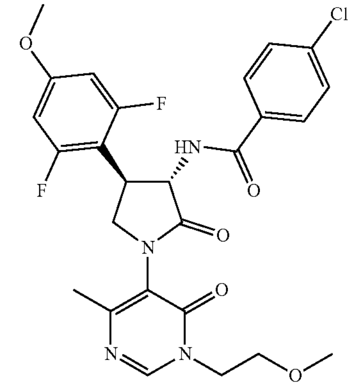 [SMILES: COCCn1cnc(C)c(N2C[C@@H](c3c(F)cc(OC)cc3F)[C@H](NC(=O)c3ccc(Cl)cc3)C2=O)c1=O] | 547.1 | Method D, RT = 1.686 min, 100%. | $^1$H NMR (400 MHz, DMSO-d$_6$) δ = 9.22-8.92 (m, 1H), 8.48-8.21 (m, 1H), 7.89-7.78 (m, 2H), 7.65-7.52 (m, 2H), 6.85-6.69 (m, 2H), 5.36-4.77 (m, 1H), 4.35-4.19 (m, 1H), 4.17-4.04 (m, 3H), 3.85-3.71 (2s, 3H), 3.65-3.53 (m, 2H), 2.47-2.38 (m, 1H), 2.36-2.24 (2s, 3H), 2.22-2.03 (m, 3H). (Mixture of interconvertible atrop isomers) |
| 522 | 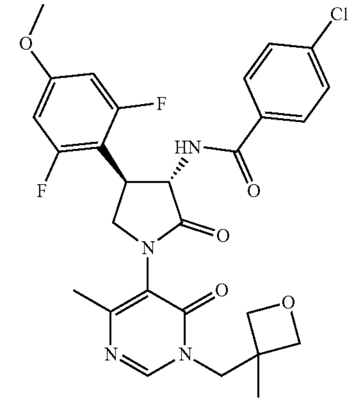 [SMILES: COc1cc(F)c([C@@H]2CN(c3c(C)ncn(CC4(C)COC4)c3=O)C(=O)[C@H]2NC(=O)c2ccc(Cl)cc2)c(F)c1] | 573.2 | Method D, RT = 1.547 min, 94%. | $^1$H NMR (400 MHz, DMSO-d$_6$) δ = 9.21-9.01 (m, 1H), 8.36-8.27 (m, 1H), 7.89-7.80 (m, 2H), 7.61-7.52 (m, 2H), 6.85-6.73 (m, 2H), 5.36-4.81 (m, 1H), 4.68 (br s, 2H), 4.33-3.98 (m, 1H), 3.97-3.86 (m, 2H), 3.81-3.73 (2s, 3H), 3.65-3.53 (m, 1H), 3.28-3.15 (m, 3H), 2.30-2.16 (2s, 3H), 0.79-0.70 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 523 | 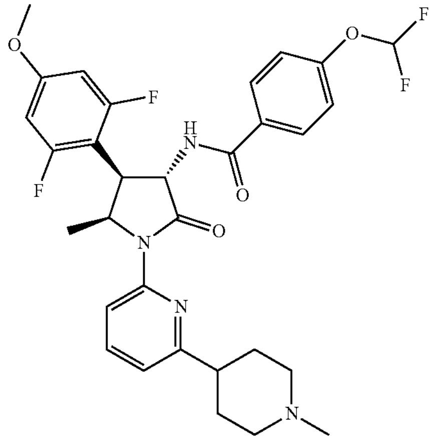 [SMILES: COc1cc(F)c([C@H]2[C@H](NC(=O)c3ccc(OC(F)F)cc3)C(=O)N(c3cccc(C4CCN(C)CC4)n3)[C@H]2C)c(F)c1] | 601.2 | Method D, RT = 1.942 min, 99%. | $^1$H NMR (400 MHz, DMSO-$d_6$) δ = 8.91 (d, J = 8.5 Hz, 1H), 8.17 (d, J = 8.5 Hz, 1H), 7.92-7.87 (m, 2H), 7.78 (dd, J = 8.5, 7.5 Hz, 1H), 7.34 (t, J = 76.0 Hz, 1H), 7.28-7.26 (m, 2H), 7.09 (d, J = 7.0 Hz, 1H), 6.84-6.77 (m, 2H), 5.67 (dd, J = 12.5, 8.5 Hz, 1H), 5.03-4.92 (m, 1H), 4.32 (dd, J = 12.8, 7.8 Hz, 1H), 3.79 (s, 3H), 2.87-2.83 (m, 2H), 2.65-2.55 (m, 1H), 2.18 (s, 3H), 1.96 (td, J = 11.4, 2.3 Hz, 2H), 1.85-1.68 (m, 4H), 1.21 (d, J = 6.5 Hz, 3H). |
| 524 | 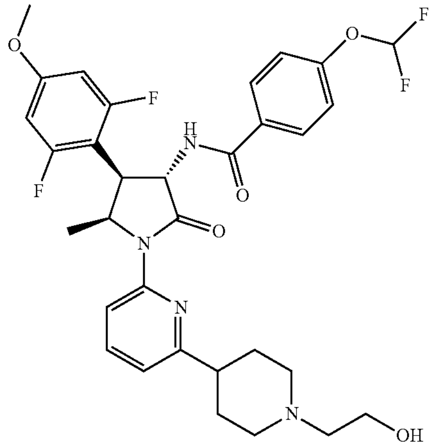 [SMILES: COc1cc(F)c([C@H]2[C@H](NC(=O)c3ccc(OC(F)F)cc3)C(=O)N(c3cccc(C4CCN(CCO)CC4)n3)[C@H]2C)c(F)c1] | 631.2 | Method D, RT = 1.87 min, 99%. | $^1$H NMR (400 MHz, DMSO-$d_6$) δ = 8.90 (d, J = 8.3 Hz, 1H), 8.17 (d, J = 8.0 Hz, 1H), 7.90 (d, J = 8.8 Hz, 2H), 7.78 (t, J = 7.9 Hz, 1H), 7.34 (t, J = 72.0 Hz, 1H), 7.26 (d, J = 8.8 Hz, 2H), 7.08 (d, J = 7.4 Hz, 1H), 6.81 (d, J = 10.8 Hz, 2H), 5.67 (dd, J = 12.5, 8.4 Hz, 1H), 5.03-4.95 (m, 1H), 4.39-4.28 (m, 2H), 3.79 (s, 3H), 3.60-3.43 (m, 2H), 3.43-3.37 (m, 1H), 3.03-2.95 (m, 2H), 2.42-2.38 (m, 2H), 2.32-2.01 (m, 2H), 1.84-1.68 (m, 4H), 1.21 (d, J = 6.4 Hz, 3H). |
| 525 | 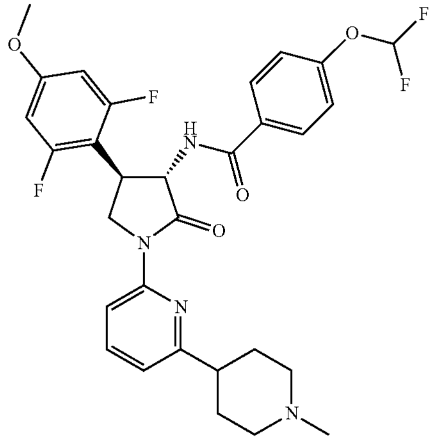 [SMILES: COc1cc(F)c([C@@H]2CN(c3cccc(C4CCN(C)CC4)n3)C(=O)[C@H]2NC(=O)c2ccc(OC(F)F)cc2)c(F)c1] | 587.2 | Method D, RT = 1.896 min, 99%. | $^1$H NMR (400 MHz, DMSO-$d_6$) δ = 9.09 (d, J = 8.3 Hz, 1H), 8.16 (d, J = 8.1 Hz, 1H), 7.89 (d, J = 8.9 Hz, 2H), 7.79 (t, J = 7.9 Hz, 1H), 7.35 (t, J = 72.0 Hz, 1H), 7.29 (d, J = 8.9 Hz, 2H), 7.10 (d, J = 7.5 Hz, 1H), 6.80 (d, J = 10.8 Hz, 2H), 5.08 (dd, J = 10.8, 8.3 Hz, 1H), 4.48 (t, J = 9.7 Hz, 1H), 4.12 (q, J = 9.8 Hz, 1H), 4.03-3.92 (m, 1H), 3.78 (s, 3H), 2.84 (m, 2H), 2.65-2.55 (m, 2H), 2.17 (s, 3H), 2.02-1.87 (m, 2H), 1.87-1.69 (m, 3H). |

TABLE 2-continued

| Ex | Structure | LCMS (M + H)+ | HPLC Method, RT (min.) & Purity | $^{1}$H NMR |
|---|---|---|---|---|
| 526 | 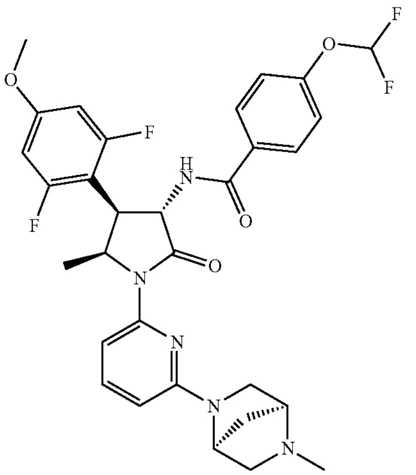 [SMILES: COc1cc(F)c([C@H]2[C@H](NC(=O)c3ccc(OC(F)F)cc3)C(=O)N(c3cccc(N4C[C@@H]5C[C@H]4CN5C)n3)[C@H]2C)c(F)c1] | 614.2 | Method D, RT = 1.645 min, 94%. | $^{1}$H NMR (400 MHz, DMSO-$d_6$) δ = 8.88 (d, J = 8.8 Hz, 1H), 7.90 (d, J = 8.8 Hz, 2H), 7.59-7.47 (m, 2H), 7.34 (t, J = 72.0 Hz, 1H), 7.28 (d, J = 8.6 Hz, 2H), 6.80 (d, J = 11.5 Hz, 2H), 6.31-6.22 (m, 1H), 5.67 (dd, J = 12.6, 8.4 Hz, 1H), 4.98-4.86 (m, 2H), 4.26 (dd, J = 12.7, 8.1 Hz, 2H), 3.80-3.74 (2s, 3H), 3.52-3.41 (m, 2H), 3.12-3.15 (m, 2H), 2.89-2.75 (2s, 3H), 2.40-2.35 (m, 1H), 2.21-2.15 (m, 1H), 1.20 (d, J = 6.4 Hz, 3H). (Mixture of interconvertible atropisomers) |
| 527 | 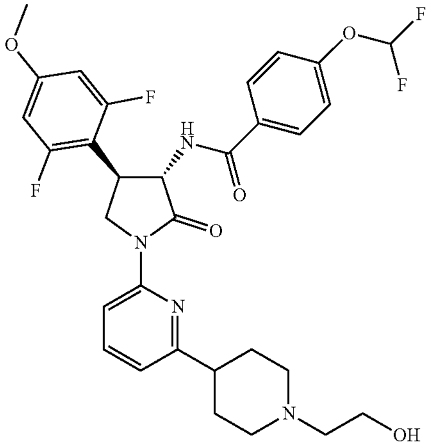 [SMILES: COc1cc(F)c([C@@H]2CN(c3cccc(C4CCN(CCO)CC4)n3)C(=O)[C@H]2NC(=O)c2ccc(OC(F)F)cc2)c(F)c1] | 617.2 | Method D, RT = 1.497 min, 98%. | $^{1}$H NMR (400 MHz, DMSO-$d_6$) δ = 9.10 (d, J = 7.8 Hz, 1H), 8.16 (d, J = 8.3 Hz, 1H), 7.95-7.86 (m, 2H), 7.80 (t, J = 7.9 Hz, 1H), 7.32-7.24 (m, 2H), 7.36 (t, J = 73.6 Hz, 1H), 7.10 (d, J = 7.6 Hz, 1H), 6.80 (d, J = 10.8 Hz, 2H), 5.08 (dd, J = 11.0, 8.6 Hz, 1H), 4.52-4.44 (m, 1H), 4.38-4.33 (m, 1H), 4.17-4.06 (m, 1H), 4.02-3.94 (m, 1H), 3.79 (s, 3H), 3.50 (t, J = 6.5 Hz, 2H), 2.99-2.95 (m, 2H), 2.65-2.56 (m, 1H), 2.41 (t, J = 6.5 Hz, 2H), 2.12-2.02 (m, 2H), 1.84-1.68 (m, 4H). |
| 528 | 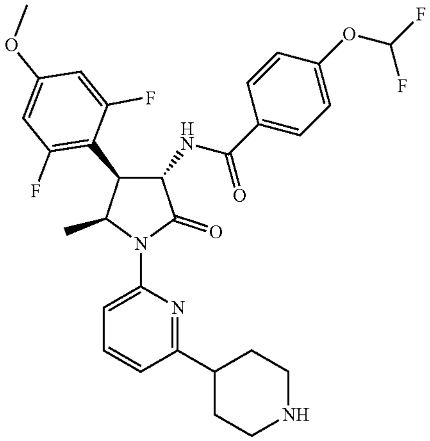 [SMILES: COc1cc(F)c([C@H]2[C@H](NC(=O)c3ccc(OC(F)F)cc3)C(=O)N(c3cccc(C4CCNCC4)n3)[C@H]2C)c(F)c1] | 587.2 | Method D, RT = 1.943 min, 99%. | $^{1}$H NMR (400 MHz, DMSO-$d_6$) δ = 8.90 (d, J = 8.3 Hz, 1H), 8.15 (d, J = 8.3 Hz, 1H), 7.89 (d, J = 8.8 Hz, 2H), 7.78 (t, J = 7.9 Hz, 1H), 7.33 (t, J = 72.0 Hz, 1H), 7.26 (d, J = 8.6 Hz, 2H), 7.06 (d, J = 7.5 Hz, 1H), 6.80 (d, J = 11.5 Hz, 2H), 5.67 (dd, J = 11.2, 8.3 Hz, 1H), 5.05-4.97 (m, 1H), 4.32 (dd, J = 12.5, 8.3 Hz, 1H), 3.79 (s, 3H), 3.05-2.97 (m, 2H), 2.77-2.70 (m, 1H), 2.62-2.54 (m, 3H), 1.80-1.71 (m, 2H), 1.66-1.52 (m, 2H), 1.20 (d, J = 6.4 Hz, 3H). |

TABLE 2-continued

| Ex | Structure | LCMS (M + H)+ | HPLC Method, RT (min.) & Purity | $^1$H NMR |
|---|---|---|---|---|
| 529 | 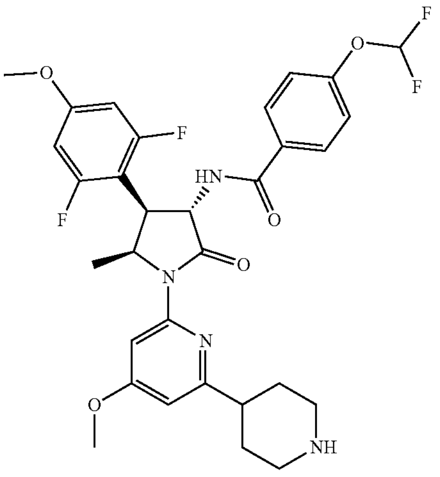 [SMILES: COc1cc(C2CCNCC2)nc(N2C(=O)[C@@H](NC(=O)c3ccc(OC(F)F)cc3)[C@H](c3c(F)cc(OC)cc3F)[C@@H]2C)c1] | 617.3 | Method-D, RT = 1.555 min, 97.7% | $^1$H NMR (400 MHz, DMSO-d$_6$) δ = 8.92 (d, J = 8.3 Hz, 1H), 7.94-7.84 (m, 3H), 7.34 (t, J = 76.0 Hz, 1H), 7.27 (d, J = 8.8 Hz, 2H), 7.02 (br s, 1H), 6.84-6.79 (m, 2H), 6.70 (d, J = 2.0 Hz, 1H), 5.65 (dd, J = 12.6, 8.2 Hz, 1H), 5.02-4.93 (m, 1H), 4.34 (dd, J = 12.7, 7.8 Hz, 1H), 3.84 (s, 3H), 3.79 (s, 3H), 3.08-2.89 (m, 4H), 2.53-2.52 (m, 1H), 2.06-1.83 (m, 4H), 1.22-1.18 (m, 3H). |
| 530 | 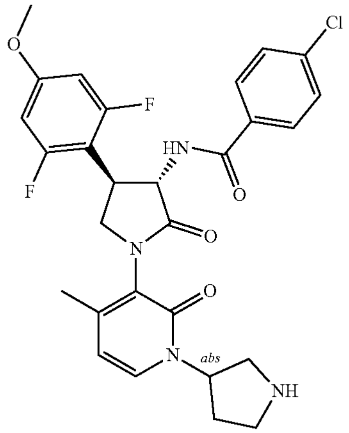 [SMILES: COc1cc(F)c([C@@H]2CN(c3c(C)ccn(C4CCNC4)c3=O)C(=O)[C@H]2NC(=O)c2ccc(Cl)cc2)c(F)c1] | 557.2 | Method D, RT = 1.679 min, 99%. | $^1$H NMR (400 MHz, DMSO-d$_6$) δ = 9.23-8.93 (m, 1H), 7.92-7.81 (m, 2H), 7.78-7.67 (m, 1H), 7.62-7.51 (m, 2H), 6.85-6.71 (m, 2H), 6.34-6.17 (m, 1H), 5.41-4.84 (m, 2H), 4.33-4.05 (m, 2H), 3.85-3.73 (2s, 3H), 3.55-3.36 (m, 2H), 3.16-3.02 (m, 2H), 2.92-2.75 (m, 2H), 2.29-2.24 (m, 1H), 2.25-2.06 (2s, 3H), 1.80-1.63 (m, 1H). (Mixture of interconvertible atropisomers) |
| 531 | 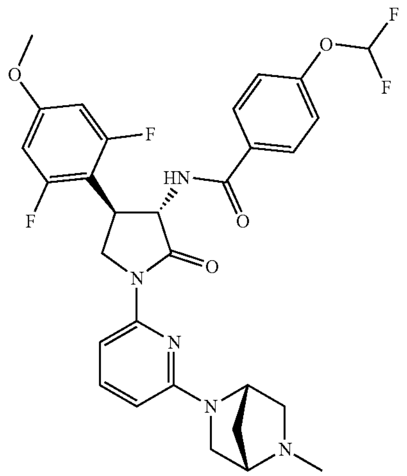 [SMILES: COc1cc(F)c([C@@H]2CN(c3cccc(N4C[C@@H]5C[C@H]4CN5C)n3)C(=O)[C@H]2NC(=O)c2ccc(OC(F)F)cc2)c(F)c1] | 600.2 | Method C, RT = 1.491 min, 99%. | $^1$H NMR (400 MHz, DMSO-d$_6$) δ = 9.06 (d, J = 8.3 Hz, 1H), 7.95-7.86 (m, 2H), 7.57-7.53 (m, 2H), 7.35 (t, J = 72.0 Hz, 1H), 7.34-7.16 (m, 2H), 6.80 (d, J = 10.8 Hz, 2H), 6.29 (dd, J = 5.3, 3.5 Hz, 1H), 5.08 (dd, J = 11.0, 8.3 Hz, 1H), 4.65-4.61 (m, 1H), 4.53-4.43 (m, 1H), 4.13-4.01 (m, 1H), 3.95-3.84 (m, 1H), 3.78 (s, 3H), 3.42-3.31 (m, 1H), 3.00-2.93 (m, 1H), 2.90-2.83 (m, 1H), 2.41 (s, 3H), 1.94-1.87 (m, 3H), 1.82-1.74 (m, 1H). |

TABLE 2-continued

| Ex | Structure | LCMS (M + H)+ | HPLC Method, RT (min.) & Purity | $^1$H NMR |
|---|---|---|---|---|
| 532 | 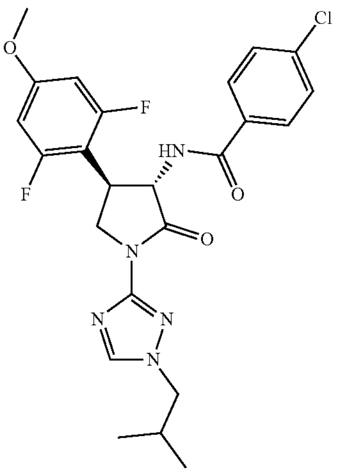 [SMILES: COc1cc(F)c([C@@H]2CN(c3ncn(CC(C)C)n3)C(=O)[C@H]2NC(=O)c2ccc(Cl)cc2)c(F)c1] | 504.1 | Method D, RT = 1.771 min, 97%. | $^1$H NMR (400 MHz, DMSO-$d_6$) δ = 9.13 (d, J = 8.3 Hz, 1H), 8.47 (s, 1H), 7.89-7.79 (m, 2H), 7.63-7.52 (m, 2H), 6.79 (d, J = 10.8 Hz, 2H), 5.00 (dd, J = 9.9, 8.9 Hz, 1H), 4.24-4.06 (m, 2H), 4.02-3.89 (m, 3H), 3.78 (s, 3H), 2.12 (m, 1H), 0.88 (d, J = 6.6 Hz, 3H), 0.86 (d, J = 6.6 Hz, 3H). |
| 533 | 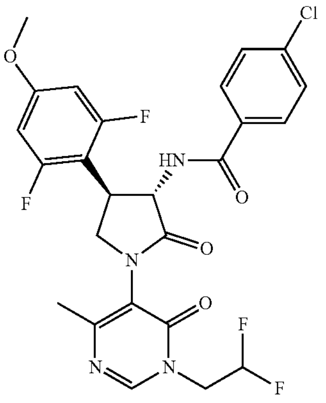 [SMILES: COc1cc(F)c([C@@H]2CN(c3c(C)ncn(CC(F)F)c3=O)C(=O)[C@H]2NC(=O)c2ccc(Cl)cc2)c(F)c1] | 553.1 | Method D, RT = 1.665 min, 100%. | $^1$H NMR (400 MHz, DMSO-$d_6$) δ = 9.22-8.96 (m, 1H), 8.51-8.30 (m, 1H), 8.00-7.73 (m, 2H), 7.63-7.41 (m, 2H), 6.85-6.70 (m, 2H), 6.42 (t, J = 52.2 Hz, 1H), 5.35-4.70 (m, 1H), 4.57-4.36 (m, 2H), 4.32-3.96 (m, 2H), 3.82-3.71 (2s, 3H), 3.67-3.51 (m, 1H), 2.33-2.14 (2s, 3H). (Mixture of interconvertible atropisomers) |
| 534 | 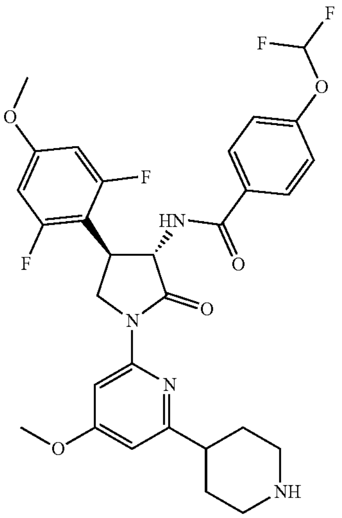 [SMILES: COc1cc(C2CCNCC2)nc(N2C[C@@H](c3c(F)cc(OC)cc3F)[C@H](NC(=O)c3ccc(OC(F)F)cc3)C2=O)c1] | 603.3 | Method D, RT = 1.486 min, 100% | $^1$H NMR (400 MHz, DMSO-$d_6$) δ = 9.13-9.08 (m, 1H), 7.90 (d, J = 8.8 Hz, 2H), 7.79 (d, J = 2.0 Hz, 1H), 7.35 (t, J = 72.0 Hz, 1H), 7.27 (d, J = 8.8 Hz, 2H), 6.80 (d, J = 10.8 Hz, 2H), 6.68 (d, J = 1.7 Hz, 1H), 5.08 (dd, J = 10.9, 8.2 Hz, 1H), 4.51-4.43 (m, 1H), 4.16-4.06 (m, 1H), 3.99-3.92 (m, 1H), 3.83 (s, 3H), 3.78 (s, 3H), 3.07-2.98 (m, 2H), 2.62-2.56 (m, 1H), 1.80-1.71 (m, 5H), 1.64 (dt, J = 9.4, 1.6 Hz, 2H). |

TABLE 2-continued

| Ex | Structure | LCMS (M + H)+ | HPLC Method, RT (min.) & Purity | $^{1}$H NMR |
|---|---|---|---|---|
| 535 | 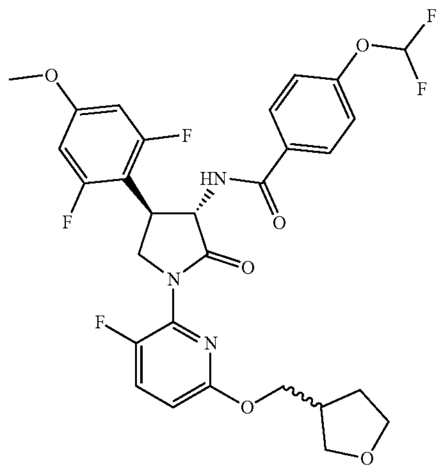 [SMILES: COc1cc(F)c([C@@H]2CN(c3nc(OCC4CCOC4)ccc3F)C(=O)[C@H]2NC(=O)c2ccc(OC(F)F)cc2)c(F)c1] | 608.2 | Method D, RT = 1.93 min, 94% | $^{1}$H NMR (400 MHz, DMSO-$d_6$) δ = 9.10 (d, J = 8.6 Hz, 1H), 7.97-7.86 (m, 3H), 7.35 (t, J = 73.2 Hz, 1H), 7.27 (d, J = 8.4 Hz, 2H), 6.85 (dd, J = 8.8, 2.7Hz, 1H), 6.80 (d, J = 10.8 Hz, 2H), 5.17-5.04 (m, 1H), 4.30-3.94 (m, 5H), 3.82-3.71 (m, 5H), 3.67-3.63 (m, 1H), 3.55-3.51 (m, 1H), 2.71-2.64 (m, 1H), 2.06-1.94 (m, 1H), 1.72-1.60 (m, 1H). |
| 536 | 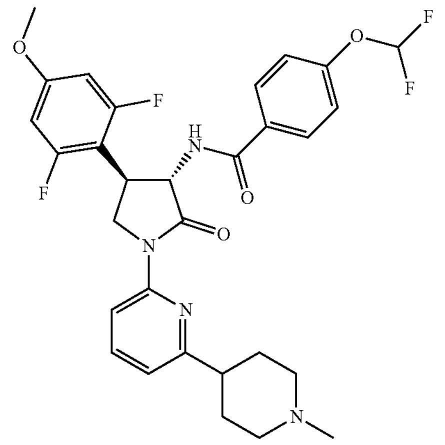 [SMILES: COc1cc(F)c([C@@H]2CN(c3cccc(C4CCN(C)CC4)n3)C(=O)[C@H]2NC(=O)c2ccc(OC(F)F)cc2)c(F)c1] | 587.2 | Method D, RT = 1.521 min, 94%. | $^{1}$H NMR (400 MHz, DMSO-$d_6$) δ = 8.75 (d, J = 7.8 Hz, 1H), 8.24 (d, J = 8.3 Hz, 1H), 7.79 (t, J = 7.5 Hz, 1H), 7.74-7.64 (m, 2H), 7.17 (d, J = 8.8 Hz, 1H), 7.31 (t, J = 73.5 Hz, 2H), 7.09 (d, J = 7.5 Hz, 1H), 6.61 (d, J = 11.0 Hz, 2H), 5.30 (t, J = 8.5 Hz, 1H), 4.47-4.24 (m, 3H), 3.70 (s, 3H), 2.97-2.87 (m, 2H), 2.65-2.58 (m, 1H), 2.25 (s, 3H), 2.15-2.00 (m, 2H), 1.90-1.67 (m, 4H). |
| 537 | 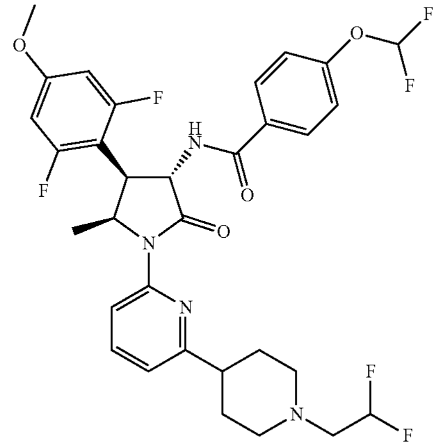 [SMILES: COc1cc(F)c([C@H]2[C@H](NC(=O)c3ccc(OC(F)F)cc3)C(=O)N(c3cccc(C4CCN(CC(F)F)CC4)n3)[C@H]2C)c(F)c1] | 651.2 | Method D, RT = 2.252 min, 94%. | $^{1}$H NMR (400 MHz, DMSO-$d_6$) δ = 8.91 (d, J = 8.5 Hz, 1H), 8.19 (d, J = 8.5 Hz, 1H), 7.83 (d, J = 9.2 Hz, 2H), 7.80 (t, J = 8.0 Hz, 1H), 7.35 (t, J = 75.3 Hz, 1H), 7.27 (d, J = 9.2 Hz, 2H), 7.11 (d, J = 7.5 Hz, 1H), 6.87-6.72 (m, 2H), 6.40-6.10 (m, 1H), 5.66 (dd, J = 12.5, 8.5 Hz, 1H), 5.06-4.91 (m, 1H), 4.33 (dd, J = 12.5, 8.0 Hz, 1H), 3.79 (s, 3H), 3.33-3.29 (m, 1H), 3.11-2.66 (m, 5H), 2.28-2.24 (m, 1H), 1.87-1.80 (m, 4H), 1.22 (d, J = 6.5 Hz, 3H). |

TABLE 2-continued

| Ex | Structure | LCMS (M + H)+ | HPLC Method, RT (min.) & Purity | $^1$H NMR |
|---|---|---|---|---|
| 538 | 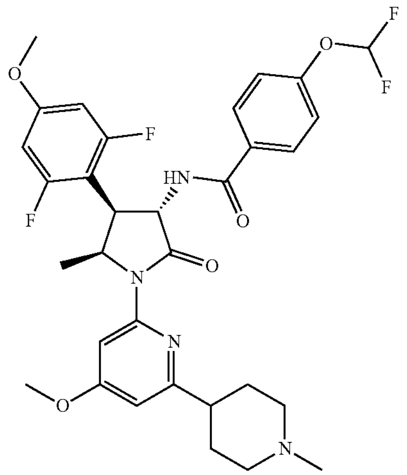 [SMILES: COc1cc(C2CCN(C)CC2)nc(N2C(=O)[C@@H](NC(=O)c3ccc(OC(F)F)cc3)[C@H](c3c(F)cc(OC)cc3F)[C@@H]2C)c1] | 631.2 | Method C, RT = 1.499 min, 95.9% | $^1$H NMR (400 MHz, DMSO-$d_6$) δ = 8.88 (d, J = 8.3 Hz, 1H), 7.89 (d, J = 8.8 Hz, 2H), 7.81 (d, J = 2.1 Hz, 1H), 7.34 (t, J = 76.0 Hz, 1H), 7.26 (d, J = 8.6 Hz, 2H), 6.80 (d, J = 11.5 Hz, 2H), 6.69 (d, J = 2.0 Hz, 1H), 5.67 (dd, J = 12.6, 8.4 Hz, 1H), 5.02-4.93 (m, 1H), 4.30 (dd, J = 12.6, 7.9 Hz, 1H), 3.82 (s, 3H), 3.78 (s, 3H), 2.84 (br d, J = 10.8 Hz, 2H), 2.18 (s, 3H), 1.99-1.96 (m, 1H), 1.97-1.92 (m, 2H), 1.82-1.70 (m, 4H), 1.19 (br d, J = 6.4 Hz, 3H). |
| 539 | 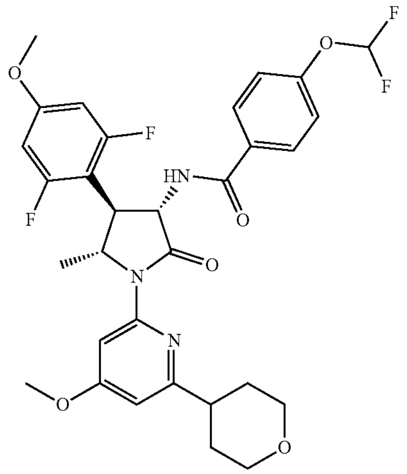 [SMILES: COc1cc(C2CCOCC2)nc(N2C(=O)[C@@H](NC(=O)c3ccc(OC(F)F)cc3)[C@H](c3c(F)cc(OC)cc3F)[C@H]2C)c1] | 618.3 | Method C, RT = 1.910 min, 93.3% | $^1$H NMR (400 MHz, DMSO-$d_6$) δ = 9.09 (d, J = 7.8 Hz, 1H), 7.93-7.88 (m, 2H), 7.40-7.37 (m, 1H), 7.34 (t, J = 76.0 Hz, 1H), 7.32-7.26 (m, 2H), 6.86-6.78 (m, 2H), 6.77-6.74 (m, 1H), 5.04-4.95 (m, 1H), 4.66-4.57 (m, 1H), 3.98-3.89 (m, 2H), 3.86-3.84 (m, 3H), 3.79 (s, 3H), 3.74-3.65 (m, 1H), 3.48-3.38 (m, 2H), 2.93-2.80 (m, 1H), 1.81-1.70 (m, 4H), 1.35 (d, J = 6.6 Hz, 3H). |
| 540 | 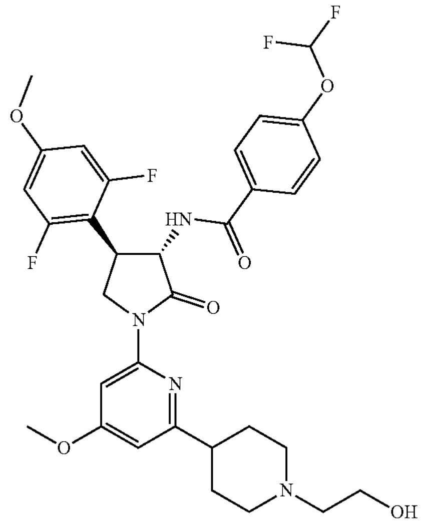 [SMILES: COc1cc(C2CCN(CCO)CC2)nc(N2C[C@@H](c3c(F)cc(OC)cc3F)[C@H](NC(=O)c3ccc(OC(F)F)cc3)C2=O)c1] | 647.2 | Method D, RT = 1.552 min, 98.4% | $^1$H NMR (400 MHz, DMSO-$d_6$) δ = 9.08 (d, J = 8.3 Hz, 1H), 7.93-7.87 (m, 2H), 7.79 (d, J = 2.2 Hz, 1H), 7.35 (t, J = 74.3 Hz, 1H), 7.29 (d, J = 8.8 Hz, 2H), 6.83-6.76 (m, 2H), 6.70 (d, J = 2.2 Hz, 1H), 5.07 (dd, J = 10.9, 8.2 Hz, 1H), 4.48 (br t, J = 9.9 Hz, 1H), 4.16-4.06 (m, 1H), 4.00-3.91 (m, 1H), 3.83 (s, 3H), 3.78 (s, 3H), 3.49 (t, J = 6.4 Hz, 3H), 2.98-2.91 (m, 2H), 2.55 (br d, J = 5.1 Hz, 1H), 2.38 (t, J = 6.5 Hz, 2H), 2.08-1.98 (m, 2H), 1.81-1.72 (m, 4H). |

TABLE 2-continued

| Ex | Structure | LCMS (M + H)+ | HPLC Method, RT (min.) & Purity | $^1$H NMR |
|---|---|---|---|---|
| 541 | 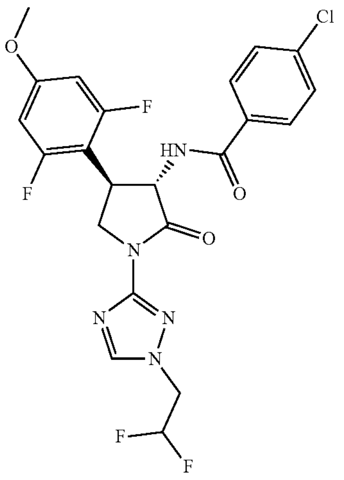 [SMILES: COc1cc(F)c([C@@H]2CN(c3ncn(CC(F)F)n3)C(=O)[C@H]2NC(=O)c2ccc(Cl)cc2)c(F)c1] | 512.1 | Method D, RT = 1.627 min, 98%. | $^1$H NMR (400 MHz, DMSO-$d_6$) δ = 9.14 (d, J = 8.3 Hz, 1H), 8.56 (s, 1H), 7.83 (d, J = 8.6 Hz, 2H), 7.58 (d, J = 8.6 Hz, 2H), 6.79 (d, J = 10.8 Hz, 2H), 6.42 (tt, J = 54.5, 9.1 Hz, 1H), 5.03-4.92 (m, 1H), 4.78-4.71 (m, 2H), 4.27-4.09 (m, 2H), 4.00-3.91 (m, 1H), 3.78 (s, 3H). |
| 542 | 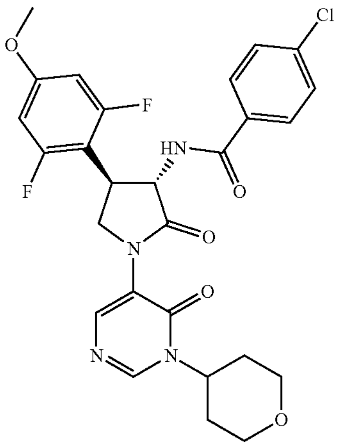 [SMILES: COc1cc(F)c([C@@H]2CN(c3cncn(C4CCOCC4)c3=O)C(=O)[C@H]2NC(=O)c2ccc(Cl)cc2)c(F)c1] | 559.1 | Method D, RT = 1.574 min, 95%. | $^1$H NMR (400 MHz, DMSO-$d_6$) δ = 9.07 (d, J = 8.5 Hz, 1H), 8.60 (s, 1H), 8.13 (s, 1H), 7.88-7.74 (m, 2H), 7.60-7.46 (m, 2H), 6.77 (d, J = 10.8 Hz, 2H), 5.11 (dd, J = 11.0, 8.5 Hz, 1H), 4.78 (t, J = 12.2, 3.8 Hz, 1H), 4.19-4.05 (m, 1H), 4.03-3.92 (m, 4H), 3.76 (s, 3H), 3.48-3.44 (m, 2H), 2.14-1.96 (m, 2H), 1.83-1.78 (m, 2H). |
| 543 | 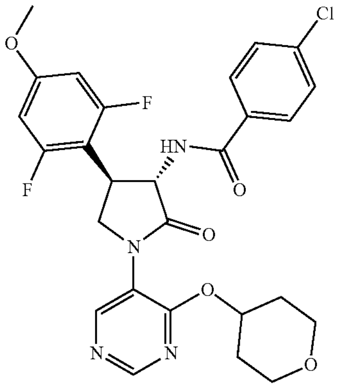 [SMILES: COc1cc(F)c([C@@H]2CN(c3cncnc3OC3CCOCC3)C(=O)[C@H]2NC(=O)c2ccc(Cl)cc2)c(F)c1] | 559.2 | Method D, RT = 1.7 min, 99%. | $^1$H NMR (400 MHz, DMSO-$d_6$) δ = 9.12 (d, J = 8.5 Hz, 1H), 8.74 (s, 1H), 8.63 (s, 1H), 7.90-7.76 (m, 2H), 7.62-7.44 (m, 2H), 6.80 (d, J = 10.8 Hz, 2H), 5.43 (t, J = 7.5 Hz, 1H), 5.09 (d, J = 10.9 Hz, 1H), 4.18 (q, J = 10.0 Hz, 1H), 4.03-3.95 (m, 2H), 3.82 (d, J = 11.3 Hz, 2H), 3.77 (s, 3H), 3.64-3.52 (m, 2H), 2.10-1.92 (m, 2H), 1.80-1.61 (m, 2H). |

TABLE 2-continued

| Ex | Structure | LCMS (M + H)+ | HPLC Method, RT (min.) & Purity | $^1$H NMR |
|---|---|---|---|---|
| 544 | 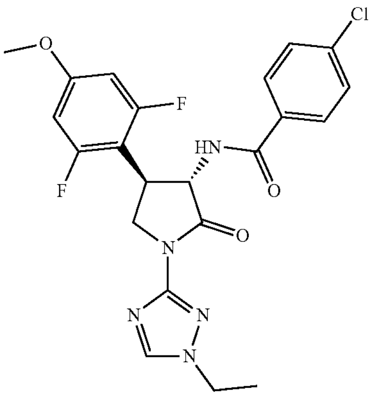 [SMILES: CCn1cnc(N2C[C@@H](c3c(F)cc(OC)cc3F)[C@H](NC(=O)c3ccc(Cl)cc3)C2=O)n1] | 476.2 | Method D, RT = 2.282 min, 99%. | $^1$H NMR (400 MHz, DMSO-d$_6$) δ = 9.12 (d, J = 8.4 Hz, 1H), 8.47 (s, 1H), 7.87-7.79 (m, J = 8.6 Hz, 2H), 7.62-7.54 (m, 2H), 6.80 (s, 1H), 6.77 (s, 1H), 4.98 (dd, J = 10.4, 8.4 Hz, 1H), 4.24-4.10 (m, 4H), 4.00-3.87 (m, 1H), 3.78 (s, 3H), 1.40 (t, J = 7.3 Hz, 3H). |
| 545 | 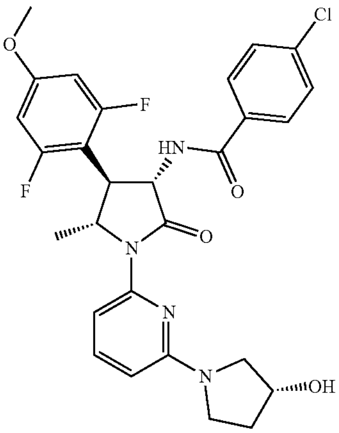 [SMILES: COc1cc(F)c([C@H]2[C@H](NC(=O)c3ccc(Cl)cc3)C(=O)N(c3cccc(N4CC[C@@H](O)C4)n3)[C@@H]2C)c(F)c1] | 557.1 | Method D, RT = 1.798 min, 96%. | $^1$H NMR (400 MHz, DMSO-d$_6$) δ = 9.13 (d, J = 8.5 Hz, 1H), 7.92-7.74 (m, 2H), 7.64-7.46 (m, 3H), 7.15 (d, J = 7.5 Hz, 1H), 6.82 (d, J = 11.3 Hz, 2H), 6.26 (d, J = 8.3 Hz, 1H), 5.00 (dd, J = 10.8, 8.5 Hz, 1H), 4.92 (d, J = 3.0 Hz, 1H), 4.62-4.48 (m, 1H), 4.37 (d, J = 1.3 Hz, 1H), 3.79 (s, 3H), 3.64 (t, J = 9.9 Hz, 1H), 3.50-3.30 (m, 4H), 2.06-1.96 (m, 1H), 1.91-1.79 (m, 1H), 1.38 (d, J = 6.0 Hz, 3H). |
| 546 | 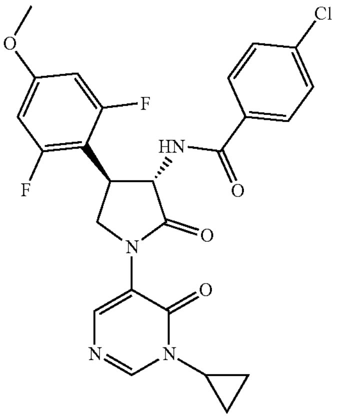 [SMILES: COc1cc(F)c([C@@H]2CN(c3cncn(C4CC4)c3=O)C(=O)[C@H]2NC(=O)c2ccc(Cl)cc2)c(F)c1] | 515.1 | Method D, RT = 1.597 min, 100%. | $^1$H NMR (400 MHz, DMSO-d$_6$) δ = 9.11 (d, J = 8.8 Hz, 1H), 7.90-7.73 (m, 2H), 7.66-7.50 (m, 3H), 7.25-7.12 (m, 1H), 6.77 (d, J = 10.8 Hz, 2H), 5.16 (dd, J = 10.3, 9.0 Hz, 1H), 4.21-4.02 (m, 2H), 3.99-3.88 (m, 1H), 3.76 (s, 3H), 3.52-3.41 (m, 1H), 1.09-1.01 (m, 2H), 0.99-0.89 (m, 2H). |

TABLE 2-continued

| Ex | Structure | LCMS (M + H)+ | HPLC Method, RT (min.) & Purity | $^1$H NMR |
|---|---|---|---|---|
| 547 | 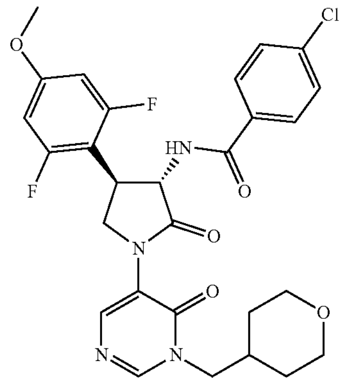 [SMILES: COc1cc(F)c([C@@H]2CN(c3cncn(CC4CCOCC4)c3=O)C(=O)[C@H]2NC(=O)c2ccc(Cl)cc2)c(F)c1] | 573.2 | Method D, RT = 1.604 min, 96%. | $^1$H NMR (400 MHz, DMSO-$d_6$) δ = 9.08 (d, J = 8.8 Hz, 1H), 8.50 (s, 1H), 8.15 (s, 1H), 7.86-7.81 (m, 2H), 7.60-7.54 (m, 2H), 6.78 (d, J = 10.8 Hz, 2H), 5.13 (dd, J = 11.2, 8.6 Hz, 1H), 4.16-4.04 (m, 1H), 4.03-3.92 (m, 2H), 3.90-3.81 (m, 4H), 3.77 (s, 3H), 3.24 (t, J = 11.5 Hz, 2H), 2.10-1.95 (m, 1H), 1.47-1.42 (m, 2H), 1.34-1.21 (m, 2H). |
| 548 | 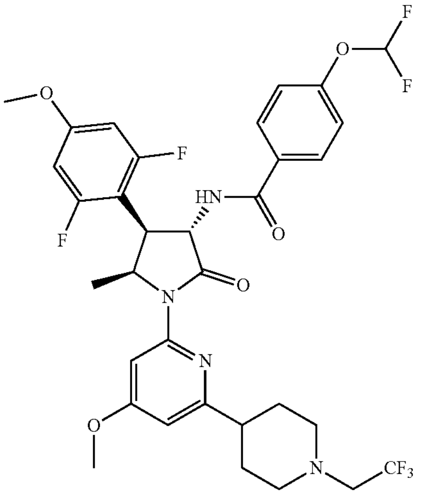 [SMILES: COc1cc(C2CCN(CC(F)(F)F)CC2)nc(N2C(=O)[C@@H](NC(=O)c3ccc(OC(F)F)cc3)[C@H](c3c(F)cc(OC)cc3F)[C@@H]2C)c1] | 699.2 | Method-D, RT = 2.434 min, 100% | $^1$H NMR (400 MHz, DMSO-$d_6$) δ = 8.93-8.87 (m, 1H), 7.90 (d, J = 8.6 Hz, 2H), 7.84-7.81 (m, 1H), 7.34 (t, J = 76.0 Hz, 1H), 7.28 (d, J = 8.6 Hz, 2H), 6.80 (d, J = 11.0 Hz, 2H), 6.73-6.70 (m, 1H), 5.67 (dd, J = 12.7, 8.3 Hz, 1H), 5.02-4.92 (m, 1H), 4.30 (dd, J = 12.7, 8.1 Hz, 1H), 3.86 (s, 3H), 3.79 (s, 3H), 3.18 (q, J = 10.2 Hz, 2H), 3.01 (br d, J = 11.5 Hz, 2H), 2.65-2.54 (m, 1H), 2.46-2.42 (m, 2H), 1.86-1.67 (m, 4H), 1.21 (d, J = 6.6 Hz, 3H). |
| 549 | 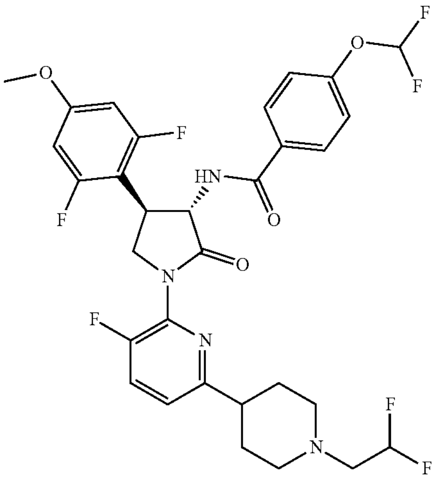 [SMILES: COc1cc(F)c([C@@H]2CN(c3nc(C4CCN(CC(F)F)CC4)ccc3F)C(=O)[C@H]2NC(=O)c2ccc(OC(F)F)cc2)c(F)c1] | 655.2 | Method D, RT = 2.089 min, 95% | $^1$H NMR (400 MHz, DMSO-$d_6$) δ = 9.10 (d, J = 8.6 Hz, 1H), 7.90 (d, J = 8.6 Hz, 2H), 7.80 (t, J = 9.0 Hz, 1H), 7.34 (t, J = 76.0 Hz, 1H), 7.34 (t, J = 71.7 Hz, 1H), 7.28 (d, J = 8.6 Hz, 2H), 6.79 (d, J = 11.0 Hz, 2H), 6.15 (tt, J = 54.3, 11.5 Hz, 1H), 5.13 (br t, J = 9.4 Hz, 1H), 4.31-4.15 (m, 2H), 4.12-4.01 (m, 1H), 3.78 (s, 3H), 3.00 (br d, J = 11.5 Hz, 2H), 2.80-2.62 (m, 3H), 2.32-2.19 (m, 2H), 1.86-1.64 (m, 4H). |

TABLE 2-continued

| Ex | Structure | LCMS (M + H)+ | HPLC Method, RT (min.) & Purity | $^1$H NMR |
|---|---|---|---|---|
| 550 | 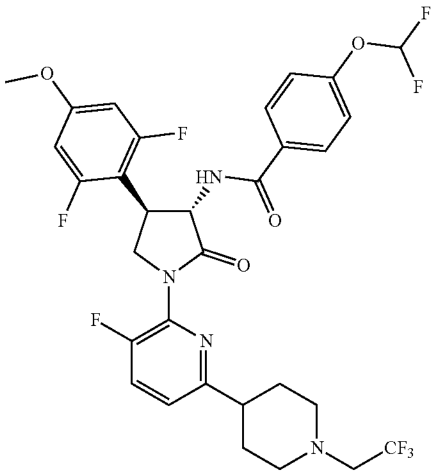 [SMILES: COc1cc(F)c([C@@H]2CN(c3nc(C4CCN(CC(F)(F)F)CC4)ccc3F)C(=O)[C@H]2NC(=O)c2ccc(OC(F)F)cc2)c(F)c1] | 673.2 | Method D, RT = 2.24 min, 96% | $^1$H NMR (400 MHz, DMSO-$d_6$) δ = 9.10 (d, J = 8.6 Hz, 1H), 7.90 (d, J = 8.6 Hz, 2H), 7.80 (dd, J = 8.6, 9.8 Hz, 1H), 7.39-7.33 (m, 1H), 7.35 (t, J = 73.6 Hz, 1H), 7.28 (d, J = 8.6 Hz, 2H), 6.79 (d, J = 10.8 Hz, 2H), 5.20-5.04 (m, 1H), 4.30-4.16 (m, 2H), 4.13-4.00 (m, 1H), 3.78 (s, 3H), 3.19 (q, J = 10.3 Hz, 2H), 3.02 (br d, J = 11.2 Hz, 2H), 2.74-2.66 (m, 1H), 2.48-2.41 (m, 2H), 1.88-1.66 (m, 4H) |
| 551 | 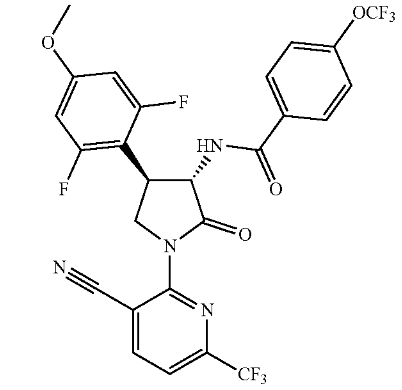 [SMILES: COc1cc(F)c([C@@H]2CN(c3nc(C(F)(F)F)ccc3C#N)C(=O)[C@H]2NC(=O)c2ccc(OC(F)(F)F)cc2)c(F)c1] | 601.1 | Method D, RT = 2.257 min, 98.7% | $^1$H NMR (400 MHz, DMSO-$d_6$) δ = 9.28 (d, J = 8.3 Hz, 1H), 8.78 (d, J = 7.8 Hz, 1H), 8.06 (d, J = 8.1 Hz, 1H), 8.01-7.88 (m, 2H), 7.51 (d, J = 8.3 Hz, 2H), 6.81 (d, J = 10.8 Hz, 2H), 5.11 (dd, J = 10.5, 8.3 Hz, 1H), 4.51-4.39 (m, 1H), 4.36-4.24 (m, 1H), 4.22-4.12 (m, 1H), 3.78 (s, 3H). |
| 552 | 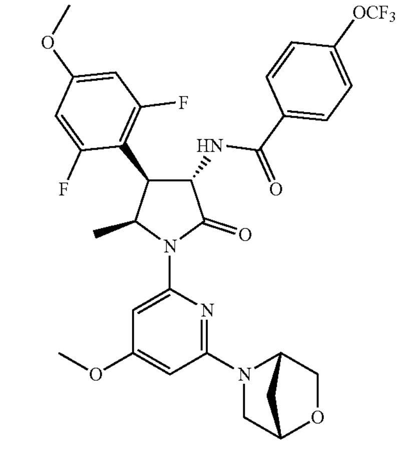 [SMILES: COc1cc(N2C[C@@H]3C[C@H]2CO3)nc(N2C(=O)[C@@H](NC(=O)c3ccc(OC(F)(F)F)cc3)[C@H](c3c(F)cc(OC)cc3F)[C@@H]2C)c1] | 649.3 | Method-C, RT = 1.916 min, 82.51% | $^1$H NMR (400 MHz, DMSO-$d_6$) δ = 8.99-8.91 (m, 1H), 7.97-7.92 (m, 2H), 7.51-7.45 (m, 2H), 7.29 (d, J = 2.0 Hz, 1H), 6.83-6.75 (m, 2H), 5.87 (d, J = 1.5 Hz, 1H), 5.71-5.63 (m, 1H), 4.92-4.82 (m, 1H), 4.79-4.75 (m, 1H), 4.65-4.61 (m, 1H), 4.28-4.20 (m, 1H), 3.80 (s, 3H), 3.78 (s, 3H), 3.70-3.63 (m, 1H), 3.47-3.41 (m, 1H), 3.25-3.15 (m, 2H), 1.90-1.80 (m, 2H), 1.21 (br d, J = 6.4 Hz, 3H). |

TABLE 2-continued

| Ex | Structure | LCMS (M + H)+ | HPLC Method, RT (min.) & Purity | $^{1}$H NMR |
|---|---|---|---|---|
| 553 | 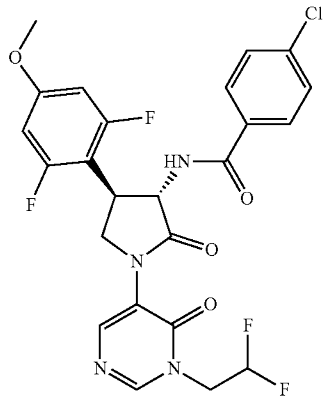 [SMILES: COc1cc(F)c([C@@H]2CN(c3cncn(CC(F)F)c3=O)C(=O)[C@H]2NC(=O)c2ccc(Cl)cc2)c(F)c1] | 539.2 | Method D, RT = 2.426 min, 99% | $^{1}$H NMR (400 MHz, DMSO-$d_6$) δ = 9.09 (d, J = 8.6 Hz, 1H), 8.51 (s, 1H), 8.19 (s, 1H), 7.86-7.81 (m, 2H), 7.60-7.54 (m, 2H), 6.77 (d, J = 10.8 Hz, 2H), 6.40 (tt, J = 56.0, 9.2 Hz, 1H), 5.12 (dd, J = 11.0, 8.6 Hz, 1H), 4.58-4.42 (m, 2H), 4.17-4.06 (m, 1H), 4.05-3.92 (m, 2H), 3.77 (s, 3H). |
| 554 | 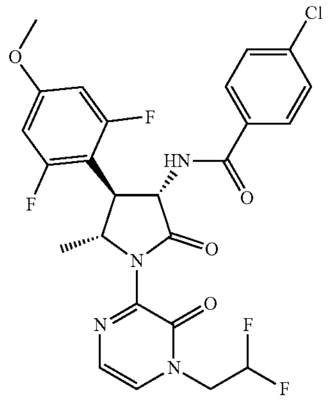 [SMILES: COc1cc(F)c([C@H]2[C@H](NC(=O)c3ccc(Cl)cc3)C(=O)N(c3nccn(CC(F)F)c3=O)[C@@H]2C)c(F)c1] | 553.1 | Method D, RT = 1.76 min, 98%. | $^{1}$H NMR (400 MHz, DMSO-$d_6$) δ = 9.15 (d, J = 8.8 Hz, 1H), 7.90-7.79 (m, 2H), 7.76 (d, J = 4.4 Hz, 1H), 7.62-7.50 (m, 2H), 7.38 (d, J = 4.4 Hz, 1H), 6.80 (d, J = 11.2 Hz, 2H), 6.41 (tt, J = 54.8, 4.3 Hz, 1H), 5.24 (dd, J = 11.2, 8.8 Hz, 1H), 4.56-4.42 (m, 3H), 3.78 (s, 3H), 3.69 (t, J = 10.4 Hz, 1H), 1.09 (d, J = 6.1 Hz, 3H). |
| 555 | 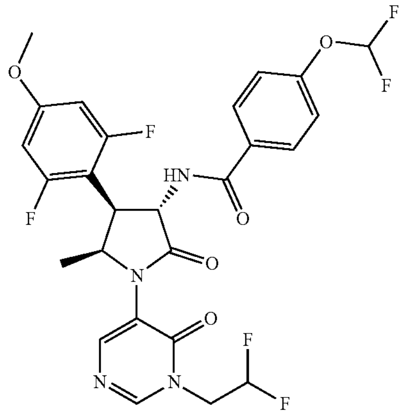 [SMILES: COc1cc(F)c([C@H]2[C@H](NC(=O)c3ccc(OC(F)F)cc3)C(=O)N(c3cncn(CC(F)F)c3=O)[C@H]2C)c(F)c1] | 585.1 | Method D, RT = 1.793 min, 100%. | $^{1}$H NMR (400 MHz, DMSO-$d_6$) δ = 8.96-8.87 (m, 1H), 8.52 (s, 1H), 7.90 (d, J = 9.9 Hz, 2H), 7.34 (t, J = 72.0 Hz, 1H), 7.27 (m, 3H), 6.80 (d, J = 9.9 Hz, 2H), 6.35 (tt, J = 54.8, 4.3 Hz, 1H), 5.69-5.57 (m, 1H), 4.84 (m, 1H), 4.48-4.26 (m, 3H), 3.78 (s, 3H), 1.19 (d, J = 6.8 Hz, 3H). |

TABLE 2-continued
| Ex | Structure | LCMS (M + H)+ | HPLC Method, RT (min.) & Purity | $^1$H NMR |
|---|---|---|---|---|
| 556 | 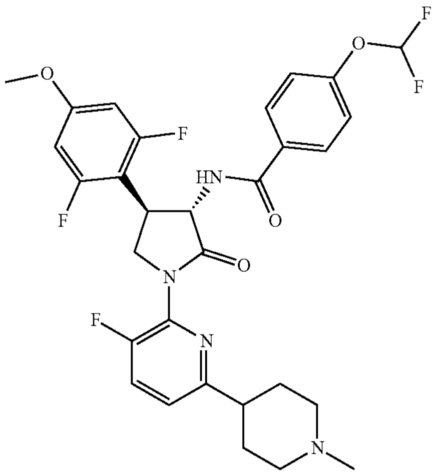 [SMILES: COc1cc(F)c([C@@H]2CN(c3nc(C4CCN(C)CC4)ccc3F)C(=O)[C@H]2NC(=O)c2ccc(OC(F)F)cc2)c(F)c1] | 605.2 | Method D, RT = 1.43 min, 93% | $^1$H NMR (400 MHz, DMSO-$d_6$) δ = 9.10 (d, J = 8.6 Hz, 1H), 7.96-7.86 (m, 2H), 7.80 (dd, J = 9.8, 8.6 Hz, 1H), 7.34 (t, J = 74.0 Hz, 1H), 7.32-7.27 (m, 3H), 6.79 (d, J = 10.8 Hz, 2H), 5.18-5.09 (m, 1H), 4.28-4.17 (m, 2H), 4.10-4.04 (m, 1H), 3.78 (s, 3H), 2.88-2.80 (m, 2H), 2.70-2.60 (m, 1H), 2.21 (s, 3H), 2.05-1.96 (m, 2H), 1.86-1.69 (m, 4H). |
| 557 | 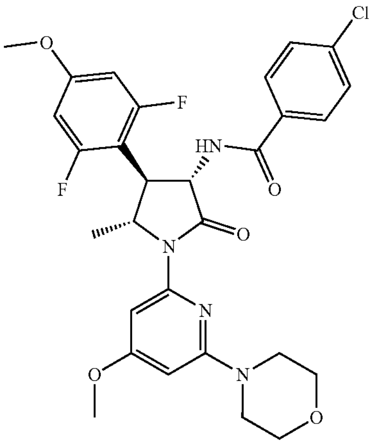 [SMILES: COc1cc(N2CCOCC2)nc(N2C(=O)[C@@H](NC(=O)c3ccc(Cl)cc3)[C@H](c3c(F)cc(OC)cc3F)[C@H]2C)c1] | 588.1 | Method-D, RT = 2.076 min, 94.45% | $^1$H NMR (400 MHz, DMSO-$d_6$) δ = 9.18-9.12 (m, 1H), 7.87-7.82 (m, 2H), 7.60-7.55 (m, 2H), 6.99-6.92 (m, 1H), 6.85-6.78 (m, 2H), 6.21-6.16 (m, 1H), 5.06-4.94 (m, 1H), 4.57-4.48 (m, 1H), 3.82 (s, 3H), 3.78 (s, 3H), 3.73-3.57 (m, 5H), 3.44-3.35 (m, 4H), 1.35 (d, J = 5.9 Hz, 3H). |
| 558 | 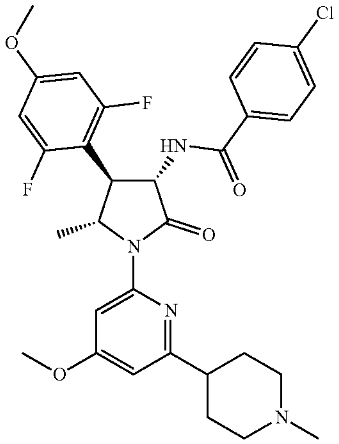 [SMILES: COc1cc(C2CCN(C)CC2)nc(N2C(=O)[C@@H](NC(=O)c3ccc(Cl)cc3)[C@H](c3c(F)cc(OC)cc3F)[C@H]2C)c1] | 600.2 | Method-D, RT = 1.712 min, 98.72% | $^1$H NMR (400 MHz, DMSO-$d_6$) δ = 9.18-9.12 (m, 1H), 7.86 (d, J = 8.6 Hz, 2H), 7.59 (d, J = 8.6 Hz, 2H), 7.36 (d, J = 2.0 Hz, 1H), 6.85-6.79 (m, 2H), 6.76-6.73 (m, 1H), 5.04-4.97 (m, 1H), 4.65-4.57 (m, 1H), 3.84 (s, 3H), 3.79 (s, 3H), 3.72-3.63 (m, 1H), 2.90-2.81 (m, 2H), 2.63-2.54 (m, 1H), 2.19 (s, 3H), 2.03-1.92 (m, 2H), 1.82-1.69 (m, 4H), 1.34 (d, J = 5.6 Hz, 3H). |

TABLE 2-continued

| Ex | Structure | LCMS (M + H)+ | HPLC Method, RT (min.) & Purity | $^1$H NMR |
|---|---|---|---|---|
| 559 | 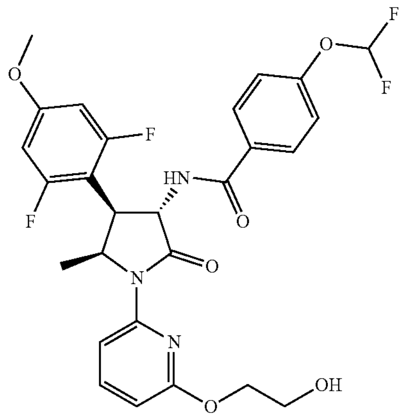 [SMILES: COc1cc(F)c([C@H]2[C@H](NC(=O)c3ccc(OC(F)F)cc3)C(=O)N(c3cccc(OCCO)n3)[C@H]2C)c(F)c1] | 564.1 | Method D, RT = 1.744 min, 95%. | $^1$H NMR (400 MHz, DMSO-$d_6$) δ = 8.90 (d, J = 8.3 Hz, 1H), 7.97-7.87 (m, 3H), 7.78 (t, J = 7.8 Hz, 1H), 7.34 (t, J = 72.9 Hz, 1H), 7.27 (d, J = 8.6 Hz, 2H), 6.81 (d, J = 11.5 Hz, 2H), 6.61 (d, J = 7.8 Hz, 1H), 5.68 (dd, J = 12.6, 8.2 Hz, 1H), 4.97-4.86 (m, 1H), 4.81 (t, J = 5.5 Hz, 1H), 4.39-4.18 (m, 3H), 3.79 (s, 3H), 3.71 (q, J = 5.1 Hz, 2H), 1.24 (d, J = 6.6 Hz, 3H). |
| 560 | 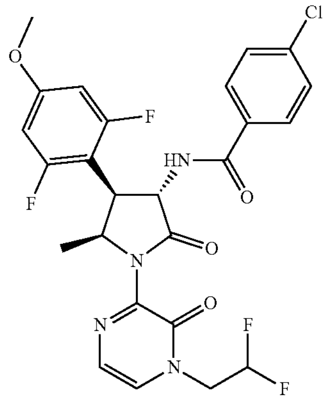 [SMILES: COc1cc(F)c([C@H]2[C@H](NC(=O)c3ccc(Cl)cc3)C(=O)N(c3nccn(CC(F)F)c3=O)[C@H]2C)c(F)c1] | 553.1 | Method D, RT = 1.727 min, 96%. | $^1$H NMR (400 MHz, DMSO-$d_6$) δ = 8.96 (d, J = 8.6 Hz, 1H), 7.85 (d, J = 8.6 Hz, 2H), 7.73 (d, J = 4.4 Hz, 1H), 7.57-7.50 (m, 2H), 7.35 (d, J = 4.4 Hz, 1H), 6.85-6.75 (m, 2H), 6.41 (tt, J = 55.5, 4.5 Hz, 1H), 5.60 (dd, J = 11.7, 8.6 Hz, 1H), 4.73-4.60 (m, 1H), 4.49 (tt, J = 14.7, 4.4 Hz, 2H), 4.37 (dd, J = 12.0, 8.3 Hz, 1H), 3.78 (s, 3H), 0.98 (d, J = 6.6 Hz, 3H). |
| 561 | 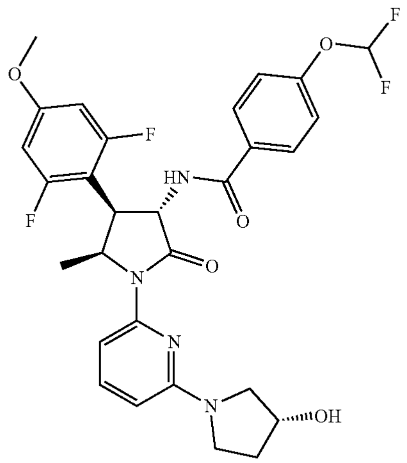 [SMILES: COc1cc(F)c([C@H]2[C@H](NC(=O)c3ccc(OC(F)F)cc3)C(=O)N(c3cccc(N4CC[C@@H](O)C4)n3)[C@H]2C)c(F)c1] | 589.2 | Method C, RT = 1.536 min, 94%. | $^1$H NMR (400 MHz, DMSO-$d_6$) δ = 8.86 (d, J = 8.1 Hz, 1H), 7.90 (d, J = 9.0 Hz, 2H), 7.57-7.49 (m, 2H), 7.35 (t, J = 73.0 Hz, 1H), 7.26 (d, J = 9.0 Hz, 2H), 6.80 (d, J = 9.0 Hz, 2H), 6.24-6.19 (m, 1H), 5.68 (m, 1H), 4.93 (t, J = 7.2 Hz, 2H), 4.38 (s, 1H), 4.28-4.24 (m, 1H), 3.78 (s, 3H), 3.53-3.34 (m, 3H), 3.30-3.22 (m, 1H), 2.06-1.97 (m, 1H), 1.92-1.87 (m, 1H), 1.24 (d, J = 6.1 Hz, 3H). |

TABLE 2-continued

| Ex | Structure | LCMS (M + H)+ | HPLC Method, RT (min.) & Purity | $^1$H NMR |
|---|---|---|---|---|
| 562 | 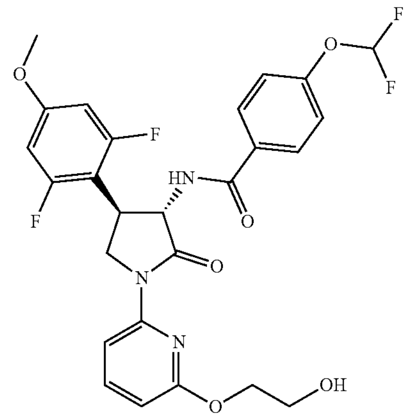 [SMILES: COc1cc(F)c([C@@H]2CN(c3cccc(OCCO)n3)C(=O)[C@H]2NC(=O)c2ccc(OC(F)F)cc2)c(F)c1] | 550.1 | Method C, RT = 1.687 min, 96%. | $^1$H NMR (400 MHz, DMSO-$d_6$) δ = 9.09 (d, J = 8.3 Hz, 1H), 7.92-7.88 (m, 3H), 7.78 (t, J = 8.1 Hz, 1H), 7.34 (t, J = 72.9 Hz, 1H), 7.27 (d, J = 8.6 Hz, 2H), 6.80 (d, J = 9.0 Hz, 2H), 6.61 (d, J = 8.1 Hz, 1H), 5.11-5.07 (m, 1H), 4.78 (t, J = 5.5 Hz, 1H), 4.48 (t, J = 9.8 Hz, 1H), 4.33-4.22 (m, 2H), 4.12 (q, J = 10.1 Hz, 1H), 4.01-3.94 (m, 1H), 3.80-3.77 (m, 3H), 3.77-3.64 (m, 2H). |
| 563 | 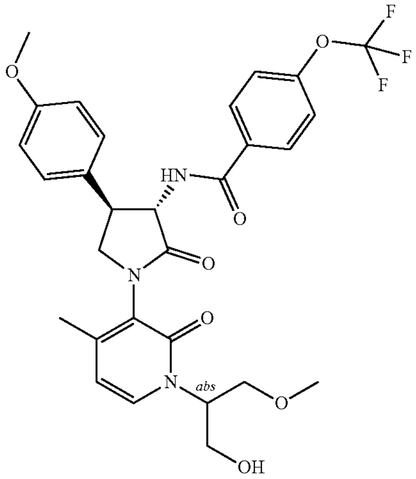 [SMILES: COCC(CO)n1ccc(C)c(N2C[C@@H](c3ccc(OC)cc3)[C@H](NC(=O)c3ccc(OC(F)(F)F)cc3)C2=O)c1=O] | 590.1 | Method D, RT = 1.729 min, 100% | $^1$H NMR (400 MHz, DMSO-$d_6$) δ = 9.07-9.00 (dd, J = 13.8, 8.8 Hz, 1H), 8.03-7.97 (m, 2H), 7.60 (d, J = 7.0 Hz, 1H), 7.53-7.44 (m, 2H), 7.39 (d, J = 8.5 Hz, 1H), 7.35-7.31 (m, 1H), 6.96-6.87 (m, 2H), 6.22 (dd, J = 7.0, 2.5 Hz, 1H), 5.27-4.67 (m, 3H), 4.15-3.81 (m, 2H), 3.79-3.58 (m, 8H), 3.24 (d, J = 1.0 Hz, 3H), 2.22-2.09 (m, 3H). (Mixture of interconvertible atrop isomers) |
| 564 | 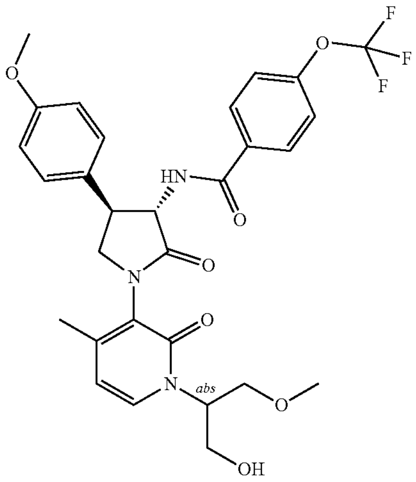 [SMILES: COCC(CO)n1ccc(C)c(N2C[C@@H](c3ccc(OC)cc3)[C@H](NC(=O)c3ccc(OC(F)(F)F)cc3)C2=O)c1=O] | 590.1 | Method D, RT = 1.675 min, 100% | $^1$H NMR (400 MHz, DMSO-$d_6$) δ = 9.07-9.00 (dd, J = 13.8, 8.8 Hz, 1H), 8.06-7.97 (m, 2H), 7.60 (dd, J = 7.0, 6.0 Hz, 1H), 7.56-7.44 (m, 2H), 7.42-7.30 (m, 2H), 6.98-6.88 (m, 2H), 6.22 (d, J = 7.5 Hz, 1H), 5.29-4.67 (m, 3H), 4.15-3.82 (m, 2H), 3.80-3.58 (m, 8H), 3.23 (d, J = 1.0 Hz, 3H), 2.23-2.08 (m, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 565 | 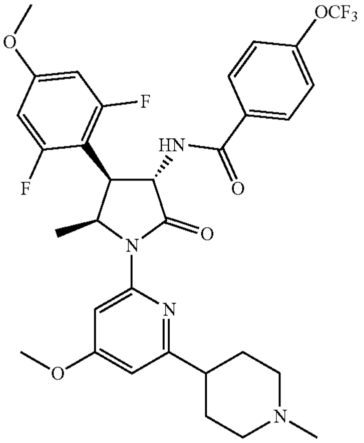 [SMILES: COc1cc(C2CCN(C)CC2)nc(N2C(=O)[C@@H](NC(=O)c3ccc(OC(F)(F)F)cc3)[C@H](c3c(F)cc(OC)cc3F)[C@@H]2C)c1] | 649.2 | Method-D, RT = 1.792 min, 96.9% | $^1$H NMR (400 MHz, DMSO-$d_6$) δ = 9.01 (d, J = 8.3 Hz, 1H), 7.95 (d, J = 11.5 Hz, 2H), 7.86 (d, J = 2.0 Hz, 1H), 7.48 (br d, J = 8.0 Hz, 2H), 6.82 (d, J = 11.5 Hz, 2H), 6.73 (d, J = 2.0 Hz, 1H), 5.66 (dd, J = 12.8, 8.3 Hz, 1H), 4.97 (quin, J = 7.0 Hz, 1H), 4.33 (dd, J = 12.8, 8.0 Hz, 1H), 3.84 (s, 3H), 3.79 (s, 3H), 2.95-2.76 (m, 3H), 2.74-2.62 (m, 4H), 2.33 (td, J = 3.7, 1.8 Hz, 1H), 2.05-1.83 (m, 4H), 1.20 (br d, J = 6.5 Hz, 3H). |
| 566 | 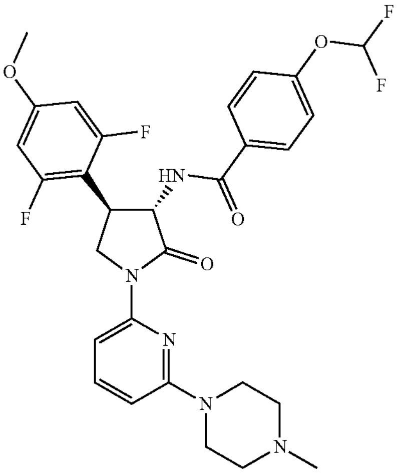 [SMILES: COc1cc(F)c([C@@H]2CN(c3cccc(N4CCN(C)CC4)n3)C(=O)[C@H]2NC(=O)c2ccc(OC(F)F)cc2)c(F)c1] | 588.2 | Method D, RT = 1.775 min, 93%. | $^1$H NMR (400 MHz, DMSO-$d_6$) δ = 9.06 (d, J = 8.3 Hz, 1H), 7.89 (d, J = 8.8 Hz, 2H), 7.62-7.57 (m, 2H), 7.35 (t, J = 73.0 Hz, 1H), 7.26 (d, J = 8.8 Hz, 2H), 6.80 (d, J = 8.8 Hz, 2H), 6.65-6.58 (m, 1H), 5.14-5.04 (m, 1H), 4.48-4.38 (m, 1H), 4.12-4.01 (m, 1H), 3.95-3.90 (m, 1H), 3.78 (s, 3H), 3.46 (m, 4H), 2.40-2.34 (m, 4H), 2.21 (s, 3H). |
| 567 | 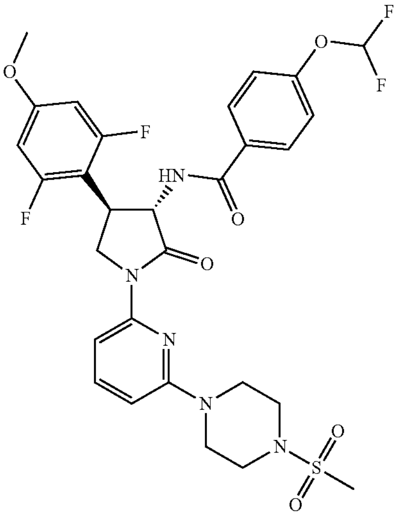 [SMILES: COc1cc(F)c([C@@H]2CN(c3cccc(N4CCN(S(C)(=O)=O)CC4)n3)C(=O)[C@H]2NC(=O)c2ccc(OC(F)F)cc2)c(F)c1] | 652.1 | Method D, RT = 1.866 min, 97%. | $^1$H NMR (400 MHz, DMSO-$d_6$) δ = 9.07 (d, J = 8.0 Hz, 1H), 7.89 (d, J = 9.0 Hz, 2H), 7.67-7.62 (m, 2H), 7.35 (t, J = 73.0 Hz, 1H), 7.26 (d, J = 8.8 Hz, 2H), 6.80 (d, J = 8.8 Hz, 2H), 6.71-6.65 (m, 1H), 5.12-5.05 (m, 1H), 4.48-4.44 (m, 1H), 4.09 (d, J = 10.0 Hz, 1H), 3.95 (d, J = 10.5 Hz, 1H), 3.78 (s, 3H), 3.65-360 (m, 4H), 3.20-3.16 (m, 4H), 2.89 (s, 3H). |

TABLE 2-continued

| Ex | Structure | LCMS (M + H)+ | HPLC Method, RT (min.) & Purity | $^1$H NMR |
|---|---|---|---|---|
| 568 | 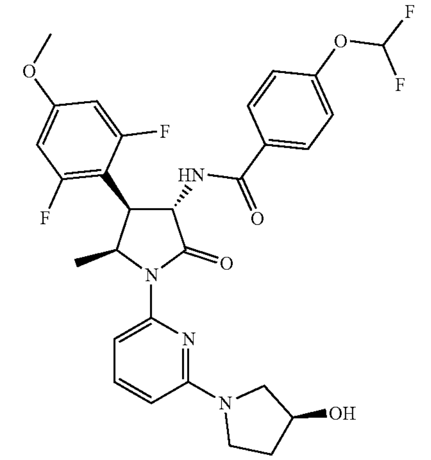 [SMILES: COc1cc(F)c([C@H]2[C@H](NC(=O)c3ccc(OC(F)F)cc3)C(=O)N(c3cccc(N4CC[C@H](O)C4)n3)[C@H]2C)c(F)c1] | 589.2 | Method D, RT = 1.829 min, 96%. | $^1$H NMR (400 MHz, DMSO-$d_6$) δ = 8.86 (d, J = 8.3 Hz, 1H), 7.89 (d, J = 9.0 Hz, 2H), 7.56-7.50 (m, 2H), 7.35 (t, J = 73.0 Hz, 1H), 7.26 (d, J = 8.8 Hz, 2H), 6.80 (d, J = 8.8 Hz, 2H), 6.21 (m, 1H), 5.68 (m, 1H), 4.98-4.85 (m, 1H), 4.41-4.35 (m, 2H), 4.31-4.22 (m, 1H), 3.78 (s, 3H), 3.51-3.38 (m, 3H), 3.34-3.26 (m, 1H), 2.07-1.83 (m, 2H), 1.24 (d, J = 6.1 Hz, 3H). |
| 569 | 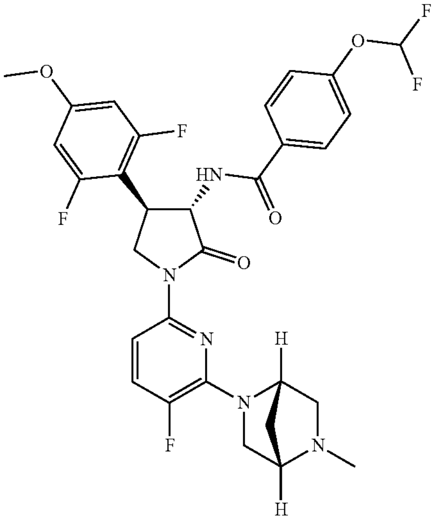 [SMILES: COc1cc(F)c([C@@H]2CN(c3ccc(F)c(N4C[C@@H]5C[C@H]4CN5C)n3)C(=O)[C@H]2NC(=O)c2ccc(OC(F)F)cc2)c(F)c1] | 618.2 | Method D, RT = 1.59 min, 95% | $^1$H NMR (400 MHz, DMSO-$d_6$) δ = 9.06 (d, J = 8.3 Hz, 1H), 7.93-7.84 (m, 2H), 7.57-7.41 (m, 2H), 7.35 (t, J = 73.6 Hz, 1H), 7.28 (d, J = 8.6 Hz, 2H), 6.79 (d, J = 10.8 Hz, 2H), 5.07 (dd, J = 10.9, 8.4 Hz, 1H), 4.63-4.60 (m, 1H), 4.44 (br t, J = 9.9 Hz, 1H), 4.12-3.96 (m, 1H), 3.92-3.83 (m, 1H), 3.78 (s, 3H), 3.62 (br dd, J = 9.7, 3.5 Hz, 1H), 3.47-3.42 (m, 1H), 3.42-3.33 (m, 1H), 2.80 (dd, J = 9.4, 1.8 Hz, 1H), 2.60 (br d, J = 10.0 Hz, 1H), 2.29 (s, 3H), 1.85-1.80 (m, 1H), 1.74-1.70 (m, 1H). |
| 570 | 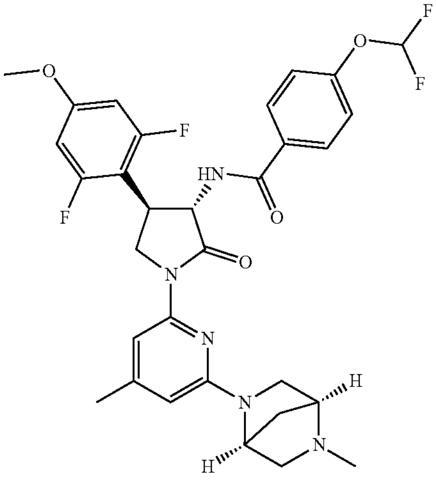 [SMILES: COc1cc(F)c([C@@H]2CN(c3cc(C)cc(N4C[C@@H]5C[C@H]4CN5C)n3)C(=O)[C@H]2NC(=O)c2ccc(OC(F)F)cc2)c(F)c1] | 614.2 | Method D, RT = 1.55 min, 98% | $^1$H NMR (400 MHz, DMSO-$d_6$) δ = 9.05 (d, J = 8.6 Hz, 1H), 7.93-7.83 (m, 2H), 7.40 (s, 1H), 7.35 (t, J = 73.6 Hz, 1H), 7.28 (d, J = 8.6 Hz, 2H), 6.79 (d, J = 10.8 Hz, 2H), 6.12 (s, 1H), 5.05 (dd, J = 11.1, 8.2 Hz, 1H), 4.58-4.54 (m, 1H), 4.47-4.42 (m, 1H), 4.07-4.01 (m, 1H), 3.89-3.80 (m, 2H), 3.78 (s, 3H), 3.45-3.40 (m, 1H), 3.26-3.19 (m, 1H), 2.79-2.77 (m, 1H), 2.45-2.41 (m, 1H), ), 2.26 (s, 3H), 2.23 (s, 3H), 1.84-1.80 (m, 1H), 1.73-1.62 (m, 1H). |

TABLE 2-continued

| Ex | Structure | LCMS (M + H)+ | HPLC Method, RT (min.) & Purity | $^1$H NMR |
|---|---|---|---|---|
| 571 | 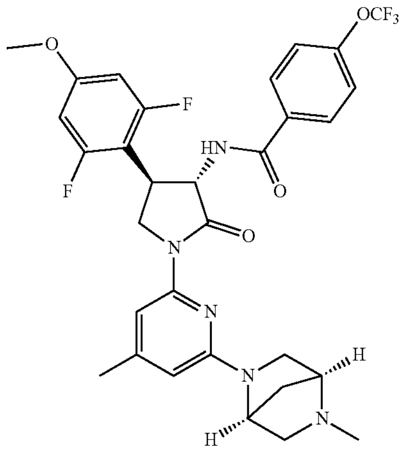 [SMILES: COc1cc(F)c([C@@H]2CN(c3cc(C)cc(N4C[C@@H]5C[C@H]4CN5C)n3)C(=O)[C@H]2NC(=O)c2ccc(OC(F)(F)F)cc2)c(F)c1] | 632.2 | Method D, RT = 1.77 min, 98% | $^1$H NMR (400 MHz, DMSO-$d_6$) δ = 9.15 (d, J = 8.3 Hz, 1H), 7.99-7.90 (m, 2H), 7.54-7.44 (m, 2H), 7.40 (s, 1H), 6.84-6.71 (m, 2H), 6.12 (s, 1H), 5.06 (dd, J = 11.0, 8.3 Hz, 1H), 4.58-4.54 (m, 1H), 4.50-4.42 (m, 1H), 4.11-4.02 (m, 1H), 3.91-3.85 (m, 1H), 3.78 (s, 3H), 3.43-3.39 (m, 2H), 3.25-3.22 (m, 1H), 2.80 (dd, J = 9.4, 2.1 Hz, 1H), 2.43 (d, J = 9.5 Hz, 1H), 2.26 (s, 3H), 2.23 (s, 3H), 1.84-1.80 (m, 1H), 1.73-1.62 (m, 1H). |
| 572 | 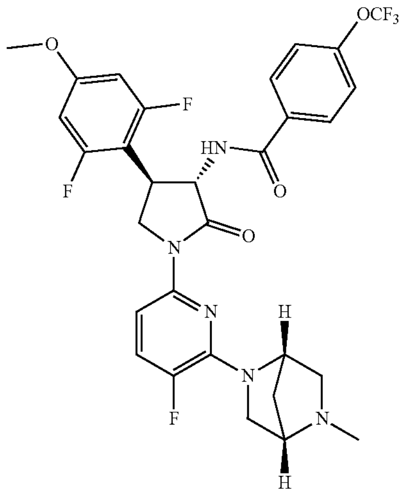 [SMILES: COc1cc(F)c([C@@H]2CN(c3ccc(F)c(N4C[C@@H]5C[C@H]4CN5C)n3)C(=O)[C@H]2NC(=O)c2ccc(OC(F)(F)F)cc2)c(F)c1] | 636.2 | Method D, RT = 1.77 min, 95% | $^1$H NMR (400 MHz, DMSO-$d_6$) δ = 9.16 (d, J = 8.3 Hz, 1H), 7.98-7.92 (m, 2H), 7.57-7.41 (m, 4H), 6.86-6.73 (m, 2H), 5.08 (dd, J = 11.0, 8.1 Hz, 1H), 4.63-4.60 (m, 1H), 4.45 (br t, J = 9.7 Hz, 1H), 4.12-4.03 (m, 1H), 3.92-3.86 (m, 1H), 3.78 (s, 3H), 3.65-3.58 (m, 1H), 3.45-3.42 (m, 1H), 3.40-3.36 (m, 1H), 2.79 (dd, J = 9.5, 2.0 Hz, 1H), 2.58 (dd, J = 9.5, 2.0 Hz, 1H), 2.28 (s, 3H), 1.85-1.77 (m, 1H), 1.74-1.66 (m, 1H). |
| 573 | 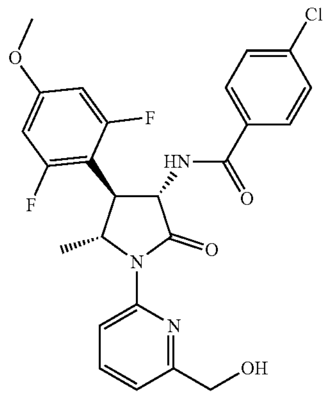 [SMILES: COc1cc(F)c([C@H]2[C@H](NC(=O)c3ccc(Cl)cc3)C(=O)N(c3cccc(CO)n3)[C@@H]2C)c(F)c1] | 502 | Method D, RT = 1.695 min, 100%. | $^1$H NMR (400 MHz, DMSO-$d_6$) δ = 9.16 (d, J = 7.8 Hz, 1H), 7.94-7.81 (m, 3H), 7.78 (d, J = 7.8 Hz, 1H), 7.62-7.52 (m, 2H), 7.32 (d, J = 7.6 Hz, 1H), 6.82 (d, J = 11.2 Hz, 2H), 5.03-4.99 (m, 1H), 4.68-4.46 (m, 3H), 3.79 (s, 3H), 3.74-3.67 (m, 1H), 3.51-3.15 (m, 1H), 1.30 (d, J = 5.9 Hz, 3H). |

TABLE 2-continued

| Ex | Structure | LCMS (M + H)+ | HPLC Method, RT (min.) & Purity | $^1$H NMR |
|---|---|---|---|---|
| 574 | 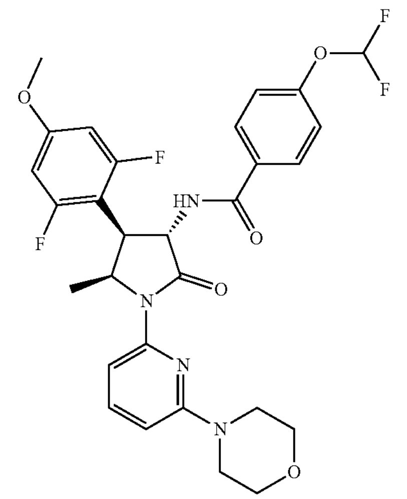 [SMILES: COc1cc(F)c([C@H]2[C@H](NC(=O)c3ccc(OC(F)F)cc3)C(=O)N(c3cccc(N4CCOCC4)n3)[C@H]2C)c(F)c1] | 589.2 | Method D, RT = 1.994 min, 97%. | $^1$H NMR (400 MHz, DMSO-d$_6$) δ = 8.88 (d, J = 8.3 Hz, 1H), 7.90 (d, J = 8.8 Hz, 2H), 7.70-7.60 (m, 2H), 7.35 (t, J = 76.0 Hz, 1H), 7.26 (d, J = 8.8 Hz, 2H), 6.79 (d, J = 8.8 Hz, 2H), 6.61 (d, J = 8.1 Hz, 1H), 5.68-5.65 (m, 1H), 4.94-4.85 (m, 1H), 4.29-4.24 (m, 1H), 3.78 (s, 3H), 3.74-3.71-3.65 (m, 4H), 3.49-3.39 (m, 4H), 1.21 (d, J = 6.4 Hz, 3H). |
| 575 | 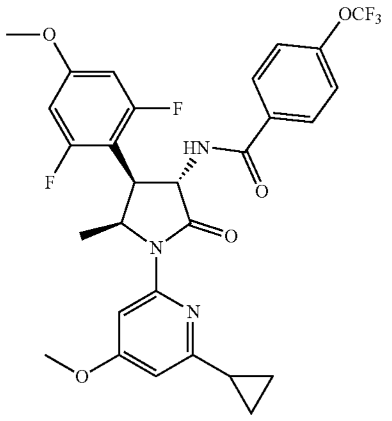 [SMILES: COc1cc(C2CC2)nc(N2C(=O)[C@@H](NC(=O)c3ccc(OC(F)(F)F)cc3)[C@H](c3c(F)cc(OC)cc3F)[C@@H]2C)c1] | 592.1 | Method-D, RT = 2.416 min, 100% | $^1$H NMR (400 MHz, DMSO-d$_6$) δ = 8.98 (d, J = 8.3 Hz, 1H), 7.98-7.92 (m, 2H), 7.74 (d, J = 2.0 Hz, 1H), 7.48 (br d, J = 8.9 Hz, 2H), 6.83-6.81 (m, 1H), 6.80-6.77 (m, 2H), 5.66 (dd, J = 12.6, 8.4 Hz, 1H), 4.92-4.80 (m, 1H), 4.26 (dd, J = 12.8, 8.0 Hz, 1H), 3.82 (s, 3H), 3.78 (s, 3H), 1.77-1.57 (m, 1H), 1.16 (d, J = 6.6 Hz, 3H), 1.00-0.88 (m, 3H), 0.87-0.80 (m, 1H). |
| 576 | 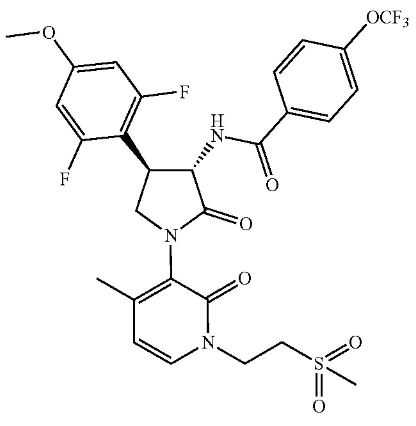 [SMILES: COc1cc(F)c([C@@H]2CN(c3c(C)ccn(CCS(C)(=O)=O)c3=O)C(=O)[C@H]2NC(=O)c2ccc(OC(F)(F)F)cc2)c(F)c1] | 644.2 | Method F, RT = 2.488 min, 99% | $^1$H NMR (400 MHz, DMSO-d$_6$) δ = 9.23-9.04 (m, 1H), 8.00-7.92 (m, 2H), 7.74-7.64 (m, 1H), 7.53-7.44 (m, 2H), 6.81-6.76 (m, 2H), 6.32-6.24 (m, 1H), 5.37-4.86 (m, 1H), 4.36-4.26 (m, 2H), 4.26-4.14 (m, 1H), 4.26-4.07 (m, 2H), 3.79-3.74 (2s, 3H), 3.61-3.53 (m, 2H), 3.07-3.04 (2s, 3H), 2.22-2.06 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 577 | 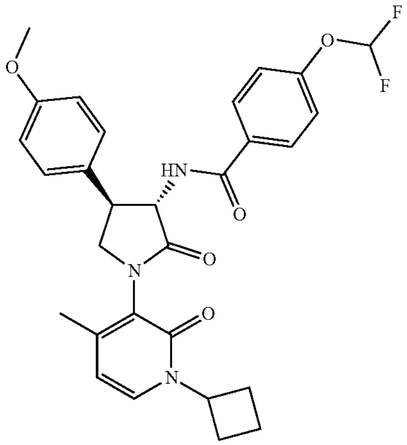 [SMILES: COc1ccc([C@@H]2CN(c3c(C)ccn(C4CCC4)c3=O)C(=O)[C@H]2NC(=O)c2ccc(OC(F)F)cc2)cc1] | 538.2 | Method D, RT = 2.596 min, 100%. | $^1$H NMR (400 MHz, DMSO-$d_6$) δ = 8.95-8.88 (m, 1H), 7.92-7.88 (m, 2H), 7.75-7.70 (m, 1H), 7.47-7.07 (m, 5H), 6.96-6.85 (m, 2H), 6.33-6.27 (m, 1H), 5.22-4.68 (m, 2H), 4.06-3.80 (m, 2H), 3.73-3.68 (2s, 3H), 3.60-3.39 (m, 1H), 2.37-2.21 (m, 4H), 2.19-2.07 (2s, 3H), 1.82-1.77 (m, 2H). (Mixture of interconvertible atrop isomers) |
| 578 | 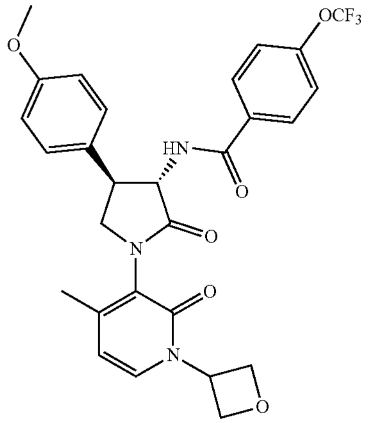 [SMILES: COc1ccc([C@@H]2CN(c3c(C)ccn(C4COC4)c3=O)C(=O)[C@H]2NC(=O)c2ccc(OC(F)(F)F)cc2)cc1] | 558.3 | Method D, RT = 2.358 min, 99%. | $^1$H NMR (400 MHz, DMSO-$d_6$) δ = 9.06-9.02 (m, 1H), 8.02-7.98 (m, 2H), 7.76-7.72 (m, 1H), 7.54-7.44 (m, 2H), 7.41-7.28 (m, 2H), 6.93-6.88 (m, 2H), 6.36-6.32 (m, 1H), 5.58-5.17 (m, 1H), 4.95-4.65 (m, 4H), 4.09-4.01 (m, 1H), 3.96-3.77 (m, 2H), 3.75-3.70 (m, 3H), 3.69-3.42 (m, 1H), 2.26-2.10 (2s, 3H). (Mixture of interconvertible atropisomers) |
| 579 | 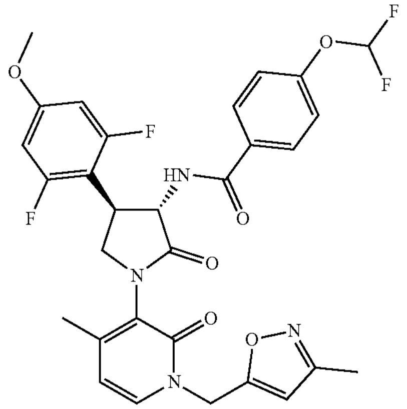 [SMILES: COc1cc(F)c([C@@H]2CN(c3c(C)ccn(Cc4cc(C)no4)c3=O)C(=O)[C@H]2NC(=O)c2ccc(OC(F)F)cc2)c(F)c1] | 615.1 | Method D, RT = 1.693 min, 94%. | $^1$H NMR (400 MHz, DMSO-$d_6$) δ = 9.11-8.92 (m, 1H), 7.93-7.85 (m, 2H), 7.82-7.73 (m, 1H), 7.54-7.11 (m, 3H), 6.82-6.72 (m, 2H), 6.36-6.24 (m, 2H), 5.37-4.83 (m, 3H), 4.32-4.04 (m, 2H), 3.79-3.74 (2s, 3H), 3.57-3.48 (m, 1H), 2.25-2.20 (2s, 3H), 2.21-2.08 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 580 | 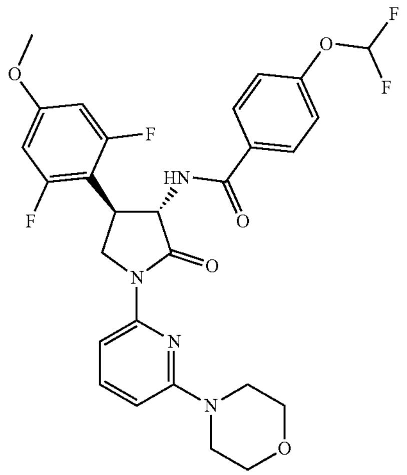 [SMILES: COc1cc(F)c([C@@H]2CN(c3cccc(N4CCOCC4)n3)C(=O)[C@H]2NC(=O)c2ccc(OC(F)F)cc2)c(F)c1] | 575.1 | Method D, RT = 1.977 min, 100%. | $^1$H NMR (400 MHz, DMSO-$d_6$) δ = 9.07 (d, J = 8.3 Hz, 1H), 7.90 (d, J = 8.6 Hz, 2H), 7.68-7.60 (m, 2H), 7.35 (t, J = 73.6 Hz, 1H), 7.28 (d, J = 8.6 Hz, 2H), 6.79 (d, J = 10.8 Hz, 2H), 6.65-6.57 (m, 1H), 5.10 (dd, J = 10.9, 8.4 Hz, 1H), 4.50-4.39 (m, 1H), 4.15-4.01 (m, 1H), 3.98-3.87 (m, 1H), 3.78 (s, 3H), 3.74-3.63 (m, 4H), 3.48-3.39 (m, 4H). |
| 581 | 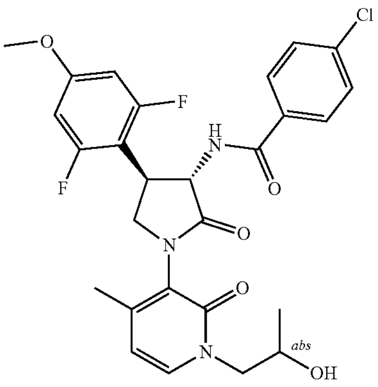 [SMILES: COc1cc(F)c([C@@H]2CN(c3c(C)ccn(CC(C)O)c3=O)C(=O)[C@H]2NC(=O)c2ccc(Cl)cc2)c(F)c1] | 546.2 | Method F, RT = 2.40 min, 99%, | $^1$H NMR (400 MHz, DMSO-$d_6$) δ = 9.20-8.90 (m, 1H), 7.91-7.74 (m, 2H), 7.64-7.36 (m, 3H), 6.82-6.64 (m, 2H), 6.27-6.07 (m, 1H), 5.36-4.81 (m, 2H), 4.28-3.82 (m, 4H), 3.80-3.73 (2s, 3H), 3.69-3.46 (m, 2H), 2.23-2.04 (2s, 3H), 1.16-0.98 (m, 3H). (Mixture of interconvertible atropisomers) |
| 582 | 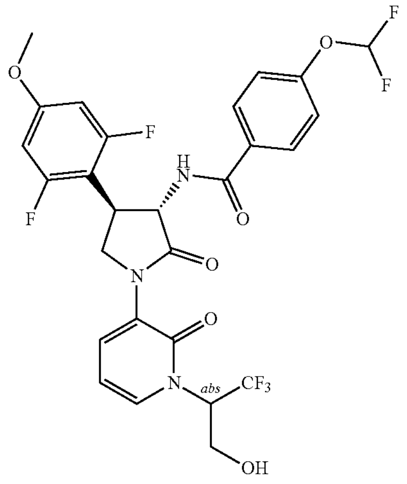 [SMILES: COc1cc(F)c([C@@H]2CN(c3cccn(C(CO)C(F)(F)F)c3=O)C(=O)[C@H]2NC(=O)c2ccc(OC(F)F)cc2)c(F)c1] | 618.2 | Method D, RT = 1.757 min, 100% | $^1$H NMR (400 MHz, DMSO-$d_6$) δ = 9.01 (br d, J = 8.5 Hz, 1H), 7.89 (d, J = 8.5 Hz, 2H), 7.74-7.61 (m, 2H), 7.35 (t, J = 76.4 Hz, 1H), 7.27 (d, J = 8.5 Hz, 2H), 6.82-6.74 (m, 1H), 6.77 (br d, J = 11.0 Hz, 1H), 6.38 (t, J = 7.0 Hz, 1H), 5.09 (br t, J = 9.3 Hz, 1H), 4.49-4.42 (m, 1H), 4.37-4.33 (m, 1H), 4.15-4.01 (m, 3H), 3.99-3.90 (m, 1H), 3.87-3.84 (m, 1H), 3.77 (s, 3H). |

TABLE 2-continued

| Ex | Structure | LCMS (M + H)+ | HPLC Method, RT (min.) & Purity | $^1$H NMR |
|---|---|---|---|---|
| 583 | 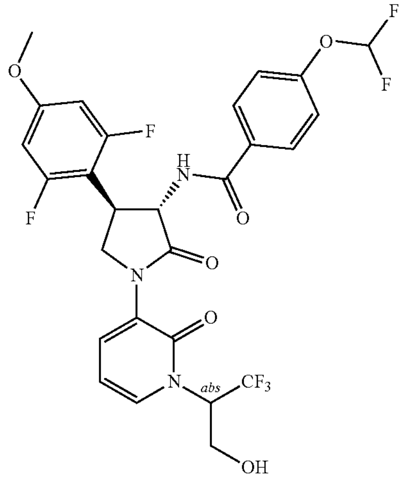 [SMILES: COc1cc(F)c([C@@H]2CN(c3cccn(C(CO)C(F)(F)F)c3=O)C(=O)[C@H]2NC(=O)c2ccc(OC(F)F)cc2)c(F)c1] | 618.2 | Method D, RT = 1.744 min, 97.2% | $^1$H NMR (400 MHz, DMSO-$d_6$) δ = 9.01 (br d, J = 8.5 Hz, 1H), 7.89 (d, J = 8.5 Hz, 2H), 7.74-7.61 (m, 2H), 7.35 (t, J = 76.4 Hz, 1H), 7.27 (d, J = 8.5 Hz, 2H), 6.82-6.74 (m, 1H), 6.77 (br d, J = 11.0 Hz, 1H), 6.38 (t, J = 7.0 Hz, 1H), 5.09 (br t, J = 9.3 Hz, 1H), 4.49-4.42 (m, 1H), 4.37-4.33 (m, 1H), 4.15-4.01 (m, 3H), 3.99-3.90 (m, 1H), 3.87-3.84 (m, 1H), 3.77 (s, 3H). |
| 584 | 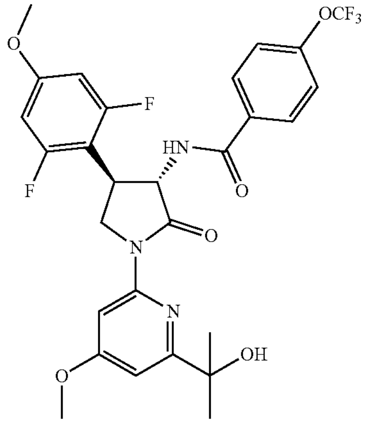 [SMILES: COc1cc(N2C[C@@H](c3c(F)cc(OC)cc3F)[C@H](NC(=O)c3ccc(OC(F)(F)F)cc3)C2=O)nc(C(C)(C)O)c1] | 596.1 | Method-D, RT = 2.103 min, 100% | $^1$H NMR (400 MHz, DMSO-$d_6$) δ = 9.18 (d, J = 8.3 Hz, 1H), 7.95 (d, J = 8.8 Hz, 2H), 7.79 (d, J = 2.0 Hz, 1H), 7.51 (d, J = 8.8 Hz, 2H), 7.04-7.02 (d, J = 2.0 Hz, 1H), 6.80 (d, J = 10.8 Hz, 2H), 5.33-5.13 (m, 1H), 5.09 (dd, J = 11.0, 8.3 Hz, 1H), 4.50 (br t, J = 9.9 Hz, 1H), 4.16-4.07 (m, 1H), 3.98-3.91 (m, 1H), 3.85 (s, 3H), 3.78 (s, 3H), 1.42 (s, 3H), 1.41 (s, 3H). |
| 585 | 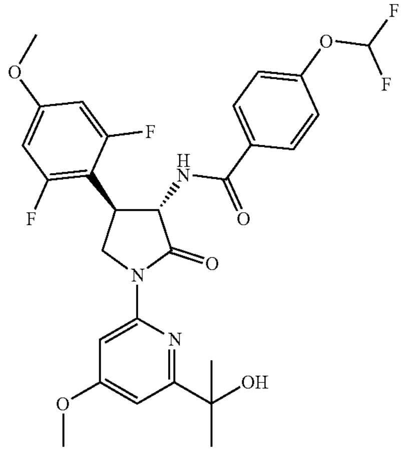 [SMILES: COc1cc(N2C[C@@H](c3c(F)cc(OC)cc3F)[C@H](NC(=O)c3ccc(OC(F)F)cc3)C2=O)nc(C(C)(C)O)c1] | 578.1 | Method-D, RT = 1.924 min, 93.8% | $^1$H NMR (400 MHz, DMSO-$d_6$) δ = 9.08 (d, J = 8.3 Hz, 1H), 7.89 (d, J = 8.8 Hz, 2H), 7.80 (d, J = 2.2 Hz, 1H), 7.34 (t, J = 76.0 Hz, 1H), 7.29 (d, J = 8.8 Hz, 2H), 7.02 (d, J = 2.2 Hz, 1H), 6.80 (d, J = 10.8 Hz, 2H), 5.33-5.13 (m, 1H), 5.07 (dd, J = 11.0, 8.1 Hz, 1H), 4.54-4.44 (m, 1H), 4.17-4.05 (m, 1H), 3.99-3.90 (m, 1H), 3.85 (s, 3H), 3.78 (s, 3H), 1.42 (s, 3H), 1.41 (s, 3H). |

TABLE 2-continued

| Ex | Structure | LCMS (M + H)+ | HPLC Method, RT (min.) & Purity | $^1$H NMR |
|---|---|---|---|---|
| 586 | 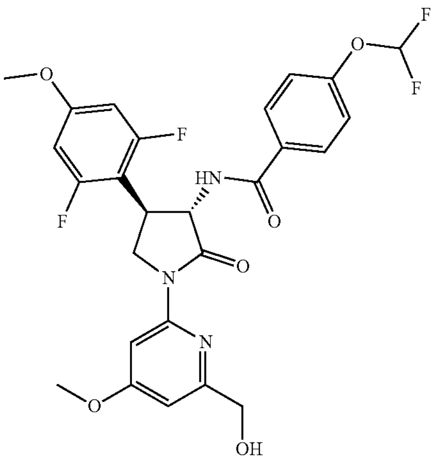 [SMILES: COc1cc(CO)nc(N2C[C@@H](c3c(F)cc(OC)cc3F)[C@H](NC(=O)c3ccc(OC(F)F)cc3)C2=O)c1] | 550.1 | Method-C, RT = 1.508 min, 98.1% | $^1$H NMR (400 MHz, DMSO-$d_6$) δ = 9.09 (d, J = 8.3 Hz, 1H), 7.89 (d, J = 8.8 Hz, 2H), 7.82 (d, J = 2.2 Hz, 1H), 7.34 (t, J = 76.0 Hz, 1H), 7.29 (d, J = 8.8 Hz, 2H), 6.88 (d, J = 2.2 Hz, 1H), 6.79 (d, J = 10.8 Hz, 2H), 5.43-5.39 (m, 1H), 5.08 (dd, J = 11.1, 8.2 Hz, 1H), 4.46 (d, J = 5.9 Hz, 2H), 4.43-4.38 (m, 1H), 4.10 (q, J = 10.1 Hz, 1H), 3.98-3.91 (m, 1H), 3.86 (s, 3H), 3.78 (s, 3H). |
| 587 | 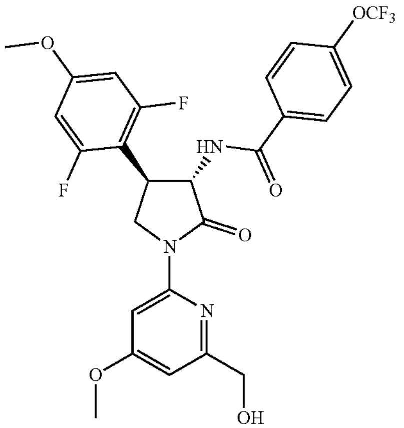 [SMILES: COc1cc(CO)nc(N2C[C@@H](c3c(F)cc(OC)cc3F)[C@H](NC(=O)c3ccc(OC(F)(F)F)cc3)C2=O)c1] | 568.1 | Method-D, RT = 1.895 min, 98.4% | $^1$H NMR (400 MHz, DMSO-$d_6$) δ = 9.19 (d, J = 8.1 Hz, 1H), 7.95 (d, J = 8.8 Hz, 2H), 7.81 (d, J = 2.0 Hz, 1H), 7.51 (d, J = 8.1 Hz, 2H), 6.88 (d, J = 2.0 Hz, 1H), 6.80 (d, J = 10.8 Hz, 2H), 5.48-5.35 (m, 1H), 5.09 (dd, J = 10.8, 8.3 Hz, 1H), 4.46 (d, J = 5.9 Hz, 2H), 4.44-4.39 (m, 1H), 4.15-4.04 (m, 1H), 3.98-3.90 (m, 1H), 3.87-3.84 (m, 3H), 3.78 (s, 3H). |
| 588 | 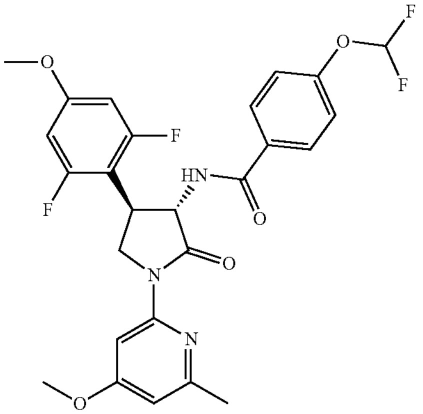 [SMILES: COc1cc(C)nc(N2C[C@@H](c3c(F)cc(OC)cc3F)[C@H](NC(=O)c3ccc(OC(F)F)cc3)C2=O)c1] | 534.1 | Method-D, RT = 2.060 min, 96.8% | $^1$H NMR (400 MHz, DMSO-$d_6$) δ = 9.09 (d, J = 8.1 Hz, 1H), 7.89 (d, J = 8.8 Hz, 2H), 7.78 (d, J = 2.2 Hz, 1H), 7.34 (t, J = 76.0 Hz, 1H), 7.29 (d, J = 8.8 Hz, 2H), 6.79 (d, J = 11.0 Hz, 2H), 6.72 (d, J = 2.2 Hz, 1H), 5.07 (dd, J = 11.0, 8.3 Hz, 1H), 4.46-4.39 (m, 1H), 4.14-4.04 (m, 1H), 3.99-3.92 (m, 1H), 3.83 (s, 3H), 3.78 (s, 3H), 2.39 (s, 3H). |

TABLE 2-continued

| Ex | Structure | LCMS (M + H)+ | HPLC Method, RT (min.) & Purity | $^1$H NMR |
|---|---|---|---|---|
| 589 | 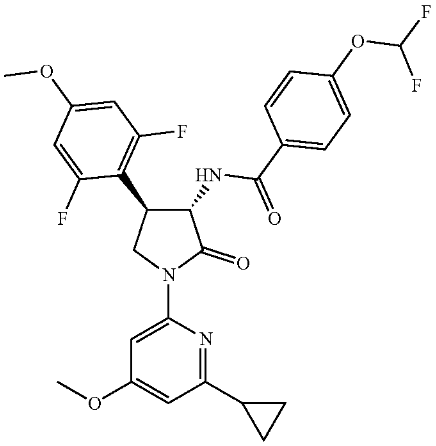 [SMILES: COc1cc(C2CC2)nc(N2C[C@@H](c3c(F)cc(OC)cc3F)[C@H](NC(=O)c3ccc(OC(F)F)cc3)C2=O)c1] | 560.2 | Method-D, RT = 2.253 min, 100% | $^1$H NMR (400 MHz, DMSO-$d_6$) δ = 9.06 (d, J = 8.3 Hz, 1H), 7.92-7.84 (m, 2H), 7.72 (d, J = 2.0 Hz, 1H), 7.34 (t, J = 76.0 Hz, 1H), 7.28 (d, J = 9.0 Hz, 2H), 6.78 (d, J = 2.0 Hz, 2H), 6.72 (d, J = 2.2 Hz, 1H), 5.06 (dd, J = 11.1, 8.4 Hz, 1H), 4.40 (t, J = 9.9 Hz, 1H), 4.07 (q, J = 10.0 Hz, 1H), 3.91-3.84 (m, 1H), 3.83 (s, 3H), 3.78 (s, 3H), 2.07-1.97 (m, 1H), 0.99-0.92 (m, 2H), 0.91-0.85 (m, 2H). |
| 590 | 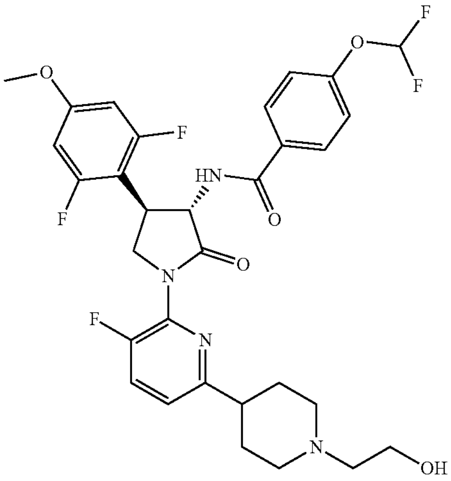 [SMILES: COc1cc(F)c([C@@H]2CN(c3nc(C4CCN(CCO)CC4)ccc3F)C(=O)[C@H]2NC(=O)c2ccc(OC(F)F)cc2)c(F)c1] | 635.2 | Method D, RT = 1.43 min, 98% | $^1$H NMR (400 MHz, DMSO-$d_6$) δ = 9.09 (d, J = 9.0 Hz, 1H), 7.95-7.84 (m, 2H), 7.78 (dd, J = 9.8, 8.5 Hz, 1H), 7.34 (t, J = 74.0 Hz, 1H), 7.32-7.27 (m, 3H), 6.79 (d, J = 10.8 Hz, 2H), 5.12-5.10 (m, 1H), 4.35 (t, J = 5.4 Hz, 1H), 4.28-4.16 (m, 2H), 4.13-3.99 (m, 1H), 3.77 (s, 3H), 3.50 (q, J = 6.4 Hz, 2H), 3.17 (d, J = 5.3 Hz, 1H), 2.99-2.89 (m, 2H), 2.71-2.64 (m, 1H), 2.40 (t, J = 6.4 Hz, 2H), 2.10-2.00 (m, 2H), 1.85-1.64 (m, 3H). |
| 591 | 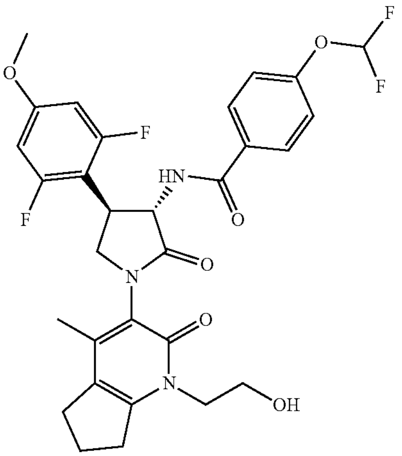 [SMILES: COc1cc(F)c([C@@H]2CN(c3c(C)c4c(n(CCO)c3=O)CCC4)C(=O)[C@H]2NC(=O)c2ccc(OC(F)F)cc2)c(F)c1] | 604.1 | Method D, RT = 1.656 min, 100% | $^1$H NMR (400 MHz, DMSO-$d_6$) δ = 9.18-8.84 (m, 1H), 7.99-7.82 (m, 2H), 7.55-7.15 (2t, J = 74.3 Hz, 1H), 7.28-7.24 (m, 2H), 6.80-6.74 (m, 2H), 5.41-4.85 (m, 2H), 4.30-3.88 (m, 4H), 3.80-3.72 (2s, 3H), 3.63 (quin, J = 5.1 Hz, 2H), 3.50-3.41 (m, 1H), 3.06 (br t, J = 7.2 Hz, 2H), 2.83-2.68 (m, 2H), 2.18-1.94 (m, 5H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 592 | 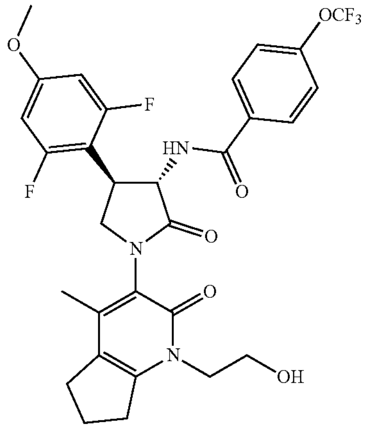 [SMILES: COc1cc(F)c([C@@H]2CN(c3c(C)c4c(n(CCO)c3=O)CCC4)C(=O)[C@H]2NC(=O)c2ccc(OC(F)(F)F)cc2)c(F)c1] | 622.1 | Method D, RT = 1.788 min, 98.6% | $^1$H NMR (400 MHz, DMSO-$d_6$) δ = 9.33-8.91 (m, 1H), 8.04-7.82 (m, 2H), 7.60-7.33 (m, 2H), 6.81-6.75 (m, 2H), 5.41-4.85 (m, 2H), 4.30-3.88 (m, 4H), 3.80-3.72 (2s, 3H), 3.64-3.61 (m, 2H), 3.50-3.41 (m, 1H), 3.08-3.04 (m, 2H), 2.83-2.68 (m, 2H), 2.18-1.94 (m, 5H). (Mixture of interconvertible atropisomers) |
| 593 | 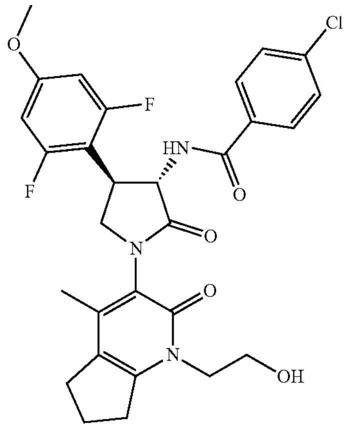 [SMILES: COc1cc(F)c([C@@H]2CN(c3c(C)c4c(n(CCO)c3=O)CCC4)C(=O)[C@H]2NC(=O)c2ccc(Cl)cc2)c(F)c1] | 572.1 | Method D, RT = 1.649 min, 99.9% | $^1$H NMR (400 MHz, DMSO-$d_6$) δ = 9.25-8.91 (m, 1H), 7.91-7.70 (m, 2H), 7.64-7.42 (m, 2H), 6.81-6.75 (m, 2H), 5.41-4.81 (m, 2H), 4.29-3.84 (m, 4H), 3.80-3.71 (2s, 3H), 3.65-3.61 (m, 2H), 3.52-3.39 (m, 1H), 3.12-2.99 (m, 2H), 2.80-2.67 (m, 2H), 2.15-1.90 (m, 5H). (Mixture of interconvertible atropisomers) |
| 594 | 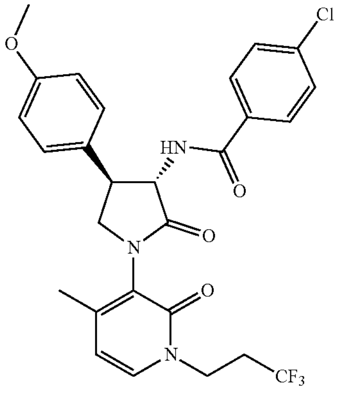 [SMILES: COc1ccc([C@@H]2CN(c3c(C)ccn(CCC(F)(F)F)c3=O)C(=O)[C@H]2NC(=O)c2ccc(Cl)cc2)cc1] | 548.2 | Method D, RT = 2.609 min, 99%. | $^1$H NMR (400 MHz, DMSO-$d_6$) δ = 9.02-8.95 (m, 1H), 7.83 (d, J = 8.5 Hz, 2H), 7.64-7.59 (m, 1H), 7.56-7.49 (m, 2H), 7.38-7.29 (m, 2H), 6.93-6.84 (m, 2H), 6.30-6.26 (m, 1H), 5.21-4.74 (m, 1H), 4.18-4.10 (m, 1H), 4.21-3.98 (m, 1H), 3.96-3.81 (m, 2H), 3.72-3.68 (2s, 3H), 3.63-3.42 (m, 1H), 2.78-2.63 (m, 2H), 2.21-2.06 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 595 | 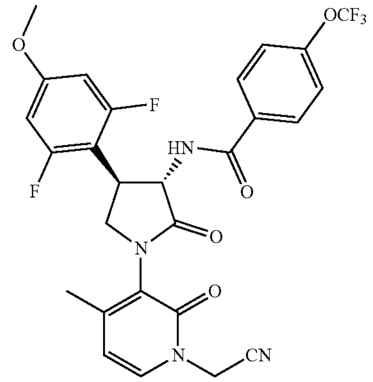 [SMILES: COc1cc(F)c([C@@H]2CN(c3c(C)ccn(CC#N)c3=O)C(=O)[C@H]2NC(=O)c2ccc(OC(F)(F)F)cc2)c(F)c1] | 577.2 | Method D, RT = 2.167 min, 99%. | $^1$H NMR (400 MHz, DMSO-$d_6$) δ = 9.35-8.94 (m, 1H), 8.02-7.91 (m, 2H), 7.78-7.71 (m, 1H), 7.54-7.44 (m, 2H), 6.85-6.73 (m, 2H), 6.43-6.32 (m, 1H), 5.39-4.82 (m, 3H), 4.33-4.22 (m, 1H), 4.20-4.05 (m, 1H), 3.81-3.74 (2s, 3H), 3.63-3.52 (m, 1H), 2.27-2.05 (2S, 3H). (Mixture of interconvertible atropisomers) |
| 596 | 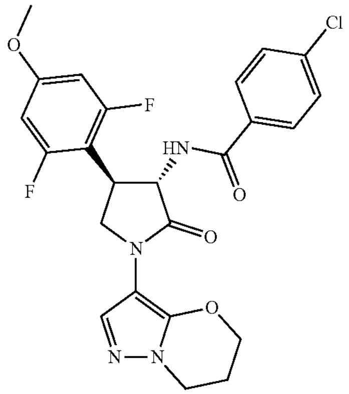 [SMILES: COc1cc(F)c([C@@H]2CN(c3cnn4c3OCCC4)C(=O)[C@H]2NC(=O)c2ccc(Cl)cc2)c(F)c1] | 503.1 | Method-D, RT = 1.319 min, 100% | $^1$H NMR (400 MHz, DMSO-$d_6$) δ = 9.05 (d, J = 8.6 Hz, 1H), 8.03 (s, 1H), 7.82 (d, J = 8.8 Hz, 2H), 7.56 (d, J = 8.6 Hz, 2H), 6.77 (d, J = 10.8 Hz, 2H), 5.00 (dd, J = 10.6, 8.7 Hz, 1H), 4.28-4.20 (m, 1H), 4.02 (q, J = 9.6 Hz, 1H), 3.91-3.84 (m, 1H), 3.79 (t, J = 7.0 Hz, 2H), 3.76 (s, 3H), 3.75-3.71 (m, 2H), 2.55-2.52 (m, 1H), 2.49-2.46 (m, 1H). |
| 597 | 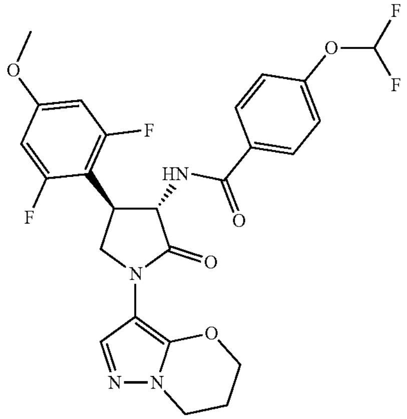 [SMILES: COc1cc(F)c([C@@H]2CN(c3cnn4c3OCCC4)C(=O)[C@H]2NC(=O)c2ccc(OC(F)F)cc2)c(F)c1] | 535.2 | Method-D, RT = 1.308 min, 93.5% | $^1$H NMR (400 MHz, DMSO-$d_6$) δ = 9.03-8.94 (m, 1H), 8.03 (s, 1H), 7.88 (d, J = 8.6 Hz, 2H), 7.34 (t, J = 76.0 Hz, 1H), 7.27 (d, J = 8.6 Hz, 2H), 6.77 (d, J = 10.8 Hz, 2H), 5.00 (dd, J = 10.6, 8.7 Hz, 1H), 4.28-4.20 (m, 1H), 4.02 (q, J = 9.6 Hz, 1H), 3.91-3.84 (m, 1H), 3.79 (t, J = 7.0 Hz, 2H), 3.76 (s, 3H), 3.75-3.71 (m, 2H), 2.55-2.52 (m, 1H), 2.49-2.46 (m, 1H). |

TABLE 2-continued

| Ex | Structure | LCMS (M + H)+ | HPLC Method, RT (min.) & Purity | $^1$H NMR |
|---|---|---|---|---|
| 598 | 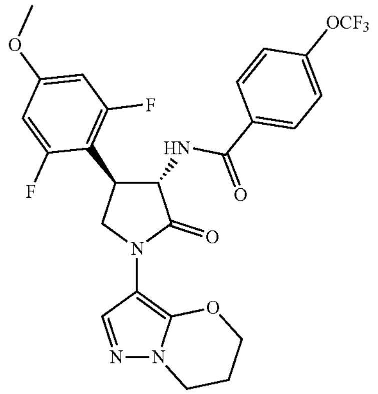 [SMILES: COc1cc(F)c([C@@H]2CN(c3cnn4c3OCCC4)C(=O)[C@H]2NC(=O)c2ccc(OC(F)(F)F)cc2)c(F)c1] | 553.1 | Method-D, RT = 1.412 min, 97% | $^1$H NMR (400 MHz, DMSO-$d_6$) δ = 9.09 (d, J = 8.6 Hz, 1H), 8.03 (s, 1H), 7.94 (d, J = 8.8 Hz, 2H), 7.49 (d, J = 8.8 Hz, 2H), 6.77 (d, J = 10.8 Hz, 2H), 5.00 (dd, J = 10.6, 8.7 Hz, 1H), 4.28-4.20 (m, 1H), 4.02 (q, J = 9.6 Hz, 1H), 3.91-3.84 (m, 1H), 3.79 (t, J = 7.0 Hz, 2H), 3.76 (s, 3H), 3.75-3.71 (m, 2H), 2.55-2.52 (m, 1H), 2.49-2.46 (m, 1H). |
| 599 | 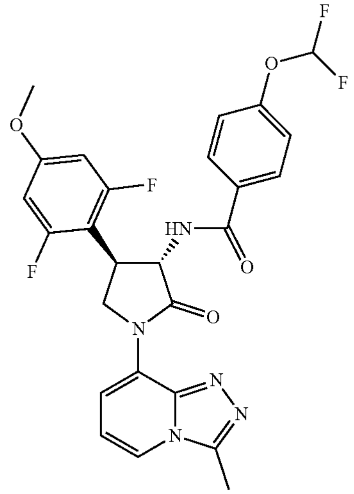 [SMILES: COc1cc(F)c([C@@H]2CN(c3cccn4c(C)nnc34)C(=O)[C@H]2NC(=O)c2ccc(OC(F)F)cc2)c(F)c1] | 544.1 | Method C, RT = 1.557 min, 99.1% | $^1$H NMR (400 MHz, DMSO-$d_6$) δ = 9.09 (d, J = 8.5 Hz, 1H), 8.30 (dd, J = 6.9, 0.9 Hz, 1H), 7.90 (d, J = 8.8 Hz, 2H), 7.67 (dd, J = 7.3, 0.9 Hz, 1H), 7.35 (t, J = 72.8 Hz, 1H), 7.28 (d, J = 8.8 Hz, 2H), 7.06 (t, J = 7.0 Hz, 1H), 6.80 (d, J = 10.8 Hz, 2H), 5.16 (dd, J = 11.1, 8.4 Hz, 1H), 4.67-4.57 (m, 1H), 4.42 (t, J = 10.3 Hz, 1H), 4.24 (q, J = 10.3 Hz, 1H), 3.78 (s, 3H), 2.71 (s, 3H). |
| 600 | 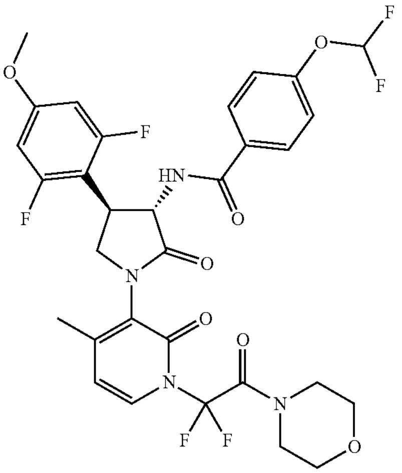 [SMILES: COc1cc(F)c([C@@H]2CN(c3c(C)ccn(C(F)(F)C(=O)N4CCOCC4)c3=O)C(=O)[C@H]2NC(=O)c2ccc(OC(F)F)cc2)c(F)c1] | 683.1 | Method D, RT = 1.644 min, 100%. | $^1$H NMR (400 MHz, DMSO-$d_6$) δ = 9.12-8.94 (m, 1H), 7.96-7.82 (m, 3H), 7.55-7.11 (m, 3H), 6.83-6.68 (m, 2H), 6.57-6.46 (m, 1H), 5.31-4.76 (m, 1H), 4.32-3.96 (m, 2H), 3.78-3.74 (2s, 3H), 3.65-3.46 (m, 6H), 3.37-3.34 (m, 1H), 2.30-2.10 (2s, 3H), 1.66-1.60 (m, 1H), 1.31-1.16 (m, 1H). (Mixture of interconvertible atrop isomers) |

TABLE 2-continued

| Ex | Structure | LCMS (M + H)+ | HPLC Method, RT (min.) & Purity | $^1$H NMR |
|---|---|---|---|---|
| 601 | 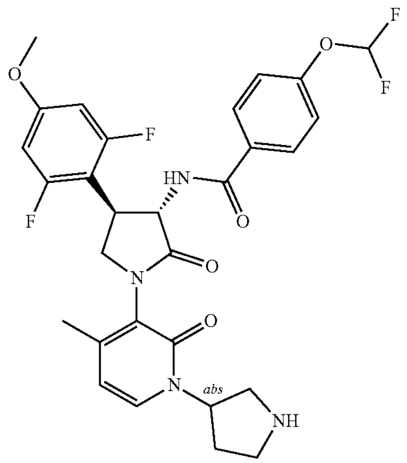 [SMILES: COc1cc(F)c([C@@H]2CN(c3c(C)ccn(C4CCNC4)c3=O)C(=O)[C@H]2NC(=O)c2ccc(OC(F)F)cc2)c(F)c1] | 589.2 | Method D, RT = 1.422 min, 100%. | $^1$H NMR (400 MHz, DMSO-$d_6$) δ = 9.13-8.89 (m, 1H), 7.96-7.83 (m, 2H), 7.77-7.67 (m, 1H), 7.54-7.10 (m, 3H), 6.84-6.70 (m, 2H), 6.33-6.22 (m, 1H), 5.36-4.84 (m, 2H), 4.27-4.10 (m, 2H), 3.78-3.75 (2s, 3H), 3.52-3.49 (m, 3H), 3.15-3.05 (m, 2H), 2.88-2.77 (m, 2H), 2.27-2.02 (2s, 3H), 1.80-1.68 (m, 1H). (Mixture of interconvertible atropisomers) |
| 602 | 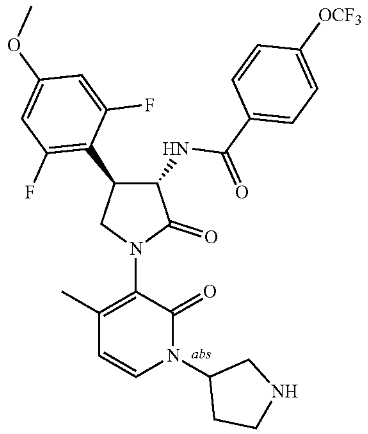 [SMILES: COc1cc(F)c([C@@H]2CN(c3c(C)ccn(C4CCNC4)c3=O)C(=O)[C@H]2NC(=O)c2ccc(OC(F)(F)F)cc2)c(F)c1] | 607.1 | Method D, RT = 1.586 min, 95%. | $^1$H NMR (400 MHz, DMSO-$d_6$) δ = 9.25-8.96 (m, 1H), 8.05-7.87 (m, 2H), 7.77-7.65 (m, 1H), 7.57-7.38 (m, 2H), 6.77 (m, 2H), 6.27 (m, 1H), 5.40-5.14 (m, 1H), 4.93-4.07 (m, 3H), 3.80-3.72 (2s, 3H), 3.53-3.49 (m, 3H), 3.13-2.99 (m, 2H), 2.90-2.74 (m, 2H), 2.27-2.00 (2s, 3H), 1.81-1.60 (m, 1H). (Mixture of interconvertible atropisomers) |
| 603 | 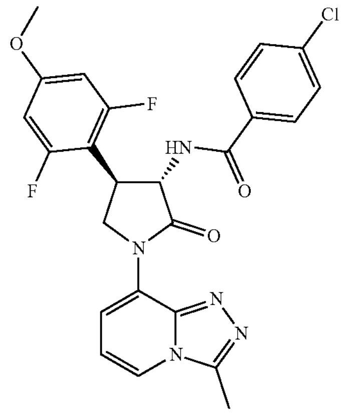 [SMILES: COc1cc(F)c([C@@H]2CN(c3cccn4c(C)nnc34)C(=O)[C@H]2NC(=O)c2ccc(Cl)cc2)c(F)c1] | 512.1 | Method C, RT = 1.625 min, 100% | $^1$H NMR (400 MHz, DMSO-$d_6$) δ = 9.16 (d, J = 8.5 Hz, 1H), 8.30 (dd, J = 6.8, 0.8 Hz, 1H), 7.94-7.80 (m, 2H), 7.68 (dd, J = 7.3, 0.8 Hz, 1H), 7.62-7.51 (m, 2H), 7.07 (t, J = 7.0 Hz, 1H), 6.81 (d, J = 10.8 Hz, 2H), 5.18 (dd, J = 11.1, 8.4 Hz, 1H), 4.70-4.55 (m, 1H), 4.42 (t, J = 10.1 Hz, 1H), 4.24 (q, J = 10.1 Hz, 1H), 3.78 (s, 3H), 2.72 (s, 3H). |

TABLE 2-continued

| Ex | Structure | LCMS (M + H)+ | HPLC Method, RT (min.) & Purity | ¹H NMR |
|---|---|---|---|---|
| 604 | 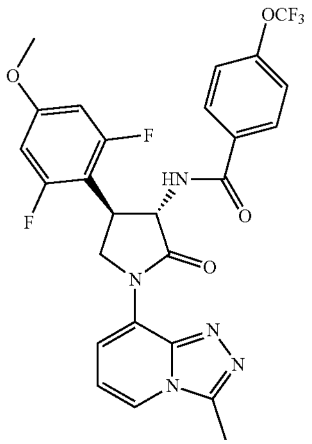 [SMILES: COc1cc(F)c([C@@H]2CN(c3cccn4c(C)nnc34)C(=O)[C@H]2NC(=O)c2ccc(OC(F)(F)F)cc2)c(F)c1] | 562.1 | Method C, RT = 1.728 min, 99.7% | $^1$H NMR (400 MHz, DMSO-$d_6$) δ = 9.20 (d, J = 8.3 Hz, 1H), 8.31 (dd, J = 6.8, 0.8 Hz, 1H), 8.04-7.87 (m, 2H), 7.68 (dd, J = 7.3, 0.8 Hz, 1H), 7.57-7.41 (m, 2H), 7.07 (t, J = 7.0 Hz, 1H), 6.81 (d, J = 10.8 Hz, 2H), 5.19 (dd, J = 11.1, 8.4 Hz, 1H), 4.68-4.55 (m, 1H), 4.42 (t, J = 10.0 Hz, 1H), 4.25 (q, J = 10.1 Hz, 1H), 3.79 (s, 3H), 2.72 (s, 3H). |
| 605 | 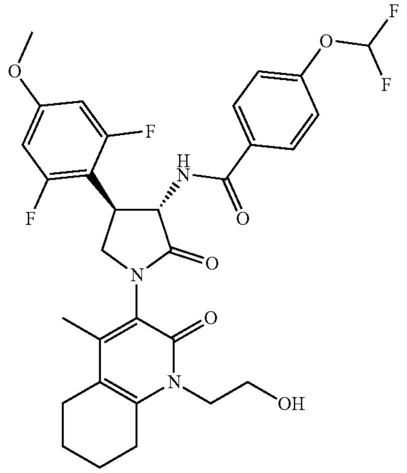 [SMILES: COc1cc(F)c([C@@H]2CN(c3c(C)c4c(n(CCO)c3=O)CCCC4)C(=O)[C@H]2NC(=O)c2ccc(OC(F)F)cc2)c(F)c1] | 618.2 | Method D, RT = 1.791 min, 99.9% | $^1$H NMR (400 MHz, DMSO-$d_6$) δ = 9.14-8.90 (m, 1H), 7.96-7.77 (m, 2H), 7.54-7.14 (2t, J = 74.3 Hz, 1H), 7.28-7.24 (m, 2H), 6.82-6.68 (m, 2H), 5.40-4.82 (m, 2H), 4.30-4.00 (m, 4H), 3.78-3.72 (2s, 3H), 3.61 (quin, J = 5.8 Hz, 2H), 3.51-3.41 (m, 1H), 2.85-2.80 (m, 2H), 2.47-2.40 (m, 2H), 2.14-1.93 (2s, 3H), 1.81-1.61 (m, 4H). (Mixture of interconvertible atrop isomers) |
| 606 | 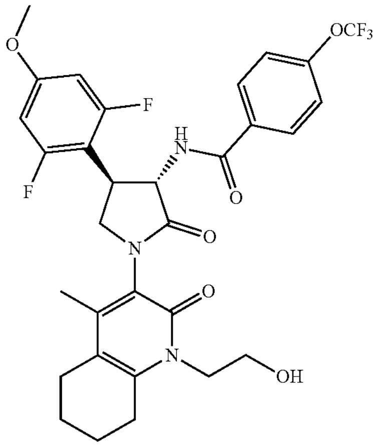 [SMILES: COc1cc(F)c([C@@H]2CN(c3c(C)c4c(n(CCO)c3=O)CCCC4)C(=O)[C@H]2NC(=O)c2ccc(OC(F)(F)F)cc2)c(F)c1] | 636.1 | Method D, RT = 1.766 min, 94.5% | $^1$H NMR (400 MHz, DMSO-$d_6$) δ = 9.26-8.98 (m, 1H), 8.02-7.84 (m, 2H), 7.56-7.37 (m, 2H), 6.84-6.66 (m, 2H), 5.41-4.80 (m, 2H), 4.28-3.99 (m, 4H), 3.81-3.73 (2s, 3H), 3.61 (quin, J = 5.8 Hz, 2H), 3.50-3.42 (m, 1H), 2.89-2.77 (m, 2H), 2.47-2.38 (m, 2H), 2.14-1.91 (2s, 3H), 1.80-1.57 (m, 4H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 607 | 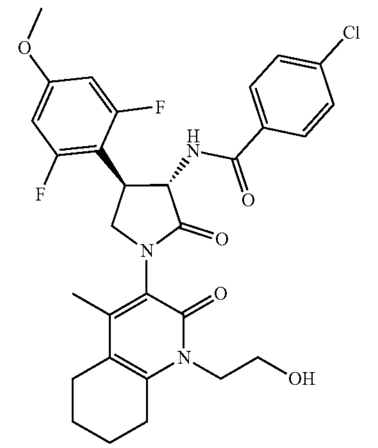 [SMILES: COc1cc(F)c([C@@H]2CN(c3c(C)c4c(n(CCO)c3=O)CCCC4)C(=O)[C@H]2NC(=O)c2ccc(Cl)cc2)c(F)c1] | 586.1 | Method D, RT = 1.629 min, 100% | $^1$H NMR (400 MHz, DMSO-$d_6$) δ = 9.21-8.93 (m, 1H), 7.92-7.76 (m, 2H), 7.67-7.46 (m, 2H), 6.83-6.69 (m, 2H), 5.41-4.87 (m, 2H), 4.29-3.99 (m, 4H), 3.79-3.72 (2s, 3H), 3.60 (quin, J = 5.8 Hz, 2H), 3.49-3.42 (m, 1H), 2.90-2.75 (m, 2H), 2.47-2.39 (m, 2H), 2.14-1.91 (2s, 3H), 1.81-1.54 (m, 4H). (Mixture of interconvertible atropisomers) |
| 608 | 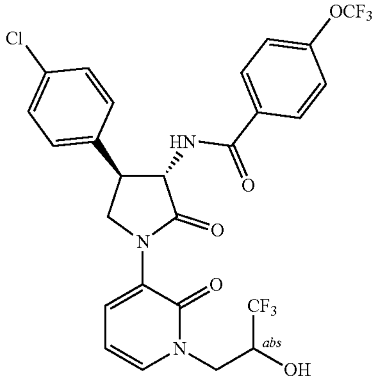 [SMILES: O=C(N[C@@H]1C(=O)N(c2cccn(CC(O)C(F)(F)F)c2=O)C[C@H]1c1ccc(Cl)cc1)c1ccc(OC(F)(F)F)cc1] | 604.2 | Method D, RT = 2.015 min, 100% | $^1$H NMR (400 MHz, DMSO-$d_6$) δ = 9.08 (d, J = 8.5 Hz, 1H), 8.03-7.96 (m, 2H), 7.72-7.64 (m, 2H), 7.49 (d, J = 9.0 Hz, 4H), 7.46-7.39 (m, 2H), 6.38 (t, J = 7.0 Hz, 1H), 5.04 (dd, J = 11.0, 8.5 Hz, 1H), 4.45 (dd, J = 13.1, 2.5 Hz, 1H), 4.40-4.28 (m, 1H), 4.19-4.09 (m, 1H), 3.92-3.79 (m, 3H), 3.51-3.40 (m, 1H). |
| 609 | 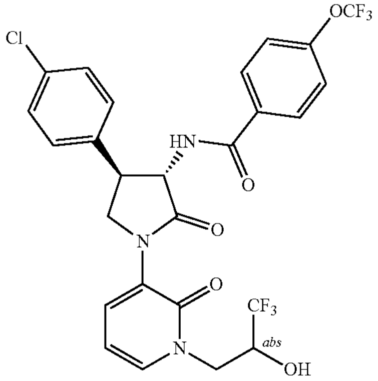 [SMILES: O=C(N[C@@H]1C(=O)N(c2cccn(CC(O)C(F)(F)F)c2=O)C[C@H]1c1ccc(Cl)cc1)c1ccc(OC(F)(F)F)cc1] | 604.2 | Method D, RT = 2.029 min, 100% | $^1$H NMR (400 MHz, DMSO-$d_6$) δ = 9.08 (d, J = 8.5 Hz, 1H), 8.03-7.96 (m, 2H), 7.72-7.64 (m, 2H), 7.49 (d, J = 9.0 Hz, 4H), 7.46-7.39 (m, 2H), 6.38 (t, J = 7.0 Hz, 1H), 5.04 (dd, J = 11.0, 8.5 Hz, 1H), 4.45 (dd, J = 13.1, 2.5 Hz, 1H), 4.40-4.28 (m, 1H), 4.19-4.09 (m, 1H), 3.92-3.79 (m, 3H), 3.51-3.40 (m, 1H). |

TABLE 2-continued

| Ex | Structure | LCMS (M + H)+ | HPLC Method, RT (min.) & Purity | $^{1}$H NMR |
|---|---|---|---|---|
| 610 | 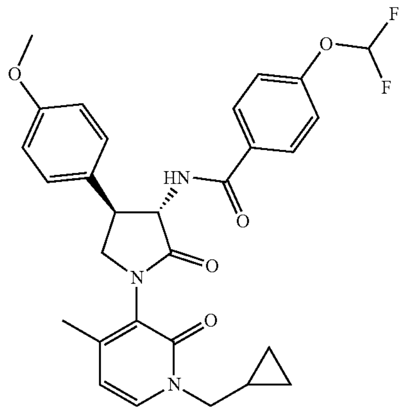 [SMILES: COc1ccc([C@@H]2CN(c3c(C)ccn(CC4CC4)c3=O)C(=O)[C@H]2NC(=O)c2ccc(OC(F)F)cc2)cc1] | 538.2 | Method F, RT = 2.51 min, 99%, | $^{1}$H NMR (400 MHz, DMSO-$d_6$) δ = 9.03 (m, 1H), 7.99-7.89 (m, 2H), 7.72-7.64 (m, 1H), 7.55-7.06 (m, 5H), 6.93-6.89 (m, 2H), 6.22 (d, J = 6.8 Hz, 1H), 5.29-4.62 (m, 1H), 4.13-3.81 (m, 2H), 3.79-3.75 (2s, 3H) 3.69-3.59 (m, 2H), 3.46-3.40 (m, 1H), 2.25-2.04 (2s, 3H), 1.22-120 (m, 1H), 0.49-0.47 (m, 4H). (Mixture of interconvertible atropisomers) |
| 611 | 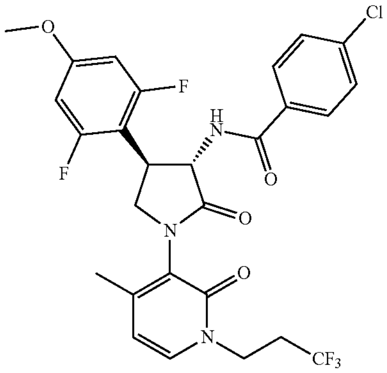 [SMILES: COc1cc(F)c([C@@H]2CN(c3c(C)ccn(CCC(F)(F)F)c3=O)C(=O)[C@H]2NC(=O)c2ccc(Cl)cc2)c(F)c1] | 584.2 | Method F, RT = 2.65 min, 99%, | $^{1}$H NMR (400 MHz, DMSO-$d_6$) δ = 9.21-9.00 (m, 1H), 7.91-7.79 (m, 2H), 7.69 (d, J = 7.0 Hz, 1H), 7.61,-7.51 (m, 2H), 6.78 (br d, J = 10.5 Hz, 2H), 6.27 (d, J = 7.0 Hz, 1H), 5.40-4.85 (m, 1H), 4.33-4.06 (m, 4H), 3.80-3.74 (2s, 3H), 3.56-3.47 (m, 1H), 2.83-2.68 (m, 2H), 2.25-2.04 (2s, 3H). (Mixture of interconvertible atrop isomers) |
| 612 | 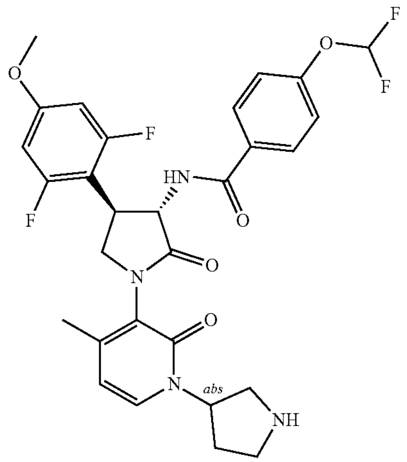 [SMILES: COc1cc(F)c([C@@H]2CN(c3c(C)ccn(C4CCNC4)c3=O)C(=O)[C@H]2NC(=O)c2ccc(OC(F)F)cc2)c(F)c1] | 589.1 | Method D, RT = 1.34 min, 93%. | $^{1}$H NMR (400 MHz, DMSO-$d_6$) δ = 9.13-8.86 (m, 1H), 7.95-7.80 (m, 2H), 7.78-7.66 (m, 1H), 7.56-7.12 (m, 3H), 6.82-6.65 (m, 2H), 6.32-6.17 (m, 1H), 5.36-4.89 (m, 2H), 4.30-4.07 (m, 3H), 3.80-3.72 (2s, 3H), 3.49 (t, J = 8.4 Hz, 1H), 3.14-3.01 (m, 2H), 2.88-2.75 (m, 2H), 2.26-2.13 (m, 4H), 1.77-1.62 (m, 1H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 613 | 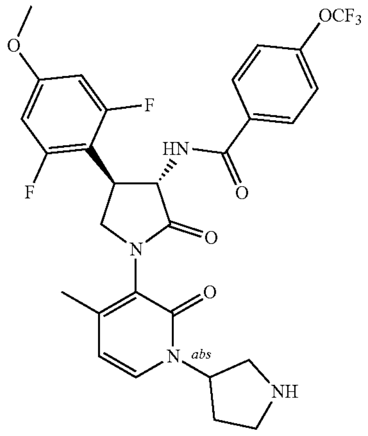 [SMILES: COc1cc(F)c([C@@H]2CN(c3c(C)ccn(C4CCNC4)c3=O)C(=O)[C@H]2NC(=O)c2ccc(OC(F)(F)F)cc2)c(F)c1] | 607.2 | Method D, RT = 1.527 min, 95%. | $^1$H NMR (400 MHz, DMSO-$d_6$) δ = 9.25-9.00 (m, 1H), 8.00-7.85 (m, 2H), 7.78-7.65 (m, 1H), 7.55-7.40 (m, 2H), 6.88-6.69 (m, 2H), 6.34-6.18 (m, 1H), 5.37-4.82 (m, 2H), 4.30-4.06 (m, 3H), 3.79-3.72 (2s, 3H), 3.50 (t, J = 8.1 Hz, 1H), 3.16-2.99 (m, 2H), 2.88-2.78 (m, 2H), 2.25-2.00 (m, 4H), 1.78-1.63 (m, 1H). (Mixture of interconvertible atropisomers) |
| 614 | 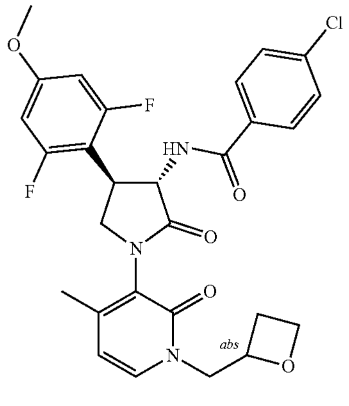 [SMILES: COc1cc(F)c([C@@H]2CN(c3c(C)ccn(CC4CCO4)c3=O)C(=O)[C@H]2NC(=O)c2ccc(Cl)cc2)c(F)c1] | 558.1 | Method D, RT = 1.611 min, 100% | $^1$H NMR (400 MHz, DMSO-$d_6$) δ = 9.21-8.94 (m, 1H), 7.90-7.78 (m, 2H), 7.71-7.48 (m, 3H), 6.83-6.70 (m, 2H), 6.31-6.15 (m, 1H), 5.35-4.83 (m, 2H), 4.53-4.45 (m, 1H), 4.39 (qd, J = 9.1, 5.7 Hz, 1H), 4.30-4.06 (m, 4H), 3.82-3.70 (2s, 3H), 3.55-3.48 (m, 1H), 2.69-2.61 (m, 1H), 2.40-2.34 (m, 1H), 2.26-2.04 (2s, 3H). (Mixture of interconvertible atropisomers) |
| 615 | 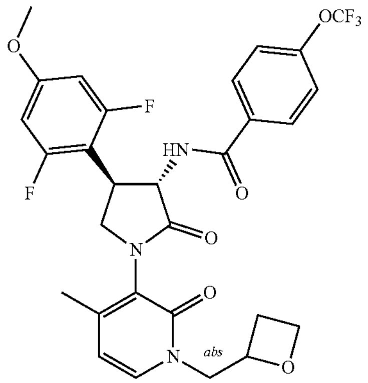 [SMILES: COc1cc(F)c([C@@H]2CN(c3c(C)ccn(CC4CCO4)c3=O)C(=O)[C@H]2NC(=O)c2ccc(OC(F)(F)F)cc2)c(F)c1] | 608.1 | Method D, RT = 1.759 min, 97.1% | $^1$H NMR (400 MHz, DMSO-$d_6$) δ = 9.28-8.90 (m, 1H), 8.03-7.84 (m, 2H), 7.70-7.56 (m, 1H), 7.52-7.37 (m, 2H), 6.86-6.65 (m, 2H), 6.30-6.15 (m, 1H), 5.41-4.80 (m, 2H), 4.55-4.45 (m, 1H), 4.43-4.33 (m, 1H), 4.31-4.06 (m, 4H), 3.82-3.70 (2s, 3H), 3.60-3.44 (m, 1H), 2.72-2.61 (m, 1H), 2.39-2.30 (m, 1H), 2.24-1.96 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 616 | 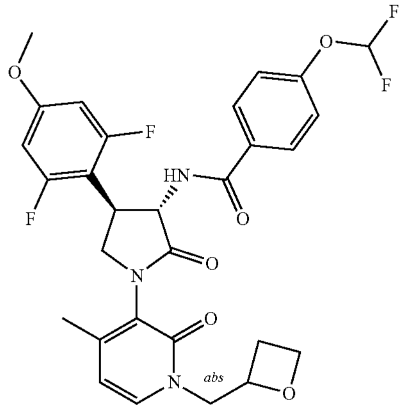 [SMILES: COc1cc(F)c([C@@H]2CN(c3c(C)ccn(CC4CCO4)c3=O)C(=O)[C@H]2NC(=O)c2ccc(OC(F)F)cc2)c(F)c1] | 590.1 | Method D, RT = 1.579 min, 100% | $^1$H NMR (400 MHz, DMSO-d$_6$) δ = 9.19-8.84 (m, 1H), 7.97-7.78 (m, 2H), 7.71-7.57 (m, 1H), 7.34 (t, J = 74.3 Hz, 1H), 7.28-7.24 (m, 2H), 6.81-6.75 (m, 2H), 6.31-6.16 (m, 1H), 5.39-4.78 (m, 2H), 4.55-4.45 (m, 1H), 4.41-4.36 (m, 1H), 4.30-4.04 (m, 4H), 3.80-3.68 (2s, 3H), 3.57-3.46 (m, 1H), 2.70-2.59 (m, 1H), 2.40-2.32 (m, 1H), 2.23-2.01 (2s, 3H). (Mixture of interconvertible atropisomers) |
| 617 | 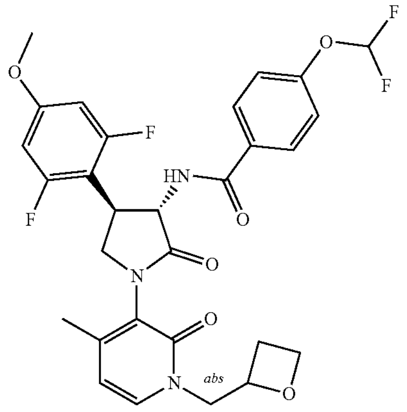 [SMILES: COc1cc(F)c([C@@H]2CN(c3c(C)ccn(CC4CCO4)c3=O)C(=O)[C@H]2NC(=O)c2ccc(OC(F)F)cc2)c(F)c1] | 590.1 | Method D, RT = 1.597 min, 100% | $^1$H NMR (400 MHz, DMSO-d$_6$) δ = 9.16-8.86 (m, 1H), 7.97-7.81 (m, 2H), 7.69-7.57 (m, 1H), 7.34 (t, J = 74.3 Hz, 1H), 7.28-7.24 (m, 2H), 6.81-6.75 (m, 2H), 6.31-6.14 (m, 1H), 5.38-4.82 (m, 2H), 4.54-4.43 (m, 1H), 4.41-4.33 (m, 1H), 4.31-4.08 (m, 4H), 3.81-3.74 (2s, 3H), 3.56-3.45 (m, 1H), 2.68-2.62 (m, 1H), 2.40-2.32 (m, 1H), 2.22-2.01 (2s, 3H). (Mixture of interconvertible atropisomers) |
| 618 | 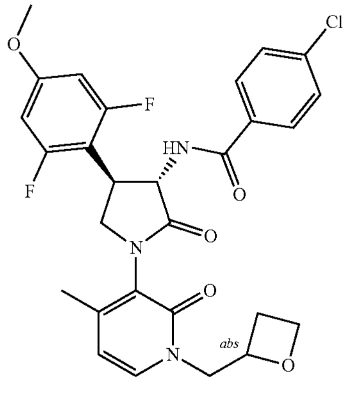 [SMILES: COc1cc(F)c([C@@H]2CN(c3c(C)ccn(CC4CCO4)c3=O)C(=O)[C@H]2NC(=O)c2ccc(Cl)cc2)c(F)c1] | 558.1 | Method D, RT = 1.616 min, 100% | $^1$H NMR (400 MHz, DMSO-d$_6$) δ = 9.23-8.86 (m, 1H), 7.93-7.76 (m, 2H), 7.71-7.38 (m, 3H), 6.81-6.75 (m, 2H), 6.32-6.12 (m, 1H), 5.41-4.78 (m, 2H), 4.57-4.44 (m, 1H), 4.42-4.31 (m, 1H), 4.29-4.06 (m, 4H), 3.81-3.70 (2s, 3H), 3.54-3.44 (m, 1H), 2.70-2.62 (m, 1H), 2.38-2.30 (m, 1H), 2.25-1.96 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 619 | 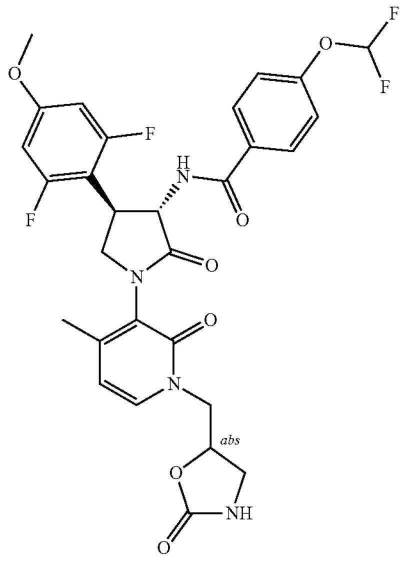 [SMILES: COc1cc(F)c([C@@H]2CN(c3c(C)ccn(CC4CNC(=O)O4)c3=O)C(=O)[C@H]2NC(=O)c2ccc(OC(F)F)cc2)c(F)c1] | 619.1 | Method D, RT = 1.484 min, 94.4% | $^1$H NMR (400 MHz, DMSO-d$_6$) δ = 9.15-8.87 (m, 1H), 7.99-7.84 (m, 2H), 7.71-7.56 (m, 2H), 7.34 (t, J = 74.3 Hz, 1H), 7.28-7.24 (m, 1H), 6.81-6.75 (m, 2H), 6.37-6.19 (m, 1H), 5.38-4.81 (m, 2H), 4.34-4.09 (m, 4H), 3.80-3.75 (2s, 3H), 3.64-3.50 (m, 3H), 3.27-3.19 (m, 1H), 2.25-2.06 (2s, 3H). (Mixture of interconvertible atropisomers) |
| 620 | 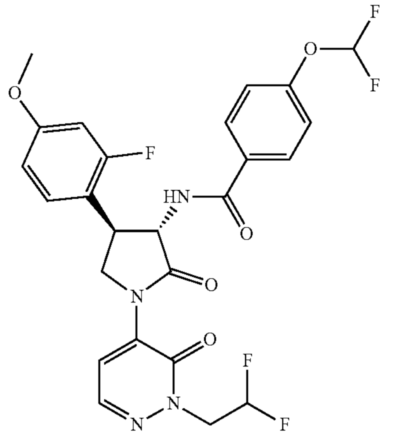 [SMILES: COc1ccc([C@@H]2CN(c3ccnn(CC(F)F)c3=O)C(=O)[C@H]2NC(=O)c2ccc(OC(F)F)cc2)c(F)c1] | 553.1 | Method D, RT = 1.75 min, 96% | $^1$H NMR (400 MHz, DMSO-d$_6$) δ = 8.97 (d, J = 8.6 Hz, 1H), 8.05 (d, J = 4.9 Hz, 1H), 7.94-7.84 (m, 2H), 7.78 (d, J = 4.6 Hz, 1H), 7.56-7.52 (m, 2H), 7.39 (t, J = 74.0 Hz, 1H), 7.27-7.25 (m, 1H) 6.85-6.77 (m, 2H), 6.40 (tt, J = 52.6, 4.8 Hz, 1H), 5.12-5.09 (m, 1H), 4.56-4.50 (m, 2H), 4.46 (t, J = 8.3 Hz, 1H), 4.07-3.90 (m, 2H), 3.74 (s, 3H). |
| 621 | 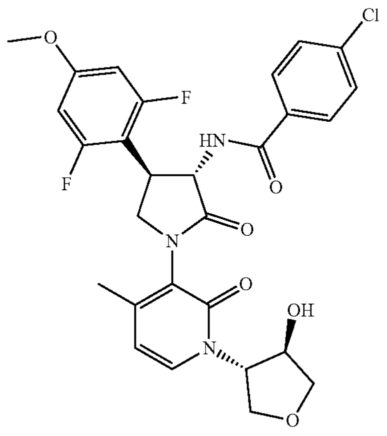 [SMILES: COc1cc(F)c([C@@H]2CN(c3c(C)ccn([C@H]4COC[C@@H]4O)c3=O)C(=O)[C@H]2NC(=O)c2ccc(Cl)cc2)c(F)c1] | 574.1 | Method D, RT = 1.59 min, 97% | $^1$H NMR (400 MHz, DMSO-d$_6$) δ = 9.21-8.94 (m, 1H), 7.90-7.75 (m, 2H), 7.63-7.35 (m, 3H), 6.86-6.69 (m, 2H), 6.35-6.22 (m, 1H), 5.36-4.84 (m, 2H), 4.37-4.04 (m, 5H), 3.91-3.83 (m, 1H), 3.86-3.82 (2s, 3H), 3.61-3.50 (m, 3H), 2.22-2.05 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 622 | 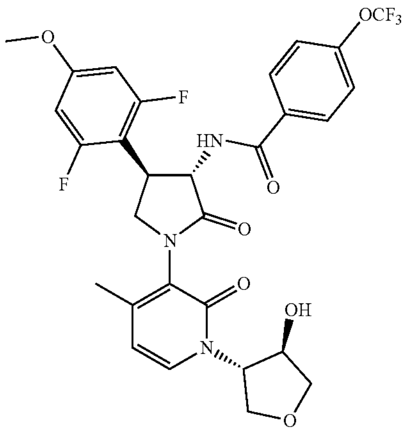 [SMILES: COc1cc(F)c([C@@H]2CN(c3c(C)ccn([C@H]4COC[C@@H]4O)c3=O)C(=O)[C@H]2NC(=O)c2ccc(OC(F)(F)F)cc2)c(F)c1] | 624.1 | Method D, RT = 1.66 min, 99% | $^1$H NMR (400 MHz, DMSO-$d_6$) δ = 9.24-8.94 (m, 1H), 8.04-7.85 (m, 2H), 7.59-7.45 (m, 3H), 6.85-6.63 (m, 2H), 6.37-6.22 (m, 1H), 5.79-5.60 (m, 1H), 5.05-4.84 (m, 2H), 4.39-4.05 (m, 5H), 3.88-3.85 (m, 1H), 3.78-3.74 (2s, 3H), 3.59-3.50 (m, 2H), 2.24-2.00 (2s, 3H). (Mixture of interconvertible atropisomers) |
| 623 | 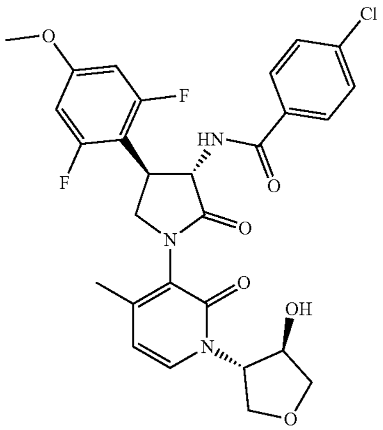 [SMILES: COc1cc(F)c([C@@H]2CN(c3c(C)ccn([C@H]4COC[C@@H]4O)c3=O)C(=O)[C@H]2NC(=O)c2ccc(Cl)cc2)c(F)c1] | 574.1 | Method D, RT = 1.53 min, 100% | $^1$H NMR (400 MHz, DMSO-$d_6$) δ = 9.25-8.90 (m, 1H), 7.92-7.76 (m, 2H), 7.65-7.53 (m, 2H), 7.53-7.38 (m, 1H), 6.85-6.69 (m, 2H), 6.36-6.23 (m, 1H), 5.50-5.30 (m, 1H), 5.0-4.28 (m, 1H), 4.34-4.03 (m, 4H), 3.89-3.80 (m, 1H), 3.78-3.74 (2s, 3H), 3.58-3.51 (m, 2H), 3.17 (s, 2H), 2.21-2.01 (2s, 3H). (Mixture of interconvertible atropisomers) |
| 624 | 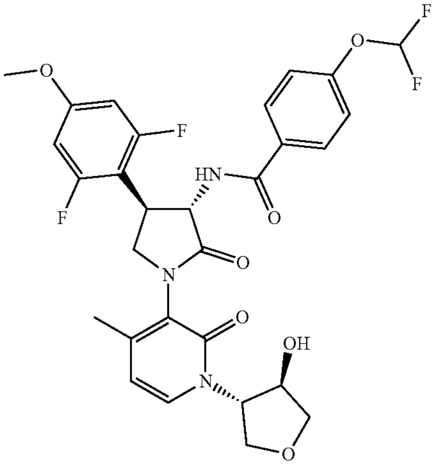 [SMILES: COc1cc(F)c([C@@H]2CN(c3c(C)ccn([C@H]4COC[C@@H]4O)c3=O)C(=O)[C@H]2NC(=O)c2ccc(OC(F)F)cc2)c(F)c1] | 606.1 | Method D, RT = 1.50 min, 99% | $^1$H NMR (400 MHz, DMSO-$d_6$) δ = 9.14-8.83 (m, 1H), 8.00-7.76 (m, 2H), 7.53-7.46 (m, 1H), 7.35 (t, J = 73.8 Hz, 1H), 7.28-7.24 (m, 2H), 6.86-6.67 (m, 2H), 6.36-6.22 (m, 1H), 5.75-5.59 (m, 1H), 5.38-4.76 (m, 2H), 4.38-4.00 (m, 5H), 3.93-3.85 (m, 1H), 3.78-3.74 (2s, 3H), 3.61-3.47 (m, 2H), 2.24-2.00 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 625 | 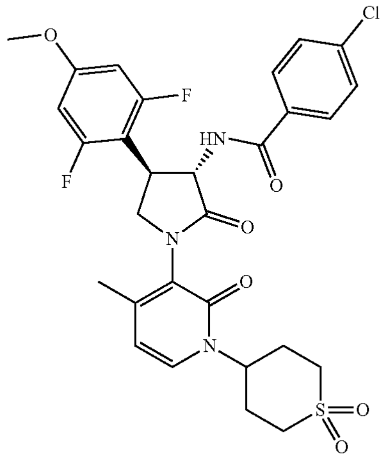 [SMILES: COc1cc(F)c([C@@H]2CN(c3c(C)ccn(C4CCS(=O)(=O)CC4)c3=O)C(=O)[C@H]2NC(=O)c2ccc(Cl)cc2)c(F)c1] | 621 | Method D, RT = 1.59 min, 100% | $^1$H NMR (400 MHz, DMSO-d$_6$) δ = 9.18-8.86 (m, 1H), 7.92-7.76 (m, 2H), 7.74-7.66 (m, 1H), 7.59-7.43 (m, 2H), 6.85-6.65 (m, 2H), 6.32-6.19 (m, 1H), 5.36-4.82 (m, 2H), 4.28-4.04 (m, 2H), 3.78-3.75 (2s, 3H), 3.54-3.42 (m, 3H), 3.22-3.13 (m, 2H), 2.43-2.29 (m, 2H), 2.19-2.0 (2s, 3H), 2.15-2.05 (m, 2H). (Mixture of interconvertible atropisomers) |
| 626 | 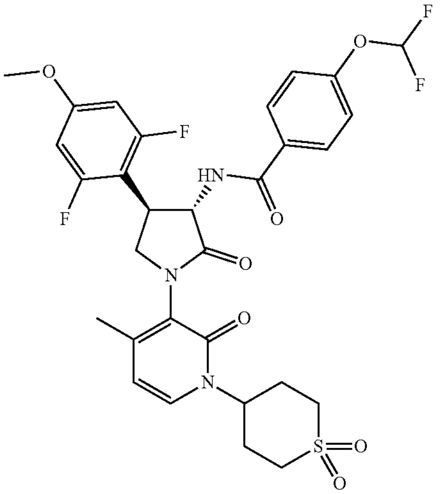 [SMILES: COc1cc(F)c([C@@H]2CN(c3c(C)ccn(C4CCS(=O)(=O)CC4)c3=O)C(=O)[C@H]2NC(=O)c2ccc(OC(F)F)cc2)c(F)c1] | 652.1 | Method D, RT = 1.57 min, 100% | $^1$H NMR (400 MHz, DMSO-d$_6$) δ = 9.11-8.81 (m, 1H), 7.96-7.81 (m, 2H), 7.75-7.62 (m, 1H), 7.28-7.23 (m, 2H), 7.35 (t, J = 73.8 Hz, 1H), 6.81-6.74 (m, 2H), 6.38-6.20 (m, 1H), 5.37-4.77 (m, 2H), 4.32-4.04 (m, 2H), 3.78-3.75 (2s, 3H), 3.56-3.40 (m, 3H), 3.23-3.11 (m, 2H), 2.43-2.25 (m, 2H), 2.19-2.0 (2s, 3H), 2.15-2.05 (m, 2H). (Mixture of interconvertible atropisomers) |
| 627 | 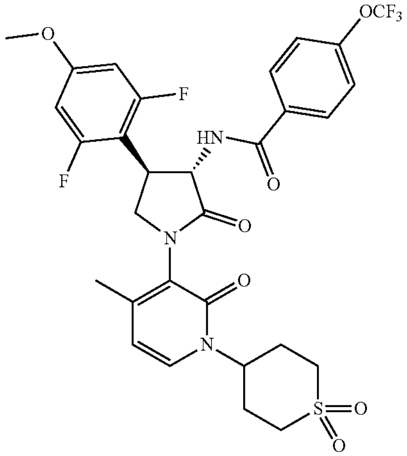 [SMILES: COc1cc(F)c([C@@H]2CN(c3c(C)ccn(C4CCS(=O)(=O)CC4)c3=O)C(=O)[C@H]2NC(=O)c2ccc(OC(F)(F)F)cc2)c(F)c1] | 670.1 | Method D, RT = 1.74 min, 98% | $^1$H NMR (400 MHz, DMSO-d$_6$) δ = 9.24-8.96 (m, 1H), 8.04-7.85 (m, 2H), 7.77-7.64 (m, 1H), 7.56-7.38 (m, 2H), 6.88-6.65 (m, 2H), 6.34-6.20 (m, 1H), 5.36-4.79 (m, 2H), 4.33-4.00 (m, 2H), 3.82-3.68 (m, 3H), 3.57-3.39 (m, 3H), 3.22-3.09 (m, 2H), 2.45-2.28 (m, 2H), 2.19-2.0 (2s, 3H), 2.15-2.05 (m, 2H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 628 | 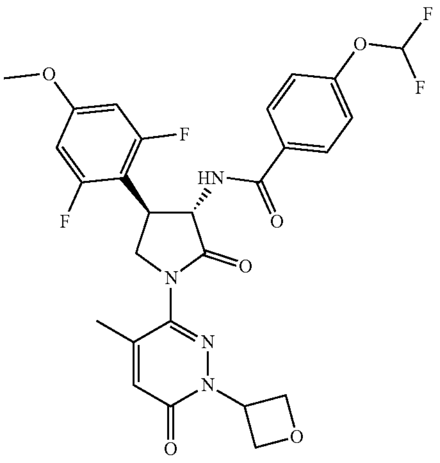 [SMILES: COc1cc(F)c([C@@H]2CN(c3nn(C4COC4)c(=O)cc3C)C(=O)[C@H]2NC(=O)c2ccc(OC(F)F)cc2)c(F)c1] | 577.1 | Method D, RT = 1.56 min, 98% | $^1$H NMR (400 MHz, DMSO-$d_6$) δ = 9.12 (d, J = 8.1 Hz, 1H), 7.95-7.82 (m, 2H), 7.28 (d, J = 8.6 Hz, 2H), 7.35 (t, J = 73.8 Hz, 1H), 6.96 (d, J = 1.2 Hz, 1H), 6.81 (d, J = 10.8 Hz, 2H), 5.77 (quin, J = 7.0 Hz, 1H), 4.91 (dd, J = 10.6, 8.2 Hz, 1H), 4.87-4.70 (m, 4H), 4.29 (q, J = 9.7 Hz, 1H), 4.15-3.97 (m, 2H), 3.77 (s, 3H), 2.24 (s, 3H). |
| 629 | 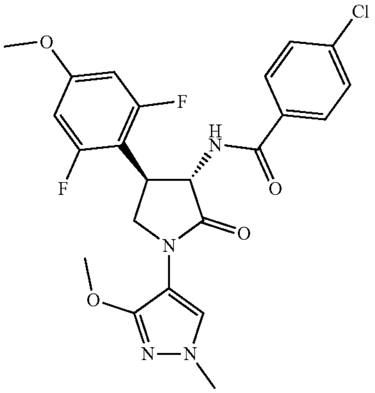 [SMILES: COc1cc(F)c([C@@H]2CN(c3cn(C)nc3OC)C(=O)[C@H]2NC(=O)c2ccc(Cl)cc2)c(F)c1] | 491.1 | Method D, RT = 1.70 min, 97% | $^1$H NMR (400 MHz, DMSO-$d_6$) δ = 9.06 (d, J = 8.6 Hz, 1H), 7.85 (s, 1H), 7.82 (d, J = 8.3 Hz, 2H), 7.56 (d, J = 8.3 Hz, 2H), 6.77 (d, J = 10.8 Hz, 2H), 5.06-4.93 (m, 1H), 4.11-3.92 (m, 2H), 3.85-3.78 (m, 4H), 3.76 (s, 3H), 3.69 (s, 3H). |
| 630 | 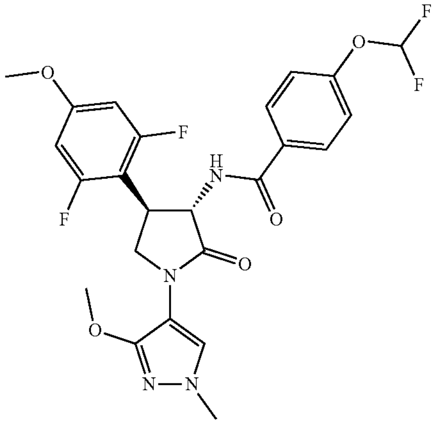 [SMILES: COc1cc(F)c([C@@H]2CN(c3cn(C)nc3OC)C(=O)[C@H]2NC(=O)c2ccc(OC(F)F)cc2)c(F)c1] | 523.1 | Method D, RT = 1.67 min, 98% | $^1$H NMR (400 MHz, DMSO-$d_6$) δ = 9.00 (d, J = 8.8 Hz, 1H), 7.92-7.81 (m, 3H), 7.34 (t, J = 72.9 Hz, 1H), 7.27 (d, J = 8.8 Hz, 2H), 6.77 (d, J = 10.8 Hz, 2H), 5.00 (dd, J = 10.3, 8.8 Hz, 1H), 4.13-3.92 (m, 2H), 3.87-3.79 (m, 4H), 3.76 (s, 3H), 3.69 (s, 3H). |

TABLE 2-continued

| Ex | Structure | LCMS (M + H)+ | HPLC Method, RT (min.) & Purity | $^1$H NMR |
|---|---|---|---|---|
| 631 | 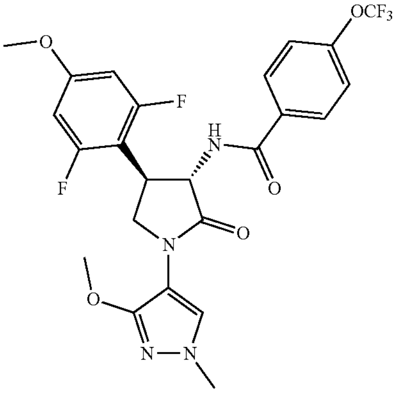 [SMILES: COc1cc(F)c([C@@H]2CN(c3cn(C)nc3OC)C(=O)[C@H]2NC(=O)c2ccc(OC(F)(F)F)cc2)c(F)c1] | 541.1 | Method D, RT = 1.84 min, 98% | $^1$H NMR (400 MHz, DMSO-$d_6$) δ = 9.10 (d, J = 8.6 Hz, 1H), 7.93 (d, J = 8.8 Hz, 2H), 7.86 (s, 1H), 7.48 (d, J = 8.6 Hz, 2H), 6.77 (d, J = 10.8 Hz, 2H), 5.01 (t, J = 9.4 Hz, 1H), 4.12-3.94 (m, 2H), 3.87-3.79 (m, 4H), 3.76 (s, 3H), 3.69 (s, 3H). |
| 632 | 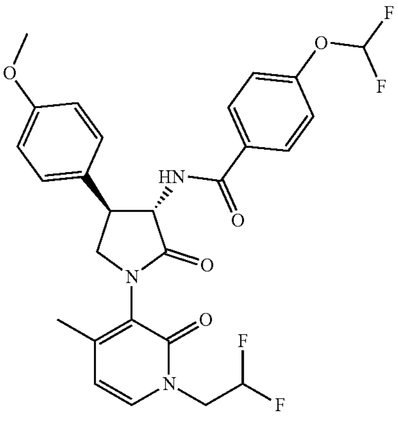 [SMILES: COc1ccc([C@@H]2CN(c3c(C)ccn(CC(F)F)c3=O)C(=O)[C@H]2NC(=O)c2ccc(OC(F)F)cc2)cc1] | 548.3 | Method D, RT = 2.482 min, 100%. | $^1$H NMR (400 MHz, DMSO-$d_6$) δ = 9.01-8.95 (m, 1H), 7.97-7.90 (m, 2H), 7.67-7.61 (m, 1H), 7.55-7.13 (m, 5H), 6.96-6.86 (m, 2H), 6.48-6.16 (m, 2H), 5.28-4.63 (m, 1H), 4.50-4.34 (m, 2H), 4.11-3.79 (m, 2H), 3.72-3.67 (2s, 3H), 3.52-3.44 (m, 1H), 2.25-2.10 (2s, 3H). (Mixture of interconvertible atropisomers) |
| 633 | 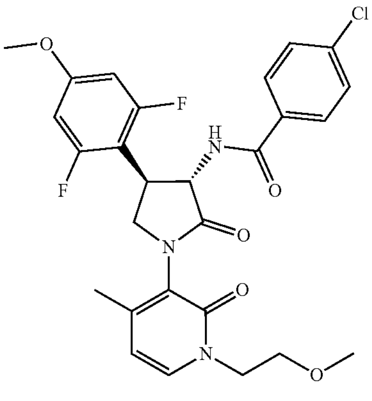 [SMILES: COCCn1ccc(C)c(N2C[C@@H](c3c(F)cc(OC)cc3F)[C@H](NC(=O)c3ccc(Cl)cc3)C2=O)c1=O] | 546.3 | Method D, RT = 1.68 min, 100% | $^1$H NMR (400 MHz, DMSO-$d_6$) δ = 9.14-8.85 (m, 1H), 7.86-7.81 (m, 2H), 7.57-7.54 (m, 3H), 6.78-6.74 (m, 2H), 6.23-6.18 (m, 1H), 5.38-4.87 (m, 1H), 4.44-4.07 (m, 4H), 3.78-3.74 (2s, 3H), 3.52-3.50 (m, 3H), 3.24 (s, 3H), 2.23-2.05 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 634 | 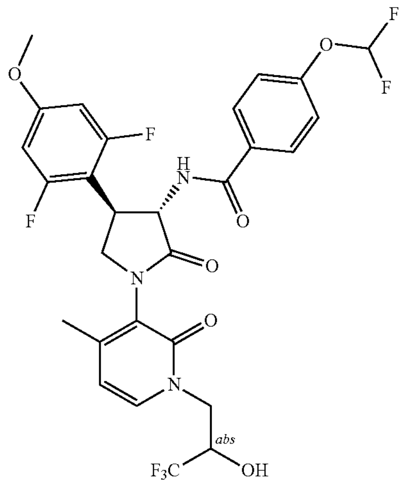 [SMILES: COc1cc(F)c([C@@H]2CN(c3c(C)ccn(CC(O)C(F)(F)F)c3=O)C(=O)[C@H]2NC(=O)c2ccc(OC(F)F)cc2)c(F)c1] | 632.2 | Method D, RT = 1.82 min, 98% | $^1$H NMR (400 MHz, DMSO-$d_6$) δ = 9.14-8.85 (m, 1H), 7.97-7.81 (m, 2H), 7.67-7.54 (m, 1H), 7.34 (t, J = 74.0 Hz, 1H), 7.28-7.24 (m, 2H), 6.83-6.61 (m, 3H), 6.33-6.18 (m, 1H), 5.38-4.81 (m, 1H), 4.44-4.07 (m, 4H), 3.86-3.71 (m, 4H), 3.52-3.50 (m, 1H), 2.23-2.05 (2s, 3H). (Mixture of interconvertible atropisomers) |
| 635 | 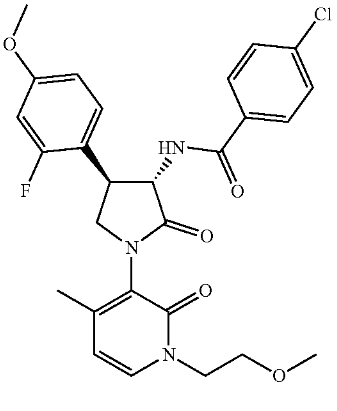 [SMILES: COCCn1ccc(C)c(N2C[C@@H](c3ccc(OC)cc3F)[C@H](NC(=O)c3ccc(Cl)cc3)C2=O)c1=O] | 528.2 | Method F, RT = 1.991 min, 99.1% | $^1$H NMR (400 MHz, DMSO-$d_6$) δ = 9.08-9.03 (m, 1H), 7.91-7.83 (m, 2H), 7.61-7.50 (m, 3H), 7.44 (t, J = 9.0 Hz, 1H), 6.87-6.77 (m, 2H), 6.21 (d, J = 7.0 Hz, 1H), 5.40-5.31 (m, 1H), 4.82 (dd, J = 11.0, 8.5 Hz, 1H), 4.20-3.91 (m, 4H), 3.77-3.72 (2s, 3H), 3.63-3.55 (m, 2H), 3.25 (s, 3H), 2.22-2.07 (2s, 3H). (Mixture of interconvertible atropisomers) |
| 636 | 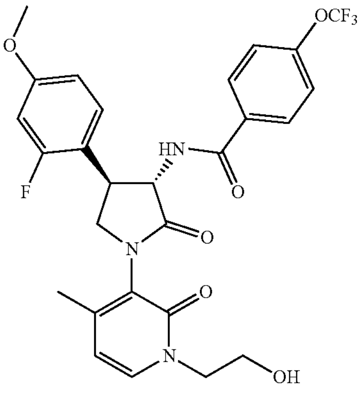 [SMILES: COc1ccc([C@@H]2CN(c3c(C)ccn(CCO)c3=O)C(=O)[C@H]2NC(=O)c2ccc(OC(F)(F)F)cc2)c(F)c1] | 564.2 | Method F, RT = 2.338 min, 99.7% | $^1$H NMR (400 MHz, DMSO-$d_6$) δ = 9.12-9.07 (m, 1H), 8.01-7.95 (m, 2H), 7.60-7.38 (m, 4H), 6.87-6.75 (m, 2H), 6.20 (d, J = 7.0 Hz, 1H), 5.38 (dd, J = 11.5, 9.5 Hz, 1H), 4.94 (br t, J = 4.5 Hz, 1H), 4.83-4.80 (m, 1H), 4.19-3.87 (m, 4H), 3.80-3.70 (2s, 3H), 3.68-3.54 (m, 2H), 2.22-2.07 (2s, 3H). (Mixture of interconvertible atrop isomers) |

TABLE 2-continued

| Ex | Structure | LCMS (M + H)+ | HPLC Method, RT (min.) & Purity | $^{1}$H NMR |
|---|---|---|---|---|
| 637 | 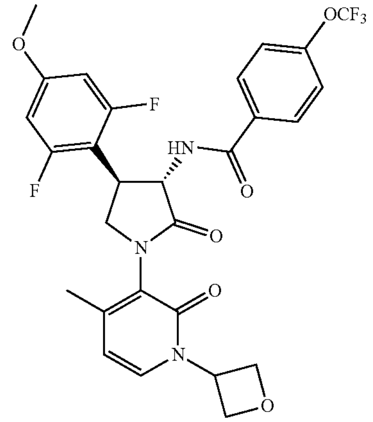 [SMILES: COc1cc(F)c([C@@H]2CN(c3c(C)ccn(C4COC4)c3=O)C(=O)[C@H]2NC(=O)c2ccc(OC(F)(F)F)cc2)c(F)c1] | 594.2 | Method F, RT = 2.526 min, 99.5% | $^{1}$H NMR (400 MHz, DMSO-d$_6$) δ = 9.23-9.05 (m, 1H), 8.00-7.91 (m, 2H), 7.76 (d, J = 7.1 Hz, 1H), 7.53-7.45 (m, 2H), 6.83-6.73 (m, 2H), 6.39-6.32 (m, 1H), 5.51 (t, J = 7.3 Hz, 1H), 4.93-4.83 (m, 3H), 4.82-4.70 (m, 2H), 4.32-4.20 (m, 1H), 4.20-4.01 (m, 2H), 3.79-3.74 (2s, 3H), 2.25-2.07 (2s, 3H). (Mixture of interconvertible atropisomers) |
| 638 | 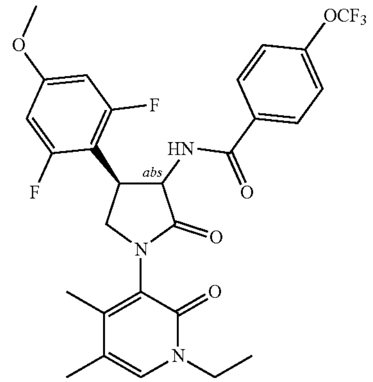 [SMILES: CCn1cc(C)c(C)c(N2C[C@@H](c3c(F)cc(OC)cc3F)C(NC(=O)c3ccc(OC(F)(F)F)cc3)C2=O)c1=O] | 580.2 | Method-D, RT = 1.890 min, 100% | $^{1}$H NMR (400 MHz, DMSO-d$_6$) δ = 9.23-9.03 (m, 1H), 7.97-7.90 (m, 2H), 7.58-7.42 (m, 3H), 6.80-6.72 (m, 2H), 5.38-4.84 (m, 1H), 4.29-4.02 (m, 2H), 3.99-3.80 (m, 2H), 3.76-3.71 (2s, 3H), 3.51-3.40 (m, 1H), 2.12 (s, 3H), 2.02-1.96 (2s, 3H), 1.24-1.16 (m, 3H). (Mixture of interconvertible atropisomers) |
| 639 | 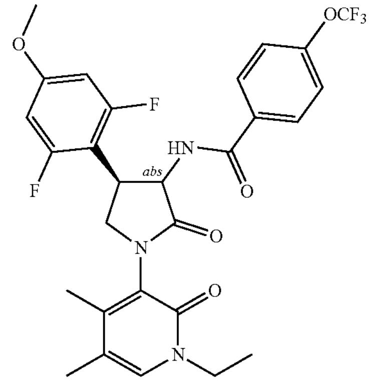 [SMILES: CCn1cc(C)c(C)c(N2C[C@@H](c3c(F)cc(OC)cc3F)C(NC(=O)c3ccc(OC(F)(F)F)cc3)C2=O)c1=O] | 580.1 | Method-D, RT = 1.891 min, 98.5% | $^{1}$H NMR (400 MHz, DMSO-d$_6$) δ = 9.25-9.04 (m, 1H), 7.99-7.90 (m, 2H), 7.60-7.43 (m, 3H), 6.81-6.73 (m, 2H), 5.40-4.83 (m, 1H), 4.30-4.05 (m, 2H), 4.00-3.82 (m, 2H), 3.77-3.74 (2s, 3H), 3.53-3.42 (m, 1H), 2.13 (s, 3H), 2.03-1.97 (2s, 3H), 1.25-1.17 (m, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 640 | 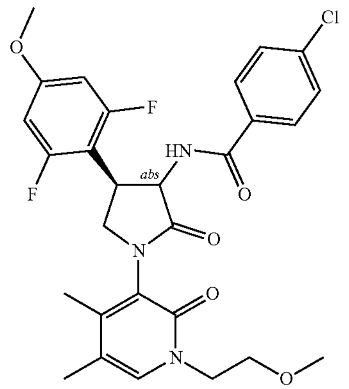 [SMILES: COCCn1cc(C)c(C)c(N2C[C@@H](c3c(F)cc(OC)cc3F)C(NC(=O)c3ccc(Cl)cc3)C2=O)c1=O] | 560.1 | Method-D, RT = 1.737 min, 100% | $^1$H NMR (400 MHz, DMSO-$d_6$) δ = 9.20-8.98 (m, 1H), 7.88-7.80 (m, 2H), 7.60 7.43 (m, 3H), 6.81-6.73 (m, 2H), 5.39-4.88 (m, 1H), 4.30-3.96 (m, 4H), 3.77-3.75 (2s, 3H), 3.60-3.54 (m, 2H), 3.52-3.43 (m, 1H), 3.24 (2s, 3H), 2.15 (s, 3H), 2.03-1.98 (2s, 3H). (Mixture of interconvertible atropisomers) |
| 641 | 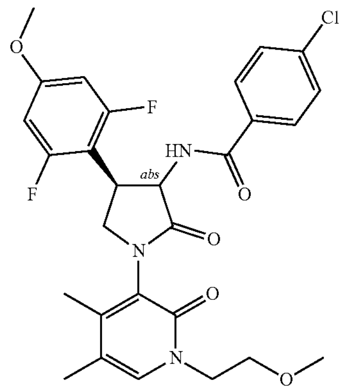 [SMILES: COCCn1cc(C)c(C)c(N2C[C@@H](c3c(F)cc(OC)cc3F)C(NC(=O)c3ccc(Cl)cc3)C2=O)c1=O] | 560.1 | Method-D, RT = 1.739 min, 98.5% | $^1$H NMR (400 MHz, DMSO-$d_6$) δ = 9.19-8.99 (m, 1H), 7.87-7.80 (m, 2H), 7.58-7.42 (m, 3H), 6.81-6.73 (m, 2H), 5.37-4.86 (m, 1H), 4.28-3.94 (m, 4H), 3.76-3.74 (2s, 3H), 3.60-3.54 (m, 2H), 3.51-3.40 (m, 1H), 3.23 (2s, 3H), 2.13 (s, 3H), 2.02-1.97 (2s, 3H). (Mixture of interconvertible atropisomers) |
| 642 | 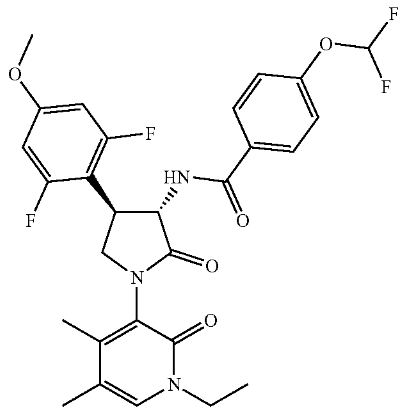 [SMILES: CCn1cc(C)c(C)c(N2C[C@@H](c3c(F)cc(OC)cc3F)[C@H](NC(=O)c3ccc(OC(F)F)cc3)C2=O)c1=O] | 562.1 | Method-D, RT = 1.725 min, 100% | $^1$H NMR (400 MHz, DMSO-$d_6$) δ = 9.14-8.96 (m, 1H), 7.94-7.86 (m, 2H), 7.60-7.50 (m, 1H), 7.51-7.13 (m, 3H), 6.81-6.72 (m, 2H), 5.40-4.86 (m, 1H), 4.31-4.05 (m, 2H), 4.01-3.82 (m, 2H), 3.78-3.73 (2s, 3H), 3.53-3.40 (m, 1H), 2.14-2.04 (2s, 3H), 2.04-1.98 (2s, 3H), 1.26-1.17 (m, 3H). (Mixture of interconvertible atrop isomers) |

TABLE 2-continued

| Ex | Structure | LCMS (M + H)+ | HPLC Method, RT (min.) & Purity | $^1$H NMR |
|---|---|---|---|---|
| 643 | 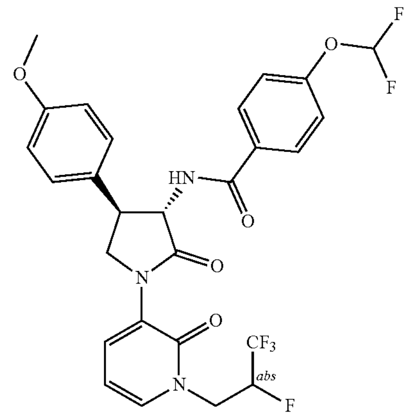 [SMILES: COc1ccc([C@@H]2CN(c3cccn(CC(F)C(F)(F)F)c3=O)C(=O)[C@H]2NC(=O)c2ccc(OC(F)F)cc2)cc1] | 582.1 | Method D, RT = 1.603 min, 100%. | $^1$H NMR (400 MHz, DMSO-d$_6$) δ = 8.92 (d, J = 9.0 Hz, 1H), 7.97-7.87 (m, 2H), 7.69 (dd, J = 6.8, 2.0 Hz, 1H), 7.64 (dd, J = 7.3, 2.0 Hz, 1H), 7.35 (t, J = 74.6 Hz, 1H), 7.35-7.33 (m, 2H), 7.26 (d, J = 8.8 Hz, 2H), 6.94-6.84 (m, 2H), 6.37 (t, J = 7.1 Hz, 1H), 5.01 (dd, J = 11.2, 8.8 Hz, 1H), 4.46-4.42 (m, 1H), 4.33-4.29 (m, 1H), 4.16 (t, J = 8.4 Hz, 1H), 3.88-3.73 (m, 3H), 3.72 (s, 3H), 3.69-3.64 (m, 1H). |
| 644 | 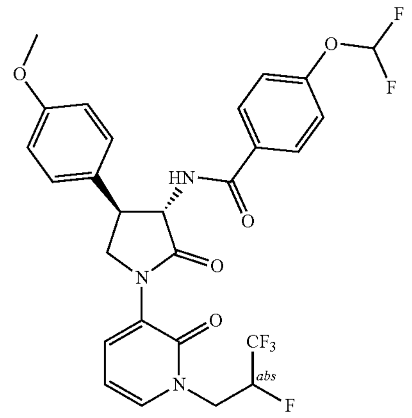 [SMILES: COc1ccc([C@@H]2CN(c3cccn(CC(F)C(F)(F)F)c3=O)C(=O)[C@H]2NC(=O)c2ccc(OC(F)F)cc2)cc1] | 582.1 | Method D, RT = 1.59 min, 100%. | $^1$H NMR (400 MHz, DMSO-d$_6$) δ = 8.94 (d, J = 8.8 Hz, 1H), 7.92 (d, J = 8.6 Hz, 2H), 7.68 (dd, J = 6.6, 1.7 Hz, 1H), 7.64 (dd, J = 7.6, 1.7 Hz, 1H), 7.35 (t, J = 74.6 Hz, 1H), 7.35-7.33 (m, 2H), 7.26 (d, J = 8.8 Hz, 2H), 6.90 (d, J = 8.6 Hz, 2H), 6.37 (t, J = 7.0 Hz, 1H), 5.04-4.95 (m, 1H), 4.44 (dd, J = 12.8, 2.6 Hz, 1H), 4.38-4.29 (m, 1H), 4.12-4.04 (m, 1H), 3.91-3.72 (m, 4H), 3.72 (s, 3H). |
| 645 | 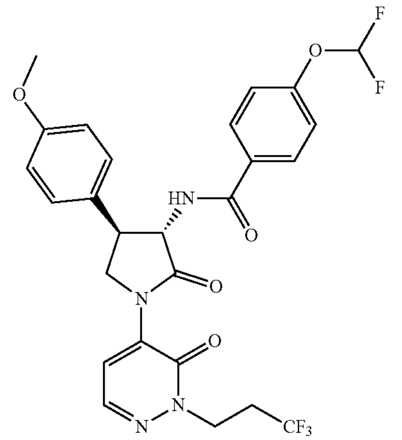 [SMILES: COc1ccc([C@@H]2CN(c3ccnn(CCC(F)(F)F)c3=O)C(=O)[C@H]2NC(=O)c2ccc(OC(F)F)cc2)cc1] | 567.1 | Method D, RT = 1.81 min, 95% | $^1$H NMR (400 MHz, DMSO-d$_6$) δ = 8.65-8.53 (m, 1H), 8.07 (d, J = 4.8 Hz, 1H), 7.77 (d, J = 4.8 Hz, 1H), 7.74-7.62 (m, 4H), 7.32 (t, J = 76.0 Hz, 1H), 7.19 (dd, J = 8.5, 2.5 Hz, 2H), 6.82 (d, J = 8.3 Hz, 2H), 5.08-4.99 (m, 1H), 4.48-4.32 (m, 4H), 4.00-3.88 (m, 1H), 3.70 (s, 3H), 2.89-2.74 (m, 2H). |

TABLE 2-continued

| Ex | Structure | LCMS (M + H)+ | HPLC Method, RT (min.) & Purity | $^1$H NMR |
|---|---|---|---|---|
| 646 | 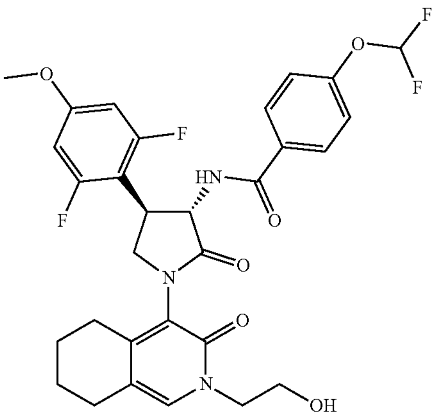 [SMILES: COc1cc(F)c([C@@H]2CN(c3c4c(cn(CCO)c3=O)CCCC4)C(=O)[C@H]2NC(=O)c2ccc(OC(F)F)cc2)c(F)c1] | 604.2 | Method D, RT = 1.649 min, 100% | $^1$H NMR (400 MHz, DMSO-$d_6$) δ = 9.13-8.87 (m, 1H), 8.01-7.81 (m, 2H), 7.47-7.43 (m, 1H), 7.34 (t, J = 74.3 Hz, 1H), 7.28-7.24 (m, 2H), 6.83-6.69 (m, 2H), 5.38-4.87 (m, 2H), 4.26-3.87 (m, 5H), 3.78-3.74 (2s, 3H), 3.67-3.59 (m, 2H), 3.53-3.43 (m, 1H), 2.71-2.65 (m, 1H), 2.55-2.50 (m, 1H), 1.83-1.49 (m, 5H). |
| 647 | 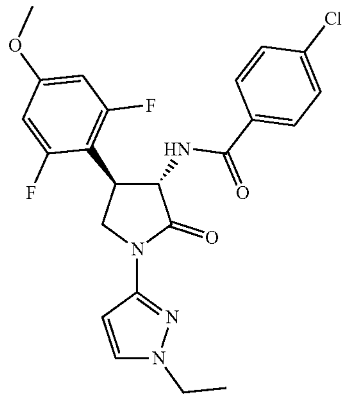 [SMILES: CCn1ccc(N2C[C@@H](c3c(F)cc(OC)cc3F)[C@H](NC(=O)c3ccc(Cl)cc3)C2=O)n1] | 475.1 | Method C, RT = 1.824 min, 100% | $^1$H NMR (400 MHz, DMSO-$d_6$) δ = 9.10 (d, J = 8.3 Hz, 1H), 7.80 (d, J = 9.0 Hz, 2H), 7.72 (d, J = 2.4 Hz, 1H), 7.60-7.48 (m, 2H), 6.78 (d, J = 10.8 Hz, 2H), 6.64 (d, J = 2.2 Hz, 1H), 4.97 (dd, J = 10.1, 8.7 Hz, 1H), 4.25-4.16 (m, 1H), 4.15-4.03 (m, 3H), 3.92-3.81 (m, 1H), 3.77 (s, 3H), 1.35 (t, J = 7.2 Hz, 3H). |
| 648 | 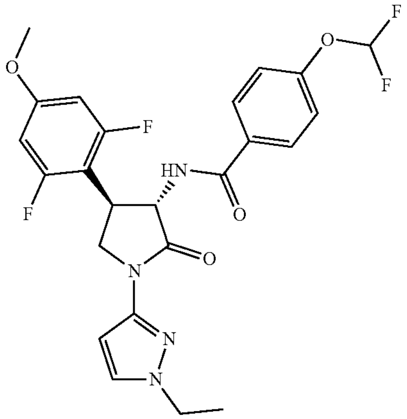 [SMILES: CCn1ccc(N2C[C@@H](c3c(F)cc(OC)cc3F)[C@H](NC(=O)c3ccc(OC(F)F)cc3)C2=O)n1] | 507.1 | Method C, RT = 1.780 min, 100% | $^1$H NMR (400 MHz, DMSO-$d_6$) δ = 9.04 (d, J = 8.6 Hz, 1H), 7.90 (d, J = 9.0 Hz, 2H), 7.72 (d, J = 2.4 Hz, 1H), 7.34 (t, J = 72.6 Hz, 1H), 7.28 (d, J = 9.0 Hz, 2H), 6.78 (d, J = 10.8 Hz, 2H), 6.65 (d, J = 2.4 Hz, 1H), 4.97 (dd, J = 10.3, 8.6 Hz, 1H), 4.27-4.16 (m, 1H), 4.16-4.01 (m, 3H), 3.90-3.81 (m, 1H), 3.77 (s, 3H), 1.35 (t, J = 7.2 Hz, 3H). |

TABLE 2-continued

| Ex | Structure | LCMS (M + H)+ | HPLC Method, RT (min.) & Purity | $^1$H NMR |
|---|---|---|---|---|
| 649 | 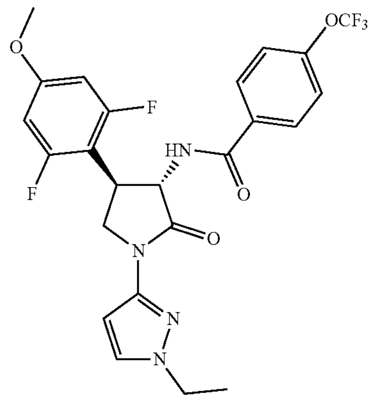 [SMILES: CCn1ccc(N2C[C@@H](c3c(F)cc(OC)cc3F)[C@H](NC(=O)c3ccc(OC(F)(F)F)cc3)C2=O)n1] | 525.1 | Method C, RT = 1.961 min, 100% | $^1$H NMR (400 MHz, DMSO-$d_6$) δ = 9.14 (d, J = 8.3 Hz, 1H), 7.91 (d, J = 8.8 Hz, 2H), 7.73 (d, J = 2.4 Hz, 1H), 7.49 (d, J = 8.8 Hz, 2H), 6.78 (d, J = 10.8 Hz, 2H), 6.65 (d, J = 2.4 Hz, 1H), 4.98 (dd, J = 10.3, 8.3 Hz, 1H), 4.28-4.16 (m, 1H), 4.16-3.98 (m, 3H), 3.86 (t, J = 9.7 Hz, 1H), 3.77 (s, 3H), 1.35 (t, J = 7.2 Hz, 3H). |
| 650 | 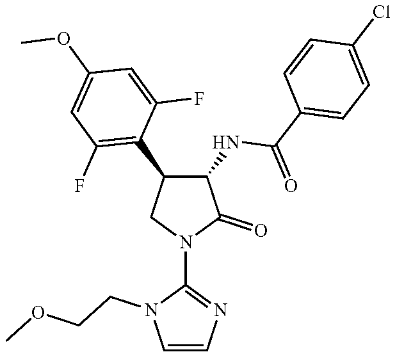 [SMILES: COCCn1ccnc1N1C[C@@H](c2c(F)cc(OC)cc2F)[C@H](NC(=O)c2ccc(Cl)cc2)C1=O] | 505.1 | Method D, RT = 1.658 min, 97.5% | $^1$H NMR (400 MHz, DMSO-$d_6$) δ = 9.14 (d, J = 8.3 Hz, 1H), 7.89-7.75 (m, 2H), 7.64-7.47 (m, 2H), 7.19 (d, J = 1.2 Hz, 1H), 6.88 (d, J = 1.2 Hz, 1H), 6.80 (d, J = 10.8 Hz, 2H), 4.87 (dd, J = 10.8, 8.1 Hz, 1H), 4.32-4.21 (m, 1H), 4.17-4.00 (m, 2H), 3.95 (br d, J = 10.0 Hz, 2H), 3.77 (s, 3H), 3.67-3.58 (m, 2H), 3.27 (s, 3H). |
| 651 | 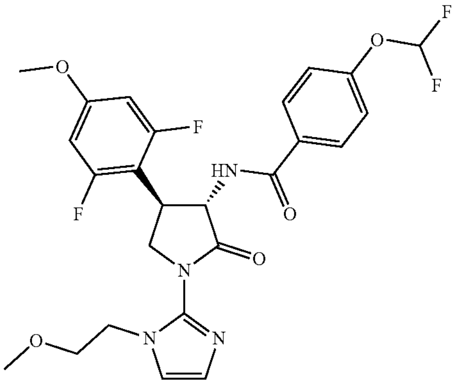 [SMILES: COCCn1ccnc1N1C[C@@H](c2c(F)cc(OC)cc2F)[C@H](NC(=O)c2ccc(OC(F)F)cc2)C1=O] | 537.2 | Method D, RT = 1.622 min, 95.9% | $^1$H NMR (400 MHz, DMSO-$d_6$) δ = 9.08 (d, J = 8.1 Hz, 1H), 7.94-7.81 (m, 2H), 7.34 (t, J = 73.4 Hz, 1H), 7.28 (d, J = 8.8 Hz, 2H), 7.19 (d, J = 1.5 Hz, 1H), 6.88 (d, J = 1.5 Hz, 1H), 6.80 (d, J = 10.8 Hz, 2H), 4.86 (dd, J = 10.8, 8.1 Hz, 1H), 4.32-4.20 (m, 1H), 4.17-4.00 (m, 2H), 3.98-3.89 (m, 2H), 3.77 (s, 3H), 3.67-3.56 (m, 2H), 3.27 (s, 3H). |
| 652 | 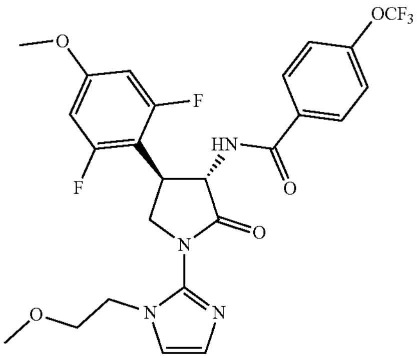 [SMILES: COCCn1ccnc1N1C[C@@H](c2c(F)cc(OC)cc2F)[C@H](NC(=O)c2ccc(OC(F)(F)F)cc2)C1=O] | 555.1 | Method D, RT = 1.809 min, 100% | $^1$H NMR (400 MHz, DMSO-$d_6$) δ = 9.18 (d, J = 8.1 Hz, 1H), 7.99-7.77 (m, 2H), 7.55-7.39 (m, 2H), 7.19 (d, J = 1.2 Hz, 1H), 6.88 (d, J = 1.2 Hz, 1H), 6.80 (d, J = 10.8 Hz, 2H), 4.88 (dd, J = 10.8, 8.1 Hz, 1H), 4.33-4.21 (m, 1H), 4.18-3.90 (m, 4H), 3.77 (s, 3H), 3.69-3.54 (m, 2H), 3.27 (s, 3H). |

TABLE 2-continued

| Ex | Structure | LCMS (M + H)+ | HPLC Method, RT (min.) & Purity | $^1$H NMR |
|---|---|---|---|---|
| 653 | 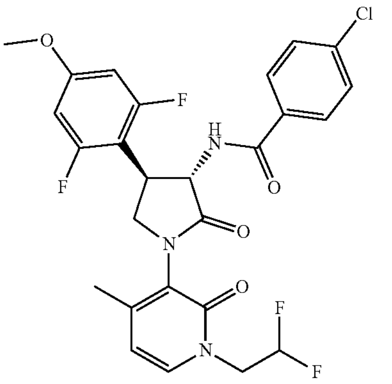 [SMILES: COc1cc(F)c([C@@H]2CN(c3c(C)ccn(CC(F)F)c3=O)C(=O)[C@H]2NC(=O)c2ccc(Cl)cc2)c(F)c1] | 552.2 | Method D, RT = 1.77 min, 100% | $^1$H NMR (400 MHz, DMSO-$d_6$) δ = 9.15-9.02 (m, 1H), 7.89-7.79 (m, 2H), 7.68-7.51 (m, 3H), 6.83-6.70 (m, 2H), 6.32-6.31 (m, 1H), 6.29 (tt, J = 54.8, 5.1 Hz, 1H), 5.32-4.85 (m, 1H), 4.40-4.05 (m, 4H), 3.78-3.74 (2s, 3H), 3.51-3.50 (m, 1H), 2.49-2.07 (2s, 3H). (Mixture of interconvertible atropisomers) |
| 654 | 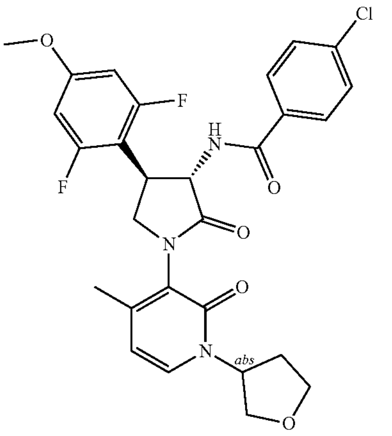 [SMILES: COc1cc(F)c([C@@H]2CN(c3c(C)ccn(C4CCOC4)c3=O)C(=O)[C@H]2NC(=O)c2ccc(Cl)cc2)c(F)c1] | 558.2 | Method D, RT = 1.69 min, 100% | $^1$H NMR (400 MHz, DMSO-$d_6$) δ = 9.04-8.98 (m, 1H), 7.87-7.82 (m, 2H), 7.59-7.52 (m, 3H), 6.81-6.57 (m, 2H), 6.32-6.27 (m, 1H), 5.41-5.32 (m, 1H), 4.90 (dd, J = 10.5, 8.5 Hz, 1H), 4.21-4.02 (m, 3H), 3.90-3.72 (m, 6H), 3.53-3.48 (m, 1H), 2.54-2.52 (m, 1H), 2.24-2.20 (2s, 3H), 2.01-1.94 (m, 1H). (Mixture of interconvertible atropisomers) |
| 655 | 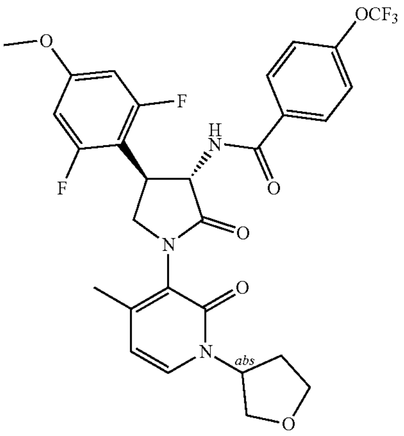 [SMILES: COc1cc(F)c([C@@H]2CN(c3c(C)ccn(C4CCOC4)c3=O)C(=O)[C@H]2NC(=O)c2ccc(OC(F)(F)F)cc2)c(F)c1] | 608.2 | Method D, RT = 1.846 min, 100% | $^1$H NMR (400 MHz, DMSO-$d_6$) δ = 9.25-9.05 (m, 1H), 8.02-7.91 (m, 2H), 7.60-7.45 (m, 3H), 6.84-6.73 (m, 2H), 6.35-6.26 (m, 1H), 5.43-4.86 (m, 2H), 4.32-4.01 (m, 3H), 3.91-3.71 (m, 6H), 3.53-3.48 (m, 1H), 2.46-2.38 (m, 1H), 2.23-2.04 (2s, 3H), 2.01-1.90 (m, 1H). (Mixture of interconvertible atrop isomers) |

TABLE 2-continued

| Ex | Structure | LCMS (M + H)+ | HPLC Method, RT (min.) & Purity | $^1$H NMR |
|---|---|---|---|---|
| 656 | 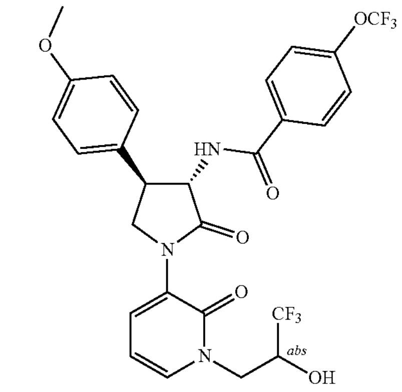 [SMILES: COc1ccc([C@@H]2CN(c3cccn(CC(O)C(F)(F)F)c3=O)C(=O)[C@H]2NC(=O)c2ccc(OC(F)(F)F)cc2)cc1] | 600.2 | Method D, RT = 1.813 min, 98.2% | $^1$H NMR (400 MHz, DMSO-$d_6$) δ = 9.05 (d, J = 9.0 Hz, 1H), 7.99 (d, J = 9.0 Hz, 2H), 7.69-7.65 (m, 2H), 7.49 (d, J = 8.5 Hz, 2H), 7.36 (d, J = 8.5 Hz, 2H), 6.91 (d, J = 9.0 Hz, 2H), 6.38 (t, J = 7.0 Hz, 1H), 5.06-4.98 (m, 1H), 4.45 (dd, J = 12.8, 2.8 Hz, 1H), 4.40-4.28 (m, 1H), 4.16-4.03 (m, 1H), 3.91-3.70 (m, 4H), 3.73 (s, 3H). |
| 657 | 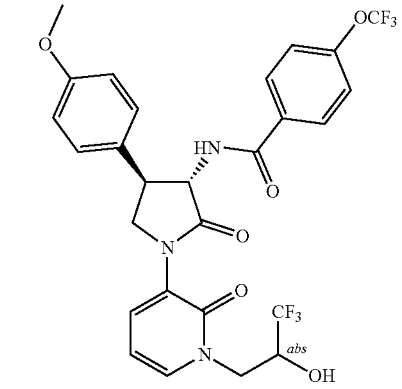 [SMILES: COc1ccc([C@@H]2CN(c3cccn(CC(O)C(F)(F)F)c3=O)C(=O)[C@H]2NC(=O)c2ccc(OC(F)(F)F)cc2)cc1] | 600.2 | Method D, RT = 1.828 min, 98.4% | $^1$H NMR (400 MHz, DMSO-$d_6$) δ = 9.03 (d, J = 8.5 Hz, 1H), 7.99 (d, J = 8.5 Hz, 2H), 7.69-7.65 (m, 2H), 7.49 (d, J = 8.5 Hz, 2H), 7.36 (d, J = 9.0 Hz, 2H), 6.91 (d, J = 9.0 Hz, 2H), 6.38 (t, J = 7.0 Hz, 1H), 5.02 (dd, J = 11.3, 8.8 Hz, 1H), 4.46 (dd, J = 13.1, 2.5 Hz, 1H), 4.39-4.28 (m, 1H), 4.17 (t, J = 8.3 Hz, 1H), 3.91-3.70 (m, 4H), 3.73 (s, 3H). |
| 658 | 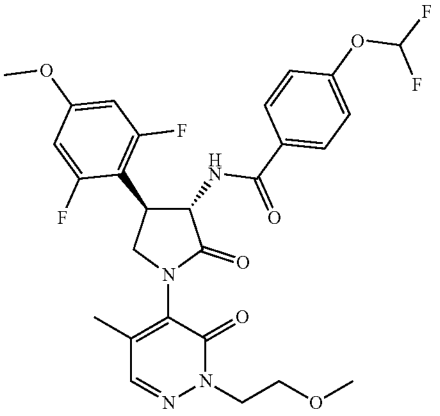 [SMILES: COCCn1ncc(C)c(N2C[C@@H](c3c(F)cc(OC)cc3F)[C@H](NC(=O)c3ccc(OC(F)F)cc3)C2=O)c1=O] | 579.2 | Method D, RT = 1.89 min, 100% | $^1$H NMR (400 MHz, DMSO-$d_6$) δ = 9.16-8.93 (m, 1H), 8.05-7.93 (m, 1H), 7.93-7.77 (m, 2H), 7.34 (t, J = 74.0 Hz, 1H), 7.27 (d, J = 8.8 Hz, 2H), 6.88-6.66 (m, 2H), 5.36-4.74 (m, 1H), 4.45-4.12 (m, 4H), 3.82-3.72 (2s, 3H), 3.72-3.51 (2s, 3H), 3.23-3.18 (2s, 3H), 2.26-2.02 (2s, 3H). (Mixture of interconvertible atrop isomers) |

TABLE 2-continued

| Ex | Structure | LCMS (M + H)+ | HPLC Method, RT (min.) & Purity | $^1$H NMR |
|---|---|---|---|---|
| 659 | 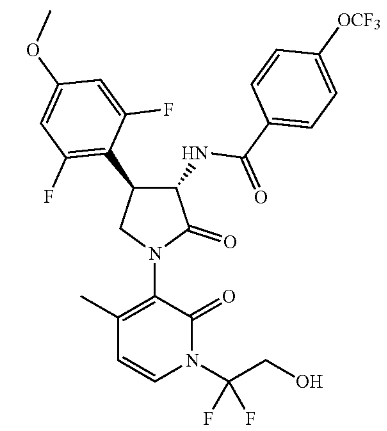 [SMILES: COc1cc(F)c([C@@H]2CN(c3c(C)ccn(C(F)(F)CO)c3=O)C(=O)[C@H]2NC(=O)c2ccc(OC(F)(F)F)cc2)c(F)c1] | 618.2 | Method D, RT = 2.709 min, 99%. | $^1$H NMR (400 MHz, DMSO-$d_6$) δ = 9.23-9.04 (m, 1H), 8.00-7.91 (m, 2H), 7.72-7.61 (m, 1H), 7.53-7.44 (m, 2H), 6.83-6.73 (m, 2H), 6.39-6.32 (m, 1H), 5.98-5.91 (m, 1H), 5.37-4.82 (m, 1H), 4.34-4.00 (m, 4H), 3.80-3.75 (2s, 3H), 3.63-3.52 (m, 1H), 2.28-2.07 (2s, 3H). (Mixture of interconvertible atropisomers) |
| 660 | 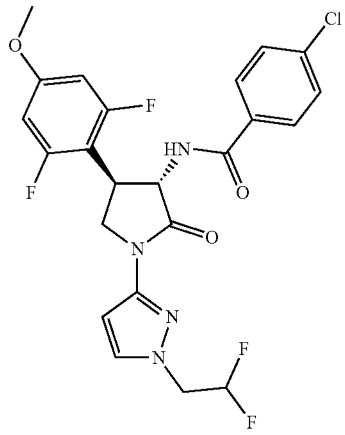 [SMILES: COc1cc(F)c([C@@H]2CN(c3ccn(CC(F)F)n3)C(=O)[C@H]2NC(=O)c2ccc(Cl)cc2)c(F)c1] | 511.1 | Method C, RT = 1.895 min, 100% | $^1$H NMR (400 MHz, DMSO-$d_6$) δ = 9.13 (d, J = 8.3 Hz, 1H), 7.83 (d, J = 8.8 Hz, 2H), 7.80 (d, J = 2.4 Hz, 1H), 7.56 (d, J = 8.8 Hz, 2H), 6.79 (d, J = 10.8 Hz, 2H), 6.75 (d, J = 2.4 Hz, 1H), 6.34 (tt, J = 55.0, 8.6 Hz, 1H), 4.96 (dd, J = 10.1, 8.4 Hz, 1H), 4.62-4.56 (m, 2H), 4.26-4.03 (m, 2H), 3.86 (t, J = 9.3 Hz, 1H), 3.77 (s, 3H). |
| 661 | 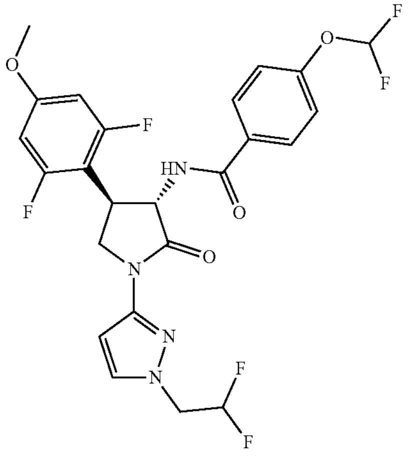 [SMILES: COc1cc(F)c([C@@H]2CN(c3ccn(CC(F)F)n3)C(=O)[C@H]2NC(=O)c2ccc(OC(F)F)cc2)c(F)c1] | 543.1 | Method C, RT = 1.852 min, 100% | $^1$H NMR (400 MHz, DMSO-$d_6$) δ = 9.06 (d, J = 8.3 Hz, 1H), 7.88 (d, J = 8.8 Hz, 2H), 7.80 (d, J = 2.4 Hz, 1H), 7.35 (t, J = 74.6 Hz, 1H), 7.26 (d, J = 8.8 Hz, 2H), 6.79 (d, J = 10.8 Hz, 2H), 6.75 (d, J = 2.2 Hz, 1H), 6.34 (tt, J = 55.0, 8.6 Hz, 1H), 4.95 (dd, J = 10.0, 8.6 Hz, 1H), 4.62-4.56 (m, 2H), 4.27-4.07 (m, 2H), 3.86 (t, J = 9.3 Hz, 1H), 3.77 (s, 3H). |

TABLE 2-continued

| Ex | Structure | LCMS (M + H)+ | HPLC Method, RT (min.) & Purity | $^1H$ NMR |
|---|---|---|---|---|
| 662 | 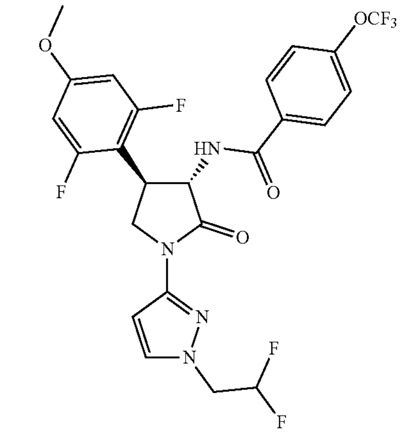 [SMILES: COc1cc(F)c([C@@H]2CN(c3ccn(CC(F)F)n3)C(=O)[C@H]2NC(=O)c2ccc(OC(F)(F)F)cc2)c(F)c1] | 561.1 | Method C, RT = 2.041 min, 97.1% | $^1H$ NMR (400 MHz, DMSO-$d_6$) δ = 9.16 (d, J = 8.3 Hz, 1H), 7.93 (d, J = 8.8 Hz, 2H), 7.80 (d, J = 2.4 Hz, 1H), 7.50 (d, J = 8.8 Hz, 2H), 6.79 (d, J = 10.8 Hz, 2H), 6.75 (d, J = 2.4 Hz, 1H), 6.34 (tt, J = 58.2, 11.0 Hz, 1H), 4.97 (dd, J = 10.0, 8.6 Hz, 1H), 4.62-4.56 (m, 2H), 4.28-4.06 (m, 2H), 3.86 (t, J = 9.5 Hz, 1H), 3.77 (s, 3H). |
| 663 | 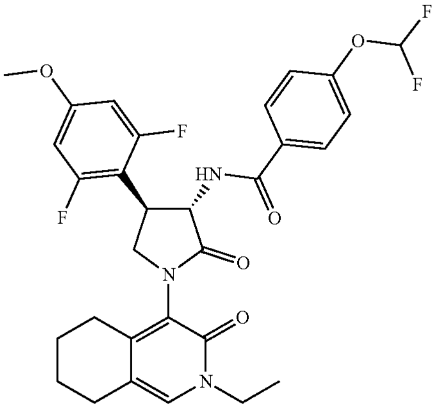 [SMILES: CCn1cc2c(c(N3C[C@@H](c4c(F)cc(OC)cc4F)[C@H](NC(=O)c4ccc(OC(F)F)cc4)C3=O)c1=O)CCCC2] | 588.1 | Method D, RT = 1.849 min, 100% | $^1H$ NMR (400 MHz, DMSO-$d_6$) δ = 9.15-8.91 (m, 1H), 7.94-7.85 (m, 2H), 7.61-7.54 (m, 1H), 7.34 (t, J = 73.4 Hz, 1H), 7.30-7.22 (m, 2H), 6.78-6.74 (m, 2H), 5.40-4.92 (m, 1H), 4.25-3.84 (m, 4H), 3.78-3.74 (m, 3H), 3.53-3.43 (m, 1H), 2.71-2.52 (m, 3H), 1.82-1.53 (m, 5H), 1.22 (2t, J = 6.8 Hz, 3H). (Mixture of interconvertible atropisomers) |
| 664 | 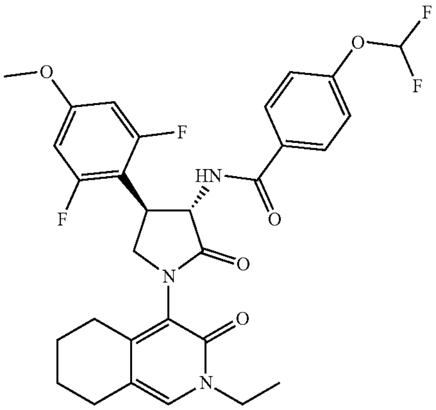 [SMILES: CCn1cc2c(c(N3C[C@@H](c4c(F)cc(OC)cc4F)[C@H](NC(=O)c4ccc(OC(F)F)cc4)C3=O)c1=O)CCCC2] | 588.1 | Method D, RT = 1.849 min, 100% | $^1H$ NMR (400 MHz, DMSO-$d_6$) δ = 9.15-8.91 (m, 1H), 7.94-7.85 (m, 2H), 7.61-7.54 (m, 1H), 7.34 (t, J = 73.4 Hz, 1H), 7.30-7.22 (m, 2H), 6.78-6.74 (m, 2H), 5.40-4.92 (m, 1H), 4.25-3.84 (m, 4H), 3.78-3.74 (m, 3H), 3.53-3.43 (m, 1H), 2.71-2.52 (m, 3H), 1.82-1.53 (m, 5H), 1.22 (2t, J = 6.8 Hz, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 665 | 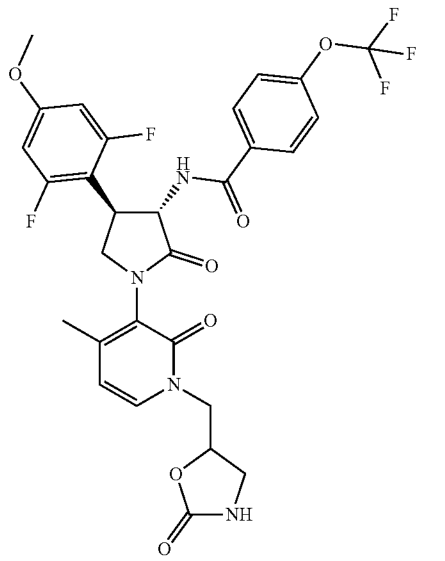 [SMILES: COc1cc(F)c([C@@H]2CN(c3c(C)ccn(CC4CNC(=O)O4)c3=O)C(=O)[C@H]2NC(=O)c2ccc(OC(F)(F)F)cc2)c(F)c1] | 619.1 | Method D, RT = 1.485 min, 95.7% | $^1$H NMR (400 MHz, DMSO-$d_6$) δ = 9.14-8.87 (m, 1H), 8.01-7.81 (m, 2H), 7.73-7.58 (m, 1H), 7.55-7.11 (m, 4H), 6.87-6.66 (m, 2H), 6.35-6.20 (m, 1H), 5.37-4.79 (m, 2H), 4.33-4.05 (m, 3H), 3.81-3.78 (2s, 3H), 3.63-3.51 (m, 2H), 3.26-3.22 (m, 2H), 2.23-2.06 (2s, 3H). (Mixture of interconvertible atropisomers) |
| 666 | 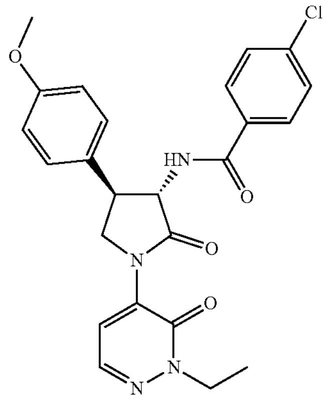 [SMILES: CCn1nccc(N2C[C@@H](c3ccc(OC)cc3)[C@H](NC(=O)c3ccc(Cl)cc3)C2=O)c1=O] | 467.1 | Method D, RT = 1.62 min, 97% | $^1$H NMR (400 MHz, DMSO-$d_6$) δ = 9.07-8.63 (m, 1H), 8.09-7.96 (m, 1H), 7.91-7.61 (m, 3H), 7.60-7.44 (m, 2H), 7.39-7.16 (m, 2H), 6.96-6.75 (m, 2H), 5.12-4.97 (m, 1H), 4.53-4.27 (m, 1H), 4.24-4.08 (m, 2H), 3.98-3.87 (m, 1H), 3.77 (s, 3H), 3.80-3.74 (m, 1H), 1.30 (t, J = 7.2 Hz, 3H). |
| 667 | 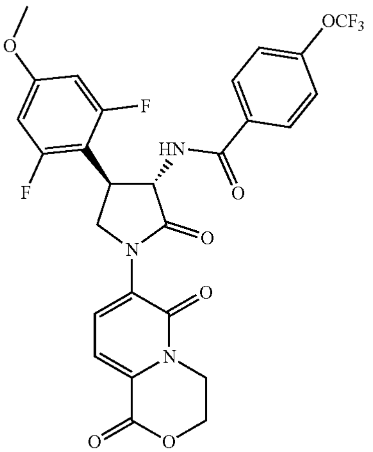 [SMILES: COc1cc(F)c([C@@H]2CN(c3ccc4n(c3=O)CCOC4=O)C(=O)[C@H]2NC(=O)c2ccc(OC(F)(F)F)cc2)c(F)c1] | 594 | Method D, RT = 1.751 min, 100% | $^1$H NMR (400 MHz, DMSO-$d_6$) δ = 9.12 (d, J = 8.3 Hz, 1H), 7.94 (d, J = 9.0 Hz, 2H), 7.83 (d, J = 7.8 Hz, 1H), 7.49 (d, J = 9.0 Hz, 2H), 7.25 (d, J = 7.8 Hz, 1H), 6.78 (d, J = 10.8 Hz, 2H), 5.11-5.00 (m, 1H), 4.68 (t, J = 5.3 Hz, 2H), 4.28-4.19 (m, 2H), 4.14-4.10 (m, 3H), 3.77 (s, 3H). |

TABLE 2-continued
| Ex | Structure | LCMS (M + H)+ | HPLC Method, RT (min.) & Purity | $^1$H NMR |
|---|---|---|---|---|
| 668 | 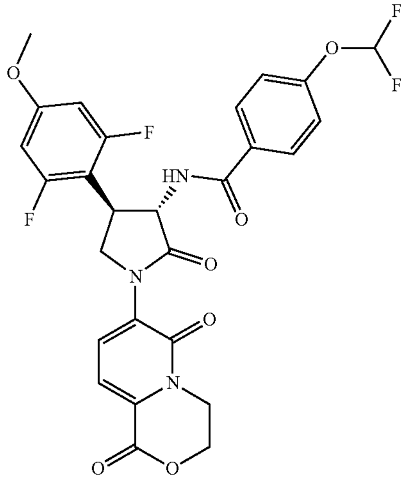 [SMILES: COc1cc(F)c([C@@H]2CN(c3ccc4n(c3=O)CCOC4=O)C(=O)[C@H]2NC(=O)c2ccc(OC(F)F)cc2)c(F)c1] | 576.1 | Method D, RT = 1.568 min, 97.9% | $^1$H NMR (400 MHz, DMSO-$d_6$) δ = 9.04 (d, J = 8.5 Hz, 1H), 7.99-7.85 (m, 2H), 7.83 (d, J = 7.6 Hz, 1H), 7.35 (t, J = 74.8 Hz, 1H), 7.27 (t, J = 7.9 Hz, 3H), 6.79 (d, J = 10.8 Hz, 2H), 5.12-4.98 (m, 1H), 4.68 (t, J = 5.2 Hz, 2H), 4.32-4.19 (m, 2H), 4.17-4.04 (m, 3H), 3.77 (s, 3H). |
| 669 | 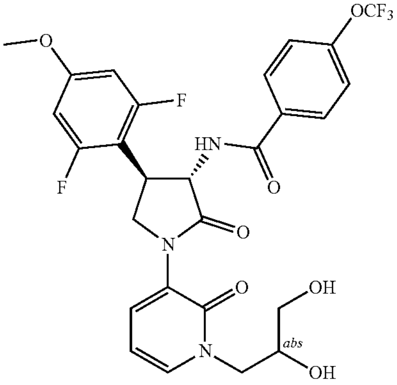 [SMILES: COc1cc(F)c([C@@H]2CN(c3cccn(CC(O)CO)c3=O)C(=O)[C@H]2NC(=O)c2ccc(OC(F)(F)F)cc2)c(F)c1] | 598.2 | Method D, RT = 1.57 min, 98% | $^1$H NMR (400 MHz, DMSO-$d_6$) δ = 9.11 (d, J = 8.5 Hz, 1H), 7.95 (d, J = 8.8 Hz, 2H), 7.62-7.58 (m, 2H), 7.49 (d, J = 8.8 Hz, 2H), 6.77 (d, J = 10.8 Hz, 2H), 6.32 (t, J = 6.9 Hz, 1H), 5.13 (dd, J =10.8, 8.5 Hz, 1H), 4.30 (dd, J =12.9, 3.4 Hz, 1H), 4.16-3.91 (m, 4H), 3.77 (s, 3H), 3.63-3.59 (m, 2H), 3.41-3.33 (m, 3H). |
| 670 | 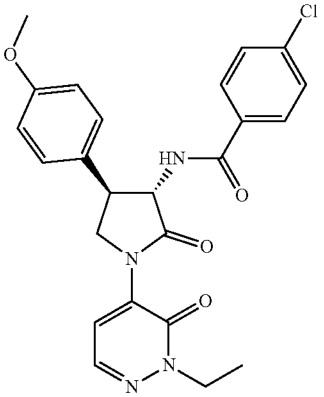 [SMILES: CCn1nccc(N2C[C@@H](c3ccc(OC)cc3)[C@H](NC(=O)c3ccc(Cl)cc3)C2=O)c1=O] | 467.1 | Method D, RT = 1.62 min, 97% | $^1$H NMR (400 MHz, DMSO-$d_6$) δ = 9.07-8.63 (m, 1H), 8.09-7.96 (m, 1H), 7.91-7.61 (m, 3H), 7.60-7.44 (m, 2H), 7.39-7.16 (m, 2H), 6.96-6.75 (m, 2H), 5.12-4.97 (m, 1H), 4.53-4.27 (m, 2H), 4.24-4.08 (m, 2H), 3.96-3.89 (m, 1H), 3.77 (s, 3H), 1.36-1.20 (t, J = 7.2 Hz, 3H). |

TABLE 2-continued

| Ex | Structure | LCMS (M + H)+ | HPLC Method, RT (min.) & Purity | $^1$H NMR |
|---|---|---|---|---|
| 671 | 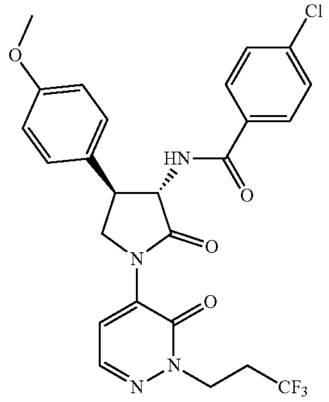 [SMILES: COc1ccc([C@@H]2CN(c3ccnn(CCC(F)(F)F)c3=O)C(=O)[C@H]2NC(=O)c2ccc(Cl)cc2)cc1] | 535.1 | Method D, RT = 1.84 min, 92% | $^1$H NMR (400 MHz, DMSO-$d_6$) δ = 9.07-8.61 (m, 1H), 8.04 (dd, J = 13.4, 4.9 Hz, 1H), 7.86 (d, J = 8.8 Hz, 2H), 7.78 (d, J = 8.8 Hz, 1H), 7.56 (d, J = 8.6 Hz, 2H), 7.36 (d, J = 8.6 Hz, 2H), 6.91 (d, J = 8.6 Hz, 2H), 5.08-4.99 (m, 1H), 4.48-4.32 (m, 3H), 4.00-3.88 (m, 1H), 3.77 (s, 3H), 3.80-3.72 (m, 1H), 2.89-2.74 (m, 2H). |
| 672 | 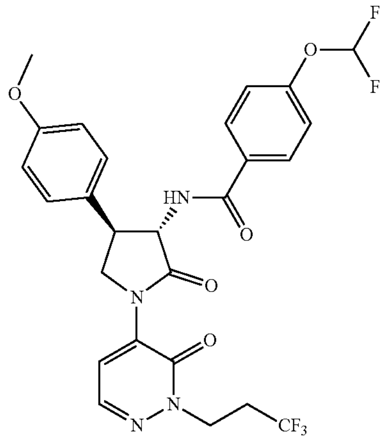 [SMILES: COc1ccc([C@@H]2CN(c3ccnn(CCC(F)(F)F)c3=O)C(=O)[C@H]2NC(=O)c2ccc(OC(F)F)cc2)cc1] | 567.1 | Method D, RT = 1.81 min, 95% | $^1$H NMR (400 MHz, DMSO-$d_6$) δ = 8.95 (d, J = 8.5 Hz, 1H), 8.04 (d, J = 4.6 Hz, 1H), 7.97-7.86 (m, 2H), 7.77 (d, J = 4.6 Hz, 1H), 7.59-7.14 (m, 5H), 7.01-6.79 (m, 2H), 5.04 (dd, J = 11.7, 8.4 Hz, 1H), 4.54-4.42 (m, 1H), 4.37 (t, J = 6.8 Hz, 2H), 3.97 (t, J = 10.4 Hz, 1H), 3.84-3.75 (m, 1H), 3.73 (s, 3H), 2.88-2.72 (m, 2H). |
| 673 | 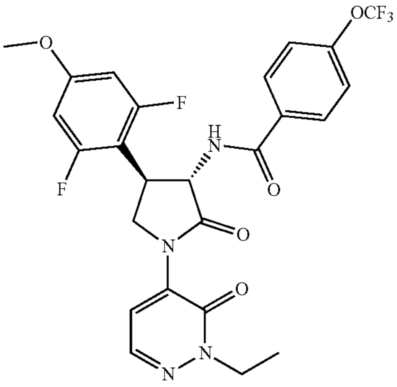 [SMILES: CCn1nccc(N2C[C@@H](c3c(F)cc(OC)cc3F)[C@H](NC(=O)c3ccc(OC(F)(F)F)cc3)C2=O)c1=O] | 553.2 | Method D, RT = 1.95 min, 100% | $^1$H NMR (400 MHz, DMSO-$d_6$) δ = 9.13 (d, J = 8.1 Hz, 1H), 8.01 (d, J = 4.6 Hz, 1H), 7.99-7.82 (m, 2H), 7.70 (d, J = 4.4 Hz, 1H), 7.49 (d, J = 8.1 Hz, 2H), 6.78 (d, J = 10.8 Hz, 2H), 5.07 (dd, J = 10.8, 8.4 Hz, 1H), 4.42-4.27 (m, 1H), 4.25-4.05 (m, 4H), 3.77 (s, 3H), 1.28 (t, J = 7.2 Hz, 3H). |

TABLE 2-continued

| Ex | Structure | LCMS (M + H)+ | HPLC Method, RT (min.) & Purity | $^1$H NMR |
|---|---|---|---|---|
| 674 | 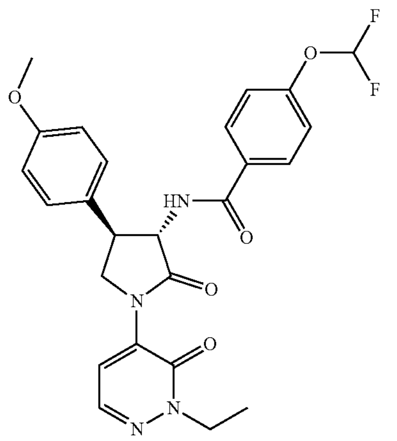 [SMILES: CCn1nccc(N2C[C@@H](c3ccc(OC)cc3)[C@H](NC(=O)c3ccc(OC(F)F)cc3)C2=O)c1=O] | 499.2 | Method D, RT = 1.66 min, 96% | $^1$H NMR (400 MHz, DMSO-$d_6$) δ = 8.94 (br d, J = 8.6 Hz, 1H), 8.00 (d, J = 4.6 Hz, 1H), 7.95-7.85 (m, 2H), 7.72 (d, J = 4.6 Hz, 1H), 7.37 (t, J = 74.5 Hz, 1H), 7.36-734 (m, 2H), 7.26-7.16 (m, 2H), 6.91 (d, J = 8.6 Hz, 2H), 5.03 (dd, J = 11.5, 8.3 Hz, 1H), 4.46 (dd, J = 9.8, 8.3 Hz, 1H), 4.14 (q, J = 7.1 Hz, 2H), 3.96 (t, J = 10.4 Hz, 1H), 3.81-3.68 (m, 1H), 3.77 (s, 3H), 1.28 (t, J = 7.1 Hz, 3H). |
| 675 | 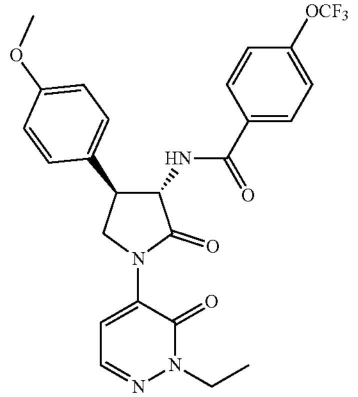 [SMILES: CCn1nccc(N2C[C@@H](c3ccc(OC)cc3)[C@H](NC(=O)c3ccc(OC(F)(F)F)cc3)C2=O)c1=O] | 517.2 | Method D, RT = 1.84 min, 96% | $^1$H NMR (400 MHz, DMSO-$d_6$) δ = 9.03 (d, J = 8.3 Hz, 1H), 8.06-7.89 (m, 3H), 7.72 (d, J = 4.6 Hz, 1H), 7.48 (d, J = 8.1 Hz, 2H), 7.36 (d, J = 8.8 Hz, 2H), 6.91 (d, J = 8.8 Hz, 2H), 5.04 (dd, J = 11.9, 8.4 Hz, 1H), 4.51-4.38 (m, 1H), 4.14 (q, J = 7.3 Hz, 2H), 3.97 (t, J = 10.3 Hz, 1H), 3.79-3.75 (m, 1H), 3.73 (s, 3H), 1.28 (t, J = 7.3 Hz, 3H). |
| 676 | 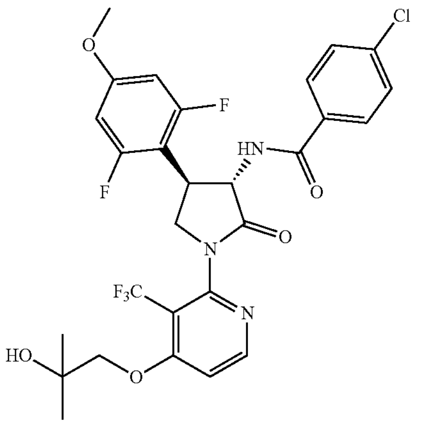 [SMILES: COc1cc(F)c([C@@H]2CN(c3nccc(OCC(C)(C)O)c3C(F)(F)F)C(=O)[C@H]2NC(=O)c2ccc(Cl)cc2)c(F)c1] | 614.2 | Method-D, RT = 2.004 min, 93.7% | $^1$H NMR (400 MHz, DMSO-$d_6$) δ = 9.15-9.10 (m, 1H), 8.51-8.47 (m, 1H), 7.86-7.78 (m, 2H), 7.58-7.52 (m, 2H), 7.28-7.23 (m, 1H), 6.83-6.74 (m, 2H), 5.14-4.96 (m, 1H), 4.65 (s, 1H), 4.43-4.18 (m, 1H), 4.14 (s, 2H), 3.99-3.82 (m, 1H), 3.77 (s, 3H), 3.75-3.71 (m, 1H), 1.22 (s, 3H), 1.17 (s, 3H). |

TABLE 2-continued

| Ex | Structure | LCMS (M + H)+ | HPLC Method, RT (min.) & Purity | $^1$H NMR |
|---|---|---|---|---|
| 677 | 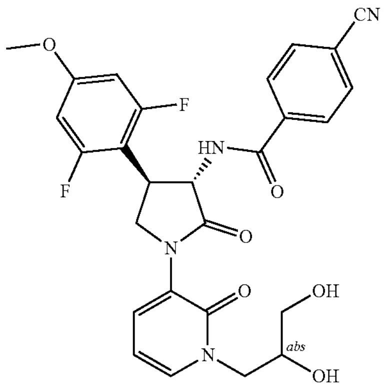 [SMILES: COc1cc(F)c([C@@H]2CN(c3cccn(CC(O)CO)c3=O)C(=O)[C@H]2NC(=O)c2ccc(C#N)cc2)c(F)c1] | 548.2 | Method D, RT = 1.42 min, 100% | $^1$H NMR (400 MHz, DMSO-$d_6$) δ = 9.07 (d, J = 8.8 Hz, 1H), 7.84 (d, J = 8.5 Hz, 2H), 7.63-7.53 (m, 4H), 6.77 (d, J = 10.5 Hz, 2H), 6.32 (t, J = 6.9 Hz, 1H), 5.12 (dd, J = 10.5, 8.6 Hz, 1H), 5.00 (br s, 1H), 4.65 (br s, 1H), 4.30-4.27 (m, 1H), 4.15-3.92 (m, 4H), 3.77 (s, 3H), 3.67-3.61 (m, 1H), 3.38-3.35 (m, 2H). |
| 678 | 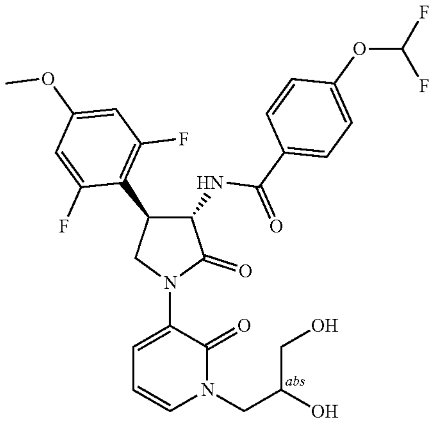 [SMILES: COc1cc(F)c([C@@H]2CN(c3cccn(CC(O)CO)c3=O)C(=O)[C@H]2NC(=O)c2ccc(OC(F)F)cc2)c(F)c1] | 580.2 | Method D, RT = 1.40 min, 98% | $^1$H NMR (400 MHz, DMSO-$d_6$) δ = 9.00 (d, J = 8.3 Hz, 1H), 7.89 (d, J = 8.8 Hz, 2H), 7.61 (dd, J = 13.0, 7.0 Hz, 2H), 7.34 (t, J = 74.0 Hz, 1H), 7.27 (d, J = 8.8 Hz, 2H), 6.77 (d, J = 10.8 Hz, 2H), 6.32 (t, J = 7.0 Hz, 1H), 5.11 (t, J = 9.6 Hz, 1H), 5.04-4.94 (m, 1H), 4.83-4.68 (m, 1H), 4.30-4.31 (m, 1H), 4.15-3.87 (m, 4H), 3.77 (s, 3H), 3.65-3.63 (m, 1H), 3.38-3.35 (m, 2H). |
| 679 | 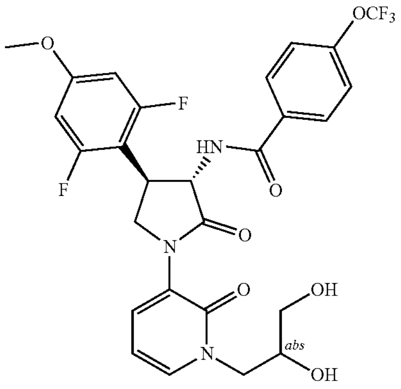 [SMILES: COc1cc(F)c([C@@H]2CN(c3cccn(CC(O)CO)c3=O)C(=O)[C@H]2NC(=O)c2ccc(OC(F)(F)F)cc2)c(F)c1] | 598.2 | Method D, RT = 1.57 min, 98% | $^1$H NMR (400 MHz, DMSO-$d_6$) δ = 9.11 (d, J = 8.5 Hz, 1H), 8.02-7.89 (m, 2H), 7.63 (dd, J = 6.5, 1.9 Hz, 1H), 7.60 (dd, J = 7.1, 1.9 Hz, 1H), 7.49 (d, J = 8.5 Hz, 2H), 6.77 (d, J = 10.8 Hz, 2H), 6.32 (t, J = 7.1 Hz, 1H), 5.13-5.09 (dd, J = 10.8, 8.9 Hz, 1H), 5.00 (d, J = 5.8 Hz, 1H), 4.74 (t, J = 5.8 Hz, 1H), 4.30 (dd, J = 12.9, 2.9 Hz, 1H), 4.15-3.92 (m, 4H), 3.76 (s, 3H), 3.64-3.60 (m, 1H), 3.41-3.36 (m, 2H). |

TABLE 2-continued

| Ex | Structure | LCMS (M + H)+ | HPLC Method, RT (min.) & Purity | $^1$H NMR |
|---|---|---|---|---|
| 680 | 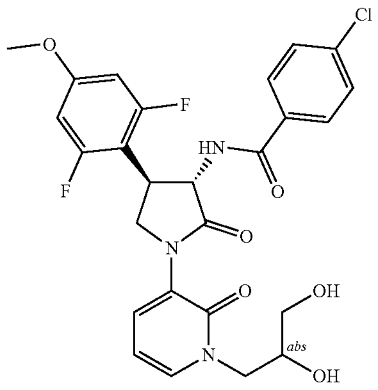 [SMILES: COc1cc(F)c([C@@H]2CN(c3cccn(CC(O)CO)c3=O)C(=O)[C@H]2NC(=O)c2ccc(Cl)cc2)c(F)c1] | 548.2 | Method D, RT = 1.42 min, 98% | $^1$H NMR (400 MHz, DMSO-$d_6$) δ = 9.06 (d, J = 8.5 Hz, 1H), 7.92-7.78 (m, 2H), 7.63 (dd, J = 6.6, 2.0 Hz, 1H), 7.59 (dd, J = 7.3, 2.0 Hz, 1H), 7.58-7.43 (m, 2H), 6.77 (d, J = 10.5 Hz, 2H), 6.32 (t, J = 7.3 Hz, 1H), 5.12-5.07 (m, 1H), 5.04-4.94 (m, 1H), 4.80-4.69 (m, 1H), 4.30-4.27 (m, 1H), 4.14-3.90 (m, 4H), 3.77 (s, 3H), 3.64-3.60 (m, 1H), 3.41-3.36 (m, 2H). |
| 681 | 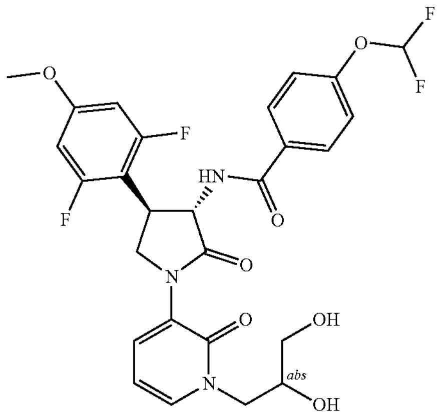 [SMILES: COc1cc(F)c([C@@H]2CN(c3cccn(CC(O)CO)c3=O)C(=O)[C@H]2NC(=O)c2ccc(OC(F)F)cc2)c(F)c1] | 580.3 | Method D, RT = 1.40 min, 98% | $^1$H NMR (400 MHz, DMSO-$d_6$) δ = 9.00 (d, J = 8.5 Hz, 1H), 7.90 (d, J = 8.8 Hz, 2H), 7.63 (dd, J = 6.8, 2.0 Hz, 2H), 7.34 (t, J = 74.0 Hz, 1H), 7.27 (d, J = 8.8 Hz, 2H), 6.78-6.75 (m, 2H), 6.32 (t, J = 7.0 Hz, 1H), 5.13-5.08 (m, 1H), 4.32-4.28 (m, 1H), 4.15-3.92 (m, 4H), 3.77 (s, 3H), 3.63-3.60 (m, 2H), 3.38-3.33 (m, 3H). |
| 682 | 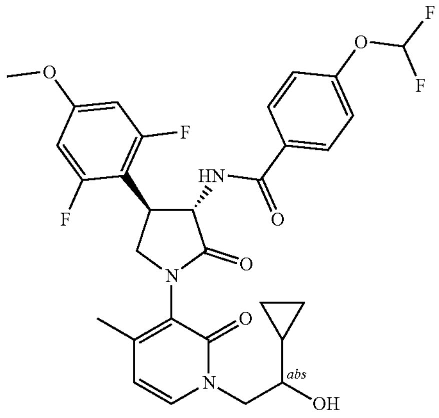 [SMILES: COc1cc(F)c([C@@H]2CN(c3c(C)ccn(CC(O)C4CC4)c3=O)C(=O)[C@H]2NC(=O)c2ccc(OC(F)F)cc2)c(F)c1] | 604.3 | Method D, RT = 1.69 min, 98% | $^1$H NMR (400 MHz, DMSO-$d_6$) δ = 9.14-8.87 (m, 1H), 7.96-7.84 (m, 2H), 7.62-7.50 (m, 1H), 7.28 (t, J = 75.1 Hz, 1H), 7.37-7.13 (m, 2H), 6.81-6.68 (m, 2H), 6.26-6.12 (m, 1H), 5.36-4.84 (m, 2H), 4.30-4.04 (m, 3H), 3.81-3.72 (2s, 3H), 3.66-3.62 (m, 1H), 3.51-3.45 (m, 1H), 3.12-3.10 (m, 1H), 2.22-2.05 (2s, 3H), 0.92-0.68 (m, 1H), 0.48-0.32 (m, 2H), 0.32-0.04 (m, 2H). (Mixture of interconvertible atropisomers) |

TABLE 2-continued

| Ex | Structure | LCMS (M + H)+ | HPLC Method, RT (min.) & Purity | $^1$H NMR |
| --- | --- | --- | --- | --- |
| 683 | 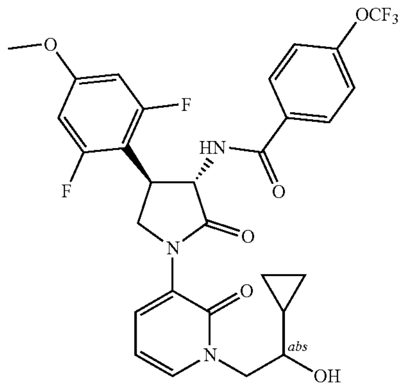 [SMILES: COc1cc(F)c([C@@H]2CN(c3cccn(CC(O)C4CC4)c3=O)C(=O)[C@H]2NC(=O)c2ccc(OC(F)(F)F)cc2)c(F)c1] | 622.3 | Method D, RT = 1.85 min, 98% | $^1$H NMR (400 MHz, DMSO-$d_6$) δ = 9.31-8.93 (m, 1H), 8.06-7.83 (m, 2H), 7.67-7.52 (m, 1H), 7.52-7.41 (m, 2H), 6.86-6.68 (m, 2H), 6.27-6.12 (m, 1H), 5.38-4.84 (m, 2H), 4.32-4.07 (m, 3H), 3.80-3.71 (2s, 3H), 3.66-3.60 (m, 1H), 3.51-3.45 (m, 1H), 3.18-3.10 (m, 2H), 2.21-1.96 (2s, 3H), 0.93-0.75 (m, 1H), 0.48-0.33 (m, 2H), 0.30-0.04 (m, 2H). (Mixture of interconvertible atropisomers) |
| 684 | 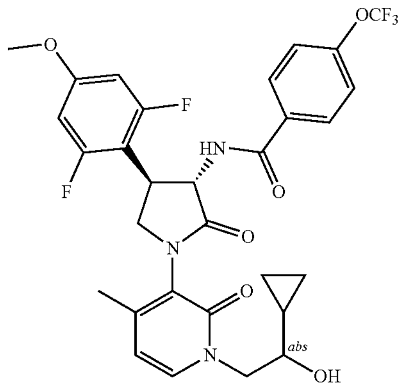 [SMILES: COc1cc(F)c([C@@H]2CN(c3c(C)ccn(CC(O)C4CC4)c3=O)C(=O)[C@H]2NC(=O)c2ccc(OC(F)(F)F)cc2)c(F)c1] | 573.2 | Method D, RT = 1.67 min, 98% | $^1$H NMR (400 MHz, DMSO-$d_6$) δ = 9.21-8.85 (m, 1H), 7.92-7.79 (m, 2H), 7.69-7.45 (m, 3H), 6.81-6.68 (m, 2H), 6.28-6.08 (m, 1H), 5.38-4.82 (m, 2H), 4.32-4.04 (m, 3H), 3.80-3.75 (2s, 3H), 3.72-3.60 (m, 1H), 3.51-3.45 (m, 1H), 3.21-3.02 (m, 1H), 2.20-1.99 (2s, 3H), 0.91-0.74 (m, 1H), 0.47-0.33 (m, 2H), 0.29-0.20 (m, 1H), 0.20-0.07 (m, 1H). (Mixture of interconvertible atropisomers) |
| 685 | 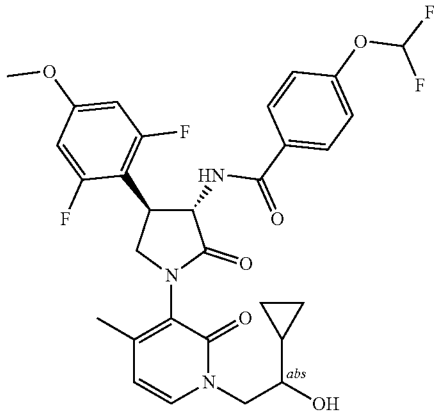 [SMILES: COc1cc(F)c([C@@H]2CN(c3c(C)ccn(CC(O)C4CC4)c3=O)C(=O)[C@H]2NC(=O)c2ccc(OC(F)F)cc2)c(F)c1] | 604.3 | Method D, RT = 1.72 min, 100% | $^1$H NMR (400 MHz, DMSO-$d_6$) δ = 9.17-8.82 (m, 1H), 8.01-7.81 (m, 2H), 7.33 (t, J = 75.1 Hz, 1H), 7.58-7.16 (m, 3H), 6.77 (dd, J = 10.6, 4.9 Hz, 2H), 6.19 (dd, J = 12.3, Hz, 1H), 5.39-4.78 (m, 2H), 4.31-4.03 (m, 3H), 3.81-3.72 (2s, 3H), 3.67-3.60 (m, 1H), 3.51-3.45 (m, 1H), 3.20-3.06 (m, 1H), 2.23-1.99 (2s, 3H), 0.91-0.71 (m, 1H), 0.48-0.33 (m, 2H), 0.31-0.21 (m, 1H), 0.19-0.07 (m, 1H). (Mixture of interconvertible atrop isomers) |

TABLE 2-continued

| Ex | Structure | LCMS (M + H)+ | HPLC Method, RT (min.) & Purity | $^1$H NMR |
|---|---|---|---|---|
| 686 | 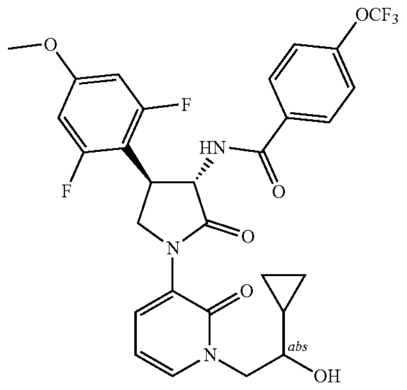 [SMILES: COc1cc(F)c([C@@H]2CN(c3cccn(CC(O)C4CC4)c3=O)C(=O)[C@H]2NC(=O)c2ccc(OC(F)(F)F)cc2)c(F)c1] | 622.3 | Method D, RT = 1.87 min, 98% | $^1$H NMR (400 MHz, DMSO-$d_6$) δ = 9.22-8.95 (m, 1H), 8.03-7.86 (m, 2H), 7.58-7.54 (m, 1H), 7.53-7.37 (m, 2H), 6.79-6.75 (m, 2H), 6.22-6.17 (m, 1H), 5.37-4.95 (m, 1H), 4.94-4.84 (m, 1H), 4.29-4.04 (m, 3H), 3.77-3.76 (2s, 3H), 3.72-3.61 (m, 1H), 3.55-3.46 (m, 1H), 3.18-3.10 (m, 1H), 2.22-2.04 (2s, 3H), 0.88-0.78 (m, 1H), 0.46-0.33 (m, 2H), 0.30-0.22 (m, 1H), 0.19-0.09 (m, 1H). (Mixture of interconvertible atropisomers) |
| 687 | 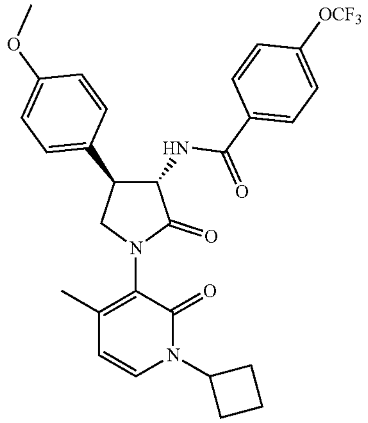 [SMILES: COc1ccc([C@@H]2CN(c3c(C)ccn(C4CCC4)c3=O)C(=O)[C@H]2NC(=O)c2ccc(OC(F)(F)F)cc2)cc1] | 556.2 | Method D, RT = 1.881 min, 100%. | $^1$H NMR (400 MHz, DMSO-$d_6$) δ = 9.14-8.91 (m, 1H), 8.08-7.92 (m, 2H), 7.79-7.62 (m, 1H), 7.50-7.46 (m, 2H), 7.42-7.23 (m, 2H), 6.93-6.89 (m, 2H), 6.34-6.14 (m, 1H), 5.28-4.65 (m, 2H), 4.12-3.82 (m, 3H), 3.78-3.48 (m, 4H), 2.36-2.24 (m, 3H), 2.21-2.08 (2s, 3H), 1.84-1.65 (m, 1H), 0.58-0.21 (m, 1H). (Mixture of interconvertible atropisomers) |
| 688 | 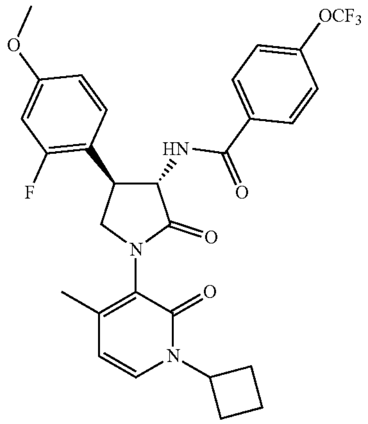 [SMILES: COc1ccc([C@@H]2CN(c3c(C)ccn(C4CCC4)c3=O)C(=O)[C@H]2NC(=O)c2ccc(OC(F)(F)F)cc2)c(F)c1] | 574.2 | Method D, RT = 2.072 min, 99%. | $^1$H NMR (400 MHz, DMSO-$d_6$) δ = 9.16-8.97 (m, 1H), 8.07-7.92 (m, 2H), 7.82-7.67 (m, 1H), 7.65-7.38 (m, 3H), 6.90-6.70 (m, 2H), 6.32-6.15 (m, 1H), 5.82-5.32 (m, 1H), 5.11-4.81 (m, 2H), 4.32-3.73 (m, 4H), 3.70-3.55 (m, 2H), 2.44-2.24 (m, 3H), 2.22-2.05 (2s, 3H), 1.99-1.72 (m, 1H), 0.54-0.22 (m, 1H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 689 | 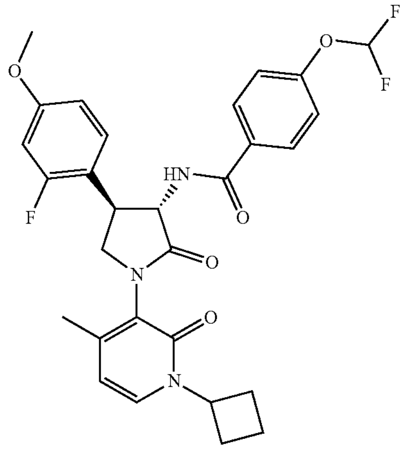 [SMILES: COc1ccc([C@@H]2CN(c3c(C)ccn(C4CCC4)c3=O)C(=O)[C@H]2NC(=O)c2ccc(OC(F)F)cc2)c(F)c1] | 556.3 | Method D, RT = 1.819 min, 96%. | $^1$H NMR (400 MHz, DMSO-$d_6$) δ = 9.05-8.85 (m, 1H), 8.00-7.87 (m, 2H), 7.81-7.65 (m, 1H), 7.59-7.39 (m, 1H), 7.38-6.92 (m, 3H), 6.87-6.66 (m, 2H), 6.33-6.19 (m, 1H), 5.42-4.81 (m, 2H), 4.20-3.89 (m, 3H), 3.78-3.74 (2s, 3H), 3.63-3.54 (m, 1H), 2.39-2.23 (m, 3H), 2.22-2.08 (2s, 3H), 1.84-1.70 (m, 1H), 0.56-0.30 (m, 1H). (Mixture of interconvertible atropisomers) |
| 690 | 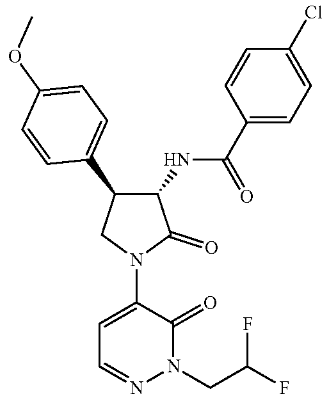 [SMILES: COc1ccc([C@@H]2CN(c3ccnn(CC(F)F)c3=O)C(=O)[C@H]2NC(=O)c2ccc(Cl)cc2)cc1] | 503.1 | Method D, RT = 1.71 min, 100% | $^1$H NMR (400 MHz, DMSO-$d_6$) δ = 8.99 (d, J = 8.6 Hz, 1H), 8.04 (d, J = 4.6 Hz, 1H), 7.91-7.83 (m, 2H), 7.78 (d, J = 4.6 Hz, 1H), 7.59-7.50 (m, 2H), 7.40-7.31 (m, 2H), 6.95-6.86 (m, 2H), 6.39 (tt, J = 54.8, 4.4 Hz, 1H), 5.04 (dd, J = 11.6, 8.4 Hz, 1H), 4.55 (dt, J = 14.5, 4.0 Hz, 2H), 4.46 (dd, J = 9.9, 8.2 Hz, 1H), 3.98 (t, J = 10.4 Hz, 1H), 3.82-3.74 (m, 1H), 3.73 (s, 3H). |
| 691 | 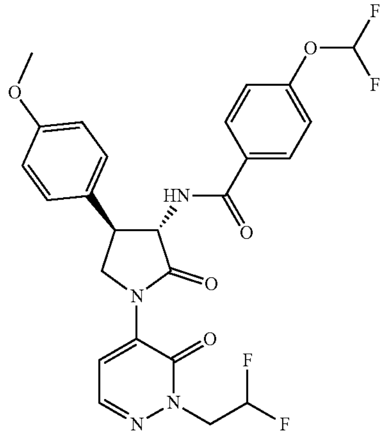 [SMILES: COc1ccc([C@@H]2CN(c3ccnn(CC(F)F)c3=O)C(=O)[C@H]2NC(=O)c2ccc(OC(F)F)cc2)cc1] | 535.1 | Method D, RT = 1.86 min, 100% | $^1$H NMR (400 MHz, DMSO-$d_6$) δ = 8.93 (d, J = 8.6 Hz, 1H), 8.04 (d, J = 4.9 Hz, 1H), 7.94-7.86 (m, 2H), 7.79 (d, J = 4.6 Hz, 1H), 7.40-7.34 (m, 2H), 7.33 (t, J = 75.1 Hz, 1H), 7.26 (d, J = 8.8 Hz, 2H), 6.95-6.86 (m, 2H), 6.39 (tt, J = 55.8, 4.4 Hz, 1H), 5.03 (dd, J = 11.6, 8.4 Hz, 1H), 4.56 (dt, J = 14.4, 4.2 Hz, 2H), 4.46 (dd, J = 9.9, 8.2 Hz, 1H), 3.98 (t, J = 10.4 Hz, 1H), 3.82-3.74 (m, 1H), 3.73 (s, 3H). |

TABLE 2-continued

| Ex | Structure | LCMS (M + H)+ | HPLC Method, RT (min.) & Purity | $^1$H NMR |
|---|---|---|---|---|
| 692 | 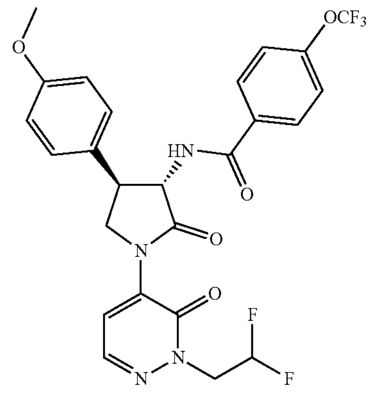 [SMILES: COc1ccc([C@@H]2CN(c3ccnn(CC(F)F)c3=O)C(=O)[C@H]2NC(=O)c2ccc(OC(F)(F)F)cc2)cc1] | 553.1 | Method D, RT = 1.86 min, 100% | $^1$H NMR (400 MHz, DMSO-$d_6$) δ = 9.04 (d, J = 8.3 Hz, 1H), 8.05 (d, J = 4.6 Hz, 1H), 8.01-7.92 (m, 2H), 7.79 (d, J = 4.6 Hz, 1H), 7.48 (d, J = 8.1 Hz, 2H), 7.41-7.29 (m, 2H), 6.96-6.85 (m, 2H), 6.40 (tt, J = 55.8, 4.3, Hz, 1H), 5.05 (dd, J = 11.6, 8.4 Hz, 1H), 4.56 (dt, J = 14.5, 4.3 Hz, 2H), 4.46 (dd, J = 9.9, 8.4 Hz, 1H), 3.98 (t, J = 10.4 Hz, 1H), 3.81-3.73 (m, 1H), 3.72 (s, 3H). |
| 693 | 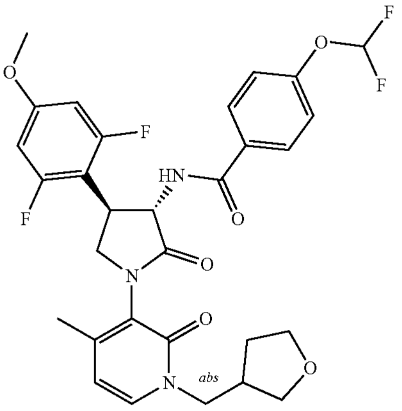 [SMILES: COc1cc(F)c([C@@H]2CN(c3c(C)ccn(CC4CCOC4)c3=O)C(=O)[C@H]2NC(=O)c2ccc(OC(F)F)cc2)c(F)c1] | 604.3 | Method D, RT = 1.629 min, 99%. | $^1$H NMR (400 MHz, DMSO-$d_6$) δ = 9.14-8.81 (m, 1H), 7.96-7.82 (m, 2H), 7.74-7.58 (m, 1H), 7.58-7.08 (m, 3H), 6.76 (m, 2H), 6.32-6.18 (m, 1H), 5.39-4.77 (m, 1H), 4.32-4.02 (m, 2H), 4.00-3.85 (m, 2H), 3.83-3.71 (m, 4H), 3.68-3.57 (m, 2H), 3.54-3.43 (m, 2H), 2.71-2.61 (m, 1H), 2.22-2.02 (2s, 3H), 1.93-1.78 (m, 1H), 1.68-1.51 (m, 1H). (Mixture of interconvertible atrop isomers) |
| 694 | 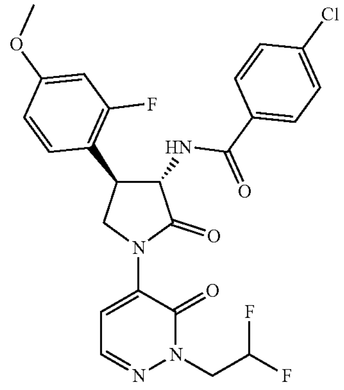 [SMILES: COc1ccc([C@@H]2CN(c3ccnn(CC(F)F)c3=O)C(=O)[C@H]2NC(=O)c2ccc(Cl)cc2)c(F)c1] | 521 | Method D, RT = 1.78 min, 100% | $^1$H NMR (400 MHz, DMSO-$d_6$) δ = 9.02 (d, J = 8.6 Hz, 1H), 8.05 (d, J = 4.6 Hz, 1H), 7.91-7.80 (m, 2H), 7.78 (d, J = 4.6 Hz, 1H), 7.61-7.43 (m, 3H), 6.90-6.75 (m, 2H), 6.39 (tt, J = 56.2, 5.1 Hz, 1H), 5.13 (dd, J = 11.1, 8.4 Hz, 1H), 4.55 (dt, J = 14.4, 4.3, Hz, 2H), 4.46 (t, J = 7.9 Hz, 1H), 4.09-3.88 (m, 2H), 3.75 (s, 3H). |

TABLE 2-continued

| Ex | Structure | LCMS (M + H)+ | HPLC Method, RT (min.) & Purity | $^1$H NMR |
|---|---|---|---|---|
| 695 | 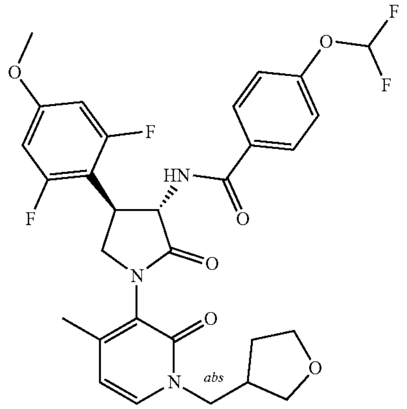 [SMILES: COc1cc(F)c([C@@H]2CN(c3c(C)ccn(CC4CCOC4)c3=O)C(=O)[C@H]2NC(=O)c2ccc(OC(F)F)cc2)c(F)c1] | 604.3 | Method D, RT = 1.619 min, 100%. | $^1$H NMR (400 MHz, DMSO-$d_6$) δ = 9.14-8.81 (m, 1H), 7.98-7.81 (m, 2H), 7.73-7.58 (m, 1H), 7.56-7.04 (m, 3H), 6.78-6.74 (m, 2H), 6.31-6.11 (m, 1H), 5.41-4.81 (m, 1H), 4.32-3.97 (m, 3H), 3.94-3.72 (m, 5H), 3.69-3.57 (m, 2H), 3.55-3.42 (m, 2H), 2.70-2.61 (m, 1H), 2.21-1.97 (2s, 3H), 1.93-1.80 (m, 1H), 1.71-1.54 (m, 1H). (Mixture of interconvertible atropisomers) |
| 696 | 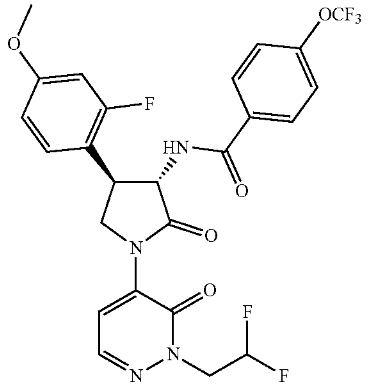 [SMILES: COc1ccc([C@@H]2CN(c3ccnn(CC(F)F)c3=O)C(=O)[C@H]2NC(=O)c2ccc(OC(F)(F)F)cc2)c(F)c1] | 571.1 | Method D, RT = 1.92 min, 100% | $^1$H NMR (400 MHz, DMSO-$d_6$) δ = 9.06 (d, J = 8.6 Hz, 1H), 8.05 (d, J = 4.9 Hz, 1H), 8.00-7.89 (m, 2H), 7.78 (d, J = 4.9 Hz, 1H), 7.54 (t, J = 8.8 Hz, 1H), 7.48 (d, J = 8.3 Hz, 2H), 6.86-6.75 (m, 2H), 6.39 (tt, J = 54.8, 5.1 Hz, 1H), 5.13 (dd, J = 11.0, 8.6 Hz, 1H), 4.55 (dt, J = 14.4, 4.2Hz, 2H), 4.47 (t, J = 7.9 Hz, 1H), 4.08-3.92 (m, 2H), 3.75 (s, 3H). |
| 697 | 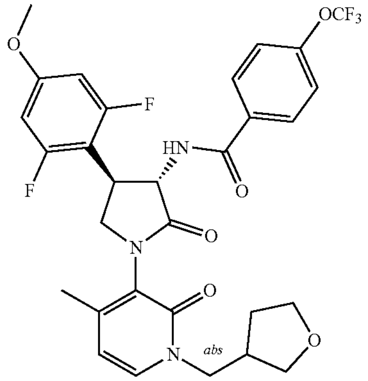 [SMILES: COc1cc(F)c([C@@H]2CN(c3c(C)ccn(CC4CCOC4)c3=O)C(=O)[C@H]2NC(=O)c2ccc(OC(F)(F)F)cc2)c(F)c1] | 622.2 | Method D, RT = 1.788 min, 97%. | $^1$H NMR (400 MHz, DMSO-$d_6$) δ = 9.23-8.92 (m, 1H), 8.05-7.87 (m, 2H), 7.78-7.61 (m, 1H), 7.55-7.37 (m, 2H), 6.78-6.73 (m, 2H), 6.30-6.13 (m, 1H), 5.38-4.81 (m, 1H), 4.31-3.95 (m, 3H), 3.93-3.83 (m, 2H), 3.75-3.70 (s, 3H), 3.67-3.58 (m, 2H), 3.53-3.43 (m, 2H), 2.72-2.64 (m, 1H), 2.24-2.02 (2s, 3H), 1.93-1.82 (m, 1H), 1.68-1.54 (m, 1H). (Mixture of interconvertible atropisomers) |

TABLE 2-continued

| Ex | Structure | LCMS (M + H)+ | HPLC Method, RT (min.) & Purity | $^1H$ NMR |
|---|---|---|---|---|
| 698 | 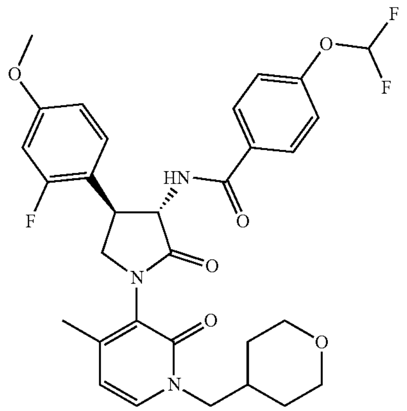 [SMILES: COc1ccc([C@@H]2CN(c3c(C)ccn(CC4CCOCC4)c3=O)C(=O)[C@H]2NC(=O)c2ccc(OC(F)F)cc2)c(F)c1] | 600.2 | Method D, RT = 1.642 min, 96%. | $^1H$ NMR (400 MHz, DMSO-$d_6$) δ = 8.97-8.92 (m, 1H), 7.98-7.83 (m, 2H), 7.60-7.58 (m, 1H), 7.56-7.13 (m, 2H), 7.10 (m, 2H), 6.87-6.70 (m, 2H), 6.22-6.19 (m, 1H), 5.43-4.74 (m, 1H), 4.19-3.87 (m, 3H), 3.87-3.70 (m, 5H), 3.62-3.37 (m, 1H), 3.26-3.15 (m, 3H), 2.23-2.06 (2s, 3H), 2.04-1.93 (m, 1H), 1.49-1.38 (m, 2H), 1.34-1.19 (m, 2H). (Mixture of interconvertible atrop isomers) |
| 699 | 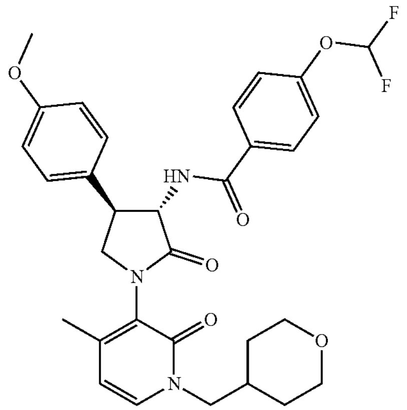 [SMILES: COc1ccc([C@@H]2CN(c3c(C)ccn(CC4CCOCC4)c3=O)C(=O)[C@H]2NC(=O)c2ccc(OC(F)F)cc2)cc1] | 582.3 | Method D, RT = 1.565 min, 94%. | $^1H$ NMR (400 MHz, DMSO-$d_6$) δ = 8.95-8.93 (m, 1H), 7.95-7.92 (m, 2H), 7.61-7.59 (m, 1H), 7.39-7.22 (m, 5H), 6.92-6.90 (m, 2H), 6.21 (d, J = 6.8 Hz, 1H), 5.32-4.58 (m, 1H), 3.94-3.69 (m, 9H), 3.67-3.38 (m, 1H), 3.30-3.18 (m, 2H), 2.23-2.06 (2s, 3H), 2.03-1.90 (m, 1H), 1.51-1.36 (m, 2H), 1.34-1.16 (m, 2H). (Mixture of interconvertible atropisomers) |
| 700 | 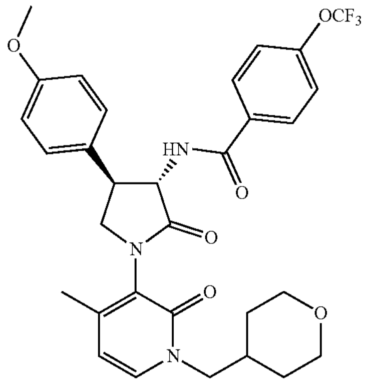 [SMILES: COc1ccc([C@@H]2CN(c3c(C)ccn(CC4CCOCC4)c3=O)C(=O)[C@H]2NC(=O)c2ccc(OC(F)(F)F)cc2)cc1] | 600.3 | Method D, RT = 1.75 min, 94%. | $^1H$ NMR (400 MHz, DMSO-$d_6$) δ = 9.05-9.03 (m, 1H), 8.02-7.97 (m, 2H), 7.61-7.59 (m, 1H), 7.49-7.47 (m, 2H), 7.40-7.30 (m, 2H), 6.93-6.90 (m, 2H), 6.21 (d, J = 6.8 Hz, 1H), 5.31-4.63 (m, 1H), 3.93-3.69 (m, 10H), 3.23 (m, 2H), 2.18-2.06 (2s, 3H), 2.03-1.89 (m, 1H), 1.51-1.36 (m, 2H), 1.32-1.21 (m, 2H). (Mixture of interconvertible atropisomers) |

TABLE 2-continued

| Ex | Structure | LCMS (M + H)+ | HPLC Method, RT (min.) & Purity | $^{1}$H NMR |
|---|---|---|---|---|
| 701 | 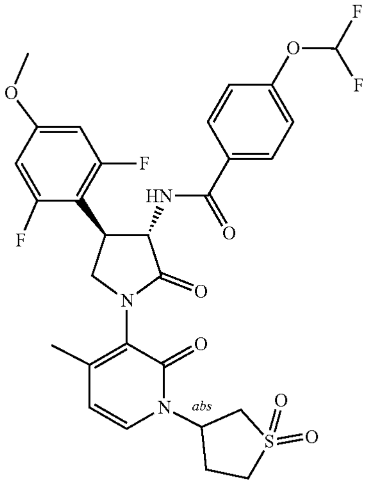 [SMILES: COc1cc(F)c([C@@H]2CN(c3c(C)ccn(C4CCS(=O)(=O)C4)c3=O)C(=O)[C@H]2NC(=O)c2ccc(OC(F)F)cc2)c(F)c1] | 638.3 | Method D, RT = 1.61 min, 100% | $^{1}$H NMR (400 MHz, DMSO-$d_6$) δ = 9.10-8.90 (m, 1H), 7.94-7.84 (m, 2H), 7.79-7.68 (m, 1H), 7.33 (t, J = 73.6 Hz, 1H), 7.26-7.24 (m, 2H), 6.81-6.68 (m, 2H), 6.40-6.29 (m, 1H), 5.49-4.75 (m, 2H), 4.31-4.04 (m, 3H), 3.78-3.74 (2s, 3H), 3.62-3.47 (m, 4H), 3.29-3.23 (m, 1H), 2.48-2.39 (m, 1H), 2.24-2.02 (2s, 3H). (Mixture of interconvertible atropisomers) |
| 702 | 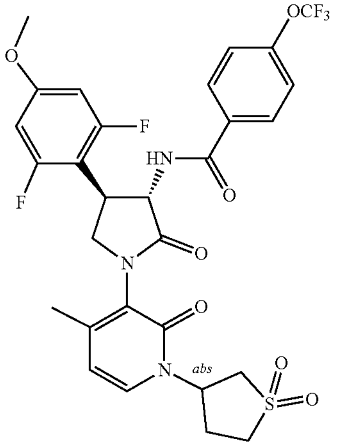 [SMILES: COc1cc(F)c([C@@H]2CN(c3c(C)ccn(C4CCS(=O)(=O)C4)c3=O)C(=O)[C@H]2NC(=O)c2ccc(OC(F)(F)F)cc2)c(F)c1] | 656.2 | Method D, RT = 1.78 min, 100% | $^{1}$H NMR (400 MHz, DMSO-$d_6$) δ = 9.19-9.00 (m, 1H), 8.00-7.88 (m, 2H), 7.77-7.67 (m, 1H), 7.52-7.41 (m, 2H), 6.82-6.70 (m, 2H), 6.40-6.28 (m, 1H), 5.46-4.81 (m, 2H), 4.29-4.05 (m, 3H), 3.78-3.74 (2s, 3H), 3.62-3.45 (m, 4H), 3.27-3.21 (m, 1H), 2.47-2.38 (m, 1H), 2.24-2.04 (2s, 3H). (Mixture of interconvertible atrop isomers) |
| 703 | 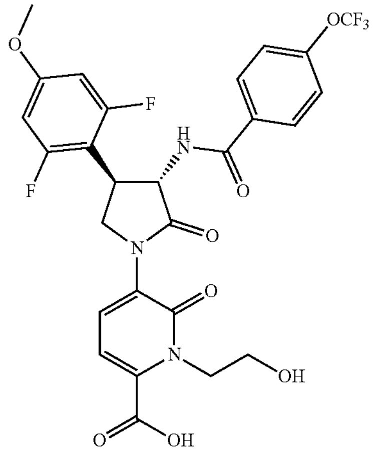 [SMILES: COc1cc(F)c([C@@H]2CN(c3ccc(C(=O)O)n(CCO)c3=O)C(=O)[C@H]2NC(=O)c2ccc(OC(F)(F)F)cc2)c(F)c1] | 612.2 | Method D, RT = 1.412 min, 95.6% | $^{1}$H NMR (400 MHz, DMSO-$d_6$) δ = 9.12 (dd, J = 14.9, 8.4 Hz, 1H), 7.95 (d, J = 8.8 Hz, 2H), 7.84-7.67 (m, 1H), 7.49 (t, J = 7.3 Hz, 2H), 7.26 (d, J = 7.5 Hz, 1H), 6.78 (t, J = 10.1 Hz, 2H), 5.20-4.98 (m, 1H), 4.68 (t, J = 5.1 Hz, 1H), 4.26-4.21 (m, 1H), 4.17-4.03 (m, 2H), 4.01-3.90 (m, 1H), 3.77 (s, 3H), 3.75-3.70 (m, 1H), 3.34-3.30 (m, 1H). |

TABLE 2-continued

| Ex | Structure | LCMS (M + H)+ | HPLC Method, RT (min.) & Purity | $^{1}$H NMR |
|---|---|---|---|---|
| 704 | 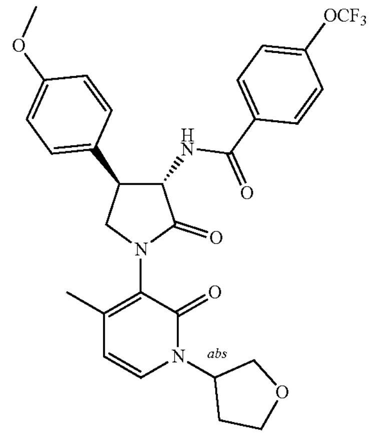 [SMILES: COc1ccc([C@@H]2CN(c3c(C)ccn(C4CCOC4)c3=O)C(=O)[C@H]2NC(=O)c2ccc(OC(F)(F)F)cc2)cc1] | 572.2 | Method D, RT = 3.00 min, 99%. | $^{1}$H NMR (400 MHz, DMSO-$d_6$) δ = 9.06-9.01 (m, 1H), 8.05-7.94 (m, 2H), 7.63-7.44 (m, 3H), 7.42-7.28 (m, 2H), 6.98-6.84 (m, 2H), 6.31-6.27 (m, 1H), 5.38-5.34 (m, 1H), 5.25-4.67 (m, 1H), 4.14-3.99 (m, 2H), 3.95-3.81 (m, 3H), 3.79-3.74 (m, 1H), 3.75-3.70 (2s, 3H), 3.67-3.45 (m, 1H), 2.48-2.39 (m, 1H), 2.26-2.08 (2s, 3H), 2.04-1.90 (m, 1H). (Mixture of interconvertible atropisomers) |
| 705 | 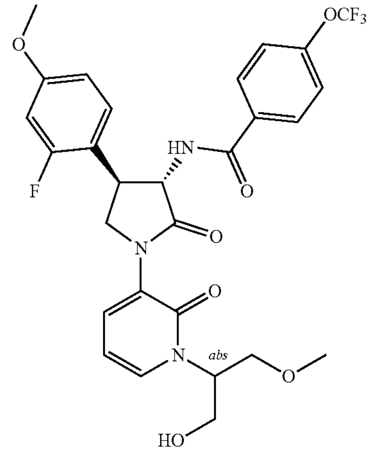 [SMILES: COCC(CO)n1cccc(N2C[C@@H](c3ccc(OC)cc3F)[C@H](NC(=O)c3ccc(OC(F)(F)F)cc3)C2=O)c1=O] | 594.2 | Method F, RT = 2.526 min, 99.9% | $^{1}$H NMR (400 MHz, DMSO-$d_6$) δ = 9.06 (d, J = 8.8 Hz, 1H), 7.98 (d, J = 8.8 Hz, 2H), 7.69 (dd, J = 7.0, 1.6 Hz, 1H), 7.57 (dd, J = 7.3, 1.6 Hz, 1H), 7.54-7.46 (m, 3H), 6.85-6.78 (m, 2H), 6.35 (t, J = 7.0 Hz, 1H), 5.20-5.01 (m, 3H), 4.19-4.12 (m, 1H), 4.06-3.96 (m, 1H), 3.80-3.64 (m, 5H), 3.75 (s, 3H), 3.24 (s, 3H). |
| 706 | 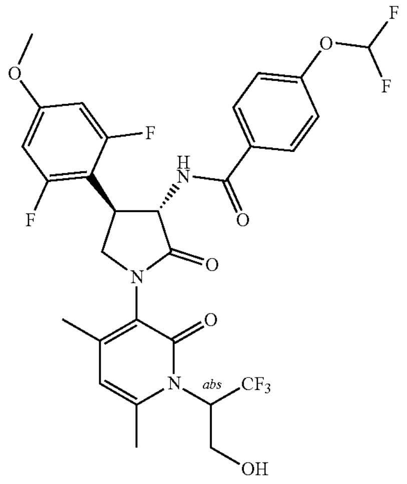 [SMILES: COc1cc(F)c([C@@H]2CN(c3c(C)cc(C)n(C(CO)C(F)(F)F)c3=O)C(=O)[C@H]2NC(=O)c2ccc(OC(F)F)cc2)c(F)c1] | 632.2 | Method D, RT = 1.765 min, 98.8% | $^{1}$H NMR (400 MHz, DMSO-$d_6$) δ = 9.15-8.83 (m, 1H), 7.97-7.79 (m, 2H), 7.69-7.56 (m, 1H), 7.35 (t, J = 74.8 Hz, 1H), 7.31-7.27 (m, 2H), 6.84-6.66 (m, 3H), 6.34-6.19 (m, 1H), 5.36-4.80 (m, 1H), 4.46-4.08 (m, 4H), 3.91-3.69 (m, 4H), 3.52-3.49 (m, 1H), 2.26-1.97 (2s, 3H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 707 | 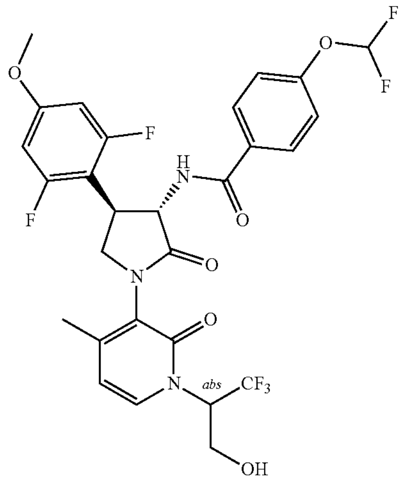 [SMILES: COc1cc(F)c([C@@H]2CN(c3c(C)ccn(C(CO)C(F)(F)F)c3=O)C(=O)[C@H]2NC(=O)c2ccc(OC(F)F)cc2)c(F)c1] | 632.3 | Method C, RT = 1.720 min, 100% | $^1$H NMR (400 MHz, DMSO-d$_6$) δ = 9.14-8.86 (m, 1H), 7.97-7.77 (m, 2H), 7.69-7.56 (m, 1H), 7.35 (t, J = 74.8 Hz, 1H), 7.31-7.27 (m, 2H), 6.85-6.53 (m, 3H), 6.34-6.15 (m, 1H), 5.38-4.78 (m, 1H), 4.47-4.01 (m, 4H), 3.91-3.69 (m, 4H), 3.56-3.47 (m, 1H), 2.25-2.04 (2s, 3H). (Mixture of interconvertible atropisomers) |
| 708 | 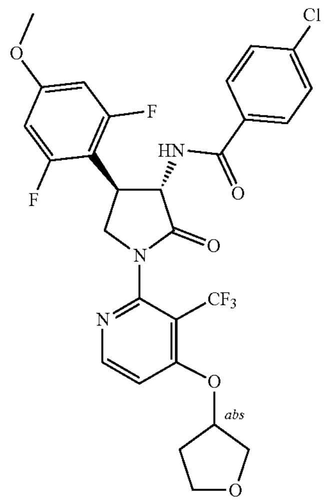 [SMILES: COc1cc(F)c([C@@H]2CN(c3nccc(OC4CCOC4)c3C(F)(F)F)C(=O)[C@H]2NC(=O)c2ccc(Cl)cc2)c(F)c1] | 612.2 | Method-D, RT = 1.918 min, 98.4% | $^1$H NMR (400 MHz, DMSO-d$_6$) δ = 9.13-9.07 (m, 1H), 8.66-8.59 (m, 1H), 7.86-7.79 (m, 2H), 7.56 (d, J = 8.6 Hz, 2H), 7.39-7.32 (m, 1H), 6.78 (d, J = 11.5 Hz, 2H), 5.39-5.34 (m, 1H), 5.14-5.04 (m, 1H), 4.48-4.13 (m, 2H), 4.01-3.73 (m, 7H), 3.33-3.30 (m, 1H), 2.35-2.27 (m, 1H), 2.12-1.91 (m, 1H). (Mixture of interconvertible atropisomers) |
| 709 | 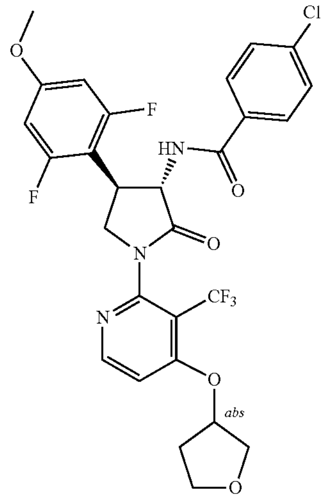 [SMILES: COc1cc(F)c([C@@H]2CN(c3nccc(OC4CCOC4)c3C(F)(F)F)C(=O)[C@H]2NC(=O)c2ccc(Cl)cc2)c(F)c1] | 612.2 | Method-D, RT = 1.918 min, 97.4% | $^1$H NMR (400 MHz, DMSO-d$_6$) δ = 9.14-9.07 (m, 1H), 8.67-8.58 (m, 1H), 7.87-7.76 (m, 2H), 7.56 (d, J = 8.6 Hz, 2H), 7.36 (br d, J = 5.6 Hz, 1H), 6.78 (d, J = 10.8 Hz, 2H), 5.39-5.31 (m, 1H), 5.13-5.02 (m, 1H), 4.47-4.13 (m, 2H), 4.01-3.73 (m, 7H), 3.33-3.30 (m, 1H), 2.37-2.22 (m, 1H), 2.09-1.94 (m, 1H). (Mixture of interconvertible atropisomers) |

TABLE 2-continued

| Ex | Structure | LCMS (M + H)+ | HPLC Method, RT (min.) & Purity | $^1$H NMR |
|---|---|---|---|---|
| 710 | 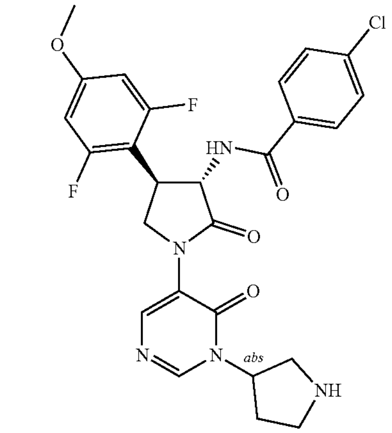 [SMILES: COc1cc(F)c([C@@H]2CN(c3cncn(C4CCNC4)c3=O)C(=O)[C@H]2NC(=O)c2ccc(Cl)cc2)c(F)c1] | 544.2 | Method D, RT = 1.207 min, 100%. | $^1$H NMR (400 MHz, DMSO-$d_6$) δ = 9.07 (d, J = 8.8 Hz, 1H), 8.53 (s, 1H), 8.12 (s, 1H), 7.89-7.74 (m, 2H), 7.62-7.50 (m, 2H), 6.77 (d, J = 10.8 Hz, 2H), 5.17-5.04 (m, 2H), 4.17-4.06 (m, 1H), 4.00-3.92 (m, 2H), 3.76 (s, 3H), 3.19-3.06 (m, 3H), 2.97 (dd, J = 11.8, 3.8 Hz, 1H), 2.89-2.79 (m, 1H), 2.30-2.18 (m, 1H), 1.92-1.88 (m, 1H). |
| 711 | 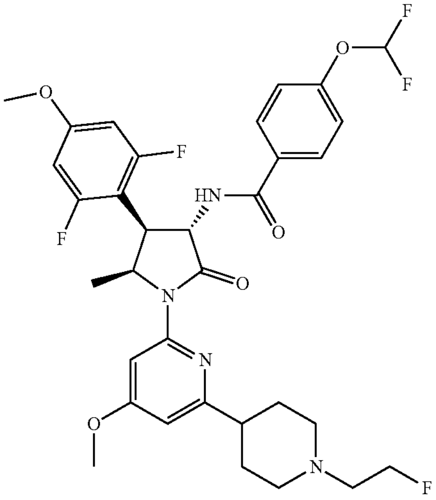 [SMILES: COc1cc(C2CCN(CCF)CC2)nc(N2C(=O)[C@@H](NC(=O)c3ccc(OC(F)F)cc3)[C@H](c3c(F)cc(OC)cc3F)[C@@H]2C)c1] | 663.3 | Method-C, RT = 1.606 min, 97.14% | $^1$H NMR (400 MHz, DMSO-$d_6$) δ = 8.88 (d, J = 8.3 Hz, 1H), 7.93-7.86 (m, 2H), 7.85-7.80 (m, 1H), 7.35 (t, J = 72 Hz, 1H), 7.30-7.23 (m, 2H), 6.84-6.76 (m, 2H), 6.72-6.68 (m, 1H), 5.67 (dd, J = 12.5, 8.3 Hz, 1H), 5.03-4.90 (m, 1H), 4.49 (dt, J = 47.2, 4.5 Hz, 2H), 4.35-4.26 (m, 1H), 3.82 (s, 3H), 3.78 (s, 3H), 2.98 (br d, J = 10.8 Hz, 2H), 2.69-2.63 (m, 1H), 2.62-2.55 (m, 2H), 2.15-2.05 (m, 2H), 1.84-1.68 (m, 4H), 1.21 (d, J = 6.2 Hz, 3H). |
| 712 | 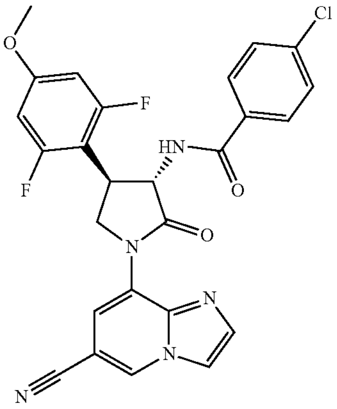 [SMILES: COc1cc(F)c([C@@H]2CN(c3cc(C#N)cn4ccnc34)C(=O)[C@H]2NC(=O)c2ccc(Cl)cc2)c(F)c1] | 522.1 | Method C, RT = 1.594 min, 96.0%. | $^1$H NMR (400 MHz, DMSO-$d_6$) δ = 9.33 (d, J = 1.0 Hz, 1H), 9.15 (d, J = 8.3 Hz, 1H), 8.14 (s, 1H), 7.85 (d, J = 8.2 Hz, 2H), 7.77 (d, J = 6.5 Hz, 2H), 7.58 (d, J = 8.5 Hz, 2H), 6.80 (d, J = 10.8 Hz, 2H), 5.17 (dd, J = 11.1, 8.6 Hz, 1H), 4.64-4.54 (m, 1H), 4.41 (t, J = 10.1 Hz, 1H), 4.23 (q, J = 10.0 Hz, 1H), 3.78 (s, 3H). |

TABLE 2-continued

| Ex | Structure | LCMS (M + H)+ | HPLC Method, RT (min.) & Purity | $^1$H NMR |
| --- | --- | --- | --- | --- |
| 713 | 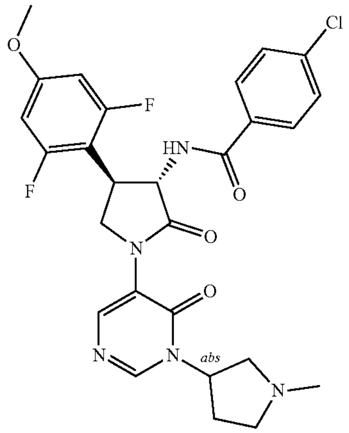 [SMILES: COc1cc(F)c([C@@H]2CN(c3cncn(C4CCN(C)C4)c3=O)C(=O)[C@H]2NC(=O)c2ccc(Cl)cc2)c(F)c1] | 558.2 | Method D, RT = 1.623 min, 99.7%. | $^1$H NMR (400 MHz, DMSO-$d_6$) δ = 9.08 (d, J = 8.5 Hz, 1H), 8.64 (s, 1H), 8.13 (s, 1H), 7.88-7.79 (m, 2H), 7.60-7.53 (m, 2H), 6.78 (d, J = 11.0 Hz, 2H), 5.26-5.17 (m, 1H), 5.12 (dd, J = 11.3, 8.8 Hz, 1H), 4.17-4.05 (m, 1H), 3.96 (d, J = 9.5 Hz, 2H), 3.77 (s, 3H), 3.06 (td, J = 8.8, 3.5 Hz, 1H), 2.92 (d, J = 9.0 Hz, 1H), 2.59-2.53 (m, 1H), 2.47-2.38 (m, 1H), 2.32 (s, 3H), 2.24 (m, 1H), 1.98-1.83 (m, 1H). |
| 714 | 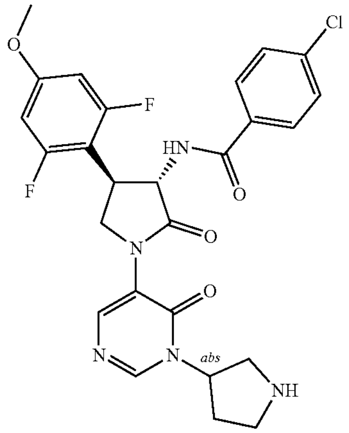 [SMILES: COc1cc(F)c([C@@H]2CN(c3cncn(C4CCNC4)c3=O)C(=O)[C@H]2NC(=O)c2ccc(Cl)cc2)c(F)c1] | 544.1 | Method D, RT = 1.204 min, 98%. | $^1$H NMR (400 MHz, DMSO-$d_6$) δ = 9.07 (d, J = 8.5 Hz, 1H), 8.53 (s, 1H), 8.13 (s, 1H), 7.89-7.76 (m, 2H), 7.64-7.46 (m, 2H), 6.77 (d, J = 10.8 Hz, 2H), 5.18-5.02 (m, 2H), 4.15-4.04 (m, 1H), 3.99-3.91 (m, 2H), 3.76 (s, 3H), 3.17-3.09 (m, 3H), 3.01 (dd, J = 12.0, 3.8 Hz, 1H), 2.91-2.82 (m, 1H), 2.30-2.20 (m, 1H), 1.94-1.86 (m, 1H). |
| 715 | 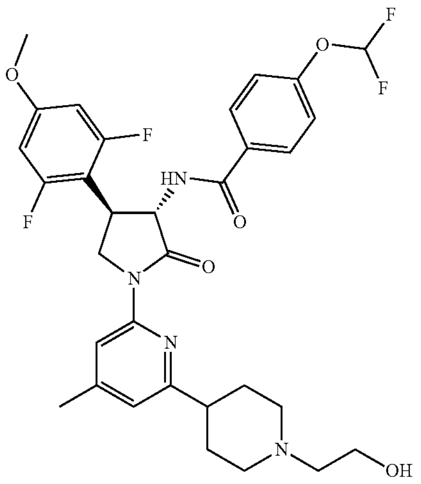 [SMILES: COc1cc(F)c([C@@H]2CN(c3cc(C)cc(C4CCN(CCO)CC4)n3)C(=O)[C@H]2NC(=O)c2ccc(OC(F)F)cc2)c(F)c1] | 631.2 | Method D, RT = 1.51 min, 96%. | $^1$H NMR (400 MHz, DMSO-$d_6$) δ = 9.11 (d, J = 8.3 Hz, 1H), 8.05 (s, 1H), 7.90 (d, J = 8.8 Hz, 2H), 7.36 (t, J = 72.0 Hz, 1H), 7.27 (d, J = 8.8 Hz, 2H), 6.97 (s, 1H), 6.81 (d, J = 10.8 Hz, 2H), 5.34 (d, J = 3.5 Hz, 1H), 5.02 (dd, J = 8.0, 10.8 Hz, 1H), 4.46 (t, J = 10.0 Hz, 1H), 4.16 (q, J = 9.8 Hz, 1H), 4.03-3.93 (m, 1H), 3.78 (s, 3H), 3.78-3.66 (m, 2H), 3.59 (d, J = 12.0 Hz, 2H), 3.22-3.14 (m, 2H), 3.12-3.01 (m, 2H), 2.93-2.84 (m, 1H), 2.36 (s, 3H), 2.13-1.95 (m, 4H). |

TABLE 2-continued

| Ex | Structure | LCMS (M + H)+ | HPLC Method, RT (min.) & Purity | $^1$H NMR |
|---|---|---|---|---|
| 716 | 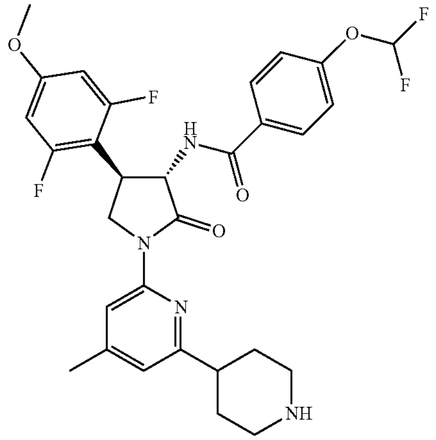 [SMILES: COc1cc(F)c([C@@H]2CN(c3cc(C)cc(C4CCNCC4)n3)C(=O)[C@H]2NC(=O)c2ccc(OC(F)F)cc2)c(F)c1] | 587.2 | Method D, RT = 1.485 min, 99%. | $^1$H NMR (400 MHz, DMSO-$d_6$) δ = 9.11 (d, J = 8.1 Hz, 1H), 8.05 (s, 1H), 7.89 (d, J = 8.8 Hz, 2H), 7.36 (t, J = 72.0 Hz, 1H), 7.29 (d, J = 8.6 Hz, 2H), 6.96 (s, 1H), 6.81 (d, J = 10.8 Hz, 2H), 5.01 (dd, J = 10.8, 8.3 Hz, 1H), 4.45 (t, J = 9.7 Hz, 1H), 4.16 (q, J = 9.8 Hz, 1H), 4.04-3.87 (m, 1H), 3.79 (s, 3H), 3.39-3.31 (m, 3H), 3.09-2.89 (m, 3H), 2.36 (s, 3H), 2.05-1.80 (m, 4H). |
| 717 | 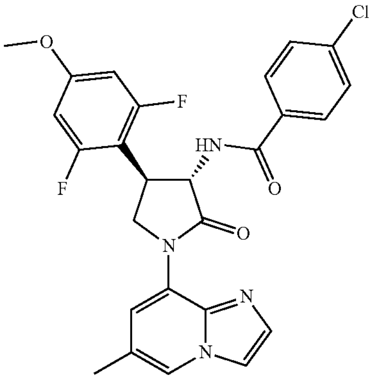 [SMILES: COc1cc(F)c([C@@H]2CN(c3cc(C)cn4ccnc34)C(=O)[C@H]2NC(=O)c2ccc(Cl)cc2)c(F)c1] | 511.12 | Method C, RT = 1.484 min, 100%. | $^1$H NMR (400 MHz, DMSO-$d_6$) δ = 9.14 (d, J = 8.5 Hz, 1H), 8.34 (s, 1H), 7.94 (d, J = 1.3 Hz, 1H), 7.91-7.79 (m, 2H), 7.63-7.48 (m, 3H), 7.37 (d, J = 1.0 Hz, 1H), 6.80 (d, J = 10.8 Hz, 2H), 5.17 (dd, J = 11.0, 8.5 Hz, 1H), 4.56-4.45 (m, 1H), 4.40 (t, J = 9.9 Hz, 1H), 4.22 (q, J = 10.0 Hz, 1H), 3.78 (s, 3H), 2.31 (s, 3H). |
| 718 | 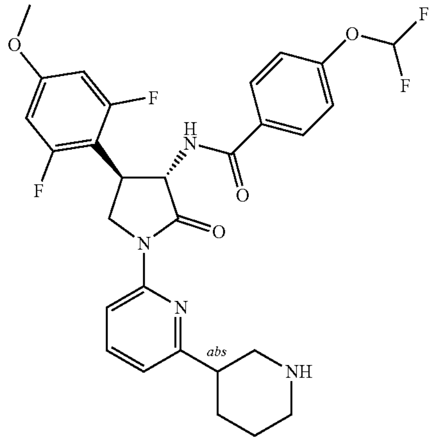 [SMILES: COc1cc(F)c([C@@H]2CN(c3cccc(C4CCCNC4)n3)C(=O)[C@H]2NC(=O)c2ccc(OC(F)F)cc2)c(F)c1] | 573.2 | Method D, RT = 1.429 min, 96%. | $^1$H NMR (400 MHz, DMSO-$d_6$) δ = 9.08 (d, J = 8.0 Hz, 1H), 8.15 (d, J = 8.3 Hz, 1H), 7.89 (d, J = 8.8 Hz, 2H), 7.78 (t, J = 8.0 Hz, 1H), 7.35 (t, J = 73.5 Hz, 1H), 7.28 (d, J = 8.8 Hz, 2H), 7.08 (d, J = 7.3 Hz, 1H), 6.79 (d, J = 10.5 Hz, 2H), 5.12-5.03 (m, 1H), 4.52-4.41 (m, 1H), 4.16-4.08 (m, 1H), 3.98 (d, J = 10.0 Hz, 1H), 3.78 (s, 3H), 3.09-3.06 (m, 1H), 2.92-2.87 (m, 1H), 2.64-2.59 (m, 1H), 2.29-2.24 (m, 1H), 1.97-1.92 (m, 1H), 1.70-1.60 (m, 2H), 1.55-1.42 (m, 3H). |

TABLE 2-continued

| Ex | Structure | LCMS (M + H)+ | HPLC Method, RT (min.) & Purity | $^1$H NMR |
|---|---|---|---|---|
| 719 | 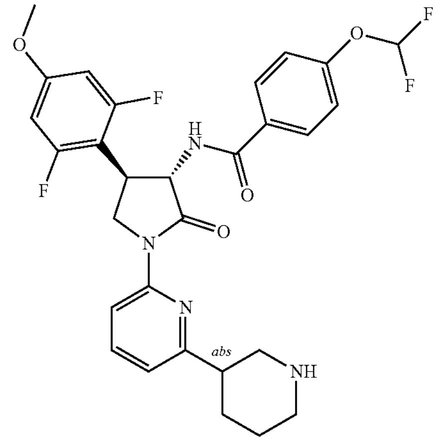 [SMILES: COc1cc(F)c([C@@H]2CN(c3cccc(C4CCCNC4)n3)C(=O)[C@H]2NC(=O)c2ccc(OC(F)F)cc2)c(F)c1] | 573.2 | Method D, RT = 1.439 min, 94%. | $^1$H NMR (400 MHz, DMSO-d$_6$) δ = 9.09 (d, J = 8.3 Hz, 1H), 8.14 (d, J = 8.3 Hz, 1H), 7.92-7.84 (m, 2H), 7.78 (t, J = 7.9 Hz, 1H), 7.35 (t, J = 73.3 Hz, 1H), 7.28 (d, J = 8.8 Hz, 2H), 7.07 (d, J = 7.5 Hz, 1H), 6.79 (d, J = 10.5 Hz, 2H), 5.07 (dd, J = 11.0, 8.3 Hz, 1H), 4.51-4.41 (m, 1H), 4.16-4.07 (m, 1H), 3.97 (t, J = 10.8 Hz, 1H), 3.78 (s, 3H), 3.10-3.07 (m, 1H), 2.92-2.87 (m, 1H), 2.65-2.58 (m, 1H), 1.97-1.90 (m, 1H), 1.76 (m, 1H), 1.69-1.58 (m, 2H), 1.55-1.34 (m, 3H). |
| 720 | 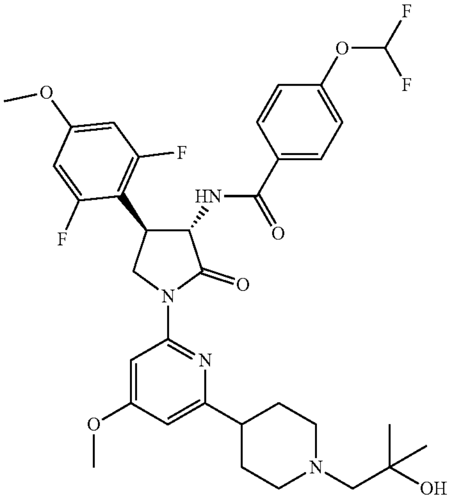 [SMILES: COc1cc(C2CCN(CC(C)(C)O)CC2)nc(N2C[C@@H](c3c(F)cc(OC)cc3F)[C@H](NC(=O)c3ccc(OC(F)F)cc3)C2=O)c1] | 675.2 | Method-D, RT = 1.799 min, 93.08% | $^1$H NMR (400 MHz, DMSO-d$_6$) δ = 9.08 (d, J = 8.5 Hz, 1H), 7.95-7.86 (m, 2H), 7.82-7.78 (m, 1H), 7.35 (t, J = 72 Hz, 1H), 7.32-7.24 (m, 2H), 6.83-6.75 (m, 2H), 6.71-6.67 (m, 1H), 5.07 (dd, J = 11.0, 8.5 Hz, 1H), 4.54-4.43 (m, 1H), 4.11 (q, J = 10.0 Hz, 1H), 3.99-3.92 (m, 1H), 3.83 (s, 3H), 3.78 (s, 3H), 3.07-2.99 (m, 2H), 2.57-2.53 (m, 1H), 2.25-2.13 (m, 4H), 1.80-1.72 (m, 4H), 1.07 (s, 6H). |
| 721 | 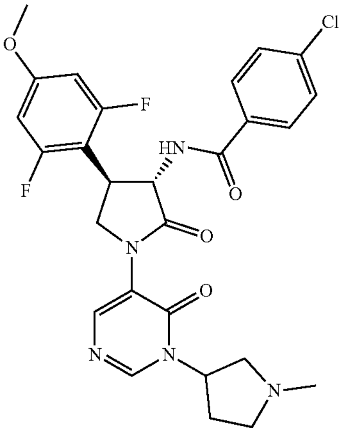 [SMILES: COc1cc(F)c([C@@H]2CN(c3cncn(C4CCN(C)C4)c3=O)C(=O)[C@H]2NC(=O)c2ccc(Cl)cc2)c(F)c1] | 558.2 | Method D, RT = 1.608 min, 97%. | $^1$H NMR (400 MHz, DMSO-d$_6$) δ = 9.08 (d, J = 8.5 Hz, 1H), 8.64 (s, 1H), 8.13 (s, 1H), 7.83 (d, J = 8.5 Hz, 2H), 7.57 (d, J = 8.5 Hz, 2H), 6.78 (d, J = 10.5 Hz, 2H), 5.25-5.16 (m, 1H), 5.12 (dd, J = 11.0, 8.5 Hz, 1H), 4.17-4.05 (m, 1H), 4.01-3.92 (m, 2H), 3.77 (s, 3H), 3.06 (td, J = 8.6, 3.3 Hz, 1H), 2.94 (d, J = 11.5 Hz, 1H), 2.58-2.53 (m, 1H), 2.47-2.38 (m, 1H), 2.32 (s, 3H), 2.28-2.19 (m, 1H), 1.94-1.79 (m, 1H). |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound, having Formula (IVa):

(IVa)

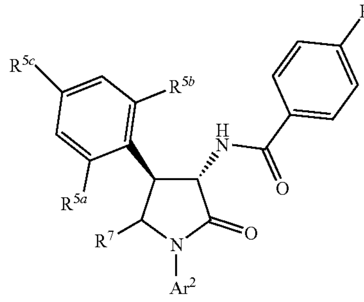

or a pharmaceutically acceptable salt thereof, wherein:

$Ar^2$ is

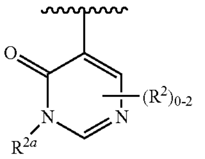

or

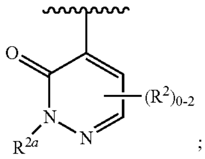

;

$R^1$ is Cl, $—CF_3$, $—OCHF_2$, or $—OCF_3$;

$R^2$ is F, Cl, $CH_2OH$, $CH_3$, $CF_3$, or $CHF_2$; and $R^{2a}$ is $—CH_3$, $—CH_2CH_3$, $—CH_2CHF_2$, $—CH_2CF_3$, $—CH_2CH_2OCH_3$, $—CH_2CH(OH)CF_3$, $—CH_2CH(OH)CH_3$, $—CH_2CH_2OH$, $—CH_2CH(CH_3)OH$, $—CH_2CH(CF_3)OH$, $—CH_2CH_2CF_3$, $—CH(CH_2OH)CH_2OCH_3$, $—CH(CH_2NH_2)OCH_3$, $—CH_2CH(CH_3)OCH_3$, or $—CH_2CH(CF_3)OCH_3$, $R^{5a}$ is hydrogen, F, or Cl;

$R^{5b}$ is hydrogen, F, or Cl;

$R^{5c}$ is Cl or $—OCH_3$; and $R^7$ is hydrogen or $CH_3$.

2. A compound, having Formula (IVb):

(IVb)

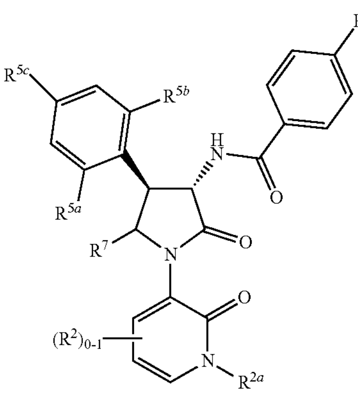

or a pharmaceutically acceptable salt thereof, wherein:

$R^1$ is Cl, $—CF_3$, $—OCHF_2$, or $—OCF_3$;

$R^2$ is cyano, F, Cl, $—CH_3$, $—CF_3$, $—CHF_2$, $—CF_3$, or $—NHC(O)CH_3$;

$R^{2a}$ is $—CH_3$, $CHF_2$, $—CH_2CH_3$, $—CH_2CN$, $—CH_2CHF_2$, $—CH_2CH_2OCH_3$, $—CH_2CH(OH)CF_3$, $—CH_2CH(OH)CH_3$, $—CH_2CH_2OH$, $—CF_2CH_2OH$, $—CH_2CH(CH_3)OH$, $—CH_2CH_2CF_3$, $—CH(CH_2OH)CH_2OCH_3$, $—CH(CH_2NH_2)OCH_3$, $—CH_2CH(CH_3)OCH_3$, $—CH_2CH(CF_3)OCH_3$, $—CH(CH_2NH_2)CH_2OCH_3$, $—CH(C(O)N(CH_3)_2)CH_2OCH_3$, $—CH_2C(CH_3)(CH_2OH)_2$, $—CH_2CH_2N(CH_3)_2$, $—CH_2CH_2S(O)_2C_{1-4}$ alkyl, $—CHR^dC(O)NR^3R^4$, $—(CH_2)_{0-1}—C_{3-6}$ cycloalkyl, $—(CH_2)_{0-3}$-heterocyclyl selected from

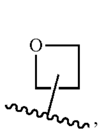,

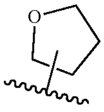, and

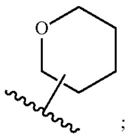;

$R^3$ and $R^4$ together with the nitrogen to which they are both attached form a heterocyclyl selected from

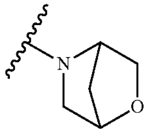

and

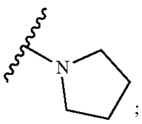;

$R^{5a}$ is hydrogen or F;

$R^{5b}$ is hydrogen or F;

$R^{5c}$ is Cl or $—OCH_3$;

$R^7$ is hydrogen or $CH_3$; and $R^d$ is $—CH_2OCH_3$.

3. A compound, having Formula (IVc):

(IVc)

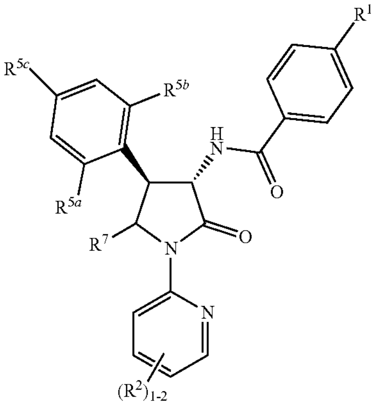

or a pharmaceutically acceptable salt thereof, wherein:

$R^1$ is Cl, $—CF_3$, $—OCHF_2$, or $—OCF_3$;

$R^2$ is cyano, F, Cl, $—CH_2OH$, $—CH_3$, $—CHF_2$, $—CF_3$, $—OCH_3$, $—OCH(CH_3)_2$, $—N^3R^4$, $(CH_3)_2(O)P—$, $C_{3-6}$ cycloalkyl,

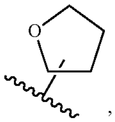, 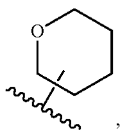, or 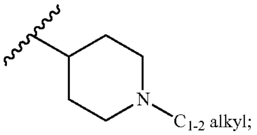

$R^3$ is hydrogen or $C_{1-4}$ alkyl substituted with 0-1 $S(O)_2C_{1-3}$ alkyl,

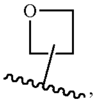, or 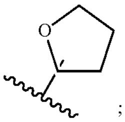;

$R^4$ is hydrogen;

alternatively, $R^3$ and $R^4$ together with the nitrogen to which they are both attached form a heterocyclyl selected from

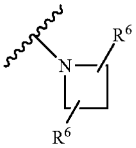, 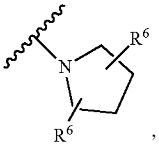, 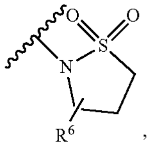, 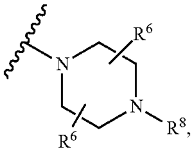 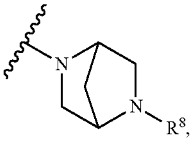 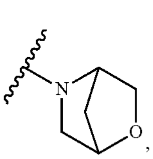, 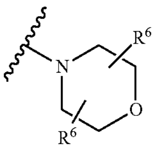, 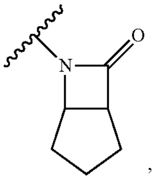, 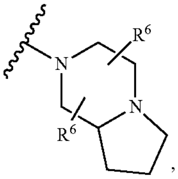, or 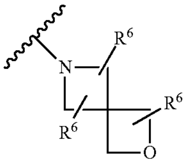;

$R^{5a}$ is hydrogen or F;

$R^{5b}$ is hydrogen or F;

$R^{5c}$ is Cl or —$OCH_3$;

$R^6$ is hydrogen, halo, oxo, —$CH_3$, —$CH_2CH_3$, or —$CH_2OH$;

$R^7$ is hydrogen or $CH_3$; and $R^8$ is hydrogen, $C_{1-2}$ alkyl, or —$S(O)_2C_{1-3}$ alkyl.

4. A compound, having Formula (IVd):

(IVd)

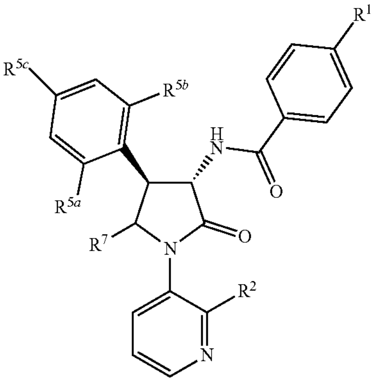

or a pharmaceutically acceptable salt thereof, wherein:

$R^1$ is Cl, —$CF_3$, —$OCHF_2$, or —$OCF_3$;

$R^2$ is —$OR^b$ or $(C_{1-2}\ alkyl)_2(O)P$—;

$R^{5a}$ is hydrogen or F;

$R^{5b}$ is hydrogen or F;

$R^{5c}$ is Cl or —$OCH_3$;

$R^7$ is hydrogen or $CH_3$;

$R^b$ is hydrogen, $C_{1-4}$ alkyl substituted with 0-3 $R^e$, or

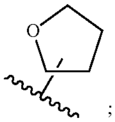;

$R^e$ is F, Cl, or —$OR^g$; and $R^g$ is hydrogen or $C_{1-3}$ alkyl.

5. A compound, having Formula (IVe):

(IVe)

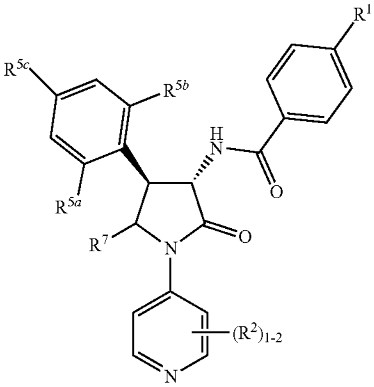

or a pharmaceutically acceptable salt thereof, wherein:

$R^1$ is Cl, —$CF_3$, —$OCHF_2$, or —$OCF_3$;

$R^2$ is cyano, F, Cl, —$CH_2OH$, —$CH_3$, —$CHF_2$, —$CF_3$, —$OCH_3$, —$OCH(CH_3)_2$, or —$NR^3R^4$;

$R^3$ is hydrogen or $C_{1-4}$ alkyl;

$R^4$ is hydrogen or $C_{1-2}$ alkyl;

alternatively, $R^3$ and $R^4$ together with the nitrogen to which they are both attached form a heterocyclyl selected from

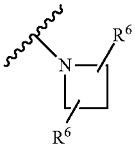,
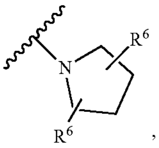,
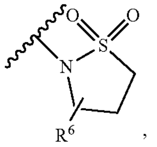,

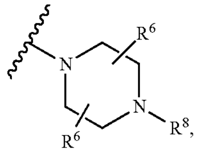
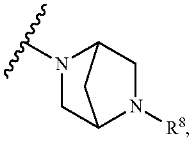

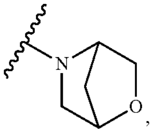,
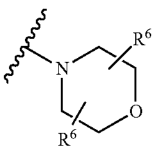,
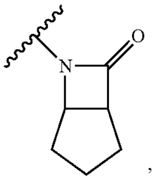,

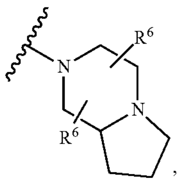, and
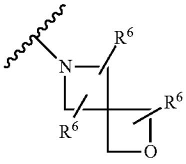;

$R^{5a}$ is hydrogen or F;

$R^{5b}$ is hydrogen or F;

$R^{5c}$ is Cl or —$OCH_3$, $R^6$ is hydrogen, halo, oxo, —$CH_3$, —$CH_2CH_3$, or —$CH_2OH$;

$R^7$ is hydrogen or $CH_3$; and $R^8$ is hydrogen, $C_{1-2}$ alkyl, or —$S(O)_2C_{1-3}$ alkyl.

6. A compound, having Formula (IVf):

(IVf)

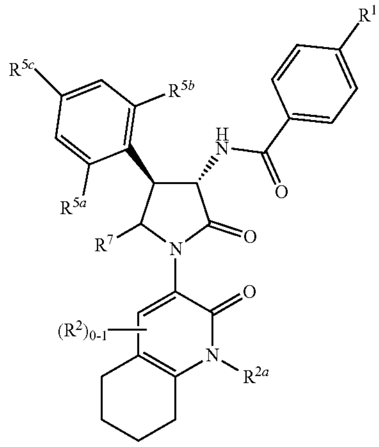

or a pharmaceutically acceptable salt thereof, wherein:

$R^1$ is Cl, —$CF_3$, —$OCH_3$, —$OCHF_2$, or —$OCF_3$;

$R^2$ is cyano, F, Cl, —$CH_2OH$, —$CH_3$, —$CHF_2$, or —$CF_3$;

$R^{2a}$ is —$CH_3$, —$CH_2CH_3$, —$CH_2CHF_2$, —$CH_2CH_2OCH_3$, —$CH_2CH(OH)CF_3$, —$CH_2CH(OH)CH_3$, —$CH_2CH_2OH$, —$CH_2CH(CH_3)OH$, or —$CH_2CH_2CF_3$;

$R^{5a}$ is hydrogen, F, or Cl;

$R^{5b}$ is hydrogen, F, or Cl; and $R^{5c}$ is Cl or —$OCH_3$; and $R^7$ is hydrogen or $CH_3$.

7. A pharmaceutical composition comprising one or more compounds according to claim 1 and a pharmaceutically acceptable carrier or diluent.

8. A method for the treatment or prophylaxis of inflammatory diseases, heart diseases, chronic airway diseases, cancers, septicemia, allergic symptoms, HIV retrovirus infection, circulatory disorders, neuroinflammation, nervous disorders, pains, prion diseases, amyloidosis, and immune disorders, comprising administrating a therapeutically effective amount of the pharmaceutical composition of claim 7 to a patient in need thereof.

9. The method of claim 8, wherein the heart disease is selected from the group consisting of angina pectoris, unstable angina, myocardial infarction, heart failure, acute coronary disease, acute heart failure, chronic heart failure, and cardiac iatrogenic damage.

10. The method of claim 9, wherein the heart failure results from hypertension, an ischemic heart disease, a non-ischemic heart disease, exposure to a cardiotoxic compound, myocarditis, Kawasaki's disease, Type I and Type II diabetes, thyroid disease, viral infection, gingivitis, drug abuse, alcohol abuse, pericarditis, atherosclerosis, vascular disease, hypertrophic cardiomyopathy, dilated cardiomyopathy, myocardial infarction, atrial fibrosis, left ventricular systolic dysfunction, left ventricular diastolic dysfunction, coronary bypass surgery, pacemaker implantation surgery, starvation, an eating disorder, muscular dystrophies, and a genetic defect.

* * * * *